United States Patent
Yokotani et al.

(10) Patent No.: US 7,999,132 B2
(45) Date of Patent: Aug. 16, 2011

(54) ANTHRANILIC ACID DERIVATIVE OR SALT THEREOF

(75) Inventors: Junichi Yokotani, Toyama (JP); Yoichi Taniguchi, Toyama (JP); Eiji Hara, Toyama (JP); Hitoshi Akitsu, Toyama (JP); Yukie Tada, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 1049 days.

(21) Appl. No.: 11/721,007

(22) PCT Filed: Dec. 6, 2005

(86) PCT No.: PCT/JP2005/022367
§ 371 (c)(1),
(2), (4) Date: Jun. 6, 2007

(87) PCT Pub. No.: WO2006/062093
PCT Pub. Date: Jun. 15, 2006

(65) Prior Publication Data
US 2009/0240052 A1 Sep. 24, 2009

(30) Foreign Application Priority Data
Dec. 7, 2004 (JP) .................................. 2004-353725

(51) Int. Cl.
C07C 233/55 (2006.01)
C07C 233/63 (2006.01)
C07C 233/81 (2006.01)
C07C 235/24 (2006.01)
C07C 311/13 (2006.01)
C07C 311/21 (2006.01)
C07C 317/50 (2006.01)

(52) U.S. Cl. ......... 562/455; 562/433; 514/561; 514/563

(58) Field of Classification Search ........................ None
See application file for complete search history.

(56) References Cited

U.S. PATENT DOCUMENTS

| | | | | |
|---|---|---|---|---|
| 6,492,547 B2 * | 12/2002 | Priepke et al. | ................. | 562/455 |
| 2002/0156061 A1 | 10/2002 | Barvian et al. | | |
| 2005/0187297 A1 * | 8/2005 | Jonsson et al. | ................. | 514/563 |

FOREIGN PATENT DOCUMENTS

| | | |
|---|---|---|
| EP | 1 101 755 A1 | 5/2001 |
| EP | 1 446 382 | 5/2003 |
| JP | 50 34028 | 4/1975 |
| WO | WO 02/064080 A2 | 8/2002 |
| WO | WO 02/064080 A3 | 8/2002 |

OTHER PUBLICATIONS

Registry File [online] American chemical Society (ACS) [retrieval date Feb. 21, 2006 (21.02.060] Retrieved from : STNEntered STN: 16.11.1984, Registry No. 30611-02-0.
Ramnath, et al. Matrix Metalloproteinase Inhibitors, Current Oncology Reports, vol. 6, pp. 96-102, 2004.
David R Close: "Matrix metalloproteinase inhibitors in rheumatic diseases", Annals of the Rheumatic Diseases, vol. 60, pp. iii62-iii67, 2001.
Poole, et al, "Proteolysis of the collagen fibril in osteoarthritis", Biochemical society Symposia, vol. 70, pp. 115-123, 2003.
Extended European Search Report issued Sep. 21, 2010, in Application No. 05814561.6-1211 / 1820795 PCT/JP2005022367.
Jeremy I. Levin , et al., "The Discovery of Anthranilic Acid-Based MMP Inhibitors. Part 1: SAR of the 3-Position", Bioorganic & Medicinal Chemistry Letters, vol. 11, XP-002599059, 2001, pp. 235-238.
U.S. Appl. No. 11/908,879, filed Sep. 17, 2007, Yokotani, et al.

* cited by examiner

*Primary Examiner* — Daniel Sullivan
*Assistant Examiner* — Yevegeny Valenrod
(74) *Attorney, Agent, or Firm* — Oblon, Spivak, McClelland, Maier & Neustadt, L.L.P.

(57) ABSTRACT

An anthranilic acid derivative represented by the general formula (X) [wherein $R^1$ represents hydrogen or a carboxy-protecting group; $R^2$ represents optionally substituted phenyl, a heterocyclic group, etc.; $R^3$ represents optionally substituted phenyl, a monocyclic heterocyclic group, etc.; $X^1$ represents carbonyl, etc.; $X^2$ represents optionally substituted alkylene group, a bond, etc.; $X^3$ represents oxygen, a bond, etc.; and $X^4$ represents a group represented by the general formula —$X^5$—$X^6$— or —$X^6$—$X^5$— (wherein $X^5$ means oxygen, a bond, etc.; and $X^6$ means optionally substituted alkylene, a bond, etc.)] or a salt of the derivative. The derivative or salt has the inhibitory activity of MMP-13 production and is hence useful as a therapeutic agent for articular rheumatism, osteoarthritis, cancer, etc.

20 Claims, No Drawings

ANTHRANILIC ACID DERIVATIVE OR SALT THEREOF

CROSS REFERENCE TO RELATED APPLICATION

This application is a 371 of PCT/JP05/022367, filed on Dec. 6, 2005, and claims priority to Japanese Patent Application No. 2004-353725, filed on Dec. 7, 2004.

TECHNICAL FIELD

The present invention relates to a novel anthranilic acid derivative or a salt thereof having the inhibitory activity of matrix metalloprotease 13 (MMP-13) production.

BACKGROUND ART

Matrix metalloproteases are a family consisting of zinc-dependent proteases whose substrates are components of extracellular matrix, and they are activated by removal of a propeptide after secretion. More than 20 members of matrix metalloproteases have been identified in human, and they are classified into collagenase (MMP-1, 8, 13), gelatinase (MMP-2, 9), stromelysin (MMP-3, 10), matrilysin (MMP-7, 26), membrane-type MMP (MMP-14, 15, 16, 17, 24, 25) according to the domain structure and substrate specificity. Overexpression of these matrix metalloproteases are observed in various cancer cells, and it is considered to be involved in the proliferation and metastasis thereof. Anticancer agents that inhibit matrix metalloprotease have been developed up to now (Non-Patent Document 1).

Matrix metalloprotease inhibitors have been developed as a therapeutic agent for rheumatoid arthritis and osteoarthritis. The articular cartilage is composed of a cartilage type II collagen network in which cartilage proteoglycans such as aggrecan and hyaluronic acid are retained. Matrix metalloprotease participates in one maintenance of the extracellular matrix. When matrix metalloprotease and TIMP (tissue inhibitor of metalloproteinases), an endogenous inhibitor thereof, are not in balance and matrix metalloprotease becomes excessively present, destruction of the cartilages and bones may progress, Particularly when collagen fibers are damaged, the joints suffer from progressive destruction as observed in rheumatoid arthritis and osteoarthritis. Accordingly, long-term suppression of the progress of joint destruction in rheumatoid arthritis and osteoarthritis can be expected by inhibiting excessive matrix metalloprotease (Non-Patent Document 2).

In osteoarthritis, the production of interleukin-1 (IL-1) and tumor necrosis factor (TNF) α also increases and extracellular matrix is degraded. The production of matrix metalloprotease is further increased by degradation products of type II collagen and fibronectin, leading to progress in degradation of matrix in the joints. When this damage of matrix exceeds a certain threshold, character of cartilage cells pathological change, and joint destruction keeps progressing. It is MMP-13 that plays a dominant role in this cleavage of type II collagen (Non-Patent Document 3).

Non-Patent Document 1: Current Oncology Reports, Vol. 6, page 96-102, 2004
Non-Patent Document 2: Annals of the Rheumatic Diseases, Vol. 60, page 62-67, 2001
Non-Patent Document 3: Biochemical Society Symposia, Vol. 70, page 115-123, 2003

DISCLOSURE OF THE INVENTION

Drugs inhibiting the production of matrix metalloproteases, particularly MMP-13, are strongly demanded.

Under the circumstances, the present inventors have conducted extensive studies, and consequently have found that an anthranilic acid derivative represented by general formula [1]

[Formula 1]

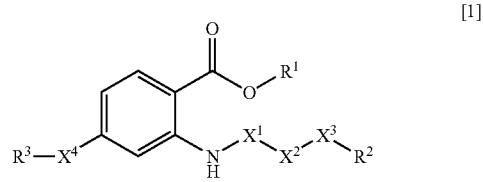

[1]

wherein, $R^1$ represents a hydrogen atom or a carboxyl protecting group; $R^2$ represents a phenyl, cycloalkyl or heterocyclic group which may be optionally substituted; $R^3$ represents a phenyl, cycloalkyl, cycloalkenyl, monocyclic heterocyclic or bicyclic heterocyclic group which may be optionally substituted; $X^1$ represents a carbonyl group or sulfonyl group; $X^2$ represents an alkylene, alkenylene or alkynylene group which may be optionally substituted or a bond; provided that when $X^1$ is a sulfonyl group and $X^4$ is a bond, $X^2$ represents an alkylene, alkenylene or alkynylene group which may be optionally substituted; $X^3$ represents an oxygen atom, a sulfur atom or a bond; $X^4$ represents a group represented by the general formula, $-X^5-X^6-$ or $-X^6-X^5-$, wherein the bond on the left side of each general formula is linked to $R^3$; and $X^5$ represents an oxygen atom, a sulfur atom, an imino group which may be optionally protected, a sulfinyl group or a sulfonyl group or a bond; $X^6$ represents an alkylene, alkenylene or alkynylene group which may be optionally substituted or a bond, or a salt thereof has the inhibitory activity of MMP-13 production and thus completed the present invention.

The novel anthranilic acid derivative or a salt thereof of the present invention has the inhibitory activity of MMP-13 production and is therefore useful as, for example, a therapeutic agent for rheumatoid arthritis, osteoarthritis, cancer and the other diseases in which MMP-13 is involved.

BEST MODE FOR CARRYING OUT THE INVENTION

Hereinbelow, compounds of the present invention are described in detail.

In the present specification, unless otherwise stated in particular, a halogen atom refers to a fluorine atom, a chlorine atom, a bromine atom and an iodine atom; an alkyl group refers to, for example, a linear or branched $C_{1-12}$ alkyl group such as methyl, ethyl, propyl, isopropyl, butyl, sec-butyl, isobutyl, tert-butyl, pentyl, isopentyl, hexyl, heptyl and octyl; a lower alkyl group refers to, for example, a linear or branched $C_{1-6}$ alkyl group such as methyl, ethyl, propyl, isopropyl, butyl, sec-butyl, Isobutyl, tert-butyl, pentyl and isopentyl; an alkenyl group refers to, for example, a linear or branched $C_{2-12}$ alkenyl group such as vinyl, allyl, propenyl, isopropenyl, butenyl, isobutenyl, pentenyl, hexenyl, heptenyl and octenyl; an alkynyl group refers to, for example, a linear or branched $C_{2-12}$ alkynyl group such as ethynyl, 2-propynyl and 2-butynyl; a cycloalkyl group refers to, for example, a $C_{3-8}$ cycloalkyl group such as cyclopropyl, cyclobutyl, cyclopentyl and cyclohexyl; a cycloalkenyl group refers to, for example, a $C_{3-8}$ cycloalkenyl group such as cyclopropenyl, cyclobutenyl, cyclopentenyl and cyclohexenyl; an alkylene group refers to, for example, a linear or branched $C_{1-6}$ alkylene group such as methylene, ethylene, propylene, butylene and hexylene; an alkenylene group refers to, for example, a linear or branched $C_{2-6}$ alkenylene group such as vinylene, propenylene, 1-butenylene and 2-butenylene; an alkynylene group refers to, for example, a linear or branched $C_{2-6}$ alkynylene group such as ethynylene, propynylene, 1-butynylene and 2-butynylene; an aryl group refers to, for example, a group such as phenyl and naphthyl; an aralkyl group refers no, for example, an ar-$C_{1-6}$ alkyl group such as benzyl, diphenylmethyl, trityl, phenethyl and naphthylmethyl; an alkoxy group refers to, for example, a linear or branched $C_{1-6}$ alkyloxy group such as methoxy, ethoxy, propoxy, isopropoxy, butoxy, isobutoxy, sec-butoxy, tert-butoxy, pentyloxy and isopentyloxy; an aryloxy group refers to, for example, a group such as phenoxy and naphthoxy; an alkoxy alkyl group refers to, for example, a $C_{1-6}$ alkyloxy $C_{1-6}$ alkyl group such as methoxymethyl and 1-ethoxyethyl; and an aralkyloxyalkyl group refers to, for example, an ar-$C_{1-6}$ alkyloxy $C_{1-6}$ alkyl group such as benzyloxymethyl and phenethyloxymethyl; an acyl group refers to, for example, a formyl group, a linear or branched $C_{2-12}$ alkanoyl group such as acetyl, propionyl and isovaleryl, an ar-$C_{1-6}$ alkylcarbonyl group such as benzylcarbonyl, a cyclic hydrocarbon carbonyl group such as benzoyl and naphthoyl, a heterocyclic carbonyl group such as nicotinoyl, thenoyl, pyrrolidinocarbonyl and furoyl, a succinyl group, a glutaryl group, a maleoyl group, a phthaloyl group and a linear or branched α-aminoalkanoyl group derived from an amino acid (Examples of the amino acid include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline.) In which the N-terminal may be optionally protected; an alkyloxycarbonyl group refers to, for example, a linear or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; an aralkyloxycarbonyl group refers to, for example, an ar-$C_{1-6}$ alkyloxycarbonyl group such as benzyloxycarbonyl and phenethyloxycarbonyl group; an aryloxycarbonyl group refers to, for example, a group such as phenyloxycarbonyl; an acyloxy group refers to, for example, a linear or branched $C_{2-6}$ alkanoyloxy group such as acetyloxy and propionyloxy and an aroyloxy group such as benzoyloxy; an acylalkyl group refers to, for example, a group such as acetylmethyl, benzoylmethyl, p-nitrobenzoylmethyl, p-bromobenzoylmethyl, p-methoxybenzoylmethyl and 1-benzoylethyl; an acyloxyalkyl group refers to, for example, a group such as acetoxymethyl, proplonyloxymethyl and pivaloyloxymethyl; an alkylthioalkyl group refers to, for example, a $C_{1-6}$ alkylthio $C_{1-6}$ alkyl group such as methylthiomethyl, ethylthiomethyl and propylthio-methyl; an arylthio group refers to, for example, a group such as phenylthio; an alkanesulfonyl group refers to, for example, a $C_{1-6}$ alkanesulfonyl group such as methanesulfonyl, ethanesulfonyl and propanesulfonyl; an arylsulfonyl group refers to, for example, a group such as benzenesulfonyl, toluenesulfonyl and naphthalenesulfonyl; an alkanesulfonyloxy group refers to, for example, a $C_{1-6}$ alkanesulfonyloxy group such as methanesulfonyloxy and ethanesulfonyloxy; an arylsulfonyloxy group refers to, for example, a group such as benzenesulfonyloxy and toluenesulfonyloxy; an arylthioalkyl group refers to, for example, a group such as phenylsulfenylmethyl and 2-(p-nitrophenylsulfenyl)ethyl; an arylsulfonylalkyl group refers to, for example, a group such as p-toluenesulfonylethyl; and an alkanesulfonamide group refers to, for example, a $C_{1-6}$ alkanesulfonamide group such as methanesulfonamide and ethanesulfonamide.

An oxygen-containing heterocyclic group refers to, for example, a group such as 2-tetrahydropyranyl and 2-tetrahydrofuranyl; a sulfur-containing heterocyclic group refers to, for example, a group such as tetrahydrothiopyranyl; a heterocyclic oxycarbonyl group refers to, for example, a group such as 2-furfuryloxycarbonyl and 8-quinolyloxycarbonyl; a nitrogen-containing heterocyclic alkyl group refers to, for example, a group such as phthalimidomethyl and succinimidomethyl; a substituted silyl group refers to, for example, a group such as trimethylsilyl, triethylsilyl and tributylsilyl; and an alkylsilylalkyl group refers to, for example, a group such as 2-(trimethylsilyl)ethyl.

A monocyclic heterocyclic group refers to, for example, a nitrogen-containing monocyclic heterocyclic group containing a nitrogen atom(s) as sole ring-member heteroatom such as pyrrolyl, pyrrolinyl, pyrrolidinyl, piperidyl, piperazinyl, imidazolyl, pyrazolyl, pyridyl, tetrahydropyridyl, pyridazinyl, pyrazinyl, pyrimidinyl, tetrazolyl, imidazolinyl, imidazolidinyl, pyrazolinyl and pyrazolidinyl group; an oxygen-containing monocyclic heterocyclic group containing an oxygen atom(s) as sole ring-member heteroatom such as furyl and pyranyl group; a sulfur-containing monocyclic heterocyclic group containing a sulfur atom(s) as sole ring-member heteroatom such as a thienyl group; a nitrogen-and-oxygen-containing monocyclic heterocyclic group containing nitrogen and oxygen atoms as sole ring-member heteroatoms such as oxazolyl, oxadiazolyl, isoxazolyl and morpholinyl group; a nitrogen-and-sulfur-containing monocyclic heterocyclic group containing nitrogen and sulfur atoms as sole ring-member heteroatoms such as thiazolyl, isothiazolyl, thiadiazolyl and thiomorpholinyl group; and an oxygen-and-sulfur-containing monocyclic heterocyclic group containing oxygen and sulfur atoms as sole ring-member heteroatoms such as a thioxanyl group.

A bicyclic heterocyclic group refers to, for example, a nitrogen-containing bicyclic heterocyclic group represented by a condensed or bridged ring containing only 1 to 3 nitrogen atom(s) as the heteroatom of the said ring such as indolyl, indolinyl, 2-oxoindolinyl, isoindolyl, indolizinyl, benzimidazolyl, benzotriazolyl, indazolyl, quinolyl, tetrahydroquinolinyl, tetrahydroisoquinolinyl, quinolizinyl, isoquinolyl, phthalazinyl, naphthyridinyl, quinoxalinyl, dihydroquinoxalinyl, quinazolinyl, cinnolinyl, quinuclidinyl and 2,3-dihydrobenzopyrrolyl group; an oxygen-containing bicyclic heterocyclic group represented by a condensed or bridged ring containing only oxygen atom(s) as the heteroatom of the said ring such as benzofuranyl, isobenzofuranyl, chromenyl, chromanyl, isochromanyl, benzo-1,3-dioxolyl, benzo-1,4-dioxanyl and 2,3-dihydrobenzofuranyl group; a sulfur-containing bicyclic heterocyclic group represented by a condensed or bridged ring containing only sulfur atom(s) as the heteroatom of the said ring such as benzothienyl and 2,3-dihydrobenzothienyl group; a nitrogen-and-oxygen-containing bicyclic heterocyclic group represented by a condensed or bridged ring containing only nitrogen and oxygen atom(s) as the heteroatom of the said ring such as benzomorpholinyl and benzomorpholinyl group; and a nitrogen-and-sulfur-containing bicyclic heterocyclic group represented by a condensed or bridged ring containing only nitrogen and sulfur atom(s) as the heteroatom of the said ring such as benzothiazolyl and benzothiadiazolyl group.

A heterocyclic group refers to, for example, a monocyclic heterocyclic group; a bicyclic heterocyclic group; a tricyclic heterocyclic group such as thianthrenyl, xanthenyl, phenoxathiinyl, carbazolyl, β-carbolinyl, phenanthridinyl, acridinyl, perimidinyl, phenathrolinyl, phenazinyl, phenothiazinyl and phenoxazinyl.

A cyclic amino group may be, for example, a saturated cyclic amino group and an unsaturated amino group, may optionally contain one or more heteroatoms such as nitrogen atom, oxygen atom and sulfur atom and carbonyl carbon in the ring, and may be monocyclic, bicyclic or tricyclic; and more specifically refers to a saturated or unsaturated monocyclic 3- to 7-membered cyclic amino group having one nitrogen atom such as aziridin-1-yl, azetidin-1-yl, pyrrolidin-1-yl, pyrrolin-1-yl, pyrrol-1-yl, dihydropyridin-1-yl, tetrahydropyridin-1-yl, piperidin-1-yl, dihydroazepin-1-yl and perhydroazepin-1-yl; a saturated or unsaturated monocyclic 3- to 7-membered cyclic amino group having 2 nitrogen atoms such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl and homopiperazin-1-yl; a saturated or unsaturated monocyclic 3- to 7-membered cyclic amino group having 3or more nitrogen atoms such as 1,2,4-triazol-1-yl, 1,2,3-triazol-1-yl, 1,2-dihydro-1,2,4-triazin-1-yl and perhydro-3-triazin-1-yl; a saturated or unsaturated monocyclic 3- to 7-membered cyclic amino group having 1 to 4 heteroatoms selected from an oxygen atom and a sulfur atom in addition to a nitrogen atom(s) such as oxazolidin-3-yl, isoxazolidin-2-yl, morpholin-4-yl, thiazolidin-3-yl, thiazolidin-2-yl, thiomorpholin-4-yl, homothiomorpholin-4-yl and 1,2,4-thiaziazolin-2-yl; a saturated or unsaturated bicyclic or tricyclic cyclic amino group such as isoindolin-2-yl, indolin-1-yl, 1H-indazol-1-yl, 1H-indol-1-yl, 1H-benzimidazol-1-yl, purin-7-yl, tetrahydroquinolin-1-yl and tetrahydroisoquinolin-2-yl; and a saturated or unsaturated 5- to 12-membered spiro or bridged cyclic amino group such as 5-azaspiro[2.4]heptan-5-yl, 2,8-diazabicyclo[4.3.0]nonan-8-yl, 3-azabicyclo[3.1.0]hexan-3-yl, 2-oxa-5,8-diazabicyclo[4.3.0]nonan-8-yl, 2,8-diazaspiro[4,4]nonan-2-yl and 7-azabicyclo[2.2.1]heptan-7-yl.

The amino protecting group includes any group which can be normally used as a protecting group of an amino group, and examples thereof include groups described in W. Greene et al., Protective Groups in Organic Synthesis, third edition, pp. 494-615, 1999, John Wiley & Sons, INC. Specific examples thereof include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group and a substituted silyl group.

The imino protecting group includes any group which can be normally used as a protecting group of an imino group, and examples thereof include groups described in w, Greene et al., Protective Groups In Organic Synthesis, third edition, pp. 494-615, 1999, John Wiley & Sons, INC, Specific examples thereof include an acyl group, an alkyloxycarbonyl group, an aralkyloxycarbonyl group, an aryloxycarbonyl group, an aralkyl group, an alkoxyalkyl group, an arylthio group, an alkanesulfonyl group, an arylsulfonyl group and a substituted silyl group.

The hydroxyl protecting group includes any group which can be normally used as a protecting group of a hydroxyl group, and examples thereof include groups described in W, Greene et al., Protective Groups in Organic Synthesis, third edition, pp. 17-245, 1999, John Wiley & Sons, INC. Specific examples thereof include an acyl group, an alkyloxycarbonyl group, an aralkyloxycarbonyl group, a heterocyclic oxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkanesulfonyl group, an arylsulfonyl group and a substituted silyl group.

The carboxyl protecting group includes any group which can be normally used as a protecting group of a carboxyl group, and examples thereof include groups described in W, Greene et al. Protective Groups in Organic Synthesis, third edition, pp. 369-453, 1999, John Wiley & Sons, INC. Specific examples thereof include an alkyl group, an aryl group, an aralkyl group, an acylalkyl group, an arylthioalkyl group, an arylsulfonylalkyl group, an oxygen-containing heterocyclic group, an alkyl silyl alkyl group, an acyloxyalkyl group, a nitrogen-containing heterocyclic alkyl group, a cycloalkyl group, an alkoxyalkyl group, an aralkyloxyalkyl group, an alkylthioalkyl group, an alkenyl group and a substituted silyl group.

The phenolic hydroxyl protecting group includes any group which can be normally used as a protecting group of a phenolic hydroxyl group, and examples thereof include groups described in W. Greene et al., Protective Groups in Organic Synthesis, third edition, pp. 246-287, 1999, John Wiley & Sons, INC, Specific examples thereof. Include an acyl group, an alkyl group, an alkenyl group, an aralkyl group, an oxygen-containing heterocyclic group, a sulfur-containing heterocyclic group, an alkoxyalkyl group, an alkanesulfonyl group, an arylsulfonyl group and a substituted silyl group.

The thiol protecting group includes any group which can be normally used as a protecting group of a thiol group, and examples thereof include groups described in W, Greene et al., Protective Groups in Organic Synthesis, third edition, pp. 454-493, 1999, John Wiley & Sons, INC. Specific examples thereof include an acyl group, an alkyl group, an alkenyl group, an aralkyl group, an alkoxyalkyl group and a substituted silyl group.

The acetylene protecting group includes any group which can be normally used as a protecting group of acetylene, and examples thereof include groups described in W, Greene et al., Protective Groups in Organic Synthesis, third edition, pp. 654-659, 1999, John Wiley & Sons, INC. Specific examples thereof. Include substituted silyl group.

Examples of a leaving group include a halogen atom, an alkanesulfonyloxy group, an arylsulfonyloxy group and an acyloxy group.

The salt of a compound of general formula [1] includes commonly known salts formed from a basic group such as an amine group or from an acidic group such as a phenolic hydroxyl group or a carboxyl group.

Examples of salts formed from a basic group include salts with a mineral acid such as hydrochloric acid, hydrogen bromide and sulfuric acid; salts with an organic carboxylic acid such as tartaric acid, formic acid, acetic acid, citric acid, trichloroacetic acid and trifluoroacetic acid and salts with a sulfonic acid such as methanesulfonic acid, benzenesulfonic acid, p-toluenesulfonic acid, mesitylenesulfonic acid and naphthalenesulfonic acid.

Examples of salts formed from an acidic group include salts with an alkali metal such as sodium and potassium; salts with an alkali earth metal such as calcium and magnesium; ammonium salt and salts with a nitrogen-containing organic base group such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine and N,N'-dibenzylethylenediamine.

Furthermore, as preferable salts of a compound of general formula [1], pharmacologically acceptable salts are included.

The phenyl, cycloalkyl and heterocyclic groups of $R^2$ in the present invention may be optionally substituted with at least one group selected from a halogen atom, a cyano group, a nitro group, an acyl group, an acyloxy group, a sulfo group, a phosphoryl group, an alkanesulfonyl group, an alkanesulfonamide group, an acetamide group, a carbamoyl group, carboxyl, amino and hydroxyl groups which may be optionally protected and alkyl, alkenyl, alkynyl, alkoxy, aryl, cyclic amino, aralkyl and heterocyclic groups which may be optionally substituted.

The phenyl, cycloalkyl, cycloalkenyl, monocyclic heterocyclic and bicyclic heterocyclic groups in $R^3$ may be optionally substituted with at least one group selected from a halogen atom, a cyano group, a nitro group, an acyl group, an acyloxy group, a sulfo group, a phosphoryl group, an amino group, an alkanesulfonyl group, an alkanesulfonamide group, an acetamide group, a dimethylamino group, a carbamoyl group, carboxyl and hydroxyl groups which may be optionally protected and an alkyl, alkenyl, alkynyl, alkoxy, aryl, aryloxy, cyclic amino, aralkyl and heterocyclic groups which may be optionally substituted.

The alkylene, alkenylene and alkynylene groups in $X^2$ and $X^6$ may be optionally substituted with at least one group selected from a halogen atom, a cyano group, a nitro group, an acyl group, a sulfo group, a phosphoryl group, an alkanesulfonyl, an alkanesulfonamide group, an acetamide group, a carbamoyl group, carboxyl, amino and hydroxyl groups which may be optionally protected and alkyl, alkenyl, alkynyl, alkoxy, aryl, cyclic amino, aralkyl and heterocyclic groups which may be optionally substituted.

Examples of the substituent of the alkyl, alkenyl, alkynyl, alkoxy, aryl, cyclic amino, aralkyl and heterocyclic groups which may be optionally substituted shown above include a halogen atom, a cyano group, a nitro group, an acyl group, a sulfo group, a phosphoryl group, a cyclic amino group, an alkanesulfonyl group, an alkanesulfonamide group, an acetamide group, an aralkyl group, a carbamoyl group, an alkyl group, an alkenyl group, an alkynyl group, an alkoxy group, an aryl group, a heterocyclic group and carboxyl, amino and hydroxyl groups which may be optionally protected.

Among the compounds of the present invention, preferable compounds include the following compounds.

The compounds in which $R^1$ is a hydrogen atom are preferable.

The compounds in which Pd is a phenyl, $C_{5-7}$ cycloalkyl or heterocyclic group which may be optionally substituted are preferable, the compounds in which $R^2$ is a phenyl or heterocyclic group which may be optionally substituted with a group selected from a halogen atom, a cyano group, a nitro group, a hydroxyl group which may be optionally protected, an alkyl group which may be optionally substituted, an alkenyl group which may be optionally substituted, an alkynyl group which may be optionally substituted, an alkoxy group which may be optionally substituted, an aryl group which may be optionally substituted, a cyclic amino group which may be optionally substituted, an aralkyl group which may be optionally substituted and a heterocyclic group which may be optionally substituted are more preferable, the compounds in which $R^2$ is a phenyl or heterocyclic group which may be optionally substituted with a group selected from a halogen atom, a nitro group, a hydroxyl group, an alkyl group which may be optionally substituted, an alkenyl group which may be optionally substituted, an alkoxy group which may be optionally substituted, an aryl group which may be optionally substituted, a cyclic amino group which may be optionally substituted and a monocyclic heterocyclic group which may be optionally substituted are still more preferable, and the compounds in which $R^2$ is a phenyl group, an oxygen-containing bicyclic heterocyclic group represented by a condensed or bridged ring containing only oxygen atom(s) as the heteroatom of the said ring, a sulfur-containing bicyclic heterocyclic group represented by a condensed or bridged ring containing only sulfur atom(s) as the heteroatom of the said ring and a nitrogen-and-sulfur-containing bicyclic heterocyclic group represented by a condensed or bridged ring containing only nitrogen and sulfur atom(s) as the heteroatom of the said ring; and these groups may be optionally substituted with a group selected from a halogen atom, a hydroxyl group, an alkyl group which may be optionally substituted with a halogen atom, an aryl group which may be optionally substituted with a halogen atom, a cyclic amino group and a nitrogen-containing monocyclic heterocyclic group containing a nitrogen atom(s) as sole ring-member heteroatom are still further more preferable.

The compounds in which $R^3$ is a phenyl, $C_{5-7}$ cycloalkyl, $C_{5-7}$ cycloalkenyl or monocyclic heterocyclic or bicyclic heterocyclic group which may be optionally substituted are preferable, the compounds in which $R^3$ is a phenyl, monocyclic heterocyclic or bicyclic heterocyclic group which may be optionally substituted with a group selected from a halogen atom, a cyano group, a nitro group, an acyl group, a hydroxyl group, an alkanesulfonyl group, an alkyl group which may be optionally substituted, an alkoxy group which may be optionally substituted, an aryl group which may be optionally substituted, an aryloxy group which may be optionally substituted and a heterocyclic group which may be optionally substituted are more preferable, the compounds in which $R^3$ is a phenyl, monocyclic heterocyclic or bicyclic heterocyclic group which may be optionally substituted with a group selected from a halogen atom, a hydroxyl group, an alkyl group which may be optionally substituted, and an alkoxy group which may be optionally substituted are still more preferable, and the compounds in which $R^3$ is phenyl groups, nitrogen-containing bicyclic heterocyclic group represented by a condensed or bridged ring containing only 1 to 3 nitrogen atom(s) as the heteroatom of the said ring, oxygen-containing bicyclic heterocyclic group represented by a condensed or bridged ring containing only oxygen atom(s) as the heteroatom of the said ring or sulfur-containing bicyclic heterocyclic group represented by a condensed or bridged ring containing only sulfur atom(s) as the heteroatom of the said ring; and these groups may be optionally substituted with a group selected from a halogen atom, a hydroxyl group, an alkyl group which may be optionally substituted with a halogen atom and an alkoxy group which may be optionally substituted with a halogen atom are still further more preferable.

The compounds in which $X^1$ is a carbonyl group are preferable.

The compounds in which $X^2$ is an alkylene, alkenylene or alkynylene group which may be optionally substituted with a group selected from an alkyl and phenyl group which may be optionally substituted or a bond are preferable, the compound in which $X^2$ is an alkylene group, an alkenylene group, an alkynylene group or a bond are more preferable, and the compounds in which $X^2$ is an alkylene group, an alkenylene group or a bond are still more preferable.

The compounds in which $X^3$ is an oxygen atom or a bond are preferable, and the compounds in which $X^3$ is a bond are more preferable.

When $X^2$ is an alkylene, alkenylene or alkynylene group which may be optionally substituted, the compounds in which $X^3$ is an oxygen atom are preferable.

The compounds in which $X^4$ is the general formula —$X^6$—$X^5$—, wherein the bond on the left side of the general formula is linked to $R^3$, and $X^5$ represents an oxygen atom, a sulfur atom, an imino group which may be optionally protected, a sulfinyl group, a sulfonyl group or a bond; $X^6$ represents an alkylene, alkenylene or alkynylene group which may be optionally substituted or a bond are preferable.

The compounds in which $X^4$ is the general formula $—X^{6p}—X^{5p}—$, wherein the bond on the left side of the general formula is linked to $R^3$; and $X^{5p}$ represents an oxygen atom, a sulfur atom, an imino group or a bond; and $X^{6p}$ represents an alkylene, alkenylene or alkynylene group which may be optionally substituted are preferable, the compounds in which $X^4$ is the general formula $—X^{6p}—X^{5q}—$, wherein the bond on the left side of the general formula is linked to $R^3$; and $X^{5q}$ represents an oxygen atom, a sulfur atom or a bond; and $X^{6p}$ means the same as above are more preferable, and the compounds in which $X^4$ is a general formula $—X^{6q}—X^{5r}—$, wherein the bond on the left side of the general formula is linked to $R^3$; and $X^{5r}$ represents a bond; and $X^{6q}$ represents an alkylene group, an alkenylene group or an alkynylene group are further preferable. The compounds in which $X^4$ is the general formula $—X^{6r}—X^{5p}—$, wherein the bond on the left side of the general formula is linked to $R^3$; and $X^{6r}$ represents a bond; and $X^{5p}$ means the same as above are preferable, and the compounds in which $X^4$ is a general formula $—X^{6r}—X^{5s}—$, wherein the bond on the left side of the general formula is linked to $R^3$; and $X^{5s}$ represents an oxygen atom or a bond; and $X^{6r}$ means the same as above are more preferable.

Examples of typical compounds, among the compounds of the present invention, include compounds of the following Tables 1 to 6.

TABLE 1

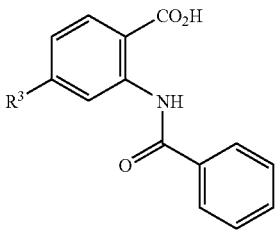

| $R^3$ |
|---|
| Phenyl |
| 4-(tert-Butyl)phenyl |
| Thiazol-2-yl |
| Thiophen-2-yl |
| Benzofuran-2-yl |
| Benzofuran-5-yl |
| 1H-benzimidazol-1-yl |
| 1H-indol-1-yl |
| 1H-indol-5-yl |
| 1H-indol-4-yl |
| 4-(Methanesulfonyl)phenyl |
| Benzothiophen-2-yl |
| Benzothiophen-5-yl |
| 3-Nitrophenyl |
| 4-Nitrophenyl |
| 4-Acetylphenyl |
| 2-Fluorophenyl |
| 3-Fluorophenyl |
| 4-Fluorophenyl |
| 2,3-Difluorophenyl |
| 2,6-Difluorophenyl |
| 3,4-Difluorophenyl |
| 2,5-Difluorophenyl |
| 3,5-Difluorophenyl |
| 2,4-Difluorophenyl |
| 2-Methoxyphenyl |
| 3-Methoxyphenyl |
| 4-Methoxyphenyl |
| 5-Chloro-2-methoxyphenyl |
| 3-Chloro-4-methoxyphenyl |

TABLE 1-continued

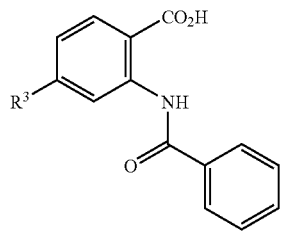

| $R^3$ |
|---|
| 2-Isopropoxyphenyl |
| 4-Isopropoxyphenyl |
| 2-(Trifluoromethoxy)phenyl |
| 3-(Trifluoromethoxy)phenyl |
| 4-(Trifluoromethoxy)phenyl |
| 4-Phenylpiperidin-1-yl |
| 4-Benzylpiperidin-1-yl |
| 2-Chlorophenyl |
| 3-Chlorophenyl |
| 4-Chlorophenyl |
| 3,5-Dichlorophenyl |
| 3,4-Dichlorophenyl |
| 2,3-Dichlorophenyl |
| 2,4-Dichlorophenyl |
| 2,5-Dichlorophenyl |
| 3-Chloro-2-fluorophenyl |
| 5-Chloro-2-fluorophenyl |
| 2-Chloro-6-fluorophenyl |
| 3-Chloro-4-fluorophenyl |
| 4-Hydroxyphenyl |
| 3-Chloro-4-hydroxyphenyl |
| 3-Cyanophenyl |
| 4-Cyanophenyl |
| 2-Methylphenyl |
| 3-Methylphenyl |
| 4-Methylphenyl |
| 2,3-Dimethylphenyl |
| 2,6-Dimethylphenyl |
| 3,4-Dimethylphenyl |
| 3,5-Dimethyl-4-hydroxyphenyl |
| 3-Fluoro-4-methylphenyl |
| 4-Fluoro-2-methylphenyl |
| 3-Fluoro-2-methylphenyl |
| 3-Chloro-4-methylphenyl |
| 5-Chloro-2-methylphenyl |
| 2-Phenoxyphenyl |
| 4-Phenoxyphenyl |
| 4-Benzoylphenyl |
| Indolin-1-yl |
| 2,3-Dihydrobenzo[1,4]dioxin-6-yl |
| Benzo[1,3]dioxol-5-yl |
| 4-(1H-pyrrol-1-yl)phenyl |
| 1,2,3,4-tetrahydroisoquinolin-2-yl |

TABLE 2

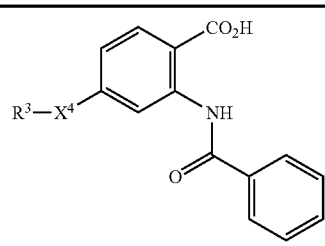

| $R^3$ | $X^4$ |
|---|---|
| Phenyl | $CH_2$ |
| Phenyl | $CH=CH$ |
| Phenyl | $C≡C$ |
| Phenyl | O |

TABLE 2-continued

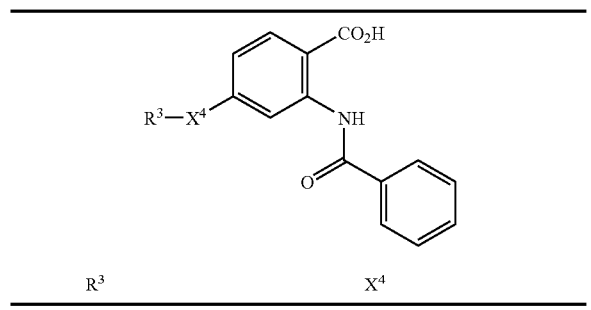

| R³ | X⁴ |
|---|---|
| Phenyl | S |
| Phenyl | NH |
| Phenyl | (CH₂)₂ |
| Phenyl | (CH₂)₃ |
| Phenyl | (CH₂)₄ |
| Phenyl | CH₂O |
| Phenyl | (CH₂)₂O |
| Phenyl | (CH₂)₃O |
| Phenyl | CH₂S |
| Phenyl | SCH₂ |
| Cyclohexyl | CH=CH |
| Cyclohexyl | CH₂CH=CH |
| Cyclohexyl | O |
| 2-Fluorophenyl | O |
| 3-Fluorophenyl | O |
| 4-Fluorophenyl | O |
| 2,3-Difluorophenyl | O |
| 2,4-Difluorophenyl | O |
| 2,5-Difluorophenyl | O |
| 2,6-Difluorophenyl | O |
| 3,4-Difluorophenyl | O |
| 3,5-Difluorophenyl | O |
| 2-Chlorophenyl | O |
| 3-Chlorophenyl | O |
| 4-Chlorophenyl | O |
| 2,3-Dichlorophenyl | O |
| 2,4-Dichlorophenyl | O |
| 2,5-Dichlorophenyl | O |
| 2,6-Dichlorophenyl | O |
| 3,4-Dichlorophenyl | O |
| 3,5-Dichlorophenyl | O |
| 3-Nitrophenyl | O |
| 4-Nitrophenyl | O |
| 2-Methylphenyl | O |
| 3-Methylphenyl | O |
| 4-Methylphenyl | O |
| 2,3-Dimethylphenyl | O |
| 2,6-Dimethylphenyl | O |
| 3,4-Dimethylphenyl | O |
| 3-(Trifluoromethoxy)phenyl | O |
| 4-(Trifluoromethoxy)phenyl | O |
| 3-Fluoro-4-methylphenyl | O |
| 4-Fluoro-2-methylphenyl | O |
| 3-Chloro-4-fluorophenyl | O |
| 5-Chloro-2-methylphenyl | O |
| 3-(Trifluoromethyl)phenyl | O |
| 4-(Trifluoromethyl)phenyl | O |
| 2,3-Dihydrobenzo[1,4]dioxin-6-yl | O |
| Benzofuran-5-yl | O |
| Benzothiophen-5-yl | O |
| Cyclohexyl | (CH₂)₂ |
| Cyclohexyl | (CH₂)₃ |
| 2-Methylphenyl | CH=CH |
| 4-Fluorophenyl | CH=CH |
| 3-Fluoro-4-methylphenyl | CH=CH |
| 3-Nitrophenyl | CH=CH |
| 4-Acetylphenyl | CH=CH |
| 3-Methoxyphenyl | CH=CH |
| 4-Methoxyphenyl | CH=CH |
| 3-Chlorophenyl | CH=CH |
| 2,3-Dihydrobenzo[1,4]dioxin-6-yl | CH=CH |
| Benzofuran-5-yl | CH=CH |
| Benzothiophen-5-yl | CH=CH |
| Benzo[1,3]dioxol-5-yl | CH=CH |
| 2,1,3-Benzothiadiazol-4-yl | CH=CH |
| 4-(Trifluoromethyl)phenyl | CH=CH |

TABLE 2-continued

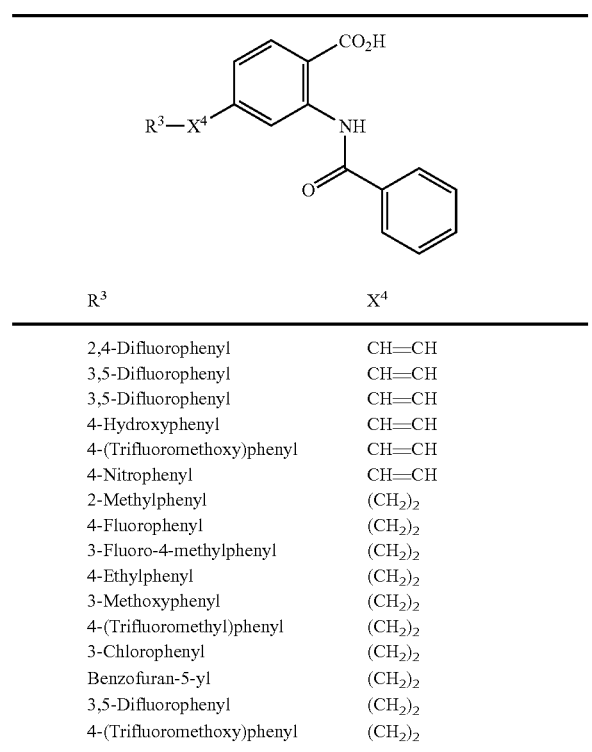

| R³ | X⁴ |
|---|---|
| 2,4-Difluorophenyl | CH=CH |
| 3,5-Difluorophenyl | CH=CH |
| 3,5-Difluorophenyl | CH=CH |
| 4-Hydroxyphenyl | CH=CH |
| 4-(Trifluoromethoxy)phenyl | CH=CH |
| 4-Nitrophenyl | CH=CH |
| 2-Methylphenyl | (CH₂)₂ |
| 4-Fluorophenyl | (CH₂)₂ |
| 3-Fluoro-4-methylphenyl | (CH₂)₂ |
| 4-Ethylphenyl | (CH₂)₂ |
| 3-Methoxyphenyl | (CH₂)₂ |
| 4-(Trifluoromethyl)phenyl | (CH₂)₂ |
| 3-Chlorophenyl | (CH₂)₂ |
| Benzofuran-5-yl | (CH₂)₂ |
| 3,5-Difluorophenyl | (CH₂)₂ |
| 4-(Trifluoromethoxy)phenyl | (CH₂)₂ |

TABLE 3

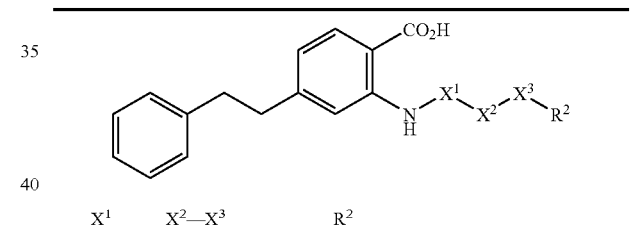

| X¹ | X²—X³ | R² |
|---|---|---|
| C=O | Bond | Cyclohexyl |
| C=O | Bond | 2-Fluorophenyl |
| C=O | Bond | 3-Fluorophenyl |
| C=O | Bond | 4-Fluorophenyl |
| C=O | Bond | 2,4-Difluorophenyl |
| C=O | Bond | 2,6-Difluorophenyl |
| C=O | Bond | 3,4-Difluorophenyl |
| C=O | Bond | 3,5-Difluorophenyl |
| C=O | Bond | 2-Chlorophenyl |
| C=O | Bond | 3-Chlorophenyl |
| C=O | Bond | 4-Chlorophenyl |
| C=O | Bond | 2,4-Dichlorophenyl |
| C=O | Bond | 2,6-Dichlorophenyl |
| C=O | Bond | 3,4-Dichlorophenyl |
| C=O | Bond | 3,5-Dichlorophenyl |
| C=O | Bond | 2-Methylphenyl |
| C=O | Bond | 3-Methylphenyl |
| C=O | Bond | 4-Methylphenyl |
| C=O | Bond | 2,3-Dimethylphenyl |
| C=O | Bond | 3,4-Dimethylphenyl |
| C=O | Bond | 3,5-Dimethylphenyl |
| C=O | Bond | 3-Nitrophenyl |
| C=O | Bond | 4-Nitrophenyl |
| C=O | Bond | 2-Hydroxyphenyl |
| C=O | Bond | 4-Hydroxyphenyl |
| C=O | Bond | 3-Biphenyl |
| C=O | Bond | 4-Biphenyl |
| C=O | Bond | Thiophen-2-yl |
| C=O | Bond | Benzofuran-2-yl |

TABLE 3-continued

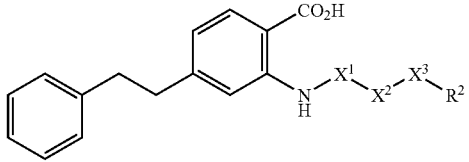

| $X^1$ | $X^2$—$X^3$ | $R^2$ |
|---|---|---|
| C=O | CH[phenyl] | Phenyl |
| C=O | Bond | Benzofuran-5-yl |
| C=O | Bond | Benzothiophen-2-yl |
| C=O | Bond | Benzothiophen-3-yl |
| C=O | Bond | Benzothiophen-5-yl |
| C=O | Bond | Benzothiazol-2-yl |
| C=O | Bond | Benzo[1,3]dioxol-5-yl |
| C=O | Bond | 2,3-Dihydrobenzo[1,4]dioxin-6-yl |
| C=O | Bond | 6-Morpholinopyridin-3-yl |
| C=O | Bond | 1-Phenyl-1H-pyrazol-5-yl |
| C=O | Bond | 6-(Piperidin-1-yl)pyridin-3-yl |
| C=O | Bond | 6-(1H-pyrrol-1-yl)pyridin-3-yl |
| C=O | Bond | 5-(1H-pyrrol-1-yl)pyridin-3-yl |
| C=O | Bond | 2-(1H-pyrrol-1-yl)pyridin-4-yl |
| C=O | Bond | 3-Phenylisoxazol-5-yl |
| C=O | Bond | 3-Phenyl-1H-pyrazol-5-yl |
| C=O | Bond | 6-Phenylpyrimidin-4-yl |
| C=O | Bond | 2-(Trifluoromethyl)phenyl |
| C=O | Bond | 3-(Trifluoromethyl)phenyl |
| C=O | Bond | 4-(Trifluoromethyl)phenyl |
| C=O | Bond | 2,4-Bis(trifluoromethyl)phenyl |
| C=O | Bond | 3,5-Bis(trifluoromethyl)phenyl |
| C=O | CH=CH (E) | Phenyl |
| C=O | CH=CH (E) | 3,4-Dimethoxyphenyl |
| C=O | CH$_2$ | Phenyl |
| C=O | CH$_2$O | Phenyl |
| C=O | CH$_2$CH=CH (E) | Phenyl |
| C=O | C(CH$_3$)=CH (E) | Phenyl |
| C=O | (CH$_2$)$_2$ | Phenyl |
| C=O | (CH$_2$)$_3$ | Phenyl |
| SO$_2$ | Bond | Phenyl |
| SO$_2$ | CH=CH | Phenyl |

TABLE 4

| $X^1$ | $X^2$—$X^3$ | $R^2$ |
|---|---|---|
| C=O | Bond | Cyclohexyl |
| C=O | Bond | 2-Fluorophenyl |
| C=O | Bond | 3-Fluorophenyl |
| C=O | Bond | 4-Fluorophenyl |
| C=O | Bond | 2,4-Difluorophenyl |
| C=O | Bond | 2,6-Difluorophenyl |
| C=O | Bond | 3,4-Difluorophenyl |
| C=O | Bond | 3,5-Difluorophenyl |
| C=O | Bond | 2-Chlorophenyl |
| C=O | Bond | 3-Chlorophenyl |
| C=O | Bond | 4-Chlorophenyl |
| C=O | Bond | 2,4-Dichlorophenyl |
| C=O | Bond | 2,6-Dichlorophenyl |
| C=O | Bond | 3,4-Dichlorophenyl |
| C=O | Bond | 3,5-Dichlorophenyl |
| C=O | Bond | 3-Methoxyphenyl |

TABLE 4-continued

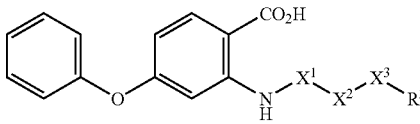

| $X^1$ | $X^2$—$X^3$ | $R^2$ |
|---|---|---|
| C=O | Bond | 4-Methoxyphenyl |
| C=O | Bond | 2-Methylphenyl |
| C=O | Bond | 3-Methylphenyl |
| C=O | Bond | 4-Methylphenyl |
| C=O | Bond | 2,3-Dimethylphenyl |
| C=O | Bond | 3,4-Dimethylphenyl |
| C=O | Bond | 3,5-Dimethylphenyl |
| C=O | Bond | 2-Biphenyl |
| C=O | Bond | 3-Biphenyl |
| C=O | Bond | 4-Biphenyl |
| C=O | Bond | 4-Morpholinophenyl |
| C=O | Bond | 3-Nitrophenyl |
| C=O | Bond | 4-Nitrophenyl |
| C=O | Bond | 2-Hydroxyphenyl |
| C=O | Bond | Thiophen-2-yl |
| C=O | Bond | Benzofuran-2-yl |
| C=O | Bond | Benzofuran-5-yl |
| C=O | Bond | Benzothiophen-2-yl |
| C=O | Bond | Benzothiophen-3-yl |
| C=O | Bond | Benzothiophen-5-yl |
| C=O | Bond | Benzothiazol-2-yl |
| C=O | Bond | 6-Phenylpyrimidin-4-yl |
| C=O | Bond | 2-Phenylthiazol-4-yl |
| C=O | Bond | Benzo[1,3]dioxol-5-yl |
| C=O | Bond | 2,3-Dihydrobenzo[1,4]dioxin-6-yl |
| C=O | Bond | 1-Methyl-1H-benzotriazol-5-yl |
| C=O | Bond | 6-Morpholinopyridin-3-yl |
| C=O | Bond | 6-(Piperidin-1-yl)pyridin-3-yl |
| C=O | Bond | 6-(1H-pyrrol-1-yl)pyridin-3-yl |
| C=O | Bond | 5-(1H-pyrrol-1-yl)pyridin-3-yl |
| C=O | Bond | 2-(1H-pyrrol-1-yl)pyridin-4-yl |
| C=O | Bond | 5-(Thiophen-2-yl)pyridin-3-yl |
| C=O | Bond | 3-Phenylisoxazol-5-yl |
| C=O | Bond | 3-Phenyl-1H-pyrazol-5-yl |
| C=O | Bond | 3-(1H-pyrrol-1-yl)phenyl |
| C=O | Bond | 4-(1H-pyrrol-1-yl)phenyl |
| C=O | Bond | 3-(1H-pyrazol-1-yl)phenyl |
| C=O | Bond | 2-(Trifluoromethyl)phenyl |
| C=O | Bond | 3-(Trifluoromethyl)phenyl |
| C=O | Bond | 4-(Trifluoromethyl)phenyl |
| C=O | Bond | 2,4-Bis(trifluoromethyl)phenyl |
| C=O | Bond | 3,5-Bis(trifluoromethyl)phenyl |
| C=O | CH=CH (E) | Phenyl |
| C=O | CH=CH (E) | 3-Chlorophenyl |
| C=O | CH=CH (E) | 4-Chlorophenyl |
| C=O | CH=CH (E) | 3,4-Dichlorophenyl |
| C=O | CH=CH (E) | 3-Methoxyphenyl |
| C=O | CH=CH (E) | Thiophen-2-yl |
| C=O | CH=CH (E) | Benzo[1,3]dioxol-5-yl |
| C=O | CH=CH (E) | 3,4-Dimethoxyphenyl |
| C=O | CH=CH (E) | 3-Nitrophenyl |
| C=O | CH=CH (E) | 4-Hydroxyphenyl |
| C=O | CH$_2$CH=CH (E) | Phenyl |
| C=O | C(CH$_3$)=CH (E) | Phenyl |
| C=O | (CH$_2$)$_2$ | Phenyl |
| C=O | (CH$_2$)$_3$ | Phenyl |
| C=O | CH$_2$O | Phenyl |
| SO$_2$ | CH$_2$ | Phenyl |
| SO$_2$ | CH=CH | Phenyl |

TABLE 5

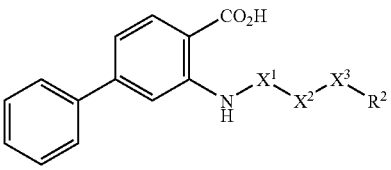

| $X^1$ | $X^2$—$X^3$ | $R^2$ |
|---|---|---|
| C=O | Bond | 2-Fluorophenyl |
| C=O | Bond | 3-Fluorophenyl |
| C=O | Bond | 4-Fluorophenyl |
| C=O | Bond | 2,4-Difluorophenyl |
| C=O | Bond | 2,6-Difluorophenyl |
| C=O | Bond | 3,4-Difluorophenyl |
| C=O | Bond | 3,5-Difluorophenyl |
| C=O | Bond | 2-Chlorophenyl |
| C=O | Bond | 3-Chlorophenyl |
| C=O | Bond | 4-Chlorophenyl |
| C=O | Bond | 2,4-Dichlorophenyl |
| C=O | Bond | 2,6-Dichlorophenyl |
| C=O | Bond | 3,4-Dichlorophenyl |
| C=O | Bond | 3,5-Dichlorophenyl |
| C=O | Bond | 3-Methoxyphenyl |
| C=O | Bond | 4-Methoxyphenyl |
| C=O | Bond | 2-Methylphenyl |
| C=O | Bond | 3-Methylphenyl |
| C=O | Bond | 4-Methylphenyl |
| C=O | Bond | 2,3-Dimethylphenyl |
| C=O | Bond | 3,4-Dimethylphenyl |
| C=O | Bond | 3,5-Dimethylphenyl |
| C=O | Bond | 3-Nitrophenyl |
| C=O | Bond | 2-Hydroxyphenyl |
| C=O | Bond | 4-Hydroxyphenyl |
| C=O | Bond | 2-Biphenyl |
| C=O | Bond | 3-Biphenyl |
| C=O | Bond | 4-Biphenyl |
| C=O | Bond | Benzofuran-2-yl |
| C=O | Bond | Benzofuran-5-yl |
| C=O | Bond | Benzothiophen-2-yl |
| C=O | Bond | Benzothiophen-3-yl |
| C=O | CH(phenyl) | Phenyl |
| C=O | Bond | Benzothiophen-5-yl |
| C=O | Bond | Benzothiazol-2-yl |
| C=O | Bond | Benzo[1,3]dioxol-5-yl |
| C=O | Bond | 2,3-Dihydrobenzo[1,4]dioxin-6-yl |
| C=O | Bond | 4-Morpholinophenyl |
| C=O | Bond | 6-(Piperidin-1-yl)pyridin-3-yl |
| C=O | Bond | 6-(1H-pyrrol-1-yl)pyridin-3-yl |
| C=O | Bond | 5-(1H-pyrrol-1-yl)pyridin-3-yl |
| C=O | Bond | 2-(1H-pyrrol-1-yl)pyridin-4-yl |
| C=O | Bond | 3-Phenylisoxazol-5-yl |
| C=O | Bond | 3-Phenyl-1H-pyrazol-5-yl |
| C=O | Bond | 3-(1H-pyrrol-1-yl)phenyl |
| C=O | Bond | 4-(1H-pyrrol-1-yl)phenyl |
| C=O | Bond | 6-Phenylpyrimidin-4-yl |
| C=O | Bond | 2-(Trifluoromethyl)phenyl |
| C=O | Bond | 3-(Trifluoromethyl)phenyl |
| C=O | Bond | 4-(Trifluoromethyl)phenyl |
| C=O | Bond | 2,4-Bis(trifluoromethyl)phenyl |
| C=O | Bond | 3,5-Bis(trifluoromethyl)phenyl |
| C=O | CH=CH (E) | Phenyl |
| C=O | CH=CH (E) | 3-Chlorophenyl |
| C=O | CH=CH (E) | 4-Chlorophenyl |
| C=O | CH=CH (E) | 3,4-Dichlorophenyl |
| C=O | CH=CH (E) | 3-Methoxyphenyl |
| C=O | CH=CH (E) | Thiophen-2-yl |
| C=O | CH=CH (E) | Benzo[1,3]dioxol-5-yl |
| C=O | CH=CH (E) | 3,4-Dimethoxyphenyl |
| C=O | CH=CH (E) | 3-Nitrophenyl |

TABLE 5-continued

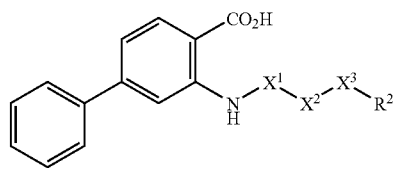

| $X^1$ | $X^2$—$X^3$ | $R^2$ |
|---|---|---|
| C=O | CH=CH (E) | 4-Hydroxyphenyl |
| C=O | $CH_2CH=CH$ (E) | Phenyl |
| C=O | $C(CH_3)=CH$ (E) | Phenyl |
| C=O | $(CH_2)_2$ | Phenyl |
| $SO_2$ | CH=CH | Phenyl |

TABLE 6

| $R^3$—$X^4$— | —$X^2$—$X^3$—$R^2$ |
|---|---|
| 3-Chlorophenyl | 4-Fluorophenyl |
| 3-Chlorophenyl | 4-Nitrophenyl |
| 3-Chlorophenyl | 4-(Trifluoromethyl)phenyl |
| 3-Chlorophenyl | 4-Hydroxyphenyl |
| 3-Chlorophenyl | 2,3-Dimethylphenyl |
| 3-Chlorophenyl | Benzothiazol-2-yl |
| 3-Chlorophenyl | 5-(1H-pyrrol-1-yl)pyridin-3-yl |
| 3-Chlorophenyl | Benzo[1,3]dioxol-5-yl |
| 3-Chlorophenyl | 2-Phenylvinyl |
| 2,4-Difluorophenyl | 4-Fluorophenyl |
| 2,4-Difluorophenyl | 4-(Trifluoromethyl)phenyl |
| 2,4-Difluorophenyl | 2,3-Dimethylphenyl |
| 2,4-Difluorophenyl | Benzothiazol-2-yl |
| 2,4-Difluorophenyl | 5-(1H-pyrrol-1-yl)pyridin-3-yl |
| 2,4-Difluorophenyl | 2-Phenylvinyl |
| 4-Hydroxyphenyl | 4-Fluorophenyl |
| 4-Hydroxyphenyl | 4-(Trifluoromethyl)phenyl |
| 4-Hydroxyphenyl | Benzothiazol-2-yl |
| 4-Hydroxyphenyl | 5-(1H-pyrrol-1-yl)pyridin-3-yl |
| 4-Hydroxyphenyl | 2-Phenylvinyl |
| Benzofuran-2-yl | 4-Fluorophenyl |
| Benzofuran-2-yl | 4-(Trifluoromethyl)phenyl |
| Benzofuran-2-yl | 2,3-Dimethylphenyl |
| Benzofuran-2-yl | Benzo[1,3]dioxol-5-yl |
| Benzofuran-2-yl | 2-Phenylvinyl |
| Benzo[1,3]dioxol-5-yl | 4-(Trifluoromethyl)phenyl |
| Benzo[1,3]dioxol-5-yl | 2,3-Dimethylphenyl |
| Benzo[1,3]dioxol-5-yl | Benzothiazol-2-yl |
| Benzo[1,3]dioxol-5-yl | Benzo[1,3]dioxol-5-yl |
| Benzo[1,3]dioxol-5-yl | 2-Phenylvinyl |
| 2-(3-Methoxyphenyl)vinyl | 4-Fluorophenyl |
| 2-(3-Methoxyphenyl)vinyl | 4-Nitrophenyl |
| 2-(3-Methoxyphenyl)vinyl | Benzothiazol-2-yl |
| 2-(3-Methoxyphenyl)vinyl | 2,3-Dimethylphenyl |
| 2-(3-Methoxyphenyl)vinyl | Benzo[1,3]dioxol-5-yl |
| 2-(3-Methoxyphenyl)vinyl | 5-(1H-pyrrol-1-yl)pyridin-3-yl |
| 2-(3-Methoxyphenyl)vinyl | 2-Phenylvinyl |

In addition, when any isomer (for example, optical isomer, geometrical isomer, tautomer and the like) is present for the compounds of general formula [1] or a salt thereof, the present invention includes those isomers and, in addition, includes solvates, hydrates and crystals of various kinds.

Next, production processes of the compounds of the present invention are described.

The compound of the present invention can be produced by combining methods well known per se together, but, for example, can be produced following the production processes shown below.

[Production Process 1]

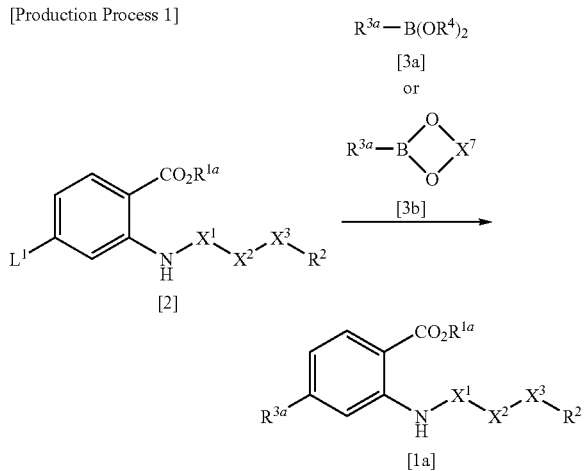

"In the formula, $R^{1a}$ represents a carboxyl protecting group; $R^{3a}$ represents a phenyl, cycloalkyl, cycloalkenyl, or monocyclic heterocyclic or bicyclic heterocyclic group linking through a ring-member carbon atom, any of which groups may be optionally substituted; $R^4$ represents a hydrogen atom or a lower alkyl group; $X^7$ represents an alkylene group which may be optionally substituted; $L^1$ represents a leaving group; and $R^2$, $X^1$, $X^2$ and $X^3$ mean the same as above,"

As a compound of general formula [3a], for example, pyridine-3-boronic acid, 3-(methanesulfonamide)phenylboronic acid, thiophene-2-boronic acid, benzofuran-2-boronic acid and 3-methoxyphenyl boronic acid are known. As a compound of general formula [3b], for example, 3-(4,4,5,5-tetramethyl-1,3,2-dioxaborolan-2-yl)furan is known. In addition, the compounds of general formulae [3a] and [3b] can be produced from corresponding halogeno compounds following a method, for example, described in JP-A-2003-206290.

The compounds of general formula [1a] can be produced by reacting a compound of general formula [2] with a compound of general formula [3a] or [3b] in the presence of or in the absence of a base, in the presence of a palladium catalyst, and in the presence of or in the absence of a ligand.

The solvent used in this reaction is not particularly limited as long as it does not adversely affect she reaction and examples thereof include water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as methylene chloride, chloroform and dichloroethane; ethers such as dioxane, tetrahydrofuran, anisole, ethylene glycol dimethyl ether, diethylene glycol dimethyl ether and diethylene glycol diethyl ether; ketones such as acetone and 2-butanone; nitrites such as acetonitrile; esters such as ethyl acetate and butyl acetate and sulfoxides such as dimethylsulfoxide and these may be optionally mixed for use.

Examples of a base optionally used in this reaction include inorganic bases such as sodium hydrogen carbonate, sodium carbonate, potassium carbonate, cesium carbonate and tripotassium phosphate and organic bases such as triethylamine and diisopropylethylamine. The used amount of the base can be 1 to 50 times mol, preferably 2 to 5 times mol for the compound of general formula [2].

The palladium catalyst used in this reaction includes metal palladium such as palladium-carbon and palladium black; inorganic palladium salts such as palladium chloride; organic palladium salts such as palladium acetate; organopalladium complex such as tetrakis(triphenylphosphine)palladium (0), bis(triphenylphosphine)palladium (II) chloride, 1,1'-bis(diphenylphosphino)ferrocene palladium (II) chloride and tris(dibenzylideneacetone)dipalladium (0) and polymer immobilized organopalladium complex such as polymer supported bis(acetato)triphenylphosphine palladium (II) and polymer supported di(acetato)dicyclohexylphenylphosphine palladium (II) and these may be optionally used in combination. The used amount of the palladium catalyst can be 0.00001 to 1 time mol, preferably 0.001 to 0.1 times mol for the compound of general formula [2].

The ligand optionally used in this reaction includes trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite and tributylphosphite; tricycloalkylphosphites such as tricyclohexylphosphite; triarylphosphite such as triphenylphosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine and triisopropylamine; 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl and 2-(di-tert-butylphosphino)biphenyl and these may be optionally used in combination. The used amount of the ligand can be 0.00001 to 1 time mol and preferably 0.001 to 0.1 time mol for the compound of general formula [2].

The used amount of the compound of general formula [3a] or [3b] can be 1 to 50 times mol and preferably 1 to 2 times mol for the compound of general formula [2].

This reaction can be preferably carried out in an Inert gas (for example, nitrogen, argon) atmosphere at 40 to 170° C. for 1 minute to 96 hours.

[Production Process 2]

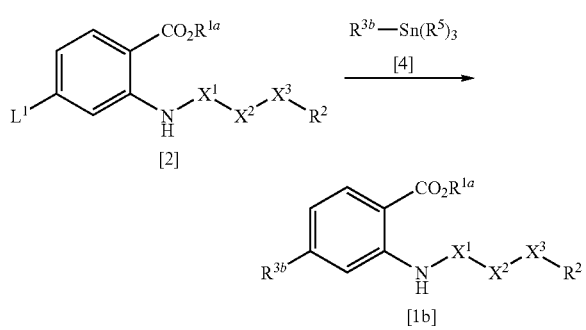

"In the formula, $R^{3b}$ represents a phenyl or monocyclic heterocyclic or bicyclic heterocyclic group linking through a ring-member carbon atom, any of which groups may be optionally substituted; and $R^5$ represents a lower alkyl group; $R^{1a}$, $R^2$, $X^1$, $X^2$, $X^3$ and $L^1$ mean the same as above."

As a compound of general formula [4], for example, 2-(tributyltin)thiazole and 2-(tributyltin)furan are known.

The compounds of general formula [1b] can be produced by reacting a compound of general formula [2] with a compound of general formula [4] In the presence of or in the absence of silver oxide, in the presence of a palladium catalyst.

The solvent used in this reaction is not particularly limited as long as it does not adversely affect the reaction and examples thereof. Include aromatic hydrocarbons such as benzene, toluene and xylene; amides such as N,N-dimethylformamide, N,N-dimethylacetamide and 1-methyl-2-pyrrolidone; ethers such as dioxane, tetrahydrofuran, anisole, ethylene glycol dimethyl ether, diethylene glycol dimethyl ether and diethylene glycol diethyl ether; nitrites such as acetonitrile and sulfoxides such as dimethylsulfoxide and these may be optionally mixed for use.

The palladium catalyst used in this reaction Includes organopalladium complexes such as tetrakis(triphenylphosphine) palladium (0), bis(triphenylphosphine)palladium (II) chloride, 1,1'-bis(diphenylphosphino)ferrocene palladium (11) chloride and tris(dibenzylideneacetone)dipalladium (0) and a polymer immobilized organopalladium complex such as a polymer supported bis(acetato)triphenylphosphine palladium (II) and a polymer supported di(acetato)dicyclohexylphenylphosphine palladium (II) and these may be optionally used in combination. The used amount of the palladium catalyst can be 0.00001 to 1 time mol, preferably 0.001 to 0.1 time mol for the compound of general formula [2].

The amount of silver oxide optionally used in this reaction can be 1 to 50 times mol, preferably 1 to 10 times mol for the compound of general formula [2].

The used amount of the compound of general formula [4] can be 1 to 50 times mol, preferably 1 to 2 times mol for the compound of general formula [2].

This reaction can be preferably carried out in an inert gas (for example, nitrogen, argon) atmosphere at 40 to 170° C. for 1 minute to 96 hours.

[Production Process 3]

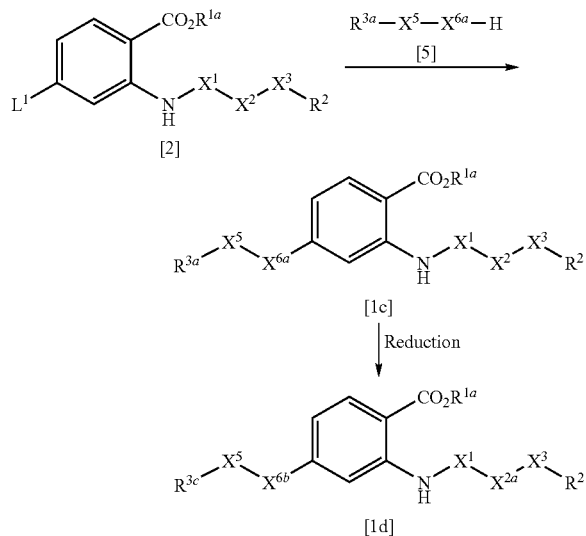

"In the formula, $R^{3c}$ represents a phenyl, cycloalkyl, or monocyclic heterocyclic or bicyclic heterocyclic group linking through a ring-member carbon atom, any of which groups may be optionally substituted; $X^{2a}$ represents an alkynyl group which may be optionally substituted or a bond; $X^{6a}$ represents an alkenylene or alkynylene group which may be optionally substituted; $X^{6b}$ represents an alkylene group which may be optionally substituted; $R^{1a}$, $R^2$, $R^{3a}$, $X^1$, $X^2$, $X^3$, $X^5$ and $L^1$ mean the same as above."

As a compound of general formula [5], for example, styrene, allylbenzene, 4-phenyl-1-butene, vinylcyclohexane and allylcyclohexane are known. In addition, the compounds of general formula [5] can be produced by a method, for example, described in "Jikken Kagaku Kouza", 4th edition, Vol. 19, pp. 298-361, 1992, Maruzen or the like method.

(3-1)

When $X^{6a}$ is an alkenylene group which may be optionally substituted, the compound of general formula [1c] can be produced by reacting a compound of general formula [2] with a compound of general formula [5] in the presence of or in the absence of a base, in the presence of or in the absence of a phase transfer catalyst, in the presence of or in the absence of a ligand, and in the presence of a palladium catalyst.

The solvent used in this reaction is not particularly limited as long as it does not adversely affect the reaction and examples thereof include water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as methylene chloride, chloroform and dichloroethane; ethers such as dioxane, tetrahydrofuran, anisole, ethylene glycol dimethyl ether, diethylene glycol dimethyl ether and diethylene glycol diethyl ether; ketones such as acetone and 2-butanone; nitriles such as acetonitrile; esters such as ethyl acetate and butyl acetate and sulfoxides such as dimethylsulfoxide and these may be optionally mixed for use.

Examples of a base optionally used in this reaction include inorganic bases such as sodium hydride, sodium hydrogen carbonate, sodium carbonate, potassium carbonate, cesium carbonate and tripotassium phosphate and organic bases such as sodium acetate, potassium acetate, sodium tert-butoxide, triethylamine, diisopropylethylamine, tributylamine and N,N-dicyclohexylmethylamine. The used amount of the base can be 1 to 50 times mol, preferably 2 to 5 times mol for the compound of general formula [2].

Examples of the phase transfer catalyst optionally used in this reaction include quaternary ammonium salts such as tetramethylammonium chloride, benzyltrimethylammonium chloride, benzyltriethylammonium chloride, benzyltributylammonium chloride, tetrabutylammonium chloride, tetrabutylammonium bromide, tetrabutylammonium hydrogen sulfate and trioctylmethylammonium chloride; N-laurylpyridinium chloride, N-lauryl-4-picolinium chloride, N-laurylpicolinium chloride and N-benzylpicolinium chloride. The used amount of the phase transfer catalyst can be 0.01 to 50 times mol, preferably 0.1 to 5 times mol for the compound of general formula [2].

The ligand optionally used in this reaction includes trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite and tributylphosphite; tricycloalkylphosphites such as tricyclohexylphosphite, triarylphosphites such as triphenylphosphite; imidazolium salts such as 1,3-bis(2,4,6-trimethylphenyl)imidazolium chloride; diketone such as acetylacetone and octafluoroacetylacetone; amines such as trimethylamine, triethylamine, tripropylamine and triisopropylamine; 1,1-bis(diphenylphosphino) ferrocene, 2,2'-bis(diphenylphosphino)-1,1'-binaphthyl, 2-dicyclohexylphosphino-2',6'-dimethoxy biphenyl, 2-dicyclohexylphosphino-2',4',6'-triisopropyl biphenyl, 2-(di-tertbutylphosphino)-2',4',6'-triisopropyl biphenyl and 2-(di-tert-butylphosphino) biphenyl and these may be optionally used in combination. The used amount of the ligand can be 0.00001 to 1 time mol and preferably 0.001 to 0.1 time mol for the compound of general formula [2].

Examples of the palladium catalyst used in this reaction include metal palladium such as palladium-carbon and palladium black; inorganic palladium salts such as palladium chloride; organic palladium salts such as palladium acetate; organopalladium complex such as tetrakis(triphenylphosphine) palladium (0), bis(triphenylphosphine)palladium (II) chloride, 1,1'-bis(diphenylphosphino)ferrocene palladium (II) chloride, (E)-di(µ-acetato) bis(o-(di-o-tolylphosphino)benzyl)dipalladium (II) and tris(dibenzylideneacetone)dipalladium (0) and polymer immobilized organopalladium complex such as polymer supported bis(acetato) triphenylphosphine palladium (II) and polymer supported di(acetato) dicyclohexylphenylphosphine palladium (II) and these may be optionally used in combination. The used amount of the palladium catalyst can be 0.00001 to 1 time mol, preferably 0.001 to 0.1 tome mol for the compound of general formula [2].

The used amount of the compound of general formula [5] can be 1 to 50 times mol and preferably 1 to 2 times mol for the compound of general formula [2].

This reaction can be preferably carried out in an Inert gas (for example, nitrogen, argon) atmosphere at 40 to 170° C. for 1 minute to 24 hours.

(3-2)

When $X^{6a}$ is an alkynylene group which may be optionally substituted, the compound of general formula [1c] can be produced by reacting a compound of general formula [2] with a compound of general formula [5] in the presence of or in the absence of a base, in the presence of or in the absence of a copper catalyst, and in the presence of a palladium catalyst.

The solvent used in this reaction is not particularly limited as long as it does not adversely affect the reaction and examples thereof. Include water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as methylene chloride, chloroform and dichloroethane; ethers such as dioxane, tetrahydrofuran, anisole, ethylene glycol dimethyl elder, diethylene glycol dimethyl ether and diethylene glycol diethyl ether; ketones such as acetone and 2-butanone; nitriles such as acetonitrile; esters such as ethyl acetate and butyl acetate and sulfoxides such as dimethylsulfoxide and these may be optionally mixed for use.

Examples of a base optionally used in this reaction include inorganic bases such as sodium hydrogen carbonate, sodium carbonate, potassium carbonate, cesium carbonate and tripotassium phosphate and organic bases such as triethylamine and diisopropylethylamine. The used amount of the base can be 1 to 50 times mol, preferably 2 to 5 times mol for the compound of general formula [2].

Examples of the copper catalyst optionally used in this reaction include copper bromide and copper iodide. The used amount of the copper catalyst can be 0.01 to 50 times mol, preferably 0.1 to 5 times mol for the compound of general formula [2].

Examples of the palladium catalyst used in this reaction include metal palladium such as palladium-carbon and palladium black; inorganic palladium salts such as palladium chloride; organic palladium salts such as palladium acetate; organopalladium complex such as tetrakis(triphenylphosphine) palladium (0), bis(triphenylphosphine)palladium (II) chloride, 1,1'-bis(diphenylphosphino)ferrocene palladium (II) chloride and tris(dibenzylideneacetone)dipalladium (0) and polymer immobilized organopalladium complex such as polymer supported bis(acetato) triphenylphosphine palladium (II) and polymer supported di(acetato) dicyclohexylphenylphosphine palladium (II) and these may be optionally used in combination. The used amount of the palladium catalyst can be 0.00001 to 1 time mol, preferably 0.001 to 0.1 time mol for the compound of general formula [2].

The used amount of the compound of general formula [5] can be 1 to 50 times mol and preferably 1 to 2 times mol for the compound of general formula [2].

This reaction can be preferably carried out in an inert gas (for example, nitrogen, argon) atmosphere at 10 to 170° C. for 1 minute to 24 hours.

(3-3)

The compounds of general formula [1d] can be produced by reducing a compound of general formula [1c]. Examples of the reducing reaction include catalytic hydrogenation reaction using a metal catalyst.

The solvent used in this reaction is not particularly limited as long as it does not adversely affect the reaction and examples thereof include water; alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; and carboxylic acids such as acetic acid and heteroaromatics such as pyridine and these may be optionally mixed for use.

Examples of the metal catalyst used in this reaction include metal palladium such as palladium-carbon and palladium black; palladium salts such as palladium oxide and palladium hydroxide, nickel metal such as Raney nickel and platinum salts such as platinum oxide. The used amount of the metal catalyst can be 0.001 to 5 times amount (W/W), preferably 0.1 to 1 time amount (W/W) for the compound of general formula [1c].

Examples of the reducing agent used in this reaction include hydrogen; formic acid; formates such as sodium formate, ammonium formate and triethylammonium formate; cyclohexene and cyclohexadiene. The used amount of the reducing agent can be 2 to 100 times mol, preferably 2 to 10 times mol for the compound of general formula [1c].

This reaction can be carried out at 0 to 200° C., preferably at 0 to 100° C. for 1 minute to 24 hours.

[Production Process 4]

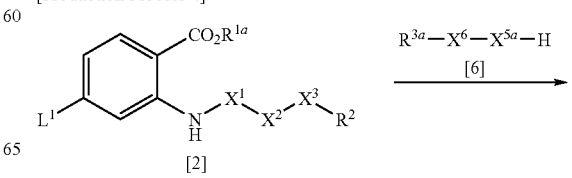

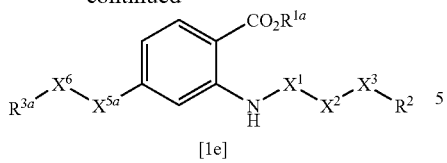

[1e]

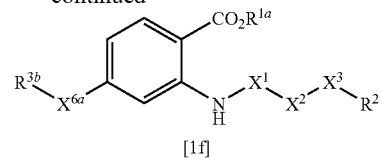

[1f]

"In the formula, $X^{5a}$ represents an oxygen atom, a sulfur atom or an imino group which may be optionally protected; $R^{1a}$, $R^2$, $R^{3a}$, $X^1$, $X^2$, $X^3$, $X^6$ and $L^1$ mean the same as above."

As a compound of general formula [6], for example, aniline, benzylamine, phenol, thiophenol and benzylmercaptan are known. In addition, for example, the compounds of general formula [6] can be produced by an ordinary method from a corresponding halogeno compound.

(4-1)

The compound of general formula [1e] can be produced by reacting a compound of general formula [2] with a compound of general formula [6] following production process (3-1).

(4-2)

When $X^{5a}$ is an oxygen atom, the compound of general formula [1e] can be produced by reacting a compound of general formula [2] with a compound of general formula [6] in the presence of or in the absence of a base, and in the presence of a copper catalyst.

The solvent used in this reaction is not particularly limited as long as it does not adversely affect the reaction and examples thereof include aromatic hydrocarbons such as benzene, toluene and xylene; amides such as N,N-dimethylformamide, N,N-dimethylacetamide and 1-methyl-2-pyrrolidone; halogenated hydrocarbons such as methylene chloride, chloroform and dichloroethane; ethers such as dioxane, tetrahydrofuran, anisole, ethylene glycol dimethyl ether, diethylene glycol dimethyl ether and diethylene glycol diethyl ether; ketones such as acetone and 2-butanone; nitriles such as acetonitrile; esters such as ethyl acetate and butyl acetate and sulfoxides such as dimethylsulfoxide and these may be optionally mixed for use.

Examples of a base optionally used in this reaction include sodium hydride and sodium. The used amount of the base can be 1 to 50 times mol, preferably 1 to 5 times mol for the compound of general formula [2].

Examples of the copper catalyst used in this reaction include copper powder and, copper iodide. The used amount of the copper catalyst can be 0.00001 to 1 time mol, preferably 0.01 to 1 time mol for the compound of general formula [2].

The used amount of the compound of general formula [6] can be 1 so 50 times mol and preferably 1 to 5 times mol for the compound of general formula [2].

This reaction can be preferably carried out at 40 to 200° C. for 30 minutes to 72 hours.

[Production Process 5]

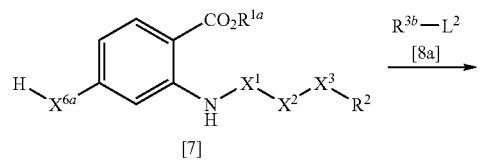

[7]

"In the formula, $L^2$ represents a leaving group; $R^{1a}$, $R^2$, $R^{3b}$, $X^1$, $X^2$, $X^3$ and $X^{6a}$ mean the same as above."

As a compound of general formula [8a], for example, 2-iodotoluene, 3-iodoanisole, 3-iodonitrobenzene and 6-iodo-2,3-dihydrobenzo[1,4]dioxin are known.

The compound of general formula [1f] can be produced by reacting a compound of general formula [7] with a compound of general formula [8a] following production process (3-1) or (3-2).

[Production Process 6]

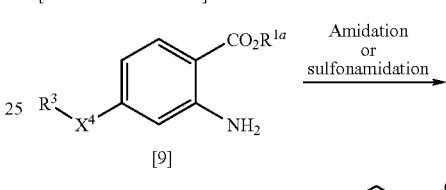

[9]

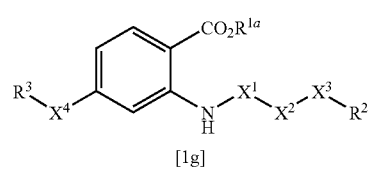

[1g]

"In the formula, $R^{1a}$, $R^2$, $R^3$, $X^1$, $X^2$, $X^3$ and $X^4$ mean the same as above."

(6-1)

When $X^1$ is a carbonyl group, the compound of general formula [1g] can be produced by amidating a compound of general formula [9]. Specifically, a method using an acid halide in the presence of or in the absence of the base, a method using an acid anhydride in the presence of or in the absence of the base and the like are included.

The solvent used in this reaction is not particularly limited as long as it does not adversely affect the reaction and examples thereof include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate and sulfoxides such as dimethylsulfoxide and these may be optionally mixed for use.

Examples of the acid halide used in this reaction include benzoyl chloride, benzoyl bromide, 2,4-difluorobenzoyl chloride, 2-naphthoyl chloride, diphenylacetyl chloride, 2,3-dihydrobenzo[1,4]dioxin-6-carbonyl chloride, cyclohexane carbonyl chloride, cyclopentylcarbonyl chloride (E)-3-phenylacryloyl chloride, phenoxyacetyl chloride, 2-furoyl chloride, 1-benzofuran-2-carbonyl chloride, 2-thenoyl chloride, nicotinoyl chloride and picolinoyl chloride. In addition, the acid halide can be produced by reacting a compound represented by general formula [38]

[Formula 2]

$$R^2\!-\!X^3\!-\!X^2\!-\!CO_2H \qquad [38]$$

"In the formula, $R^2$, $X^2$ and $X^3$ mean the same as above." with thionyl chloride, oxalyl chloride or the like. The used amount of the acid halide can be 1 to 50 times mol and preferably 1 to 5 times mol for the compound of general formula [9].

Examples of the acid anhydride used in this reaction include benzoic anhydride. In addition, acid halides can be produced from a corresponding carboxylic acid by a method, for example, described in "Shin Jikken Kagaku Kouza", Vol. 14, pp. 1120-1133, 1917, Maruzen or the like method. The used amount of the acid anhydride can be 1 to 50 nines mol and preferably 1 to 5 times mol for the compound of general formula [9].

Examples of the base optionally used in this reaction include inorganic bases such as sodium hydrogen carbonate, sodium carbonate, potassium carbonate and cesium carbonate and organic bases such as triethylamine and diisopropylethylamine. The used amount of the base can be 1 to 50 times mol and preferably 1 to 5 times mol for the compound of general formula [9].

This reaction can be carried out ordinarily at −78 to 100° C., preferably at 0 to 80° C. for 10 minutes to 24 hours.

(6-2)

When $X^1$ is a sulfonyl group, the compound of general formula [1g] can be produced, by sulfonamidating a compound of general formula [9]. Specifically, a method using a sulfonyl halide in the presence of or in the absence of the base is included.

The solvent used in this reaction is not particularly limited as long as it does not adversely affect the reaction and examples thereof include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate, sulfones such as sulfolane and sulfoxides such as dimethylsulfoxide and these may be optionally mixed for use.

Examples of the sulfonyl halide used in this reaction include benzenesulfonyl chloride and α-toluenesulfonyl chloride. In addition, a sulfonyl halide can be produced from a corresponding sulfonic acid by a method, for example, described in "Shin Jikken Kagaku Kouza", Vol. 14, pp. 1784-1792, 1978, Maruzen or the like method. The used amount of the sulfonyl halide can be 1 to 50 times mol and preferably 1 to 5 times mol for the compound of general formula [9].

Examples of the base optionally used in this reaction include inorganic bases such as sodium hydrogen carbonate, sodium carbonate, potassium carbonate and cesium carbonate and organic bases such as triethylamine and diisopropylethylamine. The used amount of the base can be 1 to 50 times mol and preferably 1 to 5 times mol for the compound of general formula [9].

This reaction can be carried out ordinarily at −78 to 100° C., preferably at 0 to 80° C. for 10 minutes to 24 hours.

[Production Process 7]

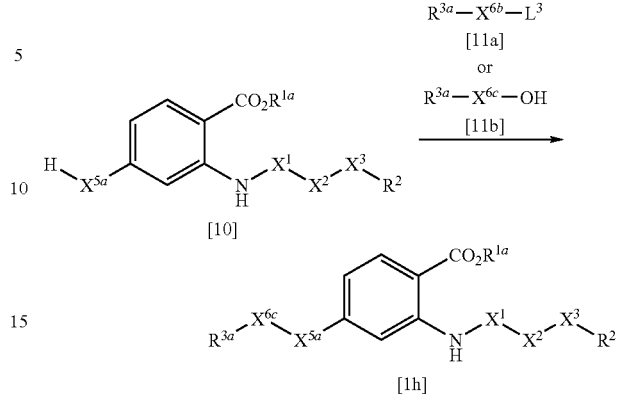

"In the formula, $X^{6c}$ represents an alkylene group which may be optionally substituted or a bond; $L^3$ represents a leaving group; $R^{1a}$, $R^2$, $R^{3a}$, $X^1$, $X^2$, $X^3$, $X^{5a}$ and $X^{6b}$ mean the same as above provided that if $X^{6c}$ represents a bond, $R^{3a}$ represents a cycloalkyl group which may be optionally substituted."

As a compound of general formula [11a], for example, benzyl bromide and (2-bromoethyl)benzene are known. As a compound of general formula [11b], for example, 3-phenyl-1-propanol and cyclohexanol are known.

(7-1)

The compounds of general formula [1h] can be produced by reacting a compound of general formula [10] with a compound of general formula [11a] in the presence of the base.

The solvent used in this reaction is not particularly limited as long as it does not adversely affect the reaction and examples thereof. Include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate, sulfones such as sulfolane and sulfoxides such as dimethylsulfoxide and these may be optionally mixed for use.

The used amount of the compound of general formula [11a] can be 1 to 20 times mol and preferably 1 to 5 times mol for the compound of general formula [10].

Examples of the base used in this reaction include organic amines such as dimethylaminopyridine, triethylamine, and pyridine; alkali metal hydrides such as sodium hydride and alkali metal carbonates such as potassium carbonate and sodium carbonate.

The used amount of the base can be 1 to 20 times mol and preferably 1 to 5 times mol for the compound of general formula [10].

This reaction can be carried out ordinarily at 0 to 200° C., preferably at 25 to 150° C. for 10 minutes to 24 hours.

(7-2)

When $X^{5a}$ is an oxygen atom or a sulfur atom, the compound of general formula [1h] can be produced by subjecting a compound of general formula [10] and a compound of general formula [11b] to Mitsunobu reaction in the presence of an azodicarbonyl compound and a phosphine.

The solvent used in this reaction is not particularly limited as long as it does not adversely affect the reaction and examples thereof include aromatic hydrocarbons such as benzene, toluene and xylene; ethers such as dioxane, tetrahydrofuran, anisole, diethylene glycol dimethyl ether, ethylene glycol monomethyl ether and ethylene glycol dimethyl ether; esters such as methyl acetate, ethyl acetate and butyl acetate; nitriles such as acetonitrile; amides such as N,N-dimethylformamide and N,N-dimethylacetamide; halogenated hydrocarbons such as chloroform, methylene chloride and these may be optionally mixed for use.

Examples of the azodicarbonyl compound used in this reaction include diethyl azodicarboxylate, diisopropyl azodicarboxylate and azodicarbonyldipiperidine. The used amount of the azodicarbonyl compound can be 1 to 5 times mol and preferably 1 to 3 times mol for the compound of general formula [10].

Examples of the phosphines used in this reaction include triarylphosphines such as triphenylphosphine and trialkylphosphines such as tributylphosphine. The used amount of the phosphines can be 1 to 5 times mol and preferably 1 to 3 times mol for the compound of general formula [10].

The used amount of the compound of general formula [11b] can be 1 to 5 times mol and preferably 1 to 3 rimes mol for the compound of general formula [10].

This reaction can be carried out ordinarily at −20 to 120° C., preferably at 0 to 50° C. for 30 minutes to 24 hours.

[Production Process 8]

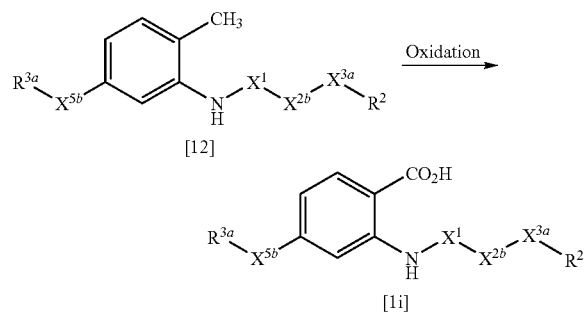

"In the formula, $X^{2b}$ represents a bond; $X^{3a}$ represents an oxygen atom or a bond; $X^{5b}$ represents an oxygen atom, a sulfonyl group or a bond; $R^2$, $R^{3a}$ and $X^1$ mean the same as above."

The compound of the general formula [1] can be produced by reacting a compound of general formula [12] with an oxidizing agent in the presence of or in the absence of an acid or a base, in the presence of or in the absence of a salt.

The solvent used in this reaction is not particularly limited as long as it does not adversely affect one reaction and examples thereof include water; halogenated hydrocarbons such as methylene chloride, chloroform and dichloroethane; aliphatic hydrocarbons such as hexane and cyclohexane, and pyridine and these may be optionally mixed for use.

Examples of the acid optionally used in this reaction include mineral acids such as hydrochloric acid and sulfuric acid and organic acids such as acetic acid. The used amount of the acid can be 1 to 1000 times mol for the compound of general formula [12].

Examples of the base optionally used in this reaction include, inorganic bases such as sodium hydroxide and potassium hydroxides, and organic base such as pyridine. The used amount of the base can be 1 to 1000 times mol for the compound of general formula [12].

Examples of the salt optionally used in this reaction include magnesium sulfate, ammonium sulfate and magnesium chloride. The used amount of the salt can be 1 to 50 times mol, preferably 1 to 10 times mol for the compound of general formula [12].

Examples of the oxidizing agent used in this reaction include chromate such as chromium oxide (VI) and sodium dichromate, and permanganate such as potassium permanganate, barium permanganate, calcium permanganate and magnesium permanganate. The used amount of the oxidizing agent can be 1 to 50 times mol, preferably 1 to 10 times mol for the compound of general formula [12].

This reaction can be carried out ordinarily at 0 to 150° C., preferably at 40 to 130° C. for 30 minutes to 48 hours.

[Production Process 9]

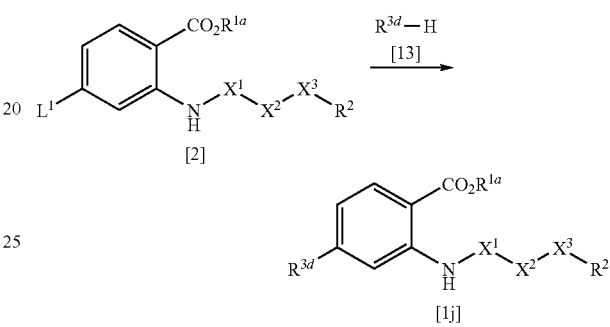

"$R^{3d}$ represents a monocyclic heterocyclic or bicyclic heterocyclic group linking through a nitrogen atom which forms the ring and which group may be optionally substituted; $R^{1a}$, $R^2$, $X^1$, $X^2$, $X^3$ and $L^1$ mean the same as above."

As a compound of general formula [13], for example, pyrrolidine, piperidine, morpholine, pyrrole, indoline, isoindoline, benzimidazole and indole are known.

The compound of general formula [1j] can be produced by reacting a compound of general formula [2] with a compound of general formula [1,3] following production process 1.

[Production Process 10]

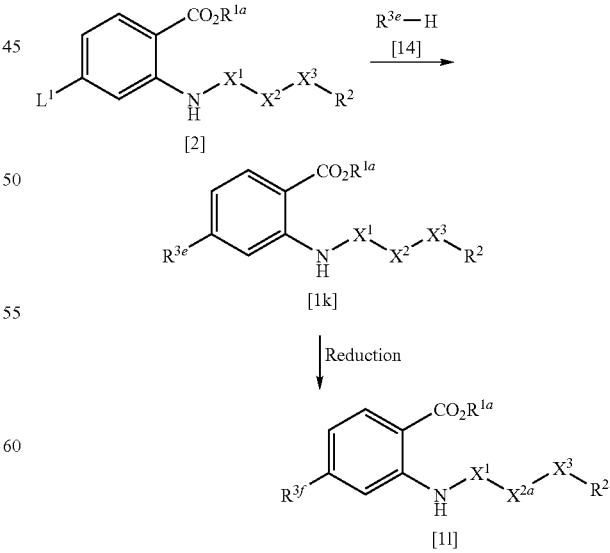

"In the formula, $R^{3e}$ represents a cycloalkenyl group which may be optionally substituted; $R^{3f}$ represents a cycloalkyl group which may be optionally substituted; $R^{1a}$, $R^2$, $X^1$, $X^2$, $X^{2a}$, $X^3$ and $L^1$ mean the same as above."

As a compound of general formula [14], for example, cyclopentene and cyclohexene are known. In addition, the compound of general formula [14] can be produced by a method, for example, described In "Jikken Kagaku Kouza", 4th edition, Vol. 19, pp. 53-298, 1992, Maruzen or the like method.

(10-1)

The compound of general formula [1k] can be produced by reacting a compound of general formula [2] with a compound of general formula [14] following production process (3-1).

(10-2)

The compound of general formula [1l] can be produced by reducing a compound of general formula [1k] following production process (3-3).

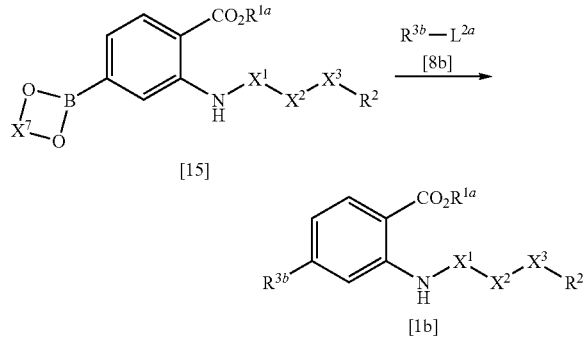

"In the formula, $L^{2a}$ represents a chlorine atom, a bromine atom or an iodine atom; $R^{1a}$, $R^2$, $R^{3b}$, $X^1$, $X^2$, $X^3$ and $X^7$ mean the same as above,"

As a compound of general formula [8b], for example, 2-iodotoluene, 3-iodoanisole, 3-iodonitrobenzene and 6-iodo-2,3-dihydrobenzo[1,4]dioxin are known.

The compound of general formula [1b] can be produced by reacting a compound of general formula [15] with a compound of general formula [8b] following production process 1.

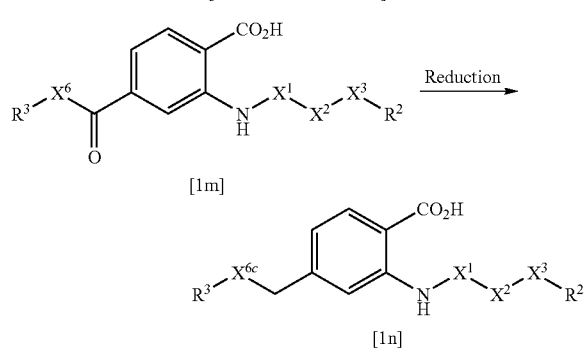

"In the formula, $R^2$, $R^3$, $X^1$, $X^2$, $X^3$, $X^6$ and $X^{6c}$ mean the same as above."

The compound of general formula [1n] can be produced by reducing a compound of general formula [1m] following production process (3-3).

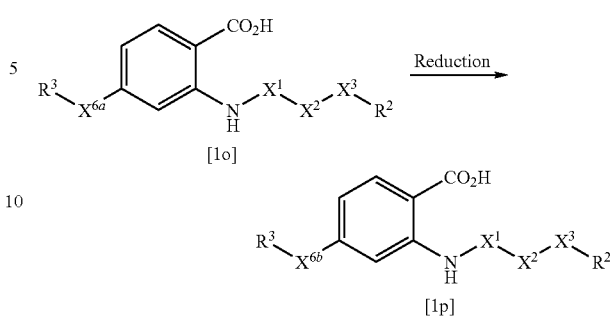

"In the formula, $R^2$, $R^3$, $X^1$, $X^2$, $X^3$, $X^{6a}$ and $X^{6b}$ mean the same as above."

The compound of general formula [1p] can be produced by reducing a compound of general formula [1o] following production process (3-3).

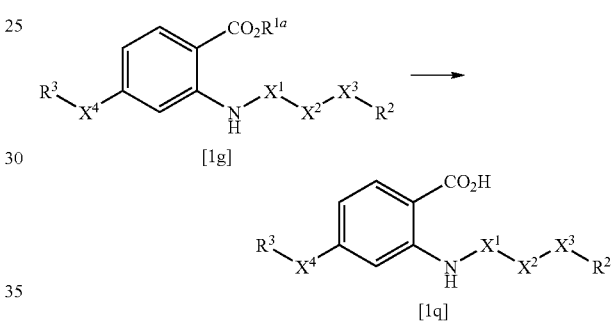

"In the formula, $R^{1a}$, $R^2$, $R^3$, $X^1$, $X^2$, $X^3$ and $X^4$ mean the same as above,"

The compound of general formula [1q] can be produced by deprotecting a compound of general formula [1g].

Examples of deprotection reaction include hydrolysis reaction using an acid or a base, dealkylation reaction using a salt and reductive dealkylation reaction including metal catalyst hydrogenation reaction.

Examples of the acid in hydrolysis reaction using an acid include formic acid, hydrochloric acid, sulfuric acid, hydrobromic acid, trifluoroacetic acid, aluminum chloride and iodinated trimethylsilane. The used amount of the acid can be 1 to 100000 times mol and preferably 1 to 1000 times mol for the compound of general formula [1g].

Examples of the base in hydrolysis reaction using a base include inorganic bases such as sodium hydroxide, potassium hydroxide and lithium hydroxide; organic bases such as sodium methoxide, sodium ethoxide and potassium tert-butoxide; carbonates such as potassium carbonate and sodium carbonate and tetrabutylammonium fluoride. The used amount of the base can be 1 to 1000 times mol and preferably 1 to 50 times mol for the compound of general formula [1g].

Examples of the salt in dealkylation reaction using a salt include lithium iodide and sodium chloride. The used amount of the salt can be 1 to 100 times mol and preferably 1 to 10 times mol for the compound of general formula [1g].

The reductive dealkylation reaction including metal catalyst hydrogenation reaction can be conducted following production process (3-3).

The solvent used in this reaction is not particularly limited as long as it does not adversely affect the reaction and examples thereof include water; alcohols such as methanol, ethanol, 2-propanol and 2-methyl-2-propanol; ethers such as dioxane, tetrahydrofuran, anisole, ethylene glycol dimethyl ether, diethylene glycol dimethyl ether and diethylene glycol diethyl ether; halogenated hydrocarbons such as methylene chloride, chloroform and dichloroethane; nitriles such as acetonitrile; aliphatic hydrocarbons such as hexane and cyclohexane; aromatic hydrocarbons such as benzene, toluene and xylene; sulfoxides such as dimethylsulfoxide; amides such as N,N-dimethylformamide; nitromethane and pyridine and these may be optionally mixed for use.

This reaction can be carried out ordinarily at −78 to 100° C., preferably at 0 to 80° C. for 10 minutes to 24 hours.

[Production Process 15]

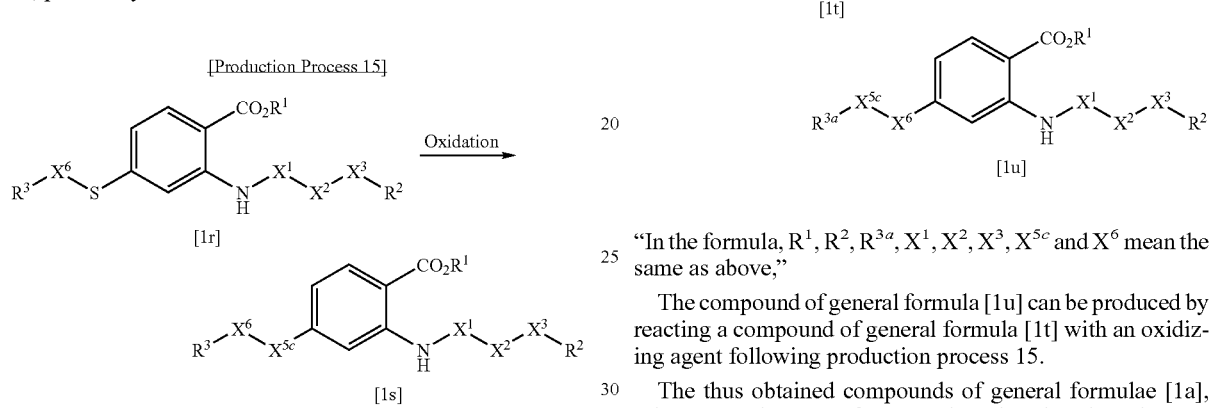

"In the formula, $X^{5c}$ represents a sulfinyl group or a sulfonyl group; $R^1$, $R^2$, $R^3$, $X^1$, $X^2$, $X^3$ and $X^6$ mean the same as above,"

The compound of general formula [1s] can be produced by reacting a compound of general formula [1r] with an oxidizing agent.

The solvent used in this reaction is not particularly limited as long as it does not adversely affect the reaction and examples thereof include water; halogenated hydrocarbons such as methylene chloride, chloroform and dichloroethane; aliphatic hydrocarbons such as hexane and cyclohexane and pyridine and these may be optionally mixed for use.

Examples of the oxidizing agent used in this reaction include hydrogen peroxide; hyperacids such as a peroxyacetic acid, perbenzoic acid and m-chloroperbenzoic acid; peroxides such as tert-butyl peroxide and sodium metaperiodate. The used amount of the oxidizing agent can be 1 to 50 times mol, preferably 1 to 10 times mol for the compound of general formula [1r].

This reaction can be carried out ordinarily at 0 to 150° C., preferably at 10 to 100° C. for 30 minutes to 48 hours.

[Production Process 16]

"In the formula, $R^1$, $R^2$, $R^{3a}$, $X^1$, $X^2$, $X^3$, $X^{5c}$ and $X^6$ mean the same as above,"

The compound of general formula [1u] can be produced by reacting a compound of general formula [1t] with an oxidizing agent following production process 15.

The thus obtained compounds of general formulae [1a], [1b], [1c], [1d], [1e], [1f], [1g], [1h], [1i], [1j], [1k], [1l], [1n], [1o], [1p], [1q], [1r], [1s], [1t] and [1u] or the salts thereof can be converted to the other compounds of general formula [1] or the salts thereof by subjecting them to reactions known per se such as condensation, addition, oxidation, reduction, rearrangement, substitution, halogenation, dehydration and hydrolysis or by combining these reactions appropriately.

In addition, when there is any isomer (for example, optical isomer, geometrical isomer, tautomer and the like) for the compounds in the production processes mentioned above, these isomers can also be used, and solvates, hydrates and crystals of various kinds can be also used.

Next, produce ion processes of the compounds of general formulae [2], [7], [9], [10], [12], [15] and [38], which are raw materials in the production of the compounds of the present invention, are described.

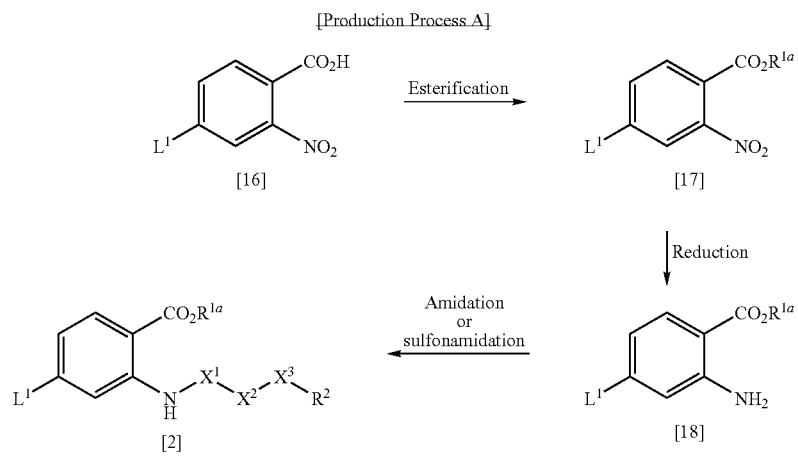

"In the formula, $R^{1a}$, $R^2$, $X^1$, $X^2$, $X^3$ and $L^1$ mean the same as above".

As a compound of general formula [16], for example, 4-chloro-2-nitrobenzoic acid and 4-bromo-2-nitrobenzoic acid are known.

(A-1)

The compound of general formula [17] can be produced by esterifying a compound of general formula [16]. This reaction can be performed by a method described in W, Greene et al., Protective Groups in Organic Synthesis, third edition, pp. 369-453, 1999, John Wiley & Sons, INC, or one like method. Specifically, methods using an alkylating agent in the presence of or in the absence of a phase transfer catalyst, in she presence of the base, a method via an acid halide of the compound of general formula [16] are Included.

The solvent used in the reaction using an alkylating agent is not particularly limited as long as it does not adversely affect the reaction and examples thereof include aromatic hydrocarbons such as benzene, toluene and xylene; amides such as N,N-dimethylformamide, N,N-dimethylacetamide and 1-methyl-2-pyrrolidone; halogenated hydrocarbons such as methylene chloride, chloroform and dichloroethane; ethers such as dioxane, tetrahydrofuran, anisole, ethylene glycol dimethyl ether, diethylene glycol dimethyl ether and diethylene glycol diethyl ether; ketones such as acetone and 2-butanone; nitriles such as acetonitrile; esters such as ethyl acetate and butyl acetate and sulfoxides such as dimethylsulfoxide and these may be optionally mixed for use.

Examples of the phase transfer catalyst optionally used in this reaction include quaternary ammonium salts such as tetramethyl ammonium chloride, benzyltrimethylammonium chloride, benzyltriethylammonium chloride, benzyltributylammonium chloride and tetrabutylammonium bromide. The used amount of the phase transfer catalyst can be 0.01 mol or more, preferably 0.1 to 5 times mol for the compound of general formula [16].

Examples of the base used in this reaction include inorganic bases such as sodium carbonate, potassium carbonate and cesium carbonate and organic bases such as triethylamine, pyridine, dimethylaminopyridine and N-methylmorpholine. The used amount of the base can be 1 to 50 times mol, preferably 1 to 5 times mol for the compound of general formula [16].

Examples of the alkylating agent used in this reaction include methyl iodide, ethyl Iodide, dimethyl sulfate, 2-bromo-2-methylpropane, benzyl chloride and benzyl bromide. The used amount of the alkylating agent can be 1 to 50 times mol, preferably 1 to 5 times mol for the compound of general formula [16].

This reaction can be carried out ordinarily at 0 to 170° C. for 1 minute to 24 hours.

For example, in a method via an acid halide, a compound of general formula [16] can be reacted with thionyl chloride, oxalyl chloride or the like to converted it to an acid halide and then reacted with alcohols such as methanol, ethanol, benzyl alcohol in the presence of or in the absence of a base.

The solvent used in this reaction is not particularly limited as long as it does not adversely affect the reaction and examples thereof include aromatic hydrocarbons such as benzene, toluene and xylene; halogenated hydrocarbons seen as methylene chloride, chloroform and dichloroethane; ethers snob as dioxane, tetrahydrofuran, anisole, ethylene glycol dimethyl ether, diethylene glycol dimethyl ether and diethylene glycol diethyl ether; ketones such as acetone and 2-butanone; nitriles such as acetonitrile; esters such as ethyl acetate and butyl acetate and sulfoxides such as dimethylsulfoxide and these may be optionally mixed for use.

Examples of the base optionally used in this reaction include inorganic bases such as sodium carbonate, potassium carbonate and cesium carbonate and organic bases such as triethylamine, pyridine, dimethylaminopyridine and N-methylmorpholine. The used amount of the base can be 1 to 50 times mol, preferably 1 to 5 times mol for the compound of general formula [16].

This reaction can be carried out ordinarily at 0 to 170° C. for 1 minute to 24 hours.

(A-2)

The compound of general formula [18] can be produced by reducing a compound of general formula [17]. This reaction can be performed by a method described in Richard C. Larock et al., Comprehensive Organic Transformations, second edition, pp. 823-827, 1999, John Wiley & Sons, INC. or the like method. Specifically, catalytic hydrogenation reaction using a metal catalyst and reductive reaction using a metal such as iron or zinc are included.

When the compound of general formula [17] is subjected to catalytic hydrogenation reaction, it can be performed following production process (3-3).

The solvent used for subjecting a compound of general formula [17] to reduction using a metal is not particularly limited as long as it does not adversely affect the reaction and examples thereof. Include wafer; alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitrites such as acetonitrile; ketones such as acetone and 2-butanone; esters such as ethyl acetate and butyl acetate and these may be optionally mixed for use.

Examples of the metal used in this reaction include iron, zinc, tin and tin (II) chloride. The used amount of the metal can be 1 to 50 times mol, preferably 1 to 10 times mol for the compound of general formula [17].

Examples of the acid optionally used in this reaction include hydrogen chloride, hydrogen bromide and acetic acid. The used amount of the acid can be 0.001 to 100 times amount (W/V), preferably 0.01 to 20 times amount (W/V) for the compound of general formula [17].

This reaction can be carried out at 0 to 200° C., preferably 0 to 100° C. for 1 minute to 24 hours.

(A-3)

The compound of general formula [2] can be produced by amidating or sulfonamidating a compound of general formula [18] following production process 6.

[Production Process B]

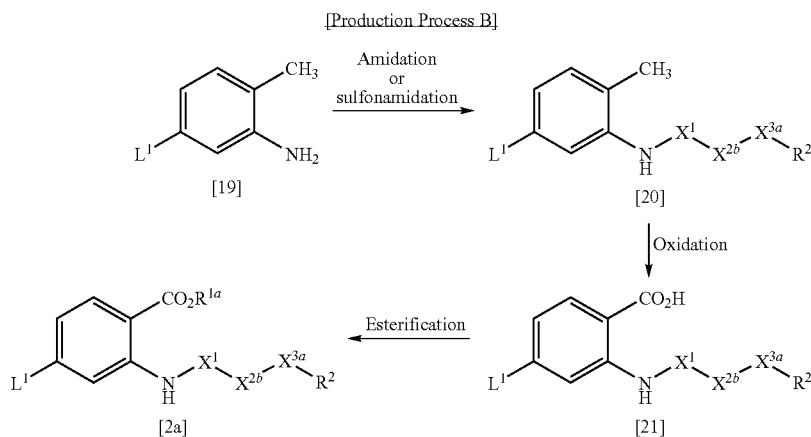

"In the formula, $R^{1a}$, $R^2$, $X^1$, $X^{2b}$, $X^{3a}$ and $L^1$ mean the same as above."

As a compound of general formula [19], for example, 5-iodo-2-methylaniline is known.

(B-1)
The compound of general formula [20] can be produced by amidating or sulfonamidating a compound of general formula [19] following production process 6.

(B-2)
The compound of general formula [21] can be produced by reacting a compound of general formula [20] with an oxidizing agent following production process 8.

(B-3)
The compound of general formula [2a] can be produced by esterifying a compound of general formula [21] following production process (A-1).

[Production Process C]

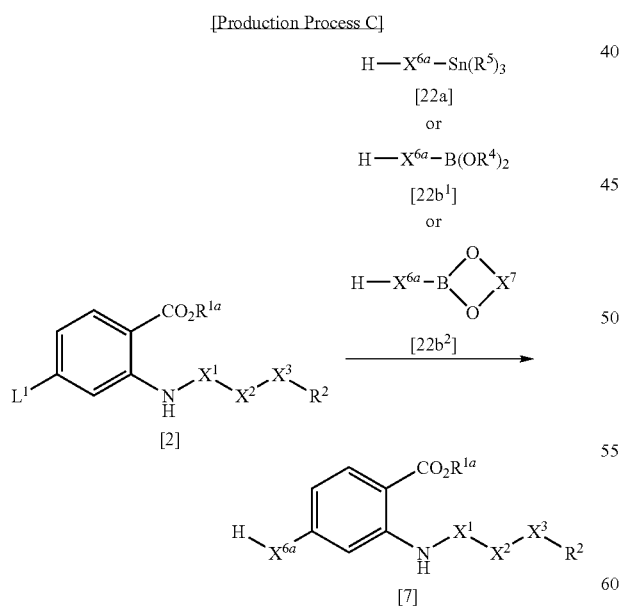

"In the formula, $R^{1a}$, $R^2$, $R^4$, $R^5$, $X^1$, $X^2$, $X^3$, $X^{6a}$, $X^7$ and $L^1$ mean the same as above."

The compound of general formula [7] can be produced by subjecting a compound of general formula [2] to coupling reaction with a compound of general formula [22a] following production process 2. In addition, it can also be produced by reacting a compound of general formula [2] with a compound of general formula [22b$^1$] or general formula [22b$^2$] following production process 1.

[Production Process D]

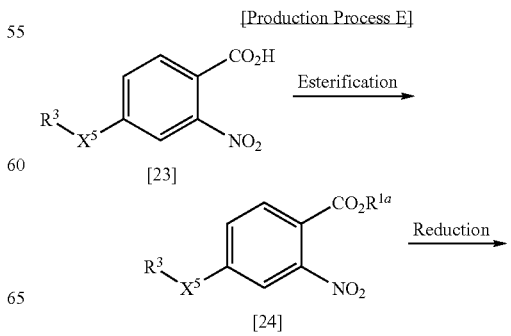

"In the formula, $R^6$ represents an acetylene protecting group; $R^{1a}$, $R^2$, $X^1$, $X^2$, $X^3$ and $L^1$ mean the same as above."

The compound of general formula [7a] can be produced by reacted a compound of general formula [2] with a compound of general formula [22c] and then by performing deprotection following production process (3-2).

Deprotection can be performed by a method described in W. Greene et al., Protective Groups In Organic Synthesis, third edition, pp. 654-659, 1999, John Wiley & Sons, INC. or the like method.

[Production Process E]

$$\underset{[23]}{\text{structure with } CO_2H, NO_2, R^3, X^5} \xrightarrow{\text{Esterification}}$$

$$\underset{[24]}{\text{structure with } CO_2R^{1a}, NO_2, R^3, X^5} \xrightarrow{\text{Reduction}}$$

37

-continued

[Structure 9a: benzene ring with CO₂R^{1a}, R³—X⁵, NH₂]

"In the formula, R$^{1a}$, R$^3$ and X$^5$ mean the same as above,"

As a compound of general formula [23], for example, 2-nitro-4-phenoxybenzoic acid [WO03/033480] is known.
(E-1)

The compound of general formula [24] can be produced by esterifying a compound of general formula [23] following production process (A-1).
(E-2)

The compound of general formula [9a] can be produced by reducing a compound of general formula [24] following production process (3-3) or (A-2).

[Production Process F]

R$^{3a}$—B(OR$^4$)$_2$
[3a]
or
R$^{3a}$—B(O)(O)X$^7$
[3b]

[17] L$^1$—benzene—CO₂R$^{1a}$, NO₂

[25] R$^{3a}$—benzene—CO₂R$^{1a}$, NO₂  →Reduction→  [9b] R$^{3a}$—benzene—CO₂R$^{1a}$, NH₂

"In the formula, R$^{1a}$, R$^{3a}$, R$^4$, X$^7$ and L$^1$ mean the same as above."
(F-1)

The compound of general formula [25] can be produced by reacting a compound of general formula [17] with a compound of general formula [3a] or general formula [3b] following production process 1.
(F-2)

The compound of general formula [9b] can be produced by reducing a compound of general formula [25] following production process (3-3) or (A-2).

[Production Process G]

[17] L$^1$—benzene—CO₂R$^{1a}$, NO₂    R$^{3b}$—Sn(R$^5$)$_3$ [4]

38

-continued

[26] R$^{3b}$—benzene—CO₂R$^{1a}$, NO₂  →Reduction→  [9c] R$^{3b}$—benzene—CO₂R$^{1a}$, NH₂

"In the formula, R$^{1a}$, R$^{3b}$, R$^5$ and L$^1$ mean the same as above,"
(G-1)

The compound of general formula [26] can be produced by reacting a compound of general formula [17] with a compound of general formula [4] following production process 2,
(G-2)

The compound of general formula [9c] can be produced by reducing a compound of general formula [26] following production process (3-3) or (A-2).

[Production Process H]

[17] L$^1$—benzene—CO₂R$^{1a}$, NO₂    R$^{3a}$—X$^{6d}$—H [27]  →

[28] R$^{3a}$—X$^{6d}$—benzene—CO₂R$^{1a}$, NO₂  →Reduction→

[9d] R$^{3c}$—X$^{6b}$—benzene—CO₂R$^{1a}$, NH₂

"In the formula, R$^{6d}$ represents an alkenylene group which may be optionally substituted; R$^{1a}$, R$^{3a}$, R$^{3c}$, X$^{6b}$ and L$^1$ mean the same as above."
(H-1)

The compound of general formula [28] can be produced by reacting a compound of general formula [17] with a compound of general formula [27] following production process (3-1).
(H-2)

The compound of general formula [9d] can be produced by reducing a compound of general formula [28] following production process (3-3).

[Production Process I]

[29] L$^4$—X$^{6b}$—benzene—CO₂R$^{1a}$, NO₂    R$^{3a}$—X$^{5a}$—H [30]  →

[31] R$^{3a}$—X$^{5a}$—X$^{6b}$—benzene—CO₂R$^{1a}$, NO₂  →Reduction→

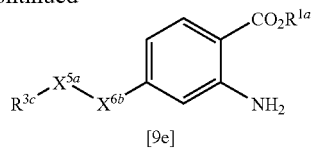

[9e]

"In the formula, $L^4$ represents a leaving group; $R^{1a}$, $R^{3a}$, $R^{3c}$, $X^{5a}$ and $X^{6b}$ mean the same as above."

As a compound of general formula [29], for example, methyl 4-(bromomethyl)-2-nitrobenzoate is known. In addition, methyl 4-(bromomethyl)-2-nitrobenzoate can be produced by esterifying 4-(bromomethyl)-2-nitrobenzoic acid according to an ordinary method described in Journal of Medicinal Chemistry, Vol. 29, pp. 589-591, 1986.

(I-1)
The compound of general formula [31] can be produced by reacting a compound of general formula [29]with a compound of general formula [30] following production process (7-1).

(I-2)
The compound of general formula [9e] can be produced by reducing a compound of general formula [31]following production process (3-3) or (A-2).

[Production Process J]

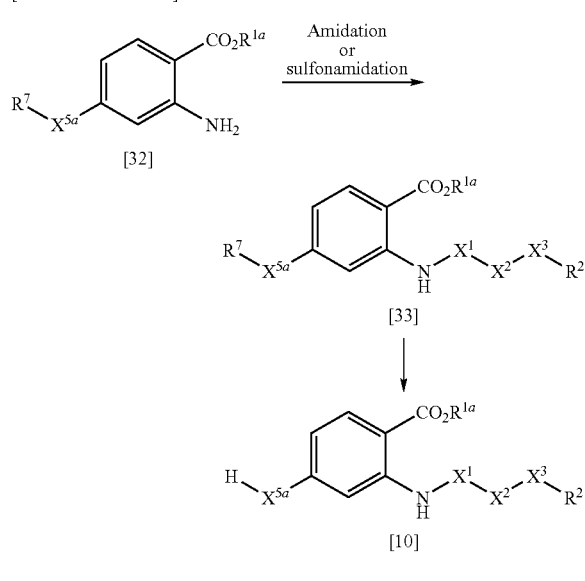

"In the formula, $R^7$ represents a phenolic hydroxyl protecting group or a thiol protecting group; $R^{1a}$, $R^2$, $X^1$, $X^2$, $X^3$ and $X^{5a}$ mean the same as above."

As a compound of general formula [32], for example, methyl 2-amino-4-methoxybenzoate [Journal of the Chemical Society, Perkin Transactions 1, Vol. 21, pp. 3261-3274, 1997] is known.

(J-2)
The compound of general formula [33] can be produced by amidating or sulfonamidating a compound of general formula [32] following production process 6.

(J-2)
The compound of general formula [10] can be produced by deprotecting a compound of general formula [33]. Deprotection of phenolic hydroxyl protecting group can be performed, for example, by a method described in W. Greene en al., Protective Groups in Organic Synthesis, third edition, pp. 249-287, 1999, John Wiley & Sons, INC. or the like method; deprotection of thiol protecting group can be performed, for example, by a method described in W. Greene et al., Protective Groups in Organic Synthesis, third edition, pp. 454-493, 1999, John Wiley & Sons, INC. or the like method.

[Production Process K]

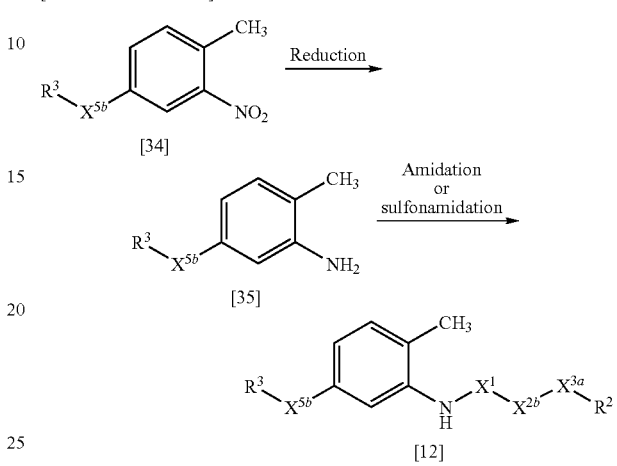

"In the formula, $R^2$, $R^3$, $X^1$, $X^{2b}$, $X^{3a}$ and $X^{5b}$ mean the same as above."

As a compound of general formula [34], for example, 1-methyl-2-nitro-4-phenoxybenzene [International Patent Publication WO02/078693] is known.

(K-1)
The compound of general formula [35] can be produced by reducing a compound of general formula [34]following production process (3-3) or (A-2).

(K-2)
The compound of general formula [1,2] can be produced by amidating or sulfonamidating a compound of general formula [35] following production process 6.

[Production Process L]

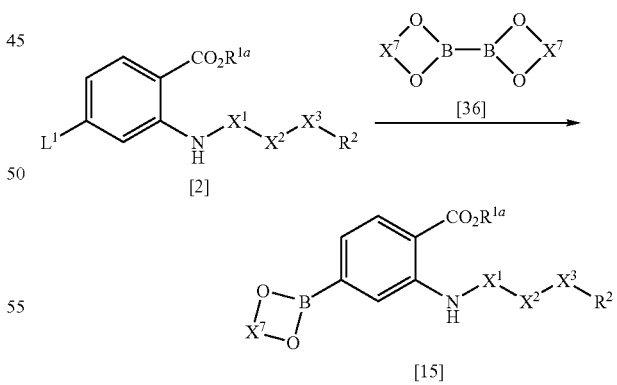

"In the formula, $R^{1a}$, $R^2$, $X^1$, $X^2$, $X^3$, $X^7$ and $L^1$ mean the same as above."

As a compound of general formula [36], for example, bis(pinacolato)diboron, bis(neopentylglylato)diboron and bis(hexyleneglycolato)diboron are known.

The compound of general formula [15] can be produced by reacting a compound of general formula [2]with a compound of general formula [36] following production process 1.

[Production Process M]

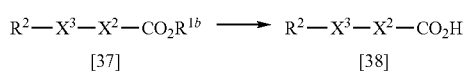

"In the formula, $R^{1b}$ represents a carboxyl protecting group; $R^2$, $X^2$ and $X^3$ mean the same as above."

As a compound of general formula [37], for example, methyl 2-(1H-pyrrol-1-yl)pyridine-4-carboxylate [International Patent Publication WO9426709] is known.

The compound of general formula [38] can be produced by deprotecting a compound of general formula following production process 14.

In the compounds used in the production processes mentioned above, compounds which can be in the form of a salt can be used as a salt. Examples of those salts include salts which are similar to the salts of the compound of general formula [1].

When there is any isomer (for example, optical isomer, geometrical isomer, tautomer and the like) for the compounds in the production processes mentioned above, these isomers can be also used. In addition, when there are solvates, hydrates and various kinds of crystals, these solvates, hydrates and various kinds of crystals can be used. Further, when the compounds used in the production process mentioned above have a protectable group, for example, an amino group, a hydroxyl group or a carboxyl group, these groups can be protected with ordinary protecting groups beforehand, and these protecting groups can be detached by methods well known per se after the reaction.

When the compounds of the present invention are used as a drug, drug adjuvants usually used for preparation such as excipient, carrier and diluent may be mixed appropriately. They can be administered orally or parenterally in the forms such as tablet, capsule, powder, syrup, granule, pill, suspension, emulsion, solution, powder preparations, suppository, eyedrop, nose drop, eardrop, patch, ointment or injection. The administration method, dosage and times of administration can be selected appropriately according to the age, weight and conditions of the patient. Ordinarily, 0.01 to 1000 mg/kg per day can be administered to an adult orally or parenterally (for example, injection, intravenous feeding and administration to a rectal part) at a time or divided to several times.

Usefulness of some representative compounds of the present invention is described in the following Test Examples.

TEST EXAMPLE 1

MMP-13 Production Inhibition Test $6.8 \times 10^3$ human cartilage derived cell line SW1353 cells were suspended in 100 μL of Dulbecco modified Eagle's medium supplemented with 10% fetal calf serum, plated on 96-well plates and cultured for 3 days. After the culture medium was changed to Dulbecco modified Eagle's medium containing 0.2% lactalbumin hydrolysate and the cells were cultured for 6 hours, best compounds were added and then IL-1β was added to obtain the final concentration of 10 ng/mL 1 hour later. 16 hours after the stimulation, supernatant was collected and the amount of MMP-13 in the culture supernatant was determined with an ELISA kit (Amersham). The inhibition rate was calculated from the amount of MMP-13 in the presence of a test compound assuming that the amount of MMP-13 was 100% in the absence of the test compound.

The results are shown in Table 7.

TABLE 7

| Example No. | Inhibition rate (%) at 30 μmol/L |
|---|---|
| 4 | 80 |
| 7 | 91 |
| 8 | 95 |
| 11 | 92 |
| 15 | 88 |
| 19 | 94 |
| 22 | 81 |
| 24 | 92 |
| 25 | 86 |
| 33 | 97 |
| 80 | 92 |
| 83 | 93 |
| 85 | 60 |
| 88 | 80 |
| 89 | 94 |
| 91 | 95 |
| 96 | 96 |
| 97 | 97 |
| 99 | 71 |
| 105 | 64 |
| 130 | 96 |
| 134 | 99 |
| 138 | 95 |
| 141 | 95 |
| 146 | 97 |
| 150 | 96 |
| 157 | 98 |
| 163 | 98 |
| 176 | 98 |
| 189 | 96 |
| 196 | 97 |
| 212 | 95 |
| 217 | 68 |
| 222 | 98 |
| 230 | 95 |
| 234 | 99 |
| 240 | 94 |
| 243 | 96 |
| 251 | 83 |
| 255 | 91 |
| 261 | 94 |
| 262 | 93 |
| 264 | 94 |
| 276 | 86 |
| 282 | 75 |
| 301 | 80 |
| 316 | 96 |
| 318 | 95 |
| 325 | 91 |
| 330 | 68 |
| 349 | 95 |
| 358 | 99 |
| 382 | 98 |
| 399 | 79 |
| 411 | 81 |
| 415 | 97 |
| 423 | 98 |
| 425 | 99 |
| 426 | 98 |
| 431 | 98 |
| 433 | 98 |
| 442 | 99 |
| 450 | 98 |
| 467 | 90 |
| 495 | 99 |
| 499 | 99 |
| 503 | 99 |
| 505 | 82 |
| 509 | 77 |
| 512 | 99 |
| 514 | 91 |
| 525 | 87 |
| 539 | 97 |
| 541 | 97 |
| 543 | 85 |
| 551 | 86 |
| 560 | 85 |

TABLE 7-continued

| Example No. | Inhibition rate (%) at 30 μmol/L |
|---|---|
| 564 | 97 |
| 570 | 98 |

TEST EXAMPLE 2

Type II Collagen-induced Arthritis in Mice

Eight-week old male DBA/1J mice were used (Charles River Laboratories Japan Inc.). 4 mg/mL bovine type II collagen (Collagen Gijutsu Kenshukai) dissolved in 0.01 mol/L of acetic acid aqueous solution and an equal amount of Freund's complete adjuvant (Chondorex) containing 1 mg/mL of killed tuberculosis bacillus were added to prepare an emulsion, and 0.1 mL thereof was intradermally injected at the base of tail. Similar treatment was conducted on the 21st day to cause arthritis. The test compound was suspended in 0.5% methylcellulose aqueous solution, and 30 mg/kg was orally administered once a day from the 21st day to the 35th day. In the control group, 0.5% methylcellulose aqueous solution was administered in the same manner. The severity of arthritis was estimated by scoring at zero point for an animal without change; one point for an animal with swelling at the one or two finger joint or light swelling only at the carpal or tarsal joint; two points for an animal with severe swelling at the carpal or tarsal joint or with swelling at three or more finger joints; three points for an animal with severe swelling along the whole foreleg or hindleg and thus counting 12 points at the maximum for the four limbs as arthritis score. Degree of bone destruction was estimated by X-ray photographs of the four limbs on the 36th day observing the interphalangeal joints of the second to fifth fingers, the metacarpophalangeal and metatarsophalangeal joints of the first to fifth fingers, carpal or tarsal parts, calcaneal bone and scoring at 0 or 0.5 point according to the absence or presence of osteoporotic image in the joint and their vicinity, 0 point for the bone image without change, one point for the partially destroyed bone image and, 2 points for the completely destroyed bone image and thus counting 105 points at the maximum for the four limbs as bone destruction score. The inhibitory rate was determined by the following expression.

Inhibitory ratio (%)=100−(score of a test compound treated group/score of the control group)×100

The compound shown in Example 25 exhibited inhibitory action on arthritis and bone destruction.

EXAMPLES

Hereinbelow, the present invention is described by way of Referential Examples and Examples, but the present invention is not limited thereto.

The mixing ratio in the eluent is a volume ratio. Unless indicated otherwise, the carrier in the silica gel column chromatography is B.W. Silica gel, BW-127ZH, manufactured by Fuji Silysia Chemical Ltd., and the carrier in the reversed-phase silica gel column chromatography is ODS-AM12S05-2520WT of YMC Co., Ltd.

Each of the symbols used in each Example has the following meaning.

Ac: acetyl, Boc: tert-butoxycarbonyl, $^t$Bu; tert-butyl, Bz: benzoyl, Eb: ethyl, Me: methyl
DMSO-d6: deuterated dimethylsulfoxide

Referential Example 1

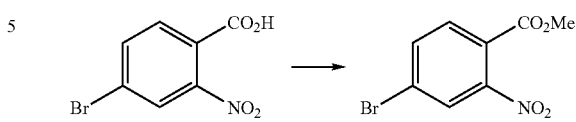

To 40 mL of acetone solution containing 4.0 g of 4-bromo-2-nitrobenzoic acid, 3.4 g of potassium carbonate and 2.3 mL of dimethyl sulfate were added at room temperature and stirred at 50° C. for 1 hour. After the reaction mixture was cooled to room temperature, the solvent was evaporated under reduced pressure. Water and ethyl acetate were added to the obtained residue. The organic layer was separated and dried over anhydrous magnesium sulfate after washed with a saturated sodium hydrogen carbonate aqueous solution, 1.0 mol/L hydrochloric acid and a saturated sodium chloride aqueous solution sequentially, and the solvent was evaporated under reduced pressure to obtain 4.1 g of methyl 4-bromo-2-nitrobenzoate as white solid.

$^1$H-NMR (CDCl$_3$) δ: 3.97 (3H, s), 7.85 (1H, d, J=8.3 Hz), 8.07 (1H, dd, J=8.3, 2.0 Hz), 8.47 (1H, d, J=2.0 Hz).

Referential Example 2

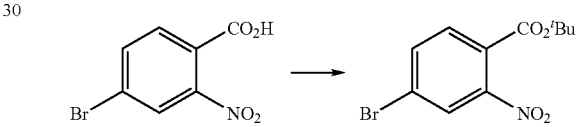

To 50 ml, of N, N-dimethylacetamide solution containing 5.0 g of 4-bromo-2-nitrobenzoic acid, 41 g of potassium carbonate, 4.6 g of benzyltriethylammonium chloride and 69 mL of 2-bromo-2-methylpropane were added at room temperature and stirred at 55° C. for 10 hours. After the reaction mixture was cooled to room temperature, 12 mL of 2-bromo-2-methylpropane was added and stirred at 55° C. for 4 hours. After the reaction mixture was cooled to room temperature, water and ethyl acetate were added. The organic layer was separated and dried over anhydrous magnesium sulfate after washed with 10% citric acid aqueous solution and a saturated sodium chloride aqueous solution sequentially, and the solvent was evaporated under reduced pressure. Methanol was added to the obtained residue and solid substances were separated by filtration to obtain 3.0 g of tert-butyl 4-bromo-2-nitrobenzoate as white solid.

$^1$H-NMR (CDCl$_3$) δ: 1.55 (9H, s), 7.63 (1H, d, J=8.3 Hz), 7.77 (1H, dd, J=8.3, 1.9 Hz), 7.95 (1H, d, J=1.9 Hz).

Referential Example 3

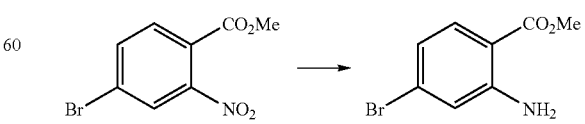

2.6 g of iron powder was added to a mixed solution of 20 mL of methanol and 20 ml, of acetic acid containing 4.0 g of methyl 4-bromo-2-nitrobenzoate, and the resulting mixture was heated to reflux for 3 hours. After the reaction mixture was cooled to room temperature, a saturated sodium hydrogen carbonate aqueous solution and ethyl acetate were added and insoluble were removed by filtration. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. Hexane was added to the obtained residue and a solid substance was separated by filtration to obtain 2.0 g of methyl 2-amino-4-bromobenzoate as white solid.

$^1$H-NMR (CDCl$_3$) δ: 3.89 (3H, s), 4.20 (2H, s), 7.26 (1H, dd, J=8.3, 2.1 Hz), 7.43 (1H, d, J=2.1 Hz), 7.47 (1H, d, J=8.3 Hz).

Referential Example 4

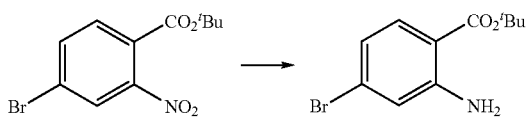

3.0 g of iron powder was added to a mixed solution of 28 mL of methanol and 28 mL of acetic acid containing 5.5 g of tert-butyl 4-bromo-2-nitrobenzoate, and the resulting mixture was heated to reflux for 1 hour. After one reaction mixture was cooled to room temperature, a saturated sodium hydrogen carbonate aqueous solution and ethyl acetate were added and insoluble were removed by filtration. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure to obtain 4.3 g of tert-butyl 2-amino-4-bromobenzoate as pale yellow oil.

$^1$H-NMR (DMSO-d$_6$) δ: 1.52 (9H, s), 6.65 (1H, dd, J=8.5, 2.0 Hz), 6.78 (2H, s), 6.98 (1H, d, J=2.0 Hz), 7.55 (1H, d, J=8.5 Hz).

Referential Example 5

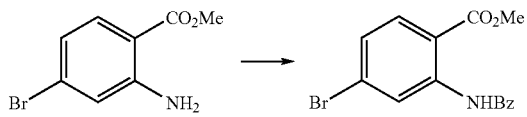

0.55 mL of benzoyl chloride was added to 10 mL of a methylene chloride solution containing 1.0 g of methyl 2-amino-4-bromobenzoate and 0.73 mL of triethylamine while ice-cooled and stirred at room temperature for 1 hour. The solvent was evaporated under reduced pressure and a saturated sodium hydrogen carbonate aqueous solution and ethyl acetate were added to the residue. The organic layer was separated and dried over anhydrous magnesium sulfate after washed with 1.0 mol/L hydrochloric acid and a saturated sodium chloride aqueous solution sequentially, and the solvent was evaporated under reduced pressure. Diisopropyl ether was added to the obtained residue and a solid substance was separated by filtration to obtain 0.9 g of methyl 2-(benzamido)-4-bromobenzoate as while solid.

$^1$H-NMR (DMSO-d$_6$) δ: 3.88 (3H, s), 7.54-7.58 (2H, m), 7.61-7.66 (1H, m), 7.77 (1H, dd, J=8.4, 2.2 Hz), 7.90 (1H, d, J=8.4 Hz), 8.00-8.02 (2H, m), 8.14 (1H, d, J=2.2 Hz), 10.18 (1H, s).

Referential Example 6

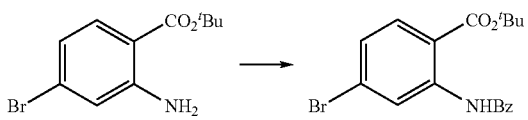

1.9 mL of benzoyl chloride was added to 42 mL of a methylene chloride solution containing 4.2 g of tert-butyl 2-amino-4-bromobenzoate and 2.6 mL of triethylamine while ice-cooled and stirred at room temperature for 2 hours. The solvent was evaporated under reduced pressure and water and ethyl acetate were added to the residue. The organic layer was separated and dried over anhydrous magnesium sulfate after washed with 10% citric acid aqueous solution and a saturated sodium chloride aqueous solution sequentially, and the solvent was evaporated under reduced pressure. Hexane and diisopropyl ether were added to the obtained residue and a solid substance was separated by filtration no obtain 4.4 g tert-butyl 2-(benzamido)-4-bromobenzoate as white solid.

$^1$H-NMR (DMSO-d$_6$) δ: 1.55 (9H, s), 7.45 (1H, dd, J=8.5, 2.1 Hz), 7.60-7.69 (3H, m), 7.89 (1H, d, J=8.5 Hz), 7.95-7.97 (2H, m), 8.78 (1H, d, J=2.1 Hz), 11.68 (1H, s).

Referential Example 7

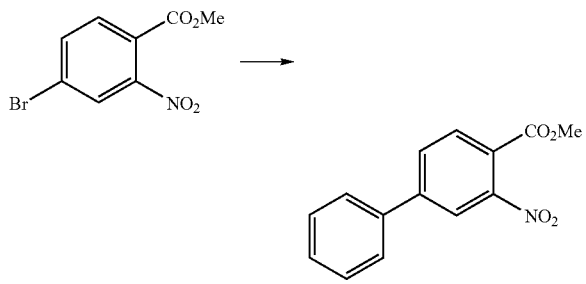

To a mixed solution of 42 mL of toluene, 16 mL of ethanol and 7.8 mL of water containing 5.2 g of methyl 4-bromo-2-nitrobenzoate, 2.9 g of dihydroxyphenyl borane, 4.2 g of sodium hydrogen carbonate and 1.1 g of tetrakis(triphenylphosphine)-palladium (0) were added sequentially and the resulting mixture was heated to reflux under nitrogen atmosphere for 2 hours. After the reaction mixture was cooled to room temperature, 1.1 g of tetrakis(triphenylphosphine) palladium (0) was added to the reaction mixture and the resulting mixture was heated to reflux under nitrogen atmosphere for 2 hours. After the reaction mixture was cooled to room temperature, 1.1 g of tetrakis(triphenylphosphine)palladium (0) was added to the reaction mixture and the resulting mixture was heated to reflux under nitrogen atmosphere for 2 hours. After the reaction mixture was cooled to room temperature, water was added. The organic layer was separated and dried over anhydrous magnesium sulfate after washed with 1.0 mol/L hydrochloric acid and a saturated sodium chloride aqueous solution sequentially, and the solvent was evaporated under reduced pressure. The obtained residue was purified with silica gel column chromatography [eluent; hexane:ethyl acetate=20:1] to obtain 4.8 g of methyl 2-nitro-4-phenylbenzoate as pale yellow oil.

$^1$H-NMR (CDCl$_3$) δ: 3.91 (3H, s), 1.41-7.53 (3H, m), 7.60-7.63 (2H, m), 7.85-7.86 (2H, m), 8.07 (1H, d, J=1.4 Hz).

Referential Example 8

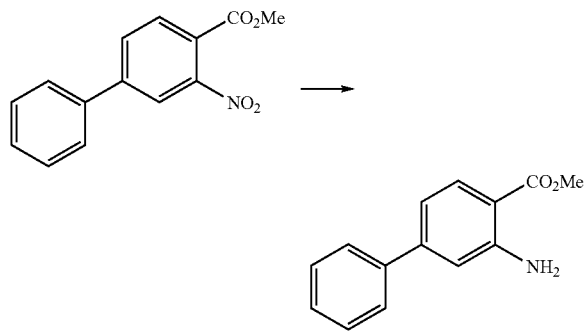

3.1 g of iron powder was added to a mixed solution of 24 mL of methanol and 24 mL of acetic acid containing 4.8 g of methyl 2-nitro-4-phenylbenzoate, and the resulting mixture was heated to reflux for 2 hours. After the reaction mixture was cooled to room temperature, insoluble were removed by filtration and a saturated sodium hydrogen carbonate aqueous solution and ethyl acetate added to the filtrate. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure, Hexane was added to the obtained residue and a solid substance was separated by filtration to obtain 1.8 g of methyl 2-amino-4-phenylbenzoate as white solid.

$^1$H-NMR (CDCl$_3$) δ: 3.89 (3H, s), 5.79 (2H, s), 6.87-6.91 (2H, m), 7.35-7.45 (3H, m), 7.57-7.61 (2H, m), 7.92 (1H, d, J=8.0 Hz).

Referential Example 9

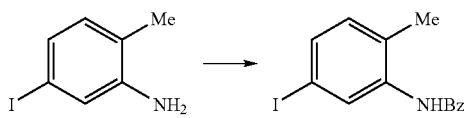

2.1 mL of benzoyl chloride was added to 70 mL of a methylene chloride solution containing 3.5 g of 5-iodo-2-methylaniline and 2.5 mL of triethylamine at room temperature and stirred at the same temperature for 30 minutes. 1.0 mol/L hydrochloric acid was added to the reaction mixture. The organic layer was separated and dried over anhydrous magnesium sulfate after washed with a saturated sodium hydrogen carbonate aqueous solution, and the solvent was evaporated under reduced pressure. Diisopropyl ether and hexane were added to the obtained residue and a solid substance was separated by filtration to obtain 4.2 g of N-(5-iodo-2-methylphenyl)benzamide as pale yellow solid.

$^1$H-NMR (CDCl$_3$) δ: 2.29 (3H, s), 6.96 (1H, d, J=8.0 Hz), 7.44 (1H, did, J=1.6, 8.6 Hz), 7.49-7.63 (4H, m), 7.86-7.88 (2H, m), 8.39 (1H, d, J=1.6 Hz).

Referential Example 10

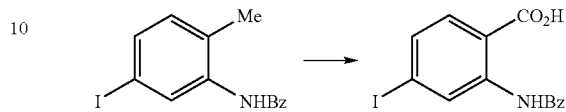

2.4 g of potassium permanganate and 1.8 g of anhydrous magnesium sulfate were added to a suspension of 40 mL of tert-butyl alcohol and 80 mL of water containing 4.2 g of N-(5-iodo-2-methylphenyl)benzamide at room temperature, and the resulting mixture was heated to reflux for 4 hours. After the reaction mixture was cooled to room temperature, 2.0 g of potassium permanganate and 1.5 g of anhydrous magnesium sulfate were added and the resulting mixture was heated to reflux for 2 hours. After the reaction mixture was cooled to room temperature, 2.0 g of potassium permanganate and 1.5 g of anhydrous magnesium sulfate were added and the resulting mixture was heated to reflux for 2 hours. After the reaction mixture was cooled to room temperature, 20 mL of ethanol was added and insoluble were removed by filtration. The solvent was evaporated under reduced pressure and 1.0 mol/L hydrochloric acid and ethyl acetate were added. The organic layer was separated and dried over anhydrous magnesium sulfate, and the solvent was evaporated under reduced pressure. Diisopropyl ether and hexane were added to the obtained residue and a solid substance was separated by filtration to obtain 3.3 g of 2-(benzamido)-4-iodobenzoic acid as pale yellow solid.

$^1$H-NMR (DMSO-d$_6$) δ: 7.58-7.69 (4H, m), 7.79 (1H, d, J=8.3 Hz), 7.94-7.96 (2H, m), 9.17 (1H, d, J=1.7 Hz), 12.17 (1H, s).

Referential Example 11

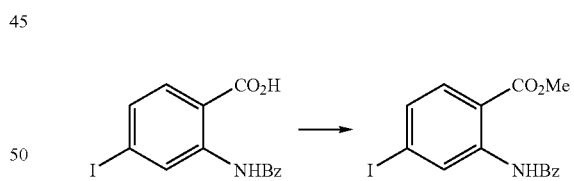

0.62 g of potassium carbonate and 0.43 ml of dimethyl sulfate were added to 15 mL of N,N-dimethylformamide solution containing 1.5 g of 2-(benzamido)-4-iodobenzoic acid at room temperature and stirred at the same temperature for 1 hour. Ethyl acetate and 1.0 mol/L hydrochloric acid were added to the reaction mixture. The organic layer was separated and dried over anhydrous magnesium sulfate, and the solvent was evaporated under reduced pressure. The obtained residual was purified with silica gel column chromatography [eluent; hexane:ethyl acetate=5:1] to obtain 1.3 g of methyl 2-(benzamido)-4-iodobenzoate as white solid.

$^1$H-NMR (DMSO-d$_6$) δ: 3.89 (3H, s), 7.59-7.69 (4H, m), 7.75 (1H, d, J=8.3 Hz), 7.95-7.98 (2H, m), 9.04 (1H, d, J=1.5 Hz), 11.61 (1H, s).

Referential Example 12

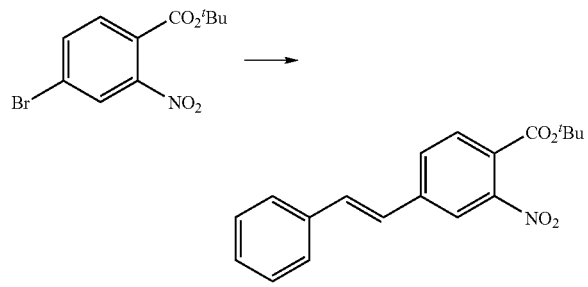

To 48 mL of N,N-dimethylacetamide solution containing 6.0 g of tert-butyl 4-bromo-2-nitrobenzoate, 2.7 mL of styrene, 2.5 g of sodium acetate, 3.2 g of tetrabutylammonium bromide and 0.22 g of palladium acetate (II) were added sequentially, and heated and stirred under nitrogen atmosphere at 90° C. for 3 hours. After the reaction mixture was cooled to room temperature, 0.45 mL of styrene and 0.22 g of palladium acetate (II) were added and heated and stirred at 110° C. for 3 hours. After the reaction mixture was cooled to room temperature, water and ethyl acetate were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [eluent; hexane:ethyl acetate=20:1] to obtain 3.8 g of tert-butyl 2-nitro-4-((E)-2-phenylvinyl)benzoate as white solid.

$^1$H-NMR (DMSO-$d_6$) δ: 1.51 (9H, s), 7.32-7.45 (1H, m), 7.59 (1H, d, J=16.6 Hz), 7.66 (2H, d, J=7.4 Hz), 7.84 (1H, d, J=8.1 Hz), 7.98 (1H, d, J=8.1, 1.5 Hz), 8.23 (1H, d, J=1.5 Hz).

Referential Example 13

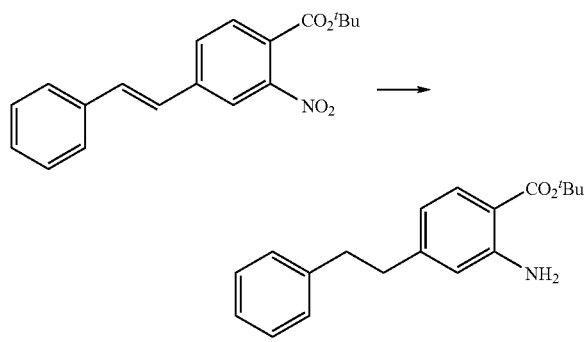

0.74 g of 5% palladium-carbon was added to a mixed solution of 56 mL of methanol and 56 mL of ethyl acetate containing 3.7 g of tert-butyl 2-nitro-4-((E)-2-phenylvinyl)benzoate and stirred under hydrogen atmosphere at room temperature for 2 hours. Insoluble were removed by filtration, and the solvent was evaporated under reduced pressure to obtain 3.4 g of tert-butyl 2-amino-4-phenethylbenzoate as white solid.

$^1$H-NMR (CDCl$_3$) δ: 1.58 (9H, s), 2.79-2.91 (4H, m), 5.63 (2H, s), 6.44-6.49 (2H, m), 7.17-7.21 (3H, m), 7.26-7.30 (2H, m), 7.72 (1H, d, J=8.4 Hz).

Referential Example 14

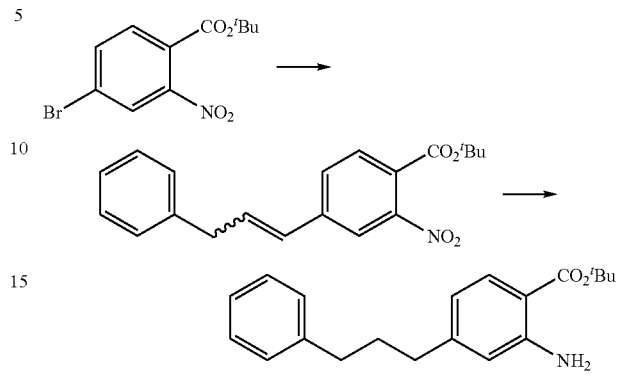

19 mg of palladium acetate (II) was added to 5 mL of toluene solution containing 0.50 g of tert-butyl 4-bromo-2-nitrobenzoate, 50 mg of tri(o-tolyl)phosphine, 0.44 mL of allylbenzene and 0.46 mL of triethylamine, and the resulting mixture was heated to reflux under nitrogen atmosphere for 2 hours. After the reaction mixture was cooled to room temperature, 20 mg of palladium acetate (II) was added and the resulting mixture was heated to reflux for 7 hours. After the reaction mixture was cooled to room temperature, Insoluble were removed by filtration, and the solvent was evaporated under reduced pressure. The obtained residue was purified with silica gel column chromatography [eluent; hexane:ethyl acetate=30:1] to obtain 0.31 g of tert-butyl 2-nitro-4-(3-phenyl-1-propenyl)benzoate.

62 mg of 5% palladium-carbon was added to 3 mL of ethyl acetate solution containing 0.31g of tert-butyl 2-nitro-4-(3-phenyl-1-propenyl)benzoate at room temperature and stirred under hydrogen atmosphere at the same temperature for 5 hours and 30 minutes. Insoluble were removed by filtration, and the solvent was evaporated under reduced pressure to obtain 0.31 g of tert-butyl 2-amino-4-(3-phenylpropyl)benzoate as yellow oil.

$^1$H-NMR (CDCl$_3$) δ: 1.57 (9H, s), 1.88-1.97 (2H, m), 2.55 (2H, t, J=7.6 Hz), 2.63 (2H, t, J=7.6 Hz), 5.64 (2H, s), 6.44-6.48 (2H, m), 7.16-7.21 (3H, m), 7.26-7.30 (2H, m), 7.72 (1H, d, J=8.0 Hz).

Referential Example 15

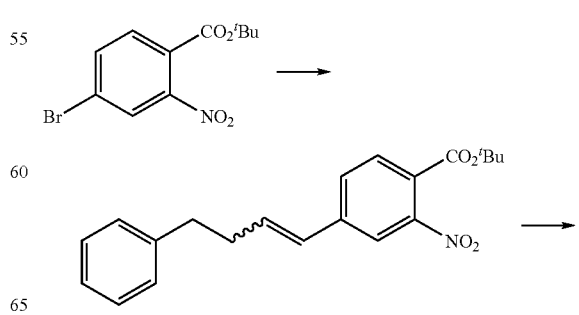

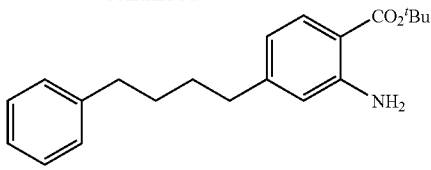

19 mg of palladium acetate (II) was added to 5 mL of toluene solution containing 0.50 g of tert-butyl 4-bromo-2-nitrobenzoate, 50 mg of tri(o-tolyl)phosphine, 0.50 mL of 4-phenyl-1-butene and 0.46 mL of triethylamine, and the resulting mixture was heated to reflux under nitrogen atmosphere for 4 hours and 30 minutes. After the reaction mixture was cooled to room temperature, 20 mg of palladium acetate (II) was added and the resulting mixture was heated to reflux for 5 hours and 30 minutes. After cooled to room temperature, the reaction mixture was purified with silica gel column chromatography [eluent; hexane:ethyl acetate=30:1] to obtain 0.35 g of tert-butyl 2-nitro-4-(4-phenyl-1-butenyl)benzoate.

70 mg of 5% palladium-carbon was added to 4 mL of ethyl acetate solution containing 0.35 g of 2-nitro-4-(4-phenyl-1-butenyl)benzoate and stirred under hydrogen atmosphere at room temperature for 8 hours. Insoluble were removed by filtration, and the solvent was evaporated under reduced pressure to obtain 0.40 g of tert-butyl 2-amino-4-(4-phenylbutyl)benzoate as yellow oil.

$^1$H-NMR (CDCl$_3$) 67: 1.57 (9H, s), 1.61-1.67 (4H, m), 2.50-2.54 (2H, m), 2.60-2.63 (2H, m), 5.63 (2H, s), 6.42-6.47 (2H, m), 7.15-7.19 (3H, m), 7.25-7.29 (2H, m), 7.70 (1H, d, J=8.0 Hz).

Referential Example 16

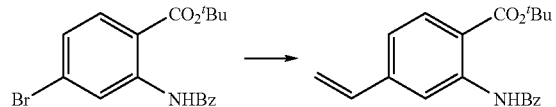

0.54 g of tetrakis(triphenylphosphine)palladium (0) was added to 35 mL of toluene solution containing 3.5 g of tert-butyl 2-(benzamido)-4-bromobenzoate and 5.0 g of tributylvinyl tin, and the resulting mixture was heated to reflux under nitrogen atmosphere for 2 hours. After the reaction mixture was cooled to room temperature, insoluble were removed by filtration, and the solvent was evaporated under reduced pressure. The obtained residue was purified with silica gel column chromatography [eluent; hexane; ethyl acetate=20:1] to obtain 1.4 g of tert-butyl 2-(benzamido)-4-vinylbenzoate as white solid.

$^1$H-NMR (CDCl$_3$) δ: 1.63 (9H, s), 5.42 (1H, d, J=11.0 Hz), 5.95 (1H, d, J=17.7 Hz), 6.77 (1H, dd, J=17.7, 11.0 Hz), 7.15 (1H, dd, J=8.2, 1.7 Hz), 7.50-7.60 (3H, m), 7.97 (1H, d, J=8.2 Hz), 8.05-8.10 (2H, m), 9.01 (1H, d, J=1.7 Hz), 12.23 (1H, s).

Referential Example 17

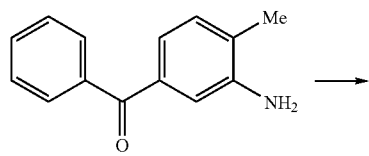

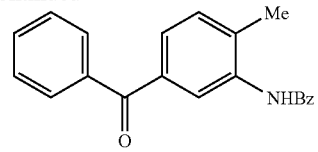

0.67 mL of triethylamine and 0.34 ml of benzoyl chloride was added to 5 mL of methylene chloride solution containing 0.51 g of 3-amino-4-methylbenzophenone while ice-cooled and stirred at room temperature for 2 hours. The solvent of the reaction mixture was evaporated under reduced pressure and ethyl acetate and 1.0 mol/L hydrochloric acid were added. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. Hexane and diisopropyl ether were added to the obtained residue and a solid substance was separated by filtration to obtain 0.71 g of N-(5-benzoyl-2-methylphenyl)benzamide as white solid.

$^1$H-NMR (CDCl$_3$) δ: 2.43 (3H, s), 7.37 (1H, d, J=7.8 Hz), 7.47-7.52 (4H, m), 7.56-7.63 (3H, m), 7.74 (1H, s), 7.82-7.86 (2H, m), 7.87-7.91 (2H, m), 8.29 (1H, s).

Referential Example 18

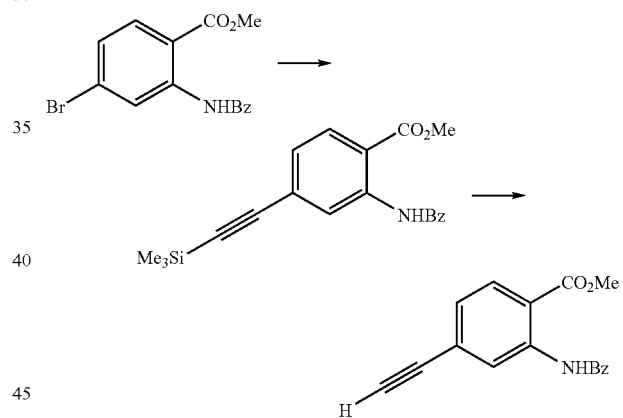

2.7 mL of (trimethylsilyl)acetylene was added to 30 mL of toluene suspension containing 3.2 g of methyl 2-(benzamido)-4-bromobenzoate, 92 mg of copper (I) iodide, 0.34 g of bis(triphenylphosphine)palladium (II) chloride and 2.7 mL of triethylamine at room temperature and stirred under nitrogen atmosphere at 70 to 80° C. for 2 hours. After the reaction mixture was cooled to room temperature, ethyl acetate and 1.0 mol/L hydrochloric acid were added and insoluble were removed by filtration. The organic layer was separated and dried over anhydrous magnesium sulfate after washed with 1.0 mol/L hydrochloric acid and a saturated sodium chloride aqueous solution sequentially, and the solvent was evaporated, under reduced pressure. Hexane and diisopropyl ether were added to the obtained residue and a solid substance was separated by filtration to obtain 3.5 g of methyl 2-(benzamido)-4-(2-(trimethylsilyl)ethynyl)benzoate as pale yellow solid.

0.68 g of potassium carbonate was added, to a solution of 17 mL of methanol and 17 mL of tetrahydrofuran containing 3.5 g of methyl 2-(benzamido)-4-(2-(trimethylsilyl)ethynyl)

benzoate and stirred at room temperature for 1 hour. The solvent was evaporated under reduced pressure and ethyl acetate and 1.0 mol/L hydrochloric acid were added and insoluble were removed by filtration. The organic layer was separated and dried over anhydrous magnesium sulfate after washed with 1.0 mol/L hydrochloric acid, and the solvent was evaporated under reduced pressure. The obtained residue was purified with silica gel column chromatography [eluent; hexane:ethyl acetate=8:1] to obtain 1.6 g of methyl 2-(benzamido)-4-ethynylbenzoate as white solid.

$^1$H-NMR (CDCl$_3$) δ: 3.25 (1H, s), 3.97 (3H, s), 7.22 (1H, dd, J=8.3, 1.5 Hz), 7.51-7.58 (3H, m), 8.02-8.06 (3H, m), 9.12 (1H, d, J=1.5 Hz), 12.02 (1H, s).

Referential Example 19

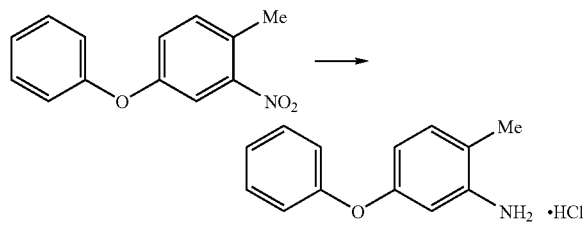

4.2 g of iron powder was added to a solution of 57 mL of methanol and 17 mL of acetic acid containing 5.7 g of 1-methyl-2-nitro-4-phenoxybenzene, and the resulting mixture was heated to reflux for 5 hours. After the reaction mixture was cooled to room temperature, ethyl acetate and a saturated sodium hydrogen carbonate aqueous solution were added and insoluble were removed by filtration. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. The obtained residue was dissolved in 60 mL of diethyl ether and 2.1 mL of hydrochloric acid was added while ice-cooled. Solid substance was separated by filtration to obtain 4.7 g of 2-methyl-5-phenoxyaniline hydrochloride as white solid.

$^1$H-NMR (DMSO-d$_6$) δ: 2.27 (3H, s), 6.82 (1H, dd, J=8.3, 2.4 Hz), 6.96 (1H, d, J=2.4 Hz), 7.03 (2H, d, J=7.5 Hz), 7.17 (1H, t, J=7.5 Hz), 7.26 (1H, d, J=8.3 Hz), 7.39-7.43 (2H, m).

Referential Example 20

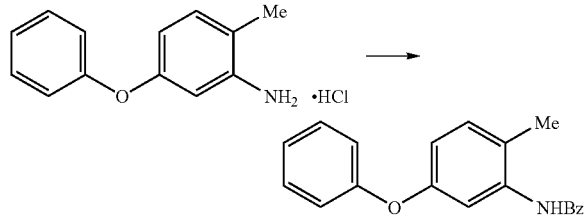

To a solution of 5 mL of N,N-dimethylformamide containing 0.50 g of 2-methyl-5-phenoxyaniline hydrochloride, 0.91 mL of triethylamine and 0.27 mL of benzoyl chloride were added sequentially while ice-cooled sequentially and stirred at room temperature for 3 hours. Ethyl acetate and 1.0 mol/L hydrochloric acid were added to the reaction mixture. The organic layer was separated and dried over anhydrous magnesium sulfate after washed with 1.0 mol/L hydrochloric acid, a saturated sodium hydrogen carbonate aqueous solution and a saturated sodium chloride aqueous solution sequentially, and the solvent was evaporated under reduced pressure. Hexane and diisopropyl ether were added to the obtained residue and a solid substance was separated by filtration to obtain 0.42 g of N-(2-methyl-5-phenoxyphenyl) benzamide as white solid.

$^1$H-NMR (CDCl$_3$) δ: 2.31 (3H, s), 6.78 (1H, dd, J=8.3, 2.4 Hz), 7.03 (2H, d, J=7.8 Hz), 7.08 (1H, t, J=7.5 Hz), 7.17 (1H, d, J=8.3 Hz), 7.30-7.34 (2H, m), 7.47-7.51 (2H, m), 7.54-7.58 (1H, m), 7.67 (1H, s), 7.78 (1H, s), 7.86 (2H, d, J=7.1 Hz).

Referential Example 21

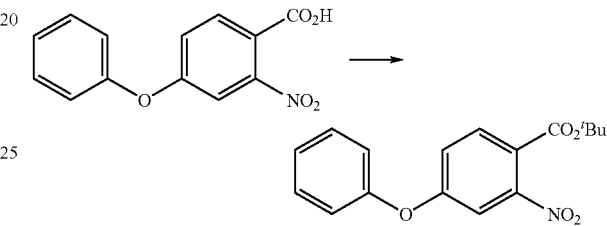

9.9 g of potassium carbonate, 0.82 g of benzyltriethylammonium chloride and 21 mL of 2-bromo-2-methylpropane were added to 14 mL of N,N-dimethylacetamide solution containing 0.93 g of 2-nitro-4-phenoxybenzoic acid at room temperature and stirred at 55° C. for 18 hours. After the reaction mixture was cooled to room temperature, water and ethyl acetate were added. The organic layer was separated and dried over anhydrous magnesium sulfate after washed with a saturated sodium hydrogen carbonate aqueous solution, 10% citric acid aqueous solution and a saturated sodium chloride aqueous solution sequentially, and the solvent was evaporated under reduced pressure to obtain 0.86 g of tert-butyl 2-nitro-4-phenoxybenzoate as white solid.

$^1$H-NMR (DMSO-d$_6$) δ: 1.48 (9H, s), 7.18-7.23 (2H, m), 7.26-7.32 (2H, m), 7.47-7.53 (2H, m), 7.54 (1H, d, J=2.4 Hz), 7.85 (1H, d, J=8.5 Hz).

Referential Example 22

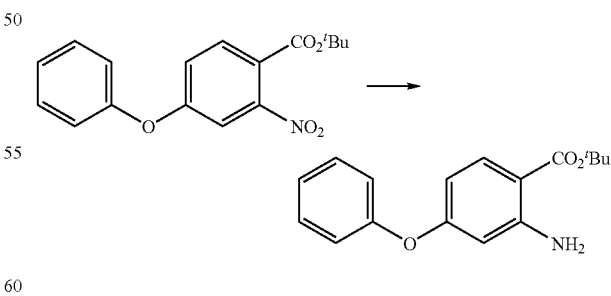

0.17 g of 5% palladium-carbon was added to a mixed solution of 8 mL of methanol and 8 mL of ethyl acetate containing 0.82 g of tert-butyl 2-nitro-4-phenoxybenzoate and stirred under hydrogen atmosphere at room temperature for 4 hours and 30 minutes. Insoluble were removed by filtration and the solvent was evaporated under reduced pressure. The obtained residue was purified with silica gel column chromatography [eluent; hexane; ethyl acetate=10:1] to obtain 0.63 g of tert-butyl 2-amino-4-phenoxybenzoate as colorless oil.

¹H-NMR (CDCl₃) δ: 1.57 (9H, s), 6.16 (1H, d, J=2.3 Hz), 6.27 (1H, dd, J=9.0, 2.3 Hz), 7.04-7.06 (2H, m), 7.14-7.18 (1H, m), 7.34-7.38 (2H, m), 7.78 (1H, d, J=9.0 Hz).

Referential Example 23

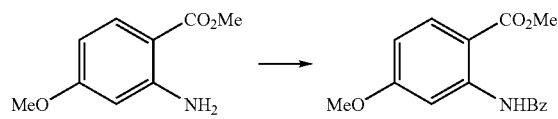

3.1 mL of triethylamine and 1.3 mL of benzoyl chloride were added to 19 mL of methylene chloride solution containing 1.9 g of methyl 2-amino-4-methoxybenzoate while ice-cooled sequentially and stirred at room temperature for 3 hours. The solvent was evaporated under reduced pressure and chloroform and 1.0 mol/L hydrochloric acid were added to the obtained residue. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. Hexane and diisopropyl ether were added to the obtained residue and a solid substance was separated by filtration to obtain 2.6 g of methyl 2-(benzamido)-4-methoxybenzoate as white solid.

¹H-NMR (CDCl₃) δ: 3.92 (3H, s), 3.93 (3H, s), 6.65 (1H, dd, J=9.0, 2.7 Hz), 7.51-7.59 (3H, m), 8.00 (1H, d, H=9.0 Hz), 8.05-8.07 (2H, m), 8.63 (1H, d, J=2.7 Hz).

Referential Example 24

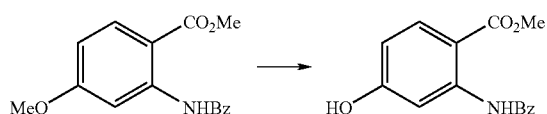

0.94 g of aluminum chloride was added to 7 mL of toluene solution containing 0.67 g of methyl 2-(benzamido)-4-methoxybenzoate at room temperature and stirred at 80° C. for 2 hours and 30 minutes. After the reaction mixture was cooled to room temperature, ethyl acetate and 1.0 mol/L hydrochloric acid were added and a solid substance was separated by filtration to obtain 0.23 g of methyl 2-(benzamido)-4-hydroxybenzoate as white solid.

¹H-NMR (CDCl₃) δ: 3.93 (3H, s), 6.68 (1H, dd, J=8.9, 2.5 Hz), 1.54-7.62 (3H, m), 8.02-8.05 (3H, m), 8.84 (1H, d, J=2.5 Hz), 9.30-9.40 (1H, broad), 12.46 (1H, s).

Referential Example 25

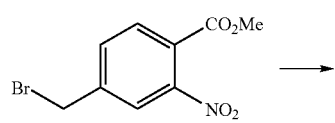

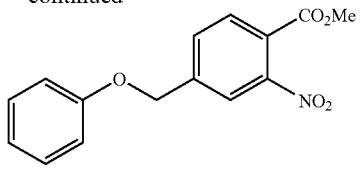

0.50 g of potassium carbonate and 0.50 g of methyl 4-(bromomethyl)-2-nitrobenzoate were added to 5 mL of N,N-dimethylformamide solution containing 0.18 g of phenol at room temperature and stirred at the same temperature for 10 hours. Ethyl acetate and 1.0 mol/L hydrochloric acid were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [eluent; hexane:ethyl acetate=6:1] to obtain 0.53 g of methyl 2-nitro-4-(phenoxymethyl)benzoate as colorless oil.

¹H-NMR (CDCl₃) δ: 3.93 (3H, s), 5.17 (2H, s), 6.95-7.03 (3H, m), 7.30-7.34 (2H, m), 7.72-7.79 (2H, m), 7.95-8.00 (1H, m).

Referential Example 26

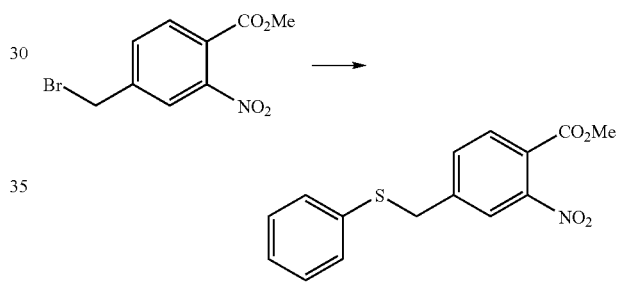

1.01 g of potassium carbonate and 0.39 mL of thiophenol were added to 10 mL of N,N-dimethylformamide solution containing 1.00 g of methyl 4-(bromomethyl)-2-nitrobenzoate at room temperature and stirred at the same temperature for 7 hours. Ethyl acetate was added to the reaction mixture and insoluble were removed by filtration and water was added. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. The obtained residue was purified with silica gel column chromatography [eluent; hexane:ethyl acetate=4:1] to obtain 0.70 g of methyl 2-nitro-4-((phenylthio)methyl)benzoate as pale yellow oil.

¹H-NMR (CDCl₃) δ: 3.86 (3H, s), 4.27 (2H, s), 6.60-6.74 (5H, m), 7.15-7.19 (2H, m), 7.82 (1H, d, J=8.3 Hz).

Referential Example 27

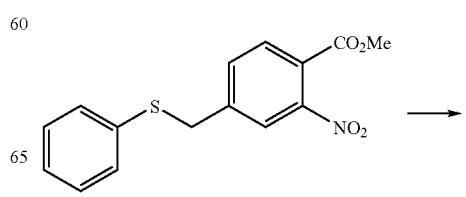

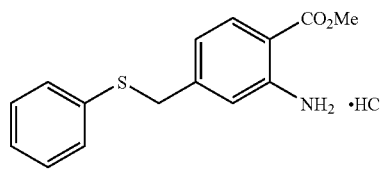

0.39 g of iron powder was added to a mixed solution of 7 mL of methanol and 2.1 mL of acetic acid containing 0.70 g of methyl 2-nitro-4-((phenylthio)methyl)benzoate, and the resulting mixture was heated to reflux for 3 hours. After the reaction mixture was cooled to room temperature, ethyl acetate and a saturated sodium hydrogen carbonate aqueous solution were added and insoluble were removed by filtration. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. The obtained residue was dissolved in 10 mL of diethyl ether and 1.2 mL of 1.9 mol/L hydrogen chloride/ethyl acetate were added while ice-cooled and a solid substance was separated by filtration to obtain 0.39 g of methyl 2-amino-4-((phenylthio)methyl)benzoate hydrochloride as white solid.

$^1$H-NMR (DMSO-$d_6$) δ: 3.76 (3H, s), 4.13 (2H, s), 4.30-4.70 (2H, broad), 6.55 (1H, dd, J=8.2, 1.7 Hz), 6.79 (1H, d, 1.7 Hz), 7.15-7.19 (1H, m), 7.26-7.33 (4H, m), 7.62 (1H, d, J=8.2 Hz).

Referential Example 28

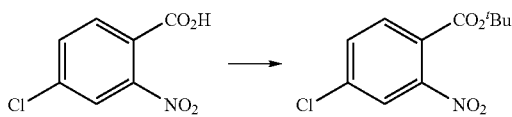

The following compound was obtained in the same manner as in Referential Example 2.

tert-Butyl 4-chloro-2-nitrobenzoate $^1$H-NMR (CDCl$_3$) δ: 1.55 (9H, s), 7.59-7.62 (1H, m), 7.70-7.73 (1H, m), 7.79 (1H, d, J=2.0 Hz).

Referential Example 29

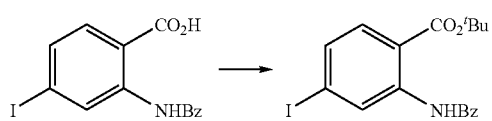

The following compound was obtained in the same manner as in Referential Example 2.

tert-Butyl 2-(benzamido)-4-iodobenzoate $^1$H-NMR (CDCl$_3$) δ: 1.62 (9H, s), 7.45 (1H, dd, J=8.5, 1.7 Hz), 7.51-7.60 (3H, m), 7.68 (1H, d, J=8.5 Hz), 8.02-8.07 (2H, m), 9.38 (1H, d, J=1.7 Hz), 12.13-12.20 (1H, broad).

Referential Example 30

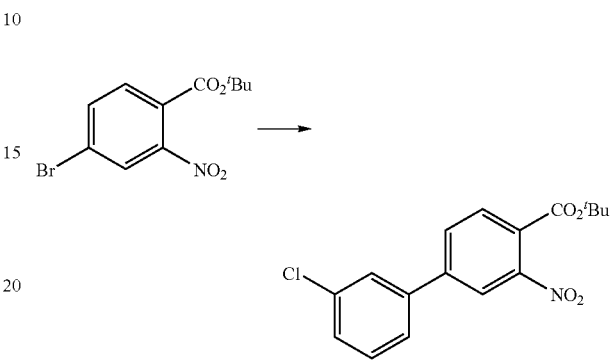

To 20 mL of toluene solution containing 2.0 g of tert-butyl 4-bromo-2-nitrobenzoate, 6.0 mL of ethanol, 3.0 mL of water, 1.2 g of 3-chlorophenylboronic acid, 1.7 g of sodium carbonate and 0.23 g of tetrakis(triphenylphosphine)palladium (0) were added sequentially, and the resulting mixture was heated to reflux under nitrogen atmosphere for 3 hours. Water was added after the reaction mixture was cooled to room temperature. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane:ethyl acetate=10:1] to obtain 0.70 g of tert-butyl 4-(3-chlorophenyl)-2-nitrobenzoate as white solid.

$^1$H-NMR (DMSO-$d_6$) δ: 1.52 (9H, s), 7.53-7.59 (2H, m), 7.77-7.82 (1H, m), 7.89-7.95 (2H, m), 8.15 (1H, dd, J=8.1, 1.6 Hz), 8.34 (1H, d, J=1.6 Hz).

Referential Example 31

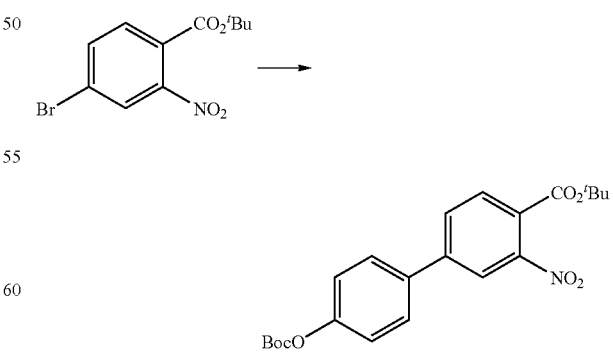

The following compound was obtained in the same manner as in Referential Example 30.

tert-Butyl 4-(4-(tert-butoxycarbonyl)oxyphenyl)-2-nitrobenzoate $^1$H-NMR (DMSO-d$_6$) δ: 1.51 (9H, s), 1.52 (9H, s), 7.36 (2H, d, J=8.8 Hz), 7.87 (2H, d, J=8.8 Hz), 7.91 (1H, d, J=8.1 Hz), 8.11 (1H, dd, J=8.1, 1.8 Hz), 8.29 (1H, d, J=1.8 Hz).

Referential Example 32

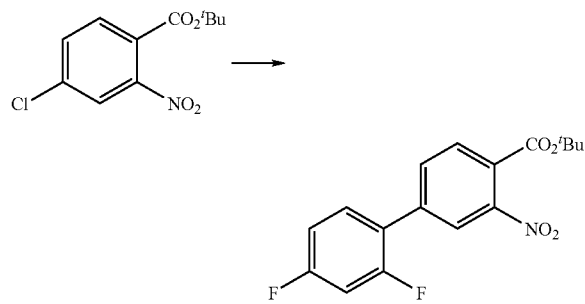

To 15 mL of toluene solution containing 1.5 g of tert-butyl 4-chloro-2-nitrobenzoate, 1.1 g of 2,4-difluorophenylboronic acid, 2.3 g of cesium carbonate, 27 mg of palladium acetate and 25 mg of 2-dicyclohexylphosphino-2',6'-dimethoxybiphenyl were added sequentially, and the resulting mixture was heated to reflux under nitrogen atmosphere for 8 hours. After the reaction mixture was cooled to room temperature, insoluble were removed by filtration and added a saturated sodium hydrogen carbonate aqueous solution. The organic layer was separated and dried over anhydrous magnesium sulfate after washed with 10% citric acid aqueous solution and a saturated sodium chloride aqueous solution sequentially, and the solvent was evaporated under reduced pressure. Hexane and diisopropyl ether were added to the obtained residue and a solid substance was separated by filtration to obtain 0.95 g of tert-butyl 4-(2,4-difluorophenyl)-2-nitrobenzoate as white solid.

$^1$H-NMR (DMSO-d$_6$) δ: 1.52 (9H, s), 7.26-7.31 (1H, m), 7.44-7.51 (1H, m), 7.72-7.79 (1H, m), 7.93 (1H, d, J=7.9 Hz), 7.98 (1H, d, J=7.9 Hz), 8.17 (1H, s).

Referential Example 33

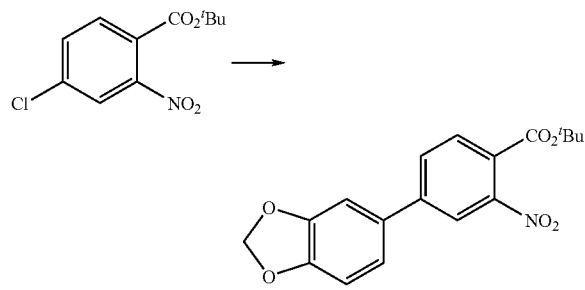

The following compound was obtained in the same manner as in Referential Example 32.

tert-Butyl 4-(benzo[1,3]dioxol-5-yl)-2-nitrobenzoate $^1$H-NMR (DMSO-d$_6$) δ: 1.51 (9H, s), 6.11 (2H, s), 7.06 (1H, d, J=8.1 Hz), 7.34 (1H, dd, J=8.1, 1.9 Hz), 7.45 (1H, d, J=1.9 Hz), 7.85 (1H, d, J=8.1 Hz), 8.04 (1H, dd, J=8.1, 1.9 Hz), 8.20 (1H, d, J=1.9 Hz).

Referential Example 34

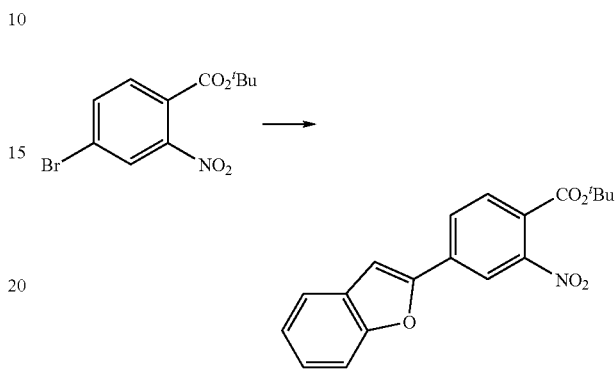

The following compound was obtained in the same manner as in Referential Example 30, tert-Butyl 4-(benzofuran-2-yl)-2-nitrobenzoate $^1$H-NMR (DMSO-d$_6$) δ: 1.53 (9H, s), 7.30-7.36 (1H, m), 7.40-7.45 (1H, m), 7.68-7.76 (1H, m), 7.75 (1H, d, J=7.3 Hz), 7.82 (1H, d, J=0.7 Hz), 7.96 (1H, d, J=8.1 Hz), 8.29 (1H, dd, J=8.1, 1.6 Hz), 8.49 (1H, d, J=1.6 Hz).

Referential Example 35

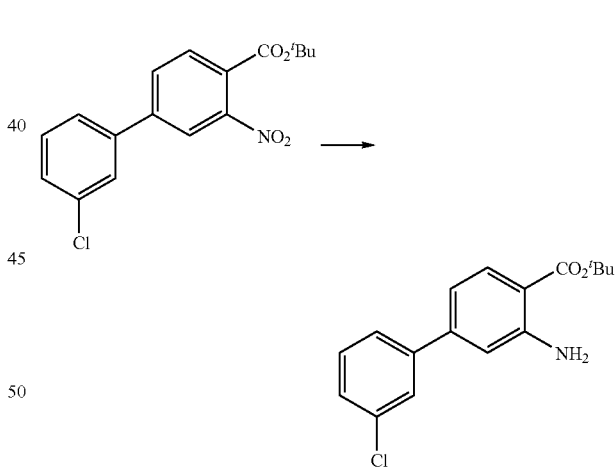

0.33 g of 10% palladium-carbon was added to a mixed solution of 11 mL of methanol and 11 mL of ethyl acetate containing 1.1 g of tert-butyl 4-(3-chlorophenyl)-2-nitrobenzoate and stirred under hydrogen atmosphere at room temperature for 3 hours. After insoluble were removed by filtration, the solvent was evaporated under reduced pressure. 11 mL of acetic acid, 11 mL of methanol and 0.33 g of 10% palladium-carbon were added to the obtained residue sequentially and stirred under hydrogen atmosphere at room temperature for 2 hours. After insoluble were removed by filtration, the solvent was evaporated under reduced pressure to obtain 0.70 g of tert-butyl 2-amino-4-(3-chlorophenyl)benzoate as white solid.

¹H-NMR (DMSO-d₆) δ: 1.55 (9H, s), 6.63-6.69 (2H, broad), 6.83 (1H, dd, J=8.5, 1.9 Hz), 7.06 (1H, d, J=1.9 Hz), 7.46 (1H, dt, J=7.8, 1.6 Hz), 7.50 (1H, t, J=7.8 Hz), 7.57 (1H, dt, J=7.8, 1.6 Hz), 7.63 (1H, t, J=1.6 Hz), 7.73 (1H, d, J=8.5 Hz).

Referential Example 36

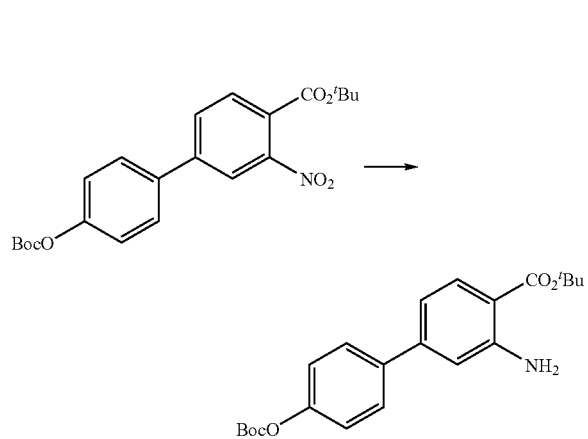

The following compound was obtained in the same manner as in Referential Example 35.

tert-butyl 2-amino-1-(4-((tert-butoxycarbonyl)oxy)phenyl)benzoate

¹H-NMR (DMSO-d₆) δ: 1.51 (9H, s), 1.55 (9H, s), 6.66-6.70 (2H, broad), 6.80 (1H, dd, J=8.5, 1.8 Hz), 7.02 (1H, d, J=1.8 Hz), 7.27-7.32 (2H, m), 7.61-7.65 (2H, m), 7.73 (1H, d, J=8.5 Hz).

Referential Example 37

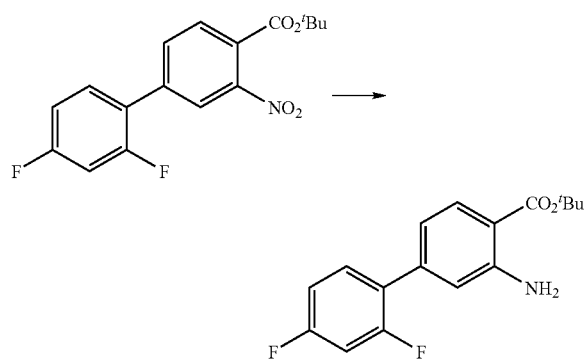

0.27 g of 10% palladium-carbon was added to a mixed solution of 9.0 mL of methanol and 9.0 mL of ethyl acetate containing 0.90 g of tert-butyl 4-(2,4-difluorophenyl)-2-nitrobenzoate and stirred under hydrogen atmosphere at room temperature for 30 minuses. After insoluble were removed by filtration, the solvent was evaporated under reduced pressure to obtain 0.80 g of tert-butyl 2-amino-4-(2,4-difluorophenyl)benzoate as white solid.

¹H-NMR (DMSO-d₆) δ: 1.55 (9H, s), 6.65 (1H, d, J=8.3 Hz), 6.66-6.73 (2H, broad), 6.91 (1H, s), 7.17-7.22 (1H, m), 7.33-7.39 (1H, m), 7.50-7.56 (1H, m), 7.72 (1H, d, J=8.3 Hz).

Referential Example 38

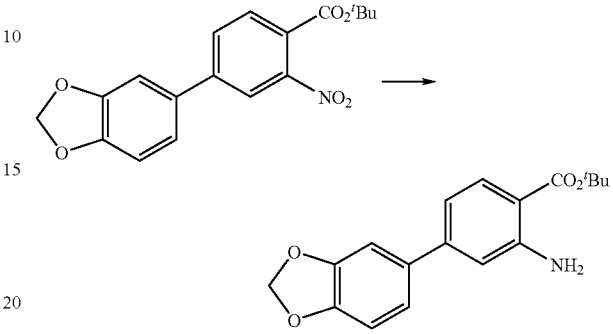

0.42 g of 10% palladium-carbon was added to a mixed solution of 14 mL of methanol and 14 mL of ethyl acetate containing 1.4 g of tert-butyl 4-(benzo[1,3]dioxol-5-yl)-2-nitrobenzoate and stirred under hydrogen atmosphere at room temperature for 2 hours. After insoluble were removed by filtration, the solvent was evaporated under reduced pressure. The obtained residue was purified with silica gel column chromatography [PSQ100B (spherical) manufactured by Fuji Silysia Chemical Ltd., eluent; hexane:ethyl acetate=20:1] to obtain 0.52 g of tert-butyl 2-amino-4-(benzo[1,3]dioxol-5-yl)benzoate as pale red solid.

¹H-NMR (DMSO-d₆) δ: 1.54 (9H, s), 6.07 (2H, s), 6.57-6.65 (2H, broad), 6.75 (1H, d, J=8.5 Hz), 6.96 (1H, s), 7.00 (1H, d, J=8.6 Hz), 7.10 (1H, d, J=8.6 Hz), 7.15 (1H, s), 7.68 (1H, d, J=8.5 Hz).

Referential Example 39

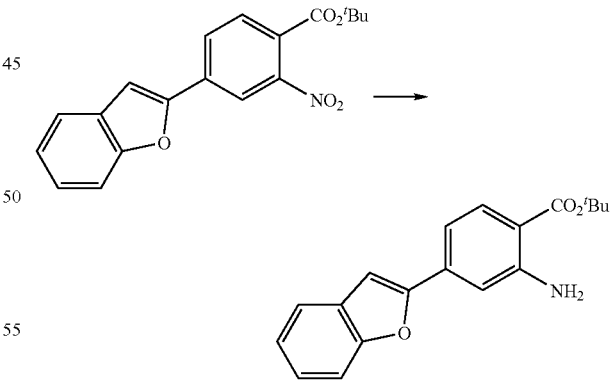

0.69 g of iron powder was added to a suspension of 7.0 mL of methanol and 7.0 mL of acetic acid containing 1.4 g of tert-butyl 4-(benzofuran-2-yl)-2-nitrobenzoate and the resulting mixture was heated to reflux for 2 hours. After the reaction mixture was cooled to room temperature, the solvent was evaporated under reduced pressure. A saturated sodium hydrogen carbonate aqueous solution and ethyl acetate were added to the obtained residue and insoluble were removed by filtration. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. Hexane was added to the obtained residue and a solid substance was separated by filtration to obtain 0.88 g of tert-butyl 2-amino-4-(benzofuran-2-yl)benzoate as white solid.

$^1$H-NMR (DMSO-d$_6$) δ: 1.56 (9H, s), 6.76-6.84 (2H, broad), 7.07 (1H, dd, J=8.5, 1.6 Hz), 7.26-7.39 (3H, m), 7.43 (1H, s), 7.64 (1H, d, J=8.1 Hz), 7.69 (1H, d, J=8.1 Hz), 7.75 (1H, d, J=8.5 Hz).

Referential Example 40

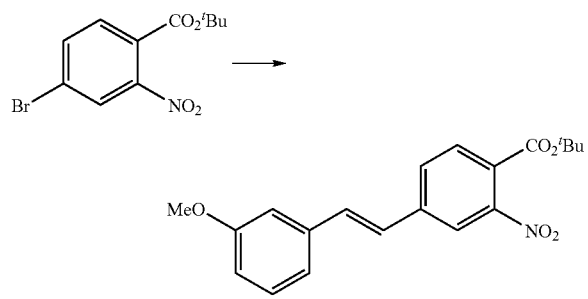

To 5 mL of N,N-dimethylacetamide solution containing 0.60 g of tert-butyl 4-bromo-2-nitrobenzoate, 0.37 mL of 3-vinylanisole, 0.47 mL of triethylamine and 0.11 g of palladium acetate were added at room temperature and stirred under nitrogen atmosphere at 110° C. for 4 hours. Ethyl acetate and water were added after the reaction mixture was cooled to room temperature. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia Chemical Ltd., eluent; hexane:ethyl acetate=10:1] to obtain 0.20 g of tert-butyl 4-((E)-2-(3-methoxyphenyl)vinyl)-2-nitrobenzoate a pale yellow solid.

$^1$H-NMR (DMSO-d$_6$) δ: 1.51 (9H, s), 3.81 (3H, s), 6.90-6.94 (1H, m), 7.20-7.27 (2H, m), 7.34 (1H, t, J=7.9 Hz), 7.43 (1H, d, J=16.6 Hz), 7.55 (1H, d, J=16.6 Hz), 7.84 (1H, d, J=8.0 Hz), 7.97 (1H, d, J=7.8 Hz), 8.21 (1H, s).

Referential Example 41

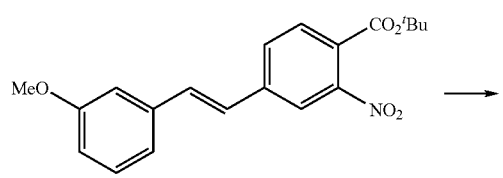

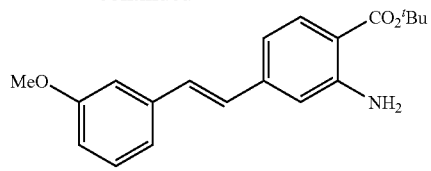

0.70 g of iron powder was added to a suspension of 7.5 mL of methanol and 7.5 mL of acetic acid containing 1.5 g of tert-butyl 4-((E)-2-(3-methoxyphenyl)vinyl)-2-nitrobenzoate, and the resulting mixture was heated to reflux for 2 hours. After the reaction mixture was cooled to room temperature, the solvent was evaporated under reduced pressure. A saturated sodium hydrogen carbonate aqueous solution and ethyl acetate were added to the obtained residue and insoluble were removed by filtration. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia Chemical Ltd., eluent; hexane:ethyl acetate=4:1] to obtain 0.44 g of tert-butyl 2-amino-4-((E)-2-(3-methoxyphenyl)vinyl)benzoate as white solid.

$^1$H-NMR (DMSO-d$_6$) δ: 1.54 (9H, s), 3.80 (3H, s), 6.57-6.65 (2H, broad), 6.80-6.92 (3H, m), 7.15-7.23 (4H, m), 7.29 (1H, t, J=8.1 Hz), 7.64 (1H, d, J=8.3 Hz).

Referential Example 42

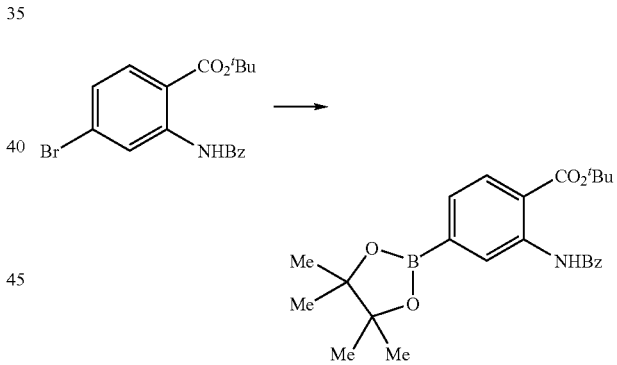

To 40 mL of dioxane solution containing 4.0 g of tert-butyl 2-(benzamido)-4-bromobenzoate, 3.1 g of potassium acetate, 5.9 g of bis(pinacolato)diboron and 0.43 g of (1,1'-bis(diphenylphosphino)ferrocene)palladium (II) dichloride-methylene chloride complex were added at room temperature sequentially, and the resulting mixture was heated to reflux for 3 hours. After the reaction mixture was cooled to room temperature, insoluble were removed by filtration, and the solvent was evaporated under reduced pressure. The obtained residue was purified with silica gel column chromatography [PSQ100B (spherical) manufactured by Fuji Silysia Chemical Ltd., eluent; hexane: ethyl acetate=4:1] to obtain 3.6 g of tert-butyl 2-(benzamido)-4-(4,4,5,5-tetramethyl-1,3,2-dioxaborolan-2-yl)benzoate as white solid.

$^1$H-NMR (DMSO-d$_6$) δ: 1.33 (12H, s), 1.54 (9H, s), 7.50 (1H, dd, J=7.8, 1.0 Hz), 7.58-7.68 (3H, m), 7.92 (1H, d, J=7.8 Hz), 7.96-8.00 (2H, m), 8.72 (1H, d, J=1.0 Hz), 11.43 (1H, s).

Referential Example 43

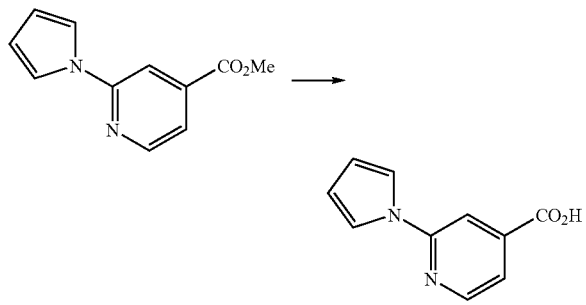

2.0 mL of 2.0 mol/L aqueous sodium hydroxide was added to a mixed solution of 4.0 mL of methanol and 4.0 mL of tetrahydrofuran containing 0.47 g of methyl 2-(1H-pyrrol-1-yl)pyridine-4-carboxylate and stirred at room temperature for 1 hour. 5.0 mL of 1.0 mol/L hydrochloric acid and ethyl acetate were added to the reaction mixture sequentially. The organic layer was separated and dried over anhydrous magnesium sulfate after washed with a saturated sodium chloride aqueous solution, and the solvent was evaporated, under reduced pressure. Diisopropyl ether was added to the obtained residue and a solid substance was removed by filtration to obtain 0.39 g of 2-(1H-pyrrol-1-yl)pyridine-4-carboxylic acid as white solid.

$^1$H-NMR (DMSO-$d_6$) δ: 6.32 (2H, t, J=2.3 Hz), 7.64 (1H, dd, J=5.1, 1.3 Hz), 7.76 (2H, t, J=2.3 Hz), 8.02 (1H, t, J=0.9 Hz), 8.60 (1H, dd, J=5.1, 0.9 Hz), 13.70-13.95 (1H, broad).

Example 1

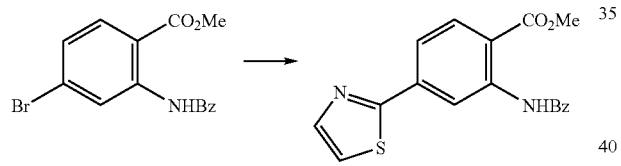

0.56 g of 2-(tributyltin)thiazole and 0.090 g of tetrakis(triphenylphosphine)palladium(0) were added to 5 mL of toluene solution containing 0.50 g of methyl 2-(benzamido)-4-bromobenzoate, and the resulting mixture was heated to reflux under nitrogen atmosphere for 6 hours. After the reaction mixture was cooled to room temperature, the solvent was evaporated under reduced pressure. The obtained residue was purified with silica gel column chromatography [eluent; hexane; ethyl acetate=3:1] to obtain 0.25 g of methyl 2-(benzamido)-4-(thiazol-2-yl)benzoate as white solid.

$^1$H-NMR (DMSO-$d_6$) δ: 3.93 (3H, s), 7.61-7.70 (3H, m), 7.82 (1H, dd, J=8.5, 1.8 Hz), 7.95 (1H, d, J=3.2 Hz), 7.99-8.01 (2H, m), 8.05 (1H, d, J=3.2 Hz), 8.13 (1H, d, J=8.5 Hz), 9.29 (1H, d, J=1.8 Hz), 11.73 (1H, s).

Example 2

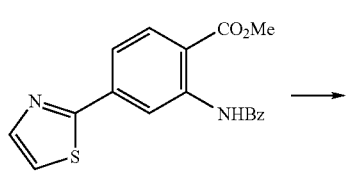

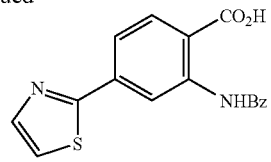

0.35 mL of 10% aqueous sodium hydroxide was added to 5 mL of ethanol suspension containing 0.25 g of methyl 2-(benzamido)-4-(thiazol-2-yl)benzoate at room temperature, and the resulting mixture was heated to reflux for 2 hours. After the reaction mixture was cooled to room temperature, 1.0 mol/L hydrochloric acid and ethyl acetate were added. The organic layer was separated and dried over anhydrous magnesium sulfate, and the solvent was evaporated under reduced pressure. Hexane and diisopropyl ether were added to the obtained residue and a solid substance was separated by filtration to obtain 0.23 g of 2-(benzamido)-4-(thiazol-2-yl)benzoic acid as white solid.

$^1$H-NMR (DMSO-$d_6$) δ: 7.61-7.70 (3H, m), 7.80 (1H, dd, J=8.3, 1.7 Hz), 7.94 (1H, d, J=3.2 Hz), 7.98-8.00 (2H, m), 8.05 (1H, d, J=3.2 Hz), 8.17 (1H, d, J=8.3 Hz), 9.43 (1H, d, J=1.7 Hz), 12.28 (1H, s).

Example 3

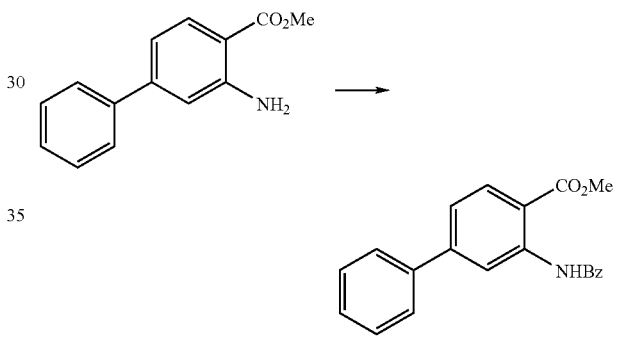

0.28 mL of benzoyl chloride was added to 10 mL of methylene chloride solution containing 0.50 g of methyl 2-amino-4-phenylbenzoate and 0.36 mL of triethylamine and stirred at room temperature overnight. The solvent was evaporated under reduced pressure and water and ethyl acetate were added. The organic layer was separated and dried over anhydrous magnesium sulfate after washed with 1.0 mol/L hydrochloric acid and a saturated sodium chloride aqueous solution sequentially, and the solvent was evaporated under reduced pressure. Hexane and diisopropyl ether were added to the obtained residue and a solid substance was separated by filtration to obtain 0.52 g of methyl 2-(benzamido)-4-phenylbenzoate as white solid.

$^1$H-NMR (CDCl$_3$) δ: 3.99 (3H, s), 7.37-7.60 (7H, m), 7.73-7.75 (2H, m), 8.07-8.10 (2H, m), 8.15 (1H, d, J=8.3 Hz), 9.29 (1H, d, J=1.7 Hz), 12.13 (1H, s).

Example 4

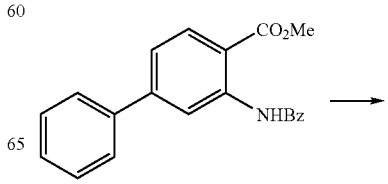

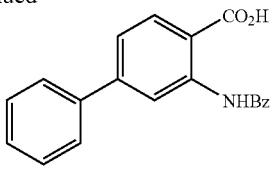

1.2 mL of 2.0 mol/L aqueous sodium hydroxide was added to a suspension of 5 mL of methanol and 2.5 mL of dioxane containing 0.50 g of methyl 2-(benzamido)-4-phenylbenzoate at room temperature and stirred at 50° C. for 30 minutes. After the reaction mixture was cooled to room temperature, 1.0 mol/L hydrochloric acid was added to adjust to pH 3 and water and ethyl acetate were added. The organic layer was separated and dried over anhydrous magnesium sulfate after washed with a saturated sodium chloride aqueous solution, and the solvent was evaporated under reduced pressure. Hexane was added to the obtained, residue and a solid substance was separated by filtration to obtain 0.36 g of 2-(benzamido)-4-phenylbenzoic acid as white solid.

$^1$H-NMR (DMSO-$d_6$) δ: 7.45-7.69 (7H, m), 7.73-7.75 (2H, m), 7.98-8.00 (2H, m), 8.15 (1H, d, J=8.1 Hz), 9.09 (1H, d, J=2.0 Hz), 12.29 (1H, s), 13.70-14.00 (1H, broad).

Example 5

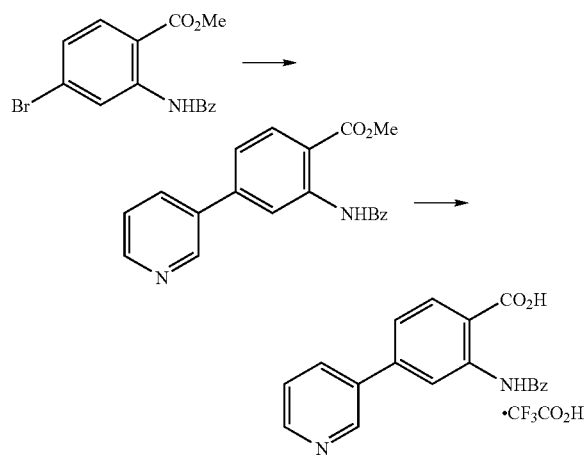

55 mg of pyridine-3-boronic acid, 88 mg of sodium hydrogen carbonate and 17 mg of tetrakis(triphenylphosphine)palladium(0) were added to a mixed solution of 2.0 mL of toluene, 0.5 mL of ethanol and 0.2 mL of water containing 100 mg of methyl 2-(benzamido)-4-bromobenzoate, and heated to reflux with stirring for 2 hours. After the reaction mixture was cooled to room temperature, 17 mg of tetrakis(triphenylphosphine)palladium(0) was added and heated to reflux with stirring for 2 hours. After the reaction mixture was cooled to room temperature, toluene and water were added. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. 3.0 mL of ethanol and 0.5 mL of 2.0 mol/L aqueous sodium hydroxide solution was added to the obtained residue and stirred at room temperature for 2 hours. The reaction mixture was purified with reversed-phase silica gel column chromatography [eluent; 30-100% acetonitrile/0.1% trifluoroacetic acid aqueous solution] to obtain 25 mg of 2-(benzamido)-4-(pyridin-3-yl)benzoic acid trifluoroacetate as white solid.

$^1$H-NMR (DMSO-$d_6$) δ: 7.45-7.49 (2H, m), 7.56 (1H, t, J=7.0 Hz), 7.63-7.69 (2H, m), 7.77 (2H, d, J=7.1 Hz), 7.97 (1H, dd, J=8.1 Hz, J=1.2 Hz), 8.09 (1H, s), 8.17 (1H, d, J=7.6 Hz), 8.65 (1H, d, J=5.1 Hz), 8.83 (1H, s), 10.25 (1H, s).

Example 6

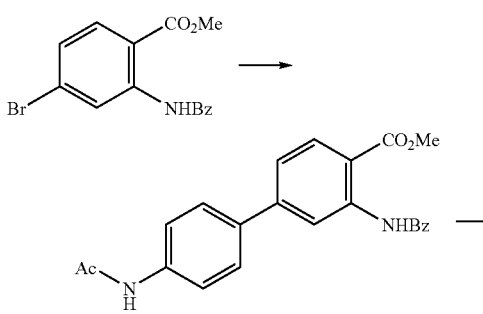

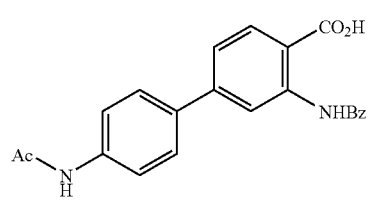

56 mg of 4-(acetamido)phenylboronic acid, 55 mg of sodium carbonate and 30 mg of polymer supported bis(acetato)triphenylphosphine palladium(11) were added to 2.5 mL of N,N-dimethylacetamide solution containing 70 mg of methyl 2-(benzamido)-4-bromobenzoate, and stirred at 90° C. for 11 hours. After the reaction mixture was cooled to room temperature, 19 mg of 4-(acetamido)phenylboronic acid was added and the mixture was stirred at 90° C. for 12 hours. After the reaction mixture was cooled to room temperature, 11 mg of sodium carbonate and 30 mg of polymer supported bis (acetato)triphenylphosphine palladium(II) were added and stirred at 90° C. for 14 hours. After the reaction mixture was cooled to room temperature, insoluble were removed by filtration and ethyl acetate and 1.2 mol/L hydrochloric acid were added. The organic layer was separated and dried over anhydrous magnesium sulfate after washed with 1.0 mol/L hydrochloric acid, a saturated sodium hydrogen carbonate aqueous solution and a saturated sodium chloride aqueous solution sequentially, and the solvent was evaporated under reduced pressure. 1 mL of 1.0 mol/L aqueous sodium hydroxide and 2 mL of ethanol were added to the obtained residue and stirred at room temperature for 1 hour. 0.6 mol/L hydrochloric acid was added, and solid substances were separated by filtration and purified with reversed-phase silica gel column chromatography [eluent; 40-100% acetonitrile/0.1% trifluoroacetic acid aqueous solution] to obtain 5.9 mg of 4-(4-(acetamido)phenyl)-2-(benzamido)benzoic acid as white solid.

$^1$H-NMR (DMSO-$d_6$) δ: 2.08 (3H, s), 7.49-7.52 (1H, m), 7.60-7.76 (7H, m), 7.99 (2H, d, J=7.6 Hz), 8.11 (1H, d, J=8.1 Hz), 9.06 (1H, d, J=1.7 Hz), 10.14 (1H, s).

Example 7

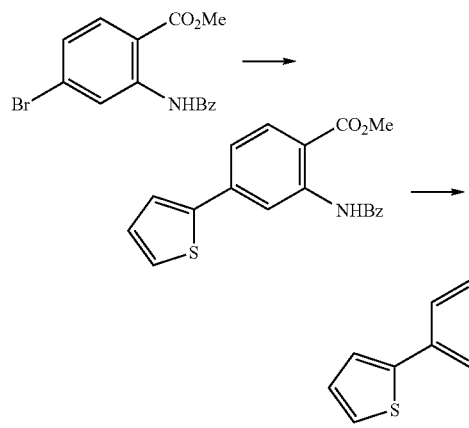

The following compound was obtained in the same manner as in Example 6.

2-(Benzamido)-4-(thiophen-2-yl)benzoic acid $^1$H-NMR (DMSO-$d_6$) δ: 7.22 (1H, t, J=4.5 Hz), 7.54-7.67 (5H, m), 7.71 (1H, d, J=4.5 Hz), 7.99 (2H, d, J=6.8 Hz), 8.08 (1H, d, J=8.6 Hz), 9.11 (1H, s).

Example 8

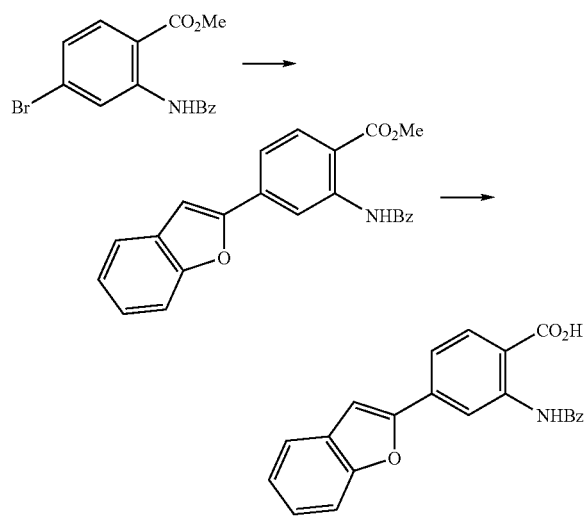

51 mg of benzofuran-2-boronic acid, 55 mg of sodium carbonate and 30 mg of polymer supported bis(acetato)triphenylphosphine palladium(II) were added to 2.5 mL of N,N-dimethylacetamide solution containing 70 mg of methyl 2-(benzamido)-4-bromobenzoate, and stirred at 90° C. for 22 hours. After the reaction mixture was cooled to room temperature, insoluble were removed by filtration and ethyl acetate and 1.2 mol/L hydrochloric acid were added. The organic layer was separated and dried over anhydrous magnesium sulfate after washed with 1.0 mol/L hydrochloric acid and a saturated sodium chloride aqueous solution sequentially, and the solvent was evaporated under reduced pressure. 1.0 mL of 1.0 mol/L aqueous sodium hydroxide and 2.0 ml, of ethanol were added to the obtained residue and stirred at room temperature for 1 hour. 0.6 mol/L hydrochloric acid was added to the reaction mixture and a solid substance was separated by filtration to obtain 11 mg of 2-(benzamido)-4-(benzofuran-2-yl)benzoic acid as whine solid.

$^1$H-NMR (DMSO-$d_6$) δ: 7.32 (1H, td, J=7.3, 0.7 Hz), 7.40 (1H, td, J=7.7, 1.1 Hz), 7.62-7.79 (7H, m), 8.01-8.03 (2H, m), 8.16 (1H, d, J=8.6 Hz), 9.33 (1H, s).

Example 9

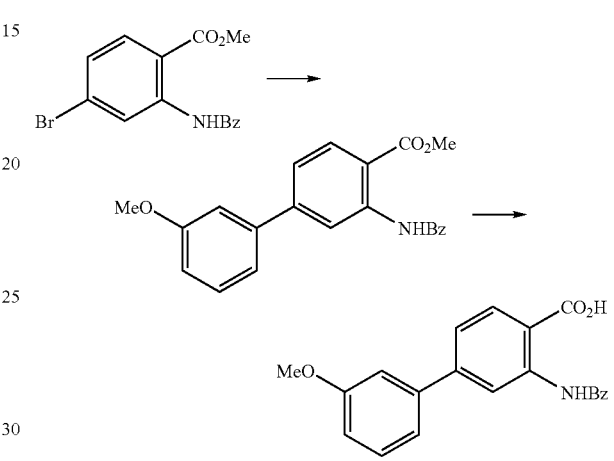

36 mg of 3-methoxyphenylboronic acid, 55 mg of sodium carbonate and 30 mg polymer supported bis(acetato)triphenylphosphine palladium(II) were added to 2.5 mL of N,N-dimethylacetamide solution containing 70 mg of methyl 2-(benzamido)-4-bromobenzoate, and stirred at 90° C. for 11 hours. After the reaction mixture was cooled to room temperature, insoluble were removed by filtration and ethyl acetate and 1.2 mol/L hydrochloric acid were added. The organic layer was separated and dried over anhydrous magnesium sulfate after washed with 1.0 mol/L hydrochloric acid, a saturated sodium hydrogen carbonate aqueous solution and a saturated sodium chloride aqueous solution sequentially, and one solvent was evaporated under reduced pressure, 1.0 mL of 1.0 mol/L aqueous sodium hydroxide and 2.0 mL of ethanol were added to the obtained residue and stirred at room temperature for 1 hour. 0.6 mol/L hydrochloric acid was added to the reaction mixture and a solid substance was separated by filtration to obtain 18 mg of 2-(benzamido)-4-(3-methoxyphenyl)benzoic acid as white solid.

$^1$H-NMR (DMSO-$d_6$) δ: 3.85 (3H, s), 7.05 (1H, ad, J=8.2, 2.6 Hz), 7.24 (1H, s), 7.30 (1H, d, J=8.1 Hz), 7.47 (1H, t, J=7.9 Hz), 7.53 (1H, dd, J=8.3, 1.5 Hz), 7.60-7.69 (3H, m), 7.99 (2H, d, J=7.1 Hz), 8.13 (1H, d, J=8.3 Hz), 9.06 (1H, s), 12.30 (1H, s).

Example 10

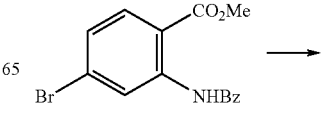

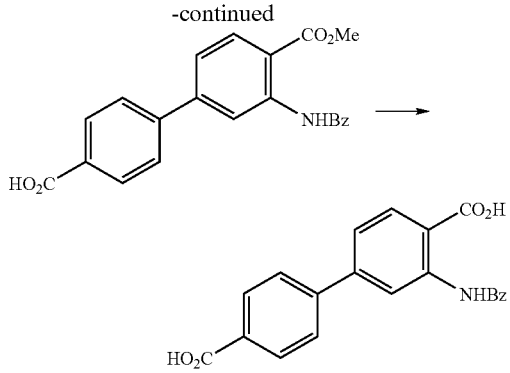

The following compound was obtained in the same manner as in Example 9.

2-(Benzamido)-4-(4-carboxyphenyl)benzoic acid $^1$H-NMR (DMSO-$d_6$) δ: 7.57-7.69 (1H, m), 7.87 (2H, d, J=8.0 Hz), 7.99-8.01 (2H, m), 8.10 (2H, d, J=8.3 Hz), 8.17 (1H, d, J=8.6 Hz), 9.13 (1H, s).

Example 11

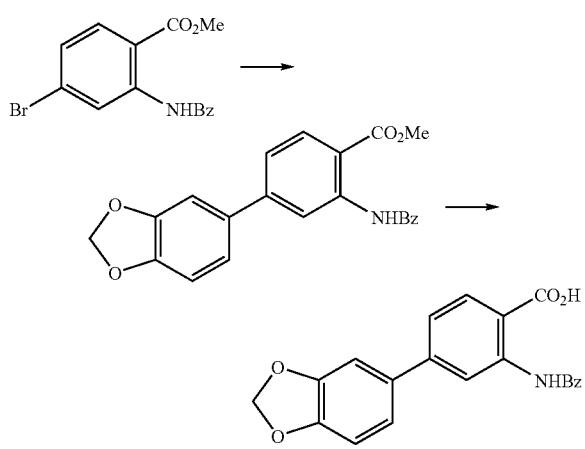

52 mg of 3,4-methylenedioxyphenylboronic acid, 55 mg of sodium carbonate and 30 mg of polymer supported bis(acetato)triphenylphosphine palladium(II) were added to 2.5 mL of N,N-dimethylacetamide solution containing 70 mg of methyl 2-(benzamido)-4-bromobenzoate, and stirred at 90° C. for 22 hours. After the reaction mixture was cooled to room temperature, insoluble were removed by filtration and ethyl acetate and 1.2 mol/L hydrochloric acid were added. The organic layer was separated and dried over anhydrous magnesium sulfate after washed with 1.0 mol/L hydrochloric acid and a saturated sodium chloride aqueous solution sequentially, and the solvent was evaporated under reduced pressure. 1.0 mL of 1.0 mol/L aqueous sodium hydroxide and 2.0 mL of ethanol were added to the obtained residue and stirred at room temperature for 1 hour. 0.6 mol/L hydrochloric acid was added to the reaction mixture and a solid substance was separated by filtration to obtain 43 mg of 2-(benzamido)-4-(benzo[1,3]dioxol-5-yl)benzoic acid as white solid.

$^1$H-NMR (DMSO-$d_6$) δ: 6.11 (2H, s), 7.08 (1H, d, J=8.1 Hz), 7.24 (1H, dd, J=8.2, 1.8 Hz), 7.30 (1H, d, J=1.7 Hz), 7.45-7.47 (1H, m), 7.59-7.69 (3H, m), 7.98-8.00 (2H, m), 8.09 (1H, d, J=8.1 Hz), 9.01 (1H, s).

Examples 12, 13

The compounds shown in Table 8 were obtained in the same manner as in Example 11.

TABLE 8

| Example No. | R³ |
|---|---|
| 12 | (5-methyl-1H-indol-5-yl) |
| 13 | (4-(methanesulfonyl)phenyl, MeO₂S-) |

2-(Benzamido)-4-(1H-indol-5-yl)benzoic acid $^1$H-NMR (DMSO-$d_6$) δ: 6.56 (1H, s), 7.43 (1H, t, J=2.7 Hz), 7.47-7.69 (6H, m), 7.94 (1H, s), 8.01 (2H, d, J=7.1 Hz), 8.12 (1H, d, J=8.3 Hz), 9.14 (1H, d, J=1.5 Hz), 11.26 (1H, s).

2-(Benzamido)-4-(4-(methanesulfonyl)phenyl)benzoic acid $^1$H-NMR (DMSO-$d_6$) δ: 3.33 (3H, s), 7.57-7.70 (4H, m), 7.99-8.01 (4H, m), 8.09 (2H, d, J=8.6 Hz), 8.19 (1H, d, J=8.3 Hz), 9.13 (1H, d, J=1.7 Hz), 12.28 (1H, s).

Example 14

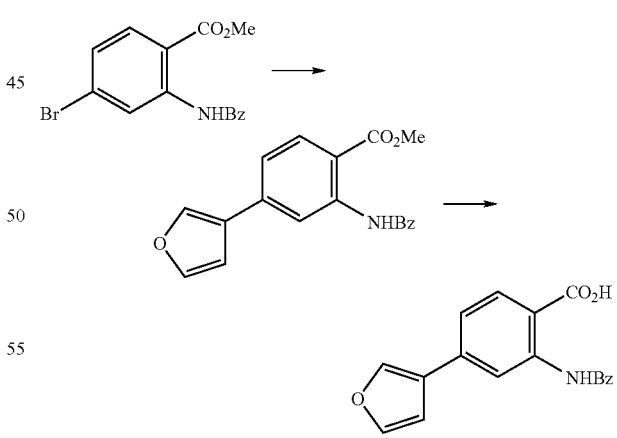

61 mg of 3-(4,4,5,5-tetramethyl-1,3,2-dioxaborolan-2-yl)furan, 65 mg of sodium carbonate and 30 mg of polymer supported bis(acetato)triphenylphosphine palladium(II) were added to 2.5 mL of N,N-dimethylacetamide solution containing 70 mg of methyl 2-(benzamido)-4-bromobenzoate, and stirred at 90° C. for 12 hours. After the reaction mixture was cooled to room temperature, 41 mg of 3-(4,4,5,5-tetramethyl-1,3,2-dioxaborolan-2-yl)furan and 22 mg of sodium carbonate were added and stirred at 90° C. for 12 hours. After the reaction mixture was cooled to room temperature, insoluble were removed by filtration and ethyl acetate and 1.0 mol/L hydrochloric acid were added. The organic layer was separated and dried over anhydrous magnesium sulfate after washed with 1.0 mol/L hydrochloric acid and a saturated sodium chloride aqueous solution sequentially, and the solvent was evaporated under reduced pressure. 1.0 mL of 2.0 mol/L aqueous sodium hydroxide and 2.0 mL of ethanol were added to the obtained residue and stirred at room temperature for 1 hour. 0.6 mol/L hydrochloric acid was added to the reaction mixture, and solid substances were separated by filtration and purified with reversed-phase silica gel column chromatography [eluent; 50-100% acetonitrile/ 0.1% trifluoroacetic acid aqueous solution] no obtain 6.2 mg of 2-(benzamido)-4-(furan-3-yl)benzoic acid as white solid.

$^1$H-NMR (DMSO-$d_6$) δ: 6.97 (1H, d, J=1.7 Hz), 7.47 (1H, dd, J=8.3, 1.7 Hz), 7.59-7.69 (3H, m), 7.83 (1H, t, J=1.6 Hz), 7.98-8.00 (2H, m), 8.06 (1H, d, J=8.3 Hz), 8.32 (1H, s), 8.94 (1H, d, J=1.7 Hz), 12.29 (1H, s).

Example 15

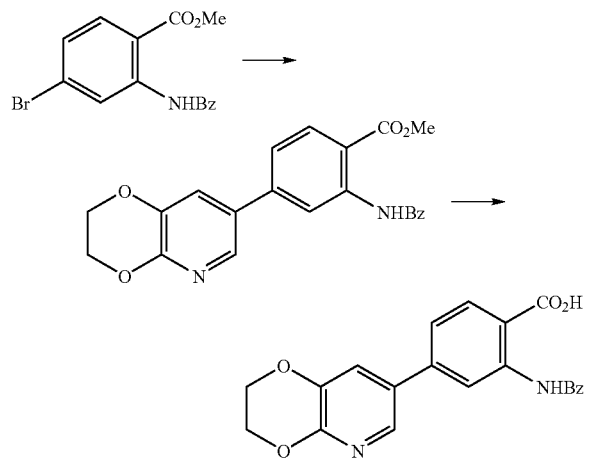

The following compound was obtained in the same manner as in Example 14.

2-(Benzamido)-4-(2,3-dihydrobenzo[1,4]dioxin-6-yl)benzoic acid $^1$H-NMR (DMSO-$d_6$) δ: 4.31 (4H, s), 7.02 (1H, d, J=8.8 Hz), 7.21-7.24 (2H, m), 7.46 (1H, dd, J=8.3, 2.0 Hz), 7.60-7.69 (3H, m), 7.97-7.99 (2H, m), 8.09 (1H, d, J=8.5 Hz), 9.02 (1H, d, J=1.7 Hz).

Example 16

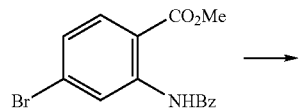

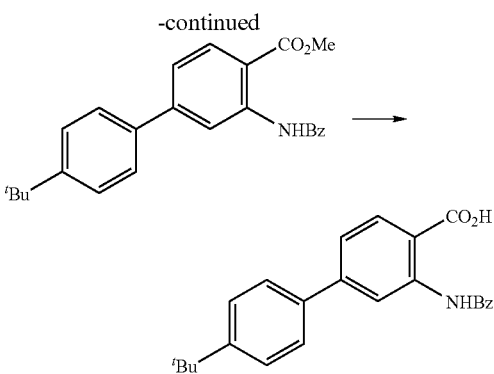

56 mg of (4-(tert-butyl)phenyl)boronic acid, 55 mg of sodium carbonate and 30 mg of polymer supported bis(acetate)triphenylphosphine palladium(11) were added to 2.5 mL of N,N-dimethylacetamide solution containing 70 mg of methyl 2-(benzamido)-4-bromobenzoate, and stirred at 90° C. for 21 hours. After the reaction mixture was cooled to room temperature, insoluble were removed by filtration and ethyl acetate and 1.0 mol/L hydrochloric acid were added. The organic layer was separated and dried over anhydrous magnesium sulfate after washed with 1.0 mol/L hydrochloric acid and a saturated sodium chloride aqueous solution sequentially, and she solvent was evaporated under reduced pressure. 1.0 mL of 2.0 mol/L aqueous sodium hydroxide and 5.0 mL of ethanol were added to the obtained residue and stirred at room temperature for 1 hour and 30 minutes. 0.5 mol/L hydrochloric acid and ethyl acetate were added to the reaction mixture. The organic layer was separated and the solvent was evaporated under reduced pressure to obtain 9.3 mg of 2-(benzamido)-4-(4-(tert-butyl)phenyl)benzoic acid as white solid.

$^1$H-NMR (DMSO-$d_6$) δ: 1.28 (9H, s), 7.41-7.57 (8H, m), 7.78-7.80 (2H, m), 7.90 (1H, dd, J=8.1, 1.7 Hz), 8.06 (1H, d, J=1.7 Hz), 9.93 (1H, s), 13.09 (1H, s).

Example 17

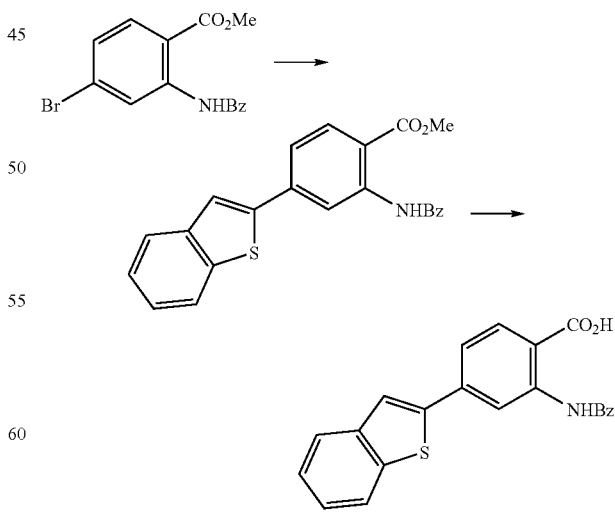

56 mg of benzothiophene-2-boronic acid, 55 mg of sodium carbonate and 30 mg of polymer supported bis(acetato)triphenylphosphine palladium(II) were added to 2.5 mL of N,N- dimethylacetamide solution containing 70 mg of methyl 2-(benzamido)-4-bromobenzoate, and stirred at 90° C. for 12 hours. After cooled to room temperature 37 mg of benzothiophene-2-boronic acid and 22 mg of sodium carbonate were added and stirred at 90° C. for 12 hours. After the reaction mixture was cooled to room temperature, insoluble were removed by filtration and ethyl acetate and 1.0 mol/L hydrochloric acid were added. The organic layer was separated, and dried over anhydrous magnesium sulfate after washed with 1.0 mol/L hydrochloric acid and a saturated sodium chloride aqueous solution sequentially, and the solvent was evaporated under reduced pressure. 1.0 mL of 2.0 mol/L aqueous sodium hydroxide and 2.0 mL of ethanol were added to the obtained residue and stirred at room temperature for 1 hour. 0.6 mol/L hydrochloric acid was added to the reaction mixture and a solid substance was separated by filtration to obtain 2.5 mg of 2-(benzamido)-4-(benzothiophen-2-yl)benzoic acid as white solid.

$^1$H-NMR (DMSO-$d_6$) δ: 7.41-7.46 (2H, m), 7.61-7.70 (4H, m), 7.94-8.06 (5H, m), 8.15 (1H, d, J=8.3 Hz), 9.24 (1H, s), 12.30-12.50 (1H, broad).

Example 18

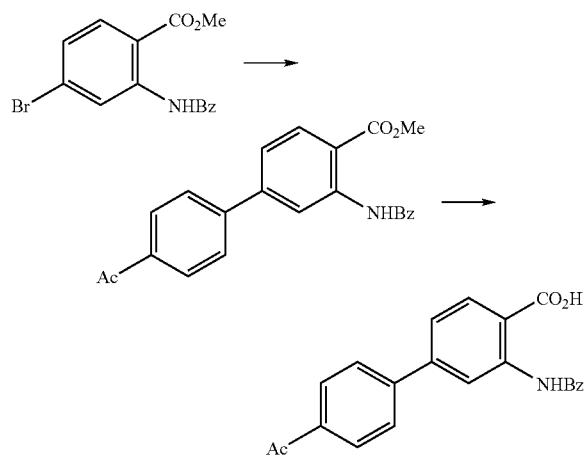

51 mg of 4-acetylphenylboronic acid, 61 mg of sodium hydrogen carbonate and 12 mg of tetrakis(triphenylphosphine)palladium(0) were added to a mixed solution of 2.0 mL of toluene, 0.6 mL of ethanol and 0.4 mL of water containing 70 mg of methyl 2-(benzamido)-1-bromobenzoate, and stirred under pressure at 160° C. for 5 minutes. After the reaction mixture was cooled to room temperature, insoluble were removed by filtration, ethyl acetate and 0.5 mol/L hydrochloric acid were added and a solid substance was separated by filtration. The obtained solid substance was added to a mixed solution of 1.0 mL of 2.0 mol/L aqueous sodium hydroxide and 5.0 mL of ethanol and stirred at room temperature for 1 hour and 30 minutes. 0.6 mol/L hydrochloric acid and ethyl acetate were added to the reaction mixture. The organic layer was separated, and the solvent was evaporated under reduced pressure to obtain 50 mg of 4-(4-acetylphenyl)-2-(benzamido)benzoic acid as white solid.

$^1$H-NMR (DMSO-$d_6$) δ: 2.64 (3H, s), 7.59-7.70 (4H, m), 7.89 (2H, d, J=8.3 Hz), 7.99-8.01 (2H, m), 8.12 (2H, d, J=8.3 Hz), 8.17 (1H, d, J=8.3 Hz), 9.14 (1H, d, J=1.7 Hz), 12.28 (1H, s), 13.80-14.10 (1H, broad).

Example 19

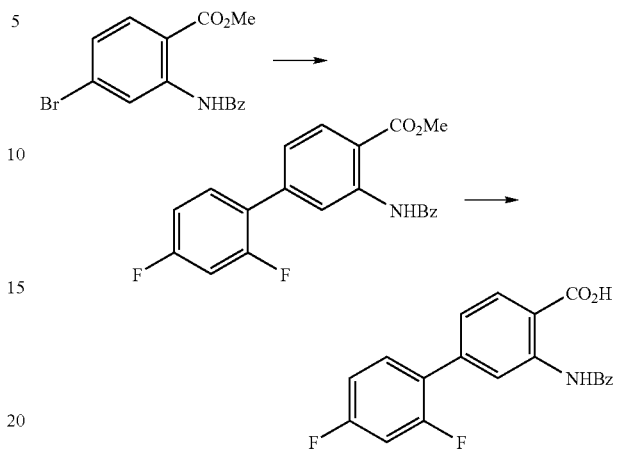

56 mg of 2,4-difluorophenylboronic acid, 63 mg of sodium carbonate and 34 mg of polymer supported bis(acetato)triphenylphosphine palladium(II) were added to 2.5 mL of N,N-dimethylacetamide solution containing 80 mg of methyl 2-(benzamido)-4-bromobenzoate, and starred at 90° C. for 20 hours. After the reaction mixture was cooled to room temperature, insoluble were removed by filtration and ethyl acetate and 1.2 mol/L hydrochloric acid were added. The organic layer was separated and dried over anhydrous magnesium sulfate after washed with 1.0 mol/L hydrochloric acid and a saturated sodium chloride aqueous solution sequentially, and the solvent was evaporated under reduced pressure. 1.0 mL of 1.0 mol/L aqueous sodium hydroxide and 4.0 mL of ethanol were added to the obtained residue and stirred at room temperature for 1 hour. 0.6 mol/L hydrochloric acid, was added to the reaction mixture and a solid substance was separated by filtration to obtain 24 mg of 2-(benzamido)-4-(2,4-difluorophenyl)benzoic acid.

$^1$H-NMR (DMSO-$d_6$) δ: 7.28 (1H, td, J=8.2 Hz, J=2.2 Hz), 7.39 (1H, dt, J=8.4, 1.6 Hz), 7.42-7.48 (1H, m), 7.59-7.70 (4H, m), 7.96-7.99 (2H, m), 8.15 (1H, d, J=8.1 Hz), 8.95 (1H, d, J=1.4 Hz), 12.24 (1H, s).

Examples 20 to 22

The compounds shown in Table 9 were obtained in the same manner as in Example 19.

TABLE 9

| Example No. | $R^3$ |
|---|---|
| 20 | ![4-fluorophenyl group] |

TABLE 9-continued

![structure with R3 and NHBz, CO2H]

| Example No. | R³ |
|---|---|
| 21 | 2-methylphenyl with OMe (ortho-OMe-methylphenyl) |
| 22 | 4-MeO-phenyl |

2-(Benzamido)-4-(4-fluorophenyl)benzoic acid $^1$H-NMR (DMSO-$d_6$) δ: 7.36-7.40 (2H, m), 7.51 (1H, dd, J=8.1, 2.0 Hz), 7.60-7.69 (3H, m), 7.77-7.81 (2H, m), 7.98-8.00 (2H, m), 8.13 (1H, d, J=8.3 Hz), 9.06 (1H, s).

2-(Benzamido)-4-(2-methoxyphenyl)benzoic acid $^1$H-NMR (DMSO-$d_6$) δ: 3.80 (3H, s), 7.09 (1H, td, J=7.4, 1.0 Hz), 7.17 (1H, d, J=7.8 Hz), 7.32-7.37 (2H, m), 7.41-7.45 (1H, m), 7.59-7.68 (3H, m), 7.96-7.98 (2H, m), 8.08 (1H, d, J=8.3 Hz), 8.88 (1H, t, J=1.6 Hz).

2-(Benzamido)-4-(4-methoxyphenyl)benzoic acid $^1$H-NMR (DMSO-$d_6$) δ: 3.83 (3H, s), 7.09-7.12 (2H, m), 7.49 (1H, dd, J=8.3, 1.7 Hz), 7.59-7.72 (5H, m), 7.98-8.00 (2H, m), 8.10 (1H, d, J=8.3 Hz), 9.06 (1H, s), 12.20-12.40 (1H, broad).

Example 23

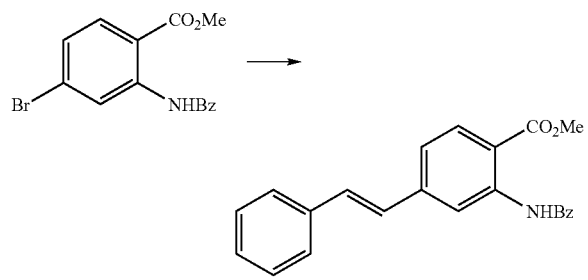

0.83 mL of triethylamine, 34 mg of palladium acetate and 0.69 mL of styrene were added to 10 mL of N,N-dimethylacetamide solution containing 1.0 g of methyl 2-(benzamido)-1-bromobenzoate and 91 mg of tri(o-tolyl)phosphine, and stirred under nitrogen atmosphere at 120° C. for 1 hour and 30 minutes. After the reaction mixture was cooled to room temperature, 0.35 mL of styrene and 5 mg of palladium acetate were added and stirred at 120° C. for 2 hours. After the reaction mixture was cooled to room temperature, ethyl acetate and 1.0 mol/L hydrochloric acid were added. The organic layer was separated and dried over anhydrous magnesium sulfate after washed with a saturated sodium chloride aqueous solution, and the solvent was evaporated under reduced pressure. The obtained residue was purified with silica gel column chromatography [eluent; hexane:ethyl acetate=8:1] to obtain 0.18 g of methyl 2-(benzamido)-4-((E)-2-phenylvinyl)benzoate as white solid.

$^1$H-NMR (CDCl$_3$) δ: 3.97 (3H, s), 7.16 (1H, d, J=16.4 Hz), 7.26-7.41 (5H, m), 7.52-7.59 (5H, m), 8.06-8.10 (3H, m), 9.17 (1H, d, J=1.4 Hz), 12.12 (1H, s).

Example 24

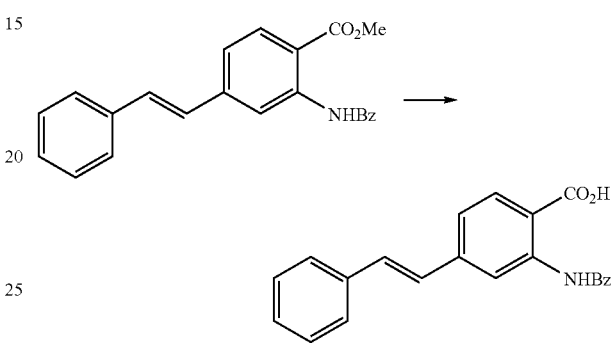

0.37 mL of 2.0 mol/L aqueous sodium hydroxide was added dropwise to a mixed solution of 2 mL of methanol and 2 mL of tetrahydrofuran containing 0.18 g of methyl 2-(benzamido)-4-((E)-2-phenylvinyl)benzoate at room temperature, and stirred at the same temperature for 7 hours. The solvent was evaporated under reduced pressure and water was added and pH was adjusted to pH 4.0 with 1.0 mol/L hydrochloric acid. Solid substances were separated by filtration and purified with silica gel column chromatography [eluent; hexane:ethyl acetate=2:1] to obtain 65 mg of 2-(benzamido)-4-((E)-2-phenylvinyl)benzoic acid as white solid.

$^1$H-NMR (DMSO-$d_6$) δ: 7.31-7.44 (5H, m), 7.49 (1H, dd, J=8.4, 1.3 Hz), 7.60-7.67 (3H, m), 7.71 (2H, d, J=7.6 Hz), 7.99 (2H, d, J=7.1 Hz), 8.06 (1H, d, J=8.4 Hz), 8.94 (1H, d, J=1.3 Hz), 12.27 (1H, s), 13.65-13.85 (1H, broad).

Example 25

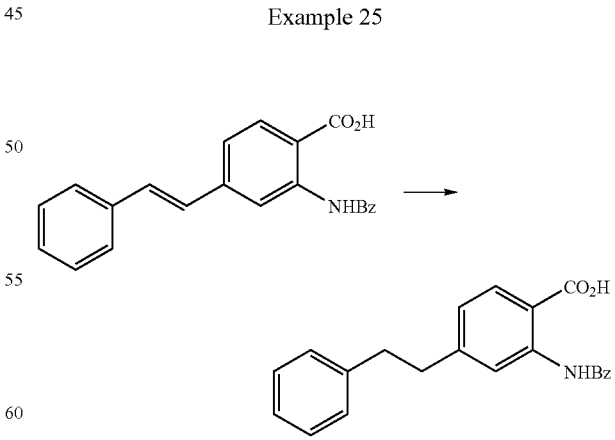

20 mg of 5% palladium-carbon was added to a mixed solution of 1 mL of methanol and 2 mL of ethyl acetate containing 0.10 g of 2-(benzamido)-4-((E)-2-phenylvinyl)benzoic acid and stirred under hydrogen atmosphere at room temperature for 5 hours. Insoluble were removed by filtration and the solvent was evaporated under reduced pressure. Hexane and diisopropyl ether were added to the obtained residue and a solid substance was separated by filtration to obtain 69 mg of 2-(benzamido)-4-phenethylbenzoic acid as white solid.

$^1$H-NMR (DMSO-$d_6$) δ: 2.91-2.99 (4H, m), 7.07 (1H, dd, J=8.1, 1.4 Hz), 7.17-7.20 (1H, m), 7.26-7.31 (4H, m), 7.58-7.67 (3H, m), 7.95-7.98 (3H, m), 8.67 (1H, d, J=1.4 Hz), 12.40-12.50 (1H, broad).

Example 26

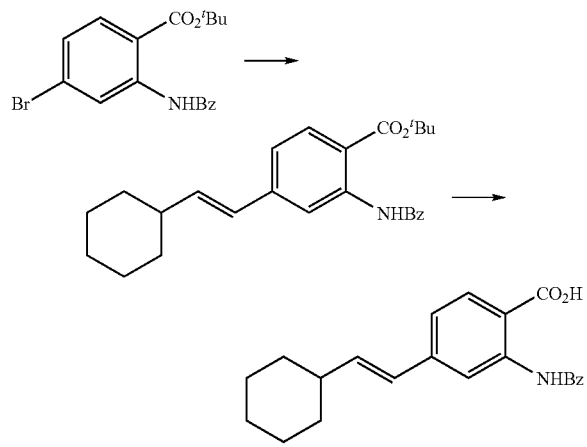

0.037 mL of vinylcyclohexane, 87 mg of cesium carbonate, 13 mg of tetrabutylammonium bromide and 21 mg of polymer supported di(acetato)dicyclohexylphosphino palladium(II) were added to 1.0 mL of toluene solution containing 50 mg of tert-butyl 2-(benzamido)-4-bromobenzoate at room temperature and stirred at 110° C. for 48 hours. After the reaction mixture was cooled to room temperature, ethyl acetate and 10% citric acid aqueous solution were added. The organic layer was separated, and the solvent was evaporated under reduced pressure after washed with 10% citric acid aqueous solution. 5 mL of trifluoroacetic acid; was added to the obtained residue and stirred at room temperature for 1 hour. The solvent was evaporated under reduced pressure, and the obtained residue was purified with reversed-phase silica gel column chromatography [eluent; 55-100% acetonitrile/ 0.1% trifluoroacetic acid aqueous solution] to obtain 2.9 mg of 2-(benzamido)-4-((E)-2-cyclohexylvinyl)benzoic acid as white solid.

$^1$H-NMR (DMSO-$d_6$) δ: 1.16-1.36 (5H, m), 1.64-1.81 (5H, m), 2.16-2.24 (1H, m), 6.42-6.44 (2H, m), 7.24 (1H, dd, J=8.3, 1.7 Hz), 7.58-7.67 (3H, m), 7.95-7.99 (3H, m), 8.76 (1H, s), 12.20-12.40 (1H, broad).

Example 27

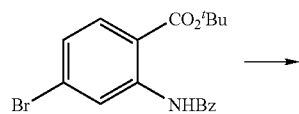

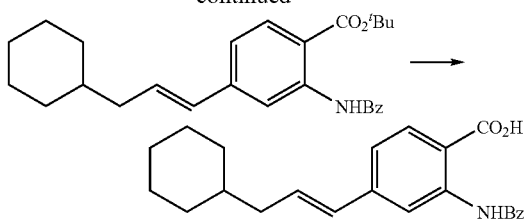

The following compound was obtained in the same manner as in Example 26.

2-(Benzamido)-4-((E)-3-cyclohexyl-1-propenyl) benzoic acid $^1$H-NMR (DMSO-$d_6$) δ: 0.92-1.28 (5H, m), 1.39-1.49 (1H, m), 1.61-1.74 (5H, m), 2.12-2.16 (2H, m), 6.45-6.47 (2H, m), 7.25 (1H, dd, J=8.3, 1.5 Hz), 7.53-7.67 (3H, m), 7.95-7.99 (3H, m), 8.75 (1H, d, J=1.5 Hz), 12.20-12.35 (1H, broad).

Example 28

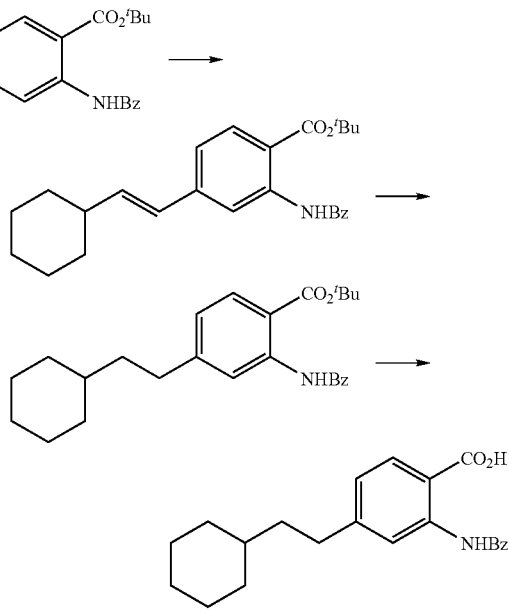

0.074 mL of vinylcyclohexane, 0.17 g cesium carbonate, 26 mg of tetrabutylammonium bromide and 42 mg of polymer supported di(acetato)dicyclohexylphosphino palladium (II) were added to 2.0 mL of toluene solution containing 0.10 g of tert-butyl 2-(benzamido)-4-bromobenzoate at room temperature and stirred at 110° C. for 48 hours. After the reaction mixture was cooled to room temperature, ethyl acetate and 10% citric acid aqueous solution were added. The organic layer was separated, and the solvent was evaporated under reduced pressure after washed with 10% citric acid aqueous solution. 2.4 mL of tetrahydrofuran, 0.6 mL of water, 0.42 g sodium formate, 0.44 mL of acetic acid and 50 mg of 3.9% palladium-carbon (ethylenediamine complex) were added to the obtained residue and stirred at 50° C. for 12 hours. After the reaction mixture was cooled to room temperature, ethyl acetate and 10% citric acid aqueous solution were added. The organic layer was separated and the solvent was evaporated under reduced pressure. 10 mL of trifluoroacetic acid was added to the obtained residue and stirred at room temperature for 1 hour, and the solvent was evaporated under reduced pressure. The obtained residue was purified with reversed-phase silica gel column chromatography [eluent; 60-100% acetonitrile/0.1% trifluoroacetic acid aqueous solution] to obtain 4.8 mg of 2-(benzamido)-4-(2-cyclohexylethyl)benzoic acid as white solid.

¹H-NMR (DMSO-d₆) δ: 0.89-0.98 (2H, m), 1.12-1.27 (4H, m), 1.48-1.78 (7H, m), 2.65-2.69 (2H, m), 7.05 (1H, dd, J=8.2, 1.6 Hz), 7.58-7.67 (3H, m), 7.94-7.97 (3H, m), 8.62 (1H, d, J=1.6 Hz), 12.20-12.35 (1H, broad).

Example 29

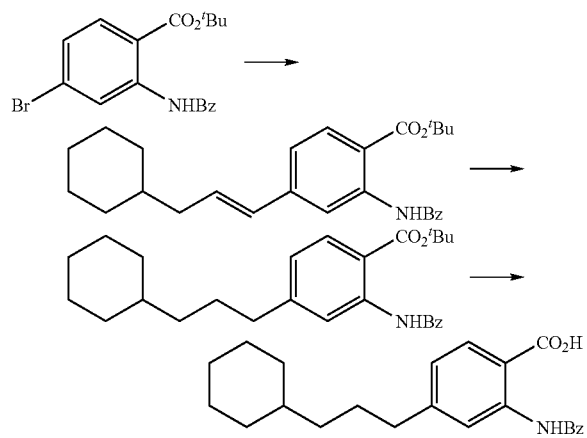

The following compound was obtained in the same manner as in Example 28.

2-(Benzamido)-4-(3-cyclohexylpropyl)benzoic acid

¹H-NMR (DMSO-d₆) δ: 0.80-0.91 (2H, m), 1.09-1.24 (6H, m), 1.59-1.70 (7H, m), 2.62-2.65 (2H, m), 7.05 (1H, dd, J=8.2, 1.6 Hz), 7.55-7.65 (3H, m), 7.94-7.98 (3H, m), 8.62 (1H, d, J=1.6 Hz), 12.25 (1H, s), 13.64 (1H, s).

Example 30

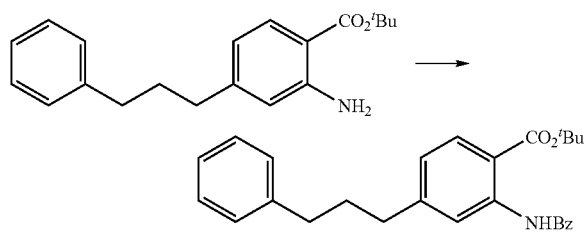

0.28 mL of triethylamine and 0.12 mL of benzoyl chloride were added to 3 mL of methylene chloride solution containing 0.31 g of tert-butyl 2-amino-4-(3-phenylpropyl)benzoate sequentially while ice-cooled and stirred at room temperature for 17 hours. The solvent was evaporated under reduced pressure, and the obtained residue was purified with silica gel column chromatography [eluent; hexane:ethyl acetate=20:1] to obtain 0.48 g of tert-butyl 2-(benzamido)-4-(3-phenylpropyl)benzoate as while solid.

¹H-NMR (CDCl₃) δ: 1.62 (9H, s), 1.96-2.05 (2H, m), 2.68 (2H, t, J=7.7 Hz), 2.72 (2H, t, J=7.8 Hz), 6.92 (1H, dd, J=8.3, 1.6 Hz), 7.18-7.22 (3H, m), 7.26-7.30 (2H, m), 7.52-7.56 (3H, m), 7.93 (1H, d, J=8.3 Hz), 8.05-8.07 (2H, m), 8.81 (1H, d, J=1.6 Hz), 12.22 (1H, s).

Example 31

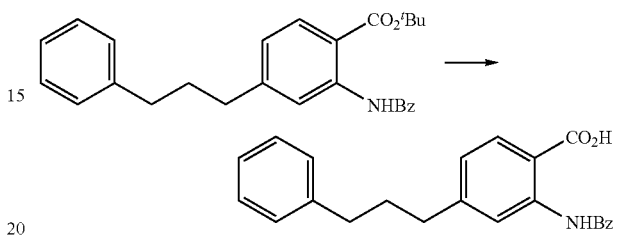

4.8 mL of trifluoroacetic acid solution containing 0.48 g of tert-butyl 2-(benzamido)-4-(3-phenylpropyl)benzoate was stirred at room temperature for 2 hours. The solvent was evaporated under reduced pressure, and the obtained residue was purified with silica gel column chromatography [eluent; hexane; ethyl acetate=1:1] to obtain 0.20 g of 2-(benzamido)-4-(3-phenylpropyl)benzoic acid as white solid.

¹H-NMR (DMSO-d₆) δ: 1.89-1.97 (2H, m), 2.65 (2H, t, J=7.9 Hz), 2.69 (2H, t, J=8.3 Hz), 7.07 (1H, dd, J=8.2, 1.6 Hz), 7.17-7.25 (3H, m), 7.28-7.32 (2H, m), 7.58-7.65 (3H, m), 7.95-7.99 (3H, m), 8.64 (1H, d, J=1.6 Hz), 12.23 (1H, s), 13.55-13.75 (1H, broad).

Example 32

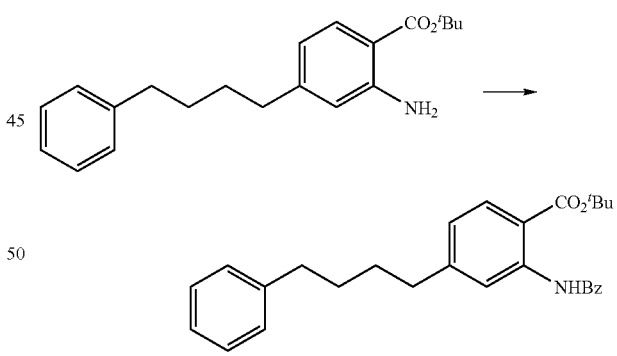

0.34 mL of triethylamine and 0.15 mL of benzoyl chloride were added to 4 mL of methylene chloride solution containing 0.40 g tert-butyl 2-amino-4-(4-phenylbutyl)benzoate while ice-cooled sequentially and stirred at room temperature for 19 hours. The solvent was evaporated under reduced pressure, and the obtained residue was purified with silica gel column chromatography [eluent; hexane:ethyl acetate=20:1] to obtain 0.50 g of tert-butyl 2-(benzamido)-4-(4-phenylbutyl)benzoate as white solid.

¹H-NMR (CDCl₃) δ: 1.55-1.73 (4H, m), 1.62 (9H, s), 2.64 (2H, t, J=7.2 Hz), 2.71 (2H, t, J=7.2 Hz), 6.90 (1H, dd, J=8.3, 1.4 Hz), 7.15-7.20 (3H, m), 7.25-7.28 (2H, m), 7.51-7.56 (3H, m), 7.92 (1H, d, J=8.3 Hz), 8.05-8.07 (2H, m), 8.80 (1H, d, J=1.4 Hz), 12.22 (1H, s).

Example 33

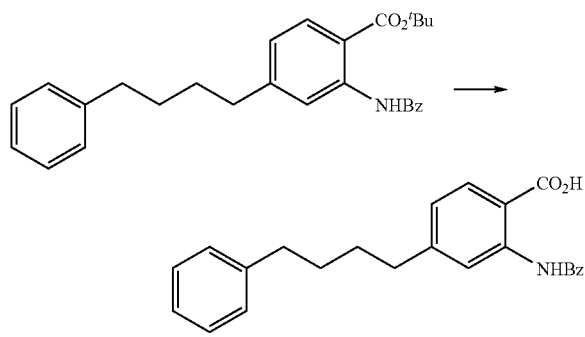

4.9 mL solution of trifluoroacetic acid containing 0.50 g of tert-butyl 2-(benzamido)-4-(4-phenylbutyl)benzoate was stirred at room temperature for 2 hours and 30 minutes. A solid substance was separated by filtration to obtain 0.16 g of 2-(benzamido)-4-(4-phenylbutyl)benzoic acid as white solid.

$^1$H-NMR (DMSO-d$_6$) δ: 1.55-1.70 (4H, m), 2.60-2.74 (4H, m), 7.04 (1H, dd, J=8.2, 1.3 Hz), 7.14-7.21 (3H, m), 7.25-7.28 (2H, m), 7.58-7.65 (3H, m), 7.94-7.98 (3H, m), 8.62 (1H, d, J=1.3 Hz), 12.22 (1H, s).

Example 34

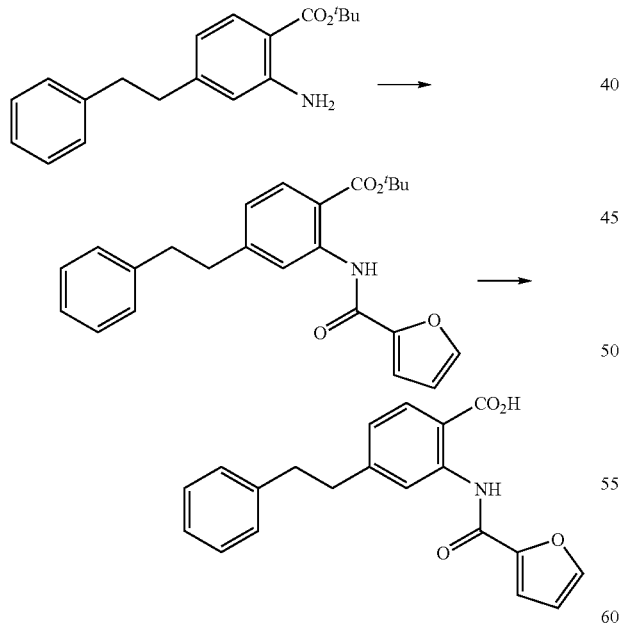

0.082 mL of triethylamine, 44 mg of 2-furoyl chloride and 2.0 mL of methylene chloride were added to 1.0 mL of methylene chloride solution containing 50 mg of tert-butyl 2-amino-4-phenethylbenzoate at room temperature and stirred at the same temperature for 2 hours. 380 mg of aminomethylated polystyrene was added to the reaction mixture and stirred at room temperature overnight. A saturated sodium hydrogen carbonate aqueous solution was added to the reaction mixture, the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(furan-2-carboxamido)-4-phenethylbenzoate.

2.0 mL of trifluoroacetic acid was added to the obtained tert-butyl 2-(furan-2-carboxamide)-4-phenethylbenzoate and stirred at room temperature for 1 hour. The solvent was evaporated under reduced pressure and diisopropyl ether was added to the obtained residue and a solid substance was separated by filtration to obtain 32 mg of 2-(furan-2-carboxamido)-4-phenethylbenzoic acid as white solid.

$^1$H-NMR (DMSO-d$_6$) δ: 2.91-2.98 (4H, m), 6.75 (1H, dd, J=3.4, 1.7 Hz), 7.07 (1H, dd, J=8.2, 1.3 Hz), 7.16-7.30 (6H, m), 7.95 (1H, d, J=8.3 Hz), 8.00 (1H, s), 8.61 (1H, s), 12.19 (1H, s), 13.50-13.70 (1H, broad).

Examples 35 to 54

The compounds shown in Table 10 were obtained in the same manner as in Example 34.

TABLE 10

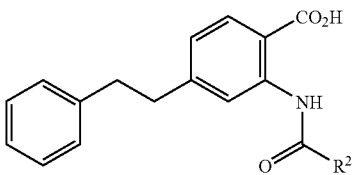

| Example No. | R$^2$ |
|---|---|
| 35 | 2,4-difluorophenyl |
| 36 | styryl (PhCH=CH–) |
| 37 | cyclohexyl |
| 38 | 4-fluorophenyl |
| 39 | 2-thienyl |
| 40 | cyclopropyl |
| 41 | phenoxyethyl |

TABLE 10-continued

| Example No. | R² |
|---|---|
| 42 | 2-methylpyridine |
| 43 | 3-methylpyridine · CF₃CO₂H |
| 44 | 1,1-diphenylethyl |
| 45 | 5-methyl-1,3-benzodioxole |
| 46 | 5-methylisoxazole |
| 47 | 3-methylbenzothiophene |
| 48 | 2-methylbenzofuran |
| 49 | 6-methyl-2,3-dihydro-1,4-benzodioxine |
| 50 | 5-methylbenzofuran |
| 51 | 5-methyl-2-morpholinopyridine |
| 52 | 5-methylbenzothiophene |
| 53 | 2-methylbenzothiazole |
| 54 | 5-methyl-1-phenylpyrazole |

2-(2,4-Difluorobenzamido)-4-phenethylbenzoic acid $^1$H-NMR (DMSO-d$_6$) δ: 2.90-3.00 (4H, m), 7.10 (1H, dd, J=8.0, 1.5 Hz), 7.16-7.20 (1H, m), 7.26-7.33 (5H, m), 7.50 (1H, ddd, J=11.4, 9.2, 2.4 Hz), 7.94 (1H, d, J=8.0 Hz), 8.01 (1H, td, J=8.8, 6.7 Hz), 8.63 (1H, s), 11.96 (1H, s), 13.54-13.64 (1H, broad).

2-(Cinnamamido)-4-phenethylbenzoic acid $^1$H-NMR (DMSO-d$_6$) δ: 2.89-2.98 (4H, m), 6.88 (1H, d, J=15.6 Hz), 7.05 (1H, dd, J=8.3, 1.5 Hz), 7.16-7.80 (5H, m), 7.42-47 (3H, m), 7.62 (1H, d, J=15.6 Hz), 7.73-7.75 (2H, m), 7.11 (1H, d, J=8.0 Hz), 3.55 (1H, s), 11.37 (1H, s), 13.40-13.60 (1H, broad).

2-(Cyclohexanecarboxamido)-4-phenethylbenzoic acid $^1$H-NMR (DMSO-d$_6$) δ: 1.17-1.47 (5H, m), 1.63-1.76 (3H, m), 1.87-1.95 (2H, m), 2.25-2.35 (1H, m), 2.86-2.92 (4H, m), 7.00 (1H, dd, J=8.0, 1.7 Hz), 7.16-7.29 (5H, m), 7.88 (1H, d, J=8.3 Hz), 8.49 (1H, s), 11.22 (1H, s), 13.35-13.55 (1H, broad).

2-(4-Fluorobenzamido)-4-phenethylbenzoic acid $^1$H-NMR (DMSO-d$_6$) δ: 2.90-3.00 (4H, m), 7.09 (1H, dd, J=8.1, 1.7 Hz), 7.16-7.20 (1H, m), 7.26-7.30 (4H, m), 7.45 (2H, t, J=8.9 Hz), 7.96 (1H, d, J=8.1 Hz), 8.00-8.04 (2H, m), 8.62 (1H, d, J=1.7 Hz), 12.16 (1H, s).

4-Phenethyl-2-(thiophene-2-carboxamido)benzoic acid $^1$H-NMR (DMSO-d$_6$) δ: 2.90-2.98 (4H, m), 7.07 (1H, dd, J=8.2, 1.6 Hz), 7.16-7.30 (6H, m), 7.74 (1H, dd, J=3.7, 1.0 Hz), 7.93-7.96 (2H, m), 8.52 (1H, s), 12.20 (1H, s).

2-(Cyclopropanecarboxamido)-4-phenethylbenzoic acid $^1$H-NMR (DMSO-d$_6$) δ: 0.85-0.87 (4H, m), 1.67-1.73 (1H, m), 2.86-2.91 (4H, m), 7.00 (1H, dd, J=8.2, 1.6 Hz), 7.15-7.29 (5H, m), 7.88 (1H, d, J=8.2 Hz), 8.41 (1H, d, J=1.6 Hz), 11.38 (1H, s), 13.35-13.60 (1H, broad).

4-Phenethyl-2-(2-phenoxyacetamido)benzoic acid $^1$H-NMR (DMSO-d$_6$) δ: 2.88-2.98 (1H, m), 9.73 (2H, s), 7.00-7.10 (4H, m), 7.16-7.37 (7H, m), 7.92 (1H, d, J=8.0 Hz), 8.63 (1H, d, J=1.7 Hz), 12.19 (1H, s), 13.50-13.75 (1H, broad).

4-Phenethyl-2-(pyridine-2-carboxamido)benzoic acid $^1$H-NMR (DMSO-d$_6$) δ: 2.92-2.99 (4H, m), 7.08-7.10 (1H, m), 7.16-7.20 (1H, m), 7.26-7.31 (4H, m), 7.67-7.70 (1H, m), 7.96 (1H, d, J=8.3 Hz), 8.09 (1H, td, J=7.7, 1.5 Hz), 8.20 (1H, d, J=7.8 Hz), 8.70-8.75 (1H, m), 8.80 (1H, d, J=1.5 Hz), 13.07 (1H, s), 13.44 (1H, s).

4-Phenethyl-2-(pyridine-3-carboxamido)benzoic acid trifluoroacetate $^1$H-NMR (DMSO-d$_6$) δ: 2.91-3.01 (4H, m), 7.11 (1H, dd, J=8.3, 1.5 Hz), 7.16-7.20 (1H, m), 7.27-7.29 (4H, m), 7.65 (1H, dd, J=7.8, 4.9 Hz), 7.97 (1H, d, J=8.3 Hz), 8.30 (1H, dt, J=8.1, 1.9 Hz), 8.60 (1H, s), 8.82 (1H, dd, J=4.9, 1.2 Hz), 9.13 (1H, d, J=2.2 Hz), 12.20 (1H, s), 13.60-13.80 (1H, broad).

4-Phenethyl-2-(2,2-diphenylacetamido)benzoic acid $^1$H-NMR (DMSO-d$_6$) δ: 2.86-2.93 (4H, m), 5.28 (1H, s), 7.02 (1H, dd, J=8.0, 1.7 Hz), 7.15-7.40 (15H, m), 7.84 (1H, d, J=8.1 Hz), 8.48 (1H, s), 11.34 (1H, s), 13.30-13.40 (1H, broad).

2-(Benzo[1,3]dioxole-5-carboxamido)-4-phenethylbenzoic acid $^1$H-NMR (DMSO-d$_6$) δ: 2.91-2.98 (4H, m), 6.16 (2H, s), 7.06 (1H, dd, J=8.1, 1.7 Hz), 7.12 (1H, d, J=8.3 Hz), 7.15-7.20 (1H, m), 7.25-7.30 (1H, m), 7.42 (1H, d, J=2.0 Hz), 7.53 (1H, dd, J=8.2, 1.8 Hz), 7.95 (1H, d, J=8.1 Hz), 8.63 (1H, s), 12.06 (1H, s).

2-(Isoxazole-5-carboxamido)-4-phenethylbenzoic acid $^1$H-NMR (DMSO-d$_6$) δ: 2.90-3.01 (4H, m), 7.14-7.30 (1H, m), 7.97 (1H, d, 8.1 Hz), 8.53 (1H, s), 8.86 (1H, d, J=1.5 Hz), 12.41 (1H, s).

2-(Benzothiophene-3-carboxamido)-4-phenethylbenzoic acid $^1$H-NMR (DMSO-d$_6$) δ: 2.94-3.01 (4H, m), 7.09 (1H, dd, J=8.2, 1.6 Hz), 7.17-7.21 (1H, m), 7.28-7.30 (4H, m), 7.47-7.54 (2H, m), 7.96 (1H, d, J=8.1 Hz), 8.11-8.13 (1H, m), 8.49-8.52 (2H, m), 8.62 (1H, d, J=1.2 Hz), 12.03 (1H, s), 13.50-13.70 (1H, broad).

2-(Benzofuran-2-carboxamido)-4-phenethylbenzoic acid $^1$H-NMR (DMSO-d$_6$) δ: 2.91-3.01 (4H, m), 7.12 (1H, dd, J=8.4, 1.6 Hz), 7.17-7.21 (1H, m), 7.26-7.29 (4H, m), 7.40 (1H, t, J=7.6 Hz), 7.54 (1H, t, J=7.2 Hz), 7.70 (1H, d, J=8.5 Hz), 7.73 (1H, s), 7.85 (1H, d, J=7.8 Hz), 7.98 (1H, d, J=8.9 Hz), 8.66 (1H, s), 12.54 (1H, s).

2-(2,3-Dihydrobenzo[1,4]dioxin-6-carboxamido)-4-phenethylbenzoic acid $^1$H-NMR (DMSO-d$_6$) δ: 2.90-2.98 (1H, m), 4.31-4.34 (4H, rip, 7.05 (2H, d, J=8.3 Hz), 7.16-7.20 (1H, ad, 7.25-7.30 (4H, m), 7.44-7.47 (2H, m), 7.94 (1H, d, J=8.3 Hz), 8.65 (1H, d, J=1.5 Hz), 12.12 (1H, s).

2-(Benzofuran-5-carboxamido)-4-phenethylbenzoic acid $^1$H-NMR (DMSO-d$_6$) δ: 2.93-3.00 (4H, m), 7.08 (1H, dd, J=8.1, 1.7 Hz), 7.15-7.21 (2H, m), 7.28-7.31 (4H, m), 7.81 (1H, d, J=8.8 Hz), 7.93 (1H, dd, 8.8, 1.9 Hz), 7.97 (1H, d, 8.3 Hz), 8.16 (1H, d, J=2.2 Hz), 8.30 (1H, d, J=1.7 Hz), 8.69 (1H, s), 12.27 (1H, s).

2-(2-Morpholinopyridine-5-carboxamido)-4-phenethylbenzoic acid $^1$H-NMR (DMSO-d$_6$) δ: 2.91-2.97 (4H, m), 3.61-3.64 (4H, m), 3.70-3.72 (4H, m), 6.98 (1H, d, J=9.0 Hz), 7.04 (1H, dd, J=8.3, 1.5 Hz), 7.16-7.20 (1H, m), 7.25-7.30 (1H, m), 7.94 (1H, d, J=8.3 Hz), 8.02 (1H, dd, J=9.0, 2.5 Hz), 8.64 (1H, d, J=1.5 Hz), 8.72 (1H, d, J=2.5 Hz), 12.00-12.10 (1H, broad).

2-(Benzothiophene-5-carboxamido)-4-phenethylbenzoic acid $^1$H-NMR (DMSO-d$_6$) δ: 2.93-3.01 (4H, m), 7.07-7.10 (1H, m), 7.17-7.22 (1H, m), 7.28-7.31 (4H, m), 7.64 (1H, d, J=5.6 Hz), 7.91-7.98 (3H, m), 8.24 (1H, d, J=8.3 Hz), 8.50 (1H, s), 8.70 (1H, s), 12.35 (1H, s).

2-(Benzothiazole-2-carboxamido)-4-phenethylbenzoic acid $^1$H-NMR (DMSO-d$_6$) δ: 2.91-3.05 (4H, m), 7.15-7.31 (6H, m), 7.62-7.71 (2H, m), 8.00 (1H, d, J=7.8 Hz), 8.19 (1H, d, J=7.8 Hz), 8.29 (1H, d, J=7.8 Hz), 8.69 (1H, s), 12.98 (1H, s).

4-Phenethyl-2-(1-phenyl-1H-pyrazole-5-carboxamido)benzoic acid $^1$H-NMR (DMSO-d$_6$) δ: 2.84-2.94 (4H, m), 7.05 (1H, d, J=2.0 Hz), 7.08 (1H, dd, J=8.1, 1.7 Hz), 7.14-7.27 (5H, m), 7.43-7.50 (5H, m), 7.86 (1H, d, J=2.2 Hz), 7.94 (1H, d, J=8.1 Hz), 8.37 (1H, s), 12.04 (1H, s).

Example 55

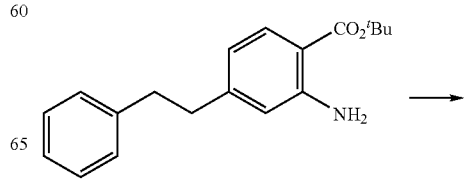

-continued

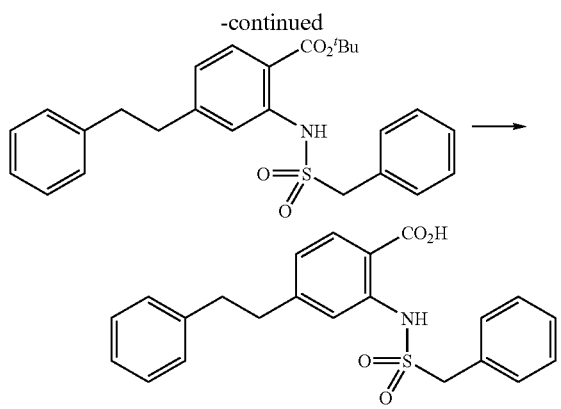

0.082 mL of triethylamine, 39 mg of benzylsulfonyl chloride and 2.0 mL of methylene chloride were added to 1.0 mL of methylene chloride solution containing 50 mg of tert-butyl 2-amino-4-phenethylbenzoate at room temperature and stirred at the same temperature for 2 hours. 380 mg of aminomethylated polystyrene was added to she reaction mixture and stirred at room temperature overnight. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(benzylsulfonamido)-4-phenethylbenzoate.

2.0 mL of trifluoroacetic acid was added to the obtained tert-butyl 2-(benzylsulfonamido)-4-phenethylbenzoate and stirred at room temperature for 1 hour. The solvent was evaporated under reduced pressure and the obtained residue was purified with reversed-phase silica gel column chromatography [eluent; 65-100% acetonitrile/0.1% trifluoroacetic acid aqueous solution] to obtain 5.1 mg of 2-(benzylsulfonamido)-4-phenethylbenzoic acid as white solid.

$^1$H-NMR (DMSO-d$_6$) δ: 2.86-2.95 (4H, m), 4.53 (2H, s), 7.03 (1H, dd, J=7.9, 1.6 Hz), 7.11-7.15 (3H, m), 7.21-7.33 (8H, m), 7.88 (1H, d, C=8.0 Hz).

Examples 56, 57

The compounds shown in Table 11 were obtained in the same manner as in Example 55.

TABLE 11

| Example No. | R² |
|---|---|
| 56 | ![structure] |

TABLE 11-continued

| Example No. | R² |
|---|---|
| 57 | ![structure] |

4-Phenethyl-2-(((E)-2-phenylvinyl)sulfonamide) benzoic acid $^1$H-NMR (DMSO-d$_6$) δ: 2.76-2.80 (2H, m), 2.90-2.94 (2H, m), 6.94 (1H, dd, J=8.1, 1.5 Hz), 7.09-7.19 (5H, m), 7.38-7.44 (5H, m), 7.72-7.77 (3H, m), 7.84 (1H, d, J=8.1 Hz), 11.02 (1H, s).

2-(Benzenesulfonamido)-4-phenethylbenzoic acid $^1$H-NMR (DMSO-d$_6$) δ: 2.78-2.82 (2H, m), 2.87-2.91 (2H, m), 6.92 (1H, d, J=8.0 Hz), 7.12-7.18 (3H, m), 7.22-7.26 (2H, m), 7.39 (1H, s), 7.52-7.56 (2H, m), 7.64 (1H, b, 7.4 Hz), 7.74-7.78 (3H, m).

Example 58

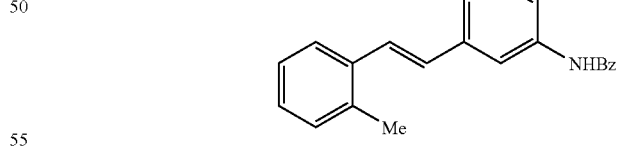

0.031 mL of 2-iodotoluene, 81 g of cesium carbonate, 12 mg of tetrabutylammonium bromide and 19 mg of polymer supported di(acetato) dicyclohexylphosphino palladium(II) were added to 1.0 mL of toluene solution containing 40 mg of tert-butyl 2-(benzamido)-4-vinylbenzoate at room temperature and stirred at 110° C. for 24 hours. After the reaction mixture was cooled to room temperature, ethyl acetate and 10% citric acid aqueous solution were added, the organic layer was separated, and the solvent was evaporated under reduced pressure after washed with 10% citric acid aqueous solution, 5 mL of trifluoroacetic acid was added to the obtained residue and stirred at room temperature for 1 hour. The solvent was evaporated under reduced pressure and the obtained residue was purified with reversed-phase silica gel column chromatography [eluent; 65-100% acetonitrile/0.1% trifluoroacetic acid aqueous solution] to obtain 2.8 mg of 2-(benzamido)-4-((E)-2-(2-methylphenyl)vinyl)benzoic acid as while solid.

$^1$H-NMR (DMSO-$d_6$) δ: 2.45 (3H, s), 7.21-7.25 (4H, m), 7.52-7.69 (5H, m), 7.76-7.78 (1H, m), 7.98-8.00 (2H, m), 8.06 (1H, d, J=8.3 Hz), 8.94 (1H, s), 12.27 (1H, s).

Examples 59 to 66

The compounds shown in Table 12 were obtained in the same manner as in Example 58.

TABLE 12

| Example No. | R$^3$ |
|---|---|
| 59 | 4-F-C$_6$H$_4$– |
| 60 | 3-F-4-Me-C$_6$H$_3$– |
| 61 | 3-O$_2$N-C$_6$H$_4$– |
| 62 | 4-Ac-C$_6$H$_4$– |
| 63 | 4-MeO-C$_6$H$_4$– |
| 64 | 3-MeO-C$_6$H$_4$– |
| 65 | 2,3-dihydrobenzo[1,4]dioxin-6-yl |
| 66 | 4-F$_3$C-C$_6$H$_4$– |

2-(Benzamido)-4-((E)-2-(4-fluorophenyl)vinyl)benzoic acid $^1$H-NMR (DMSO-$d_6$) δ: 7.23-7.42 (4H, m), 7.48 (1H, dd, J=8.2, 1.6 Hz), 7.60-7.69 (3H, m), 7.75-7.79 (2H, m), 7.99 (2H, d, J=6.8 Hz), 8.06 (1H, d, J=8.3 Hz), 8.93 (1H, s), 12.28 (1H, s).

2-(Benzamido)-4-((E)-2-(3-fluoro-4-methylphenyl)vinyl)benzoic acid $^1$H-NMR (DMSO-$d_6$) δ: 2.26 (3H, s), 7.29-7.69 (9H, m), 7.99 (2H, d, J=7.1 Hz), 8.06 (1H, d, J=8.3 Hz), 8.93 (1H, s), 12.27 (1H, s).

2-(Benzamido)-4-((E)-2-(3-nitrophenyl)vinyl)benzoic acid $^1$H-NMR (DMSO-$d_6$) δ: 7.54-7.73 (7H, m), 7.98-8.00 (2H, m), 8.09 (1H, d, J=8.3 Hz), 8.15-8.20 (2H, m), 8.56 (1H, s), 8.98 (1H, d, J=1.5 Hz), 12.24 (1H, s).

4-((E)-2-(4-acetylphenyl)vinyl)-2-(benzamido)benzoic acid $^1$H-NMR (DMSO-$d_6$) δ: 2.60 (3H, s), 7.45-7.69 (1H, m), 7.85 (2H, d, J=8.3 Hz), 7.98-8.00 (4H, m), 8.08 (1H, d, J=8.3 Hz), 8.97 (1H, d, J=1.4 Hz), 12.27 (1H, s).

2-(Benzamido)-4-((E)-2-(4-methoxyphenyl)vinyl)benzoic acid $^1$H-NMR (DMSO-$d_6$) δ: 3.80 (3H, s), 6.98 (1H, d, J=8.8 Hz), 7.18-7.22 (2H, m), 7.34 (1H, d, J=16.3 Hz), 7.44 (1H, dd, J=8.3, 1.7 Hz), 7.57-7.69 (5H, m), 7.98-8.05 (3H, m), 8.91 (1H, s), 12.29 (1H, s).

2-(Benzamido)-4-((E)-2-(3-methoxyphenyl)vinyl)benzoic acid $^1$H-NMR (DMSO-$d_6$) δ: 3.82 (3H, s), 6.89-6.91 (1H, m), 7.26-7.38 (5H, m), 7.48 (1H, dd, J=8.4, 1.6 Hz), 7.59-7.69 (3H, m), 7.98-8.00 (2H, m), 8.06 (1H, d, J=8.3 Hz), 8.94 (1H, d, J=1.7 Hz), 12.20-12.50 (1H, broad).

2-(Benzamido)-4-((E)-2-(2,3-dihydrobenzo[1,4]dioxin-6-yl)vinyl)benzoic acid $^1$H-NMR (DMSO-$d_6$) δ: 4.27 (4H, s), 6.38 (1H, d, J=8.3 Hz), 7.16-7.28 (4H, m), 7.42 (1H, dd, J=8.2, 1.3 Hz), 7.59-7.68 (3H, m), 7.98-8.04 (3H, m), 8.89 (1H, s).

2-(Benzamido)-9-((E)-2-(4-(trifluoromethyl)phenyl)vinyl)benzoic acid $^1$H-NMR (DMSO-$d_6$) δ: 7.48 (1H, d, J=16.6 Hz), 7.53-7.69 (5H, m), 7.76 (2H, d, J=8.0 Hz), 7.93 (2H, d, J=8.0 Hz), 7.98-8.00 (2H, m), 8.08 (1H, d, J=8.3 Hz), 8.97 (1H, d, J=1.5 Hz).

Example 67

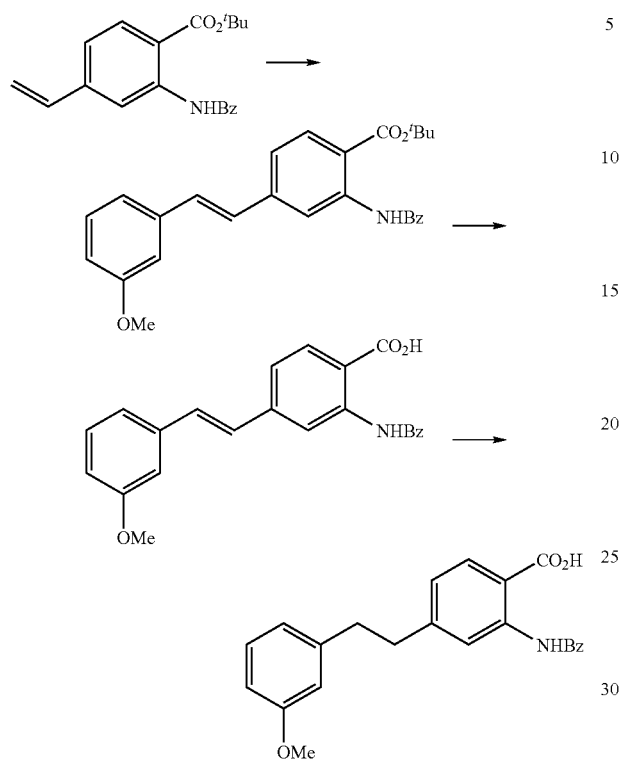

0.060 mL of 3-iodoanisole, 0.16 g of cesium carbonate, 24 mg of tetrabutylammonium bromide and 39 mg of polymer supported di(acetato)dicyclohexylphosphino palladium(II) were added to 2.0 mL of toluene solution containing 80 mg of tert-butyl 2-(benzamido)-4-vinylbenzoate at room temperature and stirred at 110° C. for 24 hours. After the reaction mixture was cooled to room temperature, ethyl acetate and 10% citric acid aqueous solution were added. The organic layer was separated, and the solvent was evaporated under reduced pressure after washed with 10% citric acid aqueous solution. 10 mL of trifluoroacetic acid was added to the obtained residue and stirred at room temperature for 1 hour. The solvent was evaporated under reduced pressure and the obtained residue was purified with reversed-phase silica gel column chromatography [eluent; 60-100% acetonitrile/0.1% trifluoroacetic acid aqueous solution] to obtain 2-(benzamido)-4-((E)-2-(3-methoxyphenyl)vinyl)benzoic acid.

1.0 mL of methanol, 2.0 mL of ethyl acetate and 2.0 mg of 5% palladium-carbon were added to the obtained 2-(benzamido)-4-((E)-2-(3-methoxyphenyl)vinyl)benzoic acid and stirred under hydrogen atmosphere at room temperature for 2 hours. Insoluble were removed by filtration, and the solvent was evaporated under reduced pressure to obtain 6.3 mg of 2-(benzamido)-4-(2-3-methoxyphenyl)ethyl)benzoic acid as white solid.

$^1$H-NMR (DMSO-$d_6$) δ: 2.87 (4H, s), 3.73 (3H, s), 6.74 (1H, ddd, J=8.2, 2.5, 1.0 Hz), 6.83-6.88 (3H, m), 7.17-7.21 (1H, m), 7.52-7.60 (3H, m), 7.92 (1H, d, J=7.8 Hz), 8.02-8.05 (2H, m), 8.61 (1H, d, J=1.7 Hz).

Examples 68 to 70

The compounds shown in Table 13 were obtained in the same manner as in Example 67.

TABLE 13

| Example No. | $R^3$ |
|---|---|
| 68 | 3-fluoro-4-methylphenyl |
| 69 | 4-ethylphenyl |
| 70 | 2-methylphenyl |

2-(Benzamido)-4-(2-(3-fluoro-4-methylphenyl)ethyl)benzoic acid $^1$H-NMR (DMSO-$d_6$) δ: 2.18 (3H, s), 2.91 (4H, s), 6.96-7.00 (2H, m), 7.05 (1H, d, J=11.0 Hz), 7.17 (1H, t, J=7.9 Hz), 7.55-7.63 (3H, m), 7.94 (1H, d, J=8.0 Hz), 8.00 (2H, d, J=6.8 Hz), 8.62 (1H, s).

2-(Benzamido)-4-(2-(4-ethylphenyl)ethyl)benzoic acid $^1$H-NMR (DMSO-$d_6$) δ: 1.15 (3H, t, J=7.6 Hz), 2.56 (2H, q, J=7.6 Hz), 2.86-2.96 (4H, m), 7.05 (1H, d, J=8.3 Hz), 7.12 (2H, d, J=7.9 Hz), 7.18 (2H, d, J=8.0 Hz), 7.57-7.66 (3H, m), 7.95-7.99 (3H, m), 8.67 (1H, s), 12.65-12.95 (1H, broad).

2-(Benzamido)-4-(2-(2-methylphenyl)ethyl)benzoic acid $^1$H-NMR (DMSO-$d_6$) δ: 2.31 (3H, s), 2.89 (4H, s), 7.05-7.21 (5H, m), 7.57-7.66 (3H, m), 7.97-7.99 (3H, m), 8.69 (1H, d, J=1.5 Hz), 12.55-12.85 (1H, broad).

Example 71

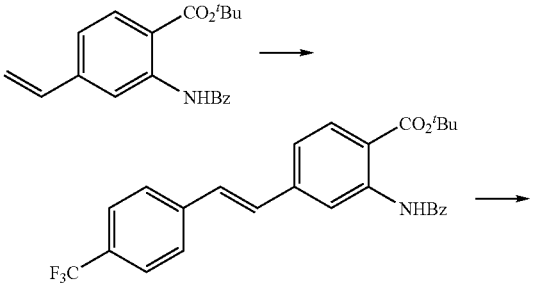

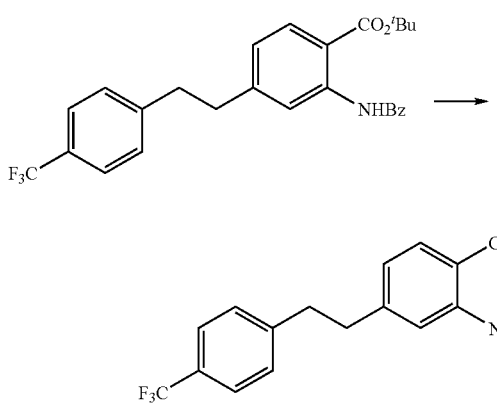

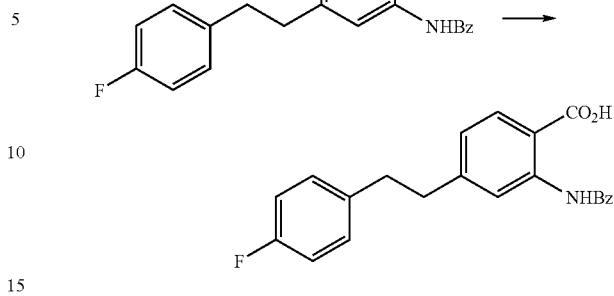

0,087 mL of 4-bromobenzotrifluoride, 0.20 g of cesium carbonate, 30 mg of tetrabutylammonium bromide and 49 mg of polymer supported di(acetato)dicyclohexylphosphino palladium(II) were added to 2.0 mL of toluene solution containing 100 mg of tert-butyl 2-(benzamido)-4-vinylbenzoate at room temperature and stirred at 110° C. for 48 hours. After the reaction mixture was cooled to room temperature, ethyl acetate and 10% citric acid aqueous solution were added. The organic layer was separated, and the solvent was evaporated under reduced pressure after washed with 10% citric acid aqueous solution. 2.4 mL of tetrahydrofuran, 0.6 mL of water, 0.42 g of sodium formate, 0.44 mL of acetic acid and 50 mg of 3.9% palladium-carbon (ethylenediamine complex) were added to the obtained residue and stirred at 50° C. for 12 hours. The reaction mixture was cooled to room temperature and ethyl acetate and 10% citric acid aqueous solution were added. The organic layer was separated and the solvent was evaporated under reduced pressure. 10 mL of trifluoroacetic acid was added to the obtained residue and stirred at room temperature for 1 hour. The solvent was evaporated under reduced pressure and the obtained residue was purified with reversed-phase silica gel column chromatography [eluent; 60-100% acetonitrile/0.1% trifluoroacetic acid aqueous solution] to obtain 21 mg of 2-(benzamido)-4-(2-(4-(trifluoromethyl)phenyl)ethyl)benzoic acid as white solid.

$^1$H-NMR (DMSO-d$_6$) δ: 3.00-3.06 (4H, m), 7.09 (1H, dd, J=8.1, 1.5 Hz), 7.50 (2H, d, J=8.1 Hz), 7.58-7.67 (5H, m), 7.95-7.98 (3H, m), 8.66 (1H, s), 12.24 (1H, s).

Example 72

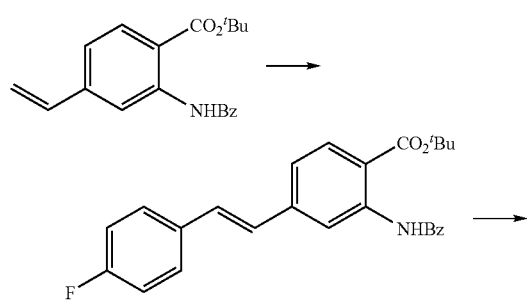

The following compound was obtained in the same manner as in Example 71.

2-(Benzamido)-4-(2-(4-fluorophenyl)ethyl)benzoic acid $^1$H-NMR (DMSO-d$_6$) δ: 2.91-2.98 (4H, m), 7.06-7.12 (3H, m), 7.28-7.31 (2H, m), 7.58-7.67 (3H, m), 7.96 (3H, d, J=7.8 Hz), 8.66 (1H, d, J=1.2 Hz), 12.21 (1H, s).

Example 73

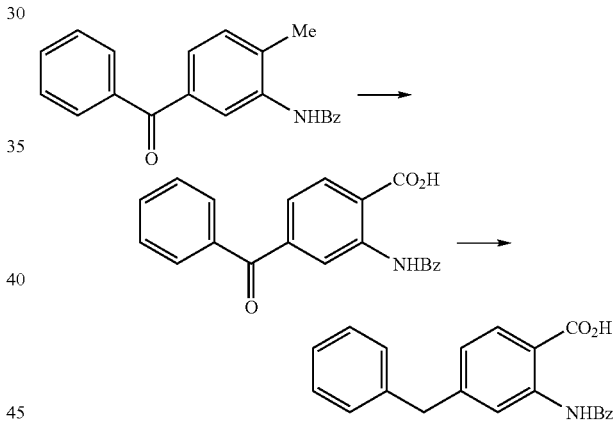

0.35 g of potassium permanganate was added to a suspension of 7 ml, of pyridine and 7 mL of water containing 0.70 g of N-((5-benzoyl-2-methyl)phenyl)benzamide at room temperature, and the resulting mixture was heated to reflux for 30 minutes. After the reaction mixture was cooled to room temperature, 0.35 g of potassium permanganate was added and the resulting mixture was heated to reflux for 30 minutes. After the reaction mixture was cooled to room temperature, 0.35 g of potassium permanganate was added and the resulting mixture was heated to reflux for 30 minutes. Ethyl acetate was added after the reaction mixture was cooled and pH was adjusted to pH 1.3 with 6.0 mol/L hydrochloric acid. Insoluble were removed by filtration. The organic layer was separated and dried over anhydrous magnesium sulfate after washed with 1.0 mol/L hydrochloric acid and a saturated sodium chloride aqueous solution sequentially, and the solvent was evaporated under reduced pressure. Hexane and diisopropyl ether were added to the obtained residue and a solid substance was separated by filtration to obtain 0.42 g of 2-(benzamido)-4-benzoylbenzoic acid as while solid.

¹H-NMR (DMSO-d₆) δ: 7.52-7.33 (9H, m), 7.95-7.97 (2H, m), 8.21 (1H, d, J=8.3 Hz), 9.05 (1H, d, J=1.7 Hz), 12.20 (1H, s).

30 mg of 5% palladium-carbon was added to a mixed solution of 1.5 mL of methanol and 2 mL of ethyl acetate containing the obtained 0.15 g of 2-(benzamido)-4-benzoyl-benzoic acid and stirred under hydrogen atmosphere at room temperature for ten hours. Insoluble were removed by filtration and the solvent was evaporated under reduced pressure. Hexane was added to the obtained residue and a solid substance was separated by filtration to obtain 0.11 g of 2-(benzamido)-4-benzylbenzoic acid as white solid.

¹H-NMR (DMSO-d₆) δ: 4.03 (2H, s), 7.0 (1H, dd, J=8.1, 1.4 Hz), 7.20-7.34 (5H, m), 7.57-7.66 (3H, m), 7.93-7.95 (2H, m), 7.98 (1H, d, J=8.1 Hz), 8.66 (1H, d, J=1.4 Hz), 12.36 (1H, s).

Example 74

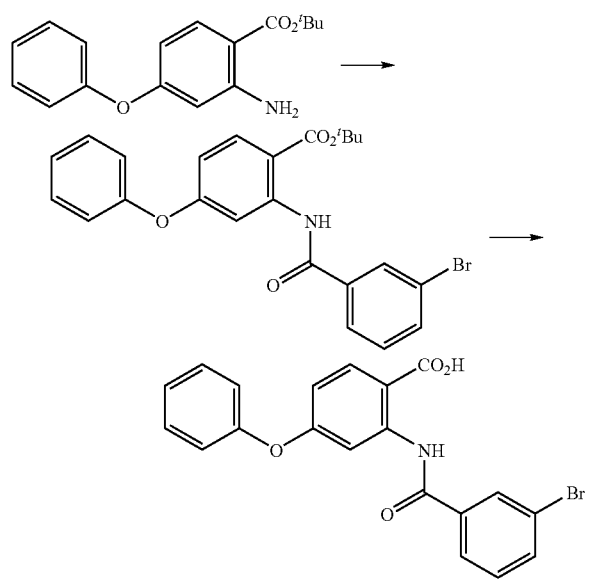

0.056 mL of triethylamine and 0.029 mL of 3-bromobenzoyl chloride were added to 3.0 mL of methylene chloride solution containing 57 mg of tert-butyl 2-amino-4-phenoxybenzoate at room temperature sequentially and stirred at the same temperature for 1 hour. A saturated sodium hydrogen carbonate aqueous solution was added to the reaction mixture. The organic layer was separated and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(3-bromobenzamido)-4-phenoxybenzoate.

5 mL of trifluoroacetic acid was added to the obtained tert-butyl 2-(3-bromobenzamido)-4-phenoxybenzoate and stirred at room temperature for 5 minutes. The solvent was evaporated under reduced pressure and diisopropyl ether was added to the obtained residue and a solid substance was separated by filtration to obtain 31 mg of 2-(3-bromobenzamido)-4-phenoxybenzoic acid as white solid.

¹H-NMR (DMSO-d₆) δ: 6.79 (1H, dd, J=8.9, 2.5 Hz), 7.15-7.22 (2H, m), 7.26-7.32 (1H, m), 7.46-7.53 (2H, m), 7.56 (1H, t, J=7.9 Hz), 7.83-7.88 (1H, m), 7.88-7.92 (1H, m), 8.05-8.10 (2H, m), 8.33 (1H, d, J=2.5 Hz), 12.44 (1H, s), 13.70-13.90 (1H, broad).

Example 75

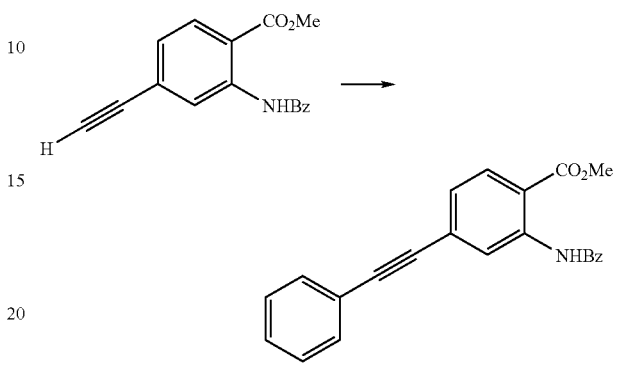

1.5 mL of toluene suspension containing 0.15 g of methyl 2-(benzamido)-4-ethynylbenzoate, 0.090 mL of iodinated benzene, 5 mg of copper(I) iodide, 20 mg of bis(triphenylphosphine)palladium(II) chloride and 0.15 mL of triethylamine was stirred under nitrogen atmosphere at room temperature for 2 hours. Ethyl acetate and 1.0 mol/L hydrochloric acid were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [eluent; hexane:ethyl acetate=8:1] to obtain 0.13 g of methyl 2-(benzamido)-4-(phenylethynyl)benzoate as white solid.

¹H-NMR (CDCl₃) δ: 3.98 (3H, s), 7.27 (1H, dd, J=8.2, 1.6 Hz), 7.37-7.39 (3H, m), 7.52-7.58 (5H, m), 8.05-8.08 (3H, m), 9.16 (1H, d, J=1.6 Hz), 12.07 (1H, s).

Example 76

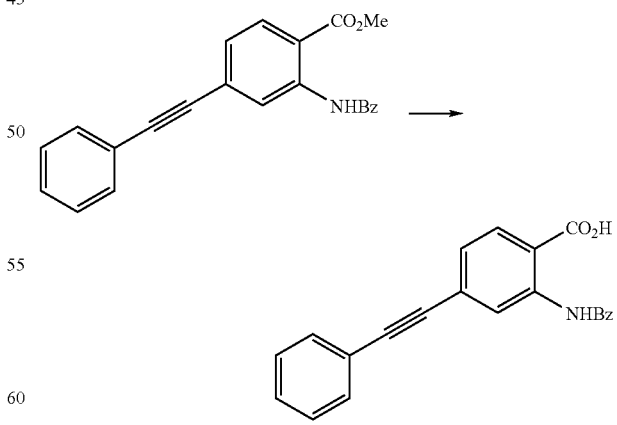

0.24 mL of 2.0 mol/L aqueous sodium hydroxide was added dropwise to a mixed solution of 1 mL of methanol and 2 mL of tetrahydrofuran containing 0.13 g of methyl 2-(benzamido)-4-(phenylethynyl)benzoate at room temperature and stirred at the same temperature for 1 hour and 30 minutes. The solvent was evaporated under reduced pressure and water was added and pH was adjusted to pH 4.0 while ice-cooled with 1.0 mol/L hydrochloric acid. A solid substance was separated by filtration to obtain 0.11 g of 2-(benzamido)-4-(phenylethynyl)benzoic acid as white solid.

$^1$H-NMR (DMSO-d$_6$) δ: 7.27 (1H, dd, J=8.0, 1.6 Hz), 7.45-7.46 (3H, m), 7.56-7.63 (5H, m), 8.03 (2H, d, J=6.8 Hz), 8.09 (1H, d, J=8.0 Hz), 8.89 (1H, d, J=1.6 Hz), 14.30-14.50 (1H, broad).

Example 77

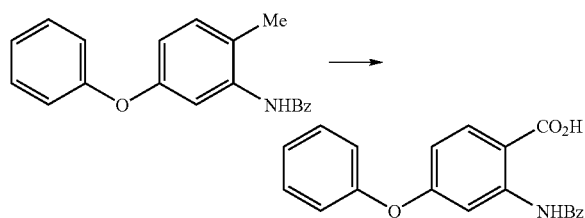

2.6 g potassium permanganate was added to a suspension of 8 mL of tert-butyl alcohol and 8 mL of wafer containing 1.7 g of N-((2-methyl-5-phenoxy)phenyl)benzamide and 2.0 g of anhydrous magnesium sulfate at room temperature, and the resulting mixture was heated to reflux for 5 hours. After the reaction mixture was cooled to room temperature, 0.86 g of potassium permanganate and 0.66 g of anhydrous magnesium sulfate were added and the resulting mixture was heated to reflux for 2 hours. After the reaction mixture was cooled to room temperature, ethyl acetate and 1.0 mol/L hydrochloric acid were added and insoluble were removed by filtration. The organic layer was separated and dried over anhydrous magnesium sulfate after washed with 1.0 mol/L hydrochloric acid and a saturated sodium chloride aqueous solution sequentially, and the solvent was evaporated under reduced pressure. The obtained residue was purified with silica gel column chromatography [eluent; hexane; ethyl acetate=2:1] to obtain 0.30 g of 2-(benzamido)-4-phenoxybenzoic acid as whine solid.

$^1$H-NMR (CDCl$_3$) δ: 6.71 (1H, dd, J=9.0, 2.5 Hz), 7.13-7.15 (2H, m), 7.21-7.25 (1H, m), 7.41-7.58 (5H, m), > 7.98-8.00 (2H, m), 8.12 (1H, d, J=9.0 Hz), 8.63 (1H, d, J=2.5 Hz), 11.94 (1H, s).

Example 78

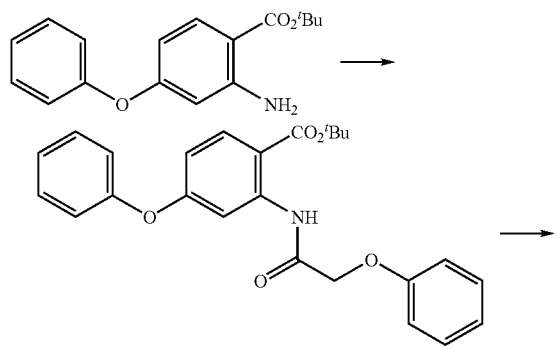

0.029 mL of 2-phenoxyacetyl chloride was added to 2.5 mL of methylene chloride solution containing 40 mg of tert-butyl 2-amino-4-phenoxybenzoate and 0.039 mL of triethylamine at room temperature and stirred at the same temperature for 2 hours. 0.25 g of aminomethylated polystyrene was added to the reaction mixture and after stirred at the same temperature overnight, 5 mL of 10% citric acid aqueous solution was added. The organic layer was separated and the solvent was evaporated under reduced pressure. The obtained residue was purified with silica gel column chromatography [Flash Tube 2008 manufactured by Trikonex Company, eluent; hexane:ethyl acetate: acetic acid=20:5:1] to obtain tert-butyl 4-phenoxy-2-(2-phenoxyacetamido)benzoate.

3 mL of trifluoroacetic acid was added to the obtained tert-butyl 4-phenoxy-2-(2-phenoxyacetamido)benzoate and stirred at room temperature for 1 hour. The solvent was evaporated 3 under reduced pressure and diisopropyl ether was added to the obtained residue and a solid substance was separated by filtration to obtain 38 mg of 4-phenoxy-2-(2-phenoxyacetamido)benzoic acid as white solid.

$^1$H-NMR (DMSO-d$_6$) δ: 4.70 (2H, s), 6.74 (1H, dd, J=9.0, 2.5 Hz), 7.01 (1H, t, J=7.4 Hz), 7.08 (2H, d, J=8.1 Hz), 7.16 (2H, d, J=7.8 Hz), 7.27 (1H, t, J=7.9 Hz), 7.35 (2H, t, J=7.9 Hz), 7.47 (2H, t, J=7.9 Hz), 8.03 (1H, d, J=9.0 Hz), 8.37 (1H, d, J=2.5 Hz), 12.32 (1H, s), 13.63 (1H, s).

Examples 79 to 97

The compounds shown in Table 14 were obtained in the same manner as in Example 78.

TABLE 14

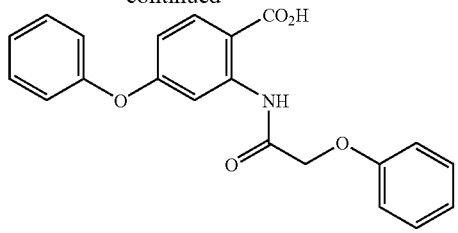

| Example No. | —X$^1$—X$^2$—X$^3$—R$^2$ |
|---|---|
| 79 | 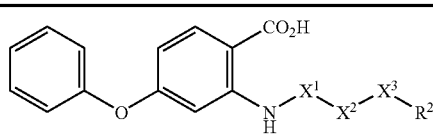 |
| 80 | |

TABLE 14-continued

[Structure: phenoxy-benzoic acid with NH-X¹-X²-X³-R² substituent]

| Example No. | —X¹—X²—X³—R² |
|---|---|
| 81 | 1-(isoxazol-5-yl)ethanone |
| 82 | 1-(2-phenylthiazol-4-yl)ethanone |
| 83 | 1-(2,3-dihydrobenzo[b][1,4]dioxin-6-yl)ethanone |
| 84 | 1-(benzo[b]thiophen-3-yl)ethanone |
| 85 | 1-cyclohexylethanone |
| 86 | 1-(thiophen-2-yl)ethanone |
| 87 | benzyl methyl sulfone |
| 88 | methyl phenyl sulfone |
| 89 | 1-(4-fluorophenyl)ethanone |
| 90 | 1-(2,4-difluorophenyl)ethanone |
| 91 | (E)-4-phenylbut-3-en-2-one |
| 92 | 1-cyclopropylethanone |
| 93 | 1-(1-methyl-1H-pyrrol-2-yl)ethanone |
| 94 | 1-(benzofuran-2-yl)ethanone |
| 95 | 1-(1-methyl-1H-benzo[d][1,2,3]triazol-5-yl)ethanone |
| 96 | 1-(benzofuran-5-yl)ethanone |
| 97 | 1-(benzo[d]thiazol-2-yl)ethanone |

4-Phenoxy-2-(pyridine-3-carboxamido)benzoic acid

¹H-NMR (DMSO-d₆) δ: 6.81 (1H, dd, J=8.8, 2.4 Hz), 7.18 (2H, d, J=7.8 Hz), 7.29 (1H, t, J=7.5 Hz), 7.48-7.51 (2H, m), 7.63 (1H, dd, J=8.0, 4.9 Hz), 8.08 (1H, d, J=8.8 Hz), 8.25 (1H, d, J=8.0 Hz), 8.34 (1H, d, J=2.4 Hz), 8.81 (1H, d, J=4.9 Hz), 9.08 (1H, d, J=1.5 Hz), 12.52 (1H, s).

2-(Benzo[1,3]dioxole-5-carboxamido)-4-phenoxybenzoic acid

¹H-NMR (DMSO-d₆) 8:6.15 (2H, s), 6.76 (1H, dd, J=8.8, 2.4 Hz), 7.10 (1H, d, J=8.1 Hz), 7.17 (2H, d, J=7.8 Hz), 7.28 (1H, t, J=7.4 Hz), 7.38 (1H, d, J=1.7 Hz), 7.47-7.50 (3H, m), 8.06 (1H, d, J=8.8 Hz), 8.36 (1H, d, J=2.4 Hz), 12.33 (1H, s), 13.55-13.80 (1H, broad).

2-(Isoxazole-5-carboxamido)-4-phenoxybenzoic acid

¹H-NMR (DMSO-d₆) δ: 6.83 (1H, dd, J=8.9, 2.5 Hz), 7.19 (2H, d, J=7.8 Hz), 7.22 (1H, t, J=1.0), 7.28-7.31 (1H, m), 7.47-7.51 (2H, d , 8.08 (1H, d, J=8.9 Hz), 8.27 (1H, d, J=2.5 Hz), 8.86 (1H, t, J=1.0), 12.63 (1H, s).

4-Phenoxy-2-(2-phenylthiazole-4-carboxamido)benzoic acid

¹H-NMR (DMSO-d₆) δ: 6.78 (1H, dd, J=8.9, 2.6 Hz), 7.20 (2H, d, J=7.8 Hz), 7.29 (1H, t, J=7.4 Hz), 7.50 (2H, t, J=7.9 Hz), 7.56-7.57 (3H, m), 8.03 (1H, d, J=8.8 Hz), 8.11-8.13 (2H, m), 8.52-8.53 (2H, m), 13.08 (1H, s), 13.69 (1H, s).

2-(2,3-Dihydrobenzo[1,4]dioxin-6-carboxamido)-4-phenoxybenzoic acid

¹H-NMR (DMSO-d₆) δ: 4.30-4.34 (4H, m), 6.75 (1H, dd, J=8.8, 2.6 Hz), 7.04 (1H, d, J=8.3 Hz), 7.17 (2H, d, J=7.8 Hz), 7.28 (1H, t, J=7.4 Hz), 7.39-7.43 (2H, m), 7.48 (2H, d, J=7.9 Hz), 8.06 (1H, d, J=8.8 Hz), 8.38 (1H, d, J=2.6 Hz), 12.31 (1H, s), 13.65 (1H, s).

2-(Benzothiophene-3-carboxamido)-4-phenoxybenzoic acid

¹H-NMR (DMSO-d₆) δ: 6.77 (1H, dd, J=8.8, 2.7 Hz), 7.20 (2H, d, J=8.0 Hz), 7.29 (1H, t, J=7.4 Hz), 7.45-7.52 (4H, m), 8.08 (1H, d, J=8.8 Hz), 8.10-8.12 (1H, m), 8.38 (1H, d, J=2.7 Hz), 8.41-8.43 (1H, m), 8.51 (1H, s), 12.25 (1H, s), 13.64 (1H, s).

2-(Cyclohexanecarboxamido)-4-phenoxybenzoic acid

¹H-NMR (DMSO-d₆) δ: 1.14-1.42 (5H, m), 1.61-1.74 (3H, m), 1.86-1.88 (2H, m), 2.23-2.30 (1H, m), 6.69 (1H, dd, J=8.8, 2.6 Hz), 7.12-7.14 (2H, m), 7.26 (1H, t, J=7.5 Hz), 7.46 (2H, t, J=7.5 Hz), 8.00 (1H, d, J=8.8 Hz), 8.24 (1H, d, J=2.6 Hz), 11.43 (1H, s), 13.47 (1H, s).

4-Phenoxy-2-(thiophene-2-carboxamido)benzoic acid

¹H-NMR (DMSO-d₆) δ: 6.76 (1H, dd, J=8.8, 2.6 Hz), 7.17 (2H, d, J=8.1 Hz), 7.26-7.30 (2H, m), 7.47-7.51 (2H, m), 7.72 (1H, d, J=3.6 Hz), 7.94 (1H, d, J=4.9 Hz), 8.06 (1H, d, J=8.8 Hz), 8.26 (1H, d, J=2.6 Hz).

2-(Benzylsulfonamido)-4-phenoxybenzoic acid

¹H-NMR (DMSO-d₆) δ: 9.65 (2H, s), 6.66 (1H, dd, J=8.9, 2.3 Hz), 7.09 (1H, d, J=2.3 Hz), 7.18 (4H, d, J=7.6 Hz), 7.28-7.33 (4H, m), 7.50 (2H, m), 7.97 (1H, d, J=8.8 Hz), 10.87 (1H, s).

2-(Benzenesulfonamido)-4-phenoxybenzoic acid

¹H-NMR (DMSO-d₆) δ: 6.70 (1H, dd, J=8.8, 2.4 Hz), 6.86 (1H, d, J=2.4 Hz), 7.05-7.07 (2H, m), 7.34 (1H, t, J=7.5 Hz), 7.50-7.60 (4H, m), 7.63-7.70 (3H, m), 7.90 (1H, d, J=8.9 Hz).

2-(4-Fluorobenzamido)-4-phenoxybenzoic acid

¹H-NMR (DMSO-d₆) δ: 6.78 (1H, dd, J=8.8, 2.5 Hz), 7.18 (2H, d, J=7.6 Hz), 7.28 (1H, t, J=7.2 Hz), 7.41-7.51 (4H, m), 7.96-8.00 (2H, m), 8.07 (1H, d, J=8.8 Hz), 8.37 (1H, d, J=2.5 Hz), 12.39 (1H, s).

2-(2,4-Difluorobenzamido)-4-phenoxybenzoic acid

¹H-NMR (DMSO-d₆) δ: 6.79 (1H, dd, J=8.8, 2.6 Hz), 7.17-7.19 (2H, m), 7.26-7.31 (2H, ml , 7.47-7.53 (3H, m), 7.97 (1H, d, J=8.8, 6.6 Hz), 8.06 (1H, d, J=8.8 Hz), 8.39 (1H, d, J=2.6 Hz), 12.16 (1H, s).

2-(Cinnamamido)-4-phenoxybenzoic acid

¹H-NMR (DMSO-d₆) δ: 6.74 (1H, dd, J=8.8, 2.4 Hz), 6.85 (1H, d, J=15.5 Hz), 7.17 (2H, d, J=7.6 Hz), 7.28 (1H, t, J=7.6 Hz), 7.42-7.51 (5H, m), 7.80 (1H, d, J=15.5 Hz), 7.72-7.74 (2H, m), 8.03 (1H, d, J=8.8 Hz), 8.35 (1H, d, J=2.4 Hz), 11.57 (1H, s).

2-(Cyclopropanecarboxamido)-4-phenoxybenzoic acid

¹H-NMR (DMSO-d₆) δ: 0.82-0.87 (4H, m), 1.64-1.70 (1H, m), 6.70 (1H, dd, J=8.8, 2.6 Hz), 7.12 (2H, d, J=8.3 Hz), 7.25 (1H, t, J=7.5 Hz), 7.46 (2H, t, J=7.9 Hz), 8.00 (1H, d, J=8.8 Hz), 8.17 (1H, d, J=2.6 Hz), 11.63 (1H, s).

2-(1-Methyl-1H-pyrrole-2-carboxamido)-4-phenoxybenzoic acid

¹H-NMR (DMSO-d₆) δ: 3.86 (3H, s), 6.15 (1H, dd, J=4.0, 2.7 Hz), 6.68 (1H, dd, J=8.9, 2.5 Hz), 6.83 (1H, dd, J=1.0, 1.6 Hz), 7.08 (1H, s), 7.16 (2H, d, J=7.6 Hz), 7.26 (1H, t, J=7.3 Hz), 7.48 (2H, h, J=7.9 Hz), 8.03 (1H, d, J=8.9 Hz), 8.33 (1H, d, J=2.5 Hz), 12.10 (1H, s).

2-(Benzofuran-2-carboxamido)-4-phenoxybenzoic acid

¹H-NMR (DMSO-d₆) δ: 6.80 (1H, dd, J=8.8, 2.4 Hz), 7.19 (2H, d, J=7.6 Hz), 7.29 (1H, t, J=7.4 Hz), 7.39 (1H, t, J=7.5 Hz), 7.48-7.56 (3H, m), 7.67-7.71 (2H, m), 7.83 (1H, d, J=7.8 Hz), 8.09 (1H, d, J=8.8 Hz), 8.39 (1H, d, J=2.4 Hz), 12.74 (1H, s).

2-(1-Methyl-1H-benzotriazole-5-carboxamido)-4-phenoxybenzoic acid

¹H-NMR (DMSO-d₆) δ: 4.37 (3H, s), 6.81 (1H, dd, J=8.8, 2.4 Hz), 7.19 (2H, d, J=7.6 Hz), 7.29 (1H, t, J=7.7 Hz), 7.50 (2H, t, J=7.9 Hz), 8.03-8.10 (3H, m), 8.40 (1H, d, J=2.4 Hz), 8.59 (1H, s).

2-(Benzofuran-5-carboxamido)-4-phenoxybenzoic acid $^1$H-NMR (DMSO-d$_6$) δ: 6.73-6.77 (1H, m), 7.08-7.29 (4H, m), 7.49 (2H, t, J=7.9 Hz), 7.78 (1H, d, J=8.6 Hz), 7.90 (1H, d, J=7.9 Hz), 8.08 (1H, d, J=8.8 Hz), 8.14 (1H, d, J=2.2 Hz), 8.27 (1H, s), 8.43 (1H, d, J=2.2 Hz).

2-(Benzothiazole-2-carboxamido)-4-phenoxybenzoic acid $^1$H-NMR (DMSO-d$_6$) δ: 6.85 (1H, dd, J=8.9, 2.5 Hz), 7.21 (2H, d, J=7.6 Hz), 7.30 (1H, t, J=7.4 Hz), 7.51 (2H, t, J=7.9 Hz), 7.61-7.70 (2H, m), 8.10 (1H, d, J=8.9 Hz), 8.18 (1H, d, J=7.6 Hz), 8.28 (1H, d, J=7.6 Hz), 8.38 (1H, d, J=2.5 Hz), 13.15 (1H, s), 13.71 (1H, s).

Example 98

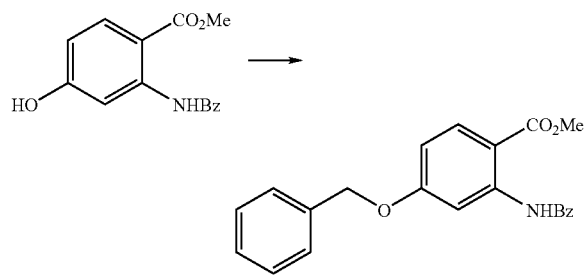

82 mg of potassium carbonate and 0.047 mL of benzyl bromide were added to 1 mL of N,N-dimethylformamide solution containing 80 mg of methyl 2-(benzamido)-4-hydroxybenzoate at room temperature and stirred at the same temperature for 3 hours. Ethyl acetate and 1.0 mol/L hydrochloric acrd were added to the reaction mixture. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. Hexane was added to the obtained residue and a solid substance was separated by filtration to obtain 75 mg of methyl 2-(benzamido)-4-(benzyloxy)benzoate as white solid.

$^1$H-NMR (CDCl$_3$) δ: 3.93 (3H, s), 5.20 (2H, 5), 6.12 (1H, dd, J=9.0, 2.5 Hz), 7.32-7.36 (1H, m), 7.39-7.42 (2H, m), 7.47-7.49 (2H, m), 7.51-7.57 (3H, m), 3.02 (1H, d, J=9.0 Hz), 8.05-8.08 (2H, m), 8.76 (1H, d, J=2.5 Hz), 12.26 (1H, s).

Example 99

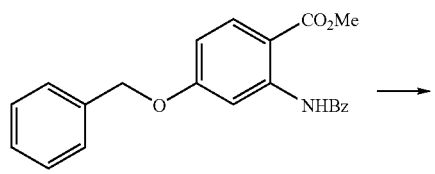

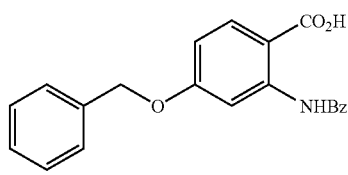

0.11 mL of 2.0 mol/L aqueous sodium hydroxide was added dropwise to a mixed solution of 1 mL of methanol and 2 mL of tetrahydrofuran containing 70 mg of methyl 2-(benzamido)-4-(benzyloxy)benzoate at room temperature, and stirred at the same temperature for 6 hours and 30 minutes, at 40° C. for 1 hour and 30 minutes and at 50° C. for 2 hours. After the reaction mixture was cooled to room temperature, the solvent was evaporated under reduced pressure and water and diethyl ether were added. The aqueous layer was separated and pH was adjusted to pH 4.0 with 1.0 mol/L hydrochloric acid. A solid substance was separated by filtration to obtain 35 mg of 2-(benzamido)-4-(benzyloxy)benzoic acid as white solid.

$^1$H-NMR (DMSO-d$_6$) δ: 5.22 (2H, s), 6.86 (1H, dd, J=8.9, 2.7 Hz), 7.34-7.38 (1H, m), 7.40-7.44 (2H, m), 7.49-7.51 (2H, m), 7.58-7.65 (3H, m), 7.95-7.97 (2H, m), 6.02 (1H, d, J=8.9 Hz), 8.52 (1H, d, J=2.7 Hz), 12.45 (1H, s), 13.30-13.70 (1H, broad).

Example 100

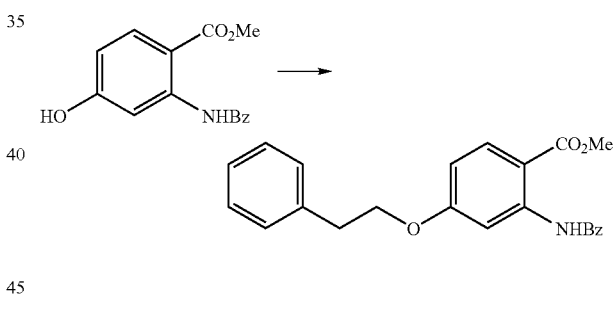

0.13 g of potassium carbonate and 0.10 mL of (2-bromoethyl)benzene were added to 2 mL of N-dimethylformamide solution containing 0.13 g of methyl 2-(benzamido)-4-hydroxybenzoate, and stirred at room temperature for 3 hours. 0.10 mL of (2-bromoethyl)benzene was added to the reaction mixture and stirred at 50° C. for 4 hours and at 80° C. for 3 hours. After the reaction mixture was cooled to room temperature, 0.10 g of potassium carbonate and 0.10 mL of (2-bromoethyl)benzene were added and stirred at 80° C. for 2 hours and 30 minutes. After the reaction mixture was cooled to room temperature, ethyl acetate and 1.0 mol/b hydrochloric acid were added. The organic layer was separated and dried over anhydrous magnesium sulfate after washed with a saturated sodium chloride aqueous solution, and the solvent was evaporated under reduced pressure. The obtained residue was purified with silica gel column chromatography [eluent; hexane:ethyl acetate=8:1] to obtain 0.13 g of methyl 2-(benzamido)-4-(phenethyloxy)benzoate as colorless oil.

$^1$H-NMR (CDCl$_3$) δ: 3.14 (2H, t, J=7.1 Hz), 3.93 (3H, s), 4.31 (2H, t, J=7.1 Hz), 6.64 (1H, dd, J=9.0, 9.5 Hz), 7.23-7.35

(5H, m), 7.50-7.56 (3H, m), 7.99 (1H, d, J=9.0 Hz), 8.04-8.07 (2H, m), 8.63 (1H, d, J=2.5 Hz), 12.24 (1H, s).

Example 101

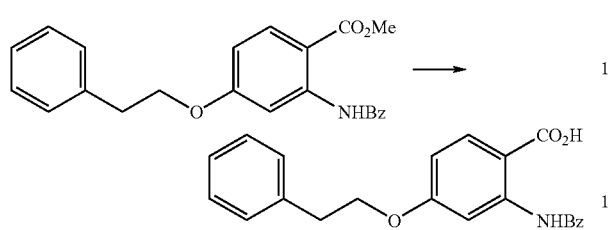

0.30 mL of 2.0 mol/L aqueous sodium hydroxide was added dropwise to a mixed solution of 2 mL of methanol and 2 mL of tetrahydrofuran containing 0.19 g of methyl 2-(benzamido)-4-(phenethyloxy)benzoate while ice-cooled, and stirred at room temperature for 14 hours and 30 minutes. The solvent was evaporated under reduced pressure and ethyl acetate and 1.0 mol/L hydrochloric acid were added. The organic layer was separated, the solvent was evaporated under reduced pressure and the residue was purified with silica gel column chromatography [eluent; hexane:ethyl acetate=2:1] to obtain 85 mg of 2-(benzamido)-4-(phenethyloxy)benzoic acid as white solid.

$^1$H-NMR (DMSO-$d_6$) δ: 3.09 (2H, t, J=6.8 Hz), 4.29 (2H, t, J=6.8 Hz), 6.78 (1H, dd, J=8.9, 2.5 Hz), 7.22-7.26 (1H, m), 7.31-7.38 (4H, m), 7.58-7.68 (3H, m), 7.94-7.96 (2H, m), 8.00 (1H, d, J=8.9 Hz), 8.42 (1H, d, J=2.5 Hz), 12.44 (1H, s).

Example 102

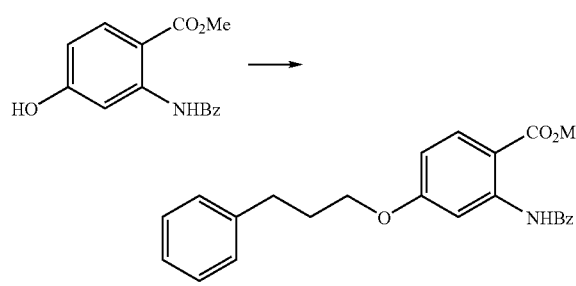

0.28 mL of 40% diisopropyl azodicarboxylate/toluene was added dropwise to 1 mL of tetrahydrofuran solution containing 0.10 g of methyl 2-(benzamido)-4-hydroxybenzoate, 0.060 mL of 3-phenyl-1-propanol and 0.15 g of triphenylphosphine at room temperature, and stirred at the same temperature for 2 hours and 30 minutes. The solvent was evaporated under reduced pressure, and the obtained residue was purified wish silica gel column chromatography [eluent; hexane:ethyl acetate=10:1] to obtain 45 mg of methyl 2-(benzamido)-4-(3-phenylpropoxy)benzoate as white solid.

$^1$H-NMR (CDCl$_3$) δ: 2.11-2.18 (2H, m), 2.83 (2H, t, J=7.7 Hz), 3.94 (3H, s), 4.12 (2H, t, J=6.2 Hz), 6.65 (1H, dd, J=9.0, 2.7 Hz), 7.18-7.31 (5H, m), 7.51-7.57 (3H, m), 8.01 (1H, d, J=9.0 Hz), 8.05-8.07 (2H, m), 8.62 (1H, d, J=2.7 Hz), 12.24 (1H, s).

Example 103

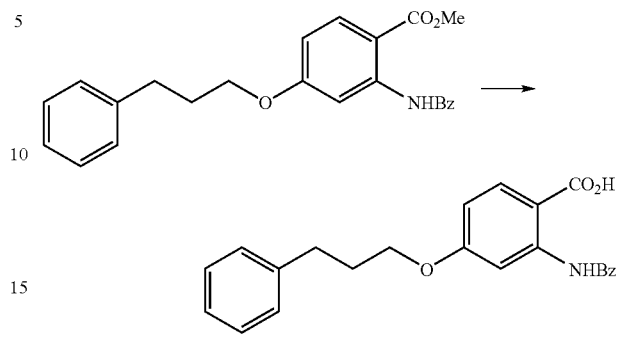

0.090 mL of 2.0 mol/L aqueous sodium hydroxide was added dropwise to a mixed solution of 1 mL of methanol and 1 mL of tetrahydrofuran containing 45 mg of methyl 2-(benzamido)-4-(3-phenylpropoxy)benzoate while ice-cooled and stirred at room temperature for 14 hours and 30 minutes. 0.15 mL of 2.0 mol/L aqueous sodium hydroxide was added dropwise and stirred at the same temperature for 5 hours and 30 minutes. The solvent was evaporated under reduced pressure and water was added and pH was adjusted to pH 4.0 with 1.0 mol/L hydrochloric acid. A solid substance was separated by filtration to obtain 32 mg of 2-(benzamido)-4-(3-phenylpropoxy)benzoic acid as white solid.

$^1$H-NMR (DMSO-$d_6$) δ: 2.01-2.08 (2H, m), 2.77 (2H, t, J=7.7 Hz), 3.99 (2H, t, J=6.2 Hz), 6.56 (1H, dd, J=8.6, 2.5 Hz), 7.17-7.21 (1H, m), 7.24-7.31 (1H, m), 7.51-7.60 (3H, m), 7.94 (1H, d, J=8.6 Hz), 8.03-8.05 (2H, m), 8.34 (1H, d, J=2.5 Hz).

Example 104

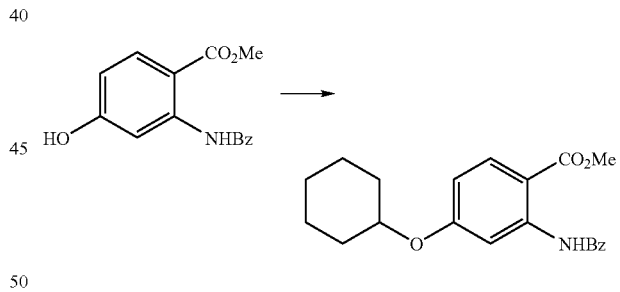

0.20 mL of 40% diisopropyl azodicarboxylate/toluene was added dropwise to 1 mL of tetrahydrofuran solution containing 90 mg of methyl 2-(benzamido)-4-hydroxybenzoate, 0.035 mL of cyclohexanol and 0.10 g of triphenylphosphine at room temperature, and stirred at the same temperature for 5 hours. Ethyl acetate and 1.0 mol/L hydrochloric acid were added to the reaction mixture. The organic layer was separated and dried over anhydrous magnesium sulfate after washed with saturated sodium hydrogen carbonate aqueous solution and saturated sodium chloride aqueous solution sequentially, and the solvent was evaporated under reduced pressure. The obtained residue was purified with silica gel column chromatography [eluent; hexane:ethyl acetate=10:1] to obtain 36 mg of methyl 2-(benzamido)-4-(cyclohexyloxy)benzoate as while solid.

$^1$H-NMR (CDCl$_3$) δ: 1.30-1.49 (4H, m), 1.54-1.64 (2H, m), 1.77-1.87 (2H, m), 1.98-2.07 (2H, m), 3.93 (3H, s), 4.45-

4.49 (1H, m), 6.63 (1H, dd, J=9.0, 2.4 Hz), 7.51-7.58 (3H, m), 7.99 (1H, d, J=9.0 Hz), 8.05-3.07 (2H, m), 8.61 (1H, d, J=2.4 Hz), 12.21 (1H, s).

Example 105

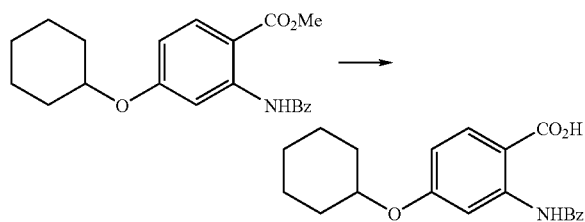

0.077 mL of 2.0 mol/L aqueous sodium hydroxide was added drop-wise to a mixed solution of 1 mL of methanol and 1 mL of tetrahydrofuran containing 35 mg of methyl 2-(benzamido)-4-(cyclohexyloxy)benzoate at room temperature and stirred at the same temperature overnight and at 40° C. for 6 hours and 30 minutes. 0.050 mL of 2.0 mol/L aqueous sodium hydroxide was added at room temperature and stirred at she same temperature for 4 hours and 30 minutes. The solvent was evaporated under reduced pressure and water was added and pH was adjusted to pH 4.0 with 1.0 mol/L hydrochloric acid. A solid substance was separated by filtration to obtain 25 mg of 2-(benzamido)-4-(cyclohexyloxy)benzoic acid as white solid.

$^1$H-NMR (DMSO-$d_6$) δ: 1.20-1.60 (6H, m), 1.68-1.78 (2H, m), 1.92-2.00 (2H, m), 4.32-4.39 (1H, m), 6.59 (1H, dd, T=8.7, 2.4 Hz), 7.52-7.59 (3H, m), 7.93 (1H, d, J=8.7 Hz), 8.01-8.03 (2H, m), 8.33 (1H, d, J=2.4 Hz).

Example 106

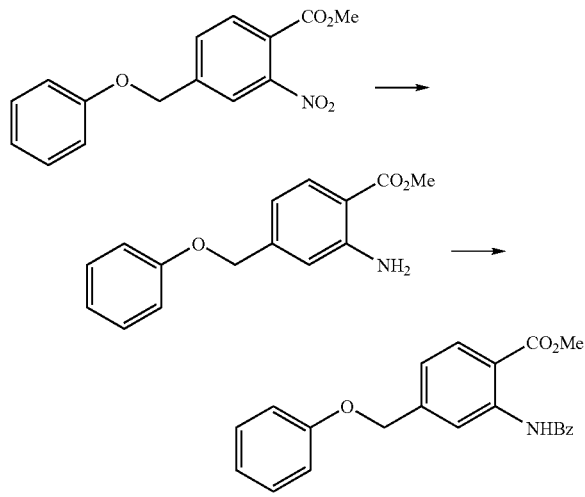

0.31 g of iron powder was added to a mixed solution of 5.3 mL of methanol and 1.6 mL of acetic acid containing 0.53 g of methyl 2-nitro-4-(phenoxymethyl)benzoate, and the resulting mixture was heated to reflux for 3 hours. The reaction mixture was cooled to room temperature and ethyl acetate and a saturated sodium hydrogen carbonate aqueous solution were added and insoluble were removed by filtration. The organic layer was separated and dried over anhydrous magnesium sulfate after washed with saturated sodium hydrogen carbonate aqueous solution and saturated sodium chloride aqueous solution sequentially, and the solvent was evaporated under reduced pressure. The obtained residue was dissolved in 5.3 mL of methylene chloride and 0.51 mL of triethylamine and 0.26 mL of benzoyl chloride were added while ice-cooled sequentially and stirred at room temperature for 15 hours. The solvent was evaporated under reduced pressure and ethyl acetate and 1.0 mol/L hydrochloric acid were added to the obtained residue. The organic layer was separated and washed with saturated sodium chloride aqueous solution and dried over anhydrous magnesium sulfate, and the solvent was evaporated under reduced pressure. Hexane and diisopropyl ether were added to the obtained residue and a solid substance was separated by filtration to obtain 0.31 g of methyl 2-(benzamido)-4-(phenoxymethyl)benzoate as white solid.

$^1$H-NMR (CDCl$_3$) δ: 3.97 (3H, s), 5.17 (2H, s), 6.95-7.00 (3H, m), 7.25-7.31 (3H, m), 7.54-7.58 (3H, m), 8.05-8.07 (2H, m), 8.10 (1H, d, J=8.3 Hz), 9.04 (1H, d, J=1.2 Hz), 12.10 (1H, s).

Example 107

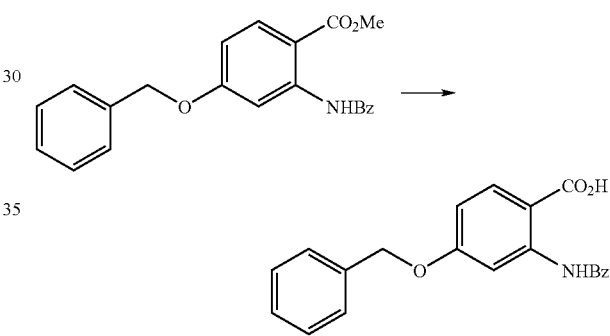

0.51 mL of 2.0 mol/b aqueous sodium hydroxide was added dropwise to a mixed solution of 3 mL of methanol and 3 mL of tetrahydrofuran containing 0.31 g of methyl 2-(benzamido)-4-(phenoxymethyl)benzoate while ice-cooled and stirred an room temperature for 5 hours and 30 minutes, the solvent was evaporated under reduced pressure and water was added and pH was adjusted to pH 4.0 with 1.0 mol/L hydrochloric acid. A solid substance was separated by filtration to obtain 0.21 g of 2-(benzamido)-1-(phenoxymethyl)benzoic acid as white solid.

$^1$H-NMR (DMSO-$d_6$) δ: 5.16 (2H, s), 6.95 (1H, t, J=7.3 Hz), 7.02-7.04 (2H, m), 7.17 (1H, dd, J=8.0, 1.2 Hz), 7.28-7.32 (2H, m), 7.54-7.61 (3H, m), 8.00-8.02 (2H, m), 8.05 (1H, d, J=8.0 Hz), 8.82 (1H, d, J=1.2 Hz).

Example 108

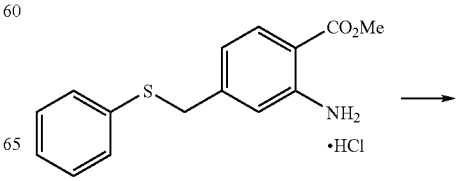

-continued

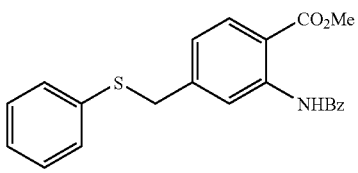

0.52 mL of triethylamine and 0.16 mL of benzoyl chloride were added to 3.8 mL of methylene chloride suspension containing 0.39 g of methyl 2-amino-4-((phenylthio)methyl)benzoate hydrochloride while ice-cooled and stirred at room temperature for 3 hours and 30 minutes. The solvent was evaporated under reduced pressure and ethyl acetate and 1.0 mol/L hydrochloric acid were added to the obtained residue. The organic layer was separated and dried over anhydrous magnesium sulfate after washed with a saturated sodium hydrogen carbonate aqueous solution and a saturated sodium chloride aqueous solution sequentially, and the solvent vas evaporated under reduced pressure, Hexane and diisopropyl ether were added to the obtained residue and a solid substance was separated by filtration to obtain 0.29 g of methyl 2-(benzamido)-4-((phenylthio)methyl)benzoate as white solid.

$^1$H-NMR (CDCl$_3$) δ: 3.95 (3H, s), 4.17 (2H, s), 7.08 (1H, dd, J=8.3, 1.6 Hz), 7.16-7.20 (1H, m), 7.24-7.27 (2H, m), 7.32-7.34 (2H, m), 7.51-7.57 (3H, m), 7.99 (1H, d, J=8.3 Hz), 8.04-8.06 (2H, m), 8.95 (1H, d, J=1.6 Hz), 12.04 (1H, s).

Example 109

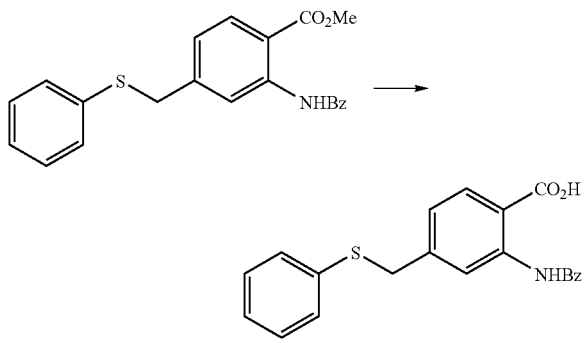

0.50 mL of 2.0 mol/L aqueous sodium hydroxide was added dropwise to a mixed solution of 3 mL of methanol and 3 mL of tetrahydrofuran containing 0.29 g of methyl 2-(benzamido)-4-((phenylthio)methyl)benzoate while ice-cooled and stirred at room temperature for 5 hours. 0.25 mL of 2.0 mol/L aqueous sodium hydroxide was added dropwise and stirred at the same temperature for 14 hours. The solvent was evaporated under reduced pressure and water was added and pH was adjusted to pH 4.0 with 1.0 mol/L hydrochloric acid. A solid substance was separated by filtration to obtain 0.28 g of 2-(benzamido)-4-((phenylthio)methyl)benzoic acid as white solid.

$^1$H-NMR (DMSO-d$_6$) δ: 4.24 (2H, s), 6.99 (1H, dd, J=7.9, 1.8 Hz), 7.15-7.19 (1H, m), 7.27-7.31 (2H, m), 7.34-7.37 (2H, m), 7.52-7.59 (3H, m), 7.93 (1H, d, J=1.9 Hz), 8.01-8.04 (2H, m), 8.76 (1H, d, J=1.8 Hz).

Example 110

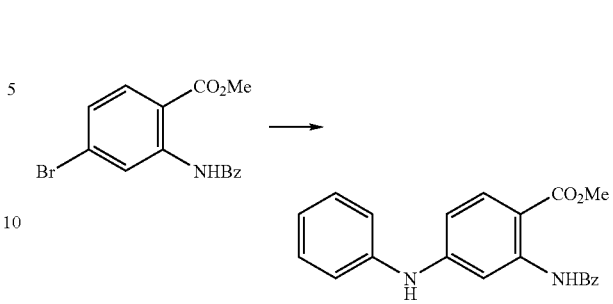

0.16 mL of aniline, 0.12 g of 1,1'-bis(diphenylphosphino)ferrocene, 0.057 g of (1,1'-bis(diphenylphosphino)ferrocene)palladium(II) dichloride methylene chloride complex and 0.17 g of sodium tert-butoxide were added to 6 mL of dioxane solution containing 0.58 g of methyl 2-(benzamido)-4-bromobenzoate, and the resulting mixture was heated to reflux under nitrogen atmosphere for 4 hours. After the reaction mixture was cooled to room temperature, 1 mL of acetic acid was added and the solvent was evaporated under reduced pressure. The obtained residue was purified with silica gel column chromatography [eluent; hexane:ethyl acetate=5:1] to obtain 0.43 g of methyl 4-(anilino)-2-(benzamido)benzoate as colorless oil.

$^1$H-NMR (DMSO-d$_6$) δ: 3.86 (3H, s), 6.79 (1H, dd, J=9.0, 2.4 Hz), 7.04 (1H, t, J=7.3 Hz), 7.25 (2K, d, J=7.6 Hz), 7.35-7.39 (2H, m), 7.59-7.68 (3H, m), 7.89 (1H, d, J=9.0 Hz), 7.95-7.97 (2H, m), 8.55 (1H, d, J=2.4 Hz), 9.03 (1H, s), 12.09 (1H, s).

Example 111

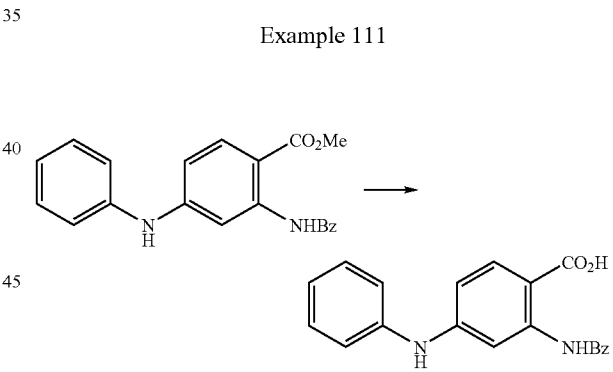

1 mL of 10% aqueous sodium hydroxide was added to 4 mL of ethanol suspension containing 0.43 g of methyl 4-(anilino)-2-(benzamido)benzoate at room, temperature, and she resulting mixture was heated to reflux for 2 hours. After the reaction mixture was cooled to room temperature, 1.0 mol/L hydrochloric acid and ethyl acetate were added. The organic layer was separated and dried over anhydrous magnesium sulfate, and the solvent was evaporated under reduced pressure. Diisopropyl ether and hexane were added to the obtained residue and a solid substance was separated by filtration to obtain 0.36 g of 4-(anilino)-2-(benzamido)benzoic acrd as white solid.

$^1$H-NMR (DMSO-d$_6$) δ: 6.78 (1H, dd, J=8.9, 2.3 Hz), 7.03 (1H, t, J=7.3 Hz), 7.25 (1H, d, J=7.8 Hz), 7.36 (2H, t, J=7.7 Hz), 7.57-7.67 (3H, m), 7.90 (1H, d, J=8.9 Hz), 7.96 (2H, d, J=7.1 Hz), 8.57 (1H, d, J=2.3 Hz), 8.97 (1H, s), 12.50 (1H, s), 12.80-13.20 (1H, broad).

Example 112

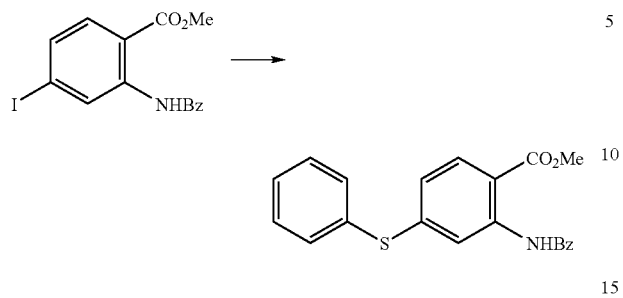

0.16 mL of thiophenol, 0.43 g of potassium carbonate and 0.030 g of copper(I) iodide were added to 6 mL of ethylene glycol dimethyl ether solution containing 0.60 g of methyl 2-(benzamido)-4-iodobenzoate, and the resulting mixture was heated to reflux under argon atmosphere for 13 hours. After the reaction mixture was cooled to room temperature, 1.0 mol/L hydrochloric acid and ethyl acetate were added. The organic layer was separated and dried over anhydrous magnesium sulfate, and the solvent was evaporated under reduced pressure. The obtained residue was purified with silica gel column chromatography [eluent; hexane:ethyl acetate=5:1] to obtain 0.30 g of methyl 2-(benzamido)-A-(phenylthio)benzoate as white solid.

$^1$H-NMR (DMSO-d$_6$) δ: 3.88 (3H, s), 6.95 (1H, dd, J=8.4, 1.8 Hz), 7.50-7.67 (8H, m), 7.91-7.96 (3H, m), 8.51 (1H, d, J=1.8 Hz), 11.73 (1H, s).

Example 113

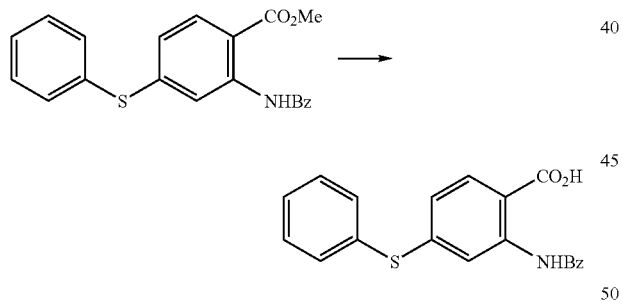

0.4 mL of 10% aqueous sodium hydroxide was added to 6 ml of ethanol suspension containing 0.30 g of methyl 2-(benzamido)-4-(phenylthio)benzoate at room temperature, and the resulting mixture was heated to reflux for 1 hour. After one reaction mixture was cooled to room temperature, 1.0 mol/b hydrochloric acid and ethyl acetate were added. The organic layer was separated and dried over anhydrous magnesium sulfate, and the solvent was evaporated under reduced pressure. Diisopropyl ether and hexane were added to the obtained residue and a solid substance was separated, by filtration to obtain 0.28 g of 2-(benzamido)-4-(phenylthio) benzoic acid as white solid.

$^1$H-NMR (DMSO-d$_6$) δ: 6.92 (1H, dd, J=8.4, 1.8 Hz), 7.47-7.67 (8H, m), 7.90-7.92 (2H, m), 7.97 (1H, d, J=8.4 Hz), 8.63 (1H, d, J=1.8 Hz), 12.25 (1H, s).

Example 114

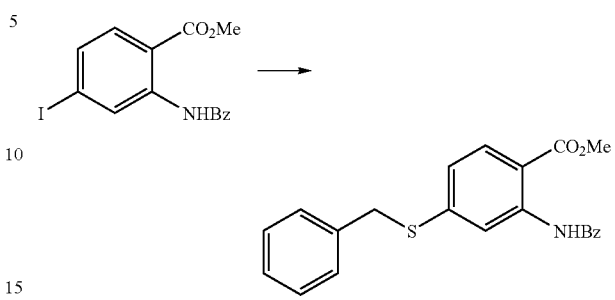

0.15 mL of triethylamine and 0.068 mL of benzyl mercaptan were added to 2 mL of toluene suspension containing 0.20 g of methyl 2-(benzamido)-4-iodobenzoate, 36 mg of 1,1'-bis (diphenylphosphino)ferrocene and 24 mg of tris(dibenzylideneacetone)dipalladium(0) and stirred under nitrogen atmosphere at 80° C. for 2 hours. Insoluble were removed by filtration and the solvent was evaporated under reduced pressure. The obtained, residue was purified with silica gel column chromatography [eluent; hexane; ethyl acetate=10:1] to obtain 0.16 g of methyl 2-(benzamido)-4-(benzylthio)benzoate as white solid.

$^1$H-NMR (CDCl$_3$) δ: 3.94 (3H, s), 4.31 (2H, s>, 6.95 (1H, dd, J=8.5, 2.0 Hz), 7.24-7.27 (1H, m), 7.30-7.34 (2H, m), 7.44-7.46 (2H, m), 7.51-7.57 (3H, m), 7.92 (1H, d, J=8.5 Hz), 8.04-8.07 (2H, m), 9.03 (1H, d, J=2.0 Hz), 12.12 (1H, s).

Example 115

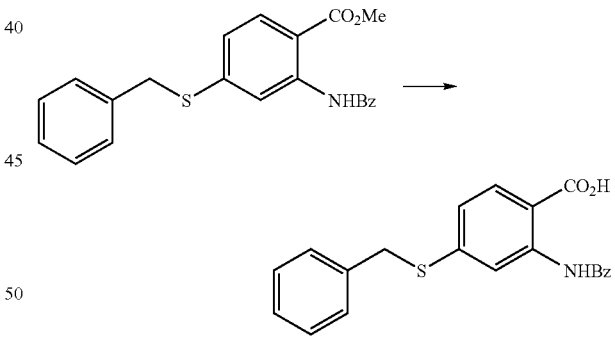

0.43 mL of 2.0 mol/L aqueous sodium hydroxide was added dropwise to a mixed solution of 1.5 mL of methanol and 1.5 mL of tetrahydrofuran containing 0.16 g of methyl 2-(benzamido)-4-(benzylthio)benzoate while ice-cooled and stirred at room temperature for 18 hours. The solvent was evaporated under reduced pressure and water was added and pH was adjusted to pH 4.0 with 1.0 mol/L hydrochloric acid. A solid substance was separated by filtration to obtain 0.14 g of 2-(benzamido)-4-(benzylthio)benzoic acid as white solid.

$^1$H-NMR (DMSO-d$_6$) δ: 4.37 (2H, s), 7.15 (1H, dd, J=8.5, 2.0 Hz), 7.24-7.28 (1H, m), 7.31-7.35 (2H, m), 7.48 (2H, d, J=7.3 Hz), 7.58-7.68 (3H, m), 7.94-7.97 (3H, m), 8.77 (1H, d, J=2.3 Hz), 12.30 (1H, s).

Example 116

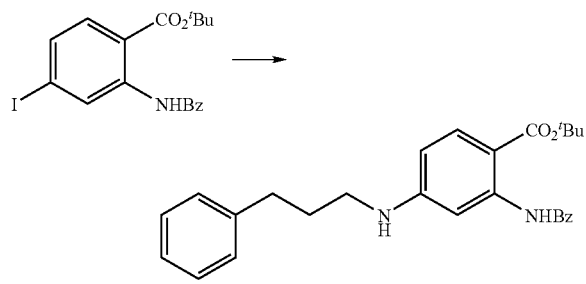

53 mg of tris(dibenzylideneacetone)dipalladium(0) and 0.17 g sodium tert-butoxide were added to 5 mL of toluene solution containing 0.50 g of tert-butyl 2-(benzamido)-4-iodobenzoate, 0.25 mL of 3-phenylpropylamine and 36 mg of rac-2,2'-bis(diphenylphosphino)-1,1-binaphthyl at room temperature and stirred at 80° C. for 7 hours. After the reaction mixture was cooled to room temperature, insoluble were removed by filtration, and the solvent was evaporated under reduced pressure. The obtained residue was purified with silica gel column chromatography [eluent; hexane:ethyl acetate=6:1] to obtain 0.11 g of tert-butyl 2-(benzamido)-4-(3-phenylpropylamino)benzoate as brown oil.

$^1$H-NMR (CDCl$_3$) δ: 1.59 (9H, s), 1.95-2.02 (2H, m), 2.72-2.77 (1H, m), 3.25-3.29 (1H, m), 6.21 (1H, dd, J=8.8, 2.6 Hz), 7.19-7.22 (3H, m), 7.26-7.32 (2H, m), 7.49-7.55 (3H, m), 7.82 (1H, d, J=8.8 Hz), 8.05-8.07 (2H, m), 8.24 (1H, d, J=2.5 Hz), 12.44-12.46 (1H, broad).

Example 117

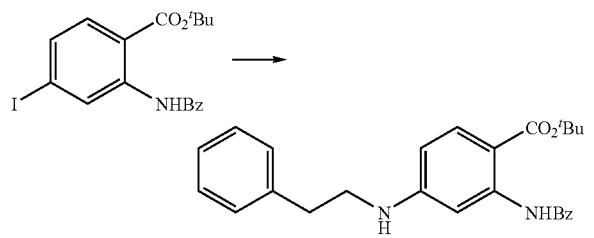

The following compound was obtained in the same manner as in Example 116.

tert-Butyl 2-(benzamido)-4-((2-phenylethyl)amino)benzoate $^1$H-NMR (CDCl$_3$) δ: 1.60 (9H, s), 2.93-2.98 (2H, m), 3.50-3.55 (2H, m), 4.23-4.28 (1H, broad), 6.25 (1H, dd, J=8.8, 2.4 Hz), 7.23-7.27 (3H, m), 7.31-7.35 (2H, m), 7.50-7.55 (3H, m), 7.83 (1H, d, J=8.8 Hz), 8.05-8.07 (2H, m), 8.27 (1H, d, J=2.4 Hz), 12.44-12.48 (1H, broad).

Example 118

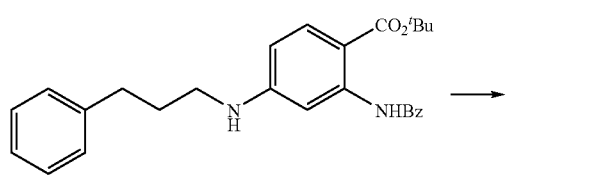

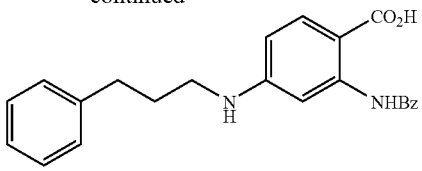

1.0 mL of trifluoroacetic acid solution containing 0.11 g of tert-butyl 2-(benzamido)-4-((3-phenylpropyl)amino)benzoate was stirred at room temperature for 2 hours. The solvent was evaporated under reduced pressure and ethyl acetate and water were added and pH was adjusted to pH 6.3 with a saturated sodium hydrogen carbonate aqueous solution. The organic layer was separated and dried over anhydrous magnesium sulfate after washed with a saturated sodium chloride aqueous solution, and the solvent was evaporated under reduced pressure, Hexane and diisopropyl ether were added to the obtained residue and a solid substance was separated by filtration to obtain 71 mg of 2-(benzamido)-4-((3-phenylpropyl)amino)benzoic acid as white solid.

$^1$H-NMR (DMSO-d$_6$) δ: 1.85-1.92 (2H, m), 2.68-2.72 (2H, m), 3.09-3.14 (2H, m), 6.33 (1H, dd, J=9.0, 2.2 Hz), 6.83-6.86 (1H, m), 7.16-7.32 (5H, m), 7.57-7.66 (3H, m), 7.77 (1H, d, J=9.0 Hz), 7.94-7.96 (2H, m), 8.08 (1H, d, J=2.2 Hz), 12.54-12.58 (1H, broad), 12.65-12.71 (1H, broad).

Example 119

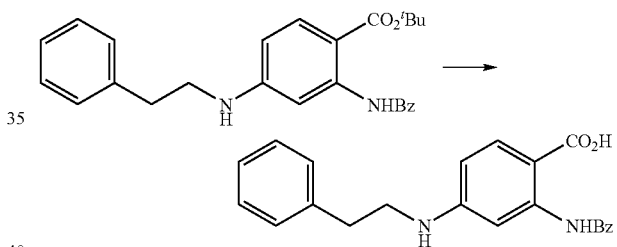

The following compound was obtained in the same manner as in Example 118.

2-(Benzamido)-4-((2-phenylethyl)amino)benzoic acid $^1$H-NMR (DMSO-d$_6$-D$_2$O) δ: 2.87-2.91 (2H, m), 3.32-3.36 (2H, m), 6.39 (1H, dd, J=9.0, 2.1 Hz), 7.21-7.26 (1H, m), 7.32-7.33 (4H, m), 7.57-7.66 (3H, m), 7.79 (1H, d, J=9.0 Hz), 7.94-7.96 (2H, m), 8.11 (1H, d, J=2.1 Hz).

Example 120

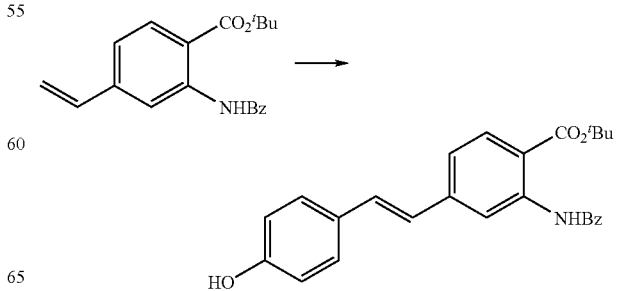

0.12 g of 4-iodophenol, 0.18 mL of tributylamine and 4.2 mg of palladium acetate were added do 2.4 mL of N,N-dimethylacetamide solution containing 0.12 g of tert-butyl 2-(benzamido)-4-vinylbenzoate sequentially at room temperature and stirred under nitrogen atmosphere at 110° C. for 6 hours. After the reaction mixture was cooled to room temperature, 10% citric acid aqueous solution and ethyl acetate were added. The organic layer was separated and dried over anhydrous magnesium sulfate after washed with 10% citric acid aqueous solution, a saturated sodium thiosulfate aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia Chemical Ltd., eluent; hexane:ethyl acetate=1:1] to obtain 0.10 g of tert-butyl 2-(benzamido)-4-((E)-2-(4-hydroxyphenyl)vinyl)benzoate as yellow solid.

$^1$H-NMR (DMSO-d$_6$) δ: 1.56 (9H, s), 6.77-6.83 (2H, m), 7.11 (1H, d, J=15.9 Hz), 7.27 (1H, d, J=15.9 Hz), 7.42 (1H, d, J=8.4 Hz), 7.50-7.55 (2H, m), 7.59-7.69 (3H, m), 7.94 (1H, d, J=8.4 Hz), 7.96-8.01 (2H, m), 8.68-8.72 (1H, m), 9.71 (1H, s), 11.70 (1H, s).

Examples 121, 122

The compounds shown in Table 15 were obtained in the same manner as in Example 120,

TABLE 15

| Example No. | R$^3$ |
|---|---|
| 121 | 2-hydroxyphenyl (structure) |
| 122 | 3,5-dichlorophenyl (structure) | tert-Butyl 2-(benzamido)-4-((E)-2-(2-hydroxyphenyl)vinyl)benzoate $^1$H-NMR (DMSO-d$_6$) δ: 1.57 (9H, s), 6.78-6.93 (2H, m), 7.10-7.18 (1H, m), 7.30 (1H, d, J=16.3 Hz), 7.41 (1H, dd, J=8.4, 1.6 Hz), 7.58-7.70 (5H, m), 7.96 (1H, d, J=8.4 Hz), 7.98-8.02 (2H, m), 8.76 (1H, d, J=1.6 Hz), 9.94 (1H, s), 11.71 (1H, s).

tert-Butyl 2-(benzamido)-4-((E)-2-(3,5-dichlorophenyl(vinyl)benzoate $^1$H-NMR (DMSO-d$_6$) δ: 1.56 (9H, s), 7.36 (1H, d, J=16.4 Hz), 7.49 (1H, dd, J=8.3, 1.2 Hz), 7.53 (1H, t, J=1.8 Hz), 7.56-7.68 (4H, m), 7.82 (2H, d, J=1.7 Hz), 7.97-8.02 (3H, m), 8.74 (1H, d, J=1.4 Hz), 11.65 (1H, s).

Example 123

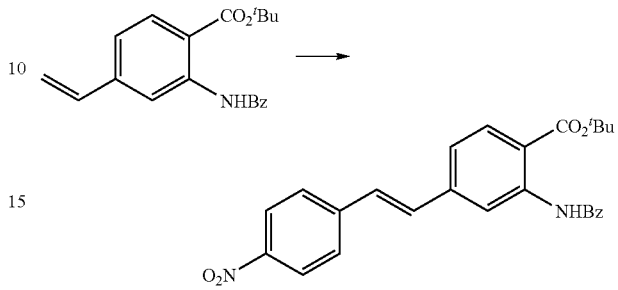

0.14 g of 1-bromo-4-nitrobenzene, 0.22 mL of tributylamine and 5.2 mg of palladium acetate were added to 2.0 mL of N,N-dimethylacetamide solution containing 0.15 g of tert-butyl 2-(benzamido)-4-vinylbenzoate at room temperature and stirred under nitrogen atmosphere at 110° C. for 1 hour and 20 minutes. After the reaction mixture was cooled to room temperature, 10% citric acid aqueous solution and ethyl acetate were added. The organic layer was separated and dried over anhydrous magnesium sulfate after washed with 10% citric acid aqueous solution, a saturated sodium thiosulfate aqueous solution and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane:ethyl acetate=4:1]to obtain 0.15 g of tert-butyl 2-(benzamido)-4-((E)-2-(4-nitrophenyl)vinyl)benzoate as yellow solid.

$^1$H-NMR (DMSO-d$_6$) δ: 1.57 (9H, s), 7.50-7.68 (6H, m), 7.96-8.02 (5H, m), 8.24-8.28 (2H, m), 8.77 (1H, 51, J=1.5 Hz), 11.64 (1H, s).

Example 124

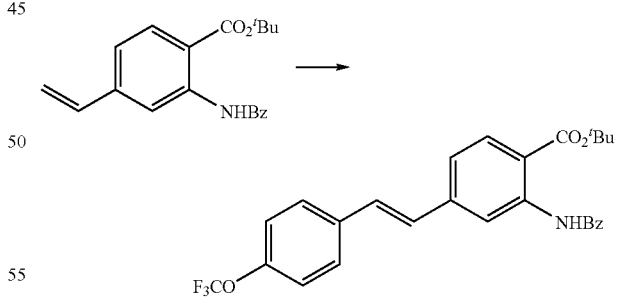

0.10 mL of 1-bromo-4-(trifluoromethoxy)benzene, 0.22 mL of tributylamine and 5.2 mg of palladium acetate were added to 2.0 mL of N,N-dimethylacetamide solution containing 0.15 g of tert-butyl 2-(benzamido)-4-vinylbenzoate at room temperature and stirred under nitrogen atmosphere at 110° C. for 3 hours. After the reaction mixture was cooled to room temperature, 0.07 mL of 1-bromo-4-(trifluoromethoxy) benzene, 0.11 mL of tributylamine and 5.2 mg of palladium acetate were added at room temperature and stirred under nitrogen atmosphere at 110° C. for 2 hours. After the reaction mixture was cooled to room temperature, 10% citric acid aqueous solution and ethyl acetate were added. The organic layer was separated and dried over anhydrous magnesium sulfate after washed with 10% citric acid aqueous solution, a saturated sodium thiosulfate aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia chemical Ltd., eluent; toluene; ethyl acetate=20:1] to obtain 0.10 g of tert-butyl 2-(benzamido)-4-((E)-2-(4-(trifluoromethoxy)phenyl)vinyl)benzoate as white solid.

$^1$H-NMR (DMSO-$d_6$) δ: 1.56 (9H, s), 7.38-7.43 (4H, m), 7.51 (1H, dd, J=8.4, 1.5 Hz), 7.59-7.70 (3H, m), 7.81-7.86 (2H, m), 7.95-8.02 (3H, m), 8.74 (1H, d, J=1.5 Hz), 11.66 (1H, s).

Example 125

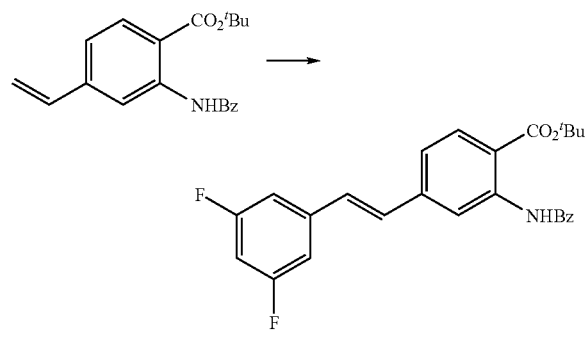

The following compound was obtained in the same manner as in Example 124.

tert-Butyl 2-(benzamido)-4-((E)-2-(3,5-difluorophenyl)vinyl)benzoate $^1$H-NMR (DMSO-$d_6$) δ: 1.56 (9H, s), 7.18 (1H, tt, J=9.3, 2.3 Hz), 7.37 (1H, d, J=16.4 Hz), 7.44-7.54 (4H, m), 7.60-7.70 (3H, m), 7.97-8.01 (3H, m), 8.74 (1H, d, J=1.4 Hz), 11.65 (1H, s).

Example 126

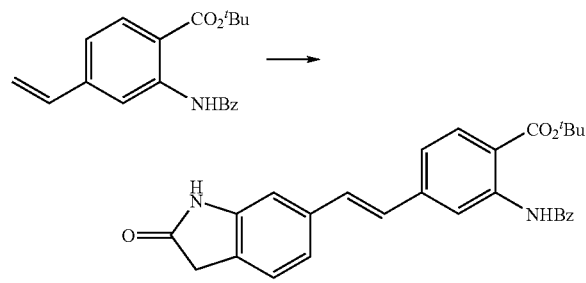

0.20 g of 6-bromo-2-oxoindoline, 0.40 mL of N,N-dicyclohexylmethylamine and 18 mg of trans-di(μ-acetato)bis-o-(di-o-tolylphosphino)benzyl dipalladium(II) were added to 2.0 mL of N,N-dimethylacetamide solution containing 0.46 g of tert-butyl 2-(benzamido)-4-vinylbenzoate at room temperature and stirred under nitrogen atmosphere at 110° C. for 7 hours. After the reaction mixture was cooled to room temperature, a saturated sodium hydrogen carbonate aqueous solution and ethyl acetate were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia chemical Ltd., eluent; hexane:ethyl acetate=1:1] to obtain 0.15 g of tert-butyl 2-(benzamido)-4-((E)-2-(2-oxoindolin-6-yl)vinyl)benzoate as green solid.

$^1$H-NMR (DMSO-$d_6$) δ: 1.56 (9H, s), 3.50 (2H, s), 7.11 (1H, s), 7.21-7.39 (4H, m), 7.50 (1H, dd, J=8.3, 1.5 Hz), 7.59-7.70 (3H, m), 7.95 (1H, d, J=8.3 Hz), 7.97-8.02 (2H, m), 8.69-8.74 (1H, m), 10.50 (1H, s), 11.65 (1H, s).

Example 127

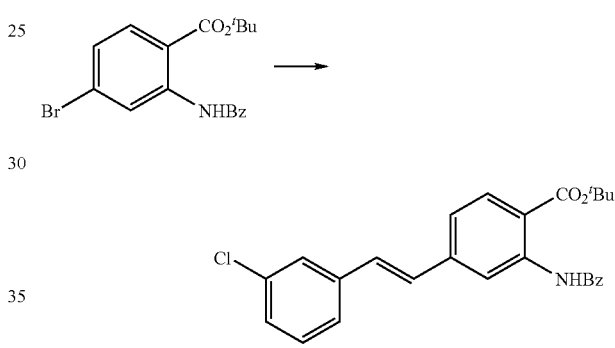

0.076 mL of 3-chlorostyrene, 0.19 mL of tributylamine, 2.9 mg of tri-tert-butylphosphine tetrafluoroborate and 4.5 mg of palladium acetate were added to 2.0 mL of N,N-dimethylacetamide solution containing 0.15 g of tert-butyl 2-(benzamido)-4-bromobenzoate at room temperature and stirred under nitrogen atmosphere at 110° C. for 4 hours and 30 minutes. After the reaction mixture was cooled to room temperature, 0.025 mL of 3-chlorostyrene, 2.9 mg of tri-tert-butylphosphine tetrafluoroborate and 4.5 mg of palladium acetate were added at room temperature and stirred under nitrogen atmosphere at 110° C. for 1 hour and 20 minutes. After the reaction mixture was cooled to room temperature, 10% citric acid aqueous solution and ethyl acetate were added. The organic layer was separated and dried over anhydrous magnesium sulfate after washed with 10% citric acid aqueous solution, a saturated sodium thiosulfate aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia Chemical Ltd., eluent; hexane:ethyl acetate=10:1] to obtain 86 mg of tert-butyl 2-(benzamido)-4-((E)-2-(3-chlorophenyl)vinyl)benzoate as white solid.

$^1$H-NMR (CDCl$_3$) δ: 1.56 (9H, s), 7.13-7.34 (5H, m), 7.40-7.45 (1H, m), 7.52-7.59 (4H, m), 8.01 (1H, d, J=8.3 Hz), 8.06-8.11 (2H, m), 9.16 (1H, d, J=1.7 Hz), 12.27 (1H, s).

Example 128

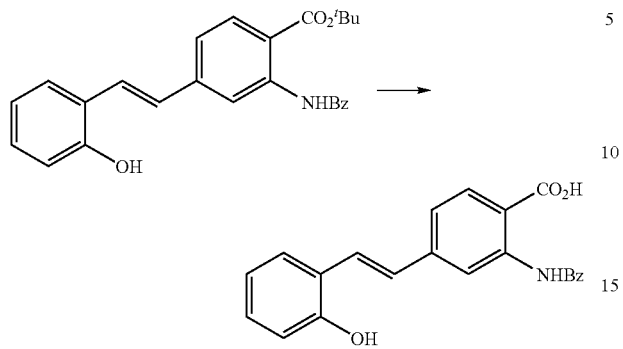

3.0 mL of trifluoroacetic acid suspension containing 0.17 g of tert-butyl 2-(benzamido)-4-((E)-2-(2-hydroxyphenyl)vinyl)benzoate was stirred at room temperature for 30 minutes. The solvent was evaporated under reduced pressure, toluene was added, and the solvent was evaporated under reduced pressure. Hexane was added to the obtained residue and a solid substance was separated by filtration to obtain 0.12 g of 2-(benzamido)-4-((E)-2-(2-hydroxyphenyl)vinyl)benzoic acid as yellow solid.

$^1$H-NMR (DMSO-$d_6$) δ: 6.79-6.94 (2H, m), 7.10-7.19 (1H, m), 7.31 (1H, d, J=16.6 Hz), 7.40 (1H, dd, J=8.4, 1.6 Hz), 7.55-7.70 (5H, m), 7.97-8.02 (2H, m), 8.05 (1H, d, J=8.4 Hz), 8.95 (1H, d, J=1.6 Hz), 9.94 (1H, s), 12.26 (1H, s).

Examples 129 to 135

The compounds shown in Table 16 were obtained in the same manner as in Example 128.

TABLE 16

| Example No. | R$^3$ |
|---|---|
| 129 | 4-nitrophenyl (O$_2$N–C$_6$H$_4$–) |
| 130 | 3,5-difluorophenyl |
| 131 | 4-(trifluoromethoxy)phenyl (F$_3$CO–C$_6$H$_4$–) |
| 132 | 4-hydroxyphenyl (HO–C$_6$H$_4$–) |
| 133 | 6-methyl-2-oxoindolin-6-yl |
| 134 | 3-chlorophenyl |
| 135 | 3,5-dichlorophenyl |

2-(Benzamido)-4-((E)-2-(4-nitrophenyl)vinyl)benzoic acid $^1$H-NMR (DMSO-$d_6$) δ: 7.50-7.70 (6H, m), 7.96-8.03 (4H, m), 8.09 (1H, d, J=8.3 Hz), 8.26 (2H, d, J=8.8 Hz), 8.99 (1H, d, J=1.4 Hz), 12.23 (1H, s).

2-(Benzamido)-4-((E)-2-(3,5-difluorophenyl)vinyl)benzoic acid $^1$H-NMR (DMSO-$d_6$) δ: 7.13-7.22 (1H, m), 7.38 (1H, d, J=16.1 Hz), 7.45-7.70 (7H, m), 7.96-8.02 (2H, m), 8.08 (1H, d, J=8.3 Hz), 8.95 (1H, s).

2-(Benzamido)-4-((E)-2-(4-(trifluoromethoxy)phenyl)vinyl)benzoic acid $^1$H-NMR (DMSO-$d_6$) δ: 7.37-7.44 (4H, m), 7.47-7.53 (1H, m), 7.58-7.70 (3H, m), 7.84 (2H, d, J=8.6 Hz), 7.96-8.02 (2H, m), 8.07 (1H, d, J=8.1 Hz), 8.95 (1H, d, J=1.4 Hz).

2-(Benzamido)-4-((E)-2-(4-hydroxyphenyl)vinyl)benzoic acid $^1$H-NMR (DMSO-$d_6$) δ: 6.80 (2H, d, J=8.5 Hz), 7.12 (1H, d, J=16.3 Hz), 7.29 (1H, d, J=16.3 Hz), 7.42 (1H, dd, J=8.5, 1.6 Hz), 7.53 (2H, d, J=8.5 Hz), 7.58-7.70 (3H, m), 7.96-8.01 (2H, m), 8.03 (1H, d, J=8.5 Hz), 8.89 (1H, d, J=1.6 Hz), 9.72 (1H, s), 12.25 (1H, s), 13.54-13.80 (1H, broad).

2-(Benzamido)-4-((E)-2-(2-oxoindolin-6-yl)vinyl)benzoic acid $^1$H-NMR (DMSO-$d_6$) δ: 3.50 (2H, s), 7.12 (1H, s), 7.21-7.40 (4H, m), 7.49 (1H, dd, J=8.3, 1.4 Hz), 7.58-7.69 (3H, m), 7.96-8.02 (2H, m), 8.05 (1H, d, J=8.3 Hz), 8.91 (1H, d, J=1.4 Hz), 10.50 (1H, s).

2-(Benzamido)-4-((E)-2-(3-chlorophenyl)vinyl)benzoic acid $^1$H-NMR (DMSO-$d_6$) δ: 7.32-7.51 (5H, m), 7.56-7.69 (4H, m), 7.81 (1H, s), 7.94-8.00 (2H, m), 8.05 (1H, d, J=8.0 Hz), 8.93 (1H, d, J=1.2 Hz), 12.23 (1H, s).

2-(Benzamido)-4-((B)-2-(3,5-dichlorophenyl(vinyl)benzoic acid $^1$H-NMR (DMSO-$d_6$) δ: 7.37 (1H, d, J=16.6 Hz), 7.49 (1H, dd, J=8.4, 1.3 Hz), 7.53 (1H, t, J=1.9 Hz), 7.58-7.68 (4H, m), 7.83 (2H, d, J=1.9 Hz), 7.97-8.01 (2H, m), 8.08 (1H, d, J=8.4 Hz), 8.95 (1H, d, J=1.3 Hz), 12.23 (1H, s).

Example 136

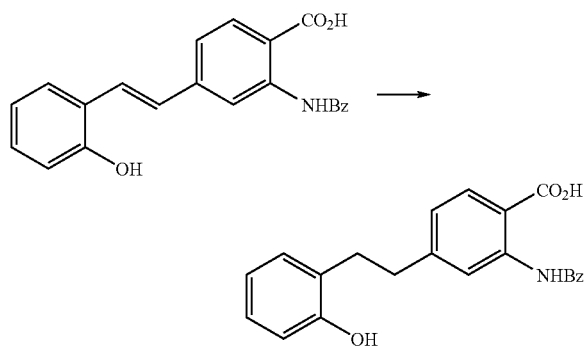

12 mg of 5% palladium-carbon was added to a mixed solution of 1.5 mL of methanol and 1.5 mL of ethyl acetate containing 60 mg of 2-(benzamido)-4-((E)-2-(2-hydroxyphenyl)vinyl)benzoic acid and stirred under hydrogen atmosphere at room temperature for 3 hours and minutes. 6.0 mg of 5% palladium-carbon was added to the reaction mixture and stirred under hydrogen atmosphere at room temperature for 3 hours and 20 minutes. 6.0 mg of 5% palladium-carbon was added to the reaction mixture and stirred under hydrogen atmosphere at room temperature for 2 hours and 40 minutes. Insoluble were removed by filtration and the solvent was evaporated under reduced pressure. Diisopropyl ether was added to the obtained residue and a solid substance was separated by filtration to obtain 47 mg of 2-(benzamido)-4-(2-(2-hydroxyphenyl(ethyl)benzoic acid as white solid.

$^1$H-NMR (DMSO-$d_6$) δ: 2.81-2.94 (4H, m), 6.68-6.72 (1H, m), 6.79-6.82 (1H, m), 6.98-7.12 (3H, m), 7.57-7.68 (3H, m), 7.95-8.01 (3H, m), 8.68 (1H, s), 9.37 (1H, s).

Examples 137 to 139

The compounds shown in Table 17 were obtained in the same manner as in Example 136.

TABLE 17

| Example No. | R³ |
|---|---|
| 137 | 3,5-difluorophenyl |
| 138 | 4-(trifluoromethoxy)phenyl |
| 139 | 4-hydroxyphenyl |

2-(Benzamido)-4-(2-(3,5-difluorophenyl)ethyl)benzoic acid $^1$H-NMR (DMSO-$d_6$) δ: 2.95-3.00 (4H, m), 6.99-7.10 (4H, m), 7.56-7.68 (3H, m), 7.94-8.00 (3H, m), 8.65 (1H, d, J=1.2 Hz).

2-(Benzamido)-4-(2-(4-(trifluoromethoxy)phenyl)ethyl)benzoic acid $^1$H-NMR (DMSO-$d_6$) δ: 2.96 (4H, s), 6.98-7.05 (1H, m), 7.24-7.30 (2H, m), 7.37-7.42 (2H, m), 7.55-7.66 (3H, m), 7.93-8.00 (3H, m), 8.64 (1H, d, J=1.5 Hz).

2-(Benzamido)-4-(2-(4-hydroxyphenyl)ethyl)benzoic acid $^1$H-NMR (DMSO-$d_6$) δ: 2.78-2.85 (2H, m), 2.87-2.95 (2H, m), 6.64-6.69 (2H, m), 7.02-7.08 (3H, m), 7.57-7.68 (3H, m), 7.93-7.99 (3H, m), 8.66 (1H, d, J=1.5 Hz), 9.15 (1H, s), 12.23 (1H, s).

Example 140

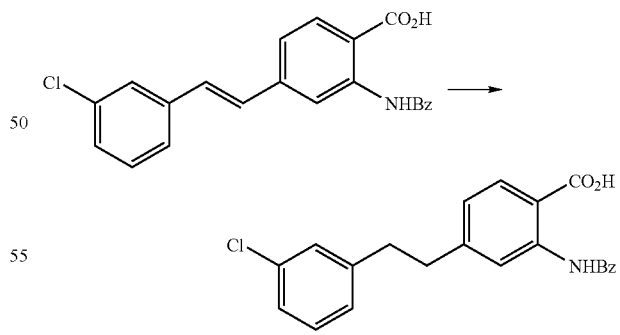

9 mg of 5% palladium-carbon was added to a mixed solution of 2.7 mL of methanol and 2.7 mL of ethyl acetate containing 30 mg of 2-benzamido-4-((E)-2-(3-chlorophenyl)vinyl)benzoic acid and stirred under hydrogen atmosphere at room temperature for 3 hours. Insoluble were removed by filtration and the solvent was evaporated under reduced pressure. The obtained residue was purified with reversed-phase silica gel column chromatography [eluent; 60-100% acetonitrile/0.1% trifluoroacetic acid aqueous solution] to obtain 2.0 mg of 2-(benzamido)-4-(2-(3-chlorophenyl)ethyl)benzoic acid as white solid.

¹H-NMR (DMSO-d₆) δ: 2.91-3.03 (4H, m), 7.09 (1H, dd, J=8.2, 1.5 Hz), 7.22-7.35 (3H, m), 7.37-7.40 (1H, m), 7.57-7.69 (3H, m), 7.94-8.02 (3H, m), 8.67 (1H, d, J=1.5 Hz), 12.22 (1H, s).

Example 141

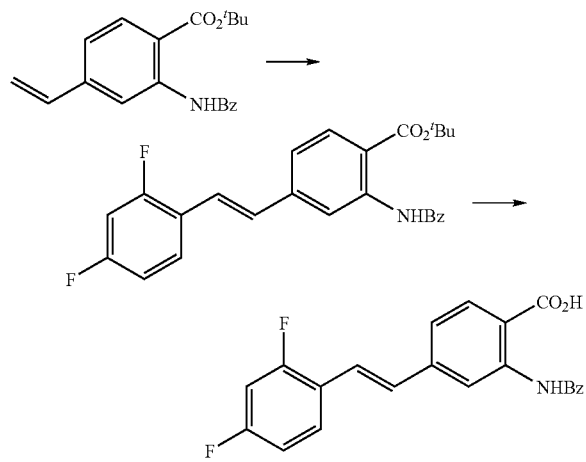

0.030 mL of 2,4-difluoroiodobenzene, 81 mg of cesium carbonate, 12 mg of tetrabutylammonium bromide and 19 mg of polymer supported bis(acetato)triphenylphosphine palladium(II) were added to 1.0 mL of toluene solution containing 40 mg of tert-butyl 2-(benzamido)-4-vinylbenzoate at room temperature and stirred at 110° C. for 24 hours. After the reaction mixture was cooled to room temperature, 19 mg of polymer supported bis(acetato)triphenylphosphine palladium(II) was added and stirred at 110° C. for 24 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. 10 mL of trifluoroacetic acid was added to the obtained residue and stirred at room temperature for 1 hour. The solvent was evaporated under reduced pressure and methanol was added to the obtained residue and a solid substance was separated by filtration to obtain 15 mg of 2-(benzamido)-4-((E)-2-(2,4-difluorophenyl)vinyl)benzoic acid as brown solid.

¹H-NMR (DMSO-d₆) δ: 7.15-7.21 (1H, m), 7.31-7.46 (3H, m), 7.50 (1H, dd, J=8.3, 1.7 Hz), 7.58-7.71 (3H, m), 7.94-8.02 (3H, m), 8.07 (1H, d, J=8.3 Hz), 8.96 (1H, s), 12.24 (1H, s), 13.70-13.90 (1H, broad).

Example 142

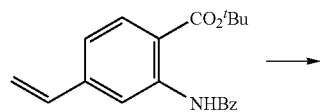

-continued

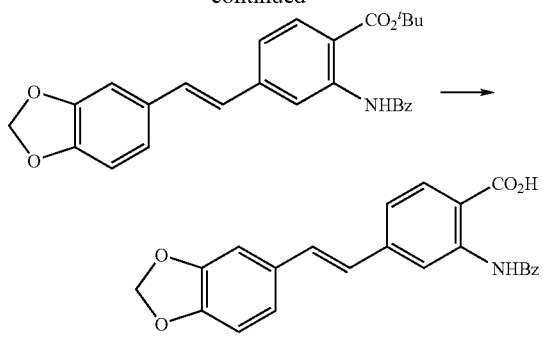

The following compound was obtained in the same manner as in Example 141.

2-(Benzamido)-4-((E)-2-(benzo[1,3]dioxol-5-yl)vinyl)benzoic acid

¹H-NMR (DMSO-d₆) δ: 6.07 (2H, s), 6.95 (1H, d, J=8.1 Hz), 7.14 (1H, dd, J=8.3, 1.5 Hz), 7.23 (1H, d, J=16.4 Hz), 7.32 (1H, d, J=16.4 Hz), 7.41 (1H, d, J=1.7 Hz), 7.44 (1H, dd, J=8.3, 1.7 Hz), 7.58-7.70 (3H, m), 7.95-8.01 (2H, m), 8.04 (1H, d, J=8.3 Hz), 8.90 (1H, d, J=1.5 Hz), 12.25 (1H, s), 13.71 (1H, s).

Example 143

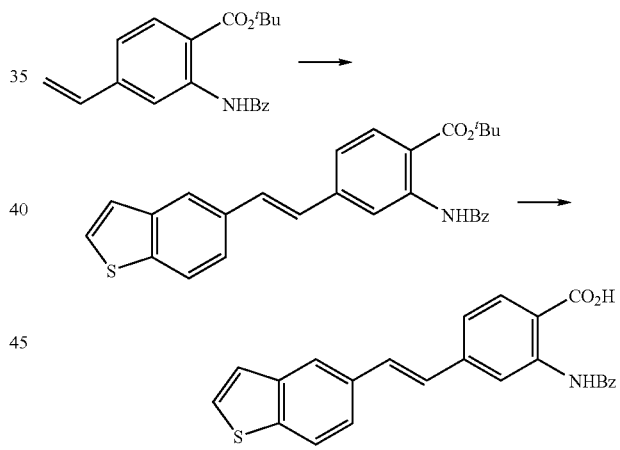

66 mg of 5-bromobenzothiophene, 0.10 g of cesium carbonate, 15 mg of tetrabutylammonium bromide and 24 mg of polymer supported bis(acetato)triphenylphosphine palladium(II) were added to 1.0 mL of toluene solution containing 50 mg of tert-butyl 2-(benzamido)-4-vinylbenzoate at room temperature and stirred at 110° C. for 24 hours. After the reaction mixture was cooled to room temperature, 24 mg of polymer supported bis(acetato)triphenylphosphine palladium(II) was added and stirred at 110° C. for 24 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium, chloride aqueous solution sequentially, and the solvent was evaporated under reduced pressure. 10 mL of trifluoroacetic acid was added, to the obtained residue and stirred at room temperature for 1 hour.

The solvent was evaporated under reduced pressure and methanol was added to the obtained residue and a solid substance was separated by filtration to obtain 26 mg of 2-(benzamido)-4-((d)-2-(benzothiophene-5-yl)vinyl)benzoic acid as white solid.

$^1$H-NMR (DMSO-d$_6$) δ: 7.41-7.70 (7H, m), 7.77 (1H, dd, J=8.5, 1.2 Hz), 7.81 (1H, d, J=5.6 Hz), 7.97-8.10 (4H, m), 8.18 (1H, d, J=1.0 Hz), 8.97 (1H, d, J=1.7 Hz), 12.26 (1H, s), 13.60-13.91 (1H, broad).

Example 144

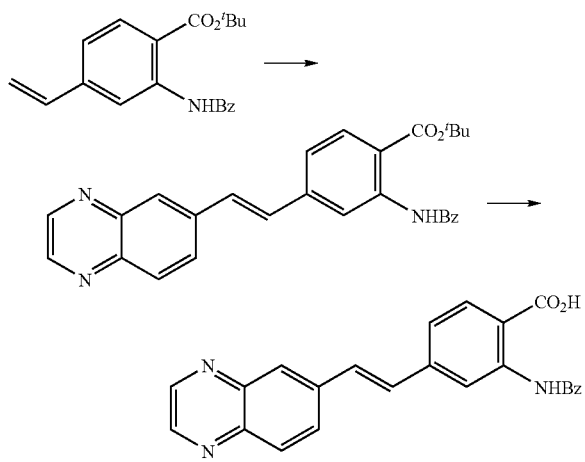

The hollowing compound was obtained in the same manner as in Example 143.

2-(Benzamido)-4-((E)-2-(quinoxalin-6-yl)vinyl)benzoic acid $^1$H-NMR (DMSO-d$_6$) δ: 7.58-7.72 (6H, m), 7.98-8.03 (2H, m), 8.08-8.13 (2H, m), 8.31-8.38 (2H, m), 8.91-9.02 (3H, m), 12.24 (1H, s), 13.70-13.90 (1H, broad).

Example 145

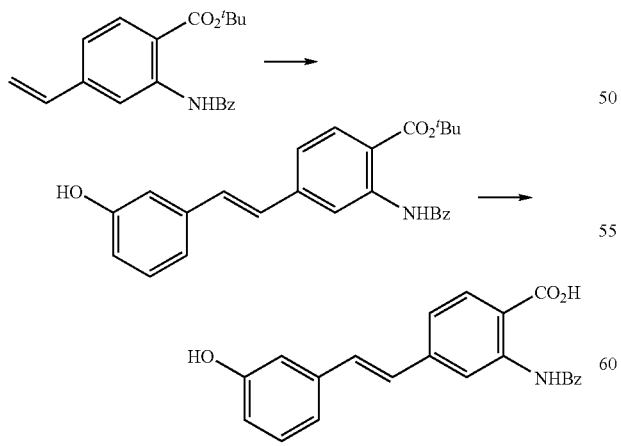

54 mg of 3-iodophenol, 81 mg of cesium carbonate, 12 mg of tetrabutylammonium bromide and 19 mg of polymer supported bis(acetato)triphenylphosphine palladium(II) were added to 1.0 mL of toluene solution containing 40 mg of tert-butyl 2-(benzamido)-4-vinylbenzoate at room temperature and stirred at 110° C. for 24 hours. After the reaction mixture was cooled to room, temperature, 19 mg of polymer supported bis(acetato)triphenylphosphine palladium(II) was added and stirred at 110° C. for 24 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. 10 mL of trifluoroacetic acid was added to the obtained residue and stirred at room temperature for 1 hour. The solvent was evaporated under reduced pressure and the obtained residue was purified with reversed-phase silica gel column chromatography [eluent; 40-90% acetonitrile/0.1% trifluoroacetic acid aqueous solution] to obtain 25 mg of 2-(benzamido)-4-((E)-2-(3-hydroxyphenyl)vinyl)benzoic acid as white solid.

$^1$H-NMR (DMSO-d$_6$) δ: 6.70-6.80 (1H, m), 7.03-7.07 (1H, m), 7.11-7.15 (1H, m), 7.18-7.33 (3H, m), 7.48 (1H, dd, J=8.4, 1.5 Hz), 7.58-7.70 (3H, m), 7.96-8.02 (2H, m), 8.05 (1H, d, J=8.4 Hz), 8.91 (1H, s), 9.50 (1H, s), 12.20-12.35 (1H, broad), 13.65-13.85 (1H, broad).

Example 146

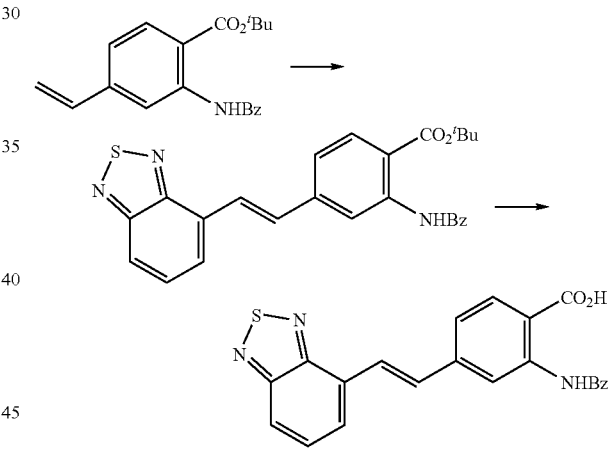

The following compound was obtained in the same manner as in Example 145.

2-(Benzamido)-4-((E)-2-(2,1,3-benzothiadiazol-4-yl)vinyl)benzoic acid $^1$H-NMR (DMSO-d$_6$) δ: 7.56-7.72 (4H, m), 7.80 (1H, dd, J=8.8, 7.1 Hz), 7.87 (1H, d, J=16.4 Hz), 7.98-8.14 (5H, m), 8.21 (1H, d, J=16.4 Hz), 9.06 (1H, s), 12.25-12.45 (1H, broad).

Example 147

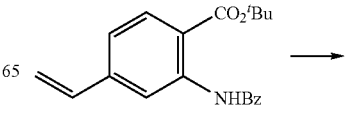

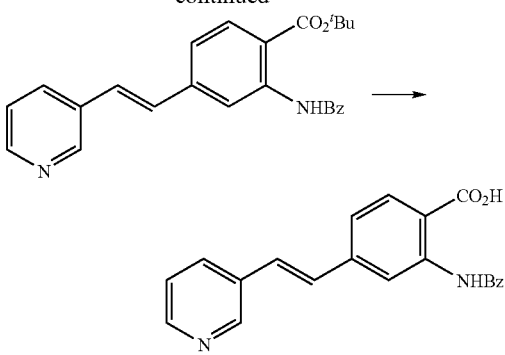

0.030 mL of 3-bromopyridine, 0.10 g of cesium carbonate, 15 mg of tetrabutylammonium bromide and 24 mg of polymer supported bis(acetato)triphenylphosphine palladium(II) were added to 1.0 mL of toluene solution containing 50 mg of tert-butyl 2-(benzamido)-4-vinylbenzoate at room temperature and stirred at 110° C. for 24 hours. After the reaction mixture was cooled to room temperature, 24 mg of polymer supported bis(acetato)triphenylphosphine palladium(11) was added and stirred at 110° C. for 24 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. 10 mL of trifluoroacetic acid was added to the obtained residue and stirred at room temperature for 1 hour. The solvent was evaporated under reduced pressure and the obtained residue was purified with reversed-phase silica gel column chromatography [eluent; 40-90% acetonitrile/0.1% trifluoroacetic acid aqueous solution]. Ethyl acetate and water were added to the obtained purified substance and pH was adjusted to pH 6.0 with a saturated sodium hydrogen carbonate aqueous solution. The organic layer was separated and dried over anhydrous magnesium sulfate after washed with water, and the solvent was evaporated under reduced pressure to obtain 2.3 mg of 2-(benzamido)-4-((E)-2-(pyridin-3-yl)vinyl)benzoic acid as white solid.

$^1$H-NMR (DMSO-$d_6$) δ: 7.39-7.70 (7H, m), 7.97-8.03 (2H, m), 8.08 (1H, d, J=8.3 Hz), 8.17 (1H, dt, J=7.9, 1.9 Hz), 8.51 (1H, dd, J=4.6, 1.5 Hz), 8.86 (1H, d, J=1.9 Hz), 8.96 (1H, d, J=1.5 Hz), 12.25-12.50 (1H, broad).

Example 148

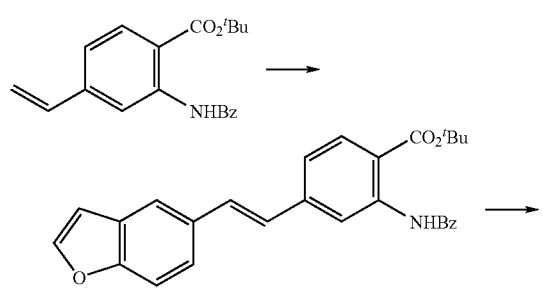

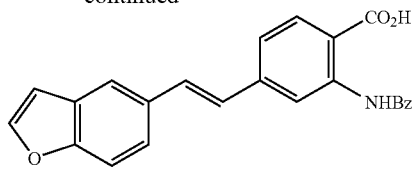

61 mg of 5-benzofuran, 0.10 g of cesium carbonate, 15 mg of tetrabutylammonium bromide and 21 mg of polymer supported bis(acetato)triphenylphosphine palladium(II) were added to 1.0 mL of toluene solution containing 50 mg of tert-butyl 2-(benzamido)-4-vinylbenzoate at room temperature and stirred at 110° C. for 24 hours. After the reaction mixture was cooled to room temperature, 24 mg of polymer supported bis(acetato)triphenylphosphine palladium(II) was added and stirred at 110° C. for 24 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. 10 mL of trifluoroacetic acid was added to the obtained residue and stirred at room temperature for 1 hour. The solvent was evaporated under reduced pressure and the obtained residue was purified with reversed-phase silica gel column chromatography [eluent; 60-100% acetonitrile/0.1% trifluoroacetic acid aqueous solution] to obtain 2.4 mg of 2-(benzamido)-4-((E)-2-(benzofuran-5-yl)vinyl)benzoic acid.

$^1$H-NMR (DMSO-$d_6$) δ: 6.97-7.02 (1H, m), 7.35 (1H, d, J=16.3 Hz), 7.46-7.53 (2H, m), 7.59-7.74 (5H, m), 7.97-8.08 (5H, m), 8.95 (1H, s), 12.29-12.47 (1H, broad).

Example 149

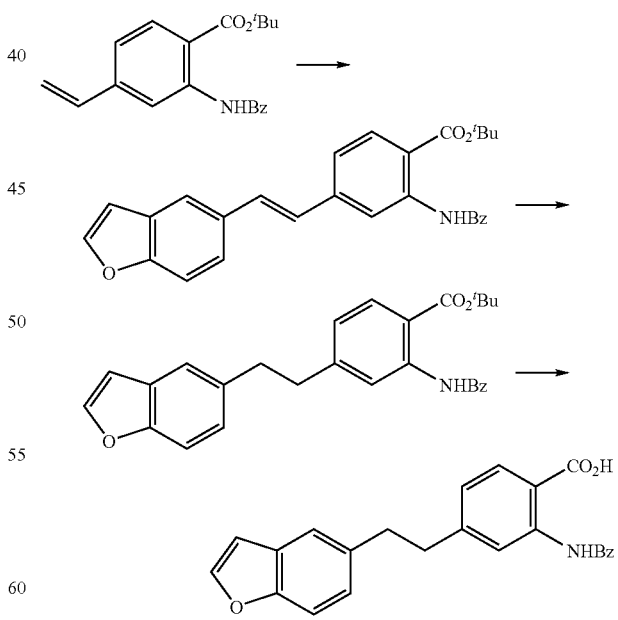

0.12 g of 5-bromobenzofuran, 0.20 g of cesium carbonate, 30 mg of tetrabutylammonium bromide and 48 mg of polymer supported di(acetato)dicyclohexylphenylphosphine palladium(II) were added to 2.0 mL of toluene solution containing 0.10 g of tert-butyl 2-(benzamido)-4-vinylbenzoate at room temperature and stirred at 110° C. for 24 hours. After the reaction mixture was cooled to room temperature, 48 mg of polymer supported di(acetato) dicyclohexylphenyl-phosphine palladium(II) was added and stirred at 110° C. for 24 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. 2.4 mL of tetrahydrofuran, 0.6 mL of water, 0.44 mL of acetic acid, 0.42 g sodium formate and 50 mg of 3.9% palladium-carbon (ethylenediamine complex) were added to the obtained residue and stirred at 50° C. for 12 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. 10 mL of trifluoroacetic acid was added to the obtained residue and stirred at room temperature for 1 hour. The solvent was evaporated under reduced pressure and the obtained residue was purified with reversed-phase silica gel column chromatography [eluent; 60-100% acetonitrile/0.1% trifluoroacetic acid aqueous solution] to obtain 8.6 mg of 2-(benzamido)-4-(2-(benzofuran-5-yl) ethyl)benzoic acid as white solid.

$^1$H-NMR (DMSO-$d_6$) δ: 3.02 (4H, s), 6.89 (1H, dd, J=2.2, 1.0 Hz), 7.09 (1H, dd, J=8.3, 1.7 Hz), 7.22 (1H, dd, J=8.3, 1.6 Hz), 7.49 (1H, d, J=8.3 Hz), 7.53 (1H, d, J=1.7 Hz), 7.57-7.69 (3H, m), 7.92-8.00 (4H, m), 8.69 (1H, d, J=1.6 Hz), 12.25 (1H, s), 13.54-13.79 (1H, broad).

Example 150

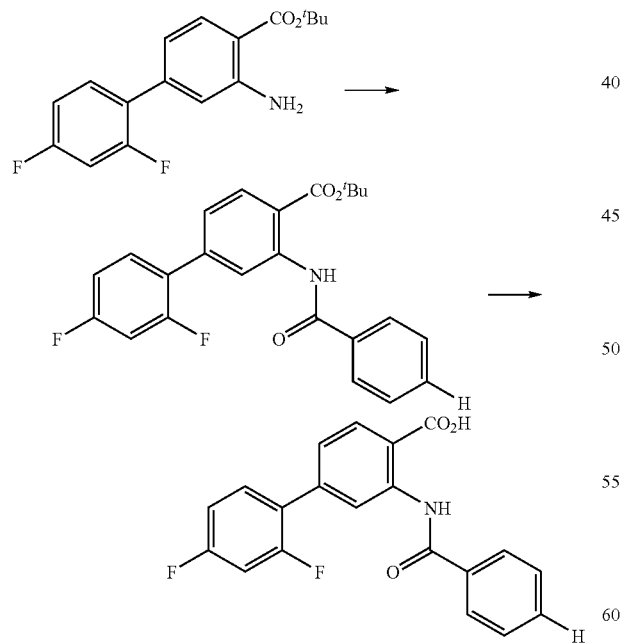

0.055 mL of triethylamine and 0.036 mL of 4-fluorobenzoyl chloride were added to 3.5 mL of methylene chloride solution containing 60 mg of tert-butyl 2-amino-4-(2,4-difluorophenyl)benzoate at room temperature sequentially and stirred at the same temperature for 1 hour. 0.014 mL of triethylamine and 0.012 mL of 4-fluorobenzoyl chloride were added to the reaction mixture at room temperature sequentially and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane: ethyl acetate=4:1] to obtain tert-butyl 4-(2,4-difluorophenyl)-2-(4-fluorobenzamido)benzoate.

10 mL of trifluoroacetic acid was added to the obtained tert-butyl 4-(2,4-difluorophenyl)-2-(4-fluorobenzamido) benzoate and stirred at room temperature for 2 hours. The solvent was evaporated under reduced pressure and diisopropyl ether was added to the obtained residue and a solid substance was separated by filtration to obtain 46 mg of 4-(2,4-difluorophenyl)-2-(4-fluorobenzamido)benzoic acid as white solid.

$^1$H-NMR (DMSO-$d_6$) δ: 7.27 (1H, td, J=8.5, 2.5 Hz), 7.36-7.50 (4H, m), 7.63-7.70 (1H, m), 8.00-8.08 (2H, m), 8.14 (1H, d, J=8.3 Hz), 8.89 (1H, s), 12.24 (1H, s).

Examples 151 to 155

The compounds shown in Table 18 were obtained in the same manner as in Example 150.

TABLE 18

| Example No. | R$^2$ |
|---|---|
| 151 | 5-methyl-1,3-benzodioxole |
| 152 | 2-methylbenzothiazole |
| 153 | 4-(trifluoromethyl)phenyl-methyl |
| 154 | 4-nitrophenyl-methyl |
| 155 | styryl |

2-(Benzo[1,3]dioxole-5-carboxamido)-4-(2,4-difluorophenyl)benzoic acid

¹H-NMR (DMSO-d₆) δ: 6.17 (2H, s), 7.13 (1H, d, J=8.0 Hz), 7.26 (1H, bd, J=8.5, 2.5 Hz), 7.36 (1H, d, J=8.3 Hz), 7.40-7.48 (2H, m), 7.52-7.57 (1H, m), 7.62-7.69 (1H, m), 8.13 (1H, d, J=8.3 Hz), 8.91 (1H, s), 12.10 (1H, s).

2-(Benzothiazole-2-carboxamido)-4-(2,4-difluorophenyl)benzoic acid

¹H-NMR (DMSO-d₆) δ: 7.24-7.32 (1H, m), 7.42-7.50 (2H, m), 7.61-7.73 (3H, m), 8.16-8.23 (2H, m), 8.27-8.32 (1H, m), 8.96-8.98 (1H, m), 13.03 (1H, s).

4-(2,4-Difluorophenyl)-2-(4-(trifluoromethyl)benzamido)benzoic acid

¹H-NMR (DMSO-d₆) δ: 7.23-7.31 (1H, m), 7.38-7.49 (2H, m), 7.64-7.71 (1H, m), 8.00 (2H, d, J=8.3 Hz), 8.13-8.18 (3H, m), 8.88-8.89 (1H, m), 12.32 (1H, s).

4-(2,4-Difluorophenyl)-2-(4-nitrobenzamido)benzoic acid

¹H-NMR (DMSO-d₆) δ: 7.22-7.32 (1H, m), 7.40-7.49 (2H, m), 7.64-7.73 (1H, m), 8.13-8.23 (3H, m), 8.42-8.47 (2H, m), 8.84-8.85 (1H, m), 12.33 (1H, s).

2-Cinnamamido-4-(2,4-difluorophenyl)benzoic acid

¹H-NMR (DMSO-d₆) δ: 6.92 (1H, d, J=15.9 Hz), 7.26 (1H, td, J=8.4, 2.3 Hz), 7.36 (1H, dt, J=8.2, 1.7 Hz), 7.39-7.99 (4H, m), 7.60-7.70 (2H, m), 7.71-7.79 (2H, m), 8.10 (1H, d, J=8.3 Hz), 8.84 (1H, s), 11.40 (1H, s).

Example 156

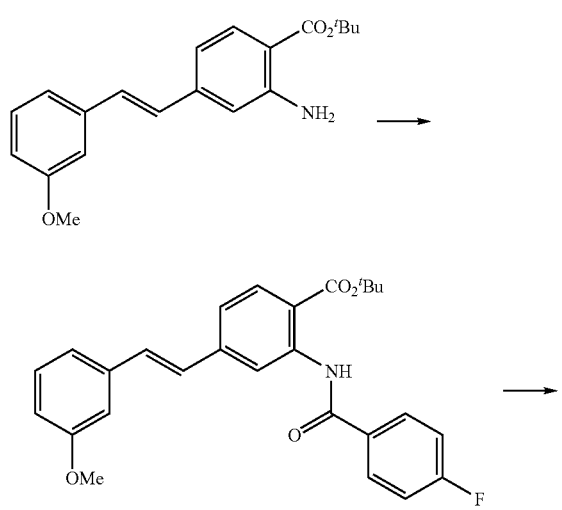

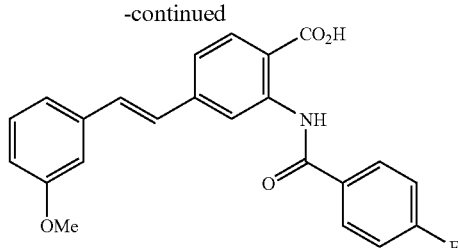

0.056 mL of triethylamine and 0.036 mL of 4-fluorobenzoyl chloride were added to 3.5 mL of methylene chloride solution containing 60 mg of tert-butyl 2-amino-4-((E)-2-(3-methoxyphenyl)vinyl)benzoate at room temperature sequentially and stirred at the same temperature for 1 hour. 0.014 mL of triethylamine and 0.012 mL of 4-fluorobenzoyl chloride were added to the reaction mixture at room temperature sequentially and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(4-fluorobenzamido)-4-((E)-2-(3-methoxyphenyl)vinyl)benzoate.

10 mL of trifluoroacetic acid was added to the obtained tert-butyl 2-(4-fluorobenzamido)-4-((E)-2-(3-methoxyphenyl)vinyl)benzoate and stirred at room temperature for 2 hours. The solvent was evaporated under reduced pressure and diisopropyl ether was added to the obtained residue and a solid substance was separated by filtration to obtain 45 mg of 2-(4-fluorobenzamido)-4-((E)-2-(3-methoxyphenyl)vinyl)benzoic acid as white solid.

¹H-NMR (DMSO-d₆) δ: 3.82 (3H, s), 6.90 (1H, dd, J=7.9, 2.3 Hz), 7.24-7.43 (4H, m), 7.43-7.52 (3H, m), 8.02-8.08 (3H, m), 8.89 (1H, s), 12.22 (1H, s).

Examples 157 to 161

The compounds shown in Table 19 were obtained in the same manner as in Example 156.

TABLE 19

| Example No. | R² |
|---|---|
| 157 | 5-methyl-benzo[1,3]dioxole |
| 158 | 2-methyl-benzothiazole |

TABLE 19-continued

[Structure: MeO-phenyl-CH=CH-phenyl(CO2H)(NH-C(=O)-R²)]

| Example No. | R² |
|---|---|
| 159 | 4-CF₃-phenyl (methyl) |
| 160 | 4-NO₂-phenyl (methyl) |
| 161 | styryl (PhCH=CH-) |

2-(Benzo[1,3]dioxole-5-carboxamido)-4-((E)-2-(3-methoxyphenyl)vinyl)benzoic acid $^1$H-NMR (DMSO-$d_6$) δ: 3.82 (3H, s), 6.17 (2H, s), 6.88-6.91 (1H, m), 7.13 (1H, d, J=8.1 Hz), 7.23-7.43 (5H, m), 7.44-7.49 (2H, m), 7.56 (1H, dd, J=8.3, 1.8 Hz), 8.04 (1H, d, J=8.3 Hz), 8.90 (1H, s), 12.10 (1H, s), 13.60-13.85 (1H, broad).

2-(Benzothiazole-2-carboxamido)-4-((E)-2-(3-methoxyphenyl)vinyl)benzoic acid $^1$H-NMR (DMSO-$d_6$) δ: 3.83 (3H, s), 6.88-6.94 (1H, m), 7.25-7.46 (5H, m), 7.54 (1H, d, J=7.9 Hz), 7.61-7.73 (2H, m), 8.09 (1H, d, J=7.9 Hz), 8.20 (1H, d, J=7.8 Hz), 8.30 (1H, d, J=7.8 Hz), 8.96 (1H, s).

4-((E)-2-(3-methoxyphenyl)vinyl)-2-(4-(trifluoromethyl)benzamido)benzoic acid $^1$H-NMR (DMSO-$d_6$) δ: 3.82 (3H, s), 6.88-6.92 (1H, m), 7.24-7.44 (5H, m), 7.39 (2H, d, J=4.9 Hz), 7.52 (1H, dd, J=8.3, 1.4 Hz), 8.01 (2H, d, J=8.2 Hz), 8.07 (1H, d, S=8.3 Hz), 8.18 (2H, d, J=8.2 Hz), 8.88 (1H, d, J=1.4 Hz), 12.30 (1H, s).

4-((E)-2-(3-methoxyphenyl)vinyl)-2-(4-nitrobenzamido)benzoic acid $^1$H-NMR (DMSO-$d_6$) δ: 3.82 (3H, s), 6.90 (1H, dd, J=7.7, 1.8 Hz), 7.20-7.46 (5H, m), 7.54 (1H, dd, J=8.3, 1.6 Hz), 8.07 (1H, d, J=8.3 Hz), 8.17-8.24 (2H, m), 8.46 (2H, d, J=8.8 Hz), 8.85 (1H, d, J=1.6 Hz), 12.32 (1H, s).

2-cinnamamido-4-((E)-2-(3-methoxyphenyl)vinyl)benzoic acid $^1$H-NMR (DMSO-$d_6$) δ: 3.82 (3H, s), 6.86-6.96 (2H, m), 7.22-7.40 (5H, m), 7.42-7.50 (4H, m), 7.65 (1H, d, J=15.6 Hz), 7.72-7.79 (2H, m), 8.01 (1H, d, J=8.3 Hz), 8.82 (1H, s), 11.38 (1H, s).

Example 162

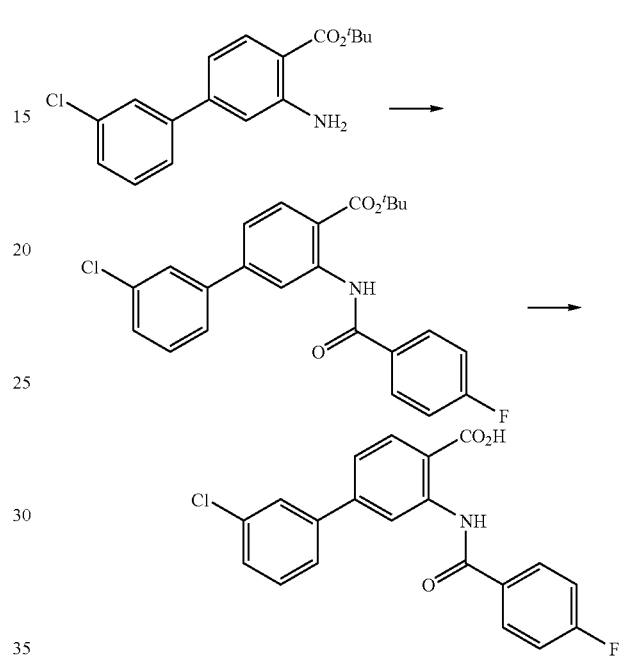

0.055 mL of triethylamine and 0.036 mL of 4-fluorobenzoyl chloride were added to 3.5 mL of methylene chloride solution containing 60 mg of tert-butyl 2-amino-4-(3-chlorophenyl)benzoate at room temperature sequentially and stirred at the same temperature for 1 hour. 0.014 mL of triethylamine and 0.012 mL of 4-fluorobenzoyl chloride were added to the reaction mixture at room temperature sequentially and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain, tert-butyl 4-(3-chlorophenyl)-2-(4-fluorobenzamido)benzoate.

10 mL of trifluoroacetic acid was added to the obtained tert-butyl 4-(3-chlorophenyl)-2-(4-fluorobenzamido)benzoate and stirred at room temperature for 2 hours. The solvent was evaporated under reduced pressure and diisopropyl ether was added to the obtained residue and a solid substance was separated by filtration to obtain 59 mg of 4-(3-chlorophenyl)-2-(4-fluorobenzamido)benzoic acid as white solid.

$^1$H-NMR (DMSO-$d_6$) δ: 7.46 (2H, t, J=8.8 Hz), 7.51-7.62 (3H, m), 7.68-7.74 (1H, m), 7.76 (1H, s), 8.05 (2H, dd, J=8.8, 5.4 Hz), 8.14 (1H, d, J=8.3 Hz), 9.01 (1H, d, J=1.7 Hz), 12.20 (1H, s).

Examples 163 to 167

The compounds shown in Table 20 were obtained in the same manner as in Example 162.

TABLE 20

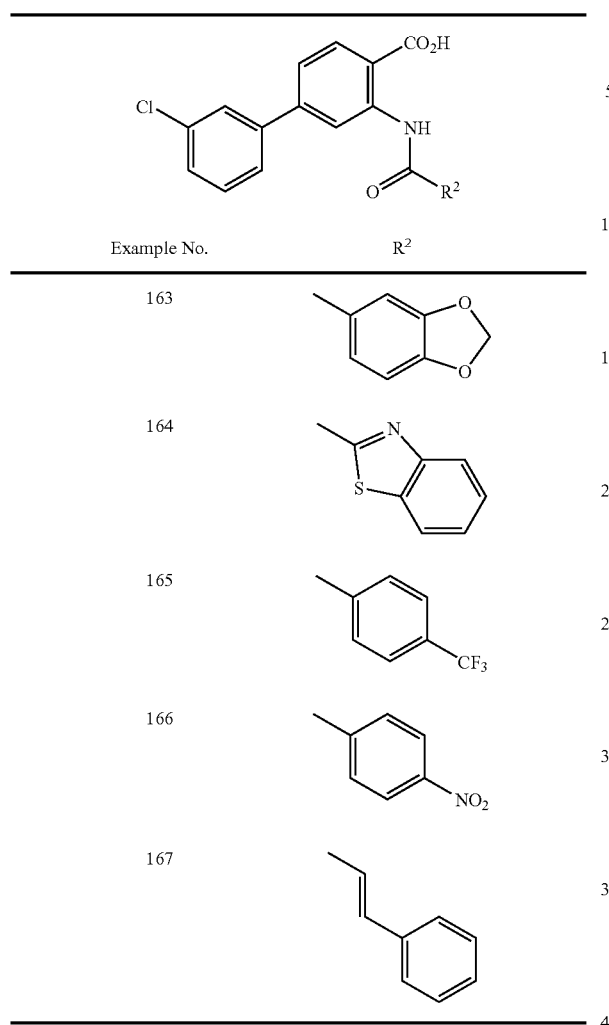

| Example No. | R² |
|---|---|
| 163 | 5-methyl-benzo[1,3]dioxole |
| 164 | 2-benzothiazolyl |
| 165 | 4-CF₃-phenyl |
| 166 | 4-NO₂-phenyl |
| 167 | styryl (PhCH=CH–) |

2-(Benzo[1,3]dioxole-5-carboxamido)-4-(3-chlorophenyl)benzoic acid

¹H-NMR (DMSO-d₆) δ: 6.17 (2H, s), 7.14 (1H, d, J=8.3 Hz), 7.45 (1H, d, J=1.7 Hz), 7.51-7.60 (4H, m), 7.70 (1H, d, J=7.6 Hz), 7.76 (1H, s), 8.13 (1H, d, J=8.3 Hz), 9.02 (1H, d, J=1.7 Hz), 12.13 (1H, s).

2-(Benzothiazole-2-carboxamido)-4-(3-chlorophenyl)benzoic acid

¹H-NMR (DMSO-d₆) δ: 7.52-7.80 (7H, m), 8.15-8.23 (2H, m), 8.30 (1H, d, J=8.0 Hz), 9.07 (1H, d, J=1.7 Hz), 13.03 (1H, s).

4-(3-Chlorophenyl)-2-(4-(trifluoromethyl)benzamido)benzoic acid

¹H-NMR (DMSO-d₆) δ: 7.52-7.62 (3H, m), 7.71 (1H, dt, J=7.5, 1.6 Hz), 7.77 (1H, t, J=1.6 Hz), 8.01 (2H, d, J=8.2 Hz), 8.15 (1H, d, J=8.3 Hz), 8.18 (2H, d, J=8.2 Hz), 8.99 (1H, d, J=2.0 Hz), 12.30 (1H, s).

4-(3-Chlorophenyl)-2-(4-nitrobenzamido)benzoic acid

¹H-NMR (DMSO-d₆) δ: 7.51-7.66 (3H, m), 7.71 (1H, d, J=7.6 Hz), 7.78 (1H, s), 8.15 (1H, d, J=8.3 Hz), 8.21 (2H, d, J=8.8 Hz), 8.45 (2H, d, J=8.8 Hz), 8.96 (1H, d, J=1.5 Hz), 12.32-12.42 (1H, broad).

4-(3-Chlorophenyl)-2-cinnamamidobenzoic acid

¹H-NMR (DMSO-d₆) δ: 6.94 (1H, d, J=15.6 Hz), 7.40-7.49 (3H, m), 7.50-7.60 (5H, m), 7.62-7.79 (5H, m), 8.10 (1H, d, J=8.3 Hz), 8.96 (1H, d, 1=1.7 Hz), 11.40 (1H, s)

Example 168

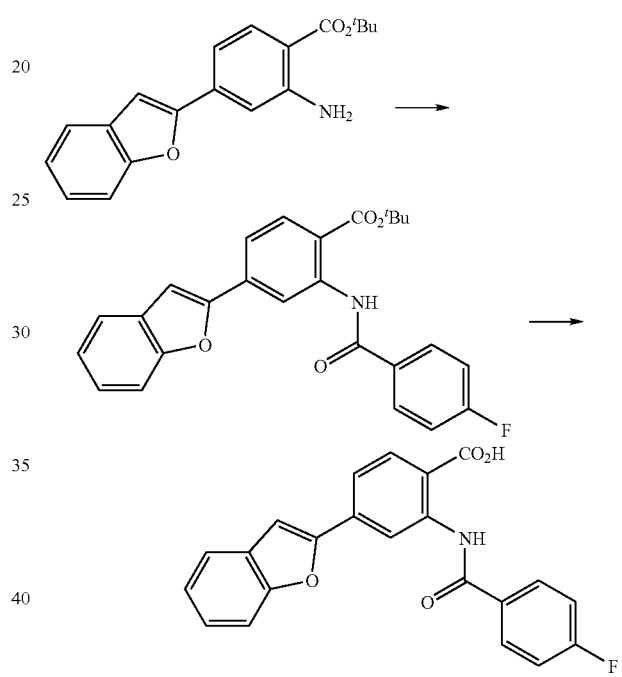

0.054 mL of triethylamine and 0.035 mL of 4-fluorobenzoyl chloride were added to 3.5 mL of methylene chloride solution containing 60 mg of tert-butyl 2-amino-4-(benzofuran-2-yl)benzoate at room temperature sequentially and stirred at the same temperature for 5 hours. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-(benzofuran-2-yl)-2-(4-fluorobenzamido)benzoate.

10 mL of trifluoroacetic acid was added to the obtained tert-butyl 4-(benzofuran-2-yl)-2-(4-fluorobenzamido)benzoate and stirred at room temperature for 2 hours. The solvent was evaporated under reduced pressure and diisopropyl ether was added to the obtained residue and a solid substance was separated by filtration to obtain 52 mg of 4-(benzofuran-2-yl)-2-(4-fluorobenzamido)benzoic acid as while solid.

¹H-NMR (DMSO-d₆) δ: 7.28-7.35 (1H, m), 7.38-7.42 (1H, m), 7.44-7.52 (2H, m), 7.63 (1H, s), 7.70-7.81 (3H, m), 8.04-8.11 (2H, m), 8.16 (1H, d, J=8.3 Hz), 9.26-9.27 (1H, m), 12.26 (1H, s).

Examples 169 to 172

The compounds shown in Table 21 were obtained in the same manner as in Example 168.

TABLE 21

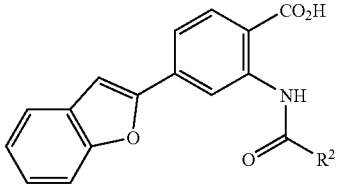

| Example No. | R² |
|---|---|
| 169 | 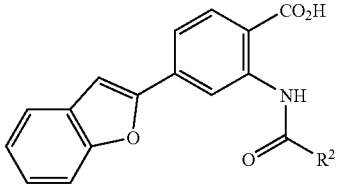 |
| 170 | 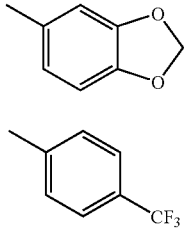 |
| 171 | 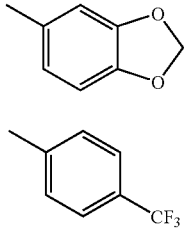 |
| 172 | 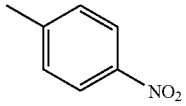 |

2-(Benzo[1,3]dioxole-5-carboxamido)-4-(benzofuran-2-yl)benzoic acid $^1$H-NMR (DMSO-d$_6$) δ: 6.18 (2H, s), 7.15 (1H, d, J=8.0 Hz), 7.28-7.35 (1H, m), 7.37-7.44 (1H, m), 7.47 (1H, d, J=1.7 Hz), 7.58 (1H, dd, J=8.2, 1.7 Hz), 7.62 (1H, s), 7.70-7.79 (3H, m), 8.15 (1H, d, J=8.2 Hz), 9.28 (1H, d, J=1.7 Hz), 12.18 (1H, s).

4-(Benzofuran-2-yl)-2-(4-(trifluoromethyl)benzamido)benzoic acid $^1$H-NMR (DMSO-d$_6$) δ: 7.29-7.35 (1H, m), 7.39-7.43 (1H, m), 7.63 (1H, d, J=0.9 Hz), 7.70-7.76 (2H, m), 7.80 (1H, dd, J=8.4, 1,7 Hz), 8.01 (2H, d, J=8.2 Hz), 8.15 (1H, d, J=8.4 Hz), 8.19 (2H, d, J=8.2 Hz), 9.24-9.26 (1H, m), 12.37 (1H, s).

4-(Benzofuran-2-yl)-2-(4-nitrobenzamido)benzoic acid $^1$H-NMR (DMSO-d$_6$) δ: 7.29-7.34 (1H, m), 7.37-7.43 (1H, m), 7.63 (1H, s), 7.70-7.74 (2H, m), 7.81 (1H, dd, J=8.4, 1.7 Hz), 8.16 (1H, d, J=8.4 Hz), 8.22 (2H, d, J=8.8 Hz), 8.45 (2H, d, J=8.8 Hz), 9.21 (1H, d, S=1.7 Hz), 12.40 (1H, s).

4-(Benzofuran-2-yl)-2-(cinnamamido)benzoic acid $^1$H-NMR (DMSO-d$_6$) δ: 6.95 (1H, d, J=15.4 Hz), 7.29-7.34 (1H, m), 7.37-7.50 (4H, m), 7.60 (1H, s), 7.66-7.81 (6H, m), 8.12 (1H, d, J=8.3 Hz), 9.21 (1H, d, J=1.7 Hz), 11.47 (1H, s).

Example 173

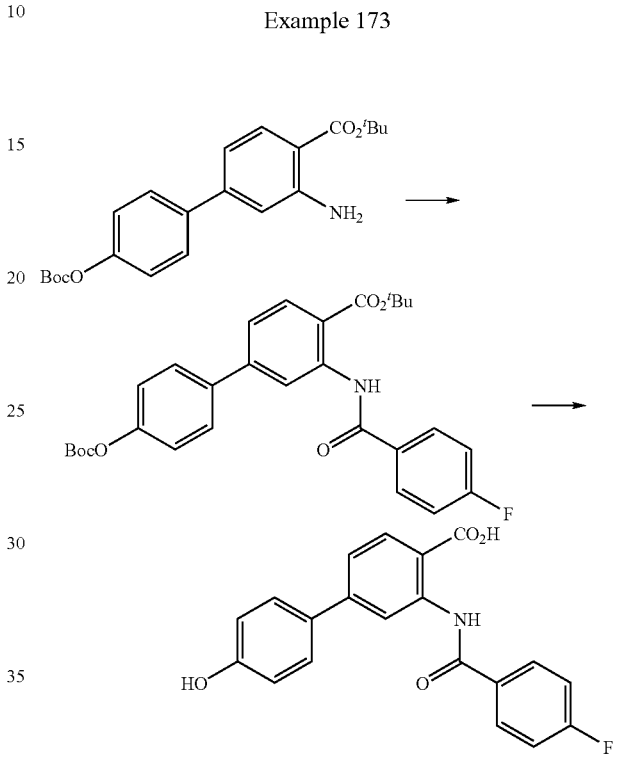

0.041 mL of triethylamine and 0.028 mL of 4-fluorobenzoyl chloride were added to 3.5 mL of methylene chloride solution containing 60 mg tert-butyl 2-amino-4-(4-tert-butoxycarbonyl)oxyphenyl)benzoate at room temperature sequentially and stirred at the same temperature for 5 hours. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=4:1]to obtain tert-butyl 4-(4-(tert-butoxycarbonyl)oxyphenyl)-2-(4-fluorobenzamido)benzoate.

10 mL of trifluoroacetic acid was added to the obtained tert-butyl 4-(4-(tert-butoxycarbonyl)oxyphenyl)-2-(4-fluorobenzamido)benzoate and stirred at room temperature for 2 hours. The solvent was evaporated under reduced pressure and diisopropyl ether was added to the obtained residue and a solid substance was separated by filtration to obtain 49 mg of 4-(4-hydroxyphenyl)-2-(4-fluorobenzamido)benzoic acid as white solid.

$^1$H-NMR (DMSO-d$_6$) δ: 6.92 (2H, d, J=8.8 Hz), 7.42-7.50 (3H, m), 7.58 (2H, d, J=8.8 Hz), 8.00-8.10 (3H, m), 8.98 (1H, d, J=1.7 Hz), 9.79 (1H, s), 12.24 (1H, s).

Examples 174 to 178

The compounds shown in Table 22 were obtained in the same mannan as in Example 173.

TABLE 22

[Structure: 4-(4-hydroxyphenyl)benzoic acid with 2-NH-C(=O)-R² substituent]

| Example No. | R² |
|---|---|
| 174 | [methylbenzo[1,3]dioxole-5-yl] |
| 175 | [benzothiazol-2-yl] |
| 176 | [4-(trifluoromethyl)phenyl] |
| 177 | [4-nitrophenyl] |
| 178 | [(E)-styryl] |

2-(Benzo[1,3]dioxole-5-carboxamido)-4-(4-hydroxyphenyl)benzoic acid

¹H-NMR (DMSO-d₆) δ: 6.17 (2H, s), 6.91 (2H, d, J=8.8 Hz), 7.13 (1H, d, J=8.4 Hz), 7.42 (1H, dd, J=8.4, 1.8 Hz), 7.45 (1H, d, J=1.8 Hz), 7.52-7.61 (3H, m), 8.07 (1H, d, J=8.3 Hz), 8.99 (1H, d, J=1.6 Hz), 9.78 (1H, s), 12.14 (1H, s), 13.55-13.85 (1H, broad).

2-(Benzothiazole-2-carboxamido)-4-(4-hydroxyphenyl)benzoic acid

¹H-NMR (DMSO-d₆) δ: 6.93 (2H, d, J=8.7 Hz), 7.52 (1H, dd, J=8.4, 1.8 Hz), 7.58-7.72 (4H, m), 8.11 (1H, d, J=8.4 Hz), 8.17-8.23 (1H, m), 8.28-8.33 (1H, m), 9.03 (1H, d, J=1.9 Hz), 9.81 (1H, s), 13.05 (1H, s), 13.60-14.00 (1H, broad).

4-(4-Hydroxyphenyl)-2-(4-(trifluoromethyl)benzamido)benzoic acid

¹H-NMR (DMSO-d₆) δ: 6.90-6.96 (2H, m), 7.48 (1H, dd, J=8.5, 1.8 Hz), 7.56-7.63 (2H, m), 8.01 (2H, d, J=8.2 Hz), 8.09 (1H, d, J=8.5 Hz), 8.17 (2H, d, J=8.2 Hz), 8.97 (1H, d, J=1.8 Hz), 9.70-9.90 (1H, broad), 12.34 (1H, s).

4-(4-Hydroxyphenyl)-2-(4-nitrobenzamido)benzoic acid

¹H-NMR (DMSO-d₆) δ: 6.90-6.95 (2H, m), 7.49 (1H, dd, J=8.3, 1.9 Hz), 7.56-7.62 (2H, m), 8.09 (1H, d, J=8.3 Hz), 8.17-8.23 (2H, m), 8.41-8.48 (2H, m), 8.94 (1H, d, J=1.9 Hz), 9.80 (1H, s), 12.35 (1H, s).

2-(Cinnamamido)-4-(4-hydroxyphenyl)benzoic acid

¹H-NMR (DMSO-d₆) δ: 6.88-6.95 (3H, m), 7.38-7.48 (4H, m), 7.53-7.59 (2H, m), 7.65 (1H, d, J=15.6 Hz), 7.72-7.78 (2H, m), 8.04 (1H, d, J=8.6 Hz), 8.92 (1H, d, J=2.0 Hz), 9.77 (1H, s), 11.43 (1H, s), 13.45-13.70 (1H, broad).

Example 179

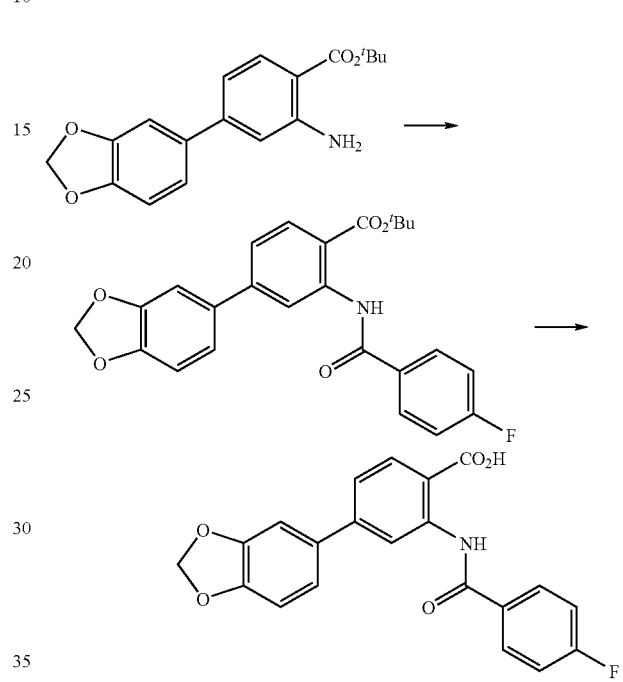

0.054 mL of triethylamine and 0.034 mL of 4-fluorobenzoyl chloride were added to 3.5 mL of methylene chloride solution containing 60 mg of tert-butyl 2-amino-4-(benzo[1,3]dioxol-5-yl)benzoate at room temperature sequentially and stirred at the same temperature for 5 hours. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-(benzo[1,3]dioxol-5-yl)-2-(4-fluorobenzamido)benzoate.

10 mL of trifluoroacetic acid was added to the obtained tert-butyl 4-(benzo[1,3]dioxol-5-yl)-2-(4-fluorobenzamido)benzoate and stirred at room temperature for 2 hours. The solvent was evaporated under reduced pressure and diisopropyl ether was added to the obtained residue and a solid substance was separated by filtration to obtain 39 mg of 4-(benzo[1,3]dioxol-5-yl)-2-(4-fluorobenzamido)benzoic acid as white solid.

¹H-NMR (DMSO-d₆) δ: 6.11 (2H, s), 7.08 (1H, d, J=8.0 Hz), 7.23 (1H, dd, J=8.0, 1.9 Hz), 7.29 (1H, d, J=1.9 Hz), 7.43-7.50 (3H, m), 8.00-8.16 (3H, m), 8.96 (1H, d, J=1.9 Hz), 12.20 (1H, s).

Examples 180 to 183

The compounds shown in Table 23 were obtained in the same manner as in Example 179.

TABLE 23

[Structure: benzo[1,3]dioxol-5-yl-benzoic acid with NH-C(=O)-R²]

| Example No. | R² |
|---|---|
| 180 | 6-methylbenzo[1,3]dioxol-5-yl |
| 181 | 2-methylbenzothiazol-5-yl |
| 182 | 4-(trifluoromethyl)phenyl |
| 183 | (E)-styryl (cinnamyl) |

2-(Benzo[1,3]dioxole-5-carboxamido)-4-(benzo[1,3]dioxol-5-yl)benzoic acid

¹H-NMR (DMSO-d₆) δ: 6.11 (2H, s), 6.17 (2H, s), 7.07 (1H, d, J=8.2 Hz), 7.13 (1H, d, J=8.2 Hz), 7.23 (1H, dd, J=8.2, 1.9 Hz), 7.28 (1H, d, J=1.9 Hz), 7.42-7.47 (2H, m), 7.55 (1H, dd, J=8.3, 1.9 Hz), 8.07 (1H, d, J=8.3 Hz), 8.97 (1H, d, J=2.0 Hz), 12.12 (1H, s), 13.65-13.85 (1H, broad).

4-(Benzo[1,3]dioxol-5-yl)-2-(benzothiazole-2-carboxamido)benzoic acid

¹H-NMR (DMSO-d₆) δ: 6.12 (2H, s), 7.09 (1H, d, J=8.0 Hz), 7.22-7.28 (1H, m), 7.31 (1H, d, J=1.5 Hz), 7.51-7.57 (1H, m), 7.60-7.75 (2H, m), 8.12 (1H, d, J=7.8 Hz), 8.16-8.24 (1H, m), 8.30 (1H, d, J=7.8 Hz), 9.02 (1H, s), 13.02 (1H, s).

4-(Benzo[1,3]dioxol-5-yl)-2-(4-(trifluoromethyl)benzamido)benzoic acid

¹H-NMR (DMSO-d₆) δ: 6.11 (2H, s), 7.08 (1H, d, J=8.1 Hz), 7.24 (1H, dd, J=8.1, 1.8 Hz), 7.30 (1H, d, J=1.8 Hz), 7.50 (1H, dd, J=8.4, 1.9 Hz), 8.01 (2H, d, J=8.3 Hz), 8.09 (1H, d, J=8.4 Hz), 8.17 (2H, d, J=8.3 Hz), 8.95 (1H, d, J=1.9 Hz), 12.35 (1H, s).

4-(Benzo[1,3]dioxol-5-yl)-2-(cinnamamido)benzoic acid

¹H-NMR (DMSO-d₆) δ: 6.11 (2H, s), 6.92 (1H, d, J=15.6 Hz), 7.07 (1H, d, J=8.1 Hz), 7.21 (1H, dd, J=8.1, 1.9 Hz), 7.27 (1H, d, J=1.9 Hz), 7.41-7.49 (4H, m), 7.65 (1H, d, J=15.6 Hz), 7.72-7.78 (2H, m), 8.04 (1H, d, J=8.3 Hz), 8.90 (1H, d, J=2.0 Hz), 11.43 (1H, s).

Example 184

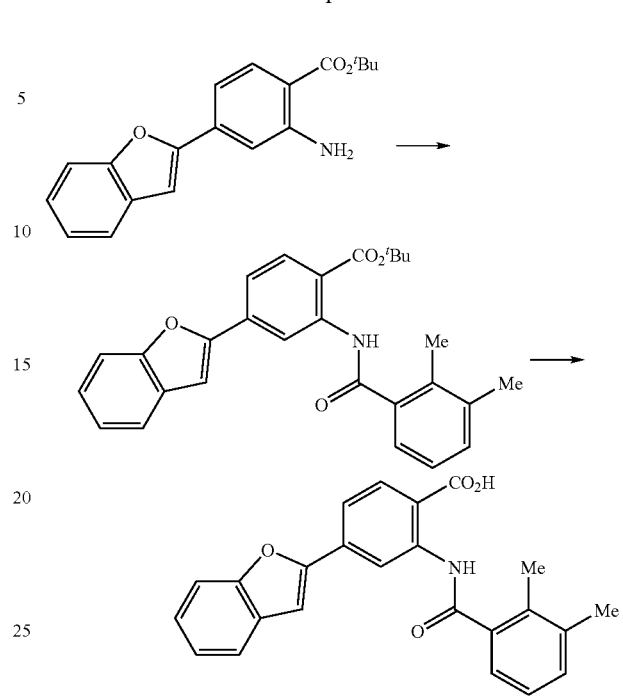

1.7 mL of methylene chloride, 1.0 μL of N,N-dimethylformamide and 0.025 mL of oxalyl chloride were added to 41 mg of 2,3-dimethylbenzoic acid at room temperature sequentially and stirred at the same temperature for 1 hour. The reaction mixture was added to a mixed solution of 2.8 mL of methylene chloride and 0.36 mL of triethylamine containing 50 mg of tert-butyl 2-amino-4-(benzofuran-2-yl)benzoate and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-(benzofuran-2-yl)-2-(2,3-dimethylbenzamido)benzoate.

10 mL of trifluoroacetic acid was added to the obtained tert-butyl 4-(benzofuran-2-yl)-2-(2,3-dimethylbenzamido)benzoate and stirred at room temperature for 2 hours. The solvent was evaporated under reduced pressure and ethyl acetate was added to the obtained residue and a solid substance was separated by filtration to obtain 15 mg of 4-(benzofuran-2-yl)-2-(2,3-dimethylbenzamido)benzoic acid as white solid.

¹H-NMR (DMSO-d₆) δ: 2.33 (3H, s), 2.35 (3H, s), 7.25 (1H, t, J=7.6 Hz), 7.29-7.46 (4H, m), 7.64 (1H, s), 7.71-7.76 (2H, m), 7.78 (1H, dd, J=8.3, 1.7 Hz), 8.13 (1H, d, J=8.3 Hz), 9.26-9.28 (1H, m), 11.65 (1H, s).

Example 185

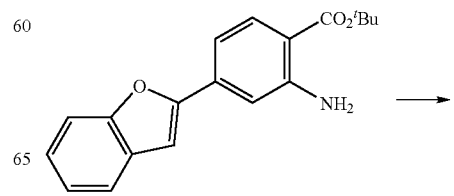

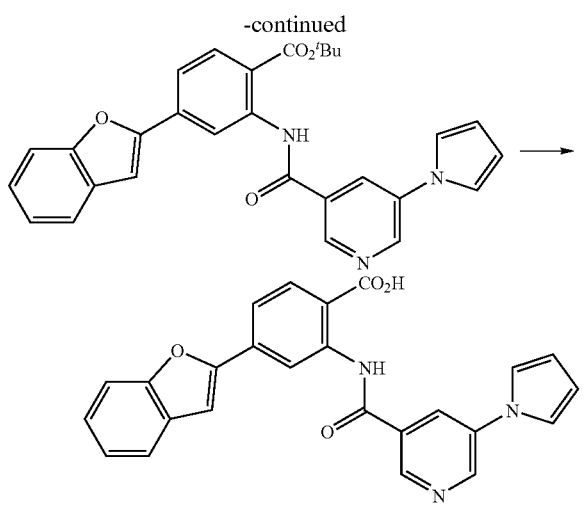

The following compound was obtained in the same manner as in Example 184.

4-(Benzofuran-2-yl)-2-(5-(1H-pyrrol-1-yl)pyridine-3-carboxamide)benzoic acid $^1$H-NMR (DMSO-d$_6$) δ: 6.39-6.41 (2H, m), 7.30-7.43 (2H, m), 7.59-7.63 (2H, m), 7.65 (1H, s), 7.71-7.76 (1H, m), 7.83 (1H, dd, J=8.4, 1.6 Hz), 8.17 (1H, d, J=8.4 Hz), 8.48-8.51 (1H, m), 9.01 (1H, d, J=1.5 Hz), 9.18 (1H, d, J=2.4 Hz), 9.22 (1H, d, J=1.4 Hz), 12.33 (1H, s).

Example 186

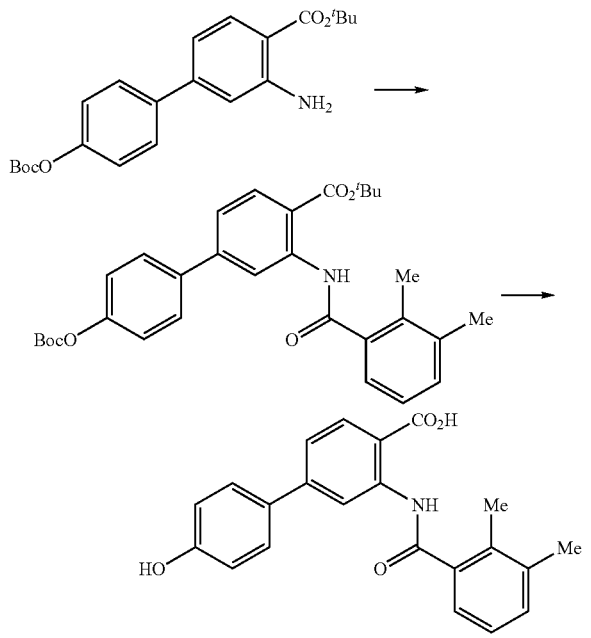

1.7 mL of methylene chloride, 1.0 μL of N,N-dimethylformamide and 0.025 mL of oxalyl chloride were added to 41 mg of 2,3-dimethylbenzoic acid at room temperature sequentially and stirred at the same temperature for 1 hour. The reaction mixture was added to a mixed solution of 62 mg of tert-butyl 2-amino-4-(4-(tert-butoxycarbonyl)oxyphenyl)benzoate, 2.8 mL of methylene chloride and 0.36 mL triethylamine and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=4:1] to obtain tert-butyl 2-(2,3-dimethylbenzamido)-4-(4-(tert-butoxycarbonyl)oxyphenyl)benzoate.

10 mL of trifluoroacetic acid was added to the obtained tert-butyl 2-(2,3-dimethylbenzamido)-4-(4-(tert-butoxycarbonyl)oxyphenyl)benzoate and stirred ah room temperature for 2 hours. The solvent was evaporated under reduced pressure and ethyl acetate was added to the obtained residue and a solid substance was separated by filtration to obtain 20 mg of 2-(2,3-dimethylbenzamido)-4-(4-hydroxyphenyl)benzoic acid as white solid.

$^1$H-NMR (DMSO-d$_6$) δ: 2.31 (3H, s), 2.33 (3H, s), 6.90-6.35 (2H, m), 7.23 (1H, t, J=7.5 Hz), 7.34 (1H, d, J=7.5 Hz), 7.40 (1H, d, J=7.5 Hz), 7.44 (1H, dd, J=8.3, 1.7 Hz), 7.56-7.60 (2H, m), 8.05 (1H, d, J=8.3 Hz), 8.97-8.99 (1H, m), 9.75-9.85 (1H, broad), 11.59 (1H, s), 13.40-13.70 (1H, broad).

Example 187

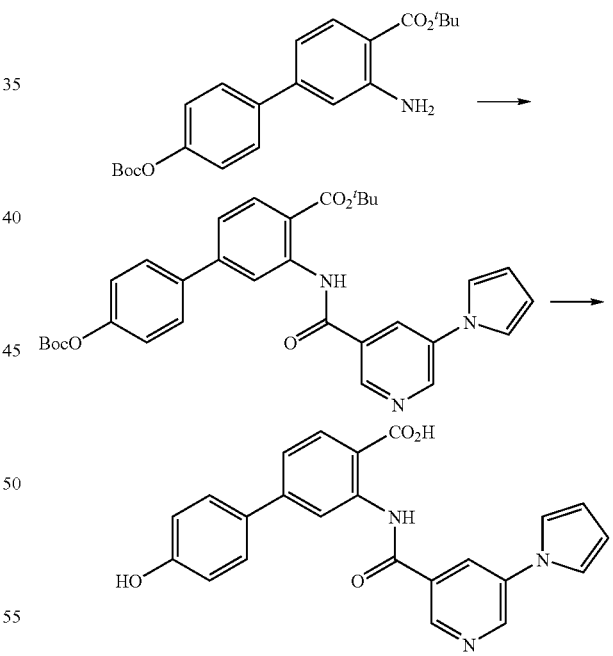

The following compound was obtained in the same manner as in Example 186.

4-(4-Hydroxyphenyl)-2-(5-(1H-pyrrol-1-yl)pyridine-3-carboxamido)benzoic acid $^1$H-NMR (DMSO-d$_6$) δ: 6.39 (2H, s), 6.93 (2H, d, J=8.5 Hz), 7.50 (1H, dd, J=8.1, 1.3 Hz), 7.56-7.65 (4H, m), 8.09

(1H, d, J=8.0 Hz), 8.47 (1H, s), 8.93-8.99 (2H, m), 9.17 (1H, d, J=2.2 Hz), 9.80 (1H, s), 12.31 (1H, s).

Example 188

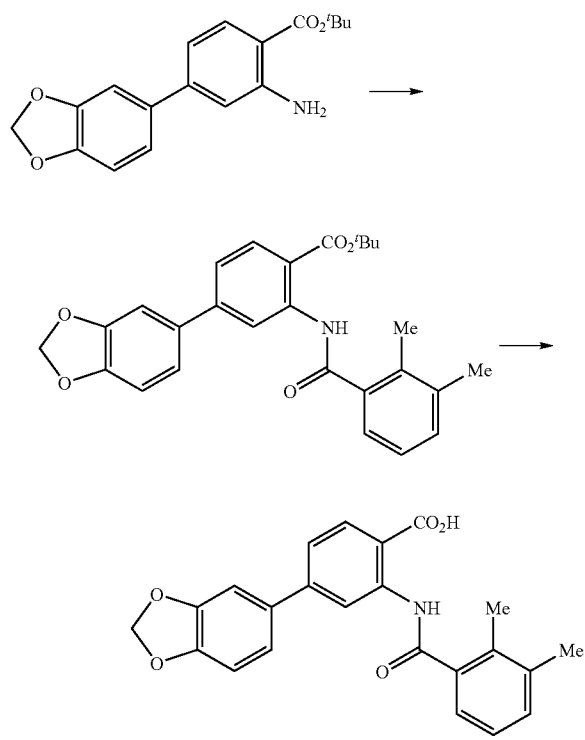

1.7 mL of methylene chloride, 1.0 µL N,N-dimethylformamide and 0.025 mL of oxalyl chloride were added to 41 mg of 2,3-dimethylbenzoic acid at room temperature sequentially and stirred ad the same temperature for 1 hour. The reaction mixture was added to a mixed solution of 50 mg of tert-butyl 2-amino-4-(benzo[1,3]dioxol-5-yl)benzoate, 2.8 mL of methylene chloride and 0.36 mL of triethylamine and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1]to obtain tert-butyl 4-(benzo[1,3]dioxol-5-yl)-2-(2,3-dimethylbenzamido)benzoate.

10 mL of trifluoroacetic acid was added to the obtained tert-butyl 4-(benzo[1,3]dioxol-5-yl)-2-(2,3-dimethylbenzamido)benzoate and stirred at room temperature for 2 hours. The solvent was evaporated under reduced pressure and methanol was added to the obtained residue and a solid substance was separated by filtration to obtain 31 mg of 4-(benzo[1,3]dioxol-5-yl)-2-(2,3-dimethylbenzamido)benzoic acid as white solid.

$^1$H-NMR (DMSO-$d_6$) δ: 2.31 (3H, s), 2.33 (3H, s), 6.11 (2H, s), 7.08 (1H, d, J=8.1 Hz), 7.20-7.27 (2H, m), 7.29 (1H, d, J=1.7 Hz), 7.34 (1H, d, J=7.3 Hz), 7.40 (1H, d, J=7.3 Hz), 7.46 (1H, dd, J=8.4, 1.8 Hz), 8.05 (1H, d, J=8.4 Hz), 8.93-9.00 (1H, broad), 11.58 (1H, s), 13.55-13.75 (1H, broad).

Example 189

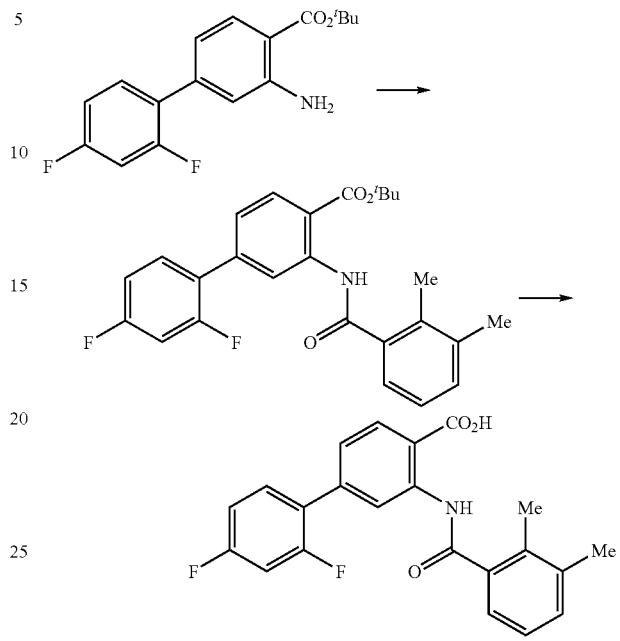

1.7 mL of methylene chloride, 1.0 µL of N,N-dimethylformamide and 0.025 mL of oxalyl chloride were added to 41 mg of 2,3-dimethylbenzoic acid at room temperature sequentially and stirred at the same temperature for 1 hour. The reaction mixture was added to a mixed solution of 49 mg of tert-butyl 2-amino-4-(2,4-difluorophenyl)benzoate, 2.8 mL of methylene chloride and 0.36 mL of triethylamine and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1]to obtain tert-butyl 4-(2,4-difluorophenyl)-2-(2,3-dimethylbenzamido)benzoate.

10 mL of trifluoroacetic acid was added to the obtained tert-butyl 4-(2,4-difluorophenyl)-2-(2,3-dimethylbenzamido)benzoate and stirred at room temperature for 2 hours. The solvent was evaporated under reduced pressure and methanol was added to the obtained residue and a solid substance was separated by filtration to obtain 17 mg of 4-(2,4-difluorophenyl)-2-(2,3-dimethylbenzamido)benzoic acid as white solid. $^1$H-NMR (DMSO-$d_6$) δ: 2.31 (3H, s), 2.31 (3H, s), 7.21-7.30 (2H, m), 7.31-7.49 (4H, m), 7.63-7.70 (1H, m), 8.11 (1H, d, J=8.0 Hz), 8.89 (1H, s), 11.58 (1H, s).

Example 190

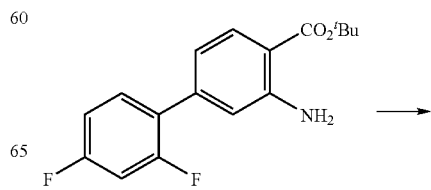

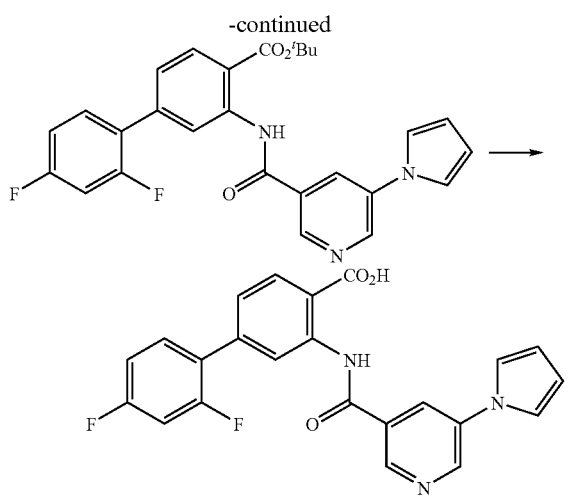

The following compound was obtained in the same manner as in Example 189.

4-(2,4-Difluorophenyl)-2-(5-(1H-pyrrol-1-yl)pyridine-3-carboxamido)benzoic acid $^1$H-NMR (DMSO-$d_6$) δ: 6.39 (2H, t, J=2.2 Hz), 7.28 (1H, td, J=8.7, 2.2 Hz), 7.42-7.48 (2H, m), 7.59 (2H, t, J=2.2 Hz), 7.68 (1H, td, J=8.7, 6.6 Hz), 8.16 (1H, d, J=8.0 Hz), 8.46 (1H, t, J=2.2 Hz), 8.85 (1H, d, J=1.4 Hz), 8.97 (1H, d, J=1.7 Hz), 9.17 (1H, d, J=2.3 Hz), 12.22 (1H, s).

Example 191

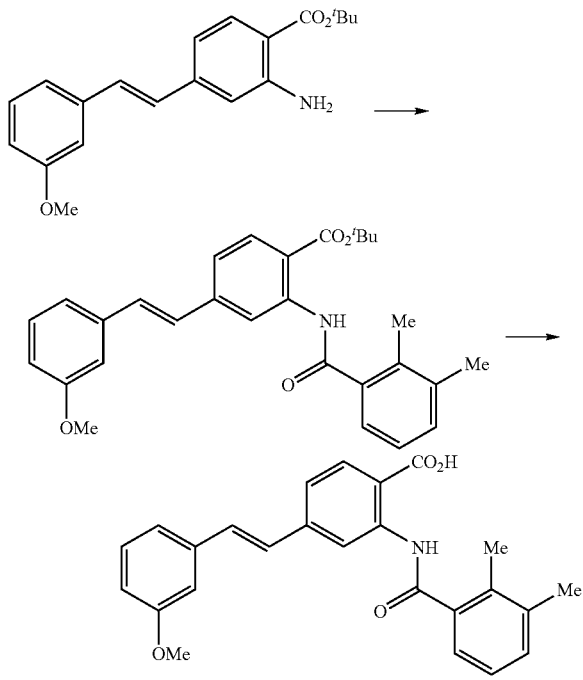

1.7 mL of methylene chloride, 1.0 μL of N,N-dimethylformamide and 0.025 mL of oxalyl chloride were added to 41 mg of 2,3-dimethylbenzoic acid at room temperature sequentially and stirred at the same temperature for 1 hour. The reaction mixture was added to a mixed solution of 52 mg of tert-butyl 2-amino-4-((E)-2-(3-methoxyphenyl)vinyl)benzoate, 2.8 mL of methylene chloride and 0.36 mL of triethylamine and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=4:1] to obtain tert-butyl 2-(2,3-dimethylbenzamido)-4-((E)-2-(3-methoxyphenyl)vinyl)benzoate.

10 mL of trifluoroacetic acid was added to the obtained tert-butyl 2-(2,3-dimethylbenzamido)-4-((E)-2-(3-methoxyphenyl)vinyl)benzoate and stirred at room temperature for 2 hours. The solvent was evaporated under reduced pressure and methanol was added to the obtained residue and a solid substance was separated by filtration to obtain 15 mg of 2-(2,3-dimethylbenzamido)-4-((E)-2-(3-methoxyphenyl)vinyl)benzoic acid as white solid.

$^1$H-NMR (DMSO-$d_6$) δ: 2.31 (3H, s), 2.33 (3H, s), 3.82 (3H, s), 6.88-6.91 (1H, m), 7.21-7.52 (9H, m), 8.02 (1H, d, J=8.3 Hz), 8.89 (1H, s), 11.59 (1H, s), 13.60 (1H, s).

Example 192

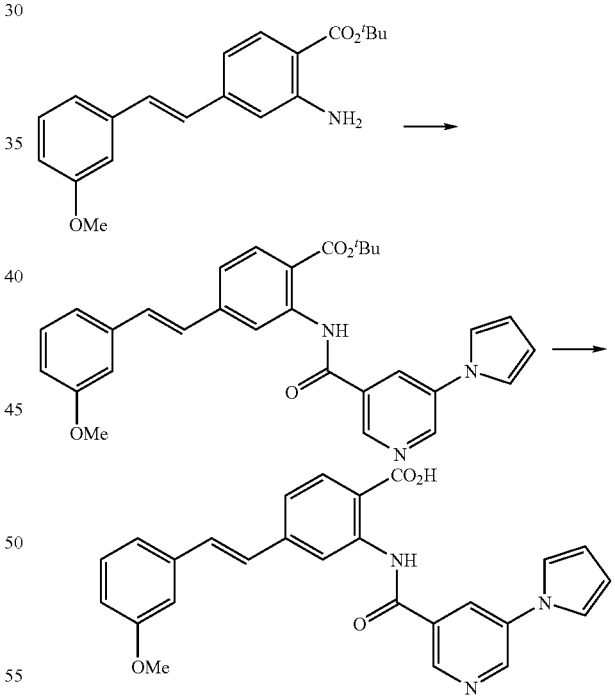

The following compound was obtained in the same manner as in Example 191.

4-((E)-2-(3-Methoxyphenyl)vinyl)-2-(5-(1H-pyrrol-1-yl)pyridine-3-carboxamido)benzoic acid $^1$H-NMR (DMSO-$d_6$) δ: 3.83 (3H, s), 6.40 (2H, t, J=2.2 Hz), 6.91 (1H, ddd, J=8.0, 2.5, 0.9 Hz), 7.25-7.44 (5H, m), 7.53 (1H, dd, J=8.3, 1.6 Hz), 7.59 (2H, t, J=2.2 Hz), 8.07 (1H, d, J=8.3 Hz), 8.45-8.47 (1H, m), 8.84 (1H, d, J=1.7 Hz), 8.99 (1H, d, J=1.6 Hz), 9.17 (1H, d, J=2.4 Hz), 12.20-12.35 (1H, broad).

Example 193

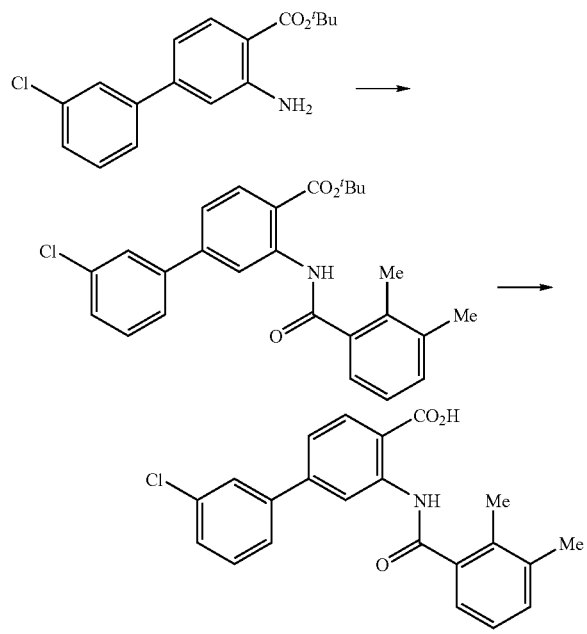

1.7 mL of methylene chloride, 1.0 µl of N,N-dimethylformamide and, 0.025 mL of oxalyl chloride were added to 41 mg of 2,3-dimethylbenzoic acid at room temperature sequentially and stirred at the same temperature for 1 hour. The reaction mixture was added to a mixed solution of 49 mg of tert-butyl 2-amino-4-(3-chlorophenyl)benzoate, 2.8 mL of methylene chloride and 0.36 mL of triethylamine and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane: ethyl acetate=4:1] to obtain tert-butyl 4-(3-chlorophenyl)-2-(2,3-dimethylbenzamido)benzoate.

10 mL of trifluoroacetic acid was added to the obtained tert-butyl 4-(3-chlorophenyl)-2-(2,3-dimethylbenzamido) benzoate and stirred at room temperature for 2 hours. The solvent was evaporated under reduced pressure and methanol was added to the obtained residue and a solid substance was separated by filtration to obtain 32 mg of 4-(3-chlorophenyl)-2-(2,3-dimethylbenzamido)benzoic acid as white solid.

$^1$H-NMR (DMSO-$d_6$) δ: 2.31 (3H, s), 2.33 (3H, s), 7.24 (1H, t, J=7.5 Hz), 7.34 (1H, d, J=7.5 Hz), 7.41 (1H, d, J=7.5 Hz), 7.52-7.61 (3H, m), 7.69-7.78 (2H, m), 8.11 (1H, d, J=8.3 Hz), 9.01 (1H, s), 11.58 (1H, s), 13.60-13.90 (1H, broad).

Examples 194, 195

The compounds shown in Table 24 were obtained in the same manner as in Example 193.

TABLE 24

| Example No. | R² |
|---|---|
| 194 | ![5-methyl-3-(1H-pyrrol-1-yl)pyridin-3-yl] |
| 195 | ![4-acetoxyphenyl/p-tolyl-OAc] |

4-(3-Chlorophenyl)-2-(5-(1H-pyrrol-1-yl)pyridine-3-carboxamido)benzoic acid $^1$H-NMR (DMSO-$d_6$) δ: 6.39 (2H, t, J=2.2 Hz), 7.52-7.64 (5H, m), 7.72 (1H, dt, J=7.6, 1.6 Hz), 7.78 (1H, t, J=1.6 Hz), 8.15 (1H, d, J=8.3 Hz), 8.46-8.48 (1H, m), 8.96 (1H, d, J=1.7 Hz), 8.99 (1H, d, J=1.7 Hz), 9.17 (1H, d, J=2.7 Hz), 12.23 (1H, s).

$^1$H-NMR (DMSO-$d_6$) δ: 2.32 (3H, s), 7.39 (2H, d, J=8.5 Hz), 7.52-7.62 (3H, m), 7.68-7.74 (1H, m), 7.77 (1H, s), 8.03 (2H, d, J=8.5 Hz), 8.14 (1H, d, J=8.3 Hz), 9.03 (1H, d, J=1.7 Hz), 12.23 (1H, s).

Example 196

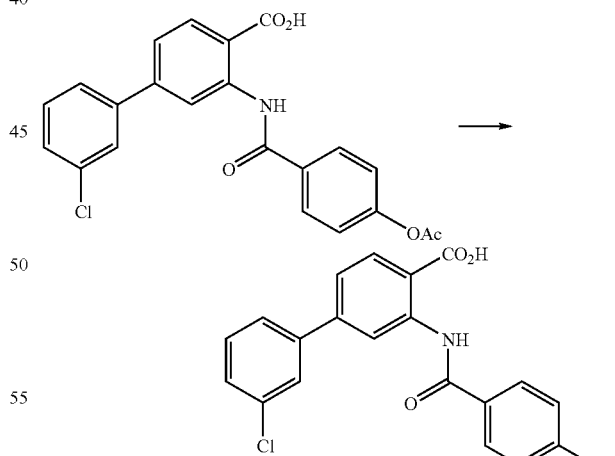

7.6 mg of potassium carbonate was added to a mixed solution of 0.5 mL of methanol and 0.5 mL of tetrahydrofuran containing 15 mg of 2-(4-acetoxybenzamido)-4-(3-chlorophenyl)benzoic acid and stirred at room temperature for 2 hours. After insoluble were removed by filtration, 10% citric acid aqueous solution was added and a solid substance was separated by filtration to obtain 10 mg of 4-(3-chlorophenyl)-2-(4-hydroxybenzamido)benzoic acid as white solid.

¹H-NMR (DMSO-d₆) δ: 6.91-6.97 (2H, m), 7.47-7.60 (3H, m), 7.69 (1H, dt, J=7.5, 1.6 Hz), 7.75 (1H, t, J=1.6 Hz), 7.83-7.89 (2H, m), 8.12 (1H, d, J=8.3 Hz), 9.07 (1H, d, J=1.9 Hz), 10.28 (1H, s).

Example 197

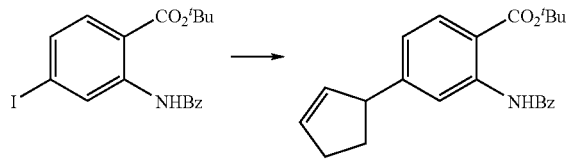

0.21 mL of cyclopentene, 0.14 g of potassium acetate, 0.13 g of tetrabutylammonium chloride, 3.1 mg of triphenylphosphine and 2.7 mg of palladium acetate were added to 1.0 mL of N-dimethylformamide solution containing 0.20 g of tert-butyl 2-(benzamido)-4-iodobenzoate at room temperature and stirred under nitrogen atmosphere at the same temperature for 17 hours. 0.21 mL of cyclopentene, 23 mg of potassium acetate, 3.1 mg of triphenylphosphine and 2.7 mg of palladium acetate were added to the reaction mixture and stirred at 70° C. for 3 hours after stirred at room temperature for 9 hours. After the reaction mixture was cooled to room temperature, ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [eluent; toluene] to obtain 94 mg of tert-butyl 2-(benzamido)-4-(2-cyclopenten-1-yl)benzoate as white solid.

¹H-NMR (CDCl₃) δ: 1.62 (9H, s), 1.72-1.84 (1H, m), 2.37-2.61 (3H, m), 3.94-4.03 (1H, m), 5.78-5.82 (1H, m), 5.98-6.03 (1H, m), 6.93 (1H, dd, J=8.3, 1.6 Hz), 7.49-7.59 (3H, m), 7.94 (1H, d, J=8.3 Hz), 8.04-8.09 (2H, m), 8.80 (1H, d, J=1.6 Hz), 12.22 (1H, s).

Example 198

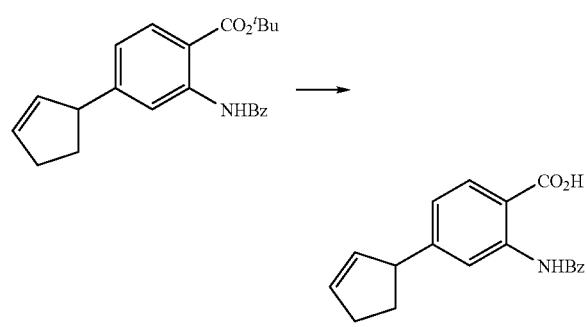

10 mL of trifluoroacetic acid solution containing 87 mg of tert-butyl 2-(benzamido)-4-(2-cyclopenten-1-yl)benzoate was stirred at room temperature for 1 hour. The solvent was evaporated under reduced pressure and methanol was added to the obtained residue and a solid substance was separated by filtration to obtain 52 mg of 2-(benzamido)-4-(2-cyclopenben-1-yl)benzoic acid as white solid.

¹H-NMR (DMSO-d₆) δ: 1.62-1.74 (1H, m), 2.35-2.55 (3H, m), 3.92-4.00 (1H, m), 5.78-5.83 (1H, ml), 6.00-6.04 (1H, m), 7.03 (1H, dd, J=8.2, 1.5 Hz), 7.57-7.68 (3H, m), 7.93-8.01 (3H, m), 8.63 (1H, d, J=1.5 Hz), 12.24 (1H, s).

Example 199

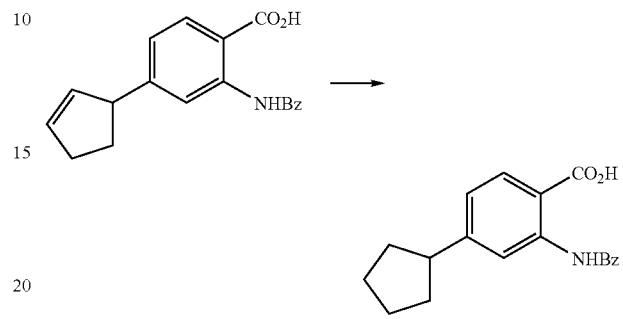

5.0 mg of 5% palladium-carbon was added to a mixed solution of 1.0 mL of methanol and 0.5 mL of ethyl acetate containing 25 mg of 2-(benzamido)-4-(2-cyclopenten-1-yl) benzoic acid and stirred at room temperature under hydrogen atmosphere for 7 hours and then at 40° C. for 8 hours and stirred at 45° C. for 15 hours. Insoluble were removed by filtration and the solvent was evaporated under reduced pressure. Methanol was added to the obtained residue and a solid substance was separated by filtration to obtain 16 mg of 2-(benzamido)-4-cyclopentyl benzoic acid as white solid.

¹H-NMR (DMSO-d₆) δ: 1.52-1.86 (6H, m), 1.98-2.12 (2H, m), 3.02-3.12 (1H, m), 7.10 (1H, dd, J=8.0, 1.6 Hz), 7.57-7.68 (3H, m), 7.94-8.00 (3H, m), 8.70 (1H, d, J=1.6 Hz), 12.22 (1H, s).

Example 200

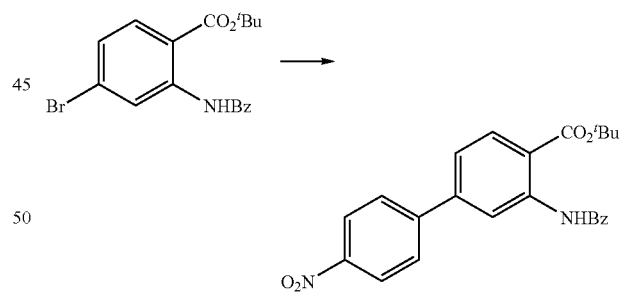

0.11 g of 4-nitrophenylboronic acid, 0.11 g of sodium hydrogen carbonate, 1.2 mL of ethanol, 0.6 mL of water and 31 mg of tetrakis(triphenylphosphine)palladium(0) were added to 4.0 mL of toluene solution containing 0.20 g of tert-butyl 2-(benzamido)-4-bromobenzoate, and the resulting mixture was heated to reflux under nitrogen atmosphere for 3 hours. A saturated sodium hydrogen carbonate aqueous solution was added after the reaction mixture was cooled to room temperature. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane:ethyl acetate=10:1] to obtain 40 mg of tert-butyl 2-(benzamido)-4-(4-nitrophenyl)benzoate as white solid.

$^1$H-NMR (DMSO-$d_6$) δ: 1.57 (9H, s), 7.60-7.70 (4H, m), 7.98-8.04 (3H, m), 8.09 (1H, d, J=8.8 Hz), 8.35-8.40 (3H, m), 8.90 (1H, d, J=1.7 Hz), 11.66 (1H, s).

Examples 201 to 205

The compounds shown in Table 25 were obtained in the same manner as in Example 200,

TABLE 25

| Example No. | $R^3$ |
|---|---|
| 201 | 4-chlorophenyl |
| 202 | 3,5-dichlorophenyl |
| 203 | 3,5-dimethyl-4-hydroxyphenyl |
| 204 | 5-methyl-2-oxoindolin |
| 205 | 3-chloro-2-fluorophenyl | tert-Butyl 2-(benzamido)-4-(4-chlorophenyl)benzoate $^1$H-NMR (DMSO-$d_6$) δ: 1.57 (9H, s), 7.55 (1H, dd, J=8.4, 1.6 Hz), 7.58-7.70 (5H, m), 7.73-7.78 (2H, m), 7.97-8.02 (2H, m), 8.04 (1H, d, J=8.4 Hz), 8.85 (1H, d, J=1.6 Hz), 11.69 (1H, s).

tert-Butyl 2-(benzamido)-4-(3,5-dichlorophenyl)benzoate $^1$H-NMR (DMSO-$d_6$) δ: 1.56 (9H, s), 7.60-7.70 (4H, m), 7.72-7.73 (1H, m), 7.77 (2H, d, J=1.7 Hz), 7.98-8.04 (3H, m), 8.77 (1H, d, J=2.0 Hz), 11.58 (1H, s).

tert-Butyl 2-(benzamido)-4-(3,5-dimethyl-4-hydroxyphenyl)benzoate $^1$H-NMR (CDCl$_3$) δ: 1.65 (9H, s), 2.33 (6H, s), 4.78 (1H, s), 7.29 (1H, dd, J=8.4, 1.8 Hz), 7.36 (2H, s), 7.51-7.60 (3H, m), 8.03 (1H, d, J=8.4 Hz), 8.06-8.11 (2H, m), 9.18 (1H, d, J=1.8 Hz), 12.28 (1H, s).

tert-Butyl 2-(benzamido)-4-(2-oxoindolin-5-yl)benzoate $^1$H-NMR (CDCl$_3$) δ: 1.65 (9H, s), 3.64 (2H, s), 6.96 (1H, d, J=8.1 Hz), 7.29 (1H, dd, J=8.5, 1.9 Hz), 7.52-7.65 (5H, m), 7.82 (1H, s), 8.05-8.11 (3H, m), 9.22 (1H, d, J=1.9 Hz), 12.30 (1H, s).

tert-Butyl 2-(benzamido)-4-(3-chloro-2-fluorophenyl)benzoate $^1$H-NMR (DMSO-$d_6$) δ: 1.57 (9H, s), 7.40 (1H, t, J=7.9 Hz), 7.43-7.47 (1H, m), 7.54-7.72 (5H, m), 7.96-8.01 (2H, m), 8.07 (1H, d, J=8.3 Hz), 8.72 (1H, s), 11.66 (1H, s).

Example 206

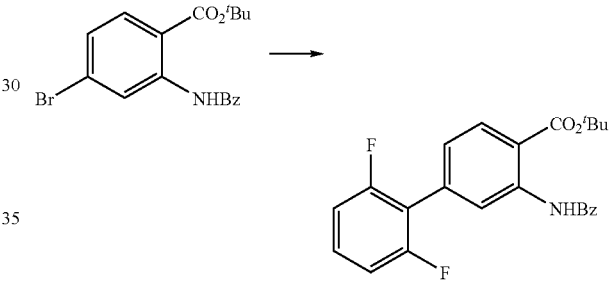

0.10 g of 2,6-difluorophenylboronic acid, 0.52 g of cesium carbonate, 2.4 mg of palladium acetate and 2.2 mg of 2-dicyclohexylphosphino-2',6'-dimethoxybiphenyl were added to 2.5 mL of toluene solution containing 0.20 g of tert-butyl 2-(benzamido)-4-bromobenzoate at room temperature sequentially, and stirred under nitrogen atmosphere at 80° C. for 1 hour and 10 minutes and then heated to reflux for 1 hour. After the reaction mixture was cooled to room temperature, 2.4 mg of palladium acetate and 2.2 mg of 2-dicyclohexylphosphino-2',6'-dimethoxybiphenyl were added and the resulting mixture was heated to reflux under nitrogen atmosphere for 1 hour. After the reaction mixture was cooled to room temperature, 2.4 mg of palladium acetate and 2.2 mg of 2-dicyclohexylphosphino-2',6'-dimethoxybiphenyl were added and the resulting mixture was heated to reflux under nitrogen atmosphere for 1 hour. After the reaction mixture was cooled to room temperature, were added 2.0 mL of toluene, 0.04 g of 2,6-difluorophenylboronic acid, 2.4 mg of palladium acetate and 2.2 mg of 2-dicyclohexylphosphino-2',6'-dimethoxybiphenyl and the resulting mixture was heated to reflux under nitrogen atmosphere for 1 hour. A saturated sodium hydrogen carbonate aqueous solution and ethyl acetate were added after the reaction mixture was cooled to room temperature. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia Chemical Ltd., eluent; hexane:ethyl acetate=20:1] to obtain 31 mg of tert-butyl 2-(benzamido)-4-(2,6-difluorophenyl)benzoate as white solid.

$^1$H-NMR (DMSO-d$_6$) δ: 1.57 (9H, s), 7.26-7.36 (3H, m), 7.53-7.67 (4H, m), 7.95-8.00 (2H, m), 8.07 (1H, d, J=8.0 Hz), 8.57-8.61 (1H, m), 11.63 (1H, s).

Example 207

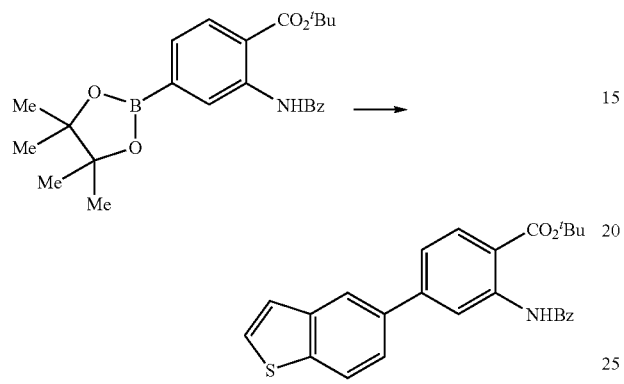

48 mg of 5-bromobenzothiophene, 40 mg of sodium hydrogen carbonate, 0.6 mL of ethanol, 0.3 mL of water and 11 mg of tetrakis(triphenylphosphine)palladium(0) were added to 1.6 mL of toluene solution containing 80 mg of tert-butyl 2-(benzamido)-4-(4,4,5,5-tetramethyl-1,3,2-dioxaborolan-2-yl)benzoate at room temperature, and the resulting mixture was heated to reflux under nitrogen atmosphere for 5 hours. Ethyl acetate and water were added after the reaction mixture was cooled to room temperature. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane; ethyl acetate=20:1] to obtain 47 mg of tert-butyl 2-(benzamido)-4-(benzothiophen-5-yl)benzoate as white solid.

$^1$H-NMR (CDCl$_3$) δ: 1.66 (9H, s), 7.40-7.44 (2H, m), 7.50 (1H, d, J=5.4 Hz), 7.51-7.61 (3H, m), 7.71 (1H, dd, J=8.5, 1.7 Hz), 7.96 (1H, d, J=8.3 Hz), 8.08-8.13 (3H, m), 8.19 (1H, d, J=1.5 Hz), 9.34 (1H, d, J=1.7 Hz), 12.31 (1H, s).

Examples 208 to 210

The compounds shown in Table 26 were obtained in the same manner as in Example 207.

TABLE 26

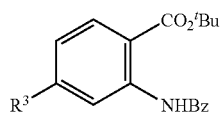

| Example No. | R$^3$ |
| --- | --- |
| 208 | ![5-methylbenzofuran] |
| 209 | ![4-methylindole] |
| 210 | ![1-(4-methylphenyl)pyrrole] | tert-Butyl 2-(benzamido)-4-(benzofuran-5-yl)benzoate $^1$H-NMR (CDCl$_3$) δ: 1.66 (9H, s), 6.84 (1H, dd, J=2.2, 1.0 Hz), 7.38 (1H, dd, J=8.3, 2.0 Hz), 7.51-7.61 (4H, m), 7.64-7.68 (2H, m), 7.96 (1H, d, J=1.5 Hz), 8.07-8.12 (3H, m), 9.30 (1H, d, J=2.0 Hz), 12.29 (1H, s).

tert-Butyl 2-(benzamido)-4-(1H-indol-4-yl)benzoate $^1$H-NMR (CDCl$_3$) δ: 1.66 (9H, s), 6.93-6.97 (1H, m), 7.24-7.36 (3H, m), 7.40-7.50 (2H, m), 7.50-7.60 (3H, m), 8.07-8.13 (2H, m), 8.13 (1H, d, J=8.3 Hz), 8.31 (1H, s), 9.33 (1H, d, J=1.5 Hz), 12.24 (1H, s).

tert-Butyl 2-(benzamido)-4-(4-(1H-pyrrol-1-yl)phenyl)benzoate $^1$H-NMR (CDCl$_3$) δ: 1.66 (9H, s), 6.38 (2H, t, J=2.2 Hz), 7.16 (2H, t, J=2.2 Hz), 7.35 (1H, dd, J=8.3, 1.7 Hz), 7.47-7.52 (2H, m), 7.52-7.61 (3H, m), 7.76-7.82 (2H, m), 8.07-8.12 (3H, m), 9.29 (1H, d, J=1.7 Hz), 12.29 (1H, s).

Example 211

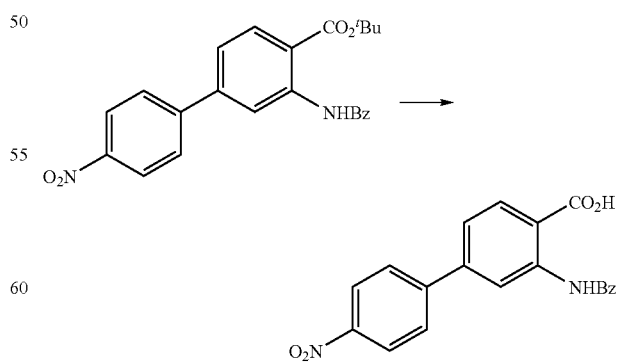

3.0 mL of trifluoroacetic acid solution containing 40 mg of tert-butyl 2-(benzamido)-4-(4-nitrophenyl)benzoate was stirred at room temperature for 1 hour. The solvent was evaporated under reduced pressure and ethyl acetate and methanol were added to she obtained residue and a solid substance was separated by filtration to obtain 15 mg of 2-(benzamido)-4-(4-nitrophenyl)benzoic acid as white solid.

$^1$H-NMR (DMSO-$d_6$) δ: 7.60-7.70 (4H, m), 7.98-8.04 (4H, m), 8.20 (1H, d, J=8.6 Hz), 8.39 (2H, d, J=8.5 Hz), 9.16 (1H, s), 12.26-12.32 (1H, broad).

Examples 212 to 221

The compounds shown in Table 27 were obtained in the same manner as in Example 211.

TABLE 27

| Example No. | R$^3$ |
|---|---|
| 212 | 4-chlorophenyl |
| 213 | 3,5-dichlorophenyl |
| 214 | 3,5-dimethyl-4-hydroxyphenyl |
| 215 | 2-oxoindolin-5-yl (5-methyl shown) |
| 216 | 3-chloro-2-fluorophenyl |
| 217 | 2,6-difluorophenyl |
| 218 | benzothiophen-5-yl |
| 219 | benzofuran-5-yl |

TABLE 27-continued

| Example No. | R$^3$ |
|---|---|
| 220 | 4-methylindol-yl |
| 221 | 1-(4-methylphenyl)pyrrol-yl |

2-(Benzamido)-4-(4-chlorophenyl)benzoic acid $^1$H-NMR (DMSO-$d_6$) δ: 7.53 (1H, dd, J=8.3, 1.8 Hz), 7.59-7.70 (5H, m), 7.75-7.79 (2H, m), 7.97-8.01 (2H, m), 8.14 (1H, d, J=8.3 Hz), 9.08 (1H, d, J=1.8 Hz), 12.28 (1H, s).

2-(Benzamido)-4-(3,5-dichlorophenyl)benzoic acid $^1$H-NMR (DMSO-$d_6$) δ: 7.58-7.70 (4H, m), 7.73 (1H, t, J=1.8 Hz), 7.77 (2H, d, J=2.0 Hz), 7.97-8.02 (2H, m), 8.14 (1H, d, J=8.3 Hz), 9.03 (1H, d, J=1.7 Hz), 12.24-12.31 (1H, broad).

2-(Benzamido)-4-(3,5-dimethyl-4-hydroxyphenyl)benzoic acid $^1$H-NMR (DMSO-$d_6$) δ: 2.26 (6H, s), 7.32 (2H, s), 7.44 (1H, dd, J=8.3, 1.8 Hz), 7.58-7.70 (3H, m), 7.96-8.02 (2H, m), 8.07 (1H, d, J=8.3 Hz), 8.60 (1H, s), 9.01 (1H, d, J=1.8 Hz), 12.27 (1H, s), 13.60-13.80 (1H, broad).

2-(Benzamido)-4-(2-oxoindolin-5-yl)benzoic acid $^1$H-NMR (DMSO-$d_6$) δ: 3.60 (2H, s), 6.97 (1H, d, J=8.1 Hz), 7.47 (1H, dd, J=8.5, 1.8 Hz), 7.56-7.70 (5H, m), 7.96-8.02 (2H, m), 8.10 (1H, d, J=8.5 Hz), 9.06 (1H, d, J=1.8 Hz), 10.57 (1H, s), 12.28 (1H, s), 13.60-13.90 (1H, broad).

2-(Benzamido)-4-(3-chloro-2-fluorophenyl)benzoic acid $^1$H-NMR (DMSO-$d_6$) δ: 7.37-7.44 (2H, m), 7.56-7.72 (5H, m), 7.95-8.00 (2H, m), 8.17 (1H, d, J=8.3 Hz), 8.97 (1H, s), 12.22-12.26 (1H, broad).

2-(Benzamido)-4-(2,6-difluorophenyl)benzoic acid $^1$H-NMR (DMSO-$d_6$) δ: 7.24-7.35 (3H, m), 7.52-7.69 (4H, m), 7.93-8.00 (2H, m), 8.17 (1H, d, J=8.3 Hz), 8.86 (1H, s), 12.24 (1H, s).

2-(Benzamido)-4-(benzothiophen-5-yl)benzoic acid $^1$H-NMR (DMSO-$d_6$) δ: 7.58-7.71 (5H, m), 7.74 (1H, dd, J=8.5, 1.7 Hz), 7.87 (1H, d, J=5.4 Hz), 7.98-8.04 (2H, m), 8.14-8.20 (2H, m), 8.27 (1H, d, J=1.4 Hz), 9.18 (1H, d, J=1.7 Hz), 12.31 (1H, s), 13.75-13.95 (1H, broad).

2-(Benzamido)-4-(benzofuran-5-yl)benzoic acid $^1$H-NMR (DMSO-d$_6$) δ: 7.09 (1H, dd, J=2.2, 1.0 Hz), 7.56 (1H, dd, J=8.3, 2.0 Hz), 7.59-7.71 (4H, m), 7.76 (1H, d, J=8.5 Hz), 7.98-8.04 (2H, mL , 8.03 (1H, d, J=1.5 Hz), 8.09 (1H, d, J=2.2 Hz), 8.15 (1H, d, J=8.3 Hz), 9.14 (1H, d, J=2.0 Hz), 12.30 (1H, s), 13.70-13.95 (1H, broad).

2-(Benzamido)-4-(1H-indol-4-yl)benzoic acid $^1$H-NMR (DMSO-d$_6$) δ: 6.75-6.79 (1H, m), 7.21-7.27 (2H, m), 7.47-7.54 (2H, m), 7.53 (1H, dd, J=8.3, 1.8 Hz), 7.58-7.70 (3H, m), 7.98-8.03 (2H, m), 8.17 (1H, d, J=8.3 Hz), 9.17 (1H, d, J=1.8 Hz), 11.37 (1H, s), 12.29 (1H, s).

2-(Benzamido)-4-(4-(1H-pyrrol-1-yl)phenyl)benzoic acid $^1$H-NMR (DMSO-d$_6$) δ: 6.32 (2H, t, J=2.2 Hz), 7.48 (2H, t, J=2.2 Hz), 7.57 (1H, dd, J=8.4, 1.9 Hz), 7.59-7.71 (3H, m), 7.74-7.80 (2H, m), 7.80-7.86 (2H, m), 7.98-8.03 (2H, m), 8.15 (1H, d, J=8.4 Hz), 9.12 (1H, d, J=1.9 Hz), 12.30 (1H, s).

Example 222

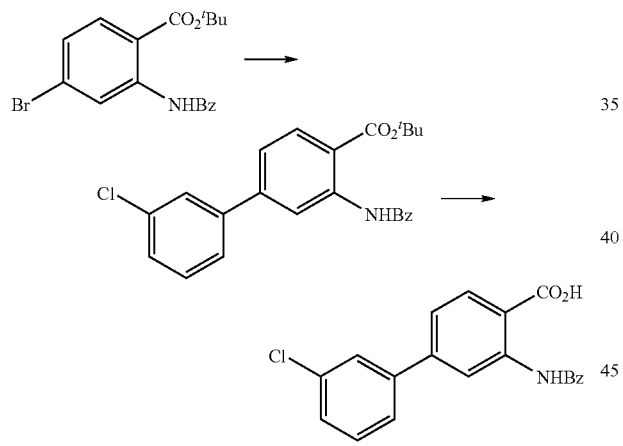

44 mp of 3-chlorophenylboronic acid, 49 mg of sodium carbonate and 6 mg of polymer supported di(acetato)dicyclohexylphenylphosphine palladium(II) were added to 2.5 mL of N,N-dimethylacetamide solution containing 70 mg of tert-butyl 2-(benzamido)-4-bromobenzoate, and stirred at 90° C. for 15 hours. After the reaction mixture was cooled to room temperature, 5.1 mg of polymer supported di(acetato) dicyclohexylphenylphosphine palladium(II) was added and stirred at 110° C. for 9 hours and 30 minutes. After the reaction mixture was cooled to room temperature, insoluble were removed by filtration and ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [Flash Tube 2008 manufactured by Tribonex Company, eluent; hexane:ethyl acetate=4:1] to obtain tert-butyl 2-(benzamido)-4-(3-chlorophenyl)benzoate.

10 mL of trifluoroacetic acid was added to the obtained tert-butyl 2-(benzamido)-4-(3-chlorophenyl)benzoate and stirred at room temperature for 1 hour. The solvent was evaporated under reduced pressure and methanol was added to the obtained residue and a solid substance was separated by filtration to obtain 21 mg of 2-(benzamido)-4-(3-chlorophenyl)benzoic acid as white solid.

$^1$H-NMR (DMSO-d$_6$) δ: 7.52-7.74 (7H, m), 7.77 (1H, s), 7.97-8.03 (2H, m), 8.14 (1H, d, J=8.3 Hz), 9.06 (1H, d, J=2.0 Hz), 12.27 (1H, s).

Examples 223 to 231

The compounds shown in Table 28 were obtained in the same manner as in Example 222.

TABLE 28

| Example No. | R$^3$ |
|---|---|
| 223 | 3-fluorophenyl |
| 224 | 2,3-difluorophenyl |
| 225 | 3,5-difluorophenyl |
| 226 | 2-hydroxyphenyl |
| 227 | 4-(1-methoxyethyl)phenyl (Me-CH(OMe)-) |
| 228 | 2-phenoxyphenyl |

TABLE 28-continued

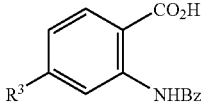

| Example No. | R³ |
|---|---|
| 229 | 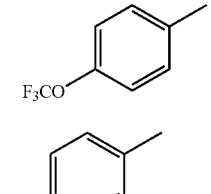 |
| 230 | Me, Me (2,3-dimethylphenyl) |
| 231 | 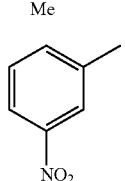 |

2-(Benzamido)-4-(3-fluorophenyl)benzoic acid $^1$H-NMR (DMSO-$d_6$) δ: 7.27-7.36 (1H, m, 7.53-7.70 (7H, m), 7.96-8.02 (2H, m), 8.14 (1H, d, J=8.0 Hz), 9.08 (1H, t, J=1.7 Hz), 12.24 (1H, s).

2-(Benzamido)-4-(2,3-difluorophenyl)benzoic acid $^1$H-NMR (DMSO-$d_6$) δ: 7.34-7.47 (3H, m), 7.50-7.70 (4H, m), 7.95-8.01 (2H, m), 8.17 (1H, d, J=8.3 Hz), 8.98 (1H, s), 12.25 (1H, s).

2-(Benzamido)-4-(3,5-difluorophenyl)benzoic acid $^1$H-NMR (DMSO-$d_6$) δ: 7.36 (1H, tt, J=9.1, 2.2 Hz), 7.43-7.51 (2H, m), 7.56-7.71 (4H, m), 7.96-8.03 (2H, m), 8.14 (1H, d, J=8.3 Hz), 9.04 (1H, d, J=1.7 Hz), 12.27 (1H, s).

2-(Benzamido)-4-(2-hydroxyphenyl)benzoic acid $^1$H-NMR (DMSO-$d_6$) δ: 6.90-7.02 (2H, m), 7.20-7.28 (1H, m), 7.32 (1H, dd, J=7.7, 1.6 Hz), 7.40 (1H, dd, J=8.3, 1.7 Hz), 7.57-7.69 (3H, m), 7.95-8.01 (2H, m), 8.07 (1H, d, J=8.3 Hz), 8.96 (1H, d, J=1.7 Hz), 9.75 (1H, s), 12.20-12.45 (1H, broad).

2-(Benzamido)-4-(4-isopropoxyphenyl)benzoic acid $^1$H-NMR (DMSO-$d_6$) δ: 1.31 (6H, d, J=6.1 Hz), 4.65-4.76 (1H, m), 7.05-7.10 (2H, m), 7.48 (1H, dd, J=8.3, 1.7 Hz), 7.59-7.70 (5H, m), 7.96-8.02 (2H, m), 8.10 (1H, d, J=8.3 Hz), 9.05 (1H, d, J=1.7 Hz), 12.32 (1H, s).

2-(Benzamido-4-(2-phenoxyphenyl)benzoic acid $^1$H-NMR (DMSO-$d_6$) δ: 6.91-6.97 (2H, m), 7.02-7.09 (2H, m), 7.29-7.50 (5H, m), 7.54-7.69 (4H, m), 7.93-8.00 (2H, m), 8.04 (1H, d, J=8.2 Hz), 8.99 (1H, d, J=1.6 Hz), 12.22 (1H, s).

2-(Benzamido)-4-(4-(trifluoromethoxy)phenyl)benzoic acid $^1$H-NMR (DMSO-$d_6$) δ: 7.51-7.57 (3H, m), 7.58-7.70 (3H, m), 7.84-7.89 (2H, m), 7.96-8.02 (2H, m), 8.15 (1H, d, J=8.3 Hz), 9.08 (1H, d, J=1.7 Hz), 12.27 (1H, s), 13.70-14.05 (1H, broad).

2-(Benzamido)-4-(2,3-dimethylphenyl)benzoic acid $^1$H-NMR (DMSO-$d_6$) δ: 2.16 (3H, s), 2.33 (3H, s), 7.09 (1H, d, J=7.1 Hz), 7.15 (1H, dd, J=8.1, 1.7 Hz), 7.17-7.27 (2H, m), 7.57-7.69 (3H, m), 7.94-7.99 (2H, m), 8.11 (1H, d, J=8.1 Hz), 8.70 (1H, d, J=1.7 Hz), 12.30 (1H, s).

2-(Benzamido)-4-(3-nitrophenyl)benzoic acid $^1$H-NMR (DMSO-$d_6$) δ: 7.59-7.71 (4H, m), 7.82-7.88 (1H, m), 7.98-8.03 (2H, m), 8.19 (1H, d, J=8.3 Hz), 8.21 (1H, ddd, J=7.8, 1.7, 1.0 Hz), 8.29-8.34 (1H, m), 8.48-8.50 (1H, m), 9.14 (1H, d, J=1.9 Hz), 12.27 (1H, s), 13.80-14.15 (1H, broad).

Example 232

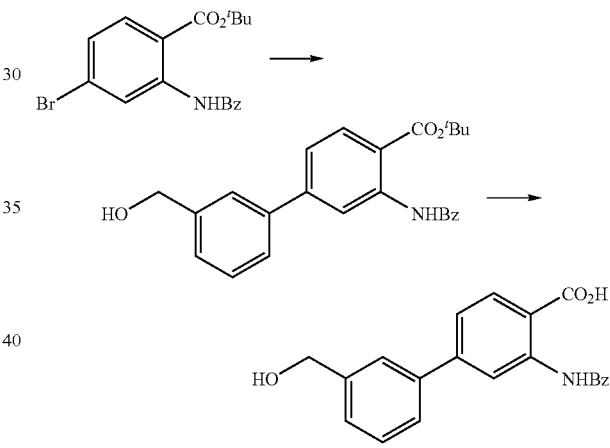

42 mg of 3-hydroxymethylphenylboronic acid, 49 mg of sodium carbonate and 6 mg of polymer supported di(acetato)dicyclohexylphenylphosphine palladium(II) were added to 2.5 mL of N,N-dimethylacetamide solution containing 70 mg of tert-butyl 2-(benzamido)-4-bromobenzoate, and stirred at 90° C. for 15 hours. After the reaction mixture was cooled do room temperature, 6 mg of polymer supported di(acetato)dicyclohexylphenylphosphine palladium(II) was added and stirred at 110° C. for 9 hours and 30 minutes. After the reaction mixture was cooled to room temperature, insoluble were removed by filtration and ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(benzamido)-4-(3-(hydroxymethyl)phenyl)benzoate.

10 mL of trifluoroacetic acid was added to the obtained tert-butyl 2-(benzamido)-4-(3-(hydroxymethyl)phenyl)benzoate and stirred at room temperature for 1 hour. The solvent was evaporated under reduced pressure and the obtained residue was purified with reversed-phase silica gel column chromatography [eluent; 60-100% acetonitrile 0.1% trifluoroacetic acid aqueous solution] to obtain 12 mg of 2-(benzamido)-4-(3-(hydroxymethyl)phenyl)benzoic acid as white solid.

$^1$H-NMR (DMSO-$d_6$) δ: 4.61 (2H, s), 5.26-5.40 (1H, broad), 7.41 (1H, d, J=7.6 Hz), 7.47-7.55 (2H, m), 7.58-7.73 (5H, m), 7.97-8.04 (2H, m), 8.15 (1H, d, J=8.3 Hz), 9.09 (1H, d, J=1.7 Hz), 12.33 (1H, s).

Examples 233 to 235

The compounds shown in Table 29 were obtained in the same manner as in Example 232.

TABLE 29

| Example No. | R³ |
|---|---|
| 233 | 2-isopropoxy-phenyl (with ortho methyl) |
| 234 | 3-(trifluoromethoxy)phenyl |
| 235 | 3-methylphenyl |

2-(Benzamido)-4-(2-isopropoxyphenyl)benzoic acid $^1$H-NMR (DMSO-$d_6$) δ: 1.26 (6H, d, J=6.1 Hz), 4.59-4.72 (1H, m), 7.05 (1H, t, J=7.3 Hz), 7.17 (1H, d, J=8.1 Hz), 7.32-7.41 (3H, m), 7.57-7.68 (3H, m), 7.95-8.01 (2H, m), 8.07 (1H, d, J=8.3 Hz), 8.98 (1H, d, J=1.7 Hz).

2-(Benzamido)-4-(3-(trifluoromethoxy)phenyl)benzoic acid $^1$H-NMR (DMSO-$d_6$) δ: 7.48 (1H, d, J=8.0 Hz), 7.57 (1H, dd, J=8.3, 1.9 Hz), 7.59-7.73 (5H, m), 7.79 (1H, d, J=7.8 Hz), 7.97-8.03 (2H, m), 8.16 (1H, d, J=8.3 Hz), 9.08 (1H, d, J=1.9 Hz), 12.35 (1H, s).

2-(Benzamido)-4-(3-Methylphenyl)benzoic acid $^1$H-NMR (DMSO-$d_6$) δ: 2.42 (3H, s), 7.28 (1H, d, J=7.6 Hz), 7.43 (1H, t, J=7.6 Hz), 7.49-7.57 (3H, m), 7.59-7.70 (3H, m), 7.97-8.02 (2H, m), 8.13 (1H, d, J=8.3 Hz), 9.07 (1H, d, J=1.7 Hz), 12.29 (1H, s).

Example 236

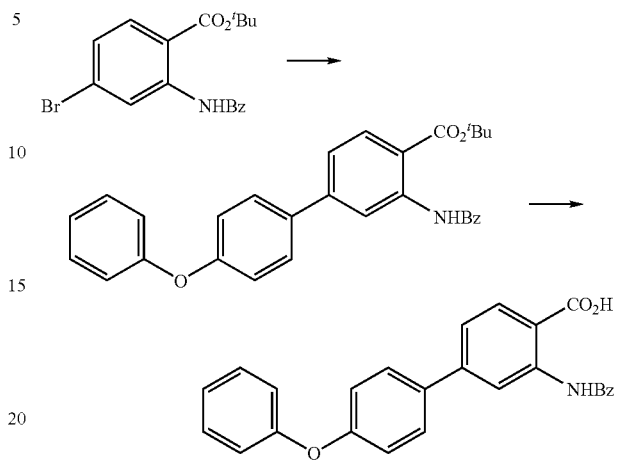

60 mg of 4-phenoxyphenylboronic acid, 49 mg of sodium carbonate and 6 mg of polymer supported di(acetato) dicyclohexylphenylphosphine palladium(II) were added to 2.5 mL of N,N-dimethylacetamide solution containing 70 mg of tert-butyl 2-(benzamido)-4-bromobenzoate, and stirred at: 110° C. for 24 hours. After the reaction mixture was cooled to room temperature, 6 mg of polymer supported di(acetato) dicyclohexylphenylphosphine palladium(II) was added and stirred at 110° C. for 24 hours. After the reaction mixture was cooled to room temperature, insoluble were removed by filtration and ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [Flash Tube 2008 manufactured by Trikonex company, eluent; hexane: ethyl acetate=4:1] to obtain tert-butyl 2-(benzamido)-4-(4-phenoxyphenyl)benzoate.

5.0 mL of trifluoroacetic acid was added to the obtained tert-butyl 2-(benzamido)-4-(4-phenoxyphenyl)benzoate and stirred at room temperature for 3 hours. The solvent was evaporated under reduced pressure, and the obtained residue was purified with silica gel column chromatography [PSQ100B (spherical) manufactured by Fuji Silysia Chemical Ltd., eluent; hexane:ethyl acetate=1:2] to obtain 8.0 mg of 2-(benzamido)-4-(4-phenoxyphenyl)benzoic acid as white solid.

$^1$H-NMR (DMSO-$d_6$) δ: 7.08-7.23 (5H, m), 7.41-7.48 (2H, m), 7.51 (1H, dd, J=8.3, 1.9 Hz), 7.58-7.70 (3H, m), 7.74-7.79 (2H, m), 7.96-8.02 (2H, m), 8.13 (1H, d, J=8.3 Hz), 9.07 (1H, d, J=1.9 Hz), 12.30 (1H, s).

Example 237

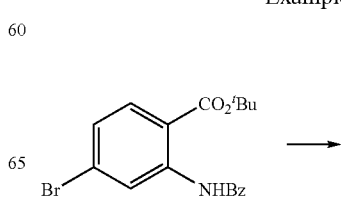

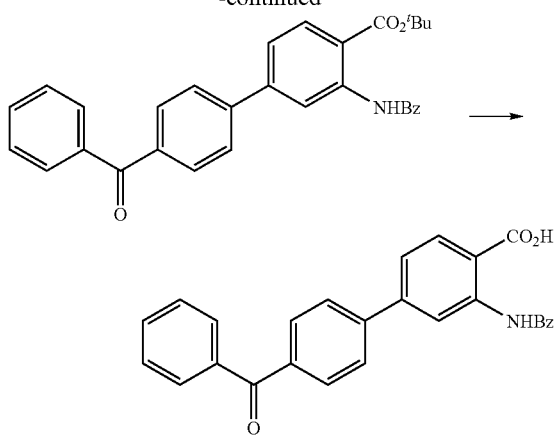

The following compound was obtained in the same manner as in Example 236.

2-(Benzamido)-4-(4-benzoylphenyl)benzoic acid $^1$H-NMR (DMSO-$d_6$) δ: 7.57-7.75 (7H, m), 7.78-7.84 (2H, m), 7.89-7.96 (4H, m), 7.98-8.03 (2H, m), 8.19 (1H, d, b=8.3 Hz), 9.17 (1H, d, J=1.5 Hz), 12.29 (1H, s).

Example 238

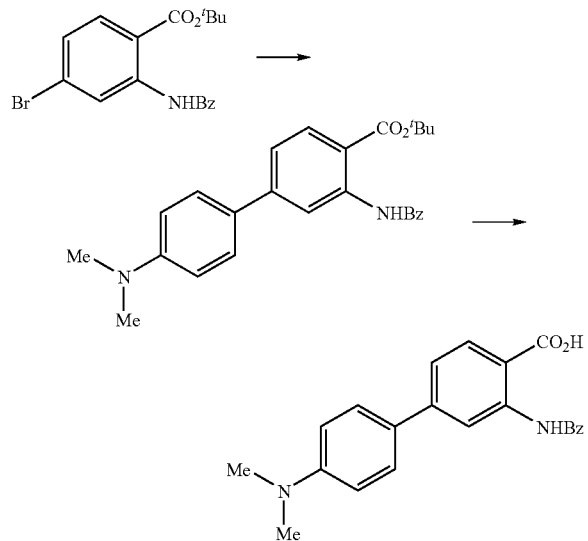

46 mg of 4-(dimethylamino)phenylboronic acid, 49 mg of sodium carbonate and 5.7 mg of polymer supported di(acetato)dicyclohexylphenylphosphine palladium(II) were added to 2.5 mL of N,N-dimethylacetamide solution containing 70 mg of tert-butyl 2-(benzamido)-4-bromobenzoate, and stirred at 110° C. for 24 hours. After the reaction mixture was cooled to room temperature 5.7 mg polymer supported di(acetato)dicyclohexylphenylphosphine palladium(II) was added and stirred at 110° C. for 24 hours, After the reaction mixture was cooled to room temperature, insoluble were removed by filtration and ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(benzamido)-4-(4-(dimethylamino)phenyl)benzoate.

5.0 mL of trifluoroacetic acid was added to the obtained tert-butyl 2-(benzamido)-4-(4-(dimethylamino)phenyl)benzoate and stirred at room temperature for 3 hours. The solvent was evaporated under reduced pressure, ethyl acetate and water were added and pH was adjusted to pH 6.5 with a saturated sodium hydrogen carbonate aqueous solution. The organic layer was separated and dried over anhydrous magnesium sulfate after washed with a saturated sodium chloride aqueous solution, and the solvent was evaporated under reduced pressure. Methanol was added to the obtained residue and a solid substance was separated by filtration to obtain 3.8 mg of 2-(benzamido)-4-(4-(dimethylamino)phenyl)benzoic acid as pale yellow solid.

$^1$H-NMR (DMSO-$d_6$) δ: 2.98 (6H, s), 6.83-6.89 (2H, m), 7.45 (1H, dd, J=8.3, 1.8 Hz), 7.58-7.69 (5H, m), 7.97-8.02 (2H, m), 8.06 (1H, d, J=8.3 Hz), 9.05 (1H, d, J=1.8 Hz), 12.32 (1H, s).

Example 239

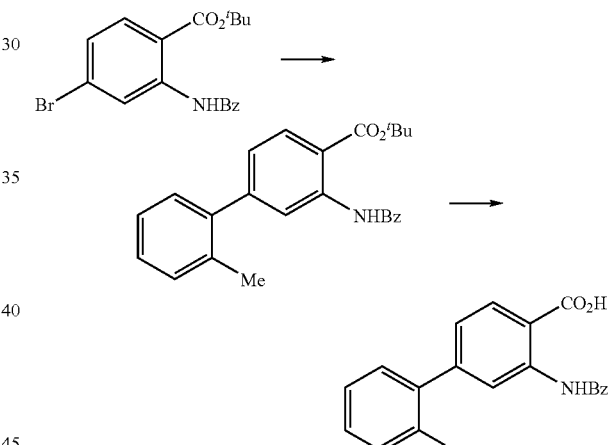

38 mg of 2-methylphenylboronic acid, 49 mg of sodium carbonate and 6 mg of polymer supported bis(acetato)triphenylphosphine palladium(II) were added to 2.5 mL of N,N-dimethylacetamide solution containing 70 mg of tert-butyl 2-(benzamido)-4-bromobenzoate, and stirred at 110° C. for 20 hours. After the reaction mixture was cooled to room temperature, 6 mg of polymer supported bis(acetato)triphenylphosphine palladium(II) was added and stirred at 110° C. for 22 hours. After the reaction mixture was cooled to room temperature, insoluble were removed by filtration and ethyl acetate and 10% citric acid aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(benzamido)-4-(2-methylphenyl)benzoate.

10 mL of trifluoroacetic acid was added no the obtained tert-butyl 2-(benzamido)-4-(2-methylphenyl)benzoate and stirred at room temperature for 1 hour. The solvent was evaporated under reduced pressure and methanol was added to the obtained residue and a solid substance was separated by filtration to obtain 14 mg of 2-(benzamido)-4-(2-methylphenyl)benzoic acid as white solid.

$^1$H-NMR (DMSO-$d_6$) δ: 2.29 (3H, s), 7.18-7.38 (5H, m), 7.57-7.69 (3H, m), 7.94-8.00 (2H, m), 8.12 (1H, d, J=8.1 Hz), 8.74 (1H, d, J=1.4 Hz), 12.27 (1H, s).

Examples 240 to 242

The compounds shown in Table 30 were obtained In the same manner as in Example 239.

TABLE 30

| Example No. | R³ |
|---|---|
| 240 | 4-methylphenyl (Me-C₆H₄-) |
| 241 | 3-cyanophenyl (NC-C₆H₄-) |
| 242 | 4-cyanophenyl (NC-C₆H₄-) |

2-(Benzamido)-4-(4-methylphenyl(benzoic acid $^1$H-NMR (DMSO-$d_6$) δ: 2.38 (3H, s), 7.35 (2H, d, J=8.0 Hz), 7.50 (1H, dd, J=8.3, 1.9 Hz), 7.58-7.70 (5H, m), 7.96-8.02 (2H, m), 8.12 (1H, d, J=8.3 Hz), 9.07 (1H, d, J=1.9 Hz), 12.33 (1H, s).

2-(Benzamido)-4-(3-cyanophenyl)benzoic acid $^1$H -NMR (DMSO-$d_6$) δ: 7.58-7.70 (4H, m), 7.76 (1H, t, J=7.8 Hz), 7.92-7.97 (1H, m), 7.97-8.02 (2H, m), 8.05-8.11 (1H, 8.16 (1H, d, J=8.3 Hz), 8.19-8.23 (1H, m), 9.08 (1H, d, J=2.0 Hz), 12.28 (1H, s).

2-(Benzamido)-4-(4-cyanophenyl)benzoic acid $^1$H-NMR (DMSO-$d_6$) δ: 7.56-7.69 (4H, m), 7.90-8.02 (6H, m), 8.16 (1H, d, J=8.3 Hz), 9.10 (1H, d, J=2.0 Hz), 12.29 (1H, s).

Example 243

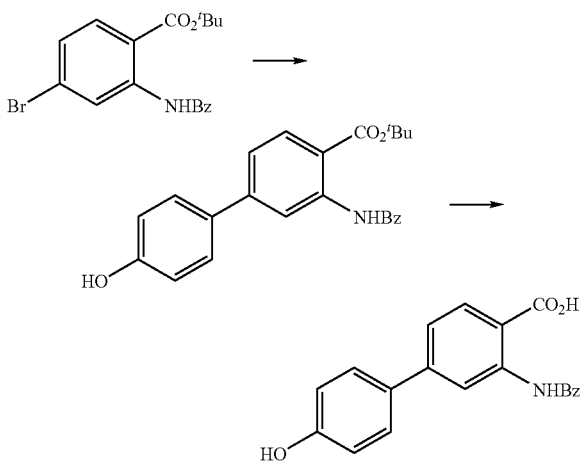

39 mg of 4-hydroxyphenylboronic acid, 49 mg of sodium carbonate and 6 mg of polymer supported bis(acetato)triphenylphosphine palladium(II) were added to 2.5 mL of N,N-dimethylacetamide solution containing 70 mg of tert-butyl 2-(benzamido)-4-bromobenzoate, and stirred at 110° C. for 20 hours. After the reaction mixture was cooled to room temperature, 6 mg of polymer supported bis(acetato)triphenylphosphine palladium(II) was added and stirred at 110° C. for 22 hours. After the reaction mixture was cooled to room temperature, insoluble were removed by filtration and ethyl acetate and 10% citric acid, aqueous solution were added. The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [Flash Tube 2008 manufactured by Trikonex company, eluent; hexane: ethyl acetate=2:1] to obtain tert-butyl 2-(benzamido)-4-(4-hydroxyphenyl)benzoate.

10 mL of trifluoroacetic acid was added to the obtained tert-butyl 2-(benzamido)-4-(4-hydroxyphenyl)benzoate and stirred at room temperature for 1 hour. The solvent was evaporated under reduced pressure and the obtained residue was purified with reversed-phase silica gel column chromatography [eluent; 55-90% acetonitrile /0.1% trifluoroacetic acid aqueous solution] to obtain 1.9 mg of 2-(benzamido)-4-(4-hydroxyphenyl)benzoic acid as while solid.

$^1$H-NMR (DMSO-$d_6$) δ: 6.88-6.96 (2H, m), 7.44 (1H, dd, J=8.3, 1.9 Hz), 7.56-7.69 (5H, m), 7.96-8.02 (2H, m), 8.08 (1H, d, J=8.3 Hz), 9.03 (1H, d, J=1.9 Hz), 9.79 (1H, s), 12.33 (1H, s).

Example 244

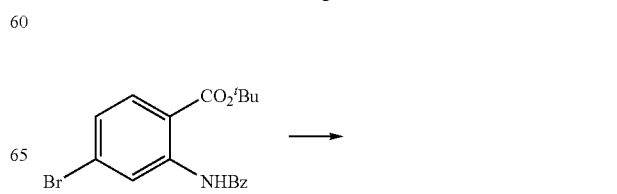

-continued

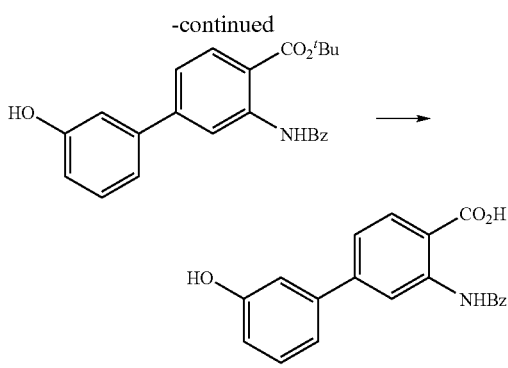

The following compound was obtained in the same manner as in Example 243.

2-(Benzamido)-4-(3-hydroxyphenyl)benzoic acid $^1$H-NMR (DMSO-d$_6$) δ: 6.86 (1H, dd, J=8.1, 1.9 Hz), 7.11-7.19 (2H, m), 7.33 (1H, t, J=7.9 Hz), 7.47 (1H, dd, J=8.1, 1.7 Hz), 7.59-7.70 (3H, m), 7.97-8.02 (2H, m), 8.13 (1H, d, J=8.1 Hz), 9.06 (1H, d, J=1.7 Hz), 9.69 (1H, s), 12.30 (1H, s).

Example 245

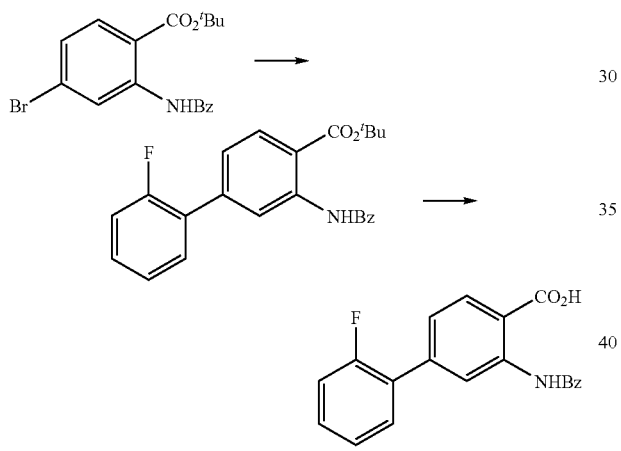

56 mg of 2-fluorophenylboronic acid, 0.10 g of sodium, hydrogen carbonate, 0.6 mL of ethanol, 0.3 mL of wafer and 23 mg of tetrakis(triphenylphosphine)palladium(0) were added to 2.1 mL of toluene solution containing 0.15 g of tert-butyl 2-(benzamido)-4-bromobenzoate, and the resulting mixture was heated to reflux for 2 hours, lifter the reaction mixture was cooled to room temperature, 17 mg of 2-fluorophenylboronic acid and 23 mg of tetrakis(triphenylphosphine )palladium(0) were added and she resulting mixture was heated to reflux for 2 hours. After the reaction mixture was cooled to room temperature, toluene and a saturated sodium hydrogen carbonate aqueous solution were added. The organic layer was separated and dried over anhydrous magnesium sulfate after washed with a saturated sodium chloride aqueous solution, and the solvent was evaporated under reduced pressure. The obtained residue was purified with silica gel column chromatography [Flash Tube 2008 manufactured by Trikonex Company, eluent; hexane:ethyl acetate=10:1] to obtain tert-butyl 2-(benzamido)-4-(2-fluorophenyl)benzoate.

10 mL of trifluoroacetic acid was added to the obtained tert-butyl 2-(benzamido)-4-(2-fluorophenyl)benzoate and stirred at room temperature for 2 hours. The solvent was evaporated under reduced pressure and toluene was added. The solvent was evaporated under reduced pressure and diisopropyl ether was added to the obtained residue and a solid substance was separated by filtration to obtain 93 mg of 2-(benzamido)-4-(2-fluorophenyl)benzoic acid as white solid.

$^1$H-NMR (DMSO-d$_6$) δ: 7.34-7.44 (3H, m), 7.47-7.55 (1H, m), 7.56-7.70 (4H, m), 7.94-8.01 (2H, m), 8.16 (1H, d, J=8.3 Hz), 8.96-9.00 (1H, m), 12.27 (1H, s).

Examples 246 to 250

The compounds shown in Table 31 were obtained in the same manner as in Example 245.

TABLE 31

R³—[ring]—CO₂H, NHBz

| Example No. | R³ |
|---|---|
| 246 | 3-fluoro-4-methylphenyl (F, Me) |
| 247 | 2-chlorophenyl (Cl) |
| 248 | 3,4-dichlorophenyl (Cl, Cl) |
| 249 | 4-chloro-2-fluoro... (Cl, F, Me) |
| 250 | 2,3-dimethylphenyl (Me, Me) |

2-(Benzamido)-4-(3-fluoro-4-methylphenyl)benzoic acid $^1$H-NMR (DMSO-d$_6$) δ: 2.28-2.34 (3H, m), 7.42-7.57 (4H, m), 7.58-7.70 (3H, m), 7.96-8.02 (2H, m), 8.12 (1H, d, J=8.3 Hz), 9.06 (1H, d, J=1.7 Hz), 12.27 (1H, s).

2-(Benzamido)-4-(2-chlorophenyl)benzoic acid $^1$H-NMR (DMSO-d$_6$) δ: 7.29 (1H, dd, J=8.3, 1.7 Hz), 7.45-7.51 (3H, m), 7.57-7.69 (4H, m), 7.94-8.00 (2H, m), 8.15 (1H, d, J=8.3 Hz), 8.84 (1H, d, J=1.7 Hz), 12.28 (1H, s).

2-(Benzamido)-4-(3,4-dichlorophenyl)benzoic acid $^1$H-NMR (DMSO-d$_6$) δ: 7.57 (1H, dd, J=8.3, 1.9 Hz), 7.58-7.70 (3H, m), 7.73 (1H, dd, J=8.3, 2.2 Hz), 7.81 (1H, d, J=8.6 Hz), 7.96-8.01 (3H, m), 8.14 (1H, d, J=8.3 Hz), 9.05 (1H, d, J=1.9 Hz), 12.24 (1H, s).

2-(Benzamido)-4-(5-chloro-2-fluorophenyl)benzoic acid $^1$H-NMR (DMSO-d$_6$) δ: 7.40-7.50 (2H, m), 7.55-7.70 (5H, m), 7.95-8.01 (2H, m), 8.16 (1H, d, J=8.0 Hz), 8.96 (1H, s), 12.27 (1H, s).

2-(Benzamido)-4-(2,6-dimethylphenyl)benzoic acid $^1$H-NMR (DMSO-d$_6$) δ: 2.03 (6H, s), 7.02 (1H, dd, J=8.1, 1.6 Hz), 7.13-7.25 (3H, m), 7.56-7.69 (3H, m), 7.93-7.99 (2H, m), 8.15 (1H, d, J=8.1 Hz), 8.53 (1H, d, J=1.6 Hz), 12.29 (1H, s).

Example 251

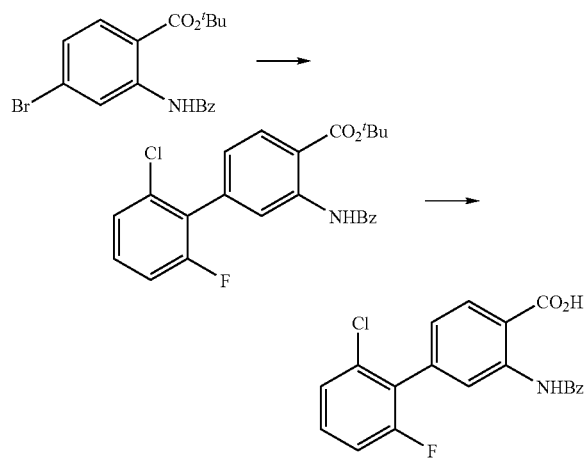

83 mg of 2-chloro-6-fluorophenylboronic acid, 0.10 g of sodium hydrogen carbonate, 0.6 mL of ethanol, 0.3 mL of wafer and 23 mg of tetrakis(triphenylphosphine)palladium(0) were added to 2.1 mL of toluene solution containing 0.15 g of tert-butyl 2-(benzamido)-4-bromobenzoate, and the resulting mixture was heated to reflux for 2 hours. After the reaction mixture was cooled to room temperature, 21 mg of 2-chloro-6-fluorophenylboronic acid and 23 mg tetrakis(triphenylphosphine)palladium(0) were added and the resulting mixture was heated to reflux for 2 hours. After the reaction mixture was cooled to room temperature, toluene and a saturated sodium, hydrogen carbonate aqueous solution were added. The organic layer was separated and dried over anhydrous magnesium sulfate after washed with saturated sodium chloride aqueous solution, and the solvent was evaporated under reduced pressure. The obtained residue was purified with silica gel column chromatography [Flash Tube 2008 manufactured by Trikonex Company, eluent; hexane:ethyl acetate=10:1] to obtain tert-butyl 2-(benzamido)-4-(2-chloro-6-fluorophenyl)benzoate.

10 mL of trifluoroacetic acid was added to the obtained tert-butyl 2-(benzamido)-4-(2-chloro-6-fluorophenyl)benzoate and stirred at room temperature for 2 hours. The solvent was evaporated under reduced pressure and toluene was added. The solvent was evaporated under reduced pressure and the obtained residue was purified with reversed-phase silica gel column chromatography [eluent; 70-100% acetonitrile/0.1% trifluoroacetic acid aqueous solution] to obtain 5.8 mg of 2-(benzamido)-4-(2-chloro-6-fluorophenyl)benzoic acid as white solid.

$^1$H-NMR (DMSO-d$_6$) δ7.23 (1H, dd, J=8.3, 1.6 Hz), 7.37-7.45 (1H, m), 7.49-7.70 (5H, m), 7.93-7.99 (2H, m), 8.17 (1H, d, J=8.3 Hz), 8.73-8.77 (1H, m), 12.28 (1H, s).

Example 252

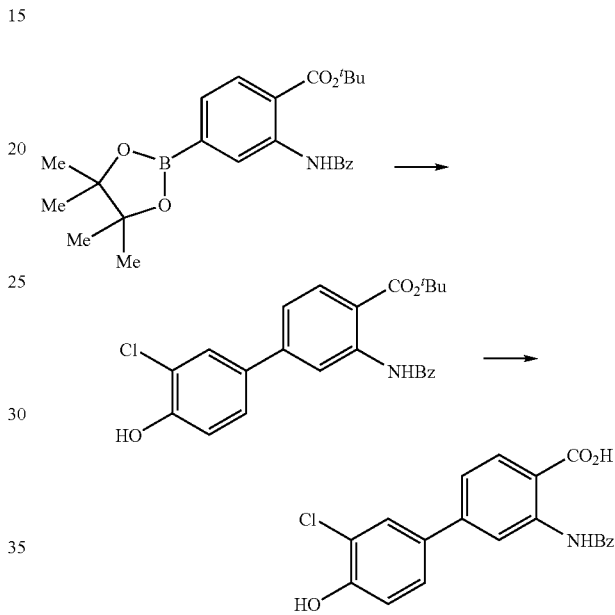

0.15 g of 4-bromo-2-chlorophenol, 0.18 g of sodium hydrogen carbonate, 0.6 mL of ethanol, 0.3 mL of water and 42 mg of tetrakis(triphenylphosphine) palladium(0) were added to 2.1 mL of toluene solution containing 0.37 g of tert-butyl 2-(benzamido)-4-(4,4,5,5-tetramethyl-1,3,2-dioxaborolan-2-yl)benzoate at room temperature, and the resulting mixture was heated to reflux for 4 hours. Toluene and a saturated sodium hydrogen carbonate aqueous solution were added after the reaction mixture was cooled to room temperature. The organic layer was separated and ethyl acetate was added after washed with a saturated sodium chloride aqueous solution and dried over anhydrous magnesium sulfate, and the solvent was evaporated under reduced pressure. Hexane was added to the obtained residue and a solid substance was separated by filtration to obtain tert-butyl 2-(benzamido)-4-(3-chloro-4-hydroxyphenyl)benzoate.

10 mL of trifluoroacetic acid was added to the obtained tert-butyl 2-(benzamido)-4-(3-chloro-4-hydroxyphenyl)benzoate and stirred at room temperature for 2 hours. The solvent was evaporated under reduced pressure and toluene was added. The solvent was evaporated under reduced pressure and diisopropyl ether was added to the obtained residue and a solid substance was separated by filtration to obtain 94 mg of 2-(benzamido)-4-(3-chloro-4-hydroxyphenyl)benzoic acid as white solid.

$^1$H-NMR (DMSO-d$_6$) δ: 7.13 (1H, d, J=8.3 Hz), 7.48 (1H, dd, J=8.3, 1.7 Hz), 7.56 (1H, dd, J=8.4, 2.3 Hz), 7.57-7.72

(4H, m), 7.96-8.01 (2H, m), 8.09 (1H, d, J=8.3 Hz), 9.01 (1H, d, J=1.7 Hz), 10.50-10.66 (1H, broad), 12.26 (1H, s).

Example 253

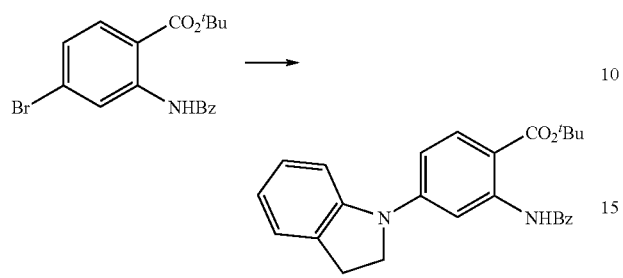

0.031 mL of indoline, 0.12 g of cesium carbonate, 1.7 mg of tris(dibenzylideneacetone)dipalladium(0), 0.8 mg of palladium acetate and 4.4 mg of 2-dicyclohexylphosphino-2',4',6'-triisopropylbiphenyl were added to 1.4 mL of toluene solution containing 70 mg of tert-butyl 2-(benzamido)-4-bromobenzoate at room temperature, and the resulting mixture was heated to reflux under nitrogen atmosphere for 3 hours. After the reaction mixture was cooled to room temperature, ethyl acetate and 10% citric acid aqueous solution were added and insoluble were removed by filtration. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane: ethyl acetate -10:1] to obtain 77 mg of tert-butyl 2-(benzamido)-4-(indolin-1-yl)benzoate as yellow oil.

$^1$H-NMR (CDCl$_3$) δ: 1.63 (3H, s), 3.17 (2H, t, J=8.4 Hz), 4.10 (2H, t, J=8.4 Hz), 6.86 (1H, td, J=7.4, 0.8 Hz), 6.96 (1H, dd, J=8.9, 2.5 Hz), 7.16-7.24 (2H, m), 7.46-7.57 (4H, m), 7.97 (1H, d, J=8.9 Hz), 8.06-8.10 (2H, m), 8.81 (1H, d, J=2.5 Hz), 12.40 (1H, s).

Example 254

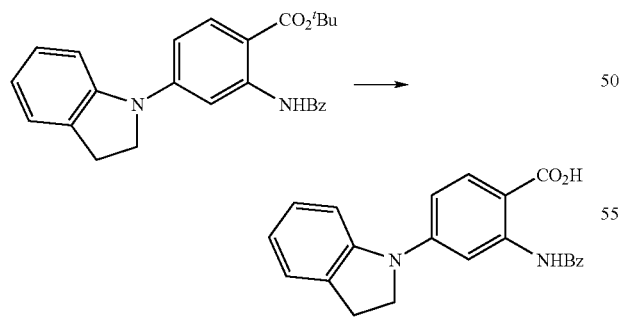

5.0 mL of trifluoroacetic acid solution containing 75 mg of tert-butyl 2-(benzamido)-4-(indolin-1-yl)benzoate was stirred at room temperature for 1 hour and 30 minutes. The solvent was evaporated under reduced pressure, ethyl acetate and water were added and pH was adjusted to pH 6.5 with a saturated sodium hydrogen carbonate aqueous solution. The organic layer was separated and dried over anhydrous magnesium sulfate after washed with water and a saturated sodium chloride aqueous solution sequentially, and the solvent was evaporated under reduced pressure. Methanol was added to the obtained residue and a solid substance was separated by filtration to obtain 51 mg of 2-(benzamido)-4-(indolin-1-yl)benzoic acid a yellow solid.

$^1$H-NMR (DMSO-d$_6$) δ: 3.17 (2H, t, J=8.4 Hz), 4.06 (2H, t, J=8.4 Hz), 6.88 (1H, t, J=7.4 Hz), 6.95 (1H, dd, J=9.0, 2.4 Hz), 7.19 (1H, t, J=7.6 Hz), 7.27 (1H, d, J=7.3 Hz), 7.48 (1H, d, J=8.0 Hz), 7.58-7.69 (3H, m), 7.96-8.02 (2H, m), 8.02 (1H, d, J=9.0 Hz), 8.82 (1H, d, J=2.4 Hz), 12.50 (1H, s), 13.26 (1H, s).

Examples 255 to 277

The compounds shown in Table 32 were obtained in the same manner as in Example 34.

TABLE 32

| Example No. | R$^2$ |
|---|---|
| 255 | 2-(trifluoromethyl)phenyl |
| 256 | benzyl |
| 257 | 2-methylphenyl |
| 258 | 3-methylphenyl |
| 259 | 4-methylphenyl |
| 260 | 4-nitrophenyl |
| 261 | 2,4-dimethylphenyl |

TABLE 32-continued
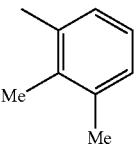
| Example No. | R² |
|---|---|
| 262 | 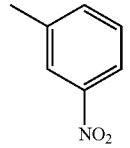 |
| 263 | 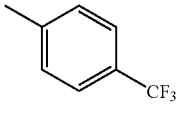 |
| 264 | 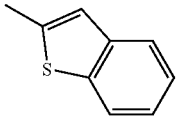 |
| 265 | 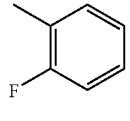 |
| 266 | 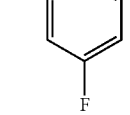 |
| 267 | 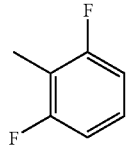 |
| 268 | 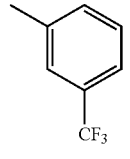 |
| 269 | 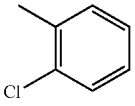 |
| 270 | 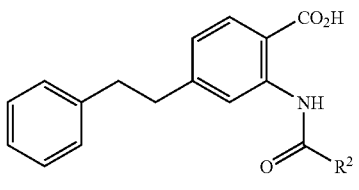 |
TABLE 32-continued
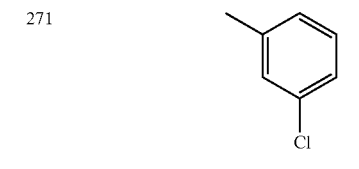
| Example No. | R² |
|---|---|
| 271 |  |
| 272 | 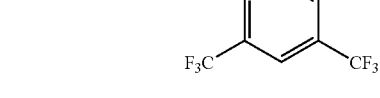 |
| 273 | 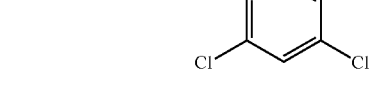 |
| 274 |  |
| 275 | 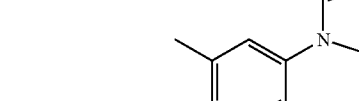 CF₃CO₂H |
| 276 |  |
| 277 |  |
4-Phenethyl-2-(2-(trifluoromethyl)benzamido)benzoic acid
¹H-NMR (DMSO-d₆) δ: 2.90-3.02 (4H, m), 7.13 (1H, dd, J=8.1, 1.7 Hz), 7.16-7.22 (1H, m), 7.26-7.32 (4H, m), 7.73-7.81 (1H, m), 7.81-7.86 (2H, m), 7.86-7.97 (2H, m), 8.49 (1H, s), 11.62 (1H, s), 13.50-13.70 (1H, broad).
4-Phenethyl-2-(2-phenylacetamido)benzoic acid
¹H-NMR (DMSO-d₆) δ: 2.82-2.94 (4H, m), 3.75 (2H, s), 6.99 (1H, dd, J=8.2, 1.5 Hz), 7.13-7.20 (1H, m), 7.20-7.32 (5H, m), 7.32-7.42 (4H, m), 7.84 (1H, d, J=8.2 Hz), 8.44 (1H, d, J=1.5 Hz), 11.16 (1H, s).
2-(2-Methylbenzamido)-4-phenethylbenzoic acid
¹H-NMR (DMSO-d₆) δ: 2.45 (3H, s), 2.90-3.02 (4H, m), 7.09 (1H, dd, J=8.3, 1.6 Hz), 7.16-7.23 (1H, m), 7.26-7.37

(6H, m), 7.40-7.50 (1H, m), 7.59 (1H, d, J=7.6 Hz), 7.94 (1H, d, J=8.3 Hz), 8.62 (1H, s), 11.62 (1H, s), 13.45-13.65 (1H, broad).

2-(3-Methylbenzamido)-4-phenethylbenzoic acid $^1$H-NMR (DMSO-d$_6$) δ: 2.42 (3H, s), 2.90-3.02 (4H, m), 7.08 (1H, dd, J=8.1, 1.6 Hz), 7.16-7.22 (1H, m), 7.25-7.32 (4H, m), 7.44-7.52 (2H, m), 7.73-7.81 (2H, m), 7.96 (1H, d, J=8.1 Hz), 8.67 (1H, d, J=1.6 Hz), 12.24 (1H, s).

2-(4-Methylbenzamido)-4-phenethylbenzoic acid $^1$H-NMR (DMSO-d$_6$) δ: 2.40 (3H, s), 2.88-3.01 (4H, m), 7.07 (1H, dd, J=8.1, 1.7 Hz), 7.15-7.22 (1H, m), 7.24-7.32 (4H, m), 7.40 (2H, d, J=8.2 Hz), 7.86 (2H, d, J=8.2 Hz), 7.95 (1H, d, J=8.1 Hz), 8.67 (1H, d, J=1.7 Hz), 12.22 (1H, s).

2-(4-Nitrobenzamido)-4-phenethylbenzoic acid $^1$H-NMR (DMSO-d$_6$) δ: 2.89-3.04 (4H, m), 7.09-7.14 (1H, m), 7.15-7.22 (1H, m), 7.25-7.32 (4H, m), 7.97 (1H, d, J=8.3 Hz), 8.19 (2H, d, J=8.8 Hz), 8.44 (2H, d, J=8.8 Hz), 8.58 (1H, d, J=1.5 Hz).

2-(3,4-Dimethylbenzamido)-4-phenethylbenzoic acid $^1$H-NMR (DMSO-d$_6$) δ: 2.32 (3H, s), 2.32 (3H, s), 2.90-3.00 (4H, m), 7.06 (1H, d, J=8.2 Hz), 7.15-7.20 (1H, m), 7.25-7.30 (4H, m), 7.35 (1H, d, J=7.7 Hz), 7.68 (1H, d, J=7.7 Hz), 7.74 (1H, s), 7.95 (1H, d, J=8.2 Hz), 8.68 (1H, s), 12.16-12.20 (1H, broad).

2-(2,3-Dimethylbenzamido)-4-phenethylbenzoic acid $^1$H-NMR (DMSO-d$_6$) δ: 2.30 (6H, s), 2.90-3.00 (4H, m), 7.06-7.11 (1H, m), 7.16-7.38 (8H, m), 7.93 (1H, d, J=8.0 Hz), 8.61 (1H, s), 11.50-11.56 (1H, broad).

2-(3-Nitrobenzamido)-4-phenethylbenzoic acid $^1$H-NMR (DMSO-d$_6$) δ: 2.90-3.05 (4H, m), 7.10-7.21 (2H, m), 7.26-7.30 (4H, m), 7.89-7.99 (2H, m), 8.36-8.42 (1H, m), 8.47-8.52 (1H, m), 8.58 (1H, d, J=1.7 Hz), 8.76 (1H, t, J=2.0 Hz), 12.36-12.48 (1H, broad).

4-Phenethyl-2-(4-(trifluoromethyl)benzamido)benzoic acid $^1$H-NMR (DMSO-d$_6$) δ: 2.90-3.02 (4H, m), 7.11 (1H, d, J=8.0 Hz), 7.16-7.21 (1H, m), 7.25-7.31 (4H, m), 7.94-8.02 (3H, m), 8.15 (2H, d, J=7.6 Hz), 8.61 (1H, s), 12.28 (1H, s).

2-(Benzothiophene-2-carboxamido)-4-phenethylbenzoic acid $^1$H-NMR (DMSO-d$_6$) δ: 2.90-3.02 (4H, m), 7.10 (1H, dd, J=8.1, 1.2 Hz), 7.17-7.21 (1H, m), 7.25-7.32 (4H, m), 7.48-7.55 (2H, m), 7.98, (1H, d, J=8.1 Hz), 8.06-8.11 (3H, m), 8.53-8.57 (1H, m), 12.34 (1H, s).

2-(2-Fluorobenzamido)-4-phenethylbenzoic acid $^1$H-NMR (DMSO-d$_6$) δ: 2.91-3.00 (4H, m), 7.10 (1H, d, J=8.0 Hz), 7.16-7.21 (1H, m), 7.25-7.31 (4H, m), 7.38-7.44 (2H, m), 7.64-7.69 (1H, m), 7.90-7.96 (2H, m), 8.66 (1H, s), 11.94-12.00 (1H, broad), 13.54-13.60 (1H, broad).

2-(3-Fluorobenzamido)-4-phenethylbenzoic acid $^1$H-NMR (DMSO-d$_6$) δ: 2.90-3.00 (4H, m), 7.10 (1H, dd, J=8.1, 1.7 Hz), 7.16-7.20 (1H, m), 7.25-7.31 (4H, m), 7.49-7.52 (1H, m), 7.64-7.73 (2H, m), 7.78-7.81 (1H, m), 7.96 (1H, d, J=8.1 Hz), 8.60-8.62 (1H, m), 12.16-12.22 (1H, broad), 13.64-13.76 (1H, broad).

2-(2,6-Difluorobenzamido)-4-phenethylbenzoic acid $^1$H-NMR (DMSO-d$_6$) δ: 2.90-3.02 (4H, m), 7.12-7.21 (2H, m), 7.26-7.33 (6H, m), 7.61-7.69 (1H, m), 7.94 (1H, d, J=8.0 Hz), 8.50 (1H, s), 11.74-11.82 (1H, broad).

4-Phenethyl-2-(3-(trifluoromethyl)benzamido)benzoic acid $^1$H-NMR (DMSO-d$_6$) δ: 2.90-3.03 (4H, m), 7.10-7.13 (1H, m), 7.16-7.21 (1H, m), 7.25-7.31 (4H, m), 7.87 (1H, t, J=7.9 Hz), 7.96 (1H, d, J=8.1 Hz), 8.04 (1H, d, J=7.8 Hz), 8.24-8.28 (2H, m), 8.60 (1H, s), 12.28-12.34 (1H, broad).

2-(2-Chlorobenzamido)-4-phenethylbenzoic acid $^1$H-NMR (DMSO-d$_6$) δ: 2.90-3.02 (4H, m), 7.12 (1H, dd, J=8.3, 1.5 Hz), 7.16-7.22 (1H, m), 7.26-7.32 (4H, m), 7.48-7.63 (3H, m), 7.71 (1H, dd, J=7.3, 1.7 Hz), 7.94 (1H, d, J=8.3 Hz), 8.53-8.59 (1H, m), 11.62-11.70 (1H, broad), 13.54-13.62 (1H, broad).

2-(3-Chlorobenzamido)-4-phenethylbenzoic acid $^1$H-NMR (DMSO-d$_6$) δ: 2.90-3.02 (1H, m), 7.10 (1H, dd, J=8.3, 1.2 Hz), 7.16-7.22 (1H, m), 7.25-7.31 (4H, m), 7.64 (1H, t, J=7.8 Hz), 7.72-7.75 (1H, m), 7.91 (1H, d, J=7.8 Hz), 7.95-7.97 (2H, m), 8.58-8.61 (1H, m), 12.18-12.24 (1H, broad).

2-(4-Chlorobenzamido)-4-phenethylbenzoic acid $^1$H-NMR (DMSO-d$_6$) δ: 2.90-3.01 (4H, m), 7.09 (1H, dd, J=8.0, 1.0 Hz), 7.16-7.20 (1H, m), 7.26-7.32 (4H, m), 7.69 (2H, d, J=8.5 Hz), 7.93-7.98 (3H, m), 8.61-8.63 (1H, m), 12.17-12.22 (1H, broad).

2-(2,4-Bis(trifluoromethyl)benzamido)-4-phenethylbenzoic acid $^1$H-NMR (DMSO-d$_6$) δ: 2.90-3.02 (4H, m), 7.14-7.22 (2H, m), 7.26-7.30 (4H, m), 7.93 (1H, d, J=8.0 Hz), 8.09 (1H, d, J=8.0 Hz), 8.24 (1H, s), 8.28 (1H, d, J=8.3 Hz), 8.36-8.39 (1H, m), 11.60-11.64 (1H, broad).

2-(2,4-Dichlorobenzamido)-4-phenethylbenoic acid $^1$H-NMR (DMSO-d$_6$) δ: 2.90-3.02 (4H, m), 7.10-7.15 (1H, m), 7.16-7.22 (1H, m), 7.26-7.32 (4H, m), 7.61 (1H, dd, J=8.4, 2.1 Hz), 7.75 (1H, d, J=8.3 Hz), 7.81 (1H, d, J=2.1 Hz), 7.93 (1H, d, J=8.3 Hz), 8.50 (1H, s), 11.62-11.68 (1H, broad).

4-Phenethyl-2-((E)-3-(pyridin-4-yl)acrylamido)benzoic acid trifluoroacetate $^1$H-NMR (DMSO-d) δ: 2.88-3.00 (4H, m), 7.09 (1H, dd, J=8.1, 1.5 Hz), 7.16-7.21 (1H, m), 7.23-7.29 (4H, m), 7.32 (1H, d, J=15.6 Hz), 7.67 (1H, d, J=15.6 Hz), 7.93 (1H, d, J=8.1 Hz), 8.00 (2H, d, J=6.2 Hz), 8.53 (1H, d, J=1.5 Hz), 8.78 (2H, d, J=6.2 Hz), 11.48 (1H, s).

4-Phenethyl-2-(5-(1H-pyrrol-1-yl)pyridine-3-carboxamido)benzoic acid $^1$H-NMR (DMSO-d$_6$) δ: 2.91-3.03 (4H, m), 6.39 (2H, t, J=2.2 Hz), 7.13 (1H, dd, J=8.1, 1.6 Hz), 7.16-7.31 (5H, m), 7.58 (2H, t, J=2.2 Hz), 7.97 (1H, d, J=8.1 Hz), 8.44 (1H, t, J=2.3 Hz), 8.57 (1H, d, J=1.6 Hz), 8.96 (1H, d, J=2.3 Hz), 9.16 (1H, d, J=2.3 Hz), 12.20 (1H, s)

4-Phenethyl-2-(2-(pyrrolidin-1-yl)pyridine-3-carboxamido)benzoic acid $^1$H-NMR (DMSO-$d_6$) δ: 1.80-1.89 (4H, m), 2.88-3.01 (4H, m), 3.32-3.42 (4H, m), 6.72 (1H, dd, J=7.4, 4.8 Hz), 7.08 (1H, dd, J=8.2, 1.7 Hz), 7.15-7.22 (1H, m), 7.24-7.31 (4H, m), 7.78 (1H, dd, J=7.4, 1.9 Hz), 7.92 (1H, d, J=8.2 Hz), 8.22 (1H, dd, J=4.8, 1.9 Hz), 8.57 (1H, s), 11.58 (1H, s).

Example 278

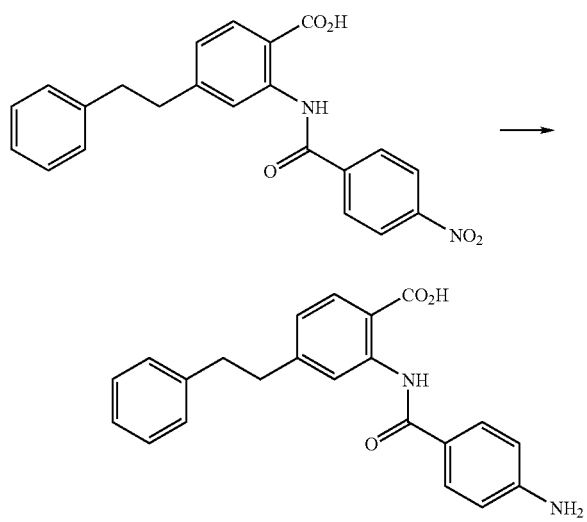

2.0 mg of 5% palladium-carbon was added to a mixed solution of 1.0 mL of methanol and 2.0 mL of ethyl acetate containing 7.0 mg of 2-(4-nitrobenzamido)-4-phenethylbenzoic acid and stirred under hydrogen atmosphere at room temperature for 2 hours. After insoluble were removed by filtration, the solvent was evaporated under reduced pressure to obtain 4.0 mg of 2-(4-aminobenzamido)-4-phenethylbenzoic acid as pale yellow solid.

$^1$H-NMR (DMSO-$d_6$) δ: 2.80-2.96 (4H, m), 5.55-5.91 (2H, broad), 6.61 (2H, d, J=8.6 Hz), 6.81 (1H, dd, J=8.0, 1.6 Hz), 7.15-7.20 (1H, m), 7.24-7.31 (4H, m), 7.74 (2H, d, J=8.6 Hz), 7.89 (1H, d, J=8.0 Hz), 8.61 (1H, d, J=1.6 Hz).

Example 279

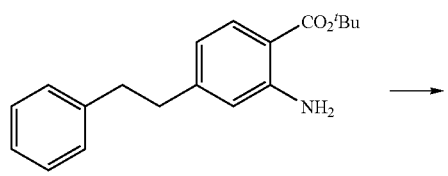

-continued

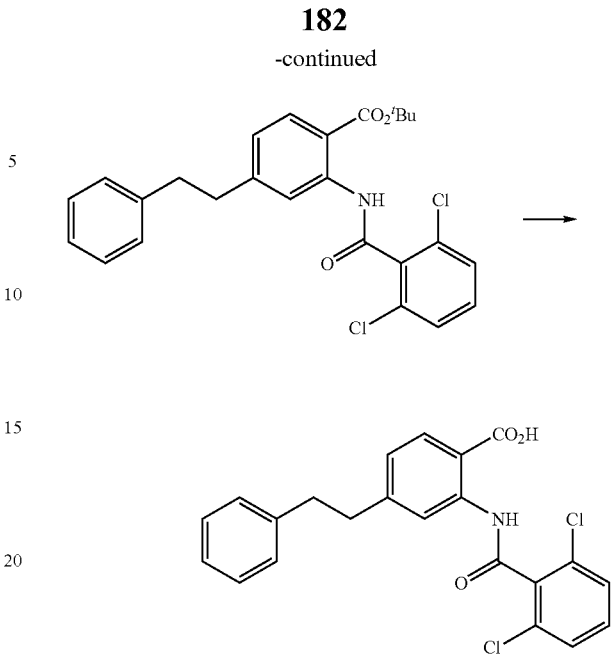

0.061 mL of pyridine and 0.086 mL of 2,6-dichlorobenzoyl chloride were added to 3.0 mL of toluene solution containing 0.15 g of tert-butyl 2-amino-4-phenethylbenzoate at room temperature sequentially, and the resulting mixture was heated to reflux for 8 hours. The reaction mixture was cooled to room temperature and a saturated sodium hydrogen carbonate aqueous solution was added. The organic layer was separated and dried over anhydrous magnesium sulfate after washed with 10% citric acid, aqueous solution and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane; ethyl acetate=4:1] to obtain tert-butyl 2-(2,6-dichlorobenzamido)-4-phenethylbenzoate.

3.0 mL of trifluoroacetic acid was added to the obtained tert-butyl 2-(2,6-dichlorobenzamido)-4-phenethylbenzoate and stirred at room temperature for 1 hour. The solvent was evaporated under reduced pressure and diisopropyl ether was added to the obtained residue and a solid substance was separated by filtration to obtain 18 mg of 2-(2,6-dichlorobenzamido)-4-phenethylbenzoic acid as white solid.

$^1$H-NMR (DMSO-$d_6$) δ: 2.91-3.02 (4H, m), 7.15-7.22 (2H, m), 7.26-7.30 (4H, m), 7.53-7.57 (1H, m), 7.61-7.64 (2H, m), 7.64 (1H, d, J=1.7 Hz), 7.94 (1H, d, J=8.0 Hz), 8.48-8.50 (1H, broad), 11.56-11.62 (1H, broad).

Example 280

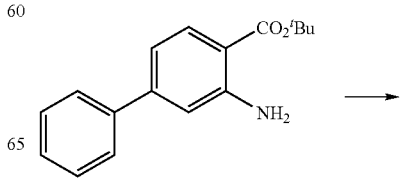

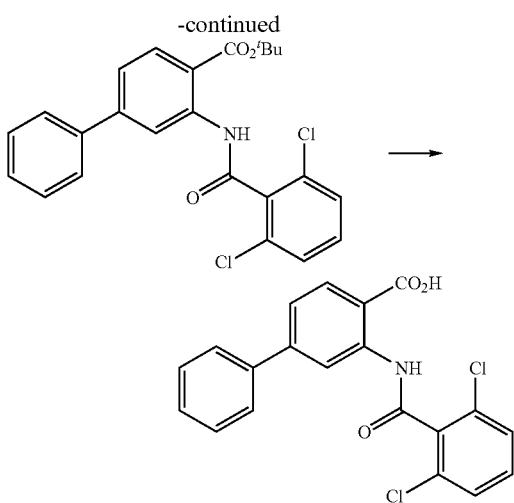

0.090 mL of pyridine and 0.12 mL of 2,6-dichlorobenzoyl chloride were added to 3.0 mL of toluene solution containing 0.15 g of tert-butyl 2-amino-4-phenylbenzoate at room temperature sequentially, and the resulting mixture was heated to reflux for 4 hours. The reaction mixture was cooled to room temperature and 0.023 mL of pyridine and 0.040 mL of 2,6-dichlorobenzoyl chloride were added sequentially and the resulting mixture was heated to reflux for 2 hours. The reaction mixture was cooled to room temperature and water was added. The organic layer was separated and dried over anhydrous sodium chloride aqueous solution, and the solvent was evaporated under reduced pressure. The obtained residue was purified with silica gel column chromatography [Flash Tube 2008 manufactured by Trikonex Company, eluent; hexane:ethyl acetate=4:1] to obtain herb-butyl 2-(2,6-dichlorobenzamido)-4-phenylbenzoate.

3.0 mL of trifluoroacetic acid was added to the obtained tert-butyl 2-(2,6-dichlorobenzamido)-4-phenylbenzoate and stirred at room temperature for 1 hour. The solvent was evaporated under reduced pressure and diisopropyl ether was added no the obtained residue and a solid substance was separated by filtration to obtain 0.10 g of 2-(2,6-dichlorobenzamido)-4-phenylbenzoic acid as white solid.

$^1$H-NMR (DMSO-$d_6$) δ: 7.46-7.65 (7H, m), 7.73 (2H, d, J=7.8 Hz), 8.12 (1H, d, J=8.3 Hz), 8.87-8.89 (1H, broad), 11.62-11.68 (1H, broad), 13.76-13.88 (1H, broad).

Example 281

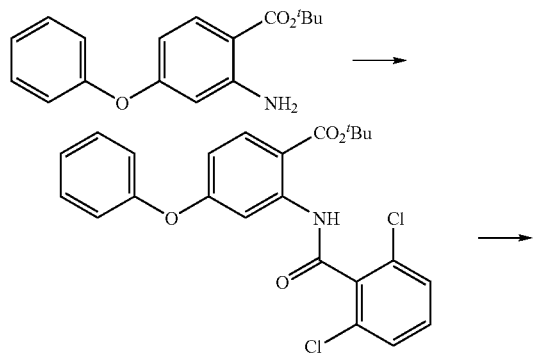

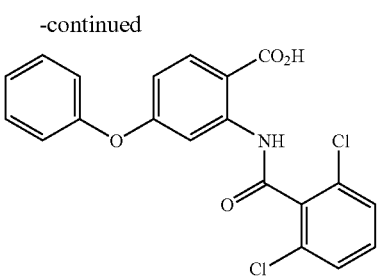

0.089 mL of pyridine and 0.11 mL of 2,6-dichlorobenzoyl chloride were added to 3.0 mL of toluene solution containing 0.15 g of tert-butyl 2-amino-4-phenoxybenzoate at room temperature sequentially, and the resulting mixture was heated to reflux for 4 hours. The reaction mixture was cooled to room temperature and 0.021 mL of pyridine and 0.037 mL of 2,6-dichlorobenzoyl chloride were added sequentially and heated to reflux for 4 hours. The reaction mixture was cooled to room temperature and water was added. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane:ethyl acetate=4:1]to obtain tert-butyl 2-(2,6-dichlorobenzamido)-4-phenoxybenzoate.

3.0 mL of trifluoroacetic acid was added to the obtained tert-butyl 2-(2,6-dichlorobenzamido)-4-phenoxybenzoate and stirred at room temperature for 1 hour. The solvent was evaporated under reduced pressure and diisopropyl ether was added to the obtained residue and a solid substance was separated by filtration to obtain 70 mg of 2-(2,6-dichlorobenzamido)-4-phenoxybenzoic acid as white solid.

$^1$H-NMR (DMSO-$d_6$) δ: 6.79 (1H, dd, J=8.9, 2.1 Hz), 7.19-7.23 (2H, m), 7.26-7.32 (1H, m), 7.48-7.57 (3H, m), 7.61-7.65 (2H, m), 8.05 (1H, d, J=8.9 Hz), 8.24-8.28 (1H, m).

Example 282

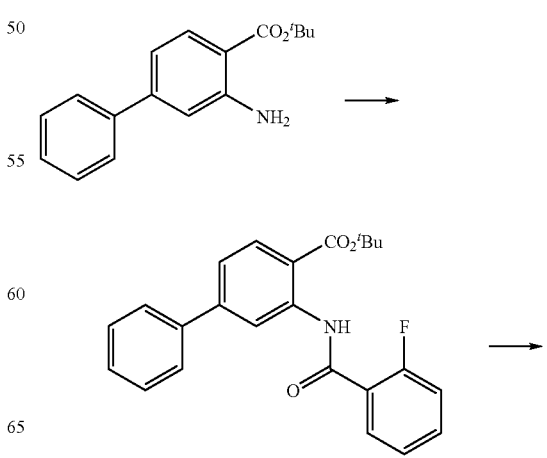

-continued

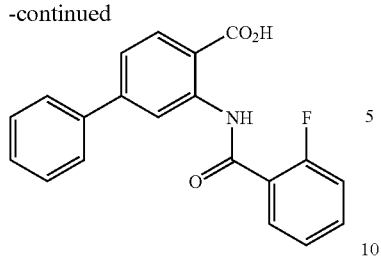

0.063 mL of triethylamine and 0.040 mL of 2-fluorobenzoyl chloride were added to 3.0 mL of Methylene chloride solution containing 60 mg of tert-butyl 2-amino-4-phenylbenzoate at room temperature sequentially and stirred at the same temperature for 1 hour. 0.51 g of aminomethylated polystyrene was added to the reaction mixture and stirred at room temperature overnight. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(2-fluorobenzamido)-4-phenylbenzoate.

10 mL of trifluoroacetic acid was added to she obtained tert-butyl 2-(2-fluorobenzamido)-4-phenylbenzoate and stirred at room temperature for 2 hours. The solvent was evaporated under reduced pressure and diisopropyl ether was added to the obtained residue and a solid substance was separated by filtration to obtain 61 mg of 2-(2-fluorobenzamido)-1-phenylbenzoic acid as white solid.

$^1$H-NMR (DMSO-$d_6$) δ: 7.39-7.50 (3H, m), 7.52-7.59 (3H, m), 7.65-7.76 (3H, m), 7.96 (1H, td, J=7.8, 1.8 Hz), 8.13 (1H, d, J=8.3 Hz), 9.07 (1H, d, J=1.7 Hz), 12.00-12.10 (1H, bread), 13.65-13.85 (1H, broad).

Examples 283 to 319

The compounds shown in Table 33 were obtained in the same manner as in Example 282.

TABLE 33

| Example No. | R² |
|---|---|
| 283 | 3-F-phenyl |
| 284 | 4-F-phenyl |
| 285 | 2-Me-4,6-diF-phenyl |
| 286 | 2,6-diF-phenyl |
| 287 | 2-Me-phenyl |
| 288 | 3,5-diMe-phenyl |
| 289 | 2,5-diMe-phenyl |
| 290 | 2-CF₃-phenyl |
| 291 | 3-CF₃-phenyl |
| 292 | 4-CF₃-phenyl |
| 293 | 2,4-diMe-phenyl |
| 294 | 2,6-diMe-phenyl |

TABLE 33-continued

| Example No. | R² |
|---|---|
| 295 | 5-methyl-2-morpholinopyridin-yl |
| 296 | cyclohexyl |
| 297 | benzyl (phenylmethyl via CH₂) |
| 298 | (E)-styryl |
| 299 | 2-ethoxyphenyl |
| 300 | furan-2-yl |
| 301 | thiophen-2-yl |
| 302 | benzo[d][1,3]dioxol-5-yl |
| 303 | 2,3-dihydrobenzo[b][1,4]dioxin-6-yl |
| 304 | benzo[b]thiophen-5-yl |
| 305 | 1-methyl-1H-benzo[d][1,2,3]triazol-5-yl |
| 306 | 3-nitrophenyl |
| 307 | benzofuran-5-yl |
| 308 | benzo[d]thiazol-2-yl |
| 309 | benzo[b]thiophen-3-yl |
| 310 | benzofuran-2-yl |
| 311 | benzo[b]thiophen-2-yl |
| 312 | 1-phenyl-1H-pyrazol-5-yl |
| 313 | diphenylmethyl (benzhydryl) |
| 314 | 2-chlorophenyl |

TABLE 33-continued

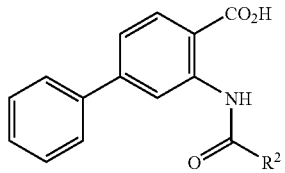

| Example No. | R² |
| --- | --- |
| 315 | 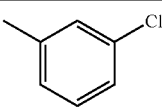 |
| 316 | 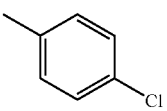 |
| 317 | 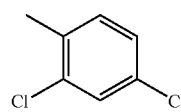 |
| 318 | 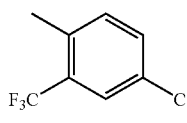 |
| 319 | 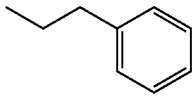 |

2-(3-Fluorobenzamido)-4-phenylbenzoic acid

¹H-NMR (DMSO-d₆) δ: 7.44-7.49 (1H, m), 7.51-7.58 (4H, m), 7.65-7.72 (1H, m), 7.72-7.77 (3H, m), 7.81-7.85 (1H, m), 8.14 (1H, d, J=8.3 Hz), 9.02 (1H, d, J=1.7 Hz), 12.25 (1H, s).

2-(4-Fluorobenzamido)-4-phenylbenzoic acid

¹H-NMR (DMSO-d₆) δ: 7.43-7.59 (6H, m), 7.71-7.77 (2H, m), 8.02-8.09 (2H, m), 8.14 (1H, d, J=8.3 Hz), 9.04 (1H, d, J=1.7 Hz), 12.24 (1H, s), 13.75-13.95 (1H, broad).

2-(2,4-Difluorobenzamido)-4-phenylbenzoic acid

¹H-NMR (DMSO-d₆) δ: 7.32 (1H, td, J=8.4, 2.4 Hz), 7.44-7.58 (5H, m), 7.70-7.76 (2H, m), 8.04 (1H, td, J=8.8, 6.6 Hz), 8.13 (1H, d, J=8.3 Hz), 9.04 (1H, d, J=2.0 Hz), 12.02-12.06 (1H, m), 13.77 (1H, s).

2-(2,6-Difluorobenzamido)-4-phenylbenzoic acid

¹H-NMR (DMSO-d₆) δ: 7.28-7.35 (2H, m), 7.44-7.50 (1H, m), 7.52-7.61 (3H, m), 7.62-7.78 (3H, m), 8.12 (1H, d, J=8.3 Hz), 8.90 (1H, s), 11.86 (1H, s), 13.70-13.95 (1H, broad).

2-(2-Methylbenzamido)-4-phenylbenzoic acid

¹H-NMR (DMSO-d₆) δ: 2.48 (3H, s), 7.33-7.39 (2H, m), 7.43-7.50 (2H, m), 7.50-7.59 (3H, m), 7.62-7.66 (1H, m), 7.71-7.76 (2H, m), 8.11 (1H, d, J=8.3 Hz), 9.03 (1H, d, J=1.7 Hz), 11.69 (1H, s), 13.71 (1H, s).

2-(3-Methylbenzamido)-4-phenylbenzoic acid

¹H-NMR (DMSO-d₆) δ: 2.43 (3H, s), 7.44-7.58 (6H, m), 7.71-7.83 (4H, m), 8.14 (1H, d, J=8.0 Hz), 9.09 (1H, d, J=1.7 Hz), 12.27 (1H, s), 13.80-13.95 (1H, broad).

2-(4-Methylbenzamido)-4-phenylbenzoic acid

¹H-NMR (DMSO-d₆) δ: 2.41 (3H, s), 7.40-7.58 (6H, m), 7.72-7.75 (2H, m), 7.89 (2H, d, J=8.3 Hz), 8.14 (1H, d, J=8.3 Hz), 9.09 (1H, d, J=1.7 Hz), 12.24 (1H, s), 13.75-13.90 (1H, broad).

4-Phenyl-2-(2-(trifluoromethyl)benzamido)benzoic acid

¹H-NMR (DMSO-d₆) δ: 7.47 (1H, tt, J=7.4, 1.5 Hz), 7.52-7.60 (3H, m), 7.70-7.94 (6H, m), 8.12 (1H, d, J=8.3 Hz), 8.88 (1H, s), 11.69 (1H, s), 13.65-13.85 (1H, broad).

4-Phenyl-2-(3-(trifluoromethyl)benzamido)benzoic acid

¹H-NMR (DMSO-d₆) δ: 7.47 (1H, tt, J=7.3, 1.5 Hz), 7.52-7.58 (3H, m), 7.72-7.77 (2H, m), 7.86-7.91 (1H, m), 8.05 (1H, d, J=8.1 Hz), 8.14 (1H, d, J=8.3 Hz), 8.27-8.32 (2H, m), 9.01 (1H, d, J=2.0 Hz), 12.38 (1H, s), 13.80-14.05 (1H, broad).

4-Phenyl-2-(4-(trifluoromethyl)benzamido)benzoic acid

¹H-NMR (DMSO-d₆) δ: 7.47 (1H, tt, J=7.6, 1.5 Hz), 7.52-7.59 (3H, m), 7.72-7.77 (2H, m), 8.01 (2H, d, J=8.3 Hz), 8.12-8.22 (3H, m), 9.02 (1H, d, J=1.7 Hz), 12.34 (1H, s).

2-(3,4-Dimethylbenzamido)-4-phenylbenzoic acid

¹H-NMR (DMSO-d₆) δ: 2.32 (3H, s), 2.33 (3H, s), 7.37 (1H, d, J=7.8 Hz), 7.44-7.58 (4H, m), 7.69-7.79 (4H, m), 8.13 (1H, d, J=8.3 Hz), 9.09 (1H, d, J=2.0 Hz), 12.25 (1H, s), 13.75-13.95 (1H, broad).

2-(2,3-Dimethylbenzamido)-4-phenylbenzoic acid

¹H-NMR (DMSO-d₆); δ: 2.31 (3H, s), 2.33 (3H, s), 7.24 (1H, t, J=7.6 Hz), 7.34 (1H, d, J=7.6 Hz), 7.41 (1H, d, J=7.6 Hz), 7.44-7.58 (4H, m), 7.71-7.75 (2H, m), 8.11 (1H, d, J=8.3 Hz), 9.03 (1H, s), 11.60 (1H, s), 13.60-13.80 (1H, broad).

2-(6-Morpholinopyridine-3-carboxamido)-4-phenylbenzoic acid

¹H-NMR (DMSO-d₆) δ: 3.60-3.75 (8H, m), 7.00 (1H, d, J=9.0 Hz), 7.43-7.58 (4H, m), 7.70-7.75 (2H, m), 8.04 (1H, dd, J=9.0, 2.5 Hz), 8.12 (1H, d, J=8.3 Hz), 8.75 (1H, d, J=2.5 Hz), 9.06 (1H, d, J=1.7 Hz), 12.08 (1H, s), 13.70-13.90 (1H, broad).

2-(Cyclohexanecarboxamido)-4-phenylbenzoic acid

¹H-NMR (DMSO-d₆) δ: 1.14-1.52 (5H, m), 1.60-1.71 (1H, m), 1.72-1.81 (2H, m), 1.88-1.99 (2H, m), 2.30-2.39 (1H, m), 7.41-7.56 (4H, m), 7.65-7.71 (2H, m), 8.06 (1H, d, J=8.3 Hz), 8.90 (1H, d, J=1.7 Hz), 11.28 (1H, s), 13.61 (1H, s),

4-Phenyl-2-(2-phenylacetamido)benzoic acid $^1$H-NMR (DMSO-d$_6$) δ: 3.80 (2H, s), 7.26-7.54 (9H, m), 7.64-7.69 (2H, m), 8.03 (1H, d, J=8.3 Hz), 8.87 (1H, d, J=1.7 Hz), 11.23 (1H, s), 13.55-13.75 (1H, broad).

2-(Cinnamamido)-4-phenylbenzoic acid $^1$H-NMR (DMSO-d$_6$) δ: 6.94 (1H, d, J=15.6 Hz), 7.41-7.57 (7H, rod , 7.66 (1H, d, J=15.6 Hz), 7.69-7.78 (4H, m), 8.10 (1H, d, J=8.3 Hz), 8.98 (1H, d, J=1.7 Hz), 11.42 (1H, s), 13.55-13.75 (1H, broad).

2-(2-Phenoxyacetamido)-4-phenylbenzoic acid $^1$H-NMR (DMSO-d$_6$) δ: 4.77 (2H, s), 7.03 (1H, t, J=7.3 Hz), 7.09-7.15 (2H, m), 7.33-7.40 (2H, m), 7.43-7.57 (4H, m), 7.67-7.73 (2H, m), 8.10 (1H, d, J=8.3 Hz), 9.06 (1H, d, J=1.7 Hz), 12.26 (1H, s), 13.82 (1H, s).

2-(Furan-2-carboxamido)-4-phenylbenzoic acid $^1$H-NMR (DMSO-d$_6$) δ: 6.77 (1H, dd, J=3.5, 1.7 Hz), 7.30 (1H, dd, J=3.5, 0.6 Hz), 7.44-7.57 (4H, m), 7.69-7.75 (2H, m), 8.02 (1H, dd, J=1.7, 0.6 Hz), 8.13 (1H, d, J=8.3 Hz), 9.03 (1H, d, J=2.0 Hz), 12.26 (1H, s), 13.79 (1H, s).

4-Phenyl-2-(thiophene-2-carboxamido)benzoic acid $^1$H-NMR (DMSO-d$_6$) δ: 7.30 (1H, dd, J=5.0, 3.8 Hz), 7.44-7.50 (1H, m), 7.50-7.58 (3H, m), 7.70-7.76 (2H, m), 7.78 (1H, dd, J=3.8, 1.1 Hz), 7.96 (1H, dd, J=5.0, 1.1 Hz), 8.13 (1H, d, J=8.3 Hz), 8.94 (1H, d, J=1.7 Hz), 12.23 (1H, s), 13.80-14.00 (1H, broad).

2-(Benzo[1,3]dioxole-5-carboxamido)-4-phenylbenzoic acid $^1$H-NMR (DMSO-d$_6$) δ: 6.17 (2H, s), 7.13 (1H, d, J=8.1 Hz), 7.43-7.59 (6H, m), 7.70-7.76 (2H, m), 8.13 (1H, d, J=8.3 Hz), 9.05 (1H, d, J=2.0 Hz), 12.14 (1H, s), 13.70-13.95 (1H, broad).

2-(2,3-Dihydrobenzo[1,4]dioxine-8-carboxamido)-4-phenylbenzoic acid $^1$H-NMR (DMSO-d$_6$) δ: 4.28-4.39 (4H, m), 7.07 (1H, d, J=8.3 Hz), 7.43-7.57 (6H, m), 7.70-7.75 (2H, m), 8.13 (1H, d, J=8.3 Hz), 9.07 (1H, d, J=1.7 Hz), 12.16 (1H, s), 13.70-13.90 (1H, broad).

2-(Benzothiophene-5-carboxamido)-4-phenylbenzoic acid $^1$H-NMR (DMSO-d$_6$) δ: 7.45-7.58 (4H, m), 7.65 (1H, d, J=5.4 Hz), 7.72-7.78 (2H, m), 7.92-7.97 (2H, m), 8.15 (1H, d, J=8.3 Hz), 8.25 (1H, d, J=8.5 Hz), 8.53 (1H, d, J=1.5 Hz), 9.11 (1H, d, J=1.7 Hz), 12.37 (1H, s).

2-(1-Methyl-1H-benzotriazole-5-carboxamido)-4-phenylbenzoic acid $^1$H-NMR (DMSO-d$_6$) δ: 4.39 (3H, s), 7.45-7.51 (1H, m), 7.53-7.59 (3H, m), 7.73-7.78 (2H, m), 8.07 (1H, d, J=8.8 Hz), 8.16 (2H, d, J=8.1 Hz), 8.66 (1H, s), 9.07 (1H, d, J=1.7 Hz), 12.37 (1H, s).

2-(3-Nitrobenzamido)-4-phenylbenzoic acid $^1$H-NMR (DMSO-d$_6$) δ: 7.48 (1H, dd, J=7.3, 1.5 Hz), 7.52-7.61 (3H, m), 7.72-7.78 (2H, m), 7.93 (1H, 1, J=8.0 Hz), 8.15 (1H, d, J=8.3 Hz), 8.41 (1H, ddd, J=8.0, 1.5, 1.0 Hz), 8.51 (1H, ddd, J=8.1, 2.4, 1.0 Hz), 8.78-8.80 (1H, m), 8.98-9.00 (1H, m), 12.42 (1H, s).

2-(Benzofuran-5-carboxamido)-4-phenylbenzoic acid $^1$H-NMR (DMSO-d$_6$) δ: 7.16 (1H, dd, J=2.2, 1.0 Hz), 7.47 (1H, tt, J=7.4, 1.5 Hz), 7.50-7.59 (3H, m), 7.72-7.78 (2H, m), 7.83 (1H, d, J=8.5 Hz), 7.96 (1H, dd, J=8.7, 1.7 Hz), 8.12-8.19 (2H, m), 8.33 (1H, d, J=1.7 Hz), 9.10 (1H, d, J=1.7 Hz), 12.31 (1H, s).

2-(Benzothiazole-2-carboxamido)-4-phenylbenzoic acid $^1$H-NMR (DMSO-d$_6$) δ: 7.46-7.51 (1H, m), 7.53-7.79 (7H, m), 8.16-8.22 (2H, m), 8.29-8.32 (1H, m), 9.10 (1H, d, J=1.7 Hz), 13.04 (1H, s).

2-(Benzothiophene-3-carboxamido)-1-phenylbenzoic acid $^1$H-NMR (DMSO-d$_6$) δ: 7.45-7.61 (6H, m), 7.73-7.80 (2H, m), 8.11-8.18 (2H, m), 8.51-8.55 (1H, m), 8.56 (1H, s), 9.04 (1H, d, J=2.0 Hz), 12.09 (1H, s).

2-(Benzofuran-2-carboxamido)-4-phenylbenzoic acid $^1$H-NMR (DMSO-d$_6$) δ: 7.37-7.48 (1H, m), 7.48 (1H, tt, J=7.4, 1.5 Hz), 7.52-7.59 (4H, m), 7.69-7.78 (4H, m), 7.86 (1H, d, J=7.8 Hz), 8.16 (1H, d, J=8.3 Hz), 9.08 (1H, d, J=1.7 Hz), 12.61 (1H, s).

2-(Benzothiophene-2-carboxamido)-4-phenylbenzoic acid $^1$H-NMR (DMSO-d$_6$) δ: 7.45-7.59 (6H, m), 7.71-7.78 (2H, m), 8.06-8.18 (4H, m), 8.95 (1H, d, J=1.5 Hz), 12.43 (1H, s).

4-Phenyl-2-(1-phenyl-1H-pyrazole-5-carboxamido)benzoic acid $^1$H-NMR (DMSO-d$_6$) δ: 7.09 (1H, d, J=2.0 Hz), 7.41-7.55 (9H, m), 7.64-7.69 (2H, m), 7.88 (1H, d, J=2.0 Hz), 8.12 (1H, d, J=8.3 Hz), 8.77 (1H, d, J=1.7 Hz), 12.12 (1H, s).

2-(2,2-Diphenylacetamido)-4-phenylbenzoic acid $^1$H-NMR (DMSO-d$_6$) δ: 5.34 (1H, s), 7.28 (1H, tt, J=7.2, 1.7 Hz), 7.33-7.54 (13H, m), 7.65-7.71 (2H, m), 8.02 (1H, d, J=8.3 Hz), 8.92 (1H, d, J=1.7 Hz), 11.42 (1H, s), 13.50-13.70 (1H, broad).

2-(2-Chlorobenzamido)-4-phenylbenzoic acid

¹H-NMR (DMSO-d₆) δ: 7.44-7.65 (7H, m), 7.71-7.78 (3H, m), 8.12 (1H, d, J=8.3 Hz), 8.97 (1H, s), 11.72 (1H, s).

2-(3-Chlorobenzamido)-4-phenylbenzoic acid

¹H-NMR (DMSO-d₆) δ: 7.44-7.50 (1H, m), 7.52-7.59 (3H, m), 7.66 (1H, t, J=7.9 Hz), 7.71-7.78 (3H, m), 7.92-7.96 (1H, m), 7.99 (9H, t, J=1.8 Hz), 8.14 (1H, d, J=8.0 Hz), 9.00 (1H, d, J=2.0 Hz), 12.27 (1H, s).

2-(4-Chlorobenzamido)-4-phenylbenzoic acid

¹H-NMR (DMSO-d₆) δ: 7.47 (1H, tt, J=7.4, 1.6 Hz), 7.52-7.59 (3H, m), 7.68-7.77 (4H, m), 7.97-8.02 (2H, m), 8.14 (1H, d, J=8.3 Hz), 9.02-9.04 (1H, m), 12.25 (1H, s).

2-(2,4-Dichlorobenzamido)-4-phenylbenzoic acid

¹H-NMR (DMSO-d₆) δ: 7.47 (1H, tt, J=7.3, 1.5 Hz), 7.52-7.59 (3H, m), 7.63 (1H, dd, J=8.3, 2.0 Hz), 7.70-7.76 (2H, m), 7.79 (1H, d, J=8.3 Hz), 7.83 (1H, d, J=2.0 Hz), 8.11 (1H, d, J=8.3 Hz), 8.91 (1H, s), 11.72 (1H, s).

4-Phenyl-2-(2,4-bis(trifluoromethyl)benzamido)benzoic acid

¹H-NMR (DMSO-d₆) δ: 7.47 (1H, tt, J=7.4, 1.6 Hz), 7.53-7.57 (2H, m), 7.60 (1H, dd, J=8.3, 1.7 Hz), 7.70-7.76 (2H, m), 8.10-8.15 (2H, m), 8.25 (1H, s), 8.28-8.33 (1H, m), 8.76 (1H, d, J=1.4 Hz), 11.69 (1H, s).

4-Phenyl-2-(3-phenylpropanamido)benzoic acid

¹H-NMR (DMSO-d₆) δ: 2.76 (2H, t, J=7.6 Hz), 2.97 (2H, t, J=7.6 Hz), 7.16-7.22 (1H, m), 7.26-7.31 (4H, m), 7.42-7.48 (2H, m), 7.50-7.56 (2H, m), 7.65-7.71 (2H, m), 8.05 (1H, d, J=8.3 Hz), 8.85 (1H, d, J=2.0 Hz), 11.23 (1H, s), 13.55-13.75 (1H, broad).

Example 320

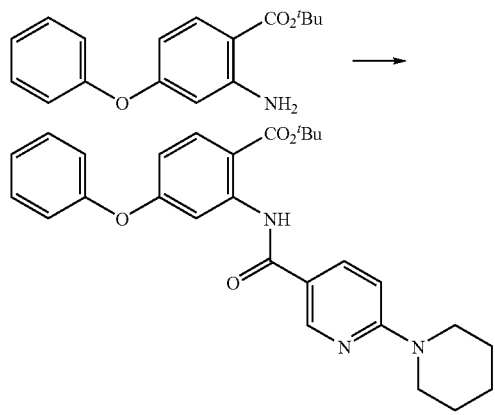

Example 321

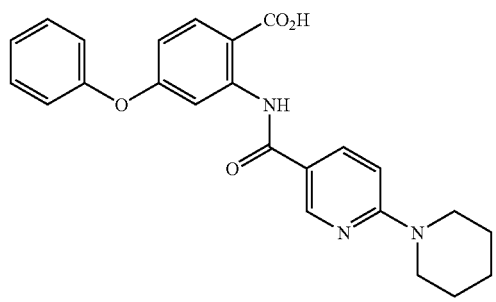

1.3 mL of methylene chloride, 1.3 μL of N,N-dimethylformamide and 0.031 mL of oxalyl chloride were added sequentially to 69 mg of 6-(piperidin-1-yl)pyridine-3-carboxylic acid at room temperature, and stirred at the same temperature for 1 hour. The reaction mixture was added to a mixed solution of 57 mg of tert-butyl 2-amino-4-phenoxybenzoate, 3.7 mL of methylene chloride and 0.22 mL of triethylamine and stirred at room temperature for 2 hours. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=8:1] to obtain tert-butyl 4-phenoxy-2-(6-(piperidin-1-yl)pyridine-3-carboxamido)benzoate.

10 mL of trifluoroacetic acid was added to the obtained tert-butyl 4-phenoxy-2-(6-(piperidin-1-yl)pyridine-3-carboxamido)benzoate and stirred at room temperature for 2 hours. The solvent was evaporated under reduced pressure and water was added and pH was adjusted to pH 6.5 with a saturated sodium hydrogen carbonate aqueous solution. A solid substance was separated by filtration to obtain 23 mg of 4-phenoxy-2-(6-(piperidin-1-yl)pyridine-3-carboxamido)benzoic acid as whine solid.

¹H-NMR (DMSO-d₆) δ: 1.47-1.70 (6H, m), 3.62-3.70 (4H, m), 6.73 (1H, dd, J=9.0, 2.6 Hz), 6.93 (1H, d, J=9.2 Hz), 7.15-7.18 (2H, m), 7.25-7.30 (1H, m), 7.45-7.52 (2H, m), 7.91 (1H, dd, J=9.2, 2.6 Hz), 8.05 (1H, d, J=9.0 Hz), 8.38 (1H, d, J=2.6 Hz), 8.63 (1H, d, J=2.6 Hz), 12.22 (1H, s).

Example 321

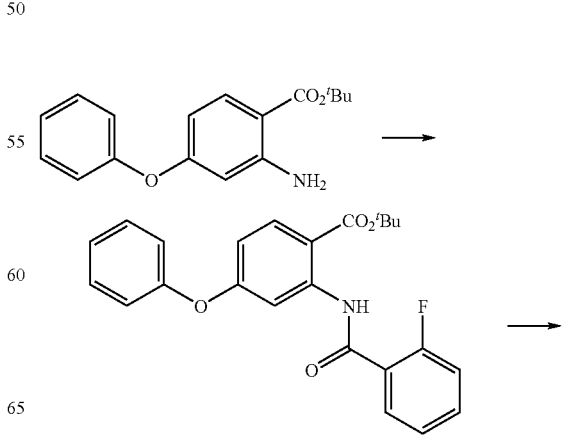

-continued

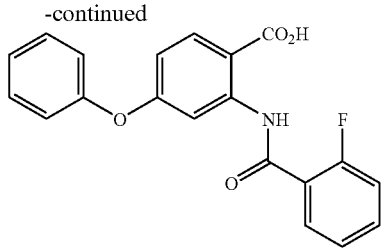

0.059 mL of triethylamine and 0.037 mL of 2-fluorobenzoyl chloride were added to 3.0 mL of methylene chloride solution containing 60 mg of tert-butyl 2-amino-4-phenoxybenzoate at room temperature sequentially and stirred at the same temperature for 2 hours. 0.48 g of aminomethylated polystyrene was added to the reaction mixture and stirred at room temperature overnight. A saturated sodium hydrogen carbonate aqueous solution was added to the reaction mixture, the organic layer was separated, and the solvent was evaporated under reduced pressure. The obtained residue was purified with silica gel column chromatography [Flash Tube 2008 manufactured by Trikonex Company, eluent; hexane: ethyl acetate=4:1] to obtain tert-butyl 2-(2-fluorobenzamido)-4-phenoxybenzoate.

10 mL of trifluoroacetic acid was added to the obtained tert-butyl 2-(2-fluorobenzamido)-4-phenoxybenzoate and stirred at room temperature for 2 hours. The solvent was evaporated under reduced pressure and diisopropyl ether was added to the obtained residue and a solid substance was separated by filtration to obtain 30 mg of 2-(2-fluorobenzamido)-4-phenoxybenzoic acid as white solid.

$^1$H-NMR (DMSO-$d_6$) δ: 6.79 (1H, dd, J=8.9, 2.5 Hz), 7.16-7.21 (2H, m), 7.25-7.31 (1H, m), 7.35-7.53 (4H, m), 7.63-7.69 (1H, m), 7.88 (1H, td, J=7.8, 1.8 Hz), 8.06 (1H, d, J=8.9 Hz), 8.41 (1H, d, J=2.5 Hz), 12.15-12.19 (1H, broad), 13.50-13.70 (1H, broad).

Examples 322 to 344

The compounds shown in Table 34 were obtained in the same manner as in Example 321.

TABLE 34

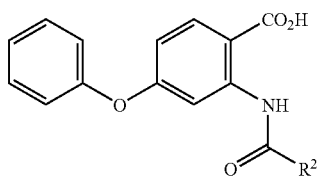

| Example No. | R$^2$ |
|---|---|
| 322 | 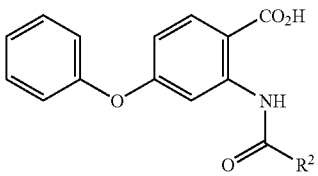 |
| 323 | 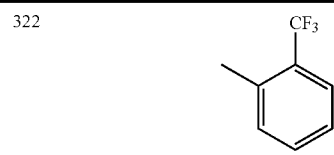 |

TABLE 34-continued

| Example No. | R$^2$ |
|---|---|
| 324 | 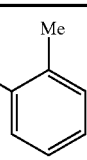 |
| 325 | 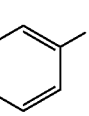 |
| 326 | 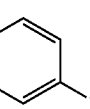 |
| 327 | 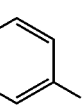 |
| 328 | 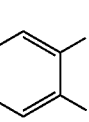 |
| 329 | 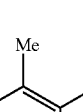 |
| 330 | 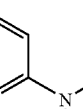 |
| 331 | 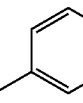 |
| 332 | 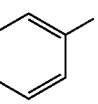 |
| 333 | 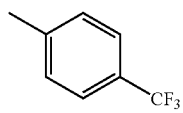 |

TABLE 34-continued

Structure: 4-phenoxy-2-(acylamino)benzoic acid core with R² substituent on the amide carbonyl.

| Example No. | R² |
|---|---|
| 334 | 3-(trifluoromethyl)phenyl with methyl (3-CF₃, methyl-substituted phenyl) — 2-methyl-5-CF₃-phenyl |
| 335 | 2-methyl-5-nitrophenyl (methyl, NO₂) |
| 336 | 2-chloro-6-methylphenyl (methyl, Cl) |
| 337 | 3-chloro-? methylphenyl (methyl, Cl) |
| 338 | 4-chloro-2-methylphenyl (methyl, Cl) |
| 339 | 2,4-dichloro-5-methylphenyl (methyl, Cl, Cl) |
| 340 | 5-methylbenzo[b]thiophen-yl |
| 341 | 2-methylbenzo[b]thiophen-yl |
| 342 | 5-methyl-1-phenyl-1H-pyrazol-yl |
| 343 | 4-methyl-2,5-bis(trifluoromethyl)phenyl (F₃C, CF₃) |
| 344 | 2-phenylethyl |

4-Phenoxy-2-(2-(trifluoromethyl)benzamido)benzoic acid

¹H-NMR (DMSO-d₆) δ: 6.77 (1H, dd, J=8.8, 2.4 Hz), 7.19 (2H, d, J=7.8 Hz), 7.28 (1H, t, J=9.4 Hz), 7.46-7.53 (2H, m), 7.74-7.87 (3H, m), 7.89 (1H, d, J=8.1 Hz), 8.04 (1H, d, J=8.8 Hz), 8.27 (1H, d, J=2.4 Hz), 11.82 (1H, s), 13.60 (1H, s).

4-Phenoxy-2-(4-(trifluoromethyl)benzamido)benzoic acid

¹H-NMR (DMSO-d₆) δ: 6.80 (1H, dd, J=8.9, 2.5 Hz), 7.16-7.22 (2H, m), 7.26-7.32 (1H, m), 7.47-7.53 (2H, m), 7.98 (2H, d, J=8.3 Hz), 8.06-8.14 (3H, m), 8.37 (1H, d, J=2.5 Hz), 12.51 (1H, s), 13.65-13.85 (1H, broad).

2-(2-Methylbenzamido)-4-phenoxybenzoic acid

¹H-NMR (DMSO-d₆) δ: 2.42 (3H, s), 6.75 (1H, dd, J=8.9, 2.7 Hz), 7.16-7.21 (2H, m), 7.25-7.36 (3H, m), 7.41-7.52 (3H, m), 7.56-7.60 (1H, m), 8.05 (1H, d, J=8.9 Hz), 8.39 (1H, d, J=2.7 Hz), 11.82 (1H, s), 13.45-13.65 (1H, broad).

2-(3-Methylbenzamido)-4-phenoxybenzoic acid

¹H-NMR (DMSO-d₆) δ: 2.40 (3H, s), 6.77 (1H, dd, J=8.8, 2.7 Hz), 7.16-7.21 (2H, m), 7.26-7.31 (1H, m), 7.94-7.53 (4H, m), 7.68-7.74 (1H, m), 7.74 (1H, s), 8.07 (1H, d, J=8.8 Hz), 8.41 (1H, d, J=2.7 Hz), 12.41 (1H, s), 13.71 (1H, s).

2-(4-Methylbenzamido)-4-phenoxybenzoic acid

¹H-NMR (DMSO-d₆) δ: 2.39 (3H, s), 6.76 (1H, dd, J=8.9, 2.6 Hz), 7.15-7.21 (2H, m), 7.26-7.31 (1H, m), 7.39 (2H, d, J=8.2 Hz), 7.46-7.52 (2H, m), 7.82 (2H, d, J=8.2 Hz), 8.07 (1H, d, J=8.9 Hz), 8.41 (1H, d, J=2.6 Hz), 12.38 (1H, s), 13.67 (1H, s).

2-(4-Nitrobenzamido)-4-phenoxybenzoic acid

¹H-NMR (DMSO-d₆) δ: 8.82 (1H, dd, J=8.9, 2.5 Hz), 7.16-7.21 (2H, m), 7.26-7.32 (1H, m), 7.46-7.53 (2H, m), 8.09 (1H, d, J=8.9 Hz), 8.12-8.17 (2H, m), 8.35 (1H, d, J=2.5 Hz), 8.40-8.45 (2H, m), 12.53 (1H, s), 13.65-13.90 (1H, broad).

2-(3,4-Dimethylbenzamido)-4-phenoxybenzoic acid

¹H-NMR (DMSO-d₆) δ: 2.30 (6H, s), 6.75 (1H, dd, J=8.9, 2.7 Hz), 7.15-7.20 (2H, m), 7.25-7.31 (1H, m), 7.34 (1H, d, J=7.8 Hz), 7.45-7.53 (2H, m), 7.64 (1H, dd, J=7.8, 1.9 Hz), 7.71 (1H, d, J=1.9 Hz), 8.06 (1H, d, J=8.9 Hz), 8.42 (1H, d, J=2.7 Hz), 12.38 (1H, s), 13.69 (1H, s).

2-(2,3-Dimethylbenzamido)-4-phenoxybenzoic acid

¹H-NMR (DMSO-d₆) δ: 2.27 (3H, s), 2.29 (3H, s), 6.75 (1H, dd, J=8.8, 2.6 Hz), 7.16-7.38 (6H, m), 7.46-7.52 (2H, m), 8.04 (1H, d, J=8.8 Hz), 8.40 (1H, d, J=2.6 Hz), 11.73 (1H, s), 13.53 (1H, s).

2-(6-Morpholinopyridine-3-carboxamido)-4-phenoxybenzoic acid

¹H-NMR (DMSO-d₆) δ: 3.57-3.75 (8H, m), 6.75 (1H, dd, J=9.0, 2.6 Hz), 6.96 (1H, d, J=9.0 Hz), 7.13-7.22 (2H, m), 7.24-7.31 (1H, m), 7.45-7.53 (2H, m), 7.97 (1H, dd, J=9.0, 2.4 Hz), 8.05 (1H, d, J=9.0 Hz), 8.37 (1H, d, J=2.6 Hz), 8.67 (1H, d, J=2.4 Hz), 12.23 (1H, s), 13.64 (1H, s).

4-Phenoxy-2-(2-phenylacetamido)benzoic acid $^1$H-NMR (DMSO-$d_6$) δ: 3.73 (2H, s), 6.69 (1H, dd, J=8.8, 2.5 Hz), 7.12 (2H, d, J=7.6 Hz), 7.22-7.38 (6H, m), 7.43-7.49 (2H, m), 7.96 (1H, d, J=8.8 Hz), 8.21 (1H, d, J=2.5 Hz), 11.35 (1H, s), 13.45 (1H, s).

2-(3-Fluorobenzamido)-4-phenoxybenzoic acid $^1$H-NMR (DMSO-$d_6$) δ: 6.80 (1H, dd, J=8.8, 2.7 Hz), 7.16-7.21 (2H, m), 7.26-7.31 (1H, m), 7.46-7.55 (3H, m), 7.62-7.70 (2H, m), 7.74-7.78 (1H, m), 8.08 (1H, d, J=8.8 Hz), 8.35 (1H, d, J=2.7 Hz), 12.42 (1H, s), 13.60-13.85 (1H, broad).

2-(2,6-Difluorobenzamido)-4-phenoxybenzoic acid $^1$H-NMR (DMSO-$d_6$) δ: 6.81 (1H, dd, J=8.8, 2.4 Hz), 7.19 (2H, d, J=7.8 Hz), 7.24-7.34 (3H, m), 7.46-7.54 (2H, m), 7.61-7.70 (1H, m), 8.05 (1H, d, J=8.8 Hz), 8.25-8.29 (1H, m), 11.99 (1H, s), 13.50-13.80 (1H, broad).

4-Phenoxy-2-(3-(trifluoromethyl)benzamido)benzoic acid $^1$H-NMR (DMSO-$d_6$) δ: 6.81 (1H, dd, J=8.8, 2.4 Hz), 7.16-7.21 (2H, m), 7.26-7.32 (1H, m), 7.46-7.53 (2H, m), 7.85 (1H, t, J=8.0 Hz), 8.03 (1H, d, J=7.8 Hz), 8.08 (1H, d, J=8.8 Hz), 8.18-8.24 (2H, m), 8.35 (1H, d, J=2.4 Hz), 12.54 (1H, s).

2-(3-Nitrobenzamido)-4-phenoxybenzoic acid $^1$H-NMR (DMSO-$d_6$) δ: 6.81 (1H, dd, J=8.8, 2.4 Hz), 7.17-7.21 (2H, m), 7.26-7.33 (1H, m), 7.46-7.54 (2H, m), 7.89 (1H, t, J=7.9 Hz), 8.08 (1H, d, J=8.8 Hz), 8.30-8.37 (8H, m), 8.46-8.50 (1H, m), 8.71 (1H, s), 12.62 (1H, s), 13.50-14.00 (1H, broad).

2-(2-Chlorobenzamido)-4-phenoxybenzoic acid $^1$H-NMR (DMSO-$d_6$) δ: 6.79 (1H, dd, J=8.9, 2.4 Hz), 7.16-7.22 (2H, m), 7.26-7.32 (1H, m), 7.46-7.63 (5H, m), 7.69 (1H, dd, J=7.4, 1.6 Hz), 8.05 (1H, d, J=8.9 Hz), 8.30-8.34 (1H, m), 11.86 (1H, s), 13.50-13.75 (1H, broad).

2-(3-Chlorobenzamido)-4-phenoxybenzoic acid $^1$H-NMR (DMSO-$d_6$) δ: 6.79 (1H, dd, J=8.8, 2.4 Hz), 7.16-7.21 (2H, m), 7.25-7.31 (1H, m), 7.45-7.53 (2H, m), 7.60-7.65 (1H, m), 7.69-7.76 (1H, m), 7.84-7.95 (2H, m), 8.07 (1H, d, J=8.8 Hz), 8.34 (1H, d, J=2.4 Hz), 12.43 (1H, s).

2-(4-Chlorobenzamido)-4-phenoxybenzoic acid $^1$H-NMR (DMSO-$d_6$) δ: 6.78 (1H, dd, J=8.9, 2.6 Hz), 7.16-7.21 (2H, m), 7.26-7.32 (1H, m), 7.46-7.52 (2H, m), 7.64-7.70 (2H, m), 7.88-7.95 (2H, m), 8.07 (1H, d, J=8.9 Hz), 8.36 (1H, d, J=2.6 Hz), 12.42 (1H, s).

2-(2,4-Dichlorobenzamido)-4-phenoxybenzoic acid $^1$H-NMR (DMSO-$d_6$) δ: 6.80 (1H, dd, J=8.8, 2.7Hz), 7.18 (2H, d, J=7.8 Hz), 7.28 (1H, t, J=7.4 Hz), 7.45-7.53 (2H, m), 7.60 (1H, dd, J=8.3, 2.2 Hz), 7.74 (1H, d, J=8.3 Hz), 7.81 (1H, d, J=1.9 Hz), 8.05 (1H, d, J=8.8 Hz), 8.26-8.28 (1H, m), 11.88 (1H, s), 13.45-13.80 (1H, broad).

2-(Benzothiophene-5-carboxamido)-4-phenoxybenzoic acid $^1$H-NMR (DMSO-$d_6$) δ: 6.78 (1H, dd, J=8.8, 2.7 Hz), 7.17-7.22 (2H, m), 7.27-7.32 (1H, m), 7.47-7.53 (2H, m), 7.62 (1H, d, J=5.4 Hz), 7.87 (1H, dd, J=8.4, 1.7 Hz), 7.93 (1H, d, J=5.4 Hz), 8.09 (1H, d, J=8.8 Hz), 8.22 (1H, d, J=8.4 Hz), 8.44 (1H, d, J=2.7 Hz), 8.47 (1H, d, J=1.7 Hz), 12.52 (1H, s).

2-(Benzothiophene-2-carboxamido)-4-phenoxybenzoic acid $^1$H-NMR (DMSO-$d_6$) δ: 6.80 (1H, dd, J=8.8, 2.6 Hz), 7.17-7.22 (2H, m), 7.26-7.32 (1H, m), 7.46-7.56 (4H, m), 8.04-8.12 (4H, m), 8.28 (1H, d, J=2.6 Hz), 12.57 (1H, s), 13.85-13.90 (1H, broad).

4-Phenoxy-2-(1-phenyl-1H-pyrazole-5-carboxamido)benzoic acid $^1$H-NMR (DMSO-$d_6$) δ: 6.73 (1H, dd, J=8.9, 2.7 Hz), 7.04 (1H, d, J=2.1 Hz), 7.10-7.15 (2H, m), 7.20-7.25 (1H, m), 7.40-7.48 (7H, m), 7.86 (1H, d, J=2.1 Hz), 8.04 (1H, d, J=8.9 Hz), 8.13 (1H, d, J=2.7 Hz), 12.22 (1H, s).

4-Phenoxy-2-(2,4-bis(trifluoromethyl)benzamido)benzoic acid $^1$H-NMR (DMSO-$d_6$) δ: 6.80 (1H, dd, J=8.9, 2.3 Hz), 7.19 (2H, d, J=7.8 Hz), 7.26-7.31 (1H, m), 7.45-7.53 (2H, m), 8.05 (1H, d, J=8.9 Hz), 8.09 (1H, d, J=7.9 Hz), 8.19 (1H, d, J=2.3 Hz), 8.23 (1H, s), 8.27 (1, d, J=7.9 Hz), 11.86 (1H, s).

4-Phenoxy-2-(3-phenylpropanamido)benzoic acid $^1$H-NMR (DMSO-$d_6$) δ: 2.69 (2H, t, J=7.7 Hz), 2.90 (2H, t, J=7.7 Hz), 6.69 (1H, dd, J=8.9, 2.5 Hz), 7.11-7.21 (3H, m), 7.21-7.31 (5H, m), 7.43-7.50 (2H, m), 7.98 (1H, d, J=8.9 Hz), 8.21 (1H, d, J=2.5 Hz), 11.36 (1H, s), 13.40-13.60 (1H, broad).

Example 345

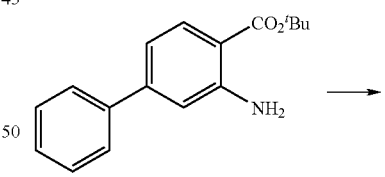

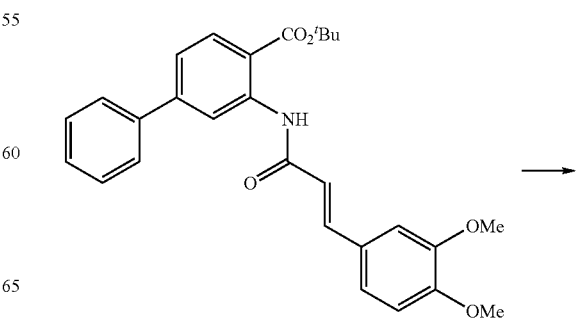

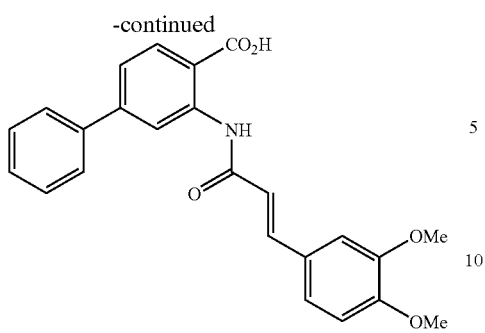

1.3 mL of methylene chloride, 1.3 μL of N,N-dimethylformamide and 0.031 mL of oxalyl chloride were added to 69 mg of 3,4-dimethoxycinnamic acid at room temperature sequentially and stirred at the same temperature for 1 hour. Tine reaction mixture was added to a mixed solution of 54 mg of tert-butyl 2-amino-4-phenylbenzoate, 3.7 mL of methylene chloride and 0.22 mL of triethylamine and stirred at room temperature for 2 hours. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=4:1] to obtain (E)-tert-butyl 2-(3-(3,4-dimethoxyphenyl)acrylamido)-4-phenylbenzoate.

10 mL of trifluoroacetic acid was added to obtain (E)-tert-butyl 2-(3-(3,4-dimethoxyphenyl)acrylamido)-4-phenylbenzoate and stirred at room temperature for 2 hours. The solvent was evaporated under reduced pressure, diisopropyl ether was added to the obtained residue, and a solid substances was separated by filtration to obtain 20 mg of (E)-2-(3-(3,4-dimethoxyphenyl)acrylamido)-4-phenylbenzoic acid as white solid.

$^1$H-NMR (DMSO-$d_6$) δ: 3.81 (3H, s), 3.85 (3H, s), 6.84 (1H, d, J=15.5 Hz), 7.01 (1H, d, J=8.3 Hz), 7.26 (1H, dd, J=8.4, 1.7 Hz), 7.40 (1H, d, J=1.5 Hz), 7.43-7.57 (4H, m), 7.59 (1H, d, J=15.5 Hz), 7.71 (2H, d, J=7.8 Hz), 8.09 (1H, d, J=8.4 Hz), 9.00 (1H, d, J=1.7 Hz), 11.37 (1H, s), 13.50-13.75 (1H, broad).

Examples 346 to 367

The compounds shown in Table 35 were obtained in the same manner as in Example 345.

TABLE 35

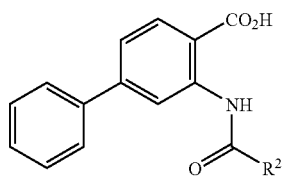

| Example No. | R² |
|---|---|
| 346 | 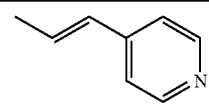 ·CF₃CO₂H |

TABLE 35-continued

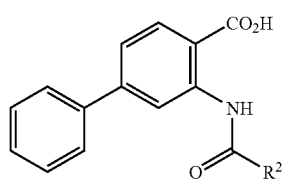

| Example No. | R² |
|---|---|
| 347 | 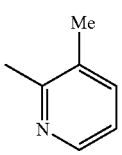 |
| 348 | 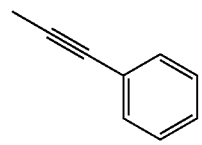 |
| 349 | 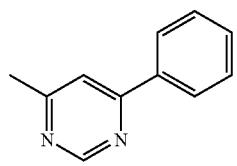 |
| 350 | 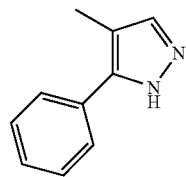 |
| 351 | 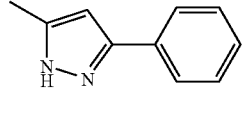 |
| 352 | 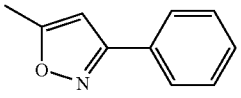 |
| 353 | 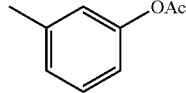 |
| 354 | 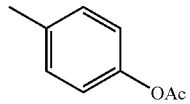 |
| 355 | 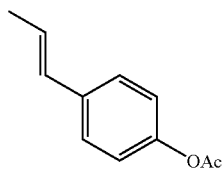 |

TABLE 35-continued

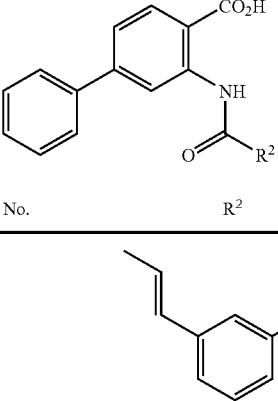

| Example No. | R² |
|---|---|
| 356 | 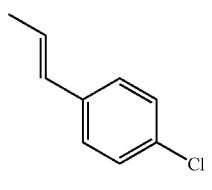 |
| 357 | 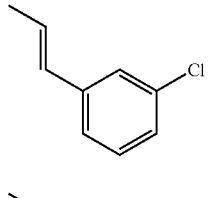 |
| 358 | 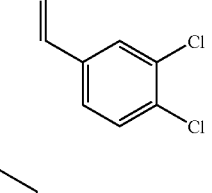 |
| 359 | 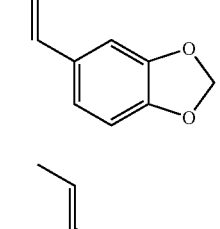 |
| 360 | 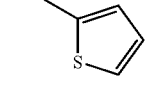 |
| 361 | 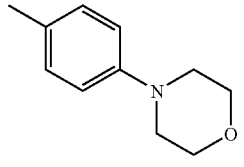 |
| 362 | 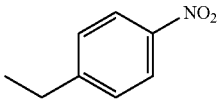 |
| 363 | 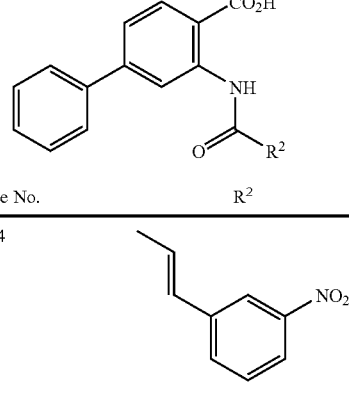 |
| 364 | 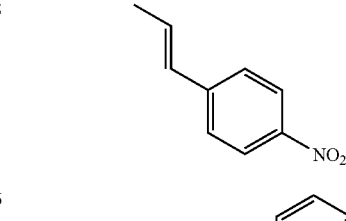 |
| 365 | 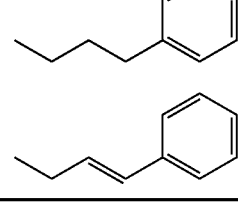 |
| 366 | 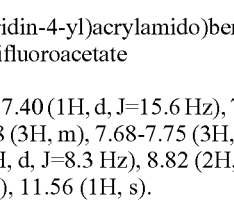 |
| 367 | |

4-Phenyl-2-((E)-3-(pyridin-4-yl)acrylamido)benzoic acid trifluoroacetate $^1$H-NMR (DMSO-d$_6$) δ: 7.40 (1H, d, J=15.6 Hz), 7.47 (1H, tt, J=7.3, 1.5 Hz), 7.51-7.58 (3H, m), 7.68-7.75 (3H, m), 8.07 (2H, d, J=6.1 Hz), 8.11 (1H, d, J=8.3 Hz), 8.82 (2H, d, J=6.1 Hz), 8.96 (1H, d, J=1.7 Hz), 11.56 (1H, s).

2-(3-Methylpyridine-2-carboxamido)-4-phenylbenzoic acid $^1$H-NMR (DMSO-d$_6$) δ: 2.71 (3H, s), 7.44-7.61 (5H, m), 7.72-7.77 (2H, m), 7.85-7.88 (1H, m), 8.12 (1H, d, J=8.0 Hz), 8.56-8.59 (1H, m), 9.20 (1H, d, J=1.7 Hz), 13.09 (1H, s), 13.45-13.70 (1H, broad).

4-Phenyl-2-(3-phenylpropiolamido)benzoic acid $^1$H-NMR (DMSO-d$_6$) δ: 6.56-6.70 (1H, m), 7.21 (1H, d, J=7.8 Hz), 7.27-7.32 (2H, m), 7.34-7.41 (3H, m), 7.61-7.70 (3H, m), 7.88-7.92 (2H, m), 8.42 (1H, d, J=7.8 Hz).

4-Phenyl-2-(6-phenylpyrimidine-4-carboxamido)benzoic acid $^1$H-NMR (DMSO-d$_6$) δ: 7.45-7.50 (1H, m), 7.54-7.66 (6H, m), 7.74-7.79 (2H, m), 8.17 (1H, d, J=8.3 Hz), 8.30-8.38 (2H, m), 8.67 (1H, d, J=1.2 Hz), 9.24 (1H, d, J=1.7 Hz), 9.49 (1H, d, J=1.2 Hz), 13.24 (1H, s).

4-Phenyl-2-(5-phenyl-1H-pyrazole-4-carboxamido)benzoic acid $^1$H-NMR (DMSO-d$_6$) δ: 7.38-7.55 (8H, m), 7.67-7.75 (4H, m), 8.08 (1H, d, J=8.3 Hz), 8.95 (1H, d, J=1.4 Hz), 11.65-11.80 (1H, broad), 12.82-12.90 (1H, broad).

4-Phenyl-2-(3-phenyl-1H-pyrazole-5-carboxamido)benzoic acid

¹H-NMR (DMSO-d₆) δ: 7.25 (1H, s), 7.38-7.59 (7H, m), 7.71-7.77 (2H, m), 7.83-7.89 (2H, m), 8.13 (1H, d, J=8.0 Hz), 9.17 (1H, s), 12.45 (1H, s), 14.01 (1H, s).

4-Phenyl-2-(3-phenylisoxazole-5-carboxamido)benzoic acid

¹H-NMR (DMSO-d₆) δ: 7.45-7.51 (1H, m), 7.53-7.63 (7H, m), 7.74 (2H, d, J=7.8 Hz), 7.98-8.05 (2H, m), 8.16 (1H, d, J=8.3 Hz), 9.05 (1H, d, J=1.7 Hz), 12.56 (1H, s), 13.75-14.10 (1H, broad).

2-(3-Acetoxybenzamido)-4-phenylbenzoic acid

¹H-NMR (DMSO-d₆) δ: 2.33 (3H, s), 7.43-7.50 (2H, m), 7.51-7.59 (3H, m), 7.67 (1H, t, J=7.9 Hz), 7.70-7.77 (3H, m), 7.35-7.30 (1H, m), 8.14 (1H, d, J=8.3 Hz), 9.03 (1H, d, J=1.7 Hz), 12.27 (1H, s), 13.75-14.05 (1H, broad).

2-(4-Acetoxybenzamido)-4-phenylbenzoic acid

¹H-NMR (DMSO-d₆) δ: 2.33 (3H, s), 7.36-7.42 (2H, m), 7.47 (1H, tt, J=7.3, 1.5 Hz), 7.51-7.59 (3H, m), 7.71-7.77 (2H, m), 8.00-8.06 (2H, m), 8.14 (1H, d, J=8.3 Hz), 9.06 (1H, d, J=2.0 Hz), 12.25 (1H, s), 13.75-13.95 (1H, broad).

2-((E)-3-(4-Acetoxyphenyl)acrylamido)-4-phenylbenzoic acid

¹H-NMR (DMSO-d₆) δ: 2.29 (3H, s), 6.92 (1H, d, J=15.7 Hz), 7.21 (2H, d, J=8.7 Hz), 7.43-7.58 (4H, m), 7.66 (1H, d, J=15.7 Hz), 7.68-7.75 (2H, m), 7.81 (2H, d, J=8.7 Hz), 8.10 (1H, d, J=8.3 Hz), 8.98 (1H, d, J=1.7 Hz), 11.43 (1H, s), 13.50-13.80 (1H, broad).

2-((E)-3-(3-Methoxyphenyl)acrylamido)-4-phenylbenzoic acid

¹H-NMR (DMSO-d₆) δ: 3.82 (3H, s), 6.96 (1H, d, J=15.6 Hz), 6.97-7.04 (1H, m), 7.28-7.39 (3H, m), 7.43-7.58 (4H, m), 7.62 (1H, d, J=15.6 Hz), 7.71 (2H, d, J=8.0 Hz), 8.09 (1H, d, J=8.3 Hz), 8.97 (1H, d, J=1.7 Hz), 11.45 (1H, s).

2-((E)-3-(4-Chlorophenyl)acrylamido)-4-phenylbenzoic acid

¹H-NMR (DMSO-d₆) δ: 6.98 (1H, d, J=15.7 Hz), 7.46 (1H, tt, J=7.3, 1.5 Hz), 7.48-7.57 (5H, m), 7.64 (1H, d, J=15.7 Hz), 7.69-7.74 (2H, m), 7.77-7.83 (2H, m), 8.10 (1H, d, J=8.3 Hz), 8.98 (1H, d, J=2.0 Hz), 11.43 (1H, s), 13.55-13.80 (1H, broad).

2-((E)-3-(3-Chlorophenyl)acrylamido)-4-phenylbenzoic acid

¹H-NMR (DMSO-d₆) δ: 7.08 (1H, d, J=15.6 Hz), 7.43-7.57 (6H, m), 7.63 (1H, d, J=15.6 Hz), 7.69-7.75 (3H, m), 7.92 (1H, s), 8.10 (1H, d, J=8.0 Hz), 8.98 (1H, s, J=2.0 Hz), 11.42 (1H, s), 13.55-13.85 (1H, broad).

2-(((E)-3-(3,4-Dichlorophenyl)acrylamido)-4-phenylbenzoic acid

¹H-NMR (DMSO-d₆) δ: 7.12 (1H, d, J=15.6 Hz), 7.46 (1H, tt, J=7.3, 1.5 Hz), 7.48-7.57 (3H, m), 7.63 (1H, d, J=15.6 Hz), 7.68-7.74 (3H, m), 7.77 (1H, dd, J=8.5, 2.0 Hz), 8.10 (1H, d, J=8.3 Hz), 8.14 (1H, d, J=2.0 Hz), 8.99 (1H, d, J=1.7 Hz), 11.43 (1H, s), 13.55-13.80 (1H, broad).

2-((E)-3-(Benzo[1,3]dioxol-5-yl)acrylamido)-4-phenylbenzoic acid

¹H-NMR (DMSO-d₆) δ: 6.10 (2H, s), 6.81 (1H, d, J=15.6 Hz), 6.98 (1H, d, J=8.1 Hz), 7.21 (1H, dd, J=8.1, 1.7 Hz), 7.43-7.51 (3H, m), 7.51-7.61 (3H, m), 7.68-7.74 (2H, m), 8.09 (1H, d, J=8.1 Hz), 9.00 (1H, d, J=1.9 Hz), 11.37 (1H, s), 13.55-13.75 (1H, broad).

9-Phenyl-2-((E)-3-(thiophen-2-yl)acrylamido)benzoic acid

¹H-NMR (DMSO-d₆) δ: 6.60 (1H, d, J=15.4 Hz), 7.17 (1H, dd, J=5.1, 3.6 Hz), 7.43-7.58 (5H, m), 7.68-7.74 (3H, m), 7.80 (1H, d, J=15.4 Hz), 8.08 (1H, d, J=8.3 Hz), 8.90 (1H, d, J=1.7 Hz), 11.30 (1H, s).

2-(4-Morpholinobenzamido)-4-phenylbenzoic acid

¹H-NMR (DMSO-d₆) δ: 3.27-3.31 (4H, m), 3.74-3.77 (4H, m), 7.10 (2H, d, J=9.0 Hz), 7.43-7.51 (2H, m), 7.51-7.58 (2H, m), 7.71-7.76 (2H, m), 7.86 (2H, d, J=9.0 Hz), 8.12 (1H, d, J=8.3 Hz), 9.12 (1H, d, J=1.7 Hz), 12.16 (1H, s).

2-(2-(4-Nitrophenyl)acetamido)-4-phenylbenzoic acid

¹H-NMR (DMSO-d₆) δ: 4.03 (2H, s), 7.42-7.54 (4H, m), 7.64-7.71 (4H, m), 8.04 (1H, d, J=8.3 Hz), 8.22-8.27 (2H, m), 8.82 (1H, d, J=1.7 Hz), 11.18 (1H, s).

2-((E)-3-(3-Nitrophenyl)acrylamido)-4-phenylbenzoic acid

¹H-NMR (DMSO-d₆) δ: 7.23 (1H, d, J=15.9 Hz), 7.43-7.58 (4H, m), 7.69-7.81 (4H, m), 8.10 (1H, d, J=8.3 Hz), 8.20-8.28 (2H, m), 8.63 (1H, t, J=1.8 Hz), 8.98 (1H, d, J=1.7 Hz), 11.52 (1H, s).

2-((E)-3-(4-Nitrophenyl)acrylamido)-4-phenylbenzoic acid

¹H-NMR (DMSO-d₆) δ: 7.20 (1H, d, J=15.6 Hz), 7.46 (1H, tt, J=7.3, 1.6 Hz), 7.50-7.57 (3H, m), 7.69-7.79 (3H, m), 8.02-8.07 (2H, m), 8.10 (1H, d, J=8.3 Hz), 8.26-8.32 (2H, m), 8.97 (1H, d, J=1.7 Hz), 11.50 (1H, s).

4-Phenyl-2-(4-phenylbutanamido)benzoic acid

¹H-NMR (DMSO-d₆) δ: 1.91-2.01 (2H, m), 2.44 (2H, t, J=7.3 Hz), 2.66 (2H, t, J=7.7 Hz), 7.15-7.33 (5H, m), 7.42-7.48 (2H, m), 7.49-7.56 (2H, m), 7.66-7.71 (2H, m), 8.06 (1H, d, J=8.3 Hz), 8.86 (1H, d, J=1.9 Hz), 11.22 (1H, s), 13.55-13.75 (1H, broad).

4-Phenyl-2-((E)-4-phenyl-3-butenamido)benzoic acid

¹H-NMR (DMSO-d₆) δ: 3.40 (2H, dd, J=7.3, 1.2 Hz), 6.45 (1H, dt, J=15.3, 7.3 Hz), 6.68 (1H, d, J=15.9 Hz), 7.25 (1H, tt,

J=7.3, 1.5 Hz), 7.32-7.37 (2H, m), 7.41-7.55 (6H, m), 7.65-7.71 (2H, m), 8.05 (1H, d, J=8.3 Hz), 8.89 (1H, d, J=2.0 Hz), 11.28 (1H, s).

Example 368

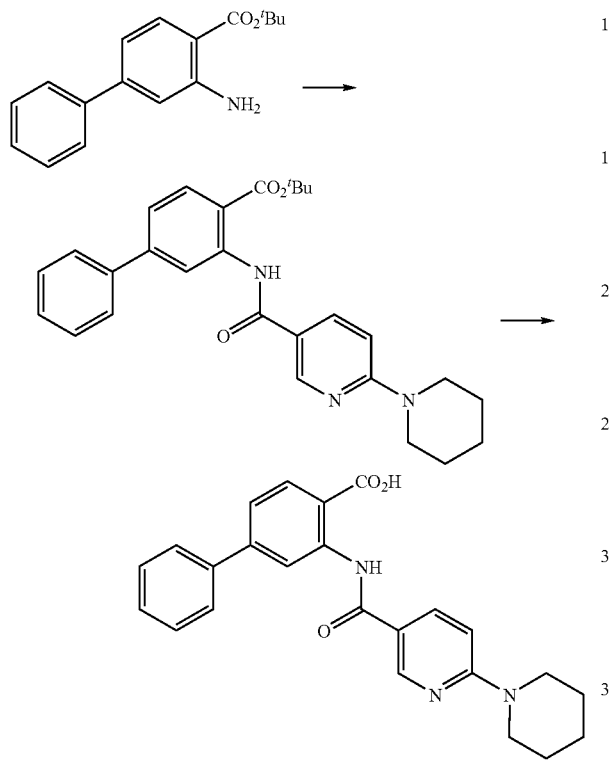

1.3 mL of methylene chloride, 1.3 µL of N,N-dimethylformamide and 3.031 mL of oxalyl chloride were sequentially added to 69 mg of 6-(piperidin-1-yl)pyridine-3-carboxylic acid at room temperature, and stirred at the same temperature for 1 hour. The reaction mixture was added to a mixed solution of 54 mg of tert-butyl 2-amino-4-phenylbenzoate, 3.7 mL of methylene chloride and 6.22 mL of triethylamine and stirred at room temperature for 2 hours. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-phenyl-2-(6-(piperidin-1-yl)pyridine-3-carboxamido)benzoate.

10 mL of trifluoroacetic acid was added to the obtained tert-butyl 4-phenyl-2-(6-(piperidin-1-yl)pyridine-3-carboxamido)benzoate and stirred at room temperature for 2 hours. The solvent was evaporated under reduced pressure and water was added and pH was adjusted to pH 6.5 with a saturated sodium hydrogen carbonate aqueous solution. A solid substance was separated by filtration to obtain 56 mg of 4-phenyl-2-(6-(piperidin-1-yl)pyridine-3-carboxamido)benzoic acid as white solid.

$^1$H-NMR (DMSO-$d_6$) δ: 1.50-1.70 (6H, m), 3.65-3.72 (4H, m), 6.99 (1H, d, J=9.3 Hz), 7.43-7.58 (4H, m), 7.70-7.76 (2H, m), 7.99 (1H, dd, J=9.3, 2.6 Hz), 8.12 (1H, d, J=8.3 Hz), 8.70 (1H, d, J=2.6 Hz), 9.07 (1H, d, J=1.7 Hz), 12.05 (1H, s).

Example 369

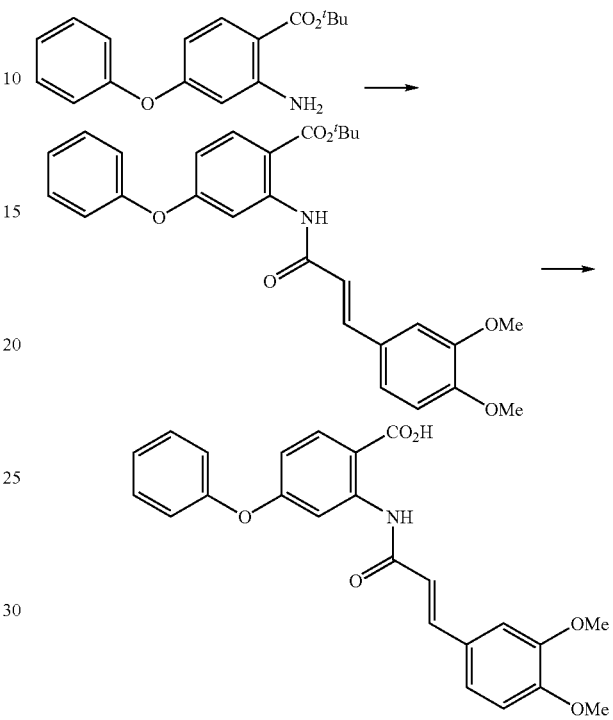

1.3 mL of methylene chloride, 1.3 µL of N,N-dimethylformamide and 0.031 mL of oxalyl chloride were added to 69 mg of 3,4-dimethoxycinnamic acid at room temperature sequentially and stirred at the same temperature for 1 hour. The reaction mixture was added to a mixed solution of 57 mg of tert-butyl 2-amino-4-phenoxybenzoate, 3.7 mL of methylene chloride and 0.22 mL of triethylamine and stirred at room temperature for 2 hours. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=4:1] to obtain tert-butyl 2-((E)-3-(3,4-dimethoxyphenyl)acrylamido)-4-phenoxybenzoate.

10 mL of trifluoroacetic acid was added to the obtained tert-butyl 2-((E)-3-(3,4-dimethoxyphenyl)acrylamido)-4-phenoxybenzoate and stirred at room temperature for 2 hours. The solvent was evaporated under reduced pressure, and diisopropyl ether was add to the obtained residue, and a solid substance was separated by filtration to obtain 13 mg of (E)-2-(3-(3,4-dimethoxyphenyl)acrylamido)-4-phenoxybenzoic acid as white solid.

$^1$H-NMR (DMSO-$d_6$) δ: 3.80 (3H, s), 3.83 (3H, s), 6.69-6.81 (2H, m), 6.99 (1H, d, J=8.5 Hz), 7.14-7.20 (2H, m), 7.22-7.31 (2H, m), 7.38 (1H, s), 7.45-7.51 (2H, m), 7.54 (1H, d, J=15.6 Hz), 8.03 (1H, d, J=8.8 Hz), 8.38 (1H, d, J=2.4 Hz), 11.50 (1H, s), 13.40-13.60 (1H, broad).

Examples 370 to 387

The compounds shown in Table 36 were obtained in the same manner as in Example 369.

TABLE 36

| Example No. | R² |
|---|---|
| 370 | 4-propenyl-pyridine · CF₃CO₂H |
| 371 | 5-methyl-3-(thiophen-2-yl)pyridine |
| 372 | 6-methyl-4-phenylpyrimidine |
| 373 | 4-methyl-3-phenyl-1H-pyrazole |
| 374 | 5-methyl-3-phenyl-1H-pyrazole |
| 375 | 5-methyl-3-phenylisoxazole |
| 376 | 3-methylphenyl acetate |
| 377 | 2-methylphenol |
| 378 | 4-methylphenyl acetate |

TABLE 36-continued

| Example No. | R² |
|---|---|
| 379 | (E)-1-(3-methoxyphenyl)propene |
| 380 | (E)-1-(4-chlorophenyl)propene |
| 381 | (E)-1-(3-chlorophenyl)propene |
| 382 | (E)-1-(3,4-dichlorophenyl)propene |
| 383 | (E)-1-(benzo[d][1,3]dioxol-5-yl)propene |
| 384 | (E)-1-(thiophen-2-yl)propene |
| 385 | 4-(4-methylphenyl)morpholine |
| 386 | 1-ethyl-4-nitrobenzene |

TABLE 36-continued

| Example No. | R² |
|---|---|
| 387 | (E)-CH=CH-CH₂-phenyl (but-2-enyl-phenyl chain) |

(Structure at top: 4-phenoxy-2-(acylamino)benzoic acid with CO₂H, NH-C(=O)-R²)

4-Phenoxy-2-((E)-3-(pyridin-4-yl)acrylamido)benzoic acid trifluoroacetate

¹H-NMR (DMSO-d₆) δ: 6.78 (1H, dd, J=8.8, 2.6 Hz), 7.15-7.20 (2H, m), 7.23-7.32 (2H, m), 7.45-7.53 (2H, m), 7.65 (1H, d, J=15.6 Hz), 7.94 (2H, d, J=6.4 Hz), 8.05 (1H, d, J=8.8 Hz), 8.34 (1H, d, J=2.6 Hz), 8.75 (2H, d, J=5.1 Hz), 11.68 (1H, s).

4-Phenoxy-2-(5-(thiophen-2-yl)pyridine-3-carboxamido)benzoic acid

¹H-NMR (DMSO-d₆) δ: 6.83 (1H, dd, J=8.8, 2.6 Hz), 7.17-7.23 (2H, m), 7.25 (1H, dd, J=5.1, 3.7 Hz), 7.27-7.33 (1H, m), 7.47-7.54 (2H, m), 7.75 (1H, dd, J=5.1, 1.1 Hz), 7.78 (1H, dd, J=3.7, 1.1 Hz), 8.09 (1H, d, J=8.8 Hz), 8.34 (1H, d, J=2.6 Hz), 8.43 (1H, t, J=2.2 Hz), 8.98 (1H, d, J=2.2 Hz), 9.14 (1H, d, J=2.2 Hz), 12.51 (1H, s).

4-Phenoxy-2-(6-phenylpyrimidine-4-carboxamido)benzoic acid

¹H-NMR (DMSO-d₆) δ: 6.85 (1H, dd, J=8.8, 2.4 Hz), 7.19-7.25 (2H, m), 7.31 (1H, t, J=7.5 Hz), 7.48-7.55 (2H, m), 7.57-7.64 (3H, m), 8.10 (1H, d, J=8.8 Hz), 8.33 (2H, dd, d -8.0, 1.7 Hz), 8.52 (1H, d, J=2.4 Hz), 8.60 (1H, d, J=1.2 Hz), 9.45 (1H, d, J=1.2 Hz), 13.33 (1H, s), 13.35-13.75 (1H, broad).

4-Phenoxy-2-(5-phenyl-1H-pyrazole-4-carboxamido)benzoic acid

¹H-NMR (DMSO-d₆) δ: 6.68 (1H, dd, J=8.8, 2.7 Hz), 7.12-7.17 (2H, m), 7.24 (1H, t, J=7.4 Hz), 7.32-7.52 (6H, m), 7.64-7.70 (2H, m), 8.00 (1H, d, J=8.8 Hz), 8.29 (1H, d, J=2.7 Hz), 11.65-12.00 (1H, broad), 13.35-13.75 (2H, broad).

4-Phenoxy-2-(3-phenyl-1H-pyrazole-5-carboxamido)benzoic acid

¹H-NMR (DMSO-d₆) δ: 6.74 (1H, dd, J=8.9, 2.6 Hz), 7.16-7.24 (3H, m), 7.28 (1H, t, J=7.4 Hz), 7.40 (1H, t, J=7.3 Hz), 7.45-7.53 (4H, m), 7.82 (2H, d, J=7.6 Hz), 8.05 (1H, d, J=8.9 Hz), 8.48-8.49 (1H, m), 12.52 (1H, s), 13.30-13.55 (1H, broad), 13.98 (1H, s).

4-Phenoxy-2-(3-phenylisoxazole-5-carboxamido)benzoic acid

¹H-NMR (DMSO-d₆) δ: 6.82 (1H, dd, J=8.9, 2.6 Hz), 7.18-7.23 (2H, m), 7.27-7.33 (1H, m), 7.47-7.62 (6H, m), 7.94-8.02 (2H, m), 8.08 (1H, d, J=8.9 Hz), 8.38 (1H, d, J=2.6 Hz), 12.66 (1H, s).

2-(3-Aceboxybenzamido)-4-phenoxybenzoic acid

¹H-NMR (DMSO-d₆) δ: 2.31 (3H, s), 6.78 (1H, dd, J=8.9, 2.7 Hz), 7.15-7.22 (2H, m), 7.28 (1H, t, J=7.6 Hz), 7.40-7.45 (1H, m), 7.46-7.53 (2H, m), 7.61-7.68 (2H, m), 7.79-7.81 (1H, m), 8.07 (1H, d, J=8.9 Hz), 8.37 (1H, d, J=2.7 Hz), 12.43 (1H, s), 13.65-13.85 (1H, broad).

2-(2-Hydroxybenzamido)-4-phenoxybenzoic acid

¹H-NMR (DMSO-d₆) δ: 6.75 (1H, ddd, J=8.8, 2.5, 0.9 Hz), 6.92-7.02 (2H, m), 7.14-7.19 (2H, m), 7.23-7.29 (1H, m), 7.39-7.51 (3H, m), 7.80 (1H, d, J=7.6 Hz), 8.04 (1H, dd, J=8.8, 0.9 Hz), 8.41 (1H, dd, J=2.5, 0.9 Hz), 11.31 (1H, s), 12.42 (1H, s).

2-(4-Acetoxybenzamido)-4-phenoxybenzoic acid

¹H-NMR (DMSO-d₆) δ: 2.31 (3H, s), 6.78 (1H, dd, J=8.9, 2.5 Hz), 7.15-7.21 (2H, m), 7.26-7.31 (1H, m), 7.33-7.39 (2H, m), 7.46-7.53 (2H, m), 7.93-7.99 (2H, m), 8.07 (1H, d, J=8.9 Hz), 8.39 (1H, d, J=2.5 Hz), 12.39 (1H, s), 13.63-13.80 (1H, broad).

2-((E)-3-(3-Methoxyphenyl)acrylamido)-4-phenoxybenzoic acid

¹H-NMR (DMSO-d₆) δ: 3.81 (3H, s), 6.74 (1H, dd, J=8.8, 2.6 Hz), 6.88 (1H, d, J=15.6 Hz), 6.99 (1H, dd, J=8.0, 1.5 Hz), 7.15-7.20 (2H, m), 7.25-7.38 (4H, m), 7.45-7.52 (2H, m), 7.57 (1H, d, J=15.6 Hz), 8.03 (1H, d, J=8.8 Hz), 8.35 (1H, d, J=2.6 Hz), 11.56 (1H, s), 13.40-13.60 (1H, broad).

2-((E)-3-(4-Chlorophenyl)acrylamido)-4-phenoxybenzoic acid

¹H-NMR (DMSO-d₆) δ: 6.74 (1H, dd, J=8.9, 2.6 Hz), 6.89 (1H, d, J=15.6 Hz), 7.15-7.20 (2H, m), 7.28 (1H, t, J=7.4 Hz), 7.45-7.52 (4H, m), 7.60 (1H, d, J=15.6 Hz), 7.76-7.79 (2H, m), 8.03 (1H, d, J=8.9 Hz), 8.35 (1H, d, J=2.6 Hz), 11.57 (1H, s), 13.40-13.65 (1H, broad).

2-((E)-3-(3-chlorophenyl)acrylamido)-4-phenoxybenzoic acid

¹H-NMR (DMSO-d₆) δ: 6.75 (1H, dd, J=8.9, 2.5 Hz), 6.99 (1H, d, J=15.6 Hz), 7.14-7.20 (2H, m), 7.28 (1H, t, J=7.4 Hz), 7.45-7.52 (4H, m), 7.59 (1H, d, J=15.6 Hz), 7.66-7.73 (1H, m), 7.90 (1H, s), 8.04 (1H, d, J=8.9 Hz), 8.35 (1H, d, J=2.5 Hz), 11.59 (1H, s).

2-((E)-3-(3,4-Dichlorophenyl)acrylamido)-4-phenoxybenzoic acid

¹H-NMR (DMSO-d₆) δ: 6.75 (1H, dd, J=9.0, 2.7 Hz), 7.04 (1H, d, J=15.6 Hz), 7.15-7.21 (2H, m), 7.28 (1H, t, J=7.4 Hz), 7.45-7.53 (2H, m), 7.58 (1H, d, J=15.6 Hz), 7.69 (1H, d, J=8.6 Hz), 7.75 (1H, dd, J=8.6, 2.0 Hz), 8.03 (1H, d, J=9.0 Hz), 8.12 (1H, d, J=2.0 Hz), 8.35 (1H, d, J=2.7 Hz), 11.60 (1H, s).

2-((E)-3-(Benzo[1,3]dioxol-5-yl)acrylamido)-4-phenoxybenzoic acid

¹H-NMR (DMSO-d₆) δ: 6.08 (2H, s), 6.68-6.77 (2H, m), 6.96 (1H, d, J=8.0 Hz), 7.14-7.22 (3H, m), 7.25-7.31 (1H, m), 7.43-7.55 (4H, m), 8.02 (1H, d, J=9.0 Hz), 8.36 (1H, d, J=2.7 Hz), 11.50 (1H, s).

4-Phenoxy-2-((E)-3-(thiophen-2-yl)acrylamido)benzoic acid $^1$H-NMR (DMSO-$d_6$) δ: 6.49 (1H, d, J=15.4 Hz), 6.73 (1H, dd, J=9.0, 2.5 Hz), 7.13-7.19 (3H, m), 7.25-7.30 (1H, m), 7.44-7.54 (3H, m), 7.71 (1H, d, J=5.1 Hz), 7.75 (1H, d, J=15.4 Hz), 8.02 (1H, d, J=9.0 Hz), 8.30 (1H, d, J=2.5 Hz), 11.50 (1H, s).

2-(4-Morpholinobenzamido)-4-phenoxybenzoic acid $^1$H-NMR (DMSO-$d_6$) δ: 3.28 (1H, t, J=4.9 Hz), 3.74 (4H, t, J=4.9 Hz), 6.72 (1H, dd, J=8.8, 2.4 Hz), 7.07 (2H, d, J=9.0 Hz), 7.14-7.20 (2H, m), 7.24-7.32 (1H, m), 7.45-7.52 (2H, m), 7.79 (2H, d, J=9.0 Hz), 8.05 (1H, d, J=8.8 Hz), 8.43 (1H, d, J=2.4 Hz), 12.28 (1H, s), 13.50-13.70 (1H, broad).

2-(2-(4-Nitrophenyl)acetamido)-4-phenoxybenzoic acid $^1$H-NMR (DMSO-$d_6$) δ: 3.96 (2H, s), 6.71 (1H, dd, J=8.9, 2.5 Hz), 7.09-7.15 (2H, m), 7.24 (1H, t, J=7.3 Hz), 7.42-7.49 (2H, m), 7.59-7.67 (2H, m), 7.97 (1H, d, J=8.9 Hz), 8.17 (1H, d, J=2.5 Hz), 8.18-8.24 (2H, m), 11.31 (1H, s), 13.40-13.55 (1H, broad).

4-Phenoxy-2-((E)-4-phenyl-3-butenamido)benzoic acid $^1$H-NMR (DMSO-$d_6$) δ: 3.35 (2H, dd, J=7.3, 1.0 Hz), 6.41 (1H, dt, J=15.9, 7.3 Hz), 6.64 (1H, d, J=15.9 Hz), 6.71 (1H, dd, J=8.9, 2.6 Hz), 7.11-7.17 (2H, m), 7.23-7.29 (2H, m), 7.31-7.37 (2H, m), 7.43-7.50 (4H, m), 7.99 (1H, d, J=8.9 Hz), 8.26 (1H, d, J=2.6 Hz), 11.48 (1H, s), 13.40-13.60 (1H, broad).

Example 388

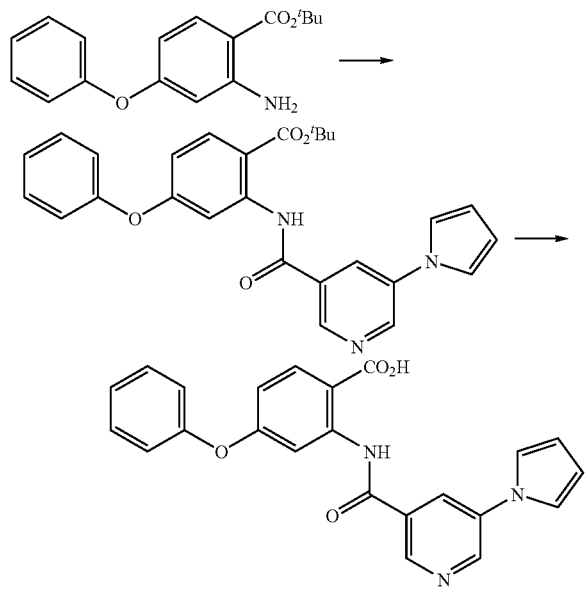

0.059 mL of triethylamine and 65 mg of 5-(1H-pyrrol-1-yl)pyridine-3-carbonyl chloride were added to 5.0 mL of methylene chloride solution containing 60 mg of tert-butyl 2-amino-4-phenoxybenzoate at room temperature sequentially and stirred at the same temperature for 2 hours, 0.029 mL of triethylamine and 22 mg of 5-(1H-pyrrol-1-yl)pyridine-3-carbonyl chloride were added to the reaction mixture at room temperature sequentially and stirred at the same temperature for 1 hour. 0.58 g aminomethylated polystyrene was added to the reaction mixture and stirred at room temperature overnight. A saturated sodium hydrogen carbonate aqueous solution was added to the reaction mixture, the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-phenoxy-2-(5-(1H-pyrrol-1-yl)pyridine-3-carboxamido)benzoate.

10 mL of trifluoroacetic acid was added to the obtained tert-butyl 4-phenoxy-2-(5-(1H-pyrrol-1-yl)pyridine-3-carboxamibo)benzoate and stirred at room temperature for 2 hours. The solvent was evaporated under reduced pressure, ethyl acetate and water were added and pH was adjusted to pH 7.0 with a saturated sodium hydrogen carbonate aqueous solution. The organic layer was separated and the solvent was evaporated under reduced pressure. Diisopropyl ether was added to the obtained residue and a solid substance was separated by filtration to obtain 7.0 mg of 4-phenoxy-2-(5-(1H-pyrrol-1-yl)pyridine-3-carboxamido)benzoic acid as white solid.

$^1$H-NMR (DMSO-$d_6$) δ: 6.37 (2H, t, J=2.2 Hz), 6.84 (1H, dd, J=8.9, 2.6 Hz), 7.17-7.22 (2H, m), 7.30 (1H, d, J=7.4 Hz), 7.47-7.54 (2H, m), 7.58 (2H, t, J=2.2 Hz), 8.09 (1H, d, J=8.9 Hz), 8.32 (1H, d, J=2.6 Hz), 8.40 (1H, t, J=2.2 Hz), 8.92 (1H, d, J=2.2 Hz), 9.15 (1H, d, J=2.2 Hz), 12.46 (1H, s).

Example 389

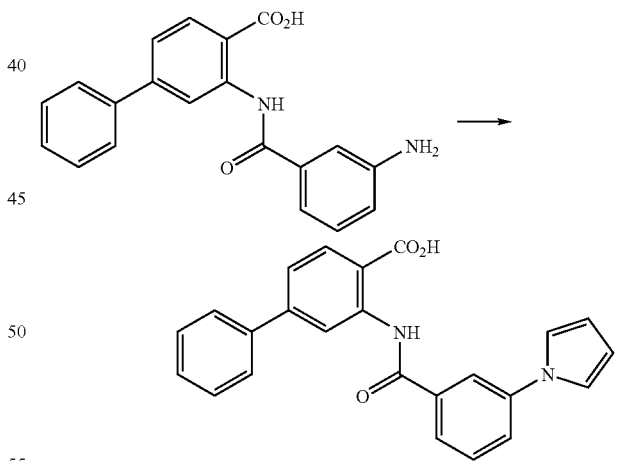

0.25 mL of acetic acid and 4.3 µL of 2,5-dimethoxytetrahydrofuran were added sequentially to 10 mg of 2-(3-aminobenzamido)-4-phenylbenzoic acid at room temperature and stirred at 90° C. for 5 minutes. Ethyl acetate and a saturated sodium hydrogen carbonate aqueous solution were added to the reaction mixture. The organic layer was separated and dried over anhydrous magnesium sulfate after washed with a saturated sodium chloride aqueous solution, and the solvent was evaporated under reduced pressure to obtain 8.3 mg of 4-phenyl-2-(3-(1H-pyrrol-1-yl)benzamido) benzoic acid as brown solid.

¹H-NMR (DMSO-d₆) δ: 6.34 (2H, t, J=2.1 Hz), 7.45-7.51 (3H, m), 7.53-7.53 (3H, m), 7.69 (1H, t, J=7.9 Hz), 7.73-7.78 (2H, m), 7.82-7.90 (2H, m), 8.11-8.18 (2H, m), 9.08 (1H, d, J=1.7 Hz), 12.37 (1H, s).

Example 390

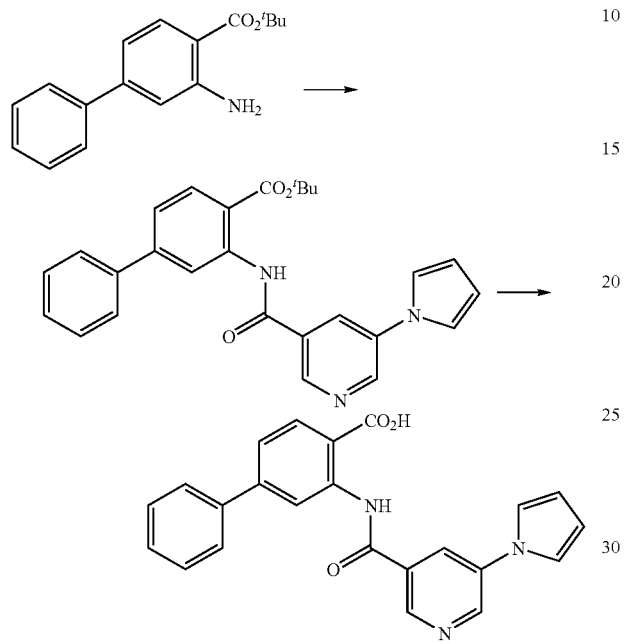

0.062 mL of triethylamine and 69 mg of 5-(1H-pyrrol-1-yl)pyridine-3-carbonyl chloride were added to 5.0 mL of methylene chloride solution containing 60 mg of tert-butyl 2-amino-4-phenylbenzoate at room temperature sequentially and stirred at the same temperature for 2 hours. 0.031 mL of triethylamine and 23 mg of 5-(1H-pyrrol-1-yl)pyridine-3-carbonyl chloride were added to the reaction mixture at room temperature sequentially and stirred at the same temperature for 1 hour. 0.62 g of aminomethylated polystyrene was added to the reaction mixture and stirred at room temperature overnight. A saturated sodium hydrogen carbonate aqueous solution was added to the reaction mixture, the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-phenyl-2-(5-(1H-pyrrol-1-yl)pyridine-3-carboxamido)benzoate.

10 mL of trifluoroacetic acid was added to the obtained tert-butyl 4-phenyl-2-(5-(1H-pyrrol-1-yl)pyridine-3-carboxamido)benzoate and stirred an room temperature for 2 hours. The solvent was evaporated under reduced pressure, ethyl acetate and water were added and pH was adjusted to pH 7.0 with a saturated sodium hydrogen carbonate aqueous solution. The organic layer was separated and the solvent was evaporated under reduced pressure. Diisopropyl ether was added to the obtained residue and a solid substance was separated by filtration to obtain 23 mg of 4-phenyl-2-(5-(1H-pyrrol-1-yl)pyridine-3-carboxamido)benzoic acid as white solid.

¹H-NMR (DMSO-d₆) δ: 6.39 (2H, t, J=2.2 Hz), 7.45-7.51 (1H, m), 7.53-7.61 (5H, m), 7.73-7.77 (2H, m), 8.15 (1H, d, J=8.3 Hz), 8.47 (1H, t, J=2.4 Hz), 8.97-9.02 (2H, m), 9.17 (1H, d, J=2.4 Hz), 12.26 (1H, s).

Example 391

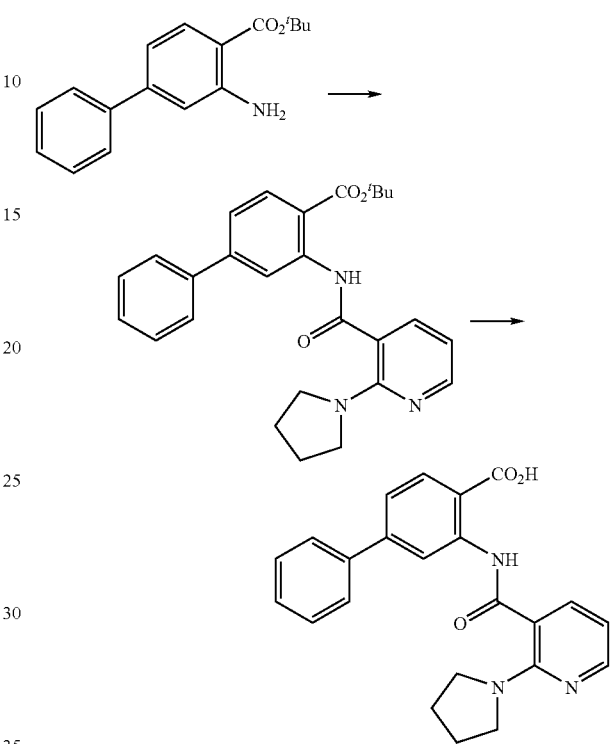

The following compound was obtained in the same manner as in Example 390.

4-Phenyl-2-(2-(pyrrolidin-1-yl)pyridine-3-carboxamido)benzoic acid

¹H-NMR (DMSO-d₆) δ: 1.80-1.89 (4H, m), 3.35-3.44 (4H, m), 6.74 (1H, dd, J=7.4, 4.9 Hz), 7.44-7.58 (4H, m), 7.69-7.74 (2H, m), 7.83 (1H, dd, J=7.4, 1.8 Hz), 8.10 (1H, d, J=8.3 Hz), 8.24 (1H, dd, J=4.9, 1.8 Hz), 9.02 (1H, s), 11.67 (1H, s).

Example 392

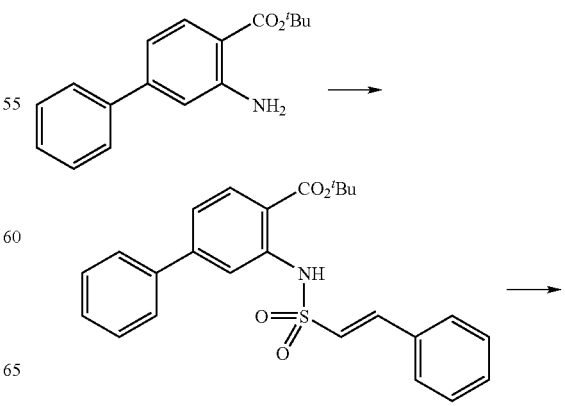

-continued

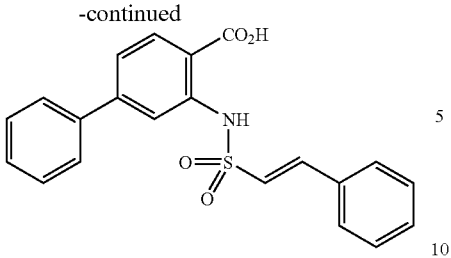

0.056 ml of triethylamine and 45 mg of ((E)-2-phenylvinyl)sulfonyl chloride were added to 3.0 mL of methylene chloride solution containing 54 mg of tert-butyl 2-amino-4-phenylbenzoate at room temperature sequentially and stirred at the same temperature for 1 hour. 0.028 mL of triethylamine and 8.1 mg of ((E)-2-phenylvinyl)sulfonyl chloride were added to the reaction mixture at room temperature sequentially and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-phenyl-2-(((E)-2-phenylvinyl)sulfonamide)benzoate.

10 mL of trifluoroacetic acid was added to the obtained tert-butyl 4-phenyl-2-(((E)-2-phenylvinyl) sulfonamido) benzoate and stirred at room temperature for 2 hours. The solvent: was evaporated under reduced pressure and diisopropyl ether was added to the obtained residue and a solid substance was separated by filtration to obtain 26 mg of 4-phenyl-2-(((E)-2-phenylvinyl)sulfonamido)benzoic acid as white solid.

$^1$H-NMR (DMSO-d$_6$) δ: 7.39-7.58 (8H, m), 7.61-7.66 (2H, m), 7.73-7.81 (4H, m), 8.05 (1H, d, J=8.3 Hz), 11.04 (1H, s).

Examples 393, 394

The compounds shown in Table 37 were obtained in the same manner as in Example 392.

TABLE 37

| Example No. | X$^1$—R$^2$ |
|---|---|
| 393 | 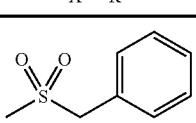 |
| 394 | 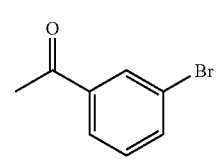 |

2-(Benzylsulfonamido)-4-phenylbenzoic acid $^1$H-NMR (DMSO-d$_6$) δ: 4.78 (2H, s), 7.23-7.33 (5H, m), 7.41-7.49 (2H, m), 7.50-7.56 (2H, m), 7.60-7.65 (2H, m), 7.67 (1H, d, J=1.7 Hz), 8.05 (1H, d, J=8.3 Hz), 10.75-10.90 (1H, broad).

2-(3-Bromobenzamido)-4-phenylbenzoic acid $^1$H-NMR (DMSO-d$_6$) δ: 7.44-7.50 (1H, m), 7.51-7.63 (4H, m), 7.70-7.77 (2H, m), 7.85-7.90 (1H, m), 7.95-8.00 (1H, m), 8.10-8.16 (2H, m), 8.99 (1H, d, J=1.7 Hz), 12.26 (1H, s), 13.75-14.00 (1H, broad).

Example 395

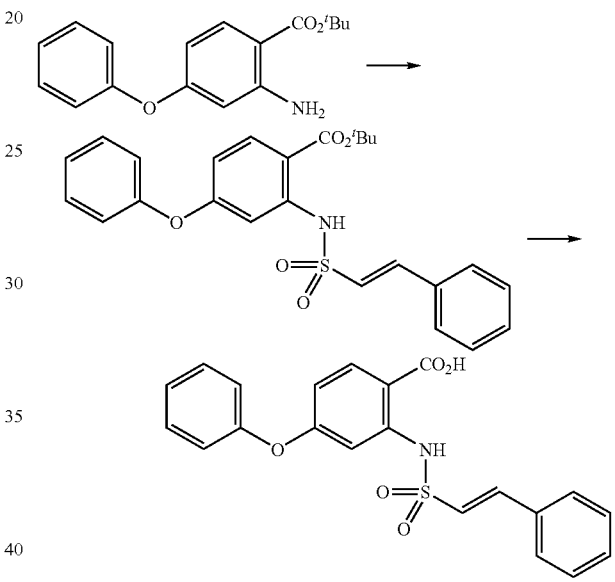

0.056 mL of triethylamine and 61 mg of ((E)-2-phenylvinyl)sulfonyl chloride were added to 5.0 mL of methylene chloride solution containing 57 mg of tert-butyl 2-amino-4-phenoxybenzoate at room, temperature sequentially and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 4-phenoxy-2-(((E)-2-phenylvinyl)sulfonamido)benzoate.

10 mL of trifluoroacetic acid was added to the obtained tert-butyl 4-phenoxy-2-(((E)-2-phenylvinyl)sulfonamido) benzoate and stirred at room temperature for 2 hours. The solvent was evaporated under reduced pressure and diisopropyl ether was added to the obtained residue and a solid substance was separated by filtration to obtain 17 mg of 4-phenoxy-2-(((E)-2-phenylvinyl)sulfonamido)benzoic acid as white solid.

$^1$H-NMR (DMSO-d$_6$) δ: 6.68 (1H, dd, J=8.8, 2.4 Hz), 6.99 (1H, d, J=2.4 Hz), 7.04-7.09 (2H, m), 7.23-7.29 (1H, m), 7.32-7.51 (7H, m), 7.64-7.70 (2H, m), 7.98 (1H, d, J=8.8 Hz), 11.16 (1H, s).

Example 396

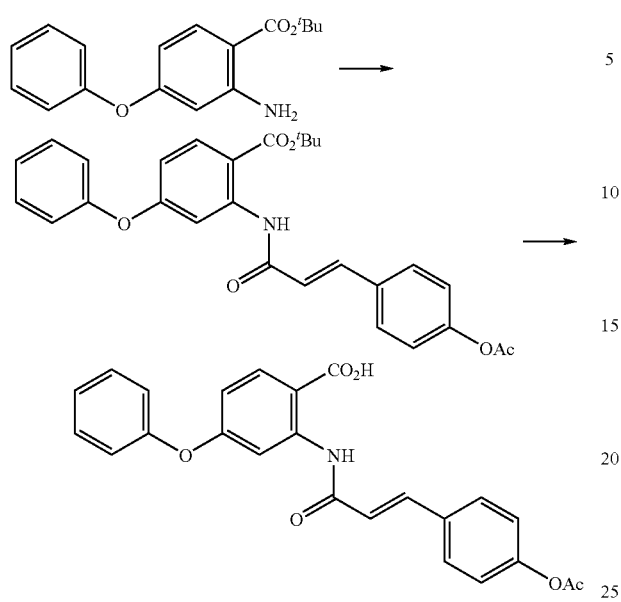

2.0 mL of methylene chloride, 3.9 μL of N,N-dimethylformamide and 0.094 mL of oxalyl chloride were added to 206 mg of 4-acetoxycinnamic acid at room temperature sequentially and stirred at the same temperature for 1 hour. The reaction mixture was added to a mixed solution of 86 mg of tert-butyl 2-amino-4-phenoxybenzoate, 3.0 mL of methylene chloride and 0.67 mL of triethylamine and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=4:1] to obtain tert-butyl 2-((E)-3-(4-acetoxyphenyl)acrylamido)-4-phenoxybenzoate.

10 mL of trifluoroacetic acid was added to the obtained tert-butyl 2-((E)-3-(4-acetoxyphenyl)acrylamido)-4-phenoxybenzoate and stirred at room temperature for 2 hours. The solvent was evaporated under reduced pressure and the obtained residue was purified with reversed-phase silica gel column chromatography [eluent; 60-100% acetonitrile/0.1% trifluoroacetic acid aqueous solution] to obtain 34 mg of 2-((E)-3-(4-acetoxyphenyl)acrylamido)-4-phenoxybenzoic acid as white solid.

$^1$H-NMR (DMSO-d$_6$) δ: 2.28 (3H, s), 6.74 (1H, dd, J=8.9, 2.5 Hz), 6.83 (1H, d, J=15.6 Hz), 7.14-7.23 (4H, m), 7.25-7.31 (1H, m), 7.45-7.52 (2H, m), 7.61 (1H, m, J=15.6 Hz), 7.76-7.82 (2H, m), 8.03 (1H, d, J=8.9 Hz), 8.35 (1H, d, J=2.5 Hz), 11.58 (1H, s), 13.40-13.65 (1H, broad).

Example 397

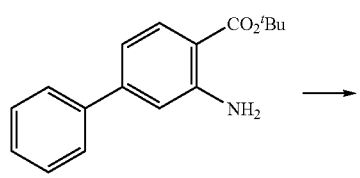

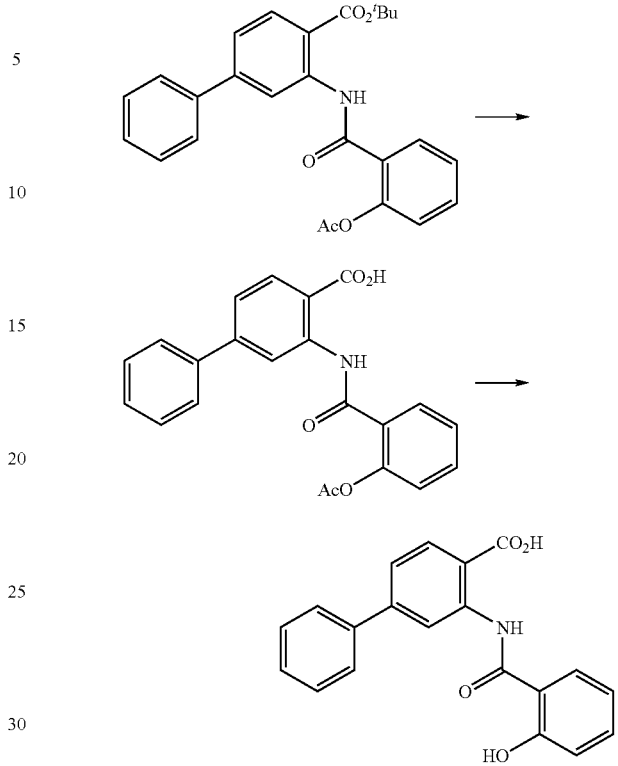

2.0 mL of methylene chloride, 3.9 μL of N,N-dimethylformamide and 0.094 mL of oxalyl chloride were added to 180 mg of 2-acetoxybenzoic acid at room temperature sequentially and stirred at the same temperature for 1 hour. The reaction mixture was added to a mixed solution of 81 mg of tert-butyl 2-amino-4-phenylbenzoate, 3.0 mL of methylene chloride and 0.67 mL triethylamine, and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(2-acetoxybenzamido)-4-phenylbenzoate.

10 mL of trifluoroacetic acid was added to the obtained tert-butyl 2-(2-acetoxybenzamido)-4-phenylbenzoate, and stirred at room temperature for 2 hours. The solvent was evaporated under reduced pressure and 0.50 mL of methanol, 0.50 mL of tetrahydrofuran and 6.1 mg of potassium carbonate were added to the obtained residue sequentially and stirred at room temperature for 2 hours. 10% citric acid aqueous solution was added to the reaction mixture and a solid substance was separated by filtration to obtain 8.2 mg of 2-(2-hydroxybenzamido)-4-phenylbenzoic acid as white solid.

$^1$H-NMR (DMSO-d$_6$) δ: 6.98-7.05 (2H, m), 7.42-7.49 (2H, m), 7.49-7.58 (3H, m), 7.71-7.76 (2H, m), 7.89-7.93 (1H, m), 8.10 (1H, d, J=8.3 Hz), 9.02 (1H, d, J=1.7 Hz), 11.46 (1H, s), 12.32 (1H, s).

Example 398

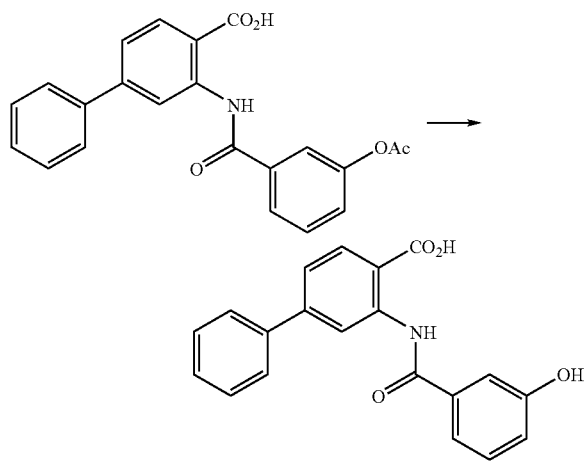

0.50 mL of methanol, 0.50 mL of tetrahydrofuran and 8.3 mg of potassium carbonate were added to 15 mg of 2-(3-acetoxybenzamido)-4-phenylbenzoic acid at room temperature sequentially and stirred at the same temperature for 2 hours. 10% citric acid aqueous solution was added to the reaction mixture and a solid substance was separated by filtration to obtain 12 mg of 2-(3-hydroxybenzamido)-4-phenylbenzoic acid as while solid.

$^1$H-NMR (DMSO-$d_6$) δ: 7.00-7.07 (1H, m), 7.35-7.59 (1H, m), 7.73 (2H, d, J=7.6 Hz), 8.14 (1H, d, J=8.0 Hz), 9.08 (1H, d, J=1.4 Hz), 9.92 (1H, s), 12.22 (1H, s).

Examples 399, 400

The compounds shown in Table 38 were obtained in the same manner as in Example 398.

TABLE 38

| Example No. | R² |
|---|---|
| 399 | 4-hydroxyphenyl |
| 400 | (E)-2-(4-hydroxyphenyl)vinyl |

2-(4-Hydroxybenzamido)-4-phenylbenzoic acid $^1$H-NMR (DMSO-$d_6$) δ: 6.94 (2H, d, J=8.8 Hz), 7.43-7.51 (2H, m), 7.54 (2H, t, J=7.6 Hz), 7.70-7.76 (2H, m), 7.85 (2H, d, J=8.8 Hz), 8.13 (1H, d, J=8.3 Hz), 9.09 (1H, d, J=1.7 Hz), 10.29 (1H, s), 12.16 (1H, s).

2-((E)-3-(4-Hydroxyphenyl)acrylamido)-4-phenylbenzoic acid $^1$H-NMR (DMSO-$d_6$) δ: 6.67 (1H, d, J=15.6 Hz), 6.82 (2H, d, J=8.5 Hz), 7.43-7.50 (2H, m), 7.50-7.62 (5H, m), 7.68-7.74 (2H, m), 8.09 (1H, d, J=8.3 Hz), 9.00 (1H, d, J=2.0 Hz), 9.98 (1H, s), 11.37 (1H, s), 13.50-13.80 (1H, broad).

Example 401

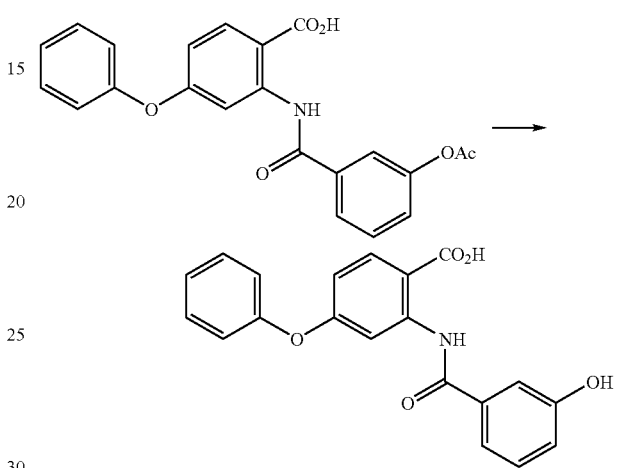

0.50 mL of methanol, 0.50 mL of tetrahydrofuran and 4.2 mg of potassium carbonate were added sequentially to 8.0 mg of 2-(3-acetoxybenzamido)-4-phenoxybenzoic acid at room temperature and stirred at the same temperature for 2 hours. 10% citric acid aqueous solution was added to the reaction mixture and a solid substance was separated by filtration to obtain 4.4 mg of 2-(3-hydroxybenzamido)-4-phenoxybenzoic acid as whine solid.

$^1$H-NMR (DMSO-$d_6$) δ: 6.76 (1H, dd, J=8.8, 2.7 Hz), 7.02 (1H, ddd, J=7.6, 2,3, 1.5 Hz), 7.15-7.21 (2H, m), 7.25-7.40 (4H, m), 7.46-7.52 (2H, m), 8.07 (1H, d, J=3.8 Hz), 8.41 (1H, d, J=2.7 Hz), 9.90 (1H, s), 12.34 (1H, s), 13.55-13.75 (1H, broad).

Examples 402, 403

The compounds shown in Table 39 were obtained in the same manner as in Example 401.

TABLE 39

| Example No. | R² |
|---|---|
| 402 | 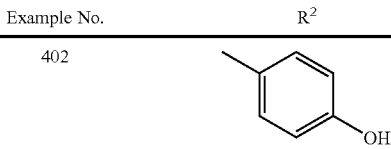 |

TABLE 39-continued

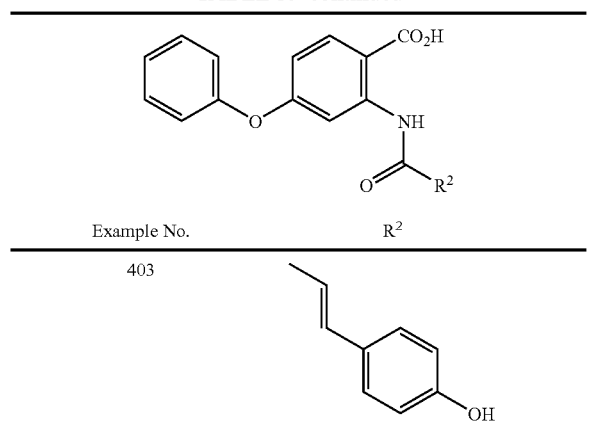

| Example No. | R² |
|---|---|
| 403 | (E)-CH=CH-C₆H₄-OH (para) |

2-(4-Hydroxybenzamido)-4-phenoxybenzoic acid

¹H-NMR (DMSO-d₆) δ: 6.73 (1H, dd, J=3.8, 2.4 Hz), 6.91 (2H, d, J=8.8 Hz), 7.15-7.19 (2H, m), 7.27 (1H, t, J=7.4 Hz), 7.45-7.52 (2H, m), 7.78 (2H, d, J=8.8 Hz), 8.05 (1H, d, J=8.8 Hz), 8.41 (1H, d, J=2.4 Hz), 10.28 (1H, s), 12.27 (1H, s).

2-((E)-3-(4-Hydroxyphenyl)acrylamido)-4-phenoxybenzoic acid

¹H-NMR (DMSO-d₆) δ: 6.58 (1H, d, J=15.6 Hz), 6.71 (1H, dd, J=8.8, 2.6 Hz), 6.80 (2H, d, J=8.6 Hz), 7.13-7.19 (2H, m), 7.24-7.30 (1H, m), 7.44-7.53 (3H, m), 7.56 (2H, d, J=8.6 Hz), 8.02 (1H, d, J=8.8 Hz), 8.35 (1H, d, J=2.6 Hz), 9.97 (1H, s), 11.60 (1H, s).

Example 404

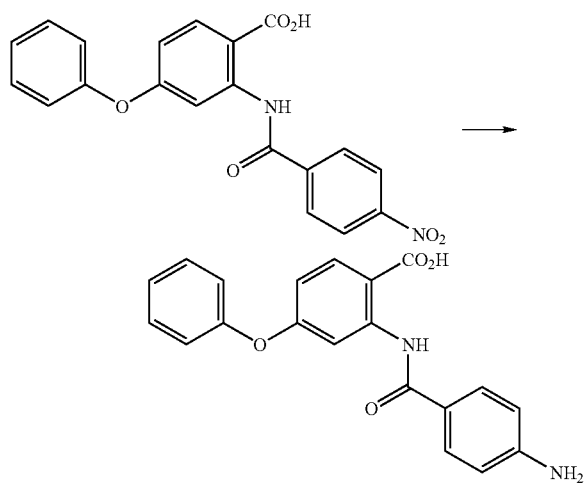

3.0 mL of methanol, 2.0 mL of ethyl acetate and 4.0 mg of 5% palladium-carbon were added to 20 mg of 2-(4-nitrobenzamido)-4-phenoxybenzoic acid at room temperature and stirred under hydrogen atmosphere at 40° C. for 8 hours. Insoluble were removed by filtration, and the solvent was evaporated under reduced pressure to obtain 20 mg of 2-(4-aminobenzamido)-4-phenoxybenzoic acid as white solid.

¹H-NMR (DMSO-d₆) δ: 6.57-6.65 (3H, m), 7.07-7.13 (2H, m), 7.20 (1H, t, J=7.4 Hz), 7.41-7.46 (2H, m), 7.67 (2H, d, J=8.8 Hz), 8.02 (1H, d, J=8.6 Hz), 8.39 (1H, d, J=2.4 Hz).

Example 405

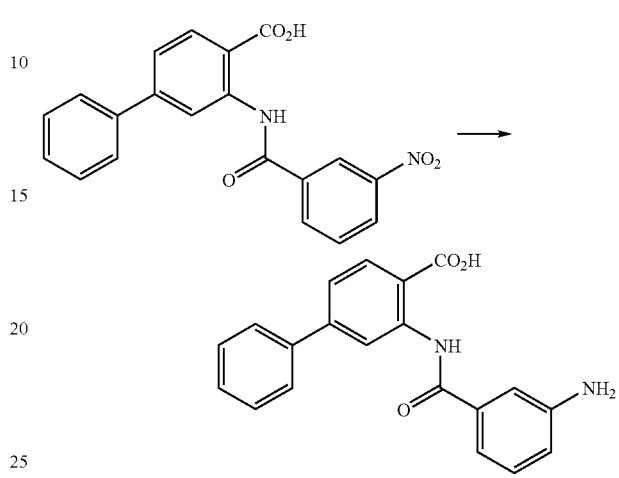

2.0 mL of methanol, 2.0 mL of ethyl acetate and 3.0 mg of 5% palladium-carbon were added to 15 mg of 2-(3-nitrobenzamido)-4-phenylbenzoic acid at room temperature and stirred under hydrogen atmosphere at 40° C. for 2 hours. Insoluble were removed by filtration, and the solvent was evaporated under reduced pressure to obtain 5.1 mg of 2-(3-aminobenzamido)-4-phenylbenzoic acid as white solid.

¹H-NMR (DMSO-d₆) δ: 6.74-6.81 (1H, m), 7.13-7.22 (3H, m), 7.36 (1H, dd, J=8.1, 1.7 Hz), 7.42 (1H, t, J=7.3 Hz), 7.49-7.54 (2H, m), 7.66-7.72 (2H, m), 8.10 (1H, d, J=8.1 Hz), 9.05 (1H, d, J=1.7 Hz).

Example 406

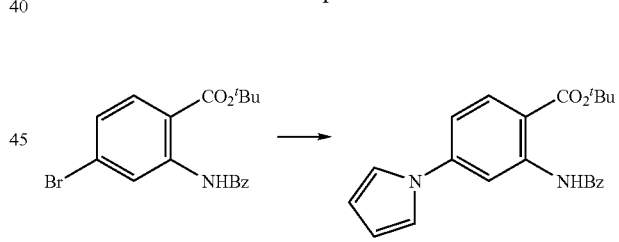

0.019 mL of 1H-pyrrole, 0.12 g of cesium carbonate, 5.1 mg of tris(dibenzylideneacetone)dipalladium(0), 1.6 mg of tri-tert-butylphosphine tetrafluoroborate and 4.4 mg of 2-dicyclohexylphosphino-2',4',6'-triisopropylbiphenyl were added to 1.4 mL of toluene solution containing 10 mg of tert-butyl 2-(benzamido)-4-bromobenzoate at room temperature, and the resulting mixture was heated to reflux under nitrogen atmosphere for 3 hours. After the reaction mixture was cooled to room temperature, 5.1 mg of tris(dibenzylideneacetone)dipalladium(0), 1.6 mg of tri-tert-butylphosphine tetrafluoroborate and 4.4 mg of 2-dicyclohexylphosphino-2',4',6'-triisopropylbiphenyl were added and the resulting mixture was heated to reflux under nitrogen atmosphere for 3 hours. After the reaction mixture was cooled to room temperature, ethyl acetate and 10% citric acid aqueous solution were added and insoluble were removed by filtration. The organic layer was separated and dried over anhydrous magnesium sulfate after washed with a saturated sodium, chloride aqueous solution, and the solvent was evaporated under reduced pressure. The obtained residue was purified with silica gel column chromatography [PSQ100B (spherical) manufactured by Fuji Silysia Chemical Ltd., eluent; hexane; ethyl acetate=10:1] to obtain 60 mg of tert-butyl 2-(benzamido)-4-(1H-pyrrol-1-yl)benzoate as white solid.

$^1$H-NMR (CDCl$_3$) δ: 1.65 (9H, s), 6.38 (2H, t, J=2.2 Hz), 7.12 (1H, dd, J=8.6, 2.3 Hz), 7.25-7.23 (2H, m), 7.51-7.61 (3H, m), 8.05-8.10 (3H, m), 9.16 (1H, d, J=2.3 Hz), 12.36 (1H, s).

Example 907

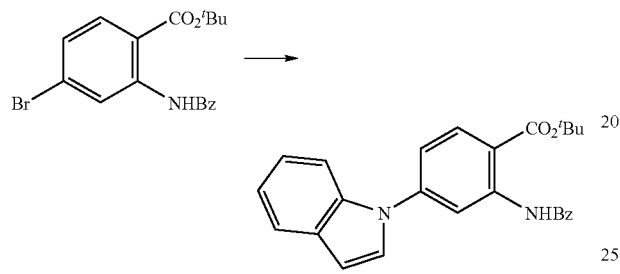

33 mg of 1H-indole, 0.12 g of cesium carbonate, 5.1 mg of tris(dibenzylideneacetone)dipalladium(0), 1.6 mg of tri-tert-butylphosphine tetrafluoroborate and 4.4 mg of 2-dicyclohexylphosphino-2',4',6'-triisopropylbiphenyl were added to 1.4 mL of toluene solution containing 70 mg of tert-butyl 2-(benzamido)-4-bromobenzoate at room temperature, and the resulting mixture was heated to reflux under nitrogen atmosphere for 4 hours. After the reaction mixture was cooled to room temperature, 33 mg of 1H-indole, 79 mg of tripotassium phosphate, 5.1 mg of tris(dibenzylideneacetone)dipalladium(0), 1.6 mg of tri-tert-butylphosphine tetrafluoroborate and 4.4 mg of 2-dicyclohexylphosphino-2',4',6'-triisopropylbiphenyl were added and the resulting mixture was heated to reflux under nitrogen atmosphere for 4 hours. After the reaction mixture was cooled to room temperature, ethyl acetate and 10% citric acid aqueous solution were added and insoluble were removed by filtration. The organic layer was separated, and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane:ethyl acetate=20:1] to obtain 45 mg of tert-butyl 2-(benzamido)-4-(1H-indol-1-yl)benzoate as colorless oil.

$^1$H-NMR (CDCl$_3$) δ: 1.67 (9H, s), 6.73 (1H, d, J=3.4 Hz), 7.18-7.22 (1H, m), 7.25-7.33 (2H, m), 7.48 (1H, d, J=3.4 Hz), 7.51-7.62 (3H, m), 7.66-7.70 (1H, m), 7.83 (1H, d, J=8.3 Hz), 8.06-8.10 (2H, m), 8.17 (1H, d, J=8.8 Hz), 9.22 (1H, d, J=2.2 Hz), 12.35 (1H, s).

Example 408

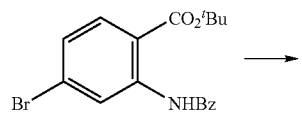

-continued

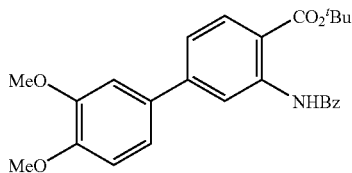

The following compound was obtained in the same manner as in Example 200.

tert-Butyl 2-(benzamido)-4-(3,4-dimethoxyphenyl)benzoate $^1$H-NMR (CDCl$_3$) δ: 1.65 (9H, s), 3.94 (3H, s), 3.99 (3H, s), 6.96 (1H, d, J=8.3 Hz), 7.23 (1H, d, J=2.2 Hz), 7.28-7.34 (2H, m), 7.51-7.61 (3H, m), 8.04-8.11 (3H, m), 9.22 (1H, d, J=2.0 Hz), 12.27 (1H, s).

Example 409

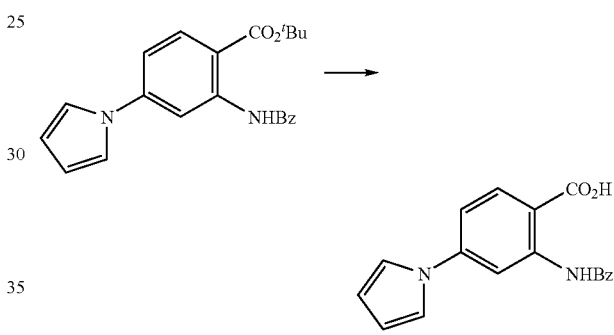

0.24 mL of 2.0 mol/L aqueous sodium hydroxide was added to a mixed solution of 1.0 mL of dioxane and 1.0 mL of methanol containing 58 mg of tert-butyl 2-(benzamido)-4-(1H-pyrrol-1-yl)benzoate and stirred at 50° C. for 1 hour and 30 minutes. After the reaction mixture was cooled to room temperature, water was added and after pH was adjusted to pH 3.0 with 1.0 mol/L hydrochloric acid, ethyl acetate was added. The organic layer was separated and dried over anhydrous magnesium sulfate after washed with water and a saturated sodium chloride aqueous solution sequentially, and the solvent was evaporated under reduced pressure. Diisopropyl ether were added to the obtained residue and a solid substance was separated by filtration to obtain 41 mg of 2-(benzamido)-4-(1H-pyrrol-1-yl)benzoic acid as white solid.

$^1$H-NMR (DMSO-d$_6$) δ: 6.37 (2H, t, J=2.2 Hz), 7.41-7.47 (3H, m), 7.59-7.71 (3H, m), 7.96-8.02 (2H, m), 8.12 (1H, d, J=8.5 Hz), 8.96 (1H, d, J=2.2 Hz), 12.40 (1H, s).

Example 410

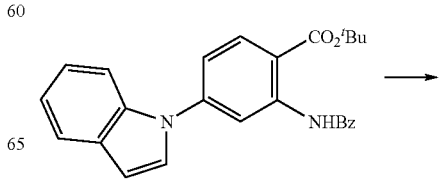

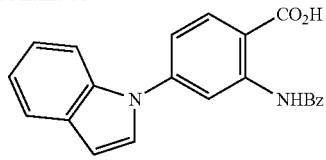

The following compound was obtained in the same manner as in Example 409.

2-(Benzamido)-4-(1H-indol-1-yl)benzoic acid

¹H-NMR (DMSO-d₆) δ: 6.81 (1H, dd, J=3.4, 0.5 Hz), 8.18-9.24 (1H, m), 7.28-7.33 (1H, m), 7.48 (1H, dd, J=8.6, 2.4 Hz), 7.59-7.73 (9H, m), 7.79 (1H, d, J=3.4 Hz), 7.85 (1H, dd, J=8.9, 0.6 Hz), 7.98-8.03 (2H, m), 8.24 (1H, d, J=8.6 Hz), 9.09 (1H, d, J=2.4 Hz), 12.46 (1H, s).

Example 411

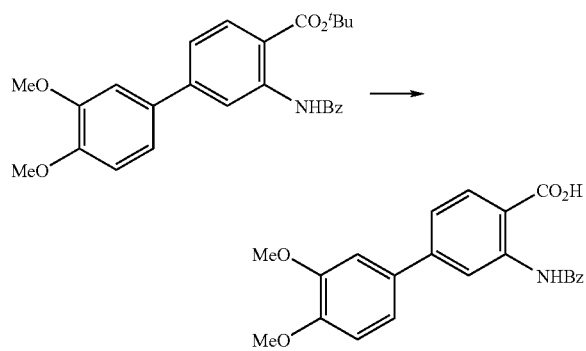

The following compound was obtained in the same manner as in Example 211.

2-(Benzamido)-4-(3,4-dimethoxyphenyl)benzoic acid

¹H-NMR (DMSO-d₆) δ: 3.83 (3H, s), 3.87 (3H, s), 7.12 (1H, d, J=9.0 Hz), 7.27-7.32 (2H, m), 7.52 (1H, dd, J=8.3, 1.8 Hz), 7.58-7.70 (3H, m), 7.97-8.02 (2H, m), 8.10 (1H, d, J=8.3 Hz), 9.04 (1H, d, J=1.8 Hz), 12.26 (1H, s).

Example 412

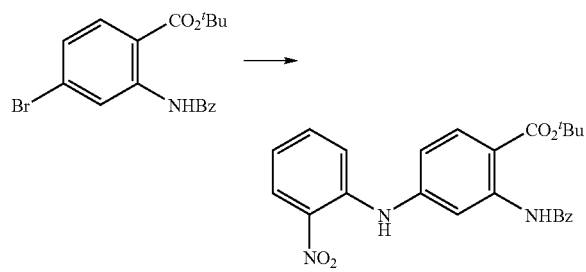

55 mg of 2-nitroaniline, 0.17 g of cesium carbonate, 2.4 mg of tris(dibenzylideneacetone)dipalladium(0), 1.2 mg of palladium acetate and 6.3 mg of 2-dicyclohexylphosphino-2',4', 6'-triisopropylbiphenyl were added to 2.0 mL of toluene solution containing 0.10 g of tert-butyl 2-(benzamido)-4-bromobenzoate at room temperature, and the resulting mixture was heated to reflux under nitrogen atmosphere for 4 hours. After the reaction mixture was cooled to room temperature, ethyl acetate and 10% citric acid aqueous solution were added and insoluble were removed by filtration. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane; ethyl acetate=1:1] to obtain 94 mg of tert-butyl 2-(benzamido)-4-(2-nitroanilino)benzoate as yellow solid.

¹H-NMR (CDCl₃) δ: 1.64 (9H, s), 6.90-6.96 (2H, m), 7.50-7.60 (4H, m), 7.66 (1H, dd, J=8.5, 1.2 Hz), 8.02 (1H, d, J=8.5 Hz), 8.02-8.08 (2H, m), 8.22 (1H, dd, J=8.7, 1.6 Hz), 8.94 (1H, d, J=2.2 Hz), 9.53 (1H, s), 12.33 (1H, s).

Example 413

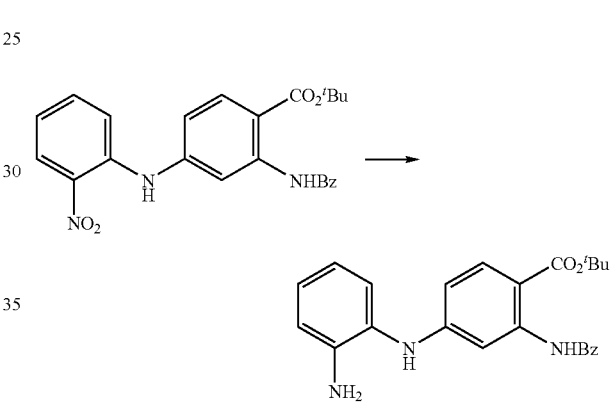

10 mg of 5% palladium-carbon was added to a mixed solution of 4.0 mL of methanol and 8.0 mL of ethyl acetate containing 50 mg of tert-butyl 2-(benzamido)-4-(2-nitroanilino)benzoate and stirred under hydrogen atmosphere at room temperature for 1 hour and 30 minutes. After insoluble were removed by filtration, the solvent was evaporated under reduced pressure to obtain 46 mg of tert-butyl 4-(2-aminoanilino)-2-(benzamido)benzoate as pale yellow solid.

¹H-NMR (CDCl₃) δ: 1.59 (9H, s), 3.79 (2H, s), 5.67 (1H, s), 6.30 (1H, dd, J=8.8, 2.3 Hz), 6.76-6.85 (2H, m), 7.06-7.12 (1H, m), 7.15-7.18 (1H, m), 7.49-7.58 (3H, m), 7.85 (1H, d, J=8.8 Hz), 8.03-8.08 (2H, m), 8.41 (1H, d, J=2.3 Hz), 12.41 (1H, s).

Example 414

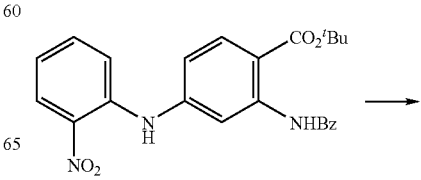

-continued

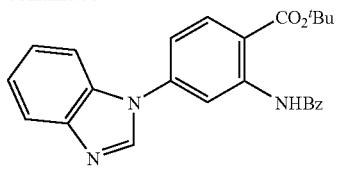

28 mg of formamidine acetate was acetate to 1.0 mL of ethylene glycol monomethyl ether solution containing 44 mg of tert-butyl 4-(2-aminoanilino)-2-(benzamido)benzoate at room temperature and stirred at 80° C. for 3 hours. After the reaction mixture was cooled to room temperature, ethyl acetate and water were added. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia Chemical Ltd., eluent; hexane:ethyl acetate=1:1] to obtain 36 mg of tert-butyl 2-(benzamido)-4-(1H-benzimidazol-1-yl)benzoate as pale yellow oil.

$^1$H-NMR (CDCl$_3$) δ: 1.68 (9H, s), 7.24-7.30 (1H, m), 7.34-7.44 (2H, m), 7.53-7.63 (3H, m), 7.78-7.82 (1H, m), 7.87-7.92 (1H, m), 8.06-8.10 (2H, m), 8.23 (1H, d, J=8.6 Hz), 8.26 (1H, s), 9.30 (1H, d, J=2.2 Hz), 12.38 (1H, s).

Example 415

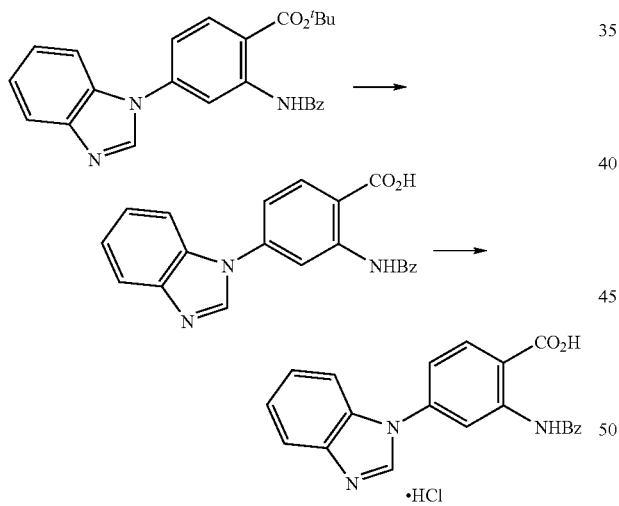

5.0 mL trifluoroacetic acid solution containing 34 mg of tert-butyl 2-(benzamido)-4-(1H-benzimidazol-1-yl)benzoate was stirred at room temperature for 1 hour and 30 minutes. The solvent was evaporated under reduced pressure and methanol was added to the obtained residue and a solid substance was separated by filtration to obtain 24 mg of 2-(benzamido)-4-(1H-benzimidazol-1-yl)benzoic acid as white solid.

0.5 mL of trifluoroacetic acid and 0.01 mL of 4.0 mol/L hydrogen chloride/dioxane were added to 1.0 mL suspension containing 15 mg of 2-(benzamido)-4-(1H-benzimidazol-1-yl)benzoic acid in ethyl acetate sequentially while ice-cooled and stirred at the same temperature for 10 minutes. A solid substance was separated by filtration to obtain 12 mg of 2-(benzamido)-4-(1H-benzimidazol-1-yl)benzoic acid hydrochloride as white solid.

$^1$H-NMR (DMSO-d$_6$) δ: 7.46-7.56 (2H, m), 7.59-7.72 (4H, m), 7.87-7.92 (2H, m), 7.98-8.03 (2H, m), 8.32 (1H, d, J=8.6 Hz), 9.15 (1H, d, J=2.2 Hz), 9.16 (1H, s), 12.38 (1H, s).

Examples 416 to 425

The compounds shown in Table 40 were obtained in the same manner as in Example 251,

TABLE 40

| Example No. | R$^3$ |
|---|---|
| 416 | 3-Cl-4-F-phenyl |
| 417 | 3,4-diF-phenyl |
| 418 | 2,5-diF-phenyl |
| 419 | 2,5-diCl-phenyl |
| 420 | 5-F-2-Me-phenyl |
| 421 | 2-OCF$_3$-phenyl |
| 422 | 2,5-diMe-phenyl |
| 423 | 2-Cl-5-MeO-phenyl |

TABLE 40-continued

| Example No. | R³ |
|---|---|
| 424 | 2,3-dichlorophenyl |
| 425 | 2,5-dichloro-4-methylphenyl (Cl, Me, Cl substitution) |

2-(Benzamido)-4-(3-chloro-4-fluorophenyl)benzoic acid

¹H-NMR (DMSO-$d_6$) δ: 7.52-7.70 (5H, m), 7.72-7.79 (1H, m), 7.93 (1H, dd, J=7.1, 2.4 Hz), 7.96-8.02 (2H, m), 8.13 (1H, d, J=8.3), 9.03 (1H, s), 12.23 (1H, s).

2-(Benzamido)-4-(3,4-difluorophenyl)benzoic acid

¹H-NMR (DMSO-$d_6$) δ: 7.54 (1H, dd, J=8.3, 1.7 Hz), 7.56-7.70 (5H, m), 7.78-7.86 (1H, m), 7.96-8.05 (2H, m), 8.13 (1H, d, J=8.3 Hz), 9.04 (1H, d, J=1.7 Hz), 12.22 (1H, s).

2-(Benzamido)-4-(2,5-difluorophenyl)benzoic acid

¹H-NMR (DMSO-$d_6$) δ: 7.33-7.52 (4H, m), 7.58-7.70 (3H, m), 7.95-8.00 (2H, m), 8.16 (1H, d, J=8.3 Hz), 8.96-8.99 (1H, m), 12.25 (1H, s).

2-(Benzamido)-1-(2,4-dichlorophenyl)benzoic acid

¹H-NMR (DMSO-$d_6$) δ: 7.28 (1H, dd, J=8.3, 1.7 Hz), 7.52 (1H, d, J=8.3 Hz), 7.56-7.70 (4H, m), 7.80 (1H, d, J=2.2 Hz), 7.94-8.00 (2H, m), 8.15 (1H, d, J=8.3 Hz), 8.82 (1H, d, J=1.7 Hz), 12.27 (1H, s).

2-(Benzamido)-4-(4-fluoro-2-methylphenyl)benzoic acid

¹H-NMR (DMSO-$d_6$) δ: 2.30 (3H, s), 7.11-7.25 (3H, m), 7.32 (1H, dd, J=8.5, 6.1 Hz), 7.57-7.69 (3H, m), 7.94-7.99 (2H, m), 8.12 (1H, d, J=8.1 Hz), 8.72 (1H, d, J=1.7 Hz), 12.26 (1H, s).

2-(Benzamido)-4-(2-trifluoromethoxyphenyl)benzoic acid

¹H-NMR (DMSO-$d_6$) δ: 7.32 (1H, dd, J=8.1, 1.6 Hz), 7.52-7.69 (7H, m), 7.95-8.00 (2H, m), 8.16 (1H, d, J=8.1 Hz), 8.91 (1H, d, J=1.6 Hz), 12.27 (1H, s).

2-(Benzamido)-4-(3,4-dimethylphenyl)benzoic acid

¹H-NMR (DMSO-$d_6$) δ: 2.29 (3H, s), 2.33 (3H, s), 7.29 (1H, d, J=7.8 Hz), 7.43-7.53 (3H, m), 7.58-7.70 (3H, m), 7.96-8.02 (2H, m), 8.11 (1H, d, J=8.3 Hz), 9.06 (1H, d, J=1.7 Hz), 12.27 (1H, s).

2-(Benzamido)-4-(3-chloro-4-methoxyphenyl)benzoic acid

¹H-NMR (DMSO-$d_6$) δ: 3.94 (3H, s), 7.32 (1H, d, J=8.7 Hz), 7.52 (1H, dd, J=8.3, 1.8 Hz), 7.58-7.74 (4H, m), 7.79 (1H, d, J=2.2 Hz), 7.96-8.02 (2H, m), 8.11 (1H, d, J=8.3 Hz), 9.04 (1H, d, J=1.8 Hz), 12.26 (1H, s), 13.70-13.95 (1H, broad).

2-(Benzamido)-4-(2,3-dichlorophenyl)benzoic acid

¹H-NMR (DMSO-$d_6$) δ: 7.29 (1H, dd, J=8.1, 1.7 Hz), 7.45 (1H, dd, J=7.8, 1.7 Hz), 7.51 (1H, t, J=7.8 Hz), 7.58-7.69 (3H, m), 7.75 (1H, dd, J=7.8, 1.7 Hz), 7.94-7.99 (2H, m), 8.15 (1H, d, J=8.1 Hz), 8.80-8.83 (1H, m), 12.27 (1H, s).

2-(Benzamido)-4-(2,5-dichlorophenyl)benzoic acid

¹H-NMR (DMSO-$d_6$) δ: 7.30 (1H, dd, J=8.2, 1.6 Hz), 7.54-7.70 (6H, m), 7.94-8.00 (2H, m), 8.15 (1H, d, J=8.2 Hz), 8.83 (1H, d, J=1.6 Hz), 12.25 (1H, s).

Example 426

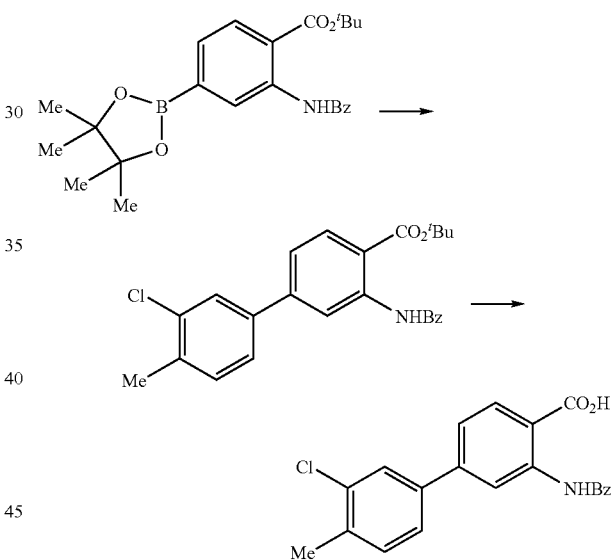

0.031 mL of 2-chloro-4-Iodotoluene, 39 mg of sodium hydrogen carbonate, 0.6 mL of ethanol, 0.3 mL of water and 11 mg of tetrakis(triphenylphosphine)palladium(0) were added to 1.6 mL of toluene solution containing 79 mg of tert-butyl 2-(benzamido)-4-(4,4,5,5-tetramethyl-1,3,2-dioxaborolan-2-yl)benzoate at room temperature, and the resulting mixture was heated to reflux for 8 hours. After the reaction mixture was cooled to room temperature, 11 mg of tetrakis(triphenylphosphine)palladium(9) was added and the resulting mixture was heated to reflux for 7 hours. After the reaction mixture was cooled to room temperature, ethyl acetate and water were added. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane:ethyl acetate=10:1] to obtain tert-butyl 2-(benzamido)-4-(3-chloro-4-methylphenyl)benzoate as white solid.

5.0 mL of trifluoroacetic acid was added to the obtained tert-butyl 2-(benzamido)-4-(3-chloro-4-Methylphenyl)benzoate and stirred at room temperature for 2 hours. The solvent was evaporated under reduced pressure and methanol was added to the obtained residue and a solid substance was separated by filtration to obtain 14 mg of 2-(benzamido)-4-(3-chloro-4-methylphenyl)benzoic acid as white solid.

$^1$H-NMR (DMSO-$d_6$) δ: 2.40 (3H, s), 7.50-7.70 (6H, m), 7.76 (1H, d, J=1.7 Hz), 7.97-8.02 (2H, m), 8.13 (1H, d, J=8.3 Hz), 9.06 (1H, d, J=1. Hz), 12.26 (1H, s).

Examples 427 to 429

The compounds shown in Table 41 were obtained in the same manner as in Example 252.

TABLE 41

| Example No. | R$^3$ |
|---|---|
| 427 | 3-chloro-2-methylphenyl |
| 428 | 5-chloro-2-methylphenyl |
| 429 | 5-chloro-2-methoxyphenyl |

2-(Benzamido)-4-(3-chloro-2-methylphenyl)benzoic acid $^1$H-NMR (DMSO-$d_6$) δ: 2.29 (3H, s), 7.20 (1H, dd, J=8.3, 1.8 Hz), 7.26 (1H, dd, J=7.7, 1.2 Hz), 7.35 (1H, dd, J=7.9, 7.7 Hz), 7.53 (1H, dd, J=7.9, 1.2 Hz), 7.58-7.69 (3H, m), 7.94-7.99 (2H, m), 8.13 (1H, d, J=8.3 Hz), 8.70-8.72 (1H, m), 12.23 (1H, s).

2-(Benzamido)-4-(5-chloro-2-Methylphenyl)benzoic acid $^1$H-NMR (DMSO-$d_6$) δ: 2.26 (3H, s), 7.23 (1H, dd, J=8.2, 1.7 Hz), 7.32 (1H, d, J=1.7 Hz), 7.37-7.44 (2H, m), 7.58-7.70 (3H, m), 7.94-8.00 (2H, m), 8.13 (1H, d, J=8.2 Hz), 8.73 (1H, s, J=1.7 Hz), 12.25 (1H, s).

2-(Benzamido)-4-(5-chloro-2-methoxyphenyl)benzoic acid $^1$H-NMR (DMSO-$d_6$) δ: 3.81 (3H, s), 7.21 (1H, d, J=8.8 Hz), 7.34 (1H, dd, J=8.2, 1.7 Hz), 7.38 (1H, d, J=2.7 Hz), 7.48 (1H, dd, J=8.8, 2.7 Hz), 7.58-7.69 (3H, m), 7.95-8.00 (2H, m), 8.09 (1H, d, J=8.2 Hz), 8.86 (1H, d, J=1.7 Hz), 12.21 (1H, s).

Example 430

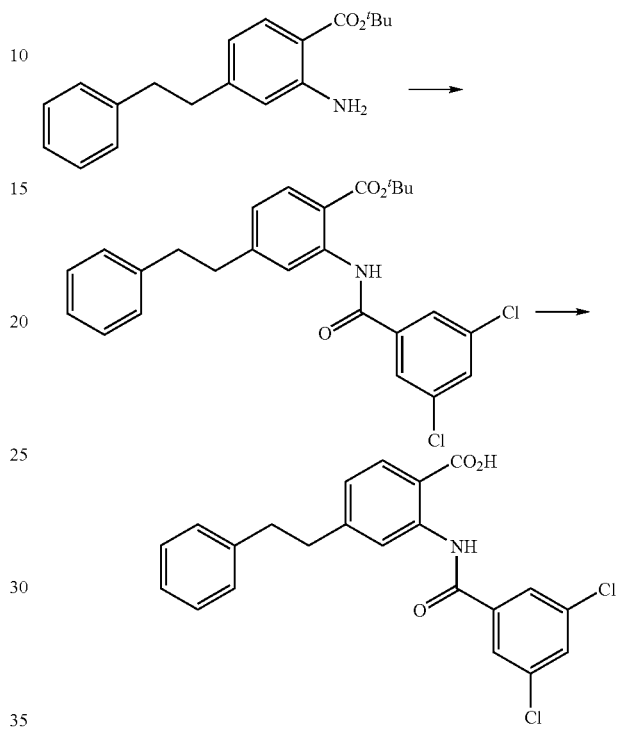

2.0 mL of methylene chloride, 2.7 μL of N,N-dimethylformamide and 0.061 mL of oxalyl chloride were sequentially added to 0.13 g of 3,5-dichlorobenzoic acid at room temperature and stirred at the same temperature for 1 hour. The reaction mixture was added to a mixed solution of 3.0 mL of methylene chloride and 0.45 mL of triethylamine containing 60 mg of tert-butyl 2-amino-4-phenethylbenzoate at room temperature and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(3,5-dichlorobenzamido)-4-phenethylbenzoate.

10 mL of trifluoroacetic acid was added to the obtained tert-butyl 2-(3,5-dichlorobenzamido)-4-phenethylbenzoate and stirred ad room temperature for 2 hours. The solvent was evaporated under reduced pressure and diisopropyl ether was added to the obtained residue and a solid substance was separated by filtration to obtain 62 mg of 2-(3,5-dichlorobenzamido)-4-phenethylbenzoic acid as white solid.

$^1$H-NMR (DMSO-$d_6$) δ: 2.89-3.02 (4H, m), 7.12 (1H, dd, J=8.0, 1.7 Hz), 7.16-7.21 (1H, m), 7.24-7.31 (4H, m), 7.91-7.97 (4H, m), 8.48-8.52 (1H, m), 12.14 (1H, s), 13.65-13.85 (1H, broad).

Examples 431 to 439

The compounds shown in Table 42 were obtained in the same manner as in Example 430.

TABLE 42

[Structure: phenethyl group on benzene ring with CO2H and NH-C(=O)-R²]

| Example No. | R² |
|---|---|
| 431 | 3,4-dichlorophenyl |
| 432 | 3,5-difluorophenyl |
| 433 | 3,4-difluorophenyl |
| 434 | 3,5-dimethylphenyl |
| 435 | 4-acetoxyphenyl |
| 436 | 6-methyl-4-phenylpyrimidin-... (4-phenyl-6-methylpyrimidinyl) |
| 437 | 5-methyl-3-phenylisoxazolyl |
| 438 | (E)-3-phenyl-2-propenyl-CH2- (styrylethyl) |
| 439 | 2-methyl-2-phenylvinyl (α-methylstyryl) |

2-(3,4-Dichlorobenzamido)-4-phenethylbenzoic acid

¹H-NMR (DMSO-d$_6$) δ: 2.89-3.02 (4H, m), 7.11 (1H, dd, J=8.1, 1.5 Hz), 7.16-7.21 (1H, m), 7.24-7.31 (4H, m), 7.88-7.91 (2H, m), 7.95 (1H, d, J=8.1 Hz), 8.13 (1H, s), 8.54 (1H, d, J=1.5 Hz), 12.17 (1H, s), 13.60-13.85 (1H, broad).

2-(3,5-Difluorobenzamido)-4-phenethylbenzoic acid

¹H-NMR (DMSO-d$_6$) δ: 2.88-3.02 (4H, m), 7.12 (1H, dd, J=8.1, 1.6 Hz), 7.15-7.21 (1H, m), 7.23-7.32 (4H, m), 7.56-7.66 (3H, m), 7.96 (1H, d, J=8.1 Hz), 8.52 (1H, d, J=1.6 Hz), 12.12 (1H, s), 13.60-13.80 (1H, broad).

2-(3,4-Difluorobenzamido)-4-phenethylbenzoic acid

¹H-NMR (DMSO-d$_6$) δ: 2.88-3.02 (4H, m), 7.10 (1H, dd, J=8.1, 1.7 Hz), 7.16-7.21 (1H, m), 7.24-7.31 (4H, m), 7.66-7.74 (1H, m), 7.79-7.85 (1H, m), 7.91-7.99 (2H, m), 8.55 (1H, d, J=1.7 Hz), 12.12 (1H, s), 13.60-13.80 (1H, broad).

2-(3,5-Dimethylbenzamido)-4-phenethylbenzoic acid

¹H-NMR (DMSO-d$_6$) δ: 2.37 (6H, s), 2.88-3.02 (4H, m), 7.07 (1H, dd, J=8.1, 1.5 Hz), 7.16-7.21 (1H, m), 7.24-7.31 (5H, m), 7.57 (2H, s), 7.95 (1H, d, J=8.1 Hz), 8.66-8.68 (1H, m), 12.19 (1H, s), 13.65-13.80 (1H, broad).

2-(4-Acetoxybenzamido)-4-phenethylbenzoic acid

¹H-NMR (DMSO-d$_6$) δ: 2.37 (3H, s), 2.89-3.02 (1H, m), 7.09 (1H, dd, J=8.3, 1.6 Hz), 7.16-7.21 (1H, m), 7.25-7.32 (4H, m), 7.35-7.40 (2H, m), 7.96 (1H, d, J=8.3 Hz), 7.96-8.03 (2H, m), 8.63-8.65 (1H, m), 12.17 (1H, s), 13.60-13.75 (1H, broad).

4-Phenethyl-2-(6-phenylpyrimidine-4-carboxamido)benzoic acid

¹H-NMR (DMSO-d$_6$) δ: 2.92-3.05 (4H, m), 7.12-7.22 (2H, m), 7.25-7.32 (4H, m), 7.58-7.67 (3H, m), 7.99 (1H, d, J=8.3 Hz), 8.30-8.37 (2H, m), 8.64 (1H, d, J=1.2 Hz), 8.82 (1H, d, J=1.5 Hz), 9.47 (1H, d, J=1.2 Hz), 13.16 (1H, s).

4-Phenethyl-2-(3-phenylisoxazole-5-carboxamido)benzoic acid

¹H-NMR (DMSO-d$_6$) δ: 2.90-3.04 (4H, m), 7.12-7.21 (2H, m), 7.25-7.32 (4H, m), 7.52-7.63 (4H, m), 7.96-8.02 (3H, m), 8.63 (1H, d, J=1.4 Hz), 12.49 (1H, s).

4-Phenethyl-2-((E)-4-phenyl-3-butenamido)benzoic acid

¹H-NMR (DMSO-d$_6$) δ: 2.84-2.97 (4H, m), 3.35-3.38 (2H, m), 6.40-6.50 (1H, m), 6.66 (1H, d, J=15.8 Hz), 7.01 (1H, dd, J=8.0, 1.6 Hz), 7.14-7.20 (1H, m), 7.21-7.30 (5H, m), 7.31-7.38 (2H, m), 7.44-7.50 (2H, m), 7.87 (1H, d, J=8.0 Hz), 8.49 (1H, d, J=1.6 Hz), 11.29 (1H, s).

2-((E)-2-Methyl-3-phenylacrylamido)-4-phenethylbenzoic acid

¹H-NMR (DMSO-d$_6$) δ: 2.19 (3H, d, J=1.2 Hz), 2.88-3.01 (4H, m), 7.05 (1H, dd, J=8.1, 1.5 Hz), 7.16-7.21 (1H, m), 7.24-7.32 (4H, m), 7.35-7.41 (1H, m), 7.43-7.53 (5H, m), 7.94 (1H, d, J=8.1 Hz), 8.65 (1H, s), 11.86 (1H, s).

Examples 440 to 446

The compounds shown in Table 43 were obtained in the same manner as in Example 369.

TABLE 43

Structure: phenyl-O-C6H3(CO2H)-NH-C(=O)-R²

| Example No. | R² |
|---|---|
| 440 | (E)-CH=CH-C6H4-4-NO2 |
| 441 | 3,5-dichlorophenyl |
| 442 | 3,4-dichlorophenyl |
| 443 | 3,5-difluorophenyl |
| 444 | 3,4-difluorophenyl |
| 445 | 3,5-dimethylphenyl |
| 446 | (E)-C(Me)=CH-phenyl |

2-((E)-3-(4-Nitrophenyl)acrylamido)-4-phenoxybenzoic acid $^1$H-NMR (DMSO-d$_6$) δ: 6.77 (1H, dd, J=8.8, 2.5 Hz), 7.12 (1H, d, J=15.6 Hz), 7.14-7.21 (2H, m), 7.28 (1H, t, J=7.5 Hz), 7.45-7.53 (2H, m), 7.71 (1H, d, J=15.6 Hz), 8.00-8.08 (3H, m), 8.26 (2H, d, J=9.0 Hz), 8.35 (1H, d, J=2.6 Hz), 11.66 (1H, s), 13.40-13.65 (1H, broad).

2-(3,5-Dichlorobenzamido)-4-phenoxybenzoic acid $^1$H-NMR (DMSO-d$_6$) δ: 6.81 (1H, dd, J=8.8, 2.7 Hz), 7.16-7.22 (2H, m), 7.29 (1H, t, J=7.4 Hz), 7.46-7.53 (2H, m), 7.88 (2H, d, J=1.8 Hz), 7.94 (1H, t, J=1.8 Hz), 8.07 (1H, d, J=8.8 Hz), 8.26 (1H, d, J=2.7 Hz), 12.43 (1H, s).

2-(3,4-Dichlorobenzamido)-4-phenoxybenzoic acid $^1$H-NMR (DMSO-d$_6$) δ: 6.80 (1H, dd, J=8.9, 2.5 Hz), 7.15-7.21 (2H, m), 7.26-7.32 (1H, m), 7.46-7.53 (2H, m), 7.84-7.92 (2H, m), 8.07 (1H, d, J=8.9 Hz), 8.09 (1H, d, J=1.9 Hz), 8.30 (1H, d, J=2.5 Hz), 12.43 (1H, s).

2-(3,5-Difluorobenzamido)-4-phenoxybenzoic acid $^1$H-NMR (DMSO-d$_6$) δ: 6.81 (1H, dd, J=8.8, 2.7 Hz), 7.15-7.22 (2H, m), 7.26-7.32 (1H, m), 7.46-7.64 (5H, m), 8.07 (1H, d, J=8.8 Hz), 8.28 (1H, d, J=2.7 Hz), 12.39 (1H, s).

2-(3,4-Difluorobenzamido)-4-phenoxybenzoic acid $^1$H-NMR (DMSO-d$_6$) δ: 6.80 (1H, dd, J=8.9, 2.5 Hz), 7.15-7.22 (2H, m), 7.25-7.32 (1H, m), 7.45-7.53 (2H, m), 7.65-7.73 (1H, m), 7.75-7.82 (1H, m), 7.88-7.94 (1H, m), 8.07 (1H, d, J=8.9 Hz), 8.30 (1H, d, J=2.5 Hz), 12.37 (1H, s).

2-(3,5-Dimethylbenzamido)-4-phenoxybenzoic acid $^1$H-NMR (DMSO-d$_6$) δ: 2.35 (6H, s), 6.76 (1H, dd, J=8.9, 2.4 Hz), 7.16-7.22 (2H, m), 7.26-7.32 (2H, m), 7.45-7.57 (9H, m), 8.06 (1H, d, J=8.9 Hz), 8.41 (1H, d, J=2.4 Hz), 12.40 (1H, s).

2-((E)-2-Methyl-3-phenylacrylamido)-4-phenoxybenzoic acid $^1$H-NMR (DMSO-d$_6$) δ: 2.16 (3H, d, J=1.5 Hz), 6.75 (1H, dd, J=8.8, 2.6 Hz), 7.15-7.19 (2H, m), 7.25-7.31 (1H, m), 7.34-7.41 (1H, m), 7.42-7.52 (7H, m), 8.05 (1H, d, J=8.8 Hz), 8.38 (1H, d, J=2.6 Hz), 12.06 (1H, s).

Examples 447 to 452

The compounds shown in Table 44 were obtained in the same manner as in Example 345.

TABLE 44

Structure: phenyl-C6H3(CO2H)-NH-C(=O)-R²

| Example No. | R² |
|---|---|
| 447 | 3,5-dichlorophenyl |
| 448 | 3,4-dichlorophenyl |

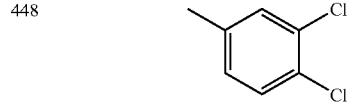

TABLE 44-continued

[Structure: benzoic acid with CO2H, NH-C(=O)-R² and phenyl substituent]

| Example No. | R² |
|---|---|
| 449 | 3,5-difluorophenyl (methyl position shown with F, F) |
| 450 | 3,4-difluorophenyl |
| 451 | 3,5-dimethylphenyl |
| 452 | (E)-1-methyl-2-phenylethenyl |

2-(3,5-Dichlorobenzamido)-4-phenylbenzoic acid $^1$H-NMR (DMSO-$d_6$) δ: 7.47 (1H, tt, J=7.3, 1.6 Hz), 7.51-7.59 (3H, m), 7.70-7.75 (2H, m), 7.94 (3H, s), 8.12 (1H, d, J=8.3 Hz), 8.90 (1H, d, J=1.7 Hz), 12.21 (1H, s).

2-(3,4-Dichlorobenzamido)-4-phenylbenzoic acid $^1$H-NMR (DMSO-$d_6$) δ: 7.44-7.50 (1H, m), 7.52-7.59 (3H, m), 7.70-7.76 (2H, m), 7.89-7.96 (2H, m), 8.13 (1H, d, J=8.3 Hz), 8.15-8.19 (1H, m), 8.95 (1H, d, J=1.7 Hz), 12.23 (1H, s).

2-(3,5-Difluorobenzamido)-4-phenylbenzoic acid $^1$H-NMR (DMSO-$d_6$) δ: 7.47 (1H, tt, J=7.2, 1.5 Hz), 7.52-7.67 (6H, m), 7.70-7.77 (2H, m), 8.13 (1H, d, J=8.8 Hz), 8.93 (1H, d, J=1.7 Hz), 12.18 (1H, s).

2-(3,4-Difluorobenzamido)-4-phenylbenzoic acid $^1$H-NMR (DMSO-$d_6$) δ: 7.44-7.50 (1H, m), 7.52-7.58 (3H, m), 7.67-7.77 (3H, m), 7.82-7.88 (1H, m), 7.94-8.02 (1H, m), 8.13 (1H, d, J=8.3 Hz), 8.96 (1H, d, J=1.7 Hz), 12.19 (1H, s).

2-(3,5-Dimethylbenzamido)-4-phenylbenzoic acid $^1$H-NMR (DMSO-$d_6$) δ: 2.38 (6H, s), 7.30 (1H, s), 7.44-7.58 (4H, m), 7.60 (2H, s), 7.70-7.76 (2H, m), 8.13 (1H, d, J=8.3 Hz), 9.08 (1H, d, J=1.7 Hz), 12.26 (1H, s).

2-((E)-2-Methyl-3-phenylacrylamido)-4-phenylbenzoic acid $^1$H-NMR (DMSO-$d_6$) δ: 2.22 (3H, d, J=1.2 Hz), 7.36-7.41 (1H, m), 7.44-7.58 (9H, m), 7.70-7.74 (2H, m), 8.12 (1H, d, J=8.3 Hz), 9.08 (1H, d, J=1.7 Hz), 11.93 (1H, s).

Example 453

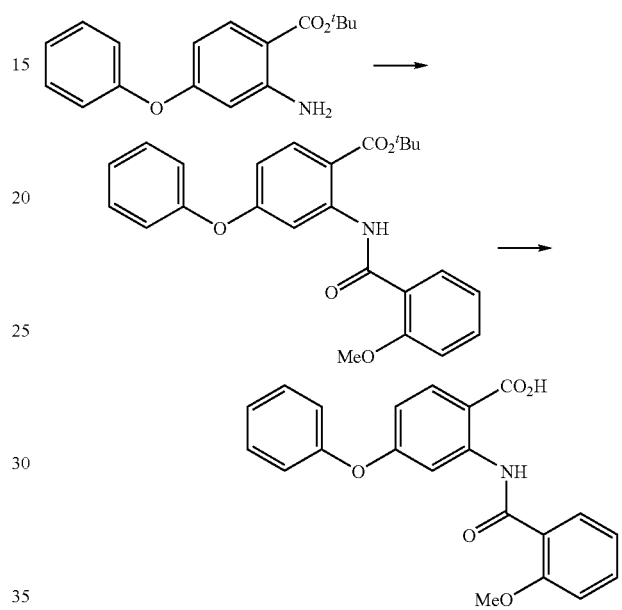

1.0 mL of methylene chloride, 2.7 pit of N,N-dimethylformamide and 0.061 mL of oxalyl chloride were added to 0.11 g of 2-methoxybenzoic acid at room temperature sequentially and stirred at the same temperature for 1 hour. The reaction mixture was added to a mixed solution of 4.0 mL of methylene chloride and 0.45 mL triethylamine containing 57 mg of tert-butyl 2-amino-4-phenoxybenzoate and stirred at room temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4:1] to obtain tert-butyl 2-(2-methoxybenzamido)-4-phenoxybenzoate.

10 mL of trifluoroacetic acid was added to the obtained tert-butyl 2-(2-methoxybenzamido)-4-phenoxybenzoate and stirred at room temperature for 3 minutes. The solvent was evaporated under reduced pressure and diisopropyl ether was added to the obtained residue and a solid substance was separated by filtration to obtain 52 mg of 2-(2-methoxybenzamido)-4-phenoxybenzoic acid as white solid.

$^1$H-NMR (DMSO-$d_6$) δ: 3.99 (3H, s), 6.74 (1H, dd, J=8.9, 2.6 Hz), 7.06-7.12 (1H, m), 7.14-7.20 (2H, m), 7.21-7.29 (2H, m), 7.44-7.52 (2H, m), 7.55-7.60 (1H, m), 7.91 (1H, dd, J=7.8, 1.7 Hz), 8.04 (1H, d, J=8.9 Hz), 8.55 (1H, d, J=2.6 Hz), 12.40 (1H, s), 13.41 (1H, s).

Example 454

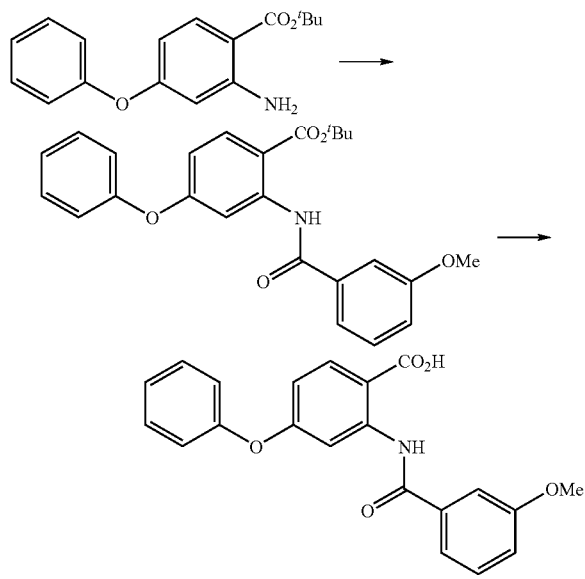

The following compound was obtained in the same manner as in Example 453.

2-(3-Methoxybenzamido)-4-phenoxybenzoic acid $^1$H-NMR (DMSO-d$_6$) δ: 3.84 (3H, s), 6.78 (1H, dd, J=8.8, 2.4 Hz), 7.16-7.24 (3H, m), 7.29 (1H, t, J=7.3 Hz), 7.43-7.55 (5H, m), 8.07 (1H, d, J=8.8 Hz), 8.40 (1H, d, J=2.4 Hz), 12.40 (1H, s), 13.65-13.85 (1H, broad).

Example 455

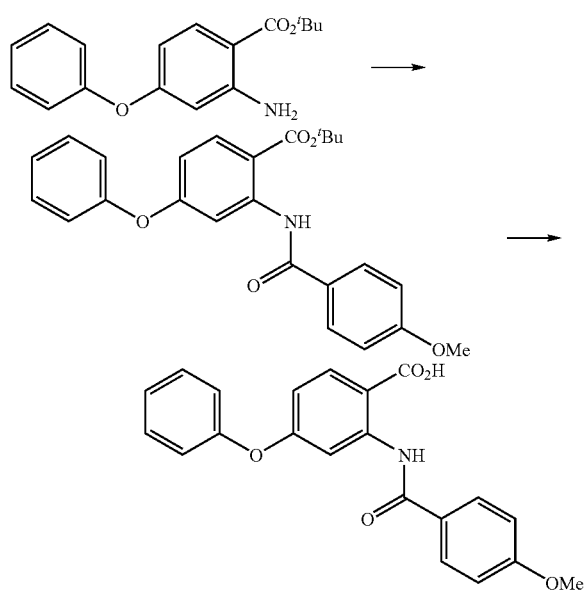

5.0 mL of methylene chloride, 0.056 mL of triethylamine and 51 mg of 4-methoxybenzoyl chloride were added sequentially to 57 mg of tert-butyl 2-amino-4-phenoxybenzoate at room temperature, and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufacture by Trikonex Company, eluent; hexane:ethyl acetate=4:1]to obtain tert-butyl 2-(4-methoxybenzamido)-4-phenoxybenzoate.

10 mL of trifluoroacetic acid was added to tert-butyl 2-(4-methoxybenzamido) 4-phenoxybenzoate and stirred at room temperature for 3 minutes. The solvent was evaporated under reduced pressure and diisopropyl ether was added to the obtained residue and a solid substance was separated by filtration to obtain 55 mg of 2-(4-methoxybenzamido)-4-phenoxybenzoic acid as white solid.

$^1$H-NMR (DMSO-d$_6$) δ: 3.85 (3H, s), 6.75 (1H, dd, J=3.0, 2.5 Hz), 7.09-7.15 (2H, m), 7.15-7.21 (2H, m), 7.28 (1H, t, J=7.4 Hz), 7.46-7.52 (2H, m), 7.86-7.93 (2H, m), 8.06 (1H, d, J=9.0 Hz), 8.41 (1H, d, J=2.5 Hz), 12.33 (1H, s), 13.55-13.75 (1H, broad).

Example 456

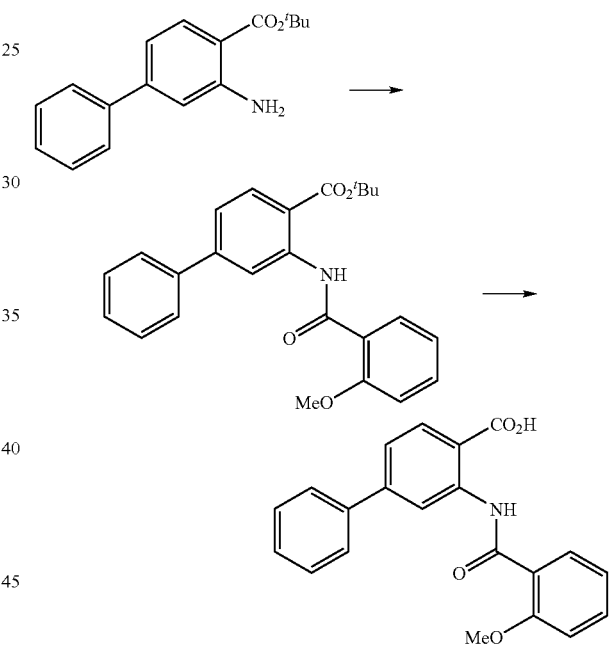

1.0 mL of methylene chloride, 2.7 μL of N,N-dimethylformamide and 0.061 mL of oxalyl chloride were added to 0.11 g of 2-methoxybenzoic acid at room temperature sequentially and stirred at the same temperature for 1 hour. The reaction mixture was added to a mixed solution of 4.0 mL of methylene chloride and 0.45 mL of triethylamine containing 54 mg of tert-butyl 2-amino-1-phenylbenzoate at room temperature and stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane:ethyl acetate=4.1] to obtain tert-butyl 2-(2-methoxybenzamido)-4-phenylbenzoate.

10 mL of trifluoroacetic acid was added to the obtained tert-butyl 2-(2-methoxybenzamido)-4-phenylbenzoate and stirred at room temperature for 3 minutes. The solvent was evaporated under reduced pressure and diisopropyl ether was added to the obtained residue and a solid substance was separated by filtration to obtain 65 mg of 2-(2-methoxybenzamido)-4-phenylbenzoic acid as white solid.

$^1$H-NMR (DMSO-d$_6$) δ: 4.03 (3H, s), 7.10-7.17 (1H, m), 7.26 (1H, d, J=8.3 Hz), 7.43-7.64 (5H, m), 7.70-7.77 (2H, m), 8.02 (1H, dd, 8=7.8, 1.7 Hz), 8.11 (1H, d, J=8.3 Hz), 9.19 (1H, d, J=1.7 Hz), 12.34 (1H, s), 13.59 (1H, s).

Example 457

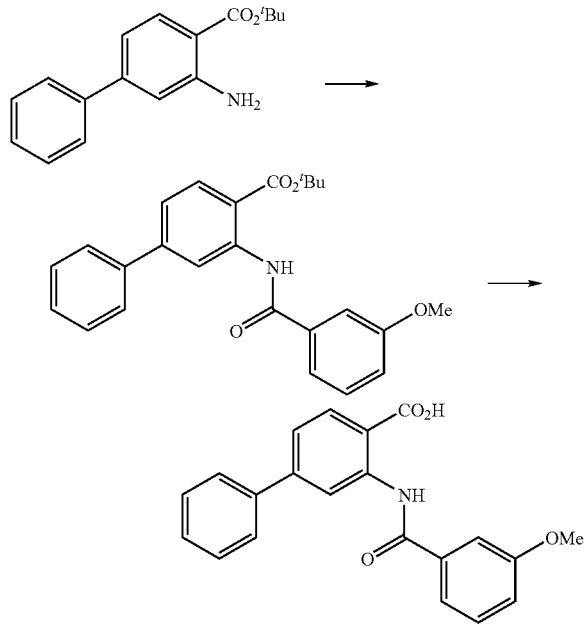

The following compound was obtained in the same manner as in Example 456.

2-(3-Methoxybenzamido)-4-phenylbenzoic acid $^1$H-NMR (DMSO-d$_6$) δ: 3.86 (3H, s), 7.22-7.26 (1H, m), 7.44-7.59 (7H, m), 7.72-7.77 (2H, m), 8.14 (1H, d, J=8.0 Hz), 9.09 (1H, d, J=1.9 Hz), 12.26 (1H, s), 13.80-14.00 (1H, broad).

Examples 458, 459

The compounds shown in Table 45 were obtained in the same manner as in Example 34.

TABLE 45

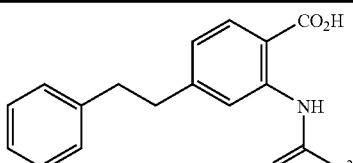

| Example No. | R$^2$ |
|---|---|
| 458 | ![phenethyl] |

TABLE 45-continued

| Example No. | R$^2$ |
|---|---|
| 459 | 3,5-bis(CF$_3$)phenyl |

4-Phenethyl-2-(3-phenylpropanamido)benzoic acid $^1$H-NMR (DMSO-d$_6$) δ: 2.71 (2H, t, J=7.7 Hz), 2.84-2.96 (4H, m), 2.94 (2H, t, J=7.7 Hz), 7.00 (1H, dd, J=) 8.2, 1.6 Hz), 7.15-7.31 (10H, m), 7.87 (1H, d, J=8.2 Hz), 8.43 (1H, d, J=1.6 Hz), 11.15 (1H, s), 13.45 (1H, s).

4-Phenethyl-2-(3,5-bis(trifluoromethyl)benzamido)benzoic acid $^1$H-NMR (DMSO-d$_6$) δ: 2.90-3.04 (4H, m), 7.14 (1H, dd, J=8.1, 1.7 Hz), 7.15-7.21 (1H, m), 7.24-7.32 (4H, m), 7.96 (1H, d, J=8.1 Hz), 8.45 (1H, s), 8.49-8.52 (1H, m), 8.54 (2H, s), 12.32 (1H, s), 13.70-13.90 (1H, broad).

Example 460

The following compound was obtained in the same manner as in Example 282.

4-Phenyl-2-(3,5-bis(trifluoromethyl)benzamido)benzoic acid $^1$H-NMR (DMSO-d$_6$) δ: 7.45-7.51 (1H, m), 7.52-7.61 (3H, m), 7.71-7.77 (2H, m), 8.13 (1H, d, J=8.1 Hz), 8.46 (1H, s), 8.56 (2H, s), 8.91 (1H, d, J=1.7 Hz), 12.38 (1H, s).

Example 461

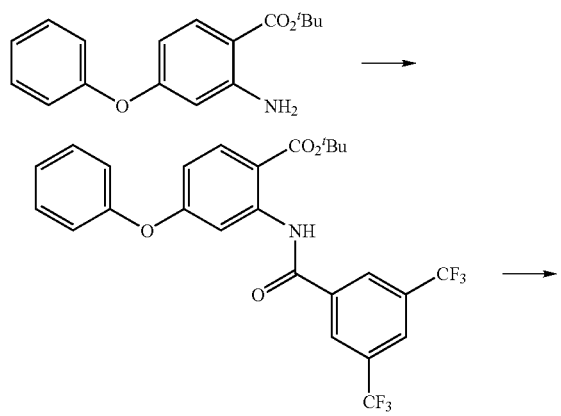

The following compound was obtained in the same manner as in Example 321.

4-Phenoxy-2-(3,5-bis(trifluoromethyl)benzamido)benzoic acid $^1$H-NMR (DMSO-d$_6$) δ: 6.84 (1H, dd, J=8.9, 2.6 Hz), 7.17-7.22 (2H, m), 7.27-7.33 (1H, m), 7.47-7.54 (2H, m), 8.08 (1H, d, J=8.9 Hz), 8.28 (1H, d, J=2.6 Hz), 8.44 (1H, s), 8.50 (2H, s), 12.63 (1H, s).

Example 462

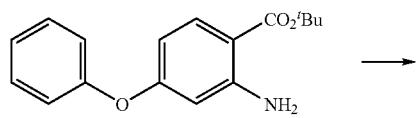

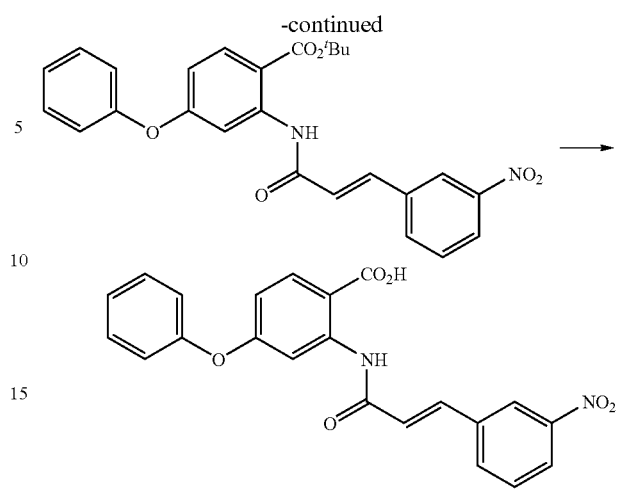

The following compound was obtained in the same manner as in Example 396.

2-((E)-3-(3-Nitrophenyl)acrylamido)-4-phenoxybenzoic acid $^1$H-NMR (DMSO-d$_6$) δ: 6.76 (1H, dd, J=8.9, 2.7 Hz), 7.12-7.22 (3H, m), 7.28 (1H, t, J=7.4 Hz), 7.46-7.51 (2H, m), 7.68-7.78 (2H, m), 8.04 (1H, d, J=8.9 Hz), 8.18-8.29 (2H, m), 8.35 (1H, d, J=2.7 Hz), 8.61 (1H, s), 11.61 (1H, s).

Example 463

5.0 mL of methylene chloride, 0.049 mL of triethylamine and 45 mg of 4-methoxybenzoyl chloride were added sequentially to 40 mg of methyl 2-amino-4-phenylbenzoate at room temperature and stirred at the same temperature for 1 hour. A saturated sodium hydrogen carbonate aqueous solution was added to the reaction mixture, and the organic layer was separated, and the solvent was evaporated under reduced pressure.

The obtained residue was purified with silica gel column chromatography [Flash Tube 2008 manufactured by Trikonex Company, eluent; hexane:ethyl acetate=4:1]to obtain methyl 2-(4-methoxybenzamido)-4-phenylbenzoate.

1.0 mL of 2.0 mol/L aqueous sodium hydroxide and 3.0 mL of ethanol were added to the obtained methyl 2-(4-methoxybenzamido)-4-phenylbenzoate and stirred at 40° C. for 2 hours. After the reaction mixture was cooled to room temperature, 8.0 mL of 0.38 mol/L hydrochloric acid and 10 mL of ethyl acetate were added. The organic layer was separated and dried over anhydrous magnesium sulfate, and the solvent was evaporated under reduced pressure. The obtained residue was purified with reversed-phase silica gel column chromatography [eluent; 55-100% acetonitrile /0.1% trifluoroacetic acid aqueous solution] to obtain 6.1 mg of 2-(4-methoxybenzamido)-4-phenylbenzoic acid as white solid.

$^1$H-NMR (DMSO-$d_6$) δ: 3.86 (3H, s), 7.15 (2H, d, J=8.8 Hz), 7.44-7.57 (4H, m), 7.73 (2H, d, J=7.4 Hz), 7.95 (2H, d, J=8.8 Hz), 8.13 (1H, d, J=8.3 Hz), 9.09 (1H, d, J=1.4 Hz), 12.21 (1H, s), 13.70-13.30 (1H, broad).

Example 464

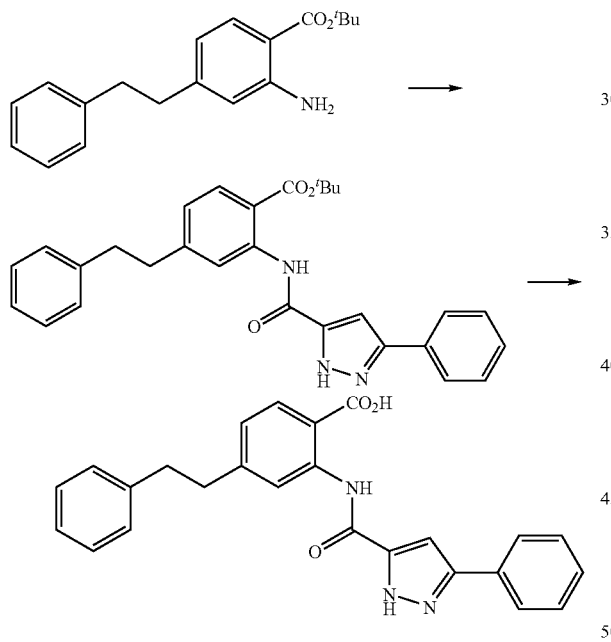

2.0 mL of methylene chloride, 2.7 μL of N,N-dimethylformamide and 0.061 mL of oxalyl chloride were sequentially added to 0.13 g of 3-phenyl-1H-pyrazole-5-carboxylic acid at room temperature and stirred at the same temperature for 1 hour. The reaction mixture was added to a mixed solution of 3.0 mL of methylene chloride and 0.45 mL of triethylamine containing 60 mg of tert-butyl 2-amino-4-phenethylbenzoate at room temperature was stirred at the same temperature for 1 hour. A saturated sodium hydrogen carbonate aqueous solution was added to the reaction mixture, and the organic layer was separated, and the solvent was evaporated under reduced pressure. The obtained residue was purified with silica gel column chromatography [Flash Tube 2008 manufactured by Trikonex Company, eluent; hexane; ethyl acetate=4.1] to obtain tert-butyl 4-phenethyl-2-(3-phenyl-1H-pyrazole-5-carboxamido)benzoate.

10 mL of trifluoroacetic acid was added to the obtained tert-butyl 4-phenethyl-2-(3-phenyl-1H-pyrazole-5-carboxamido)benzoate and stirred at room temperature for 2 hours. The solvent was evaporated under reduced pressure, and the obtained residue was purified with silica gel column chromatography [Flash Tube 2008 manufactured by Trikonex Company, eluent; ethyl acetate] to obtain 2.6 mg of 4-phenethyl-2-(3-phenyl-1H-pyrazole-5-carboxamido)benzoic acid as white solid.

$^1$H-NMR (DMSO-$d_6$) δ: 2.89-3.04 (4H, m), 7.05 (1H, d, J=7.7 Hz), 7.15-7.33 (6H, m), 7.38-7.44 (1H, m), 7.47-7.53 (8H, m), 7.84 (2H, d, J=7.6 Hz), 7.95 (1H, d, J=7.7 Hz), 8.74 (1H, s), 12.39 (1H, s), 13.96 (1H, s).

Example 465

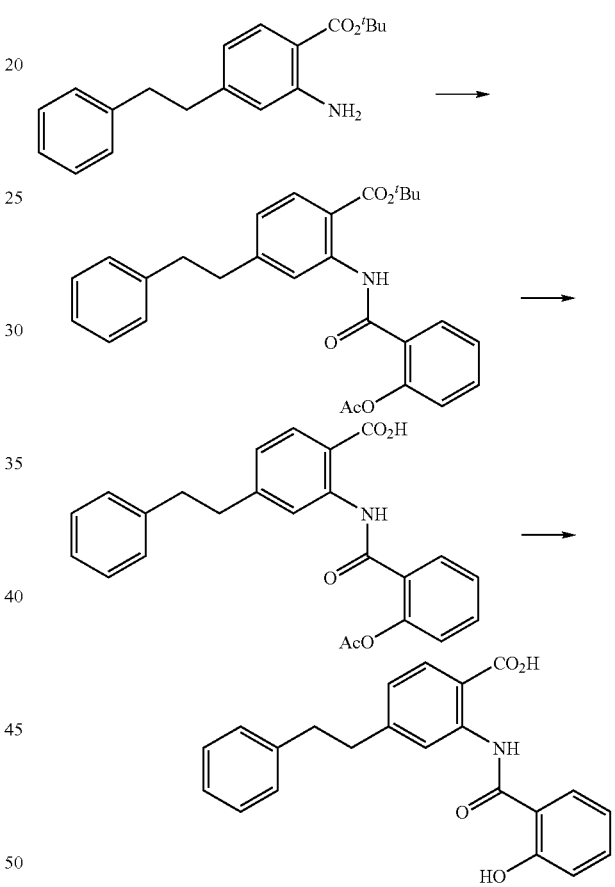

2.0 mL of methylene chloride, 2.7 μL of N,N-dimethylformamide and 0.061 mL of oxalyl chloride were added to 0.13 g of 2-acetoxybenzoic acid at room temperature sequentially and stirred at the same temperature for 1 hour. The reaction mixture was added to a mixed solution of 3.0 mL of methylene chloride and 0.45 mL of triethylamine containing 60 mg of tert-butyl 2-amino-4-phenethylbenzoate at room temperature and stirred at the same temperature for 1 hour. A saturated sodium hydrogen carbonate aqueous solution was added to the reaction mixture, and the organic layer was separated, and the solvent was evaporated under reduced, pressure. The obtained residue was purified with silica gel column chromatography [Flash Tube 2008 manufactured by Trikonex Company, eluent; hexane; ethyl acetate=4:1] to obtain tert-butyl 2-(2-acetoxybenzamido)-4-phenethylbenzoate.

10 mL of trifluoroacetic acid was added to the obtained tert-butyl 2-(2-acetoxybenzamido)-4-phenethylbenzoate and stirred at room temperature for 2 hours. The solvent was evaporated under reduced pressure and 0.50 mL of methanol, 0.50 mL of tetrahydrofuran and 10 mg of potassium carbonate were added to the obtained residue sequentially and stirred at room temperature for 3 hours. After insoluble were removed by filtration, 3.0 mL of 10% citric acid aqueous solution was added and a solid; substance was separated, by filtration to obtain 11 mg of 2-(2-hydroxybenzamido)-4-phenethylbenzoic acid as white solid.

$^1$H-NMR (DMSO-$d_6$) δ: 2.88-3.02 (4H, m), 6.95-7.03 (2H, m), 7.07 (1H, dd, J=8.1, 1.4 Hz), 7.15-7.21 (1H, m), 7.24-7.32 (4H, m), 7.41-7.47 (1H, m), 7.87 (1H, dd, J=7.9, 1.6 Hz), 7.92 (1H, d, J=8.1 Hz), 8.59 (1H, d, J=1.4 Hz), 11.46 (1H, s), 12.22 (1H, s).

Example 466

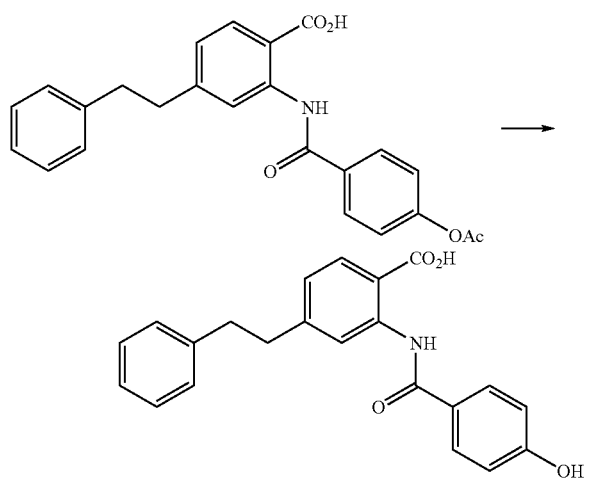

10 mg of potassium carbonate were added to a mixed solution of 1.0 mL of methanol and 1.0 mL of tetrahydrofuran containing 20 mg of 2-(4-acetoxybenzamido)-4-phenethylbenzoic acid and stirred at room temperature for 3 hours. After insoluble were removed by filtration, 3.0 mL of 10% citric acid aqueous solution was added and a solid substance was separated by filtration to obtain 15 mg of 2-(4-hydroxybenzamido)-4-phenethylbenzoic acid as white solid.

$^1$H-NMR (DMSO-$d_6$) δ: 2.88-3.00 (4H, m), 6.93 (2H, d, J=8.8 Hz), 7.04 (1H, dd, J=8.1, 1.6 Hz), 7.15-7.21 (1H, m), 7.24-7.32 (4H, m), 7.82 (2H, d, J=8.8 Hz), 7.94 (1H, d, J=8.1 Hz), 8.68 (1H, d, J=1.6 Hz), 10.26 (1H, s), 12.09 (1H, s), 13.50-13.80 (1H, broad).

Example 467

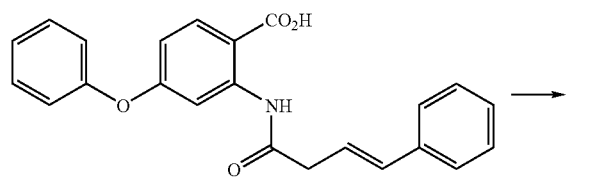

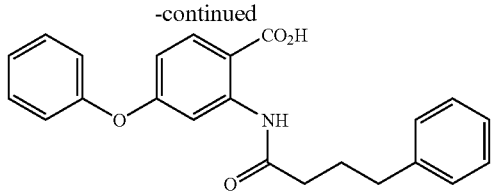

1.3 mg of 10% palladium-carbon was added to a mixed solution of 1.0 mL of methanol and 1.0 mL of ethyl acetate containing 10 mg of 4-phenoxy-2-((E)-4-phenyl-3-butenamido)benzoic acid and stirred under hydrogen atmosphere at room temperature for 6 hours. After insoluble were removed by filtration, the solvent was evaporated under reduced pressure. Hexane and diisopropyl ether were added to the obtained residue and a solid substance was separated by filtration to obtain 4.6 mg of 4-phenoxy-2-(4-phenylbutanamido)benzoic acid as white solid.

$^1$H-NMR (DMSO-$d_6$) δ: 1.83-1.94 (2H, m), 2.28 (2H, t, J=7.6 Hz), 2.60 (2H, t, J=7.7 Hz), 6.49-6.57 (1H, m), 7.02 (2H, d, J=7.8 Hz), 7.11-7.31 (6H, m), 7.35-7.43 (2H, m), 7.95 (1H, d, J=8.6 Hz), 8.17 (1H, d, J=2.4 Hz).

Example 468

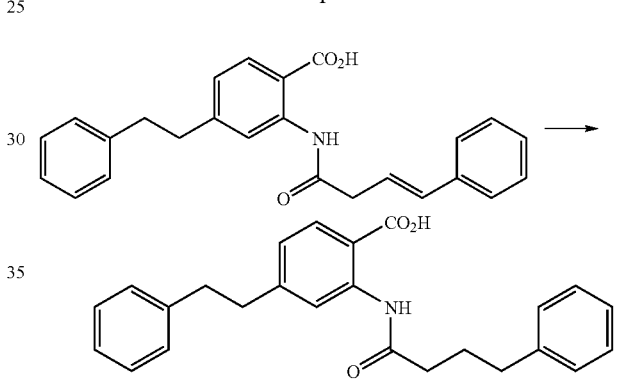

1.0 mg of 10% palladium-carbon was added to a mixed solution of 0.50 mL of methanol and 0.50 mL ethyl acetate containing 8.0 mg of 4-phenethyl-2-((E)-4-phenyl-3-butenamido)benzoic acid and stirred under hydrogen atmosphere at room temperature for 1 hour and 30 minutes. After insoluble were removed by filtration, the solvent was evaporated under reduced pressure and the obtained residue was purified with silica gel column chromatography [Flash Tube 2003 manufactured by Trikonex Company, eluent; ethyl acetate] to obtain 4.6 mg of 4-phenethyl-2-(4-phenylbutanamido)benzoic acid as white solid.

$^1$H-NMR (DMSO-$d_6$) δ ($D_2O$ treatment): 1.86-2.02 (2H, m), 2.39 (2H, t, J=7.3 Hz), 2.64 (2H, t, J=7.6 Hz), 2.85-2.96 (4H, m), 6.56 (1H, s), 7.01 (1H, d, J=8.2 Hz), 7.14-7.34 (9H, m), 7.87 (1H, d, J=8.2 Hz), 8.43 (1H, s).

Example 469

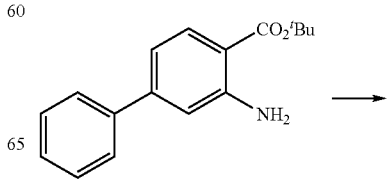

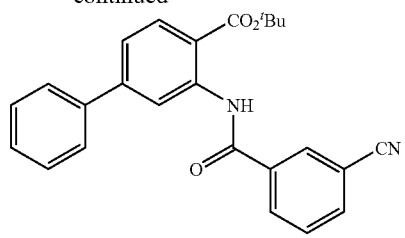

2.5 mL of methylene chloride, 0.015 mL of N,N-dimethylformamide and 0.095 mL of oxalyl chloride were added to 0.17 g of 3-cyanobenzoic acid at room temperature sequentially and stirred at the same temperature for 30 minutes. The reaction mixture was added to a mixed solution of 2.0 mL of methylene chloride and 0.35 mL of triethylamine containing 0.25 g of tert-butyl 2-amino-4-phenylbenzoate at room temperature and stirred at the same temperature for 10 minutes. Ethyl acetate, 1.0 mol/L hydrochloric acid and tetrahydrofuran were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; chloroform] to obtain 0.29 g of tert-butyl 2-(3-cyanobenzamido)-4-phenylbenzoate as white solid.

$^1$H-NMR (CDCl$_3$) δ: 1.66 (9H, s), 7.37-7.44 (2, m), 7.45-7.52 (2H, m), 7.66-7.74 (3H, m), 7.84-7.87 (1H, m), 8.10 (1H, d, J=8.3 Hz), 8.28-8.31 (1H, m), 8.37 (1H, t, J=1.5 Hz), 9.19 (1H, d, J=1.9 Hz), 12.44 (1H, s).

Examples 410 to 476

The compounds shown in Table 46 were obtained in the same manner as in Example 469.

TABLE 46

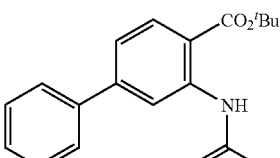

| Example No. | R² |
|---|---|
| 470 | 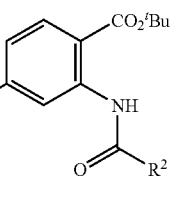 |
| 471 | 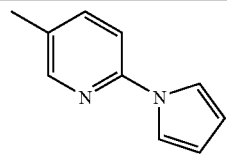 |

TABLE 46-continued

| Example No. | R² |
|---|---|
| 472 | 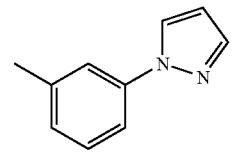 |
| 473 | 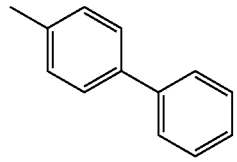 |
| 474 | 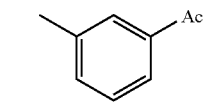 |
| 475 | 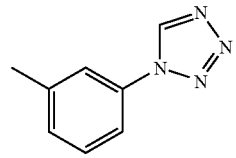 |
| 476 | 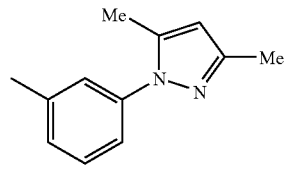 | tert-Butyl 4-phenyl-2-(6-(1H-pyrrol-1-yl)pyridine-3-carboxamido)benzoate $^1$H-NMR (CDCl$_3$) δ: 1.66 (9H, s), 6.41 (2H, t, J=2.3 Hz), 7.37 (1H, dd, J=8.5, 2.0 Hz), 7.38-7.50 (4H, m), 7.61 (2H, t, J=2.3 Hz), 7.70-7.74 (2H, m), 8.10 (1H, d, J=8.5 Hz), 8.43 (1H, dd, J=8.8, 2.4 Hz), 9.15 (1H, d, J=2.4 Hz), 9.23 (1H, d, J=2.0 Hz), 12.44 (1H, s).

tert-Butyl 4-phenyl-2-(2-(1H-pyrrol-1-yl)pyridine-4-carboxamido)benzoate $^1$H-NMR (CDCl$_3$) δ: 1.68 (9H, s), 6.40 (2H, t, J=2.3 Hz), 7.38-7.52 (4H, m), 7.64 (2H, t, J=2.3 Hz), 7.68 (1H, dd, J=5.2, 1.4 Hz), 7.71-7.75 (2H, m), 8.00 (1H, s), 8.12 (1H, d, J=8.3 Hz), 8.64 (1H, d, J=5.2 Hz), 9.22 (1H, d, J=2.0 Hz), 12.59 (1H, s).

tert-Butyl 4-phenyl-2-(3-(1H-pyrazol-1-yl)benzamido)benzoate $^1$H-NMR (CDCl$_3$) δ: 1.67 (9H, s), 6.51-6.53 (1H, m), 7.35-7.44 (2H, m), 7.45-7.51 (2H, m), 7.62-7.68 (1H, m), 7.70-7.78 (3H, m), 7.94-8.00 (1H, m), 8.04-8.12 (3H, m), 8.36-8.38 (1H, m), 9.25 (1H, d, J=1.7 Hz), 12.42 (1H, s).

tert-Butyl 2-(biphenyl-4-carboxamido)-4-phenylbenzoate $^1$H-NMR (CDCl$_3$) δ: 1.67 (9H, s), 7.36 (1H, dd, J=8.4, 1.8 Hz), 7.37-7.44 (2H, m), 7.45-7.53 (4H, m), 7.65-7.70 (2H, m), 7.72-7.80 (4H, m), 8.10 (1H, d, J=8.4 Hz), 8.14-8.18 (2H, m), 9.28 (m, d, J=1.8 Hz), 12.33 (1H, s).

tert-Butyl 2-(3-acetylbenzamido)-4-phenylbenzoate $^1$H-NMR (CDCl$_3$) δ: 1.66 (9H, s), 2.72 (3H, s), 7.36-7.44 (2H, m), 7.45-7.51 (2H, m), 7.67 (1H, t, J=7.8 Hz), 7.70-7.76 (2H, m), 8.11 (1H, d, J=8.3 Hz), 8.16-8.22 (1H, m), 8.25-8.30 (1H, m), 8.68-8.72 (1H, m), 9.25 (1H, d, J=1.9 Hz), 12.49 (1H, s).

tert-Butyl 4-phenyl-2-(3-(1H-tetrazol-1-yl)benzamido)benzoate $^1$H-NMR (CDCl$_3$) δ: 1.67 (9H, s), 7.38-7.45 (2H, m), 7.46-7.53 (2H, m), 7.70-7.75 (2H, m), 7.81 (1H, t, J=7.9 Hz), 8.03-8.07 (1H, m), 8.12 (1H, d, J=8.3 Hz), 8.21-8.24 (1H, m), 8.42 (1H, t, J=1.8 Hz), 9.13 (1H, s), 9.22 (1H, d, J=1.7 Hz), 12.57 (1H, s).

tert-Butyl 2-(3-(3,5-dimethyl-1H-pyrazol-1-yl)benzamido)-4-phenylbenzoate $^1$H-NMR (CDCl$_3$) δ: 1.65 (9H, s), 2.32 (3H, s), 2.46 (3H, s), 6.05 (1H, s), 7.36 (1H, dd, J=8.3, 1.9 Hz), 7.36-7.43 (1H, m), 7.44-7.50 (2H, m), 7.64 (1H, t, J=7.9 Hz), 7.70-7.74 (2H, m), 7.74-7.79 (1H, m), 8.02-8.07 (1H, m), 8.09 (1H, d, J=8.3 Hz), 8.12 (1H, t, J=1.7 Hz), 9.25 (1H, d, J=1.7 Hz), 12.40 (1H, s).

Example 477

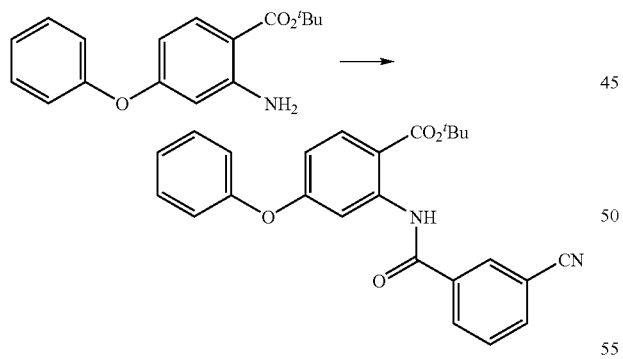

To 0.17 g of 3-cyanobenzoic acid were added 2.5 mL of methylene chloride, 0.015 mL of N,N-dimethylformamide and 0.095 mL of oxalyl chloride at room temperature sequentially and stirred at the same temperature for 30 minutes. The reaction mixture was added to a mixed solution of 3.0 mL of methylene chloride and 0.35 mL of triethylamine containing 0.26 g of tert-butyl 2-amino-4-phenoxybenzoate at room temperature and stirred at the same temperature for 10 minutes. Ethyl acetate, 1.0 mol/L hydrochloric acid and tetrahydrofuran were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; chloroform] to obtain 0.20 g of tert-butyl 2-(3-cyanobenzamido)-4-phenoxybenzoate as white solid.

$^1$H-NMR (CDCl$_3$) δ: 1.63 (9H, s), 6.70 (1H, dd, J=8.9, 2.9 Hz), 7.08-7.13 (2H, m), 7.18-7.24 (1H, m), 7.38-7.45 (2H, m), 7.62-7.68 (1H, m), 7.83 (1H, dt, J=7.6, 1.5 Hz), 8.00 (1H, d, J=8.9 Hz), 8.21-8.26 (1H, m), 8.31 (1H, t, J=1.5 Hz), 8.53 (1H, d, J=2.7 Hz), 12.48 (1H, s).

Examples 478 to 484

The compounds shown in Table 47 were obtained in the same manner as in Example 477.

TABLE 47

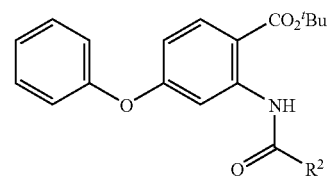

| Example No. | R$^2$ |
|---|---|
| 478 | (5-methyl-2-(1H-pyrrol-1-yl)pyridine) |
| 479 | (4-methyl-2-(1H-pyrrol-1-yl)pyridine) |
| 480 | (3-methyl-2-(1H-pyrrol-1-yl)pyridine) |
| 481 | (3-methyl-1-(1H-pyrazol-1-yl)phenyl) |
| 482 | (4-methylbiphenyl) |
| 483 | (3-methyl-Ac-phenyl) |

TABLE 47-continued

[Structure: phenoxy-benzoate with CO₂ᵗBu and NH-C(=O)-R²]

| Example No. | R² |
|---|---|
| 484 | [3,5-dimethyl-1-(m-tolyl)-1H-pyrazol-4-yl structure with two Me groups] | tert-Butyl 4-phenoxy-2-(6-(1H-pyrrol-1-yl)pyridine-3-carboxamido)benzoate

¹H-NMR (CDCl₃) δ: 1.63 (9H, s), 6.40 (2H, t, J=2.3 Hz), 6.69 (1H, dd, J=8.9, 2.5 Hz), 7.08-7.14 (2H, m), 7.18-7.24 (1H, m), 7.38-7.45 (3H, m), 7.59 (2H, t, J=2.3 Hz), 8.00 (1H, d, J=8.9 Hz), 8.37 (1H, dd, J=8.8, 2.4 Hz), 8.56 (1H, d, J=2.5 Hz), 9.09 (1H, d, J=2.4 Hz), 12.48 (1H, s).

tert-Butyl 4-phenoxy-2-(2-(1H-pyrrol-1-yl)pyridine-4-carboxamido)benzoate

¹H-NMR (CDCl₃) δ: 1.64 (9H, s), 6.39 (2H, t, J=2.2 Hz), 6.72 (1H, dd, J=8.9, 2.5 Hz), 7.08-7.14 (2H, m), 7.18-7.25 (1H, m), 7.38-7.46 (2H, m), 7.60-7.64 (3H, m), 7.93 (1H, s), 8.01 (1H, d, J=8.8 Hz), 8.54 (1H, d, J=2.5 Hz), 8.60 (1H, d, J=5.1 Hz), 12.62 (1H, s).

tert-Butyl 4-phenoxy-2-(2-(1H-pyrrol-1-yl)pyridine-3-carboxamido) benzoate

¹H-NMR (CDCl₃) δ: 1.49 (9H, s), 6.22 (2H, t, J=2.3 Hz), 6.63 (1H, dd, J=8.9, 2.5 Hz), 7.06-7.14 (2H, m), 7.16-7.24 (3H, m), 7.30 (1H, dd, J=7.7, 4.9 Hz), 7.37-7.44 (2H, m), 7.88 (1H, d, J=8.9 Hz), 8.05 (1H, dd, J=7.7, 1.8 Hz), 8.51 (1H, d, J=2.5 Hz), 8.59 (1H, dd, J=4.9, 1.8 Hz), 11.62 (1H, s).

tert-Butyl 4-phenoxy-2-(3-(1H-pyrazol-1-yl)benzamido)benzoate

¹H-NMR (CDCl₃) δ: 1.63 (9H, s), 6.51 (1H, t, J=2.1 Hz), 6.69 (1H, dd, J=8.9, 2.4 Hz), 7.09-7.14 (2H, m), 7.21 (1H, t, J=7.3 Hz), 7.38-7.44 (2H, m), 7.61 (1H, t, J=7.9 Hz), 7.75 (1H, d, J=1.5 Hz), 7.88-7.92 (1H, m), 8.00 (1H, d, J=8.9 Hz), 8.02-8.07 (2H, m), 8.28-8.31 (1H, m), 8.58 (1H, d, J=2.4 Hz), 12.45 (1H, s).

tert-Butyl 2-(biphenyl-4-carboxamido)-4-phenoxybenzoate

¹H-NMR (CDCl₃) δ: 1.63 (9H, s), 6.67 (1H, dd, J=8.9, 2.5 Hz), 7.08-7.14 (2H, m), 7.16-7.23 (1H, m), 7.36-7.52 (5H, m), 7.63-7.68 (2H, m), 7.72-7.78 (2H, m), 7.99 (1H, d, J=8.9 Hz), 8.07-8.13 (2H, m), 8.62 (1H, d, J=2.5 Hz), 12.37 (1H, s).

tert-Butyl 2-(3-acetylbenzamido)-4-phenoxybenzoate

¹H-NMR (CDCl₃) δ: 1.63 (9H, s), 2.70 (3H, s), 6.69 (1H, dd, J=9.0, 2.7 Hz), 7.10-7.15 (2H, m), 7.18-7.23 (1H, m), 7.38-7.45 (2H, m), 7.63 (1H, t, J=7.8 Hz), 8.00 (1H, d, J=9.0 Hz), 8.14-8.19 (1H, m), 8.20-8.24 (1H, m), 8.57 (1H, d, J=2.7 Hz), 8.62-8.64 (1H, m), 12.52 (1H, s).

tert-Butyl 2-(3-(3,5-dimethyl-1H-pyrazol-1-yl)benzamido)-4-phenoxybenzoate

¹H-NMR (CDCl₃) δ: 1.61 (9H, s), 2.31 (3H, s), 2.44 (3H, s), 6.03 (1H, s), 6.67 (1H, dd, J=8.9, 2.5 Hz), 7.08-7.13 (2H, m), 7.16-7.22 (1H, m), 7.37-7.43 (2H, m), 7.60 (1H, t, J=7.9 Hz), 7.72-7.76 (1H, m), 7.96-8.01 (2H, m), 8.06 (1H, t, J=1.8 Hz), 8.59 (1H, d, J=2.5 Hz), 12.43 (1H, s).

Example 485

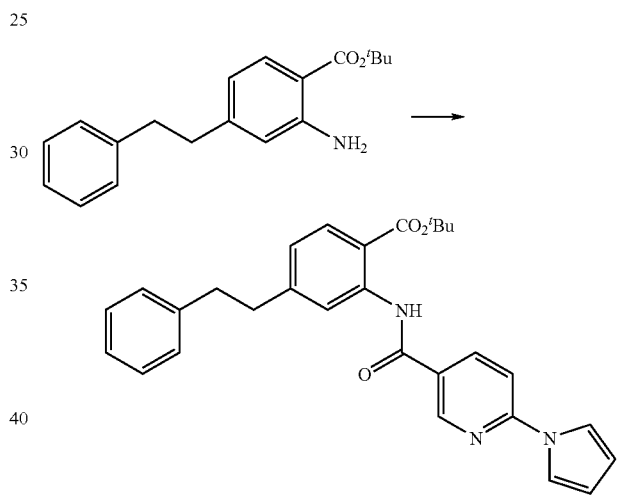

0.015 mL of N,N-dimethylformamide was added to a mixed solution of 2.0 mL of methylene chloride and 0.024 mL of oxalyl chloride containing 47 mg of 6-(1H-pyrrol-1-yl)pyridine-3-carboxylic acid and stirred at room temperature for 30 minutes. 74 mg of tert-butyl 2-amino-4-phenethylbenzoate and 0.090 mL of triethylamine were added to the reaction mixture at room temperature sequentially and stirred at the same temperature for 1 hour and 40 minutes. 1.0 mol/L hydrochloric acid and ethyl acetate were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; chloroform] to obtain 62 mg of tert-butyl 4-phenethyl-2-(6-(1H-pyrrol-1-yl)pyridine-3-carboxamido)benzoate as white solid.

¹H-NMR (CDCl₃) δ: 1.63 (9H, s), 2.90-3.08 (4H, m), 6.41 (2H, t, J=2.3 Hz), 6.90 (1H, dd, J=8.1, 1.7 Hz), 7.17-7.32 (5H, m), 7.46 (1H, d, J=8.9 Hz), 7.60 (2H, d, J=2.3 Hz), 7.93 (1H, d, J=8.1 Hz), 8.41 (1H, dd, J=8.7, 2.3 Hz), 8.83 (1H, d, J=1.7 Hz), 9.13 (1H, d, J=2.3 Hz), 12.40 (1H, s).

Examples 486 to 488

The compounds shown in Table 48 were obtained in the same manner as in Example 485.

TABLE 48

| Example No. | R² |
|---|---|
| 486 | 4-methyl-2-(1H-pyrrol-1-yl)pyridin-? |
| 487 | 3-methylbiphenyl |
| 488 | 4-methylbiphenyl | tert-Butyl 4-phenethyl-2-(2-(1H-pyrrol-1-yl)pyridine-4-carboxamido) benzoate

¹H-NMR (CDCl₃) δ: 1.64 (9H, s), 2.94-3.05 (4H, m), 6.40 (2H, t, J=2.3 Hz), 6.94 (1H, dd, J=8.2, 1.7 Hz), 7.18-7.33 (5H, m), 7.63 (2H, t, J=2.3 Hz), 7.66 (1H, dd, J=5.1, 1.5 Hz), 7.94 (1H, d, J=8.2 Hz), 7.97-7.99 (1H, m), 8.63 (1H, d, J=5.1 Hz), 8.81 (1H, d, J=1.7 Hz), 12.55 (1H, s).

tert-Butyl 2-(biphenyl-3-carboxamido)-4-phenethylbenzoate

¹H-NMR (CDCl₃) δ: 1.64 (9H, s), 2.94-3.06 (4H, m), 6.89 (1H, dd, J=8.2, 1.6 Hz), 7.16-7.34 (5H, m), 7.35-7.43 (1H, m), 7.45-7.52 (2H, m), 7.61 (1H, t, J=7.7 Hz), 7.70-7.75 (2H, m), 7.78-7.84 (1H, m), 7.93 (1H, d, J=8.2 Hz), 8.80-8.05 (1H, m), 8.36 (1H, t, J=1.7 Hz), 8.88 (1H, d, J=1.6 Hz), 12.38 (1H, s).

tert-Butyl 2-(biphenyl-4-carboxamido)-4-phenethylbenzoate

¹H-NMR (CDCl₃) δ: 1.64 (9H, s), 2.92-3.06 (4H, m), 6.89 (1H, dd, J=8.1, 1.6 Hz), 7.16-7.34 (5H, m), 7.37-7.44 (1H, m), 7.45-7.53 (2H, m), 7.64-7.70 (2H, m), 7.74-7.80 (2H, m), 7.93 (1H, d, J=8.1 Hz), 8.12-8.17 (2H, m), 8.89 (1H, d, J=1.6 Hz), 12.30 (1H, s).

Example 489

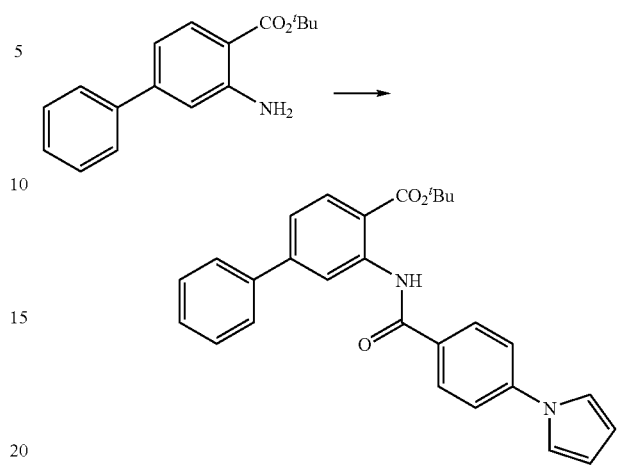

0.015 mL of N,N-dimethylformamide was added to a mixed solution of 2.0 mL of methylene chloride and 0.024 mL of oxalyl chloride containing 47 mg of 4-(1H-pyrrol-1-yl)benzoic acid and stirred at room temperature for 30 minutes. 67 mg of tert-butyl 2-amino-4-phenylbenzoate and 0.090 mL of triethylamine were added to the reaction mixture at room temperature sequentially and stirred at the same temperature for 30 minutes. Ethyl acetate and 1.0 mol/L hydrochloric acid were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; chloroform] to obtain 64 mg of tert-butyl 4-phenyl-2-(4-(1H-pyrrol-1-yl)benzamido)benzoate as white solid.

¹H-NMR (CDCl₃) δ: 1.66 (9H, s), 6.40 (2H t, J=2.2 Hz), 7.20 (2H, t, J=2.2 Hz), 7.35 (1H, dd, J=8.3, 1.8 Hz), 7.37-7.43 (1H, m), 7.44-7.50 (2H, m), 7.54-7.59 (2H, m), 7.71-7.76 (2H, m), 8.10 (1H, d, J=8.3 Hz), 8.14-8.18 (2H, m), 9.26 (1H, d, J=1.8 Hz), 12.33 (1H, s).

Example 490

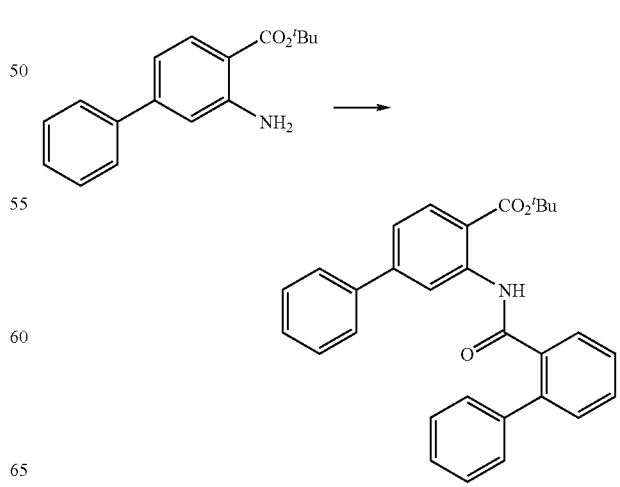

The following compound was obtained in the same manner as in Example 489.

tert-Butyl 2-(biphenyl-2-carboxamido)-4-phenylbenzoate $^1$H-NMR (CDCl$_3$) δ: 1.52 (9H, s), 7.20-7.40 (5H, m), 7.40-7.58 (7H, m), 7.64-7.70 (2H, m), 7.74-7.78 (1H, m), 7.93 (1H, d, J=8.3 Hz), 9.10 (1H, s), 11.26 (1H, s).

Example 491

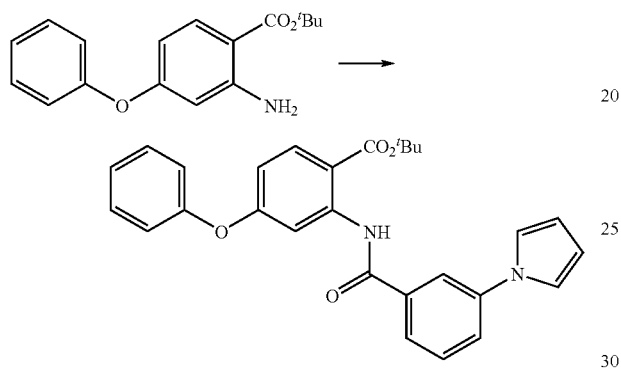

0.015 mL of N,N-dimethylformamide was added to a mixed solution of 2.0 mL of methylene chloride and 0.024 mL of oxalyl chloride containing 47 mg of 3-(1H-pyrrol-1-yl)benzoic acid and stirred at room temperature for 30 minutes, 71 mg of tert-butyl 2-amino-4-phenoxybenzoate and 0.090 mL of triethylamine were added to the reaction mixture at room temperature sequentially and stirred at the same temperature for 30 minutes. Ethyl acetate and 1.0 mol/L hydrochloric acid were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane: ethyl acetate=40:1] to obtain 31 mg of tert-butyl 4-phenoxy-2-(3-(1H-pyrrol-1-yl)benzamido)benzoate as white solid.

$^1$H-NMR (CDCl$_3$) δ: 1.63 (9H, s), 6.38 (2H, t, J=2.2 Hz), 6.68 (1H, dd, J=8.9, 2.5 Hz), 7.09-7.14 (2H, m), 7.17-7.24 (3H, m), 7.37-7.44 (2H, m), 7.55-7.60 (2H, m), 7.84-7.88 (1H, m), 8.00 (1H, d, J=8.9 Hz), 8.09-8.11 (1H, m), 8.58 (1H, d, J=2.5 Hz), 12.46 (1H, s).

Example 492

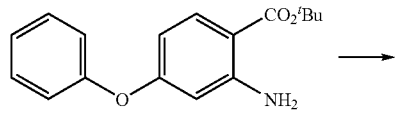

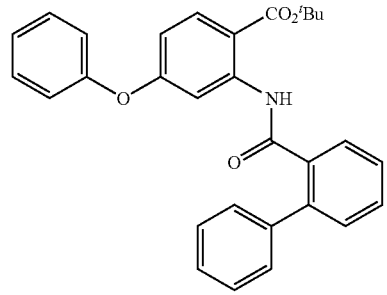

The following compound was obtained in the same manner as in Example 491.

tert-Butyl 2-(biphenyl-2-carboxamido)-4-phenoxybenzoate $^1$H-NMR (CDCl$_3$) δ: 1.48 (9H, s), 6.54 (1H, dd, J=9.0, 2.6 Hz), 7.02-7.08 (2H, m), 7.16 (1H, t, J=7.4 Hz), 7.21-7.40 (5H, m), 7.41-7.56 (5H, m), 7.69-7.73 (1H, m), 7.81 (1H, d, J=9.0 Hz), 8.47-8.52 (1H, broad), 11.23-11.27 (1H, broad).

Example 493

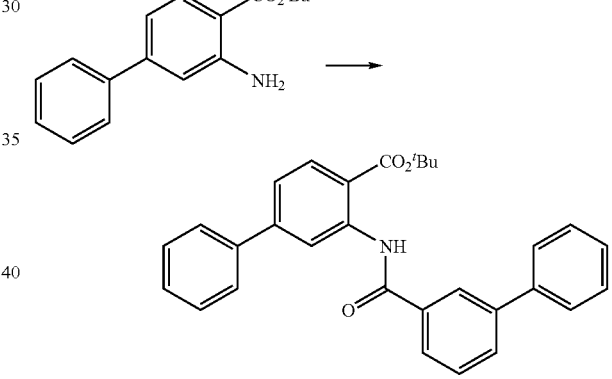

4.0 mL of methylene chloride, 0.015 mL of N,N-dimethylformamide and 0.050 mL of oxalyl chloride were added to 99 mg of 3-biphenylcarboxylic acid at room temperature sequentially and stirred at the same temperature for 20 minutes. 0.16 mL of triethylamine and 0.12 g of tert-butyl 2-amino-1-phenylbenzoate were added to the reaction mixture at room temperature sequentially and stirred at the same temperature for 10 minutes. Ethyl acetate and 1.0 mol/L hydrochloric acid were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; chloroform] to obtain 0.14 g of tert-butyl 2-(biphenyl-3-carboxamido)-4-phenylbenzoate as white solid.

$^1$H-NMR (CDCl$_3$) δ: 1.67 (9H, s), 7.34-7.43 (3H, m), 7.45-7.51 (4H, m), 7.62 (1H, t, J=7.7 Hz), 7.70-7.76 (4H, m), 7.82 (1H, ddd, J=7.7, 1.8, 1.0 Hz), 8.04 (1H, ddd, J=7.8, 1.8, 1.0 Hz), 8.10 (1H, d, J=8.3 Hz), 8.37-8.40 (1H, m), 9.28 (1H, d, J=1.7 Hz), 12.42 (1H, s).

Example 494

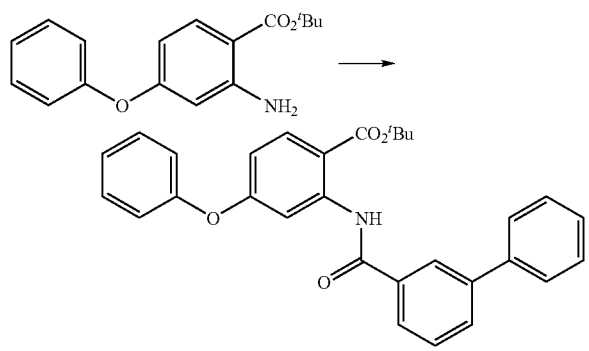

4.0 mL of methylene chloride, 0.015 mL of N-dimethylformamide and 0.050 mL of oxalyl chloride were added to 99 mg of 3-biphenylcarboxylic acid at room temperature sequentially and stirred at the same temperature for 20 minutes. 0.16 mL of triethylamine and 0.13 g of tert-butyl 2-amino-4-phenoxybenzoate were added to the reaction mixture at room temperature sequentially and stirred at the same temperature for 10 minutes. Ethyl acetate and 1.0 mol/L hydrochloric acid were added to the reaction mixture. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; chloroform] to obtain 14 mg of tert-butyl 2-(biphenyl-3-carboxamido)-4-phenoxybenzoate as white solid.

$^1$H-NMR (CDCl$_3$) δ: 1.63 (9H, s), 6.68 (1H, dd, J=8.9, 2.5 Hz), 7.08-7.15 (2H, m), 7.16-7.22 (1H, m), 7.35-7.52 (5H, m), 7.58 (1H, t, J=7.7 Hz), 7.68-7.14 (2H, m), 7.77-7.82 (1H, m), 7.95-8.04 (2H, m), 8.30-8.32 (1H, m), 8.61 (1H, d, J=2.5 Hz), 12.46 (1H, s).

Example 495

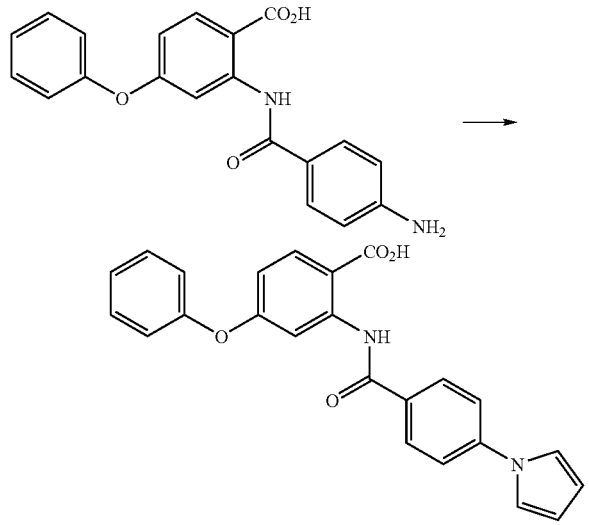

0.25 mL of acetic acid and 4.1 μL of 2,5-dimethoxytetrahydrofuran were added sequentially to 10 mg of 2-(4-aminobenzamido)-4-phenoxybenzoic acid at room temperature and stirred at 90° C. for 5 minutes. After the reaction mixture was cooled so room temperature, ethyl acetate and a saturated sodium hydrogen carbonate aqueous solution were added. The organic layer was separated and dried over anhydrous magnesium sulfate after washed with a saturated sodium chloride aqueous solution, and the solvent was evaporated under reduced pressure. The obtained residue was purified wish silica gel column chromatography [PSQ100B (spherical) manufactured by Fuji Silysia Chemical Ltd., eluent; ethyl acetate] to obtain 3.8 mg of 4-phenoxy-2-(4-(1H-pyrrol-1-yl)benzamido)benzoic acid a brown solid.

$^1$H-NMR (DMSO-d$_6$) δ: 6.33 (2H, t, J=2.2 Hz), 6.78 (1H, dd, J=8.8, 2.6 Hz), 7.16-7.21 (2H, m), 7.28 (1H, t, J=7.4 Hz), 7.46-7.53 (2H, m), 7.53 (2H, t, J=2.2 Hz), 7.80-7.85 (2H, m), 7.96-8.01 (2H, m), 8.08 (1H, d, J=8.8 Hz), 8.41 (1H, d, J=2.6 Hz), 12.49 (1H, s).

Example 496

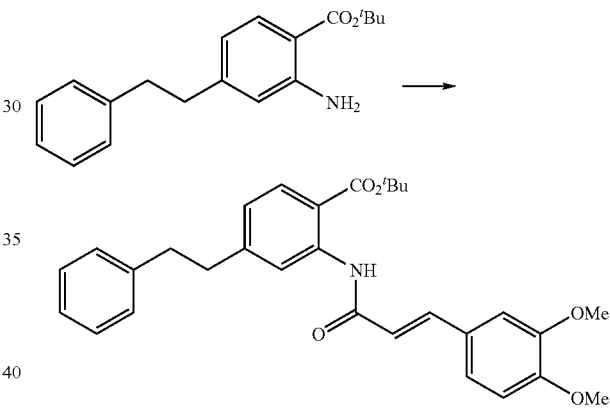

1.0 mL of Methylene chloride, 0.010 mL of N,N-dimethylformamide and 0.064 mL of oxalyl chloride were added to 0.13 g of 3,4-dimethoxycinnamic acid at room temperature sequentially and stirred at the same temperature for 1 hour. The reaction mixture was added to a mixed solution of 1.5 mL of methylene chloride and 0.14 mL of triethylamine containing 0.15 g or tert-butyl 2-amino-4-phenethylbenzoate while ice-cooled and stirred at room temperature overnight. The solvent was evaporated under reduced pressure and ethyl acetate and 10% critic acid aqueous solution were added. The organic layer was separated and dried over anhydrous magnesium sulfate after washed, with 10% citric acid aqueous solution, a saturated sodium hydrogen carbonate aqueous solution and a saturated sodium chloride aqueous solution sequentially, and the solvent was evaporated under reduced pressure. The obtained residue was purified with silica gel column chromatography [PSQ100B (spherical) manufactured by Fuji Silysia chemical Ltd., eluent; hexane:ethyl acetate=4:1] to obtain 0.12 g of tert-butyl 2-((E)-3-(3,4-dimethoxyphenyl)acrylamido)-4-phenethylbenzoate as white solid.

$^1$H-NMR (CDCl$_3$) δ: 1.63 (9H, s), 2.94-3.01 (4H, m), 3.93 (3H, s), 3.97 (3H, s), 6.51 (1H, d, J=15.5 Hz), 6.86 (1H, dd, J=8.3, 1.3 Hz), 6.89 (1H, d, J=8.3 Hz), 7.13 (1H, d, J=1.7 Hz), 7.16-7.32 (6H, m), 7.71 (1H, d, J=15.5 Hz), 7.89 (1H, d, J=8.3 Hz), 8.82 (1H, d, J=1.3 Hz), 11.45 (1H, s).

Example 497

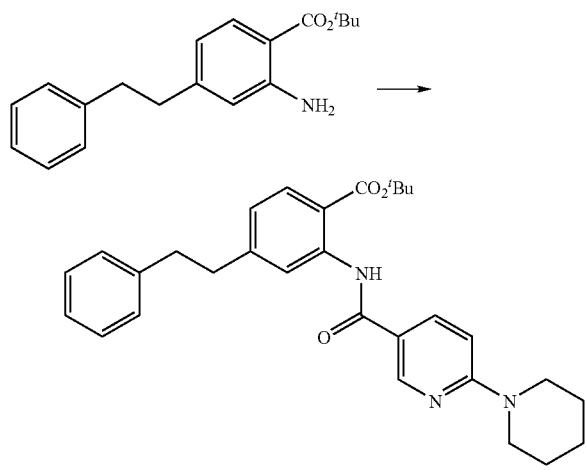

1.5 mL of methylene chloride, 0.010 mL of N,N-dimethylformamide and 0.062 mL of oxalyl chloride were added sequentially to 0.13 g of 6-(piperidin-1-yl)pyridine-3-carboxylic acid at room temperature and stirred at the same temperature for 1 hour and 30 minutes. The solvent was evaporated under reduced pressure, 1.5 mL of methylene chloride was added and, while ice-cooled, the mixture was added to a mixed solution of 1.5 mL of methylene chloride and 0.14 mL of triethylamine containing 0.15 g of tert-butyl 2-amino-4-phenethylbenzoate and stirred at room temperature overnight. The solvent was evaporated under reduced pressure and ethyl acetate and 10% citric acid aqueous solution v/ere added. The organic layer was separated and dried over anhydrous magnesium sulfate after washed with a saturated sodium hydrogen carbonate aqueous solution and a saturated sodium chloride aqueous solution sequentially, and the solvent was evaporated under reduced pressure. Hexane and diisopropyl ether were added to the obtained residue and a solid substance was separated by filtration to obtain 0.17 g of tert-butyl 4-phenethyl-2-(6-(piperidin-1-yl)pyridine-3-carboxamido)benzoate as whine solid.

$^1$H-NMR (CDCl$_3$) δ: 1.52-1.77 (6H, m), 1.61 (9H, s), 2.97 (4H, s), 3.66-3.73 (4H, m), 6.70 (1H, d, J=9.2 Hz), 6.84 (1H, dd, J=8.2, 1.7 Hz), 7.17-7.31 (5H, m), 7.90 (1H, d, J=8.2 Hz), 8.10 (1H, dd, J=9.2, 2.7 Hz), 8.86 (1H, d, J=1.7 Hz), 8.89 (1H, d, J=2.7 Hz), 12.11 (1H, s).

Example 498

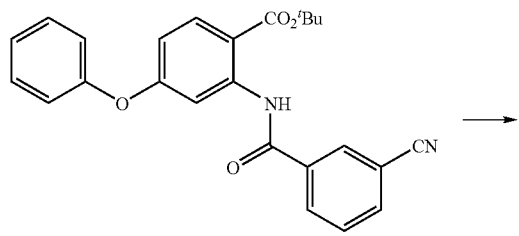

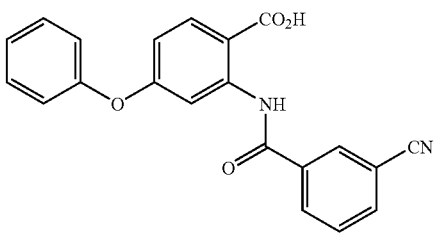

0.5 mL of trifluoroacetic acid was added to 0.5 mL of methylene chloride solution containing 10 mg of tert-butyl 2-(3-cyanobenzamido)-4-phenoxybenzoate and stirred at room temperature for 2 hours. The solvent was evaporated under reduced pressure and diisopropyl ether was added to the obtained residue and a solid substance was separated by filtration to obtain 5.0 mg of 2-(3-cyanobenzamido)-4-phenoxybenzoic acid as white solid.

$^1$H-NMR (DMSO-d$_6$) δ: 6.81 (1H, dd, J=8.9, 2.6 Hz), 7.16-7.20 (2H, m), 7.29 (1H, t, J=7.2 Hz), 7.47-7.52 (2H, m), 7.81 (1H, t, J=7.8 Hz), 8.08 (1H, d, J=8.9 Hz), 8.12 (1H, d, J=7.8 Hz), 8.20 (1H, d, J=8.0 Hz), 8.29 (1H, s), 8.31 (1H, d, J=2.6 Hz), 12.48 (1H, s).

Examples 499 to 507

The compounds shown in Table 49 were obtained in the same manner as in Example 498.

TABLE 49

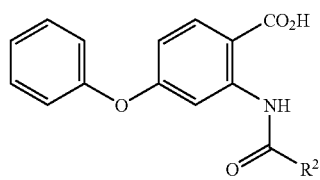

| Example No. | R$^2$ |
|---|---|
| 499 | 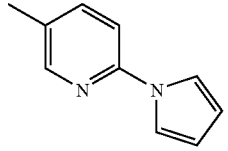 |
| 500 | 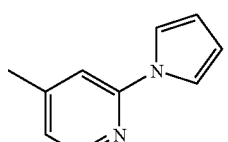 |
| 501 | 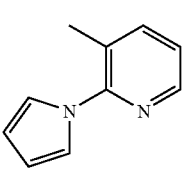 |

TABLE 49-continued

[Structure: phenoxy-substituted benzoic acid with NHC(O)R² group]

| Example No. | R² |
|---|---|
| 502 | 3-(1H-pyrazol-1-yl)phenyl |
| 503 | 3-biphenyl |
| 504 | 4-biphenyl |
| 505 | 3-acetylphenyl |
| 506 | 3-(3,5-dimethyl-1H-pyrazol-1-yl)phenyl |
| 507 | 2-biphenyl |

4-Phenoxy-2-(6-(1H-pyrrol-1-yl)pyridine-3-carboxamido)benzoic acid

¹H-NMR (DMSO-d₆) δ: 6.37 (2H, t, J=2.3 Hz), 6.81 (1H, dd, J=8.9, 2.6 Hz), 7.16-7.22 (2H, m), 7.26-7.32 (1H, m), 7.46-7.54 (2H, m), 7.78 (2H, t, J=2.3 Hz), 7.92 (1H, d, J=8.8 Hz), 8.09 (1H, d, J=9.0 Hz), 8.30-8.36 (2H, m), 8.92 (1H, d, J=2.4 Hz), 12.40 (1H, s).

4-Phenoxy-2-(2-(1H-pyrrol-1-yl)pyridine-4-carboxamido)benzoic acid

¹H-NMR (DMSO-d₆) δ: 6.35 (2K, b, J=2.3 Hz), 6.85 (1H, dd, J=8.9, 2.7 Hz), 7.16-7.24 (2H, m), 7.26-7.34 (1H, m), 7.46-7.54 (2H, m), 7.61 (1H, dd, J=5.1, 1.2 Hz), 7.74 (2H, t, J=2.3 Hz), 8.05 (1H, s), 8.10 (1H, d, J=8.9 Hz), 8.32 (1H, d, J=2.7 Hz), 8.66 (1H, d, J=5.1 Hz), 12.50 (1H, s).

4-Phenoxy-2-(2-(1H-pyrrol-1-yl)pyridine-3-carboxamido)benzoic acid

¹H-NMR (DMSO-d₆) δ: 6.21 (2H, t, J=2.2 Hz), 6.75 (1H, dd, J=8.9, 2.7 Hz), 7.16-7.22 (4H, m), 7.25-7.30 (1H, m), 7.46-7.54 (3H, m), 7.98 (1H, d, J=8.9 Hz), 8.15-8.22 (2H, m), 8.64 (1H, dd, J=4.9, 1.7 Hz), 11.67 (1H, s).

4-Phenoxy-2-(3-(1H-pyrazol-1-yl)benzamido)benzoic acid

¹H-NMR (DMSO-d₆) δ: 6.60 (1H, dd, J=2.6, 1.8 Hz), 6.80 (1H, dd, J=8.9, 2.6 Hz), 7.16-7.23 (2H, m), 7.27-7.32 (1H, m), 7.46-7.55 (2H, m), 7.71 (1H, t, J=7.9 Hz), 7.80-7.86 (2H, m), 8.07-8.13 (2H, m), 8.41-8.42 (2H, m), 8.61 (1H, d, J=2.4 Hz), 12.53 (1H, s).

2-(Biphenyl-3-carboxamido)-4-phenoxybenzoic acid

¹H-NMR (DMSO-d₆) δ: 6.79 (1H, dd, J=8.8, 2.7 Hz), 7.17-7.22 (2H, m), 7.26-7.33 (1H, m), 7.43 (1H, tt, J=7.4, 1.5 Hz), 7.46-7.55 (4H, m), 7.68 (1H, t, J=7.8 Hz), 7.72-7.77 (2H, m), 7.90-7.97 (2H, m), 8.08 (1H, d, J=8.8 Hz), 8.19 (1H, t, J=1.7 Hz), 8.43 (1H, d, J=2.7 Hz), 12.54 (1H, s).

2-(Biphenyl-4-carboxamido)-4-phenoxybenzoic acid

¹H-NMR (DMSO-d₆) δ: 6.78 (1H, dd, J=8.9, 2.5 Hz), 7.16-7.22 (2H, m), 7.26-7.32 (1H, m), 7.41-7.55 (5H, m), 7.75-7.80 (2H, m), 7.87-7.93 (2H, m), 7.98-8.04 (2H, m), 8.09 (1H, d, J=8.9 Hz), 8.43 (1H, d, J=2.5 Hz), 12.48 (1H, s).

2-(3-Acetylbenzamido)-4-phenoxybenzoic acid

¹H-NMR (DMSO-d₆) δ: 2.66 (3H, s), 6.80 (1H, dd, J=8.9, 2.6 Hz), 7.16-7.22 (2H, m), 7.26-7.32 (1H, m), 7.46-7.54 (2H, m), 7.75 (1H, t, J=7.8 Hz), 8.09 (1H, d, J=8.9 Hz), 8.15-8.19 (1H, m), 8.20-8.24 (1H, m), 8.40 (1H, d, J=2.6 Hz), 8.48-8.51 (1H, m), 12.58 (1H, s), 13.60-14.00 (1H, broad).

2-(3-(3,5-Dimethyl-1H-pyrazol-1-yl)benzamido)-4-phenoxybenzoic acid

¹H-NMR (DMSO-d₆) δ: 2.20 (3H, s), 2.37 (3H, s), 6.13 (1H, s), 6.79 (1H, dd, J=8.9, 2.5 Hz), 7.17-7.21 (2H, m), 7.26-7.32 (1H, m), 7.46-7.53 (2H, m), 7.70 (1H, t, J=7.8 Hz), 7.76-7.81 (1H, m), 7.88-7.93 (1H, m), 7.99 (1H, b, J=2.0 Hz), 8.08 (1H, d, J=8.9 Hz), 8.40 (1H, d, J=2.5 Hz), 12.46 (1H, s), 13.50-14.00 (1H, broad).

2-(Biphenyl-2-carboxamido)-4-phenoxybenzoic acid

¹H-NMR (DMSO-d₆) δ: 6.66 (1H, dd, J=8.8, 2.4 Hz), 7.11-7.16 (2H, m), 7.22-7.43 (6H, m), 7.44-7.55 (4H, m), 7.62 (1H, td, J=7.6, 7.5 Hz), 7.67 (1H, dd, J=7.6, 1.2 Hz), 7.91 (1H, d, J=8.8 Hz), 8.22 (1H, s), 11.44 (1H, s), 13.30-13.60 (1H, broad).

Example 508

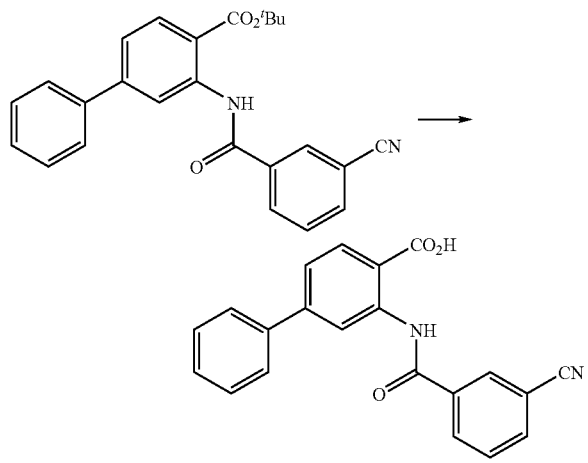

0.5 mL of trifluoroacetic acid was added to 0.5 mL of methylene chloride solution containing 10 mg of tert-butyl 2-(3-cyanobenzamido)-4-phenylbenzoate and stirred at room temperature for 1 hour and 30 minutes. The solvent was evaporated under reduced pressure and diisopropyl ether was added to the obtained residue and a solid substance was separated by filtration to obtain 7.6 mg of 2-(3-cyanobenzamido)-4-phenylbenzoic acid as white solid.

$^1$H-NMR (DMSO-d$_6$) δ: 7.44-7.50 (1H, m), 7.52-7.60 (3H, m), 7.72-7.77 (2H, m), 7.84 (1H, t, J=7.9 Hz), 8.12-8.18 (2H, m), 8.25-8.30 (1H, m), 8.35-8.38 (1H, m), 8.95 (1H, d, J=1.7 Hz), 12.24 (1H, s).

Examples 509 to 516

The compounds shown in Table 50 were obtained in the same manner as in Example 508.

TABLE 50

| Example No. | R$^2$ |
|---|---|
| 509 | (5-methyl-2-(1H-pyrrol-1-yl)pyridin-3-yl) |
| 510 | (4-methyl-2-(1H-pyrrol-1-yl)pyridin-3-yl) |
| 511 | (3-(1H-pyrazol-1-yl)phenyl, methyl-substituted) |
| 512 | (methylbiphenyl) |
| 513 | (4-methylbiphenyl) |
| 514 | (3-acetylphenyl, methyl-substituted) |
| 515 | (3-(3,5-dimethyl-1H-pyrazol-1-yl)phenyl, methyl-substituted) |
| 516 | (2'-methylbiphenyl) |

4-Phenyl-2-(6-(1H-pyrrol-1-yl)pyridine-3-carboxamido) benzoic acid $^1$H-NMR (DMSO-d$_6$) δ: 6.38 (2H, t, J=2.1 Hz), 7.44-7.50 (1H, m), 7.52-7.58 (3H, m), 7.71-7.76 (2H, m), 7.80 (2H, t, J=2.1 Hz), 7.96 (1H, d, J=8.6 Hz), 8.15 (1H, d, J=8.3 Hz), 8.40 (1H, dd, J=8.6, 2.4 Hz), 8.98-9.02 (2H, m), 12.25 (1H, s).

4-Phenyl-2-(2-(1H-pyrrol-1-yl)pyridine-4-carboxamido)benzoic acid $^1$H-NMR (DMSO-d$_6$) δ: 6.37 (2H, t, J=2.3 Hz), 7.48 (1H, tt, J=7.3, 1.6 Hz), 7.53-7.62 (3H, m), 7.69 (1H, dd, J=5.1, 1.4 Hz), 7.74-7.78 (4H, m), 8.13 (1H, s), 8.16 (1H, d, J=8.3 Hz), 8.69 (1H, dd, J=5.1, 0.8 Hz), 8.98 (1H, d, J=1.7 Hz), 12.29 (1H, s).

4-Phenyl-2-(3-(1H-pyrazol-1-yl)benzamido)benzoic acid $^1$H-NMR (DMSO-$d_6$) δ: 6.62 (1H, dd, J=2.4, 2.0 Hz), 7.45-7.51 (1H, m), 7.53-7.60 (3H, m), 7.72-7.78 (3H, m), 7.82-7.84 (1H, m), 7.88-7.94 (1H, m), 8.10-8.17 (2H, m), 8.49 (1H, t, J=1.8 Hz), 8.63 (1H, d, J=2.4 Hz), 9.09 (1H, d, J=1.7 Hz), 12.38 (1H, s).

2-(Biphenyl-3-carboxamido)-4-phenylbenzoic acid $^1$H-NMR (DMSO-$d_6$) δ: 7.42-7.60 (7H, m), 7.69-7.80 (5H, m), 7.94-8.02 (2H, m), 8.15 (1H, d, J=8.3 Hz), 8.26 (1H, s), 9.11 (1H, d, J=1.7 Hz), 12.40 (1H, s).

2-(Biphenyl-4-carboxamido)-4-phenylbenzoic acid $^1$H -NMR (DMSO-$d_6$) δ: 7.42-7.60 (7H, m), 7.74-7.82 (4H, m), 7.90-7.95 (2H, m), 8.06-8.11 (2H, m), 8.16 (1H, d, J=8.3 Hz), 9.11 (1H, d, J=1.7 Hz), 12.34 (1H, s).

2-(3-Acetylbenzamido)-4-phenylbenzoic acid $^1$H-NMR (DMSO-$d_6$) δ: 2.69 (3H, s), 7.45-7.50 (1H, m), 7.52-7.59 (3H, m), 7.72-7.82 (3H, m), 8.15 (1H, d, J=8.3 Hz), 8.24 (2H, dd, J=7.8, 1.7 Hz), 8.57 (1H, t, J=1.7 Hz), 9.07 (1H, d, J=2.0 Hz), 12.41 (1H, s).

2-(3-(3,5-Dimethyl-1H-pyrazol-1-yl)benzamido)-4-phenylbenzoic acid $^1$H-NMR (DMSO-$d_6$) δ: 2.21 (3H, s), 2.39 (3H, d, J=0.5 Hz), 6.14 (1H, s), 7.47 (1H, tt, J=7.3, 1.5 Hz), 7.52-7.58 (3H, m), 7.70-7.77 (3H, m), 7.79-7.82 (1H, m), 7.96-7.99 (1H, m), 8.06-8.07 (1H, m), 8.14 (1H, d, J=8.3 Hz), 9.05-9.07 (1H, m), 12.30 (1H, s).

2-(Biphenyl-2-carboxamido)-4-phenylbenzoic acid $^1$H-NMR (DMSO-$d_6$) δ: 7.29 (1H, tt, J=7.2, 1.7 Hz), 7.34-7.48 (6H, m), 7.48-7.59 (4H, m), 7.61-7.70 (3H, m), 7.73 (1H, dd, J=7.6, 1.2 Hz), 7.99 (1H, d, J=8.3 Hz), 8.85 (1H, s), 11.35 (1H, s), 13.40-13.80 (1H, broad).

Example 517

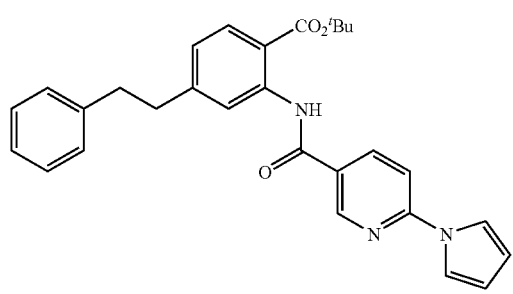

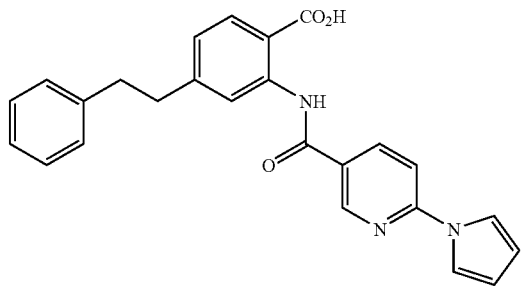

1.0 mL of trifluoroacetic acid was added to 1.0 mL of methylene chloride solution containing 20 mg of tert-butyl 4-phenethyl-2-(6-(1H-pyrrol-1-yl)pyridine-3-carboxamido)benzoate and stirred at room temperature for 1 hour and 30 minutes. Tine solvent was evaporated under reduced pressure and diisopropyl ether was added to the obtained residue and a solid substance was separated by filtration to obtain 17 mg of 4-phenethyl-2-(6-(1H-pyrrol-1-yl)pyridine-3-carboxamido)benzoic acid as white solid.

$^1$H-NMR (DMSO-$d_6$) δ: 2.90-3.02 (4H, m), 6.38 (2H, t, J=2.3 Hz), 7.11 (1H, dd, J=8.3, 1.6 Hz), 7.15-7.24 (1H, m), 7.25-7.32 (4H, m), 7.79 (2H, t, J=2.3 Hz), 7.94 (1H, d, J=8.7 Hz), 7.97 (1H, d, J=8.3 Hz), 8.37 (1H, dd, J=8.7, 2.3 Hz), 8.58-8.61 (1H, m), 8.97 (1H, d, J=2.3 Hz), 12.15 (1H, s), 13.60-13.80 (1H, broad).

Examples 518 to 521

The compounds shown in Table 51 were obtained in the same manner as in Example 517.

TABLE 51

| Example No. | R$^2$ |
|---|---|
| 518 | ![4-methyl-2-(1H-pyrrol-1-yl)pyridine] |
| 519 | ![3-methylbiphenyl] |
| 520 | ![4-methylbiphenyl] |

TABLE 51-continued

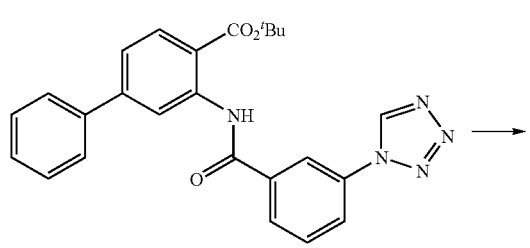

| Example No. | R² |
|---|---|
| 521 | 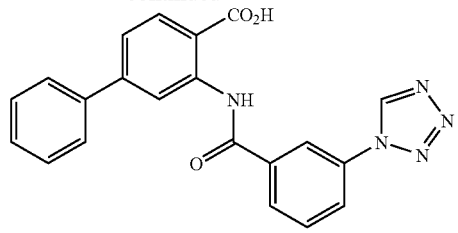 |

4-Phenethyl-2-(2-(1H-pyrrol-1-yl)pyridine-4-carboxamido)benzoic acid

¹H-NMR (DMSO-d₆) δ: 2.90-3.04 (4H, m), 6.37 (2H, t, J=2.3 Hz), 7.12-7.22 (2H, m), 7.25-7.32 (4H, m), 7.66 (1H, dd, J=5.1, 1.5 Hz), 7.74 (2H, t, J=2.3 Hz), 7.97 (1H, d, J=8.3 Hz), 8.10 (1H, s), 8.56 (1H, d, J=1.5 Hz), 8.67 (1H, d, J=5.1 Hz), 12.21 (1H, s).

2-(Biphenyl-3-carboxamido)-4-phenethylbenzoic acid

¹H-NMR (DMSO-d₆) δ: 2.88-3.04 (4H, m), 7.10 (1H, dd, J=8.3, 1.5 Hz), 7.15-7.24 (1H, m), 7.24-7.33 (4H, m), 7.41-7.46 (1H, m), 7.51-7.55 (2H, m), 7.70 (1H, t, J=7.7 Hz), 7.73-7.78 (2H, m), 7.92-8.00 (3H, m), 8.23 (1H, s), 8.70 (1H, s), 12.31 (1H, s), 13.50-14.00 (1H, broad).

2-(Biphenyl-4-carboxamido)-4-phenethylbenzoic acid

1H-NMR (DMSO-d₆) δ: 2.90-3.01 (4H, m), 7.09 (1H, dd, J=8.1, 1.5 Hz), 7.15-7.25 (1H, m), 7.25-7.30 (4H, m), 7.44 (1H, tt, J=7.3, 1.4 Hz), 7.49-7.56 (2H, m), 7.76-7.80 (2H, m), 7.88-7.94 (2H, m), 7.97 (1H, d, J=8.1 Hz), 8.03-8.08 (2H, m), 8.70 (1H, d, J=1.5 Hz), 12.27 (1H, s).

2-((E)-3-(3,4-Dimethoxyphenyl)acrylamido)-4-phenethylbenzoic acid

¹H-NMR (DMSO-d₆) δ: 2.89-2.98 (4H, m), 3.81 (3H, s), 3.84 (3H, s), 6.79 (1H, d, J=15.5 Hz), 7.00 (1H, d, J=8.5 Hz), 7.04 (1H, dd, J=8.3, 1.4 Hz), 7.15-7.20 (1H, m), 7.23-7.30 (5H, m), 7.38 (1H, d, J=1.7 Hz), 7.56 (1H, d, J=15.5 Hz), 7.91 (1H, d, J=8.3 Hz), 8.58 (1H, d, J=1.4 Hz), 11.30 (1H, s).

Example 522

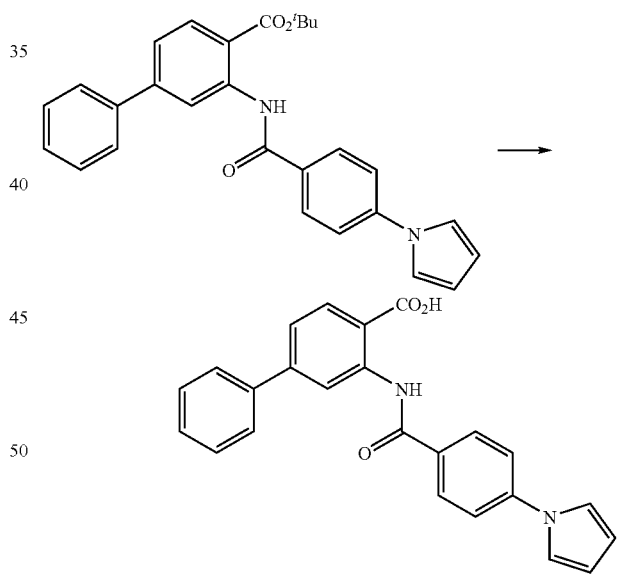

1.0 mL of trifluoroacetic acid was added to 1.0 mL of methylene chloride solution containing 20 mg of tert-butyl 4-phenyl-2-(3-(1H-tetrazol-1-yl)benzamido)benzoate and stirred an room temperature for 1 hour. The solvent was evaporated under reduced pressure and ethyl acetate and tetrahydrofuran were added to the obtained residue and headed to 50° C., Insoluble were removed by filtration at the same temperature, and the solvent was evaporated under reduced pressure. Tetrahydrofuran was added to the obtained residue and a solid substance was separated by filtration to obtain 5.0 mg of 4-phenyl-2-(3-(1H-tetrazol-1-yl)benzamido)benzoic acid as white solid.

¹H-NMR (DMSO-d₆) δ: 7.48 (1H, tt, J=7.3, 1.5 Hz), 7.53-7.60 (3H, m), 7.72-7.78 (2H, m), 7.92 (1H, t, J=7.9 Hz), 8.15 (2H, d, J=8.3 Hz), 8.20-8.24 (1H, m), 8.54 (1H, t, J=1.8 Hz), 9.04 (1H, d, J=1.7 Hz), 10.23 (1H, s), 12.44 (1H, s).

Example 523

1.0 mL of methanol and 0.5 mL of 2.0 mol/L aqueous sodium hydroxide were added to 1.0 mL of dioxane solution containing 20 mg of tert-butyl 4-phenyl-2-(4-(1H-pyrrol-1-yl)benzamido)benzoate at room temperature and stirred at 50° C. for 30 minutes. Ethyl acetate and 1.0 mol/L hydrochloric acid were added after the reaction mixture was cooled to room temperature. The organic layer was separated and dried over anhydrous magnesium sulfate after washed with a saturated sodium chloride aqueous solution, and the solvent was evaporated under reduced pressure, Diisopropyl ether were added to toe obtained residue and a solid substance was

273 separated by filtration to obtain 15 mg of 4-phenyl-2-(4-(1H-pyrrol-1-yl)benzamido)benzoic acid as white solid.

$^1$H-NMR (DMSO-d$_6$) δ: 6.34 (2H, t, J=2.2 Hz), 7.47 (1H, tt, J=7.3, 1.5 Hz), 7.50-7.59 (5H, m), 7.72-7.78 (2H, m), 7.83-7.88 (2H, m), 8.03-8.09 (2H, m), 8.15 (1H, d, J=8.5 Hz), 9.09 (1H, d, J=2.0 Hz), 12.33 (1H, s).

Example 524

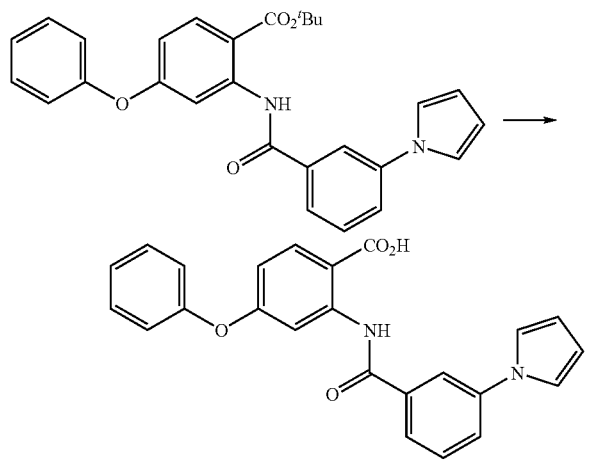

1.0 mL of methanol and 0.5 mL of 2.0 mol/L aqueous sodium hydroxide were added to 1.0 mL of dioxane solution containing 20 mg of tert-butyl 4-phenoxy-2-(3-(1H-pyrrol-1-yl)benzamido)benzoate at room temperature and stirred at 50° C. for 30 minutes. After the reaction mixture was cooled to room temperature, ethyl acetate and 1.0 mol/L hydrochloric acid were added. The organic layer was separated and dried over anhydrous magnesium sulfate after washed with a saturated sodium chloride aqueous solution, and the solvent was evaporated under reduced pressure. Diisopropyl ether were added to the obtained residue and a solid substance was separated by filtration to obtain 7.6 mg of 4-phenoxy-2-(3-(1H-pyrrol-1-yl)benzamido)benzoic acid as white solid.

$^1$H-NMR (DMSO-d$_6$) δ: 6.32 (2H, t, J=2.2 Hz), 6.80 (1H, dd, J=8.9, 2.7 Hz), 7.16-7.22 (2H, m), 7.26-7.32 (1H, m), 7.46 (2H, t, J=2.2 Hz), 7.47-7.54 (2H, m), 7.66 (1H, t, J=7.9 Hz), 7.74-7.80 (1H, m), 7.84-7.88 (1H, m), 8.05 (1H, t, J=1.8 Hz), 8.09 (1H, d, J=8.9 Hz), 8.39 (1H, d, J=2.7 Hz), 12.52 (1H, s).

Example 525

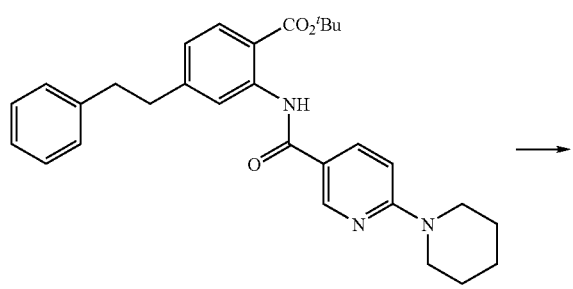

274

-continued

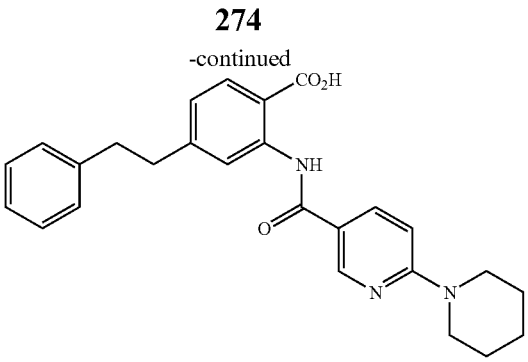

1.7 mL of trifluoroacetic acid was added to 0.17 g of tert-butyl 4-phenethyl-2-(6-(piperidin-1-yl)pyridine-3-carboxamido)benzoate and stirred at room temperature for 3 hours. The solvent was evaporated under reduced pressure, and hexane and diisopropyl ether were added to the obtained residue and a solid substance was separated by filtration. Ethyl acetate and water were added to the obtained solid substance and pH was adjusted to pH 6.8 with a saturated sodium hydrogen carbonate aqueous solution. A solid substance was separated by filtration to obtain 65 mg of 4-phenethyl-2-(6-(piperidin-1-yl)pyridine-3-carboxamido)benzoic acid as white solid.

$^1$H-NMR (DMSO-d$_6$) δ: 1.51-1.68 (6H, m), 2.88-2.97 (4, m), 3.62-3.72 (4H, m), 6.94 (1H, d, J=9.3 Hz), 7.01 (1H, d, J=8.1 Hz), 7.16-7.20 (1H, m), 7.25-7.30 (4H, m), 7.94 (1H, d, J=8.0 Hz), 7.94-8.00 (1H, m), 8.65 (1H, s), 8.69 (1H, d, J=2.4 Hz), 12.30-12.50 (1H, broad).

Example 526

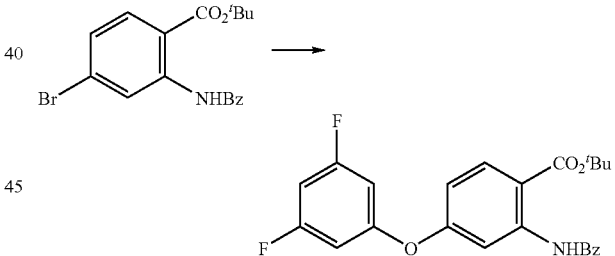

29 mg of 3,5-difluorophenol, 79 mg of tripotassium phosphate, 4.7 mg of 2-(di-tert-butylphosphino)-2', 4', 6'-triisopropylbiphenyl and 6.8 mg of tris(dibenzylideneacetone)dipalladium(0) were added to 1.4 mL of toluene solution containing 70 mg of tert-butyl 2-(benzamido)-4-bromobenzoate at room temperature, and the resulting mixture was heated to reflux under nitrogen atmosphere for 3 hours. After the reaction mixture was cooled to room temperature, ethyl acetate and 10% citric acid aqueous solution were added and insoluble were removed by filtration. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd, eluent; hexane:ethyl acetate=10:1] to obtain 71 mg of tert-butyl 2-(benzamido)-4-(3,5-difluorophenoxy)benzoate as colorless oil.

¹H-NMR (CDCl₃) δ: 1.64 (9H, s), 6.56-6.63 (3H, m), 6.73 (1H, dd, J=8.8, 2.4 Hz), 7.50-7.60 (3H, m), 8.01-8.07 (3H, m), 8.70 (1H, d, J=2.4 Hz), 12.34 (1H, s).

Examples 527 to 533

The compounds shown in Table 58 were obtained in the same manner as in Example 526.

TABLE 52

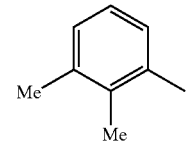

| Example No. | R³ |
|---|---|
| 527 | 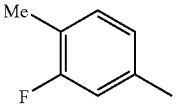 |
| 528 | 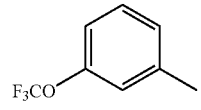 |
| 529 | 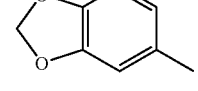 |
| 530 | 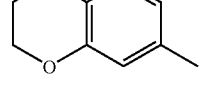 |
| 531 | 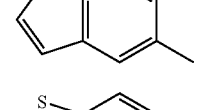 |
| 532 | 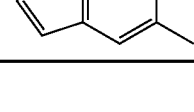 |
| 533 | 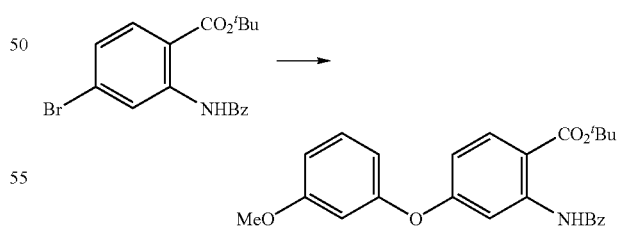 | tert-Butyl 2-(benzamido)-4-(2,3-dimethylphenoxy)benzoate

¹H-NMR (CDCl₃) δ: 1.61 (9H, s), 2.12 (3H, s), 2.33 (3H, s), 6.50 (1H, dd, J=8.9, 2.5 Hz), 6.89 (1H, d, J=7.8 Hz), 7.04 (1H, d, J=7.6 Hz), 7.10-7.15 (1H, m), 7.48-7.58 (3H, m), 7.94 (1H, d, J=8.9 Hz), 8.00-8.05 (2H, m), 8.53 (1H, d, J=2.5 Hz), 12.31 (1H, s).

tert-Butyl 2-(benzamido)-4-(3-fluoro-4-methylphenoxy)benzoate

¹H-NMR (CDCl₃) δ: 1.62 (9H, s), 2.26 (3H, d, J=1.7 Hz), 6.67 (1H, dd, J=8.9, 2.5 Hz), 6.75-6.83 (2H, m), 7.18 (1H, t, J=8.5 Hz), 7.48-7.59 (3H, m), 7.99 (1H, d, J=8.9 Hz), 7.99-8.05 (2H, m), 8.61 (1H, d, J=2.5 Hz), 12.32 (1H, s).

tert-Butyl 2-(benzamido)-4-(3-(trifluoromethoxy)phenoxy)benzoate

¹H-NMR (CDCl₃) δ: 1.63 (9H, s), 6.69 (1H, dd, J=8.9, 2.7 Hz), 6.94-6.98 (1H, m), 7.00-7.06 (2H, m), 7.39 (1H, t, J=8.3 Hz), 7.49-7.60 (3H, m), 8.00-8.06 (3H, m), 8.67 (1H, d, J=2.7 Hz), 12.32 (1H, s).

tert-Butyl 2-(benzamido)-4-(benzo[1,3]dioxol-5-yloxy)benzoate

¹H-NMR (CDCl₃) δ: 1.61 (9H, s), 6.00 (2H, s), 6.58 (1H, dd, J=8.3, 2.4 Hz), 6.61-6.66 (2H, m), 6.80 (1H, d, J=8.3 Hz), 7.48-7.58 (3H, m), 7.97 (1H, d, J=9.0 Hz), 8.00-8.05 (2H, m), 8.56 (1H, d, J=2.7 Hz), 12.31 (1H, s).

tert-butyl 2-(benzamido)-4-(2,3-dihydrobenzo[1,4]dioxin-6-yloxy)benzoate

¹H-NMR (CDCl₃) δ: 1.61 (9H, s), 4.27 (4H, s), 6.58-6.67 (3H, m), 6.87 (1H, d, J=8.8 Hz), 7.48-7.58 (3H, m), 7.96 (1H, d, J=9.0 Hz), 8.00-8.05 (2H, m), 8.57 (1H, d, J=2.4 Hz), 12.30 (1H, s).

tert-Butyl 2-(benzamido)-4-(benzofuran-5-yloxy)benzoate

¹H-NMR (CDCl₃) δ: 1.61 (9H, s), 6.64 (1H, dd, J=9.0, 2.7 Hz), 6.75 (1H, dd, J=2.2, 1.0 Hz), 7.07 (1H, dd, J=8.8, 2.4 Hz), 7.33 (1H, d, J=2.4 Hz), 7.47-7.57 (4H, m), 7.66 (1H, d, J=2.2 Hz), 7.97 (1H, d, J=9.0 Hz), 7.98-8.04 (2H, m), 8.58 (1H, d, J=2.7 Hz), 12.31 (1H, s).

tert-Butyl 2-(benzamido)-4-(benzothiophen-5-yloxy)benzoate

¹H-NMR (CDCl₃) δ: 1.62 (9H, s), 6.67 (1H, dd, J=8.9, 2.5 Hz), 7.15 (1H, dd, J=8.9, 2.1 Hz), 7.27-7.30 (1H, m), 7.48-7.58 (5H, m), 7.88 (1H, d, J=8.5 Hz), 7.98 (1H, d, J=8.8 Hz), 7.99-8.04 (2H, m), 8.63 (1H, d, J=2.5 Hz), 12.32 (1H, s).

Example 534

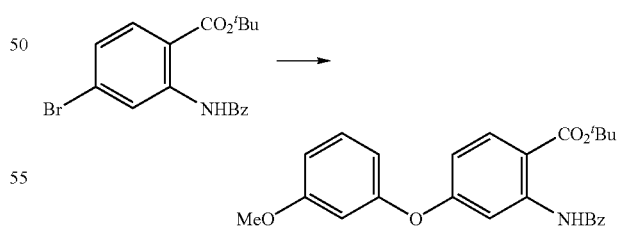

6.0 mg of palladium acetate was added to 5 mL of toluene suspension containing 0.50 g tert-butyl 2-(benzamido)-4-bromobenzoate, 0.18 mL of 3-methoxyphenol, 17 mg of 2-(di-tert-butylphosphino)-2',4',6'-triisopropylbiphenyl and 0.57 g of tripotassium phosphate at room temperature, and the resulting mixture was heated to reflux under nitrogen atmosphere for 5 hours. After the reaction mixture was cooled no room temperature, ethyl acetate and 10% citric acid aqueous solution were added and insoluble were removed by filtration.

The organic layer was separated and dried over anhydrous magnesium sulfate after washed with 10% citric acid aqueous solution and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane:ethyl acetate=6:1]to obtain 0.32 g of tert-butyl 2-(benzamido)-4-(3-methoxyphenoxy)benzoate as white solid.

$^1$H-NMR (CDCl$_3$) δ: 1.62 (9H, s), 3.80 (3H, s), 6.64-6.76 (4H, m), 7.28 (1H, t, J=8.0 Hz), 7.48-7.59 (3H, m), 7.98 (1H, d, J=8.8 Hz), 8.01-8.06 (2H, m), 8.63 (1H, d, J=2.7 Hz), 12.30 (1H, s).

Example 535

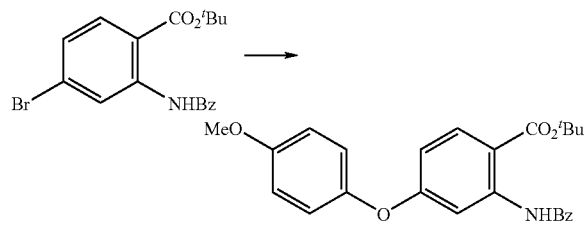

The following compound was obtained in one same manner as in Example 534.

tert-Butyl 2-(benzamido)-4-(4-methoxyphenoxy)benzoate $^1$H-NMR (CDCl$_3$) δ: 1.61 (9H, s), 3.82 (3H, s), 6.62 (1H, dd, J=9.0, 2.7 Hz), 6.90-6.96 (2H, m), 7.02-7.08 (2H, m), 7.48-7.58 (3H, m), 7.96 (1H, d, J=9.0 Hz), 7.99-8.06 (2H, m), 8.54 (1H, d, J=2.7 Hz), 12.31 (1H, s).

Example 536

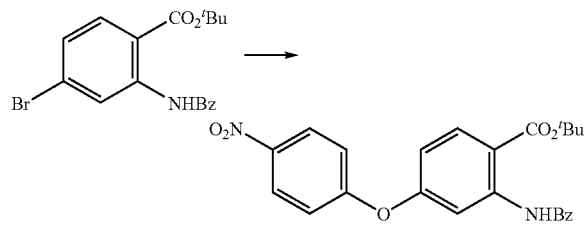

31 mg of 4-nitrophenol was added to 1.0 mL of toluene suspension containing of 8.9 mg of 60% sodium hydride at room temperature, and the resulting mixture was heated to reflux under nitrogen atmosphere for 15 minutes. After the reaction mixture was cooled to room temperature, 0.5 mL of toluene solution containing 3.8 mg of 2-(di-tert-butylphosphino)-2',4',6'-triisopropylbiphenyl, 1.3 mg of palladium acetate and 56 mg of tert-butyl 2-(benzamido)-4-bromobenzoate were added and the resulting mixture was heated to reflux under nitrogen atmosphere for 3 hours. After the reaction mixture was cooled to room temperature, 1.3 mg of tri-tert-butylphosphine tetrafluoroborate and 4.1 mg of tris (dibenzylideneacetone)dipalladium(0) were added and the resulting mixture was heated to reflux under nitrogen atmosphere for 4 hours. After the reaction mixture was cooled to room temperature, 10% citric acid aqueous solution and ethyl acetate were added and insoluble were removed by filtration. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia chemical Ltd., eluent; hexane:ethyl acetate=10:1] to obtain 18 mg of tert-butyl 2-(benzamido)-4-(4-nitrophenoxy)benzoate as white solid.

$^1$H-NMR (CDCl$_3$) δ: 1.65 (9H, s), 6.79 (1H, dd, J=8.8, 2.4 Hz), 7.12-7.17 (2H, m), 7.50-7.61 (3H, m), 8.01-8.06 (2H, m), 8.09 (1H, d, J=8.8 Hz), 8.23-8.29 (2H, m), 8.74 (1H, d, J=2.4 Hz), 12.36 (1H, s).

Example 537

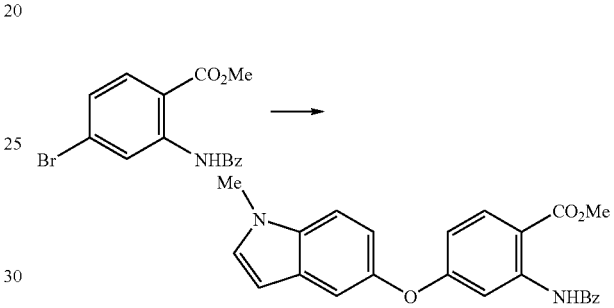

26 mg of 5-hydroxy-1-methyl-1H-indole, 64 mg of tripotassium phosphate, 3.8 mg of 2-(di-tert-butylphosphino)-2', 4',6'-triisopropylbiphenyl and 5.5 mg of tris(dibenzylideneacetone) dipalladium (0) were added to 1.0 mL of toluene solution containing 50 mg of methyl 2-(benzamido)-4-bromobenzoate at zoom temperature, and the resulting mixture was heated to reflux under nitrogen atmosphere for 2 hours. After the reaction mixture was cooled to room temperature, ethyl acetate and 10% citric acid aqueous solution were added and insoluble were removed by filtration. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia chemical Ltd., eluent; hexane:ethyl acetate=5:1] to obtain 53 mg of methyl 2-(benzamido)-4-(1-methyl-1H-indol-5-yloxy)benzoate as pale yellow solid.

$^1$H-NMR (CDCl$_3$) δ: 3.83 (3H, s), 3.93 (3H, s), 6.47 (1H, dd, J=3.1, 0.9 Hz), 6.63 (1H, dd, J=9.0, 2.6 Hz), 7.02 (1H, dd, J=8.8, 2.2 Hz), 7.10 (1H, d, J=2.9 Hz), 7.32-7.38 (2H, m), 7.47-7.57 (3H, m), 7.97-8.03 (3H, m), 8.58 (1H, d, J=2.6 Hz), 12.14 (1H, s).

Example 538

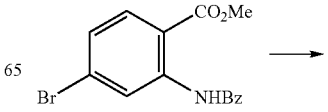

-continued

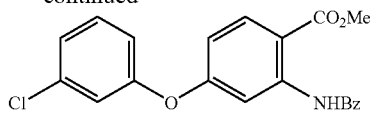

The following compound was obtained in the same manner as in Example 537.

Methyl 2-(benzamido)-4-(3-chlorophenoxy)benzoate $^1$H-NMR (CDCl$_3$) δ: 3.96 (3H, s), 6.70 (1H, dd, J=9.0, 2.5 Hz). 7.01 (1H, ddd, J=8.1, 2.1, 0.9 Hz), 7.10 (1H, t, J=2.1 Hz), 7.17 (1H, ddd, J=8.1, 2.1, 0.9 Hz), 7.33 (1H, t, J=8.1 Hz), 7.48-7.59 (3H, m), 8.00-8.05 (2H, m), 8.07 (1H, d, J=9.0 Hz), 8.65 (1H, d, J=2.5 Hz), 12.17 (1H, s).

Example 539

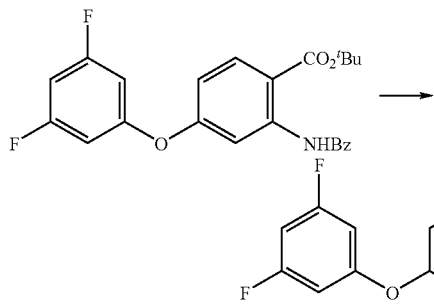

5.0 mL of trifluoroacetic acid solution containing 69 mg of tert-butyl 2-(benzamido)-4-(3,5-difluorophenoxy)benzoate was stirred at room temperature for 2 hours. The solvent was evaporated under reduced pressure and diisopropyl ether was added to the obtained residue and a solid substance was separated by filtration to obtain 41 mg of 2-(benzamido)-4-(3,5-difluorophenoxy)benzoic acid as white solid.

$^1$H-NMR (DMSO-d$_6$) δ: 6.90 (1H, dd, J=8.8, 2.4 Hz), 6.96-7.04 (2H, m), 7.17 (1H, tt, J=9.4, 2.3 Hz), 7.56-7.69 (3H, m), 7.91-7.97 (2H, m), 8.12 (1H, d, J=8.8 Hz), 8.48 (1H, d, J=2.7 Hz), 12.42 (1H, s).

Examples 540 so 549

The compounds shown in Table 53 were obtained in the same manner as in Example 539.

TABLE 53

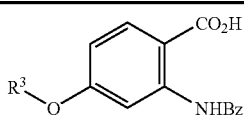

| Example No. | R$^3$ |
|---|---|
| 540 | O$_2$N-⌬-CH$_3$ |

TABLE 53-continued

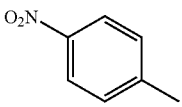

| Example No. | R$^3$ |
|---|---|
| 541 | 2,3-dimethylphenyl (Me, Me) |
| 542 | 2-methyl-4-fluorophenyl (Me, F) |
| 543 | 3-methoxyphenyl (MeO) |
| 544 | 4-methoxyphenyl (MeO) |
| 545 | 3-trifluoromethoxyphenyl (F$_3$CO) |
| 546 | benzo[1,3]dioxol-5-yl |
| 547 | 2,3-dihydrobenzo[1,4]dioxin-6-yl |
| 548 | benzofuran-5-yl |
| 549 | benzothiophen-5-yl |

2-(Benzamido)-4-(4-nitrophenoxy)benzoic acid $^1$H-NMR (DMSO-d$_6$) δ: 6.98 (1H, dd, J=8.7, 2.5 Hz), 7.33-7.38 (2H, m), 7.57-7.69 (3H, m), 7.91-7.97 (2H, m), 8.17 (1H, d, J=8.7 Hz), 8.30-8.36 (2H, m), 8.54 (1H, d, J=2.5 Hz), 12.46 (1H, s).

2-(Benzamido)-4-(2,3-dimethylphenoxy)benzoic acid $^1$H-NMR (DMSO-d$_6$) δ: 2.07 (3H, s), 2.31 (3H, s), 6.63 (1H, dd, J=8.9, 2.7 Hz), 6.94 (1H, d, J=7.7 Hz), 7.13 (1H, d, J=7.5 Hz), 7.17-7.22 (1H, m), 7.55-7.68 (3H, m), 7.90-7.94

(2H, m), 8.04 (1H, d, J=8.9 Hz), 8.33 (1H, d, J=2.7 Hz), 12.41 (1H, s), 13.50-13.70 (1H, broad).

2-(Benzamido)-4-(3-fluoro-4-methylphenoxy)benzoic acid $^1$H-NMR (DMSO-d$_6$) δ: 2.26 (3H, d, J=1.7 Hz), 6.79 (1H, dd, J=8.9, 2.5 Hz), 6.94 (1H, dd, J=8.3, 2.2 Hz), 7.07 (1H, dd, J=10.6, 2.3 Hz), 7.35-7.41 (1H, m), 7.56-7.68 (3H, m), 7.90-7.95 (2H, m), 8.08 (1H, d, J=8.9 Hz), 8.42 (1H, d, J=2.5 Hz), 12.42 (1H, s).

2-(Benzamido)-4-(3-methoxyphenoxy)benzoic acid $^1$H-NMR (DMSO-d$_6$) δ: 3.78 (3H, s), 6.70-6.88 (4H, m), 7.38 (1H, t, J=8.2 Hz), 7.55-7.68 (3H, m), 7.91-7.95 (2H, m), 8.07 (1H, d, J=8.8 Hz), 8.43 (1H, d, J=2.4 Hz), 12.41 (1H, s).

2-(Benzamido)-4-(4-methoxyphenoxy)benzoic acid $^1$H-NMR (DMSO-d$_6$) δ: 3.79 (3H, s), 6.71 (1H, dd, J=8.9, 2.7 Hz), 7.01-7.06 (2H, m), 7.11-7.17 (2H, m), 7.55-7.68 (3H, m), 7.89-7.95 (2H, m), 8.05 (1H, d, J=8.9 Hz), 8.36 (1H, d, J=2.7 Hz), 12.41 (1H, s).

2-(Benzamido)-4-(3-(trifluoromethoxy)phenoxy)benzoic acid $^1$H-NMR (DMSO-d$_6$) δ: 6.85 (1H, dd, J=8.8, 2.6 Hz), 7.20-7.31 (3H, m), 7.56-7.69 (4H, m), 7.90-7.96 (2H, m), 8.11 (1H, d, J=8.8 Hz), 8.46 (1H, d, J=2.6 Hz), 12.43 (1H, s).

2-(Benzamido)-4-(benzo[1,3]dioxol-5-yloxy)benzoic acid $^1$H-NMR (DMSO-d$_6$) δ: 6.10 (2H, s), 6.65 (1H, dd, J=8.3, 2.3 Hz), 6.73 (1H, dd, J=8.8, 2.7 Hz), 6.87 (1H, d, J=2.3 Hz), 6.99 (1H, d, J=8.3 Hz), 7.56-7.68 (3H, m), 7.90-7.96 (2H, m), 8.05 (1H, d, J=8.8 Hz), 8.38 (1H, d, J=2.7 Hz), 12.42 (1H, s), 13.55-13.75 (1H, broad).

2-(Benzamido)-4-(2,3-dihydrobenzo[1,4]dioxin-6-yloxy)benzoic acid $^1$H-NMR (DMSO-d$_6$) δ: 4.25-4.31 (4H, m), 6.65 (1H, dd, J=8.7, 2.8 Hz), 6.69-6.74 (2H, m), 6.95 (1H, d, J=8.5 Hz), 7.56-7.68 (3H, m), 7.90-7.96 (2H, m), 8.05 (1H, d, J=8.8 Hz), 8.38 (1H, d, J=2.7 Hz), 12.42 (1H, s).

2-(Benzamido)-4-(benzofuran-5-yloxy)benzoic acid $^1$H-NMR (DMSO-d$_6$) δ: 6.76 (1H, dd, J=8.9, 2.5 Hz), 7.00 (1H, dd, J=2.2, 1.0 Hz), 7.15 (1H, dd, J=8.9, 2.5 Hz), 7.49 (1H, d, J=2.5 Hz), 7.54-7.67 (3H, m), 7.71 (1H, d, J=8.9 Hz), 7.88-7.93 (2H, m), 8.06 (1H, d, J=8.9 Hz), 8.09 (1H, d, J=2.2 Hz), 8.39 (1H, d, J=2.5 Hz), 12.42 (1H, s), 13.50-13.75 (1H, broad).

2-(Benzamido)-4-(benzothiophen-5-yloxy)benzoic acid $^1$H-NMR (DMSO-d$_6$) δ: 6.81 (1H, dd, J=8.9, 2.7 Hz), 7.23 (1H, dd, J=8.7, 2.3 Hz), 7.47 (1H, dd, J=5.5, 0.6 Hz), 7.54-7.67 (3H, m), 7.70 (1H, d, J=2.3 Hz), 7.88 (1H, d, J=5.5 Hz), 7.88-7.93 (2H, m), 8.08 (1H, d, J=8.8 Hz), 8.11 (1H, d, J=8.5 Hz), 8.42 (1H, d, J=2.7 Hz), 12.42 (1H, s).

Example 550

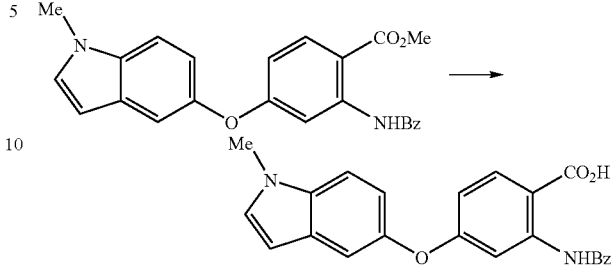

0.094 mL of 2.0 mol/L aqueous sodium hydroxide was added to a mixed solution of 1.5 mL of dioxane and 1.5 mL of methanol containing 50 mg of methyl 2-(benzamido)-4-(1-methyl-1H-indol-5-yloxy)benzoate at room temperature, stirred at 50° C. for 1 hour, and 0.031 mL of 2.0 mol/L aqueous sodium hydroxide was added at the same temperature and then stirred at 50° C. for 30 minutes. After the reaction mixture was cooled to room temperature, water was added and pH was adjusted to pH 3.5 with 1.0 mol/L hydrochloric acid and ethyl acetate was added. The organic layer was separated and dried over anhydrous magnesium sulfate after washed with water and a saturated sodium chloride aqueous solution sequentially, and the solvent was evaporated under reduced pressure. Hexane was added to the obtained residue and a solid substance was separated by filtration to obtain 37 mg of 2-(benzamido)-4-(1-methyl-1H-indol-5-yloxy)benzoic acid as white solid.

$^1$H-NMR (DMSO-d$_6$) δ: 3.84 (3H, s), 6.45 (1H, d, J=2.9 Hz), 6.71 (1H, dd, J=8.8, 2.3 Hz), 6.98 (1H, dd, J=8.8, 2.2 Hz), 7.35 (1H, d, J=2.2 Hz), 7.42 (1H, d, J=2.9 Hz), 7.51-7.67 (4H, m), 7.87-7.92 (2H, m), 8.03 (1H, d, J=8.8 Hz), 8.36 (1H, d, J=2.3 Hz), 12.43 (1H, s), 13.45-13.70 (1H, broad).

Example 551

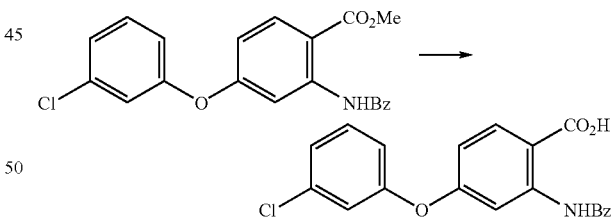

0.16 mL of 2.0 mol/L aqueous sodium hydroxide was added to a mixed solution of 1.0 mL of methanol and 1.0 mL of tetrahydrofuran containing 0.10 g of methyl 2-(benzamido)-4-(3-chlorophenoxy)benzoate while ice-cooled and stirred at room temperature for 5 hours. The reaction mixture was added to water and 1.0 mol/L hydrochloric acid while ice-cooled, and a solid substance was separated by filtration to obtain 92 mg of 2-(benzamido)-4-(3-chlorophenoxy)benzoic acid as white solid.

$^1$H-NMR (DMSO-d$_6$) δ: 6.83 (1H, dd, J=8.8, 2.4 Hz), 7.15-7.18 (1H, m), 7.29-7.32 (1H, m), 7.33-7.37 (1H, m), 7.51 (1H, t, J=8.2 Hz), 7.57-7.68 (3H, m), 7.91-7.96 (2H, m), 8.10 (1H, d, J=8.8 Hz), 8.44 (1H, d, J=2.4 Hz), 12.42 (1H, s), 13.59-13.92 (1H, broad).

Example 552

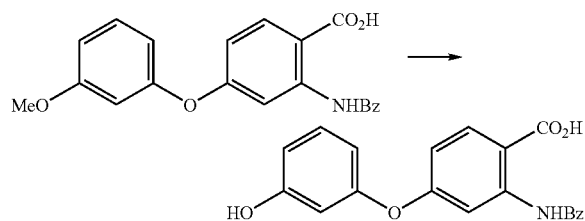

0.22 g of aluminum chloride was added to 1.0 ml of toluene solution containing 0.10 g of 2-(benzamido)-4-(3-methoxyphenoxy)benzoic acid at room temperature and stirred at 80° C. for 8 hours. After the reaction mixture was cooled to room temperature, ethyl acetate and 1.0 mol/b hydrochloric acid were added. The organic layer was separated, and dried over anhydrous magnesium sulfate after washed with 1.0 mol/L hydrochloric acid and a saturated sodium chloride aqueous solution sequentially, and the solvent was evaporated under reduced pressure. The obtained residue was purified with silica gel column chromatography [Flash Tube 2008 manufactured by Trikonex Company, eluent; hexane:ethyl acetate; acetic acid=15:10:1] to obtain 54 mg of 2-(benzamido)-4-(3-hydroxyphenoxy)benzoic acid as white solid.

$^1$H-NMR (DMSO-$d_6$) δ: 6.52 (1H, t, J=2.2 Hz), 6.55-6.60 (1H, m), 6.64-6.70 (1H, m), 6.78 (1H, dd, J=8.9, 2.5 Hz), 7.26 (1H, t, J=8.0 Hz), 7.54-7.71 (3H, m), 7.89-7.99 (2H, m), 8.07 (1H, d, J=8.9 Hz), 8.42 (1H, d, J=2.5 Hz), 9.77 (1H, s), 12.43 (1H, s).

Example 553

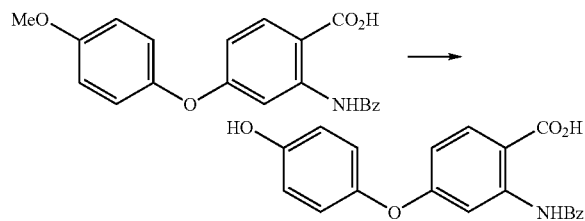

The following compound was obtained in the same manner as in Example 552.

2-(Benzamido)-4-(4-hydroxyphenoxy)benzoic acid $^1$H-NMR (DMSO-$d_6$) δ: 6.69 (1H, dd, J=8.8, 2.7 Hz), 6.82-6.88 (2H, m), 6.97-7.04 (2H, m), 7.54-7.68 (3H, m), 7.90-7.95 (2H, m), 8.03 (1H, d, J=8.8 Hz), 8.34 (1H, d, J=2.7 Hz), 9.51 (1H, s), 12.44 (1H, s).

Example 554

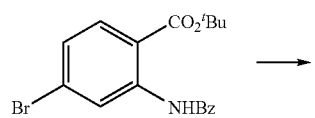

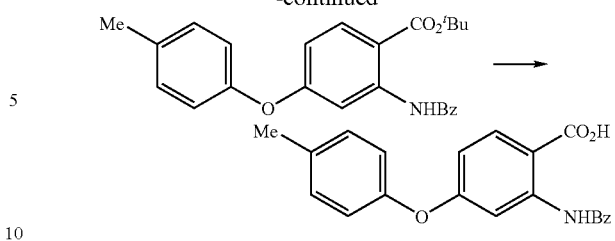

0.023 mL of p-cresol, 79 mg of tripotassium phosphate, 2.4 mg of 2-(di-tert-butylphosphino)-2',4',6'-triisopropylbiphenyl and 0.8 mg of palladium acetate were added to 1.4 mL of toluene solution containing 70 mg of tert-butyl 2-(benzamido)-4-bromobenzoate at room temperature, and the resulting mixture was heated to reflux under nitrogen atmosphere for 1 hour. After the reaction mixture was cooled to room temperature, 4.7 mg of 2-(di-tert-butylphosphino)-2',4',6'-triisopropylbiphenyl and 1.7 mg of palladium acetate were added and the resulting mixture was heated to reflux under nitrogen atmosphere for 6 hours. After the reaction mixture was cooled to room temperature, ethyl acetate and 10% citric acid aqueous solution were added. The organic layer was separated and dried over anhydrous magnesium sulfate after washed with a saturated sodium chloride aqueous solution, and the solvent was evaporated under reduced pressure. The obtained residue was purified with silica gel column chromatography [Flash Tube 2008 manufactured by Trikonex Company, eluent; hexane; ethyl acetate=4:1] to obtain tert-butyl 2-(benzamido)-4-(4-methylphenoxy)benzoate.

5.0 mL of trifluoroacetic acid was added to the obtained tert-butyl 2-(benzamido)-4-(4-methylphenoxy)benzoate and stirred at room temperature for 3 hours. The solvent was evaporated under reduced pressure and methanol was added to the obtained residue and a solid substance was separated by filtration to obtain 6.2 mg of 2-(benzamido)-4-(4-Methylphenoxy)benzoic acid as white solid.

$^1$H-NMR (DMSO-$d_6$) δ: 2.35 (3H, s), 6.74 (1H, dd, J=8.8, 2.6 Hz), 7.05-7.10 (2H, m), 7.26-7.32 (2H, m), 7.56-7.68 (3H, m), 7.90-7.95 (2H, m), 8.05 (1H, d, J=8.8 Hz), 8.39 (1H, d, J=2.6 Hz), 12.43 (1H, s).

Examples 555, 556

The compounds shown in Table 54 were obtained in the same manner as in Example 554.

TABLE 54

| Example No. | R³ |
|---|---|
| 555 | 2-chloro-methylphenyl (o-Cl, methyl) |
| 556 | 4-chloro-methylphenyl (p-Cl, methyl) |

2-(Benzamido)-4-(2-chlorophenoxy)benzoic acid $^1$H-NMR (DMSO-$d_6$) δ: 6.73 (1H, dd, J=8.8, 2.5 Hz), 7.33-7.42 (2H, m), 7.45-7.53 (1H, m), 7.54-7.72 (4H, m), 7.87-7.96 (2H, m), 8.08 (1H, d, J=8.8 Hz), 8.36 (1H, d, J=2.5 Hz), 12.42 (1H, s), 13.59-13.84 (1H, broad).

2-(Benzamido)-4-(4-chlorophenoxy)benzoic acid $^1$H-NMR (DMSO-$d_6$) δ: 6.81 (1H, dd, J=8.8, 2.4 Hz), 7.18-7.26 (2H, m), 7.50-7.69 (5H, m), 7.88-7.97 (2H, m), 8.09 (1H, d, J=8.8 Hz), 8.42 (1H, d, J=2.4 Hz), 12.41 (1H, s), 13.60-13.85 (1H, broad).

Example 557

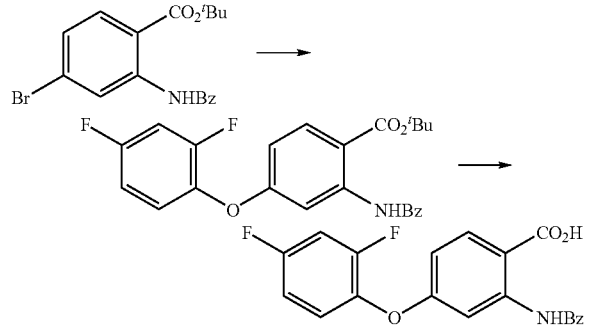

0.018 mL of 2,4-difluorophenol was added to 1 mL of toluene suspension containing 10 mg of 60% sodium hydride at room temperature, and the resulting mixture was heated to reflux under nitrogen atmosphere for 15 minutes. After the reaction mixture was cooled to room temperature, 0.5 mL of toluene solution containing 4.7 mg of 2-(di-tert-butylphosphino)-2',4',6'-triisopropylbiphenyl, 1.7 mg of palladium acetate and 70 mg of tert-butyl 2-(benzamido)-4-bromobenzoate was added and the resulting mixture was heated to reflux under nitrogen atmosphere for 4 hours. After the reaction mixture was cooled to room temperature, 4.5 mg of 60% sodium hydride, 4.7 mg of 2-(di-tert-butylphosphino)-2',4',6'-triisopropylbiphenyl and 1.7 mg of palladium acetate were added and the resulting mixture was heated to reflux under nitrogen atmosphere for 2 hours. After the reaction mixture was cooled to room temperature, 0.018 mL of 2,4-difluorophenol, 7.4 mg of 60% sodium hydride, 4.7 mg of 2-(di-tert-butylphosphino)-2',4',6'-triisopropylbiphenyl and 1.7 mg of palladium acetate were added and the resulting mixture was heated to reflux under nitrogen atmosphere for 2 hours. After the reaction mixture was cooled to room temperature, 1.6 mg of tri-tert-butylphosphine tetrafluoroborate and 5.1 mg of tris(dibenzylideneacetone)dipalladium(0) were added, and the resulting mixture was heated to reflux under nitrogen atmosphere for 1 hour and 30 minutes. 10% citric acid aqueous solution and ethyl acetate were added after the reaction mixture was cooled to room temperature. The organic layer was separated and dried over anhydrous magnesium sulfate after washed with a saturated sodium chloride aqueous solution, and the solvent was evaporated under reduced pressure. The obtained residue was purified with silica gel column chromatography [Flash Tube 2008 manufactured by Trikonex Company, eluent; hexane:ethyl acetate=4:1]to obtain tert-butyl 2-(benzamido)-4-(2,4-difluorophenoxy)benzoate.

5.0 mL of trifluoroacetic acid was added to the obtained tert-butyl 2-(benzamido)-4-(2,4-difluorophenoxy)benzoate and stirred at room temperature for 3 hours. The solvent was evaporated under reduced pressure and diisopropyl ether was added to the obtained residue and a solid substance was separated by filtration no obtain 3.8 mg of 2-(benzamido)-4-(2,4-difluorophenoxy)benzoic acid as pale yellow solid.

$^1$H-NMR (DMSO-$d_6$) δ: 6.79 (1H, dd, J=8.8, 2.7 Hz), 7.20-7.28 (1H, m), 7.46-7.52 (1H, m), 7.54-7.68 (4H, m), 7.90-7.95 (2H, m), 8.07 (1H, d, J=8.8 Hz), 8.38 (1H, d, J=2.7 Hz), 12.44 (1H, s).

Example 558

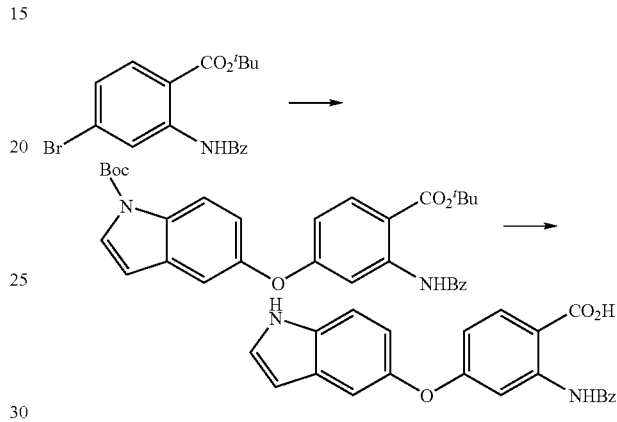

52 mg of tert-butyl 5-hydroxy-1H-indole-1-carboxylate, 79 mg of tripotassium phosphate, 4.7 mg of 2-(di-tert-butylphosphino)-2',4',6'-triisopropylbiphenyl and 6.8 mg of tris (dibenzylideneacetone)dipalladium(0) were added to 1.4 mL of toluene solution containing 70 mg of tert-butyl 2-(benzamido)-4-bromobenzoate at room temperature, and the resulting mixture was heated to reflux under nitrogen atmosphere for 2 hours and 30 minutes. After the reaction mixture was cooled to room temperature, ethyl acetate and 10% citric acid aqueous solution were added and insoluble were removed by filtration. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane:ethyl acetate=10:1] to obtain tert-butyl 5-(3-(benzamido)-4-(tert-butoxycarbonyl)phenoxy)-1H-indole-1-carboxylase.

1.0 mL of trifluoroacetic acid was added to 4.0 mL of methylene chloride solution containing the obtained tert-butyl 5-(3-(benzamido)-4-(tert-butoxycarbonyl)phenoxy)-1H-indole-1-carboxylate while ice-cooled and stirred at the same temperature for 2 hours and 30 minutes. After the reaction mixture was warmed to room temperature, ethyl acetate and a saturated sodium hydrogen carbonate aqueous solution were added. The aqueous layer was separated and washed with ethyl acetate after adjusted to pH 6.5 with 6.0 mol/L hydrochloric acid and allowed to stand still for 17 hours. A solid substance was separated by filtration to obtain 10 mg of 2-(benzamido)-4-(1H-indol-5-yloxy)benzoic acid as white solid.

$^1$H-NMR (DMSO-$d_6$) δ: 6.41-6.43 (1H, m), 6.54 (1H, dd, J=8.6, 2.7 Hz), 6.87 (1H, dd, J=8.6, 2.3 Hz), 7.25 (1H, d, J=2.2 Hz), 7.39-7.41 (1H, m), 7.43 (1H, d, J=8.5 Hz), 7.46-7.59 (3H, m), 7.96-8.04 (3H, m), 8.30 (1H, d, J=2.4 Hz;, 11.19 (1H, s).

Example 559

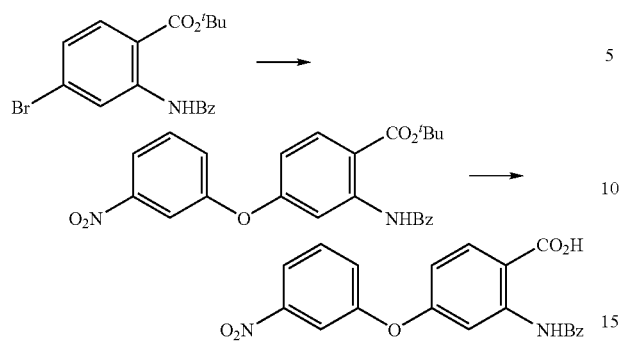

31 mg of 3-nitrophenol, 79 mg of tripotassium phosphate, 4.7 mg of 2-(di-tert-butylphosphino)-2',4',6'-triisopropylbiphenyl and 6.8 mg of tris(dibenzylideneacetone)dipalladium (0) were added to 1.4 mL of toluene solution containing 70 mg of tert-butyl 2-(benzamido)-4-bromobenzoate at room temperature, and the resulting mixture was heated to reflux under nitrogen atmosphere for 2 hours. After the reaction mixture was cooled to room temperature, 4.7 mg of 2-(di-tert-butylphosphino)-2',4',6'-triisopropylbiphenyl and 6.8 mg of tris(dibenzylideneacetone)dipalladium(0) were added and the resulting mixture was heated to reflux under nitrogen atmosphere for 1 hour. After the reaction mixture was cooled to room temperature, ethyl acetate and 10% citric acid aqueous solution were added and insoluble were removed by filtration. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane; ethyl acetate=10:1) to obtain tert-butyl 2-(benzamido)-4-(3-nitrophenoxy)benzoate.

5.0 mL of trifluoroacetic acid was added to the obtained tert-butyl 2-(benzamido)-4-(3-nitrophenoxy)benzoate and stirred at room temperature for 3 hours. The solvent was evaporated under reduced pressure and diisopropyl ether was added to the obtained residue and a solid substance was separated by filtration to obtain 34 mg of 2-(benzamido)-4-(3-nitrophenoxy)benzoic acid as pale yellow solid.

$^1$H-NMR (DMSO-$d_6$) δ: 6.91 (1H, dd, J=8.8, 2.6 Hz), 7.56-7.71 (4H, m), 7.78 (1H, t, J=8.2 Hz), 7.90-7.98 (3H, m), 8.10-8.16 (2H, m), 8.49 (1H, d, J=2.6 Hz), 12.41 (1H, s).

Examples 560 to 570

The compounds shown in Table 55 were obtained in the same manner as in Example 559.

TABLE 55

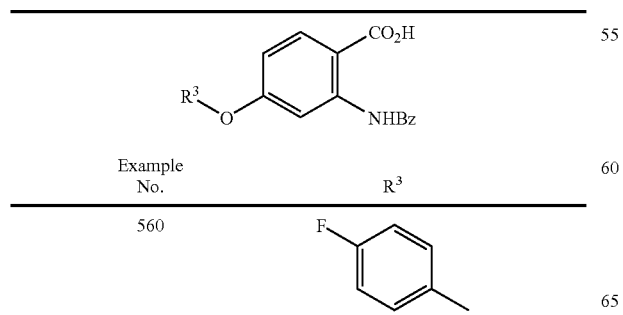

| Example No. | R³ |
|---|---|
| 560 | 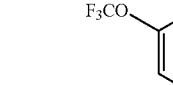 |
| 561 |  |
| 562 |  |
| 563 |  |
| 564 |  |
| 565 |  |
| 566 |  |
| 567 |  |
| 568 |  |
| 569 |  |
| 570 |  |

2-(Benzamido)-4-(4-fluorophenoxy)benzoic acid $^1$H-NMR (DMSO-$d_6$) δ: 6.76 (1H, dd, J=8.9, 2.7 Hz), 7.21-7.28 (2H, m), 7.29-7.37 (2H, m), 7.55-7.68 (3H, m), 7.90-7.95 (2H, m), 8.07 (1H, d, J=8.9 Hz), 8.39 (1H, d, J=2.7 Hz), 12.41 (1H, s).

2-(Benzamido)-4-(4-(trifluoromethoxy)phenoxy)benzoic acid $^1$H-NMR (DMSO-$d_6$) δ: 6.82 (1H, dd, J=8.9, 2.7 Hz), 7.28-7.34 (2H, m), 7.46-7.52 (2H, m), 7.56-7.69 (3H, m), 7.90-7.96 (2H, m), 8.10 (1H, d, J=8.9 Hz), 8.44 (1H, d, J=2.7 Hz), 12.41 (1H, s).

2-(Benzamido)-4-(2-methylphenoxy)benzoic acid $^1$H-NMR (DMSO-$d_6$) δ: 2.16 (3H, s), 6.67 (1H, dd, J=8.9, 2.7 Hz), 7.08-7.13 (1H, m), 7.21-7.26 (1H, m), 7.29-7.34 (1H, m), 7.38-7.41 (1H, m), 7.55-7.68 (3H, m), 7.89-7.95 (2H, m), 8.05 (1H, d, J=8.9 Hz), 8.32 (1H, d, J=2.7 Hz), 12.41 (1H, s).

2-(Benzamido)-4-(3-methylphenoxy)benzoic acid $^1$H-NMR (DMSO-$d_6$) δ: 2.34 (3H, s), 6.76 (1H, dd, J=9.0, 2.6 Hz), 6.94-7.02 (2H, m), 7.07-7.12 (1H, m), 7.36 (1H, dd, J=8.0, 7.7 Hz), 7.56-7.68 (3H, m), 7.90-7.96 (2H, m), 8.07 (1H, d, J=9.0 Hz), 8.41 (1H, d, J=2.6 Hz), 12.41 (1H, s).

2-(Benzamido)-4-(2,6-dimethylphenoxy)benzoic acid $^1$H-NMR (DMSO-$d_6$) δ: 2.10 (6H, s), 6.58 (1H, dd, J=9.0, 2.5 Hz), 7.14-7.25 (3H, m), 7.55-7.68 (3H, m), 7.89-7.95 (2H, m), 8.04 (1H, d, J=9.0 Hz), 8.25 (1H, d, J=2.5 Hz), 12.43 (1H, s).

2-(Benzamido)-4-(3-fluorophenoxy)benzoic acid $^1$H-NMR (DMSO-$d_6$) δ: 6.84 (1H, dd, J=8.8, 2.4 Hz), 7.00-7.05 (1H, m), 7.08-7.16 (2H, m), 7.48-7.68 (4H, m), 7.90-7.96 (2H, m), 8.10 (1H, d, J=8.8 Hz), 8.45 (1H, d, J=2.4 Hz), 12.41 (1H, s).

2-(Benzamido)-4-(2-fluorophenoxy)benzoic acid $^1$H-NMR (DMSO-$d_6$) δ: 6.79 (1H, dd, J=8.8, 2.6 Hz), 7.29-7.51 (4H, m), 7.55-7.69 (3H, m), 7.89-7.95 (2H, m), 8.08 (1H, d, J=8.8 Hz), 8.39 (1H, d, J=2.6 Hz), 12.41 (1H, s).

2-(Benzamido)-4-(2,6-difluorophenoxy)benzoic acid $^1$H-NMR (DMSO-$d_6$) δ: 6.85 (1H, dd, J=9.0, 2.7 Hz), 7.34-7.51 (3H, m), 7.55-7.68 (3H, m), 7.89-7.95 (2H, m), 8.09 (1H, d, J=9.0 Hz), 8.42 (1H, d, J=2.7 Hz), 12.43 (1H, s).

2-(Benzamido)-4-(3,4-dimethylphenoxy)benzoic acid $^1$H-NMR (DMSO-$d_6$) δ: 2.24 (6H, a), 6.72 (1H, dd, J=8.9, 2.7 Hz), 6.89 (1H, dd, J=8.1, 2.5 Hz), 6.98 (1H, d, J=2.5 Hz), 7.23 (1H, d, J=8.1 Hz), 7.56-7.68 (3H, m), 7.90-7.95 (2H, m), 8.05 (1H, d, J=8.9 Hz), 8.39 (1H, d, J=2.7 Hz), 12.40 (1H, s).

2-(Benzamido)-4-(3-(trifluoromethyl)phenoxy)benzoic acid $^1$H-NMR (DMSO-$d_6$) δ: 6.85 (1H, dd, J=9.0, 2.7 Hz), 7.48-7.52 (1H, m), 7.54-7.68 (5H, m), 7.72 (1H, t, J=7.9 Hz), 7.90-7.95 (2H, m), 8.11 (1H, d, J=9.0 Hz), 8.46 (1H, d, J=2.7 Hz), 12.41 (1H, s).

2-(Benzamido)-4-(4-(trifluoromethyl)phenoxy)benzoic acid $^1$H-NMR (DMSO-$d_6$) δ: 6.90 (1H, dd, J=8.8, 2.6 Hz), 7.33-7.39 (2H, m), 7.56-7.69 (3H, m), 7.81-7.88 (2H, m), 7.91-7.96 (2H, m), 8.13 (1H, d, J=8.8 Hz), 8.50 (1H, d, J=2.6 Hz), 12.41 (1H, s), 13.70-13.95 (1H, broad).

Example 571

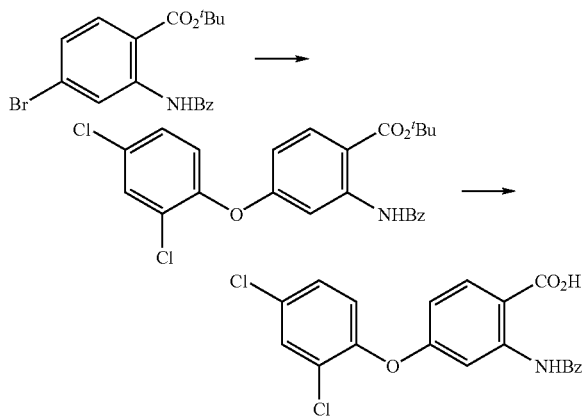

91 mg of 2,4-dichlorophenol was added to 2.1 mL of toluene suspension containing 22 mg of 60% sodium hydride at room temperature, and the resulting mixture was heated to reflux under nitrogen atmosphere for 15 minutes. After the reaction mixture was cooled to room temperature, 70 mg of tert-butyl 2-(benzamido)-4-bromobenzoate, 4.7 mg of 2-(di-tert-butylphosphine)-2',4',6'-triisopropylbiphenyl and 6.8 mg of tris(dibenzylideneacetone)dipalladium(0) were added and the resulting mixture was heated to reflux under nitrogen atmosphere for 6 hours. After the reaction mixture was cooled to room temperature, 61 mg of 2,4-dichlorophenol, 15 mg of 60% sodium hydride, 4.7 mg of 2-(di-tert-butylphosphino)-2', 4',6'-triisopropylbiphenyl and 6.8 mg of tris(dibenzylideneacetone)dipalladium(0) were added and the resulting mixture was heated to reflux under nitrogen atmosphere for 10 hours. After the reaction mixture was cooled to room temperature, 10% citric acid aqueous solution and ethyl acetate were added and insoluble were removed by filtration. The organic layer was separated and dried over anhydrous magnesium sulfate after washed with a saturated, sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane; ethyl acetate=20:1] to obtain tert-butyl 2-(benzamido)-4-(2, 4-dichlorophenoxy)benzoate.

5.0 mL of trifluoroacetic acid was added to the obtained tert-butyl 2-(benzamido)-4-(2,4-dichlorophenoxy)benzoate and stirred at room temperature for 2 hours. The solvent was evaporated under reduced pressure and the obtained residue was purified with reversed-phase silica gel column chromatography [eluent; 80-100% acetonitrile/0.1% trifluoroacetic acid aqueous solution] to obtain 8.7 mg of 2-(benzamido)-4-(2,4-dichlorophenoxy)benzoic acid as white solid.

$^1$H-NMR (DMSO-$d_6$) δ: 6.77 (1H, dd, J=8.8, 2.7 Hz), 7.41 (1H, d, J=8.8 Hz), 7.53-7.68 (4H, m), 7.88 (1H, d, J=2.4 Hz), 7.90-7.95 (2H, m), 8.08 (1H, d, J=8.8 Hz), 8.36 (1H, d, J=2.7 Hz), 12.43 (1H, s).

Examples 572 to 583

The compounds shown in Table 56 were obtained in the same manner as in Example 571.

TABLE 56

Structure: benzoic acid with CO2H, NHBz, and R3-O- substituents

| Example No. | R3 |
|---|---|
| 572 | 2,3-difluorophenyl |
| 573 | 3-chloro-2-fluorophenyl |
| 574 | 3-chloro-4-fluorophenyl |
| 575 | 3,5-dichlorophenyl |
| 576 | 4-fluoro-2-methylphenyl |
| 577 | 3,4-difluorophenyl |
| 578 | 2,5-difluorophenyl |
| 579 | 4-chloro-2-methylphenyl |
| 580 | 3,4-dichlorophenyl |
| 581 | 2,3-dichlorophenyl |
| 582 | 2,5-dichlorophenyl |
| 583 | 2,6-dichlorophenyl |

2-(Benzamido)-4-(2,3-difluorophenoxy)benzoic acid $^1$H-NMR (DMSO-d$_6$) δ: 6.86 (1H, dd, J=8.9, 2.7 Hz), 7.20-7.26 (1H, m), 7.30-7.48 (2H, m), 7.56-7.68 (3H, m), 7.90-7.95 (2H, m), 8.10 (1H, d, J=8.9 Hz), 8.44 (1H, d, J=2.7 Hz), 12.41 (1H, s).

2-(Benzamido)-4-(3-chloro-2-fluorophenoxy)benzoic acid $^1$H-NMR (DMSO-d$_6$) δ: 6.84 (1H, dd, J=8.8, 2.7 Hz), 7.32-7.43 (2H, m), 7.53-7.69 (4H, m), 7.90-7.96 (2H, m), 8.10 (1H, d, J=8.8 Hz), 8.43 (1H, d, J=2.7 Hz), 12.42 (1H, s).

2-(Benzamido)-4-(3-chloro-4-fluorophenoxy)benzoic acid $^1$H-NMR (DMSO-d$_6$) δ: 6.81 (1H, dd, J=8.8, 2.7 Hz), 7.21-7.28 (1H, m), 7.52-7.69 (5H, m), 7.90-7.96 (2H, m), 8.09 (1H, d, J=8.8 Hz), 8.42 (1H, d, J=2.7 Hz), 12.41 (1H, s).

2-(Benzamido)-4-(3,5-dichlorophenoxy)benzoic acid $^1$H-NMR (DMSO-d$_6$) δ: 6.88 (1H, dd, J=8.8, 2.6 Hz), 7.32 (2H, d, J=1.9 Hz), 7.52 (1H, t, J=1.9 Hz), 7.56-7.69 (3H, m), 7.91-7.97 (2H, m), 8.12 (1H, d, J=8.8 Hz), 8.46 (1H, d, J=2.6 Hz), 12.42 (1H, s).

2-(Benzamido)-4-(4-fluoro-2-Methylphenoxy)benzoic acid $^1$H-NMR (DMSO-d$_6$) δ: 2.15 (3H, s), 6.67 (1H, dd, J=8.9, 2.5 Hz), 7.11-7.20 (2H, m), 7.27-7.31 (1H, m), 7.55-7.68 (3H, m), 7.89-7.95 (2H, m), 8.05 (1H, d, J=8.9 Hz), 8.31 (1H, d, J=2.5 Hz), 12.43 (1H, s).

2-(Benzamido)-4-(3,4-difluorophenoxy)benzoic acid $^1$H-NMR (DMSO-d$_6$) δ: 6.81 (1H, dd, J=8.8, 2.7 Hz), 7.04-7.11 (1H, m), 7.42-7.48 (1H, m), 7.52-7.69 (4H, m), 7.90-7.96 (2H, m), 8.09 (1H, d, J=8.8 Hz), 8.42 (1H, d, J=2.7 Hz), 12.42 (1H, s).

2-(Benzamido)-4-(2,5-difluorophenoxy)benzoic acid $^1$H-NMR (DMSO-d$_6$) δ: 6.84 (1H, dd, J=8.8, 2.7 Hz), 7.21-7.28 (1H, m), 7.38-7.44 (1H, m), 7.51-7.69 (4H, m), 7.90-7.96 (2H, m), 8.09 (1H, d, J=8.8 Hz), 8.43 (1H, d, J=2.7 Hz), 12.42 (1H, s).

2-(Benzamido)-4-(5-chloro-2-methylphenoxy)benzoic acid $^1$H-NMR (DMSO-$d_6$) δ: 2.15 (3H, s), 6.72 (1H, dd, J=8.9, 2.7 Hz), 7.22 (1H, d, J=2.2 Hz), 7.30 (1H, dd, J=8.3, 2.2 Hz), 7.44 (1H, d, J=8.3 Hz), 7.55-7.68 (3H, m), 7.90-7.95 (2H, m<, 8.08 (1H, d, J=8.9 Hz), 8.34 (1H, d, J=2.7 Hz), 12.42 (1H, s).

2-(Benzamido)-4-(3,4-dichlorophenoxy)benzoic acid $^1$H-NMR (DMSO-$d_6$) δ: 6.86 (1H, dd, J=9.0, 2.5 Hz), 7.22 (1H, dd, J=8.9, 2.7 Hz), 7.54-7.69 (4H, m), 7.74 (1H, d, J=8.9 Hz), 7.90-7.96 (2H, m), 8.10 (1H, d, J=9.0 Hz), 8.45 (1H, d, J=2.5 Hz), 12.41 (1H, s).

2-(Benzamido)-4-(2,3-dichlorophenoxy)benzoic acid $^1$H-NMR (DMSO-$d_6$) δ: 6.78 (1H, dd, J=8.8, 2.6 Hz), 7.36 (1H, dd, J=8.3, 1.2 Hz), 7.50 (1H, t, J=8.2 Hz), 7.56-7.69 (4H, m), 7.90-7.96 (2H, m), 8.09 (1H, d, J=8.8 Hz), 8.38 (1H, d, J=2.6 Hz), 12.44 (1H, s).

2-(Benzamido)-1-(2,5-dichlorophenoxy)benzoic acid $^1$H-NMR (DMSO-$d_6$) δ: 6.78 (1H, dd, J=8.9, 2.7 Hz), 7.46 (1H, dd, J=8.8, 2.5 Hz), 7.54 (1H, d, J=2.5 Hz), 7.56-7.69 (3H, m), 7.73 (1H, d, J=8.8 Hz), 7.90-7.96 (2H, m), 8.09 (1H, d, J=8.9 Hz), 8.38 (1H, d, J=2.7 Hz), 12.41 (1H, s).

2-(Benzamido)-4-(2,6-dichlorophenoxy)benzoic acid $^1$H-NMR (DMSO-$d_6$) δ: 6.70 (1H, dd, J=8.8, 2.7 Hz), 7.46 (1H, t, J=8.3 Hz), 7.55-7.68 (3H, m), 7.71 (2H, d, J=8.3 Hz), 7.89-7.96 (2H, m), 8.08 (1H, d, J=8.8 Hz), 8.31 (1H, d, J=2.7 Hz), 12.49 (1H, s).

Example 584

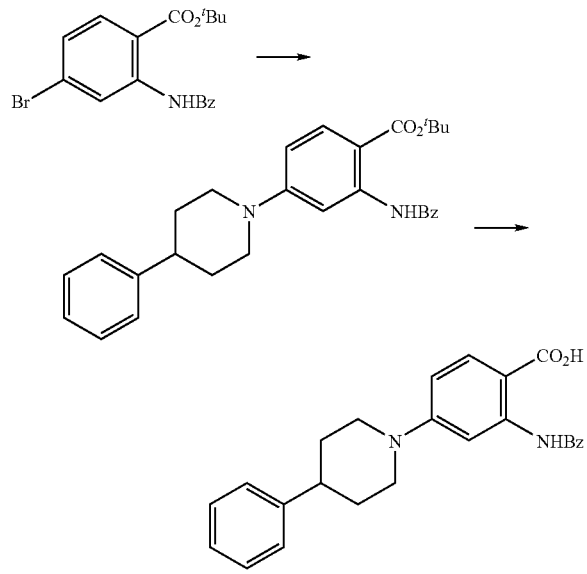

86 mg of 4-phenylpiperidine, 0.22 g of cesium carbonate, 2.4 mg of tris(dibenzylideneacetone)dipalladium(0), 1.2 mg of palladium acetate and 6.3 mg of 2-dicyclohexylphosphino-2',4',6'-triisopropylbiphenyl were added to 3.0 mL of toluene solution containing 0.10 g of tert-butyl 2-(benzamido)-4-bromobenzoate, and the resulting mixture was heated to reflux for 2 hours. After the reaction mixture was cooled to room temperature, 2.4 mg of tris(dibenzylideneacetone)dipalladium(0), 1.2 mg of palladium acetate and 6.3 mg of 2-dicyclohexylphosphino-2',4',6'-triisopropylbiphenyl were added and the resulting mixture was heated to reflux for 6 hours. After the reaction mixture was cooled to room temperature, ethyl acetate and 10% citric acid aqueous solution were added. The organic layer was separated and dried over anhydrous magnesium sulfate after washed with a saturated sodium chloride aqueous solution, and the solvent was evaporated under reduced pressure. The obtained residue was purified with silica gel column chromatography [PSQ100B (spherical) manufactured by Fuji Silysia Chemical Ltd., eluent; hexane:ethyl acetate=10:1] to obtain tert-butyl 2-(benzamido)-4-(4-phenylpiperidin-1-yl)benzoate as pale yellow solid.

5.0 mL of trifluoroacetic acid was added to the obtained tert-butyl 2-(benzamido)-4-(4-phenylpiperidin-1-yl)benzoate and stirred at room temperature for 3 hours, the solvent was evaporated under reduced pressure, ethyl acetate and water were added and pH was adjusted to pH 6.5 with a saturated sodium hydrogen carbonate aqueous solution. The organic layer was separated and dried over anhydrous magnesium sulfate after washed with water and a saturated sodium chloride aqueous solution sequentially, and the solvent was evaporated under reduced pressure. Diisopropyl ether was added to the obtained residue and a solid substance was separated by filtration to obtain 20 mg of 2-(benzamido)-4-(4-phenylpiperidin-1-yl)benzoic acid as white solid.

$^1$H-NMR (DMSO-$d_6$) δ: 1.65-1.78 (2H, m), 1.86-1.95 (2H, m), 2.76-2.87 (1H, m), 2.97-3.08 (2H, m), 4.01-4.11 (2H, m), 6.78 (1H, dd, J=9.1, 2.5 Hz), 7.17-7.23 (1H, m), 7.25-7.34 (4H, m), 7.56-7.68 (3H, m), 7.88 (1H, d, J=9.1 Hz), 7.94-7.99 (2H, m), 8.47 (1H, d, J=2.5 Hz), 12.53 (1H, s).

Examples 585 to 588

The compounds shown in Table 57 were obtained in the same manner as in Example 584.

TABLE 57

| Example No. | R$^3$ |
|---|---|
| 585 | 1-methyl-1,2,3,4-tetrahydroisoquinolin-7-yl |
| 586 | 4-benzyl-1-methylpiperidin-? |
| 587 | (1-methylpiperidin-4-yl)(phenyl)methanone-yl |

TABLE 57-continued

[Structure: benzene ring with CO₂H, R³, NHBz]

| Example No. | R³ |
|---|---|
| 588 | [1-methyl-4-phenyl-1,2,3,6-tetrahydropyridinyl structure] |

2-(Benzamido)-4-(1,2,3,4-tetrahydroisoquinolin-2-yl)benzoic acid $^1$H-NMR (DMSO-$d_6$) δ: 2.95-3.01 (2H, m), 3.64-3.70 (2H, m), 4.58 (2H, s), 6.77 (1H, dd, J=9.0, 2.6 Hz), 7.18-7.32 (4H, m), 7.57-7.68 (3H, m), 7.90 (1H, d, J=9.0 Hz), 7.95-8.00 (2H, m), 8.45 (1H, d, J=2.6 Hz), 12.53 (1H, s), 12.97 (1H, s).

2-(Benzamido)-4-(4-benzylpiperidin-1-yl)benzoic acid $^1$H-NMR (DMSO-$d_6$) δ: 1.17-1.31 (2H, m), 1.62-1.71 (2H, m), 1.74-1.88 (1H, m), 2.50-2.57 (2H, m), 2.82-2.92 (2H, m), 3.86-3.96 (2H, m), 6.69 (1H, dd, J=9.3, 2.5 Hz), 7.16-7.22 (3H, m), 7.26-7.32 (2H, m), 7.56-7.67 (3H, m), 7.84 (1H, d, J=9.3 Hz), 7.92-7.98 (2H, m), 8.39 (1H, d, J=2.5 Hz), 12.49 (1H, s), 12.94 (1H, s).

2-(Benzamido)-4-(4-benzoylpiperidin-1-yl)benzoic acid $^1$H-NMR (DMSO-$d_6$) δ: 1.58-1.72 (2H, m), 1.86-1.95 (2H, m), 3.10-3.21 (2H, m), 3.73-3.83 (1H, m), 3.93-4.03 (2H, m), 6.76 (1H, dd, J=9.1, 2.4 Hz), 7.53-7.70 (6H, m), 7.87 (1H, d, J=9.1 Hz), 7.93-7.98 (2H, m), 8.01-8.06 (2H, m), 8.43 (1H, d, J=2.4 Hz), 12.49 (1H, s), 12.90-13.15 (1H, broad).

2-(benzamido)-4-(4-phenyl-1,2,3,6-tetrahydropyridin-1-yl)benzoic acid $^1$H-NMR (DMSO-$d_6$) δ: 2.64-2.72 (2H, m), 3.65-3.71 (2H, m), 4.02-4.09 (2H, m), 6.32-6.37 (1H, m), 6.78 (1H, dd, J=9.1, 2.5 Hz), 7.25-7.32 (1H, m), 7.35-7.41 (2H, m), 7.48-7.53 (2H, m), 7.57-7.68 (3H, m), 7.90 (1H, d, J=9.1 Hz), 7.95-8.00 (2H, m), 8.47 (1H, d, J=2.5 Hz), 12.53 (1H, s), 12.90-13.15 (1H, broad).

INDUSTRIAL APPLICABILITY

The compounds of general formula [1] of the present invention or the sails thereof have the inhibitory activity of MMP-13 production and therefore they are useful as, for example, therapeutic agents for rheumatoid arthritis, osteoarthritis, cancer and the other diseases in which MMP-13 is involved.

The invention claimed is:

1. An anthranilic acid compound represented by formula (I):

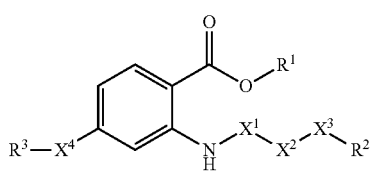

wherein, $R^1$ represents a hydrogen atom or a carboxyl protecting group;

$R^2$ represents a phenyl, cycloalkyl or heterocyclic group which is optionally substituted with at least one group selected from the group consisting of a halogen atom; a cyano group; a nitro group; an acyl group; an acyloxy group; a sulfo group; a phosphoryl group; an alkanesulfonyl group; an alkanesulfonamide group; an acetamide group; a carbamoyl group; a carboxyl group that is optionally protected; an amino group that is optionally protected; a hydroxyl group that is optionally protected; an alkyl group that is optionally substituted; an alkenyl group that is optionally substituted; an alkynyl group that is optionally substituted; an alkoxy group that is optionally substituted; an aryl group that is optionally substituted; a cyclic amino group that is optionally substituted; an aralkyl group that is optionally substituted; and a heterocyclic group that is optionally substituted;

$R^3$ represents a phenyl, cycloalkyl, cycloalkenyl, indolyl, indolinyl, 2-oxoindolinyl, isoindolyl, indolizinyl, benzimidazolyl, benzotriazolyl, indazolyl, quinolyl, tetrahydroquinolinyl, tetrahydroisoquinolinyl, quinolizinyl, isoquinolyl, phthalazinyl, naphthyridinyl, quinoxalinyl, dihydroquinoxalinyl, quinazolinyl, cinnolinyl, quinuclidinyl, 2,3-dihydrobenzopyrrolyl, benzofuranyl, isobenzofuranyl, chromenyl, chromanyl, isochromanyl, benzo-1,3-dioxolyl, benzo-1,4-dioxanyl, 2,3-dihydrobenzofuranyl, benzothienyl, 2,3-dihydrobenzothienyl, benzomorpholinyl, benzomorpholonyl, benzothiazolyl, benzothiadiazolyl or monocyclic heterocyclic group which is optionally substituted;

$X^1$ represents a carbonyl group or a sulfonyl group;

$X^2$ represents an alkylene, alkenylene or alkynylene group which is optionally substituted or a bond; provided that when $X^1$ is a sulfonyl group and $X^4$ is a bond, $X^2$ represents an alkylene, alkenylene or alkynylene group which is optionally substituted;

$X^3$ represents an oxygen atom, a sulfur atom or a bond; and $X^4$ represents a group represented by the general formula, —$X^5$—$X^6$— or —$X^6$—$X^5$—, wherein the bond on the left side of each general formula is linked to $R^3$; and $X^5$ represents an oxygen atom, a sulfur atom, an imino group which is optionally protected, a sulfinyl group, a sulfonyl group or a bond; and $X^6$ represents an alkylene, alkenylene or alkynylene group which is optionally substituted or a bond or a salt thereof.

2. The anthranilic acid compound or a salt thereof according to claim 1 wherein $X^1$ is a carbonyl group.

3. The anthranilic acid compound or a salt thereof according to claim 1, wherein $R^1$ represents a hydrogen atom;

$R^2$ represents a phenyl or heterocyclic group which is optionally substituted with a group selected from a halogen atom, a cyano group, a nitro group, a hydroxyl group which is optionally protected, an alkyl group which is optionally substituted, an alkenyl group which is optionally substituted, an alkynyl group which is optionally substituted, an alkoxy group which is optionally substituted, an aryl group which is optionally substituted, a cyclic amino group which is optionally substituted, an aralkyl group which is optionally substituted and a heterocyclic group which is optionally substituted;

$R^3$ represents a phenyl, indolyl, indolinyl, 2-oxoindolinyl, isoindolyl, indolizinyl, benzimidazolyl, benzotriazolyl, indazolyl, quinolyl, tetrahydroquinolinyl, tetrahydroisoquinolinyl, quinolizinyl, isoquinolyl, phthalazinyl, naphthyridinyl, quinoxalinyl, dihydroquinoxalinyl, quinazolinyl, cinnolinyl, quinuclidinyl, 2,3-dihydrobenzopyrrolyl, benzofuranyl, isobenzofuranyl, chromenyl, chromanyl, isochromanyl, benzo-1,3-dioxolyl, benzo-1,4-dioxanyl, 2,3-dihydrobenzofuranyl, benzothienyl, 2,3-dihydrobenzothienyl, benzomorpholinyl, benzomorpholonyl, benzothiazolyl, benzothiadiazolyl or monocyclic heterocyclic group which is optionally substituted with a group selected from a halogen atom, a hydroxyl group, an alkyl group which is optionally substituted and an alkoxy group which is optionally substituted;

$X^2$ represents an alkylene group, an alkenylene group, an alkynylene group or a bond;

provided that when $X^1$ is a sulfonyl group and $X^4$ is a bond, $X^2$ represents an alkylene group, an alkenylene group or an alkynylene group;

$X^3$ represents an oxygen atom or a bond; and $X^4$ represents the general formula —$X^6$—$X^5$—, wherein the bond on the left side of the general formula is linked to $R^3$; and $X^5$ represents an oxygen atom, a sulfur atom, an imino group which is optionally protected, a sulfinyl group, a sulfonyl group or a bond; and $X^6$ represents an alkylene, alkenylene or alkynylene group which is optionally substituted or a bond.

4. The anthranilic acid compound or a salt thereof according to claim 1, wherein $R^3$ represents a phenyl, indolyl, indolinyl, 2-oxoindolinyl, isoindolyl, indolizinyl, benzimidazolyl, benzotriazolyl, indazolyl, quinolyl, tetrahydroquinolinyl, tetrahydroisoquinolinyl, quinolizinyl, isoquinolyl, phthalazinyl, naphthyridinyl, quinoxalinyl, dihydroquinoxalinyl, quinazolinyl, cinnolinyl, quinuclidinyl, 2,3-dihydrobenzopyrrolyl, benzofuranyl, isobenzofuranyl, chromenyl, chromanyl, isochromanyl, benzo-1,3-dioxolyl, benzo-1,4-dioxanyl, 2,3-dihydrobenzofuranyl, benzothienyl, 2,3-dihydrobenzothienyl, benzomorpholinyl, benzomorpholonyl, benzothiazolyl or benzothiadiazolyl group; and these groups are optionally substituted with a group selected from a halogen atom, a hydroxyl group, an alkyl group which is optionally substituted with a halogen atom and an alkoxy group which is optionally substituted with a halogen atom.

5. The anthranilic acid compound or a salt thereof according to claim 1, wherein $X^4$ represents the general formula —$X^{6P}$—$X^{5q}$—, wherein the bond on the left side of the general formula is linked to $R^3$; and $X^{5q}$ represents an oxygen atom, a sulfur atom or a bond; and $X^{6p}$ represents an alkylene, alkenylene or alkynylene group which is optionally substituted.

6. The anthranilic acid compound or salts thereof according to claim 1, wherein $X^4$ represents the general formula —$X^{6r}$—$X^{5s}$—, wherein the bond on the left side of the general formula is linked to $R^3$; and $X^{5s}$ represents an oxygen atom or a bond; and $X^{6r}$ represents a bond.

7. A matrix metalloprotease 13 production inhibitor which comprises the anthranilic acid compound or a salt thereof according to claim 1.

8. A therapeutic agent for rheumatoid arthritis which comprises the anthranilic acid compound or a salt thereof according to claim 1.

9. The anthranilic acid compound or salt thereof according to claim 1, wherein $X^2$ represents an alkylene group, an alkenylene group, or a bond.

10. The anthranilic acid compound or salt thereof according to claim 1, wherein $X^3$ represents an oxygen atom or a bond.

11. The anthranilic acid compound or salt thereof according to claim 1, wherein $X^3$ represents a bond.

12. The anthranilic acid compound or salt thereof according to claim 1, wherein $X^1$ is a carbonyl group;

—$X^2$—$X^3$—, together, represents a bond;

$X^4$ represents $CH_2$, CH=CH, C≡O, S, NH, $(CH_2)_2$, $(CH_2)_3$, $(CH_2)_4$, $CH_2O$, $(CH_2)_2O$, $(CH_2)_3O$, $CH_2S$, $SCH_2$, or $CH_2CH=CH$;

$R^1$ is hydrogen; and $R^2$ is phenyl.

13. The anthranilic acid compound or salt thereof according to claim 1, wherein

—$X^2$—$X^3$—, together, represents a bond, CH=CH(E), $CH_2$, $CH_2O$, $CH_2CH=CH(E)$, $C(CH_3)=CH(E)$, $(CH_2)_2$, $(CH_2)_3$ or

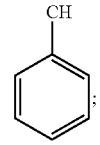

$X^4$ represents $(CH_2)_2$;

$R^1$ is hydrogen; and $R^3$ is phenyl.

14. The anthranilic acid compound or salt thereof according to claim 13, wherein $X^1$ represents a carbonyl group.

15. The anthranilic acid compound or salt thereof according to claim 13, wherein $X^1$ represents a sulfonyl group.

16. The anthranilic acid compound or salt thereof according to claim 1, wherein —$X^2$—$X^3$—, together, represents a bond, CH=CH(E), $CH_2CH=CH(E)$, $C(CH_3)=CH(E)$, $CH_2$, $(CH_2)_2$, $(CH_2)_3$, or $CH_2O$;

$X^4$ represents O;

$R^1$ is hydrogen; and $R^3$ is phenyl.

17. The anthranilic acid compound or salt thereof according to claim 16, wherein $X^1$ represents a carbonyl group.

18. The anthranilic acid compound or salt thereof according to claim 16, wherein $X^1$ represents a sulfonyl group;

$R^2$ represents a phenyl group; and

—$X^2$—$X^3$—, together, represents CH=CH or $CH_2$.

19. The anthranilic acid compound or salt thereof according to claim 1, wherein —$X^2$—$X^3$—, together, represents a bond, CH=CH(E), $CH_2CH=CH(E)$, $C(CH_3)=CH(E)$, $(CH_2)_2$, CH=CH, or

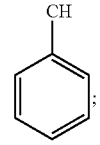

$X^4$ represents a bond;

$R^1$ represents hydrogen; and $R^3$ represents a phenyl group.

20. The anthranilic acid compound or salt thereof according to claim 19, wherein $X^1$ represents a carbonyl group; and —$X^2$—$X^3$—, together, represents a bond, CH=CH(E), $CH_2CH=CH(E)$, $C(CH_3)=CH(E)$, or

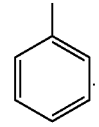

* * * * *